US012453724B2

(12) United States Patent
Blizzard et al.

(10) Patent No.: US 12,453,724 B2
(45) Date of Patent: Oct. 28, 2025

(54) OCULAR IMPLANT CONTAINING A TYROSINE KINASE INHIBITOR

(71) Applicant: OCULAR THERAPEUTIX, INC., Bedford, WA (US)

(72) Inventors: Charles D. Blizzard, Bedford, MA (US); Erica Kahn, Bedford, MA (US); Peter Jarrett, Bedford, MA (US); Rabia Gurses-Ozden, Bedford, MA (US); Rami El-Hayek, Bedford, MA (US); Elizabeth Braun, Bedford, MA (US); Joseph Iacona, Bedford, MA (US); Chintan Patel, Bedford, MA (US); Mark Ransbottom, Bedford, MA (US); Olivia Sherman, Bedford, MA (US); William Isom, Bedford, WA (US)

(73) Assignee: OCULAR THERAPEUTIX, INC., Bedford, MA (US)

( * ) Notice: Subject to any disclaimer, the term of this patent is extended or adjusted under 35 U.S.C. 154(b) by 0 days.

(21) Appl. No.: 19/174,612

(22) Filed: Apr. 9, 2025

(65) Prior Publication Data

US 2025/0235438 A1 Jul. 24, 2025

Related U.S. Application Data

(63) Continuation of application No. PCT/US2024/023688, filed on Apr. 9, 2024.

(60) Provisional application No. 63/609,334, filed on Dec. 12, 2023, provisional application No. 63/546,064, filed on Oct. 27, 2023, provisional application No. 63/458,558, filed on Apr. 11, 2023.

(51) Int. Cl.
*A61K 31/4439* (2006.01)
*A61K 9/00* (2006.01)
*A61K 47/34* (2017.01)

(52) U.S. Cl.
CPC ........ *A61K 31/4439* (2013.01); *A61K 9/0051* (2013.01); *A61K 47/34* (2013.01)

(58) Field of Classification Search
CPC ... A61K 31/4439; A61K 9/0051; A61K 47/34
See application file for complete search history.

(56) References Cited

U.S. PATENT DOCUMENTS

| | | | |
|---|---|---|---|
| 3,949,750 | A | 4/1976 | Freeman |
| 3,993,071 | A | 11/1976 | Higuchi et al. |
| 4,915,684 | A | 4/1990 | Mackeen et al. |

(Continued)

FOREIGN PATENT DOCUMENTS

| | | |
|---|---|---|
| CN | 104884049 | 9/2015 |
| CN | 107205922 | 9/2017 |

(Continued)

OTHER PUBLICATIONS

European Search Report for Application No. 21164737.5 dated Aug. 18, 2021, 4 pgs.

(Continued)

*Primary Examiner* — Carlos A Azpuru
(74) *Attorney, Agent, or Firm* — Lowenstein Sandler LLP

(57) ABSTRACT

The invention relates to a sustained release biodegradable ocular implant containing axitinib dispersed in a hydrogel for the treatment of a retinal disease for an extended period of time.

12 Claims, 36 Drawing Sheets

(A)

(B)

(56) References Cited

U.S. PATENT DOCUMENTS

| | | | |
|---|---|---|---|
| 5,469,867 | A | 11/1995 | Schmitt |
| 5,902,598 | A | 5/1999 | Chen et al. |
| 6,027,470 | A | 2/2000 | Mendius |
| 6,196,993 | B1 | 3/2001 | Cohan et al. |
| 6,509,327 | B1 | 1/2003 | Cagle et al. |
| 6,534,524 | B1 | 3/2003 | Kania et al. |
| 6,646,001 | B2 | 11/2003 | Hellberg et al. |
| 6,726,918 | B1 | 4/2004 | Wong et al. |
| 6,899,717 | B2 | 5/2005 | Weber et al. |
| 6,982,090 | B2 | 1/2006 | Gillespie |
| 7,090,681 | B2 | 8/2006 | Weber et al. |
| 7,998,497 | B2 | 8/2011 | de Juan, Jr. et al. |
| 8,034,366 | B2 | 10/2011 | Shiah et al. |
| 8,034,370 | B2 | 10/2011 | Shiah et al. |
| 8,039,470 | B2 | 10/2011 | Liang et al. |
| 8,409,606 | B2 | 4/2013 | Sawhney et al. |
| 8,506,987 | B2 | 8/2013 | Shiah et al. |
| 8,512,738 | B2 | 8/2013 | Hughes et al. |
| 8,512,749 | B2 | 8/2013 | Edelman et al. |
| 8,524,709 | B2 | 9/2013 | Liang et al. |
| 8,535,705 | B2 | 9/2013 | Edelman et al. |
| 8,563,027 | B2 | 10/2013 | Sawhney et al. |
| 8,685,435 | B2 | 4/2014 | Nivaggioli et al. |
| 8,791,140 | B2 | 7/2014 | Campeta et al. |
| 8,808,225 | B2 | 8/2014 | Prausnitz et al. |
| 8,956,655 | B2 | 2/2015 | Lyons et al. |
| 8,961,501 | B2 | 2/2015 | Jarrett et al. |
| 9,125,807 | B2 | 9/2015 | Sawhney et al. |
| 9,192,511 | B2 | 11/2015 | Shiah et al. |
| 9,205,150 | B2 | 12/2015 | El-Hayek et al. |
| 9,254,267 | B2 | 2/2016 | Sawhney |
| 9,278,139 | B2 | 3/2016 | Rau et al. |
| 9,320,647 | B2 | 4/2016 | Lerner et al. |
| 9,370,485 | B2 | 6/2016 | Sawhney et al. |
| 9,447,469 | B2 | 9/2016 | Lamont |
| 9,463,114 | B2 | 10/2016 | Odrich et al. |
| 9,504,653 | B2 | 11/2016 | Liu et al. |
| 9,539,259 | B2 | 1/2017 | Zack et al. |
| 9,572,800 | B2 | 2/2017 | Zarnitsyn et al. |
| 9,636,189 | B2 | 5/2017 | Ahari et al. |
| 9,775,906 | B2 | 10/2017 | Sawhney et al. |
| 9,849,082 | B2 | 12/2017 | de Juan, Jr. et al. |
| 9,931,330 | B2 | 4/2018 | Zarnitsyn et al. |
| 9,980,901 | B2 | 5/2018 | Ni |
| 10,010,610 | B2 | 7/2018 | Horn |
| 10,076,526 | B2 | 9/2018 | Shiah et al. |
| 10,111,886 | B2 | 10/2018 | Ng et al. |
| 10,119,202 | B2 | 11/2018 | Mao et al. |
| 10,226,417 | B2 | 3/2019 | Jarrett et al. |
| 10,251,954 | B2 | 4/2019 | Sawhney et al. |
| 10,300,014 | B2 | 5/2019 | de Juan, Jr. et al. |
| 10,420,724 | B2 | 9/2019 | Jarrett et al. |
| 10,570,202 | B2 | 2/2020 | Martini et al. |
| 10,617,563 | B2 | 4/2020 | Jarrett et al. |
| 10,688,092 | B2 | 6/2020 | Ni et al. |
| 10,702,539 | B2 | 7/2020 | Shiah et al. |
| 10,786,462 | B2 | 9/2020 | Jarrett et al. |
| 10,869,924 | B2 | 12/2020 | Andrews et al. |
| 10,874,605 | B2 | 12/2020 | Nivaggioli et al. |
| 10,874,606 | B2 | 12/2020 | de Juan, Jr. et al. |
| 10,905,765 | B2 | 2/2021 | Jarrett et al. |
| 11,053,224 | B2 | 7/2021 | Liang et al. |
| 11,129,690 | B2 | 9/2021 | Fisher |
| 11,439,592 | B2 | 9/2022 | Blizzard et al. |
| 11,534,396 | B2 | 12/2022 | Blizzard et al. |
| 12,161,753 | B2 * | 12/2024 | Blizzard ................. A61P 27/02 |
| 12,357,565 | B2 | 7/2025 | Blizzard et al. |
| 2002/0169409 | A1 | 11/2002 | Gillespie |
| 2003/0065060 | A1 | 4/2003 | Qvist et al. |
| 2003/0108511 | A1 | 6/2003 | Sawhney |
| 2004/0175410 | A1 | 9/2004 | Ashton et al. |
| 2005/0197614 | A1 | 9/2005 | Pritchard et al. |
| 2005/0232972 | A1 | 10/2005 | Odrich |
| 2005/0244475 | A1 | 11/2005 | Edelman et al. |
| 2005/0283109 | A1 | 12/2005 | Peyman |
| 2006/0094763 | A1 | 5/2006 | Ye et al. |
| 2006/0095108 | A1 | 5/2006 | Chowdhury et al. |
| 2007/0298075 | A1 | 12/2007 | Borgia et al. |
| 2008/0124400 | A1 | 5/2008 | Liggins et al. |
| 2008/0140192 | A1 | 6/2008 | Humayun et al. |
| 2008/0247984 | A1 | 10/2008 | Messersmith et al. |
| 2009/0227981 | A1 | 9/2009 | Bennett |
| 2012/0059338 | A1 | 3/2012 | Beeley et al. |
| 2012/0156259 | A1 | 6/2012 | Rau et al. |
| 2014/0128478 | A1 | 5/2014 | Asgharian et al. |
| 2015/0037422 | A1 | 2/2015 | Kaplan et al. |
| 2016/0296627 | A1 | 10/2016 | Garcia et al. |
| 2016/0331738 | A1 | 11/2016 | Jarrett et al. |
| 2017/0182173 | A1 | 6/2017 | Ng et al. |
| 2018/0085307 | A1 | 3/2018 | Sawhney et al. |
| 2018/0353431 | A1 | 12/2018 | Guo et al. |
| 2019/0070339 | A1 | 3/2019 | Gerecht et al. |
| 2019/0336441 | A1 | 11/2019 | Whitcup et al. |
| 2019/0365737 | A1 | 12/2019 | Haniuda et al. |
| 2019/0388522 | A1 | 12/2019 | Burian et al. |
| 2020/0306182 | A1 | 10/2020 | Das et al. |
| 2020/0337989 | A1 | 10/2020 | Jarrett et al. |
| 2021/0007973 | A1 | 1/2021 | Patel et al. |
| 2021/0017266 | A1 | 1/2021 | Racine et al. |
| 2021/0078970 | A1 | 3/2021 | Lu et al. |
| 2022/0054476 | A1 | 2/2022 | Rosen et al. |
| 2022/0054477 | A1 | 2/2022 | Rosen et al. |
| 2022/0054478 | A1 | 2/2022 | Rosen et al. |
| 2022/0062273 | A1 | 3/2022 | Sprogøe et al. |
| 2022/0080044 | A1 | 3/2022 | Chen et al. |
| 2023/0116809 | A1 | 4/2023 | Knappe et al. |
| 2023/0140691 | A1 | 5/2023 | Byrne et al. |
| 2023/0302156 | A1 | 9/2023 | Jiang et al. |
| 2023/0338286 | A1 | 10/2023 | Bassett et al. |

FOREIGN PATENT DOCUMENTS

| | | | |
|---|---|---|---|
| CN | 109982683 | | 7/2019 |
| CN | 116419755 | | 7/2023 |
| WO | 02/43785 | | 6/2002 |
| WO | 2005/107708 | A1 | 11/2005 |
| WO | 2009/008946 | | 1/2009 |
| WO | 2010/093873 | | 8/2010 |
| WO | 2010111449 | | 9/2010 |
| WO | 2013/039706 | | 3/2013 |
| WO | 2013/086015 | | 6/2013 |
| WO | 2013/188273 | | 12/2013 |
| WO | 2014152959 | A1 | 9/2014 |
| WO | 2015/108787 | A2 | 7/2015 |
| WO | 2016/094646 | | 6/2016 |
| WO | 2016/178150 | A1 | 11/2016 |
| WO | 2016/183296 | | 11/2016 |
| WO | 2016176579 | A1 | 11/2016 |
| WO | 2017/015591 | | 1/2017 |
| WO | 2017/015616 | | 1/2017 |
| WO | 2017/091749 | | 6/2017 |
| WO | 2018/058048 | | 3/2018 |
| WO | 2018/183984 | A1 | 3/2018 |
| WO | 2019/094652 | | 5/2019 |
| WO | 2019/200181 | A1 | 10/2019 |
| WO | 2020/219890 | | 10/2020 |
| WO | 2020243608 | | 12/2020 |
| WO | 2021/195163 | A1 | 9/2021 |
| WO | 2022/093818 | | 5/2022 |
| WO | WO2022/093818 | A1 * | 5/2022 |
| WO | 2022/204374 | A1 | 9/2022 |
| WO | 2023/064578 | A1 | 4/2023 |
| WO | 2023/107478 | A1 | 6/2023 |
| WO | 2024/081410 | A1 | 4/2024 |

OTHER PUBLICATIONS

Avery, et al., "Preliminary Findings from a Phase 1 Trial Evaluating the Safety, Tolerability and Biological Activity of OTX-TKI, a Hydrogel-Based, Sustained-Release Intravitreal Axitinib Implant, in Subjects with Neovascular Age- Related Macular Degeneration," Retina Society Annual Scientific Meeting, 2020.

(56) References Cited

OTHER PUBLICATIONS

Avery, Robert L., "Safety and Efficacy of OTX-TKI, a Novel Tyrosine Kinase Inhibitor Hydrogel Intravitreal Implant," Annual VIT Buckle Society Meeting, Apr. 2020.
Csaky, et al., "Evaluating Safety, Tolerability and Biological Activity of OTX-TKI, a Hydrogel-Based, Sustained-Relese Intravitreal Axitinib Implant, in Subjects with Neovascular Age-Releated Macular Degeneration Preliminary Findings from a Phase 1 Trial," Euretina Congress 2020.
Mattessich, et al., "Transforming Drug Delivery Leveraging a Novel Technology Platform," Sep. 2020.
International Search Report for PCT/US2021/023806 mailed Jul. 9, 2021, 4 pages.
Written Opinion of the International Searching Authority for PCT/US2021/023806 mailed Jul. 9, 2021, 9 pages.
Mattessich, et al., "Transforming Drug Delivery Leveraging a Novel Technology Platform," Oct. 10, 2020.
El-Hayek, et al., "Efficacy of a 6 month Sustained Hydrogel Delivery System for Tyrosine Kinase Inhibitors in a VEGF Induced Retinal Leakage Model," Association for Research in Vision and Ophthalmology 2017 Annual Meeting; Baltimore, MD, May 7-11, 2017.
Jarrett, P., et al., "Tolerability of a 6 month Sustained Hydrogel Delivery System for Tyrosine Kinase Inhibitors in Dutch Belted Rabbits," Association for Research in Vision and Ophthamology 2017 Annual Meeting; Baltimore, MD May 7-11, 2017.
Jarrett, T., et al., "Pharmacokinetics of a 6 month Sustained Hydrogel Delivery System for Tyrosine Kinase Inhibitors in Dutch Belted Rabbits," Association for Research in Vision and Ophthamology 2017 Annual Meeting; Baltimore, MD May 7-11, 2017.
El-Hayek, et al., "Effectiveness of Sustained release TKI Hydrogel Combined with Bevacizumab in a VEGF Induced Retinal Leakage Model Through 12 Months," Association for Research in Vision and Ophthalmology 2018 Annual Meeting; Honolulu, HI, April 29-May 3, 2018.
Jarrett, P, et al., "Efficacy and Tolerability of OTX-TKI, a Sustained Hydrogel Delivery System for a Tyrosine Kinase Inhibitor, in a VEGF-Induced Retinal Leakage Model through 12 Months," presented at the ARVO Annual Meeting May 2018.
Jarrett, P., et al., "Efficacy & Tolerability of OTX-TKI, a Sustained Hydrogel Delivery System for a Tyrosine Kinase Inhibitor, in a VEGF Induced Retinal Leakage Model: 1 Year Results," Association for Research in Vision and Ophthalmology, Canada Apr. 28-May 2, 2019.
Csaky, et al., "Evaluating safety, tolerability and biological activity of OTX-TKI, a hydrogel-based, sustained-release intravitreal axitinib implant, in subjects with neovascular age-releated mascular degeneraiton (nAMD)—preliminary findings from phase 1 trail," Prize Paper Session 2: New Drug Treatment and Technology Session.
Ocular TTherapeutix™ Reports Second Quarter 2020 Financial Results and Business Update, Newly Published Physician Fee Schedules for 0356T for the Administration of Intracanalicular Inserts to Support Ongoing DEXTENZA® Launch, Firefox, 9 pgs.
Kim et al., "Persistent Remnants of Dexamethasone Intravitreal Implant (Ozurdex)", Retina, The Journal of Retinal and Vitreous Diseases, vol. 00, No. 00, Feb. 13, 2020, pp. 1-6, published by Retina.
Gillies et al., "A Randomized Clinical Trial of Intravitreal Bevacizumab versus Intravitreal Dexamethasone for Diabetic Macular Edema", Opthamology, vol. 121, No. 12, Dec. 2014, pp. 2473-2481, published by American Academy of Opthamology.
Bacharach et al., "Phase 3, Randomized, 20-Month Study of the Efficacy and Safety of Bimatoprost Implant in Patients with Open-Angle Glaucoma and Ocular Hypertension (ARTEMIS 2)", Drugs, vol. 81 No. 17, pp. 2017-2033, published by Adis.
Rahic et al., "Novel Drug Delivery Systems Fighting Glaucoma: Formulation Obstacles and Solutions", Pharmaceutics, vol. 13, No. 28, pp. 1-58, published by MDPI.
Pardo-Lopez et al., "Anterior chamber migration of dexametasona intravitreal implant (Ozurdex)", Graefe's Archive for Clinical and Experimental Opthalmology, Nov. 2011, vol. 250, pp. 1703-1704, Published by Springer.
Narvekar et al., "Axitinib-Loaded Poly(Lactic-Co-Glycolic Acid) Nanoparticles for Age-Related Macular Degeneration: Formulation development and In Vitro Characterization", ASSAY and Druge Development Technologies, May/Jun. 2019, pp. 167-177, vol. 17, No. 4.
Das, et al., "A review of emerging tyrosine kinase inhibitors as durable treatment of neovascular age-related mascular degeneration", Expert Opinion on Emerging Drugs, 2023, 9 pgs.
Bao, Zhi et al., "Preparation of axitnib in biodegradable drug membranes for ocular surface", Chin J. Clin. Pharmacol, vol. 33, No. 17, Sep. 2017, 4 pages.
Kahn, Erica et al., "A Safety and Pharmacokinetic Study of a Novel Hydrogel-based Axitnib Intravitreal Implant (OTX-TKI) in Non-Human Primates", Investigative Ophthamology & Visual Science, Jun. 2022, vol. 63, 4 pages.
Giddabasappa et al., "Axitinib inhibits retinal and choroidal neovascularization in in vitro and in vivo models", Experimental Eye Research, 2016, pp. 373-379. vol. 145, Elsevier.
International Search Report and Written Opinion of International Application No. PCT/US2024/023688 mailed Jun. 18, 2024, 17 pgs.
Campeta et al., Journal of Pharmaceutical Sciences, Development of a Targeted Polymorph Screening Approach for a Complex Polymorphic and Highly Solvating API:, Sep. 2010, 3874-3886, vol. 99, No. 9.
Chekal et al., Organic Process Research & Development, "The Challenges of Developing an API Crystallization Process for a Complex Polymorphic and Highly Solvating System, Part I", 2009, 1327-1337, vol. 13.
Ren et al., Cocrystallization of axitinib with carboxylic acids: preparation, crystal structures and dissolution behavior:, Cryst Eng Comm., 2021, 5504-5515, vol. 23.
Kolb et al., "Click Chemistry: Diverse Chemical Function from a Few (2001). Click Chemistry: Diverse Chemical Function from a Few Good Reactions", Angewandte Chemie International Edition, 2001, 2004-2021, vol. 40 No. 11.
Short, "Selected Aspects of Ocular Toxicity Studies With a Focus on High-Quality Pathology Reports: A Pathology/Toxicology Consultant's Perspective", Toxicologic Pathology, 2021. 673-699, vol. 49, No. 3.
Lorget et al., "Characterization of the pH and Temperature in the Rabbit, Pig, and Monkey Eye: Key Parameters for the Development of Long-Acting Delivery Ocular Strategies", Molecular Pharmaceutics, 2891-2896, vol. 13, No. 9.
Landers III et al., Determination of Retinal and Vitreous Temperature in Vitrectomy:, Retina, Jan. 2012, 172-176, vol. 32, No. 1.

* cited by examiner

ArmWidth*ArmLength*5+Center^2 = "Surface Area End Face"
Perimiter*ImplantLength+2*SurfaceAreaEndFace = "Total Implant Surface Area'

| Implant Length (mm) | Ave Arm Width (mm) | Ave Arm Length (mm) | Average Center (mm) | Perimeter (mm) | Surface Area End Face (mm2) | Total Implant Surface Area (mm2) |
|---|---|---|---|---|---|---|
| 10.06 | 0.14 | 0.36 | 0.38 | 4.81 | 0.39 | 49.17 |

Axitinib

N-succinoyloxymethyl prodrug

N-mPEG-oxymethyl prodrug

LC/MS REPORT

| | | | |
|---|---|---|---|
| Sample Name | : A022213435 | Operator | : NITISH |
| Location | : Vial 42 | Injection Date | : 01-09-2022 |
| Inj. Vol | : 3µL | Injection Time | : 5:59:02 PM |
| Acq Method | : XT-095-FA-2022.M | | |
| Data file | : D:\DATA\SEP-2022\AR0222RD0027337.D | | |

Sample Info :

| # | Meas. Ret | Area | Area % |
|---|---|---|---|
| 1 | 2.428 | 0.838 | 0.025 |
| 2 | 2.528 | 2.392 | 0.072 |
| 3 | 2.595 | 64.206 | 1.921 |
| 4 | 2.838 | 3174.725 | 95.007 |
| 5 | 3.159 | 28.462 | 0.852 |
| 6 | 3.253 | 57.749 | 1.728 |
| 7 | 3.855 | 10.599 | 0.317 |
| 8 | 3.982 | 1.946 | 0.058 |
| 9 | 4.067 | 0.661 | 0.020 |

MASS REPORT

Data File: AR0222RD0027337.D Instrument LC-MSD-Trap-XCT_Plus

Method: XT-095-FA-2022.M Sample Name A022213435

| # | Meas. Ret | Area | Area % |
|---|---|---|---|
| 1 | 2.586 | 39.915 | 2.464 |
| 2 | 2.959 | 2.438 | 0.150 |
| 3 | 3.028 | 1547.869 | 95.536 |
| 4 | 3.163 | 12.796 | 0.790 |
| 5 | 3.300 | 10.486 | 0.647 |
| 6 | 3.397 | 6.699 | 0.413 |

1 Detector A Channel 1 / 225nm

Peak Table

Detector A Channel 1 / 225nm

| Peak# | Ret. Time (min) | RRT | Height | Area | Area% | Name |
|---|---|---|---|---|---|---|
| 1 | 5.142 | 0.580 | 444 | 2387 | 0.034 | |
| 2 | 6.306 | 0.712 | 22170 | 166152 | 2.346 | |
| 3 | 7.192 | 0.811 | 1522 | 9222 | 0.130 | |
| 4 | 8.109 | 0.915 | 1697 | 9895 | 0.140 | |
| 5 | 8.563 | 1.000 | 1037912 | 6627115 | 93.576 | Axitinib-N-(mPEG)1-oxy methyl produng |
| 6 | 9246 | 1.043 | 966 | 8446 | 0.119 | |
| 7 | 9.609 | 1.091 | 2881 | 17758 | 0.251 | |
| 8 | 9.858 | 1.112 | 742 | 5114 | 0.072 | |
| 9 | 10.016 | 1.130 | 634 | 3995 | 0.056 | |
| 10 | 10.311 | 1.186 | 2734 | 19745 | 0.279 | |
| 11 | 10.732 | 1.211 | 4085 | 27845 | 0.393 | |
| 12 | 11.956 | 1.349 | 696 | 4636 | 0.065 | |
| 13 | 12.096 | 1.365 | 243 | 1452 | 0.020 | |
| 14 | 13.829 | 1.560 | 41 | 5399 | 0.076 | |
| 15 | 16.442 | 1.855 | 2389 | 59362 | 0.838 | |
| 16 | 16.952 | 1.913 | 5252 | 86092 | 1.216 | |
| 17 | 18.971 | 2.140 | 43 | 2470 | 0.035 | |
| 18 | 23.082 | 2.604 | 1368 | 21459 | 0.303 | |
| 19 | 28.827 | 3.252 | 213 | 3554 | 0.050 | |
| Total | | | 1086031 | 7062096 | 100.000 | |

Peak Results

| | RT | Area | % Area | Height (µV) |
|---|---|---|---|---|
| 1 | 1.344 | 2592698 | 99.33 | 1544053 |
| 2 | 1.440 | 3864 | 0.15 | 2503 |
| 3 | 1.502 | 2334 | 0.09 | 1103 |
| 4 | 1.601 | 7956 | 0.30 | 5715 |
| 5 | 1.873 | 3321 | 0.13 | 973 |

Peak Table

PDA Ch1 225nm

| Peak# | Ret. Time (min | RRT | Height | Area | Area% | Name |
|---|---|---|---|---|---|---|
| 1 | 5.671 | 0.607 | 389 | 2566 | 0.043 | |
| 2 | 6.516 | 0.697 | 686 | 5003 | 0.083 | |
| 3 | 9.147 | 0.979 | 4261 | 17316 | 0.288 | |
| 4 | 9.344 | 1.000 | 925661 | 5964638 | 99.348 | Axitinib-N-(mPEG)1-oxy methyl prodrug |
| 5 | 10.546 | 1.129 | 427 | 2298 | 0.038 | |
| 6 | 11.359 | 1.216 | 1331 | 8842 | 0.147 | |
| 7 | 15.677 | 1.678 | 303 | 1540 | 0.026 | |
| 8 | 20.371 | 2.180 | 362 | 1609 | 0.027 | |
| Total | | | 933419 | 6003812 | 100.000 | |

OCULAR IMPLANT CONTAINING A TYROSINE KINASE INHIBITOR

This application incorporates by reference for all purposes U.S. Provisional Applications No. 63/458,558 filed Apr. 11, 2023, 63/546,064 filed Oct. 27, 2023, and 63/609,334 filed Dec. 12, 2023.

TECHNICAL FIELD

The present invention relates to a sustained release biodegradable ocular implant containing a tyrosine kinase inhibitor (TKI) such as axitinib for the treatment of ocular diseases, including neovascular (wet) age-related macular degeneration (AMD. According to the present invention, ocular diseases are treated by injecting an implant containing TKI, into the eye, where the implant releases the TKI over an extended period of time.

BACKGROUND

Macular diseases, including AMD, are among the leading causes of visual impairment and irreversible blindness in the world for people over the age of 50. Specifically, AMD was one of the most common retinal diseases in the United States (US) in 2019, affecting approximately 16.9 million people, and this is expected to grow to 18.8 million people in 2024 (Market Scope, Ophthalmic Comprehensive Reports. 2019 Retinal Pharmaceuticals Market Report: A Global Analysis for 2018 to 219 September 2019). AMD can be subdivided into different disease stages. Early AMD is characterized by the presence of a few (<20) medium-size drusen or retinal pigmentary abnormalities. Intermediate AMD is characterized by at least one large druse, numerous medium-size drusen, or geographic atrophy that does not extend to the center of the macula. Advanced or late AMD can be either non-neovascular (dry, atrophic, or non-exudative) or neovascular (wet or exudative). Advanced non-neovascular AMD is characterized by drusen and geographic atrophy extending to the center of the macula. Advanced neovascular AMD is characterized by choroidal neovascularization and its sequelae (Jager et al., Age-related macular degeneration. N Engl J Med. 2008; 358(24):2606-17).

The more advanced form of wet AMD is characterized by an increase in vascular endothelial growth factor (VEGF), which promotes the growth of new vessels (angiogenesis) that grow beneath the retina and leak blood and fluid into and below the macular and subretinal space. Successful interference of this pathway has been achieved with the development of inhibitors of vascular endothelial growth factor subtypes, i.e., VEGF inhibitors, initially used to treat various cancers. Photodynamic therapy in combination with anti-VEGF and steroid administration are currently reserved as a second-line therapy for patients not responding to monotherapy with an anti-VEGF agent (Al-Zamil et al., Recent developments in age-related macular degeneration: a review. Clin Interv Aging. 2017; 12:1313-30).

Other common retinal diseases are diabetic eye diseases such as diabetic retinopathy (DR). DR was one of the most common retinal diseases in the US in 2019, affecting approximately 8 million people, and this is expected to grow to 8.8 million people in 2024 (Market Scope 2019, supra). The condition is characterized by blood vessel leakage, blockage, or proliferation of neovascularization, which can progress to vision impairment and ultimately vision loss. The disease can be categorized in non-proliferative diabetic retinopathy (NPDR) and proliferative diabetic retinopathy (PDR). As the NPDR progresses in severity, there is an increased risk of developing the more serious proliferative stages until loss of vision. Diabetic macular edema (DME) can occur at any stage of DR, and is characterized by a decrease in retinal tension and an increase in vascular pressure caused by the upregulation of VEGF, retinal vascular autoregulation (Browning et al., Diabetic macular edema: evidence-based management, 2018 Indian journal of ophthalmology, 66(1), p. 1736), and inflammatory cytokines and chemokines (Miller et al., Diabetic macular edema: current understanding, pharmacologic treatment options, and developing therapies. 2018, Asia-Pacific Journal of Ophthalmology, 7(1): 28-35). The changes that occur from these inflammatory and vasogenic mediators result in the breakdown of the blood retinal barrier (BRB) in the vascular endothelium (Miller et al, supra). Hard exudates enter into the extracellular space causing blurred and distorted central vision, resulting in a decrease in the patient's visual acuity (Schmidt-Erfurth et al., guidelines for the Management of Diabetic Macular Edema by the European Society of Retina Specialists (EURETINA). 2017, Ophthalmologica, 237(4): 185-222). On average, a patient will experience an 8% decrease in visual acuity after 3 years following the start of the condition.

The basis of all available treatments for DR is to try to control the metabolic functions of hyperglycemia and blood pressure (Browning et al., supra). Anti-VEGF therapy is currently considered a first line therapy in the standard of care treatment of DME as it is proven to be less destructive and damaging than other treatment methods (Schmidt-Erfurth et al., supra). Anti-VEGF therapy and pan retinal photocoagulation are commonly used for the treatment of PDR (Brown et al., Evaluation of intravitreal aflibercept for the treatment of severe nonproliferative diabetic retinopathy: results from the PANORAMA randomized clinical trial; JAMA Ophthalmol 2021 Sep. 1; 139(9):946-955). In recent years, there has been a shift to treat moderate to severe NDPR with anti-VEGF. Studies have shown that early Intervention would reduce progression to PDR (Arabi et al., Update on management of non-proliferative diabetic retinopathy without diabetic macular edema; is there a paradigm shift? J. Ophthalmic Vis. Res. 2022; 17(1):108-117)).

A further common ocular disease is retinal vein occlusion (RVO). RVO affected approximately 1.3 million people in the US in 2019 and is predicted to affect 1.4 million people in the US in 2024 (Market Scope 2019, supra), RVO is a chronic condition in which the retinal circulation contains a blockage leading to leakage, retinal thickening, and visual impairment (Ip and Hendrick, Retinal Vein Occlusion Review. 2018, Asia-Pacific Journal of Ophthalmology, 7(1): 40-45; Pierru et al., Occlusions veineuses rétiniennes retinal vein occlusions. 2017, Journal Français d'Ophtalmologie, 40(8):696-705). The condition is typically seen in patients 55 and older who have a pre-existing condition such as high blood pressure, diabetes, and glaucoma. RVO does not have a projected course as it can either deteriorate a patient's vision quickly or remain asymptomatic. Prognosis of RVO and associated treatment options depend on the classification of the disease as the different variants have different risk factors despite behaving similarly. Classification of the disease is categorized depending on the location of the impaired retinal circulation: branch retinal vein occlusion (BRVO), hemiretinal vein occlusion (HRVO), and central retinal vein occlusion (CRVO). BRVO is more common affecting 0.4% worldwide and CRVO affecting 0.08% worldwide. Studies show that BRVO is more prevalent in Asian and Hispanic groups compared to Caucasians (Ip and Hendrick, supra).

Treatment of RVO currently includes symptomatic maintenance of the condition to avoid further complications, macular edema, and neovascular glaucoma. Anti-VEGF treatment is currently the standard of care treatment and may temporarily improve vision. Other treatment options include lasers, steroids, and surgery (Pierru et al., supra).

Anti-VEGF agents are currently considered the standard of care treatment for wet AMD, DME, DR, and RVO. The first treatment approved for wet AMD by the FDA in 2004 was MACUGEN® (pegaptanib sodium injection by Bausch & Lomb). Since then, LUCENTIS® (ranibizumab injection by Genentech, Inc.) and EYLEA® (aflibercept intravitreal injection by Regeneron Pharmaceuticals, Inc.) have been approved for the treatment of wet AMD in 2006, and 2011 respectively, as well as DME and macular edema following RVO. The recommended dose for EYLEA® is 2 mg (0.05 mL) administered by intravitreal injection every 4 weeks (1 month) for the first 3 months, followed by 2 mg (0.05 mL) Intravitreal injection every 8 weeks (2 months) (EYLEA® prescribing information, November 2011). Additionally, in October 2019, BEOVU® (brolucizumab injection by Novartis Pharmaceuticals Corp) was approved by the FDA for the treatment of wet AMD, Other developments are reported in Amadio et al., Targeting VEGF in eye neovascularization: What's new?: A comprehensive review on current therapies and oligonucleotide-based Interventions under development. 2016, Pharmacological Research, 103: 253-69.

Tyrosine kinase inhibitors (TKI) were developed as chemotherapeutics that inhibit signaling of receptor tyrosine kinases (RTKs), which are a family of tyrosine protein kinases. RTKs span the cell membrane with an intracellular (internal) and extracellular (external) portion. Upon ligand binding to the extracellular portion, receptor tyrosine kinases dimerize and initiate an intracellular signaling cascade driven by autophosphorylation using the coenzyme messenger adenosine triphosphate (ATP). Many of the RTK ligands are growth factors such as VEGF, VEGF relates to a family of proteins binding to VEGF-receptor (VEGFR) types, i.e. VEGFR1-3 (all RTKs), thereby inducing angiogenesis, VEGF-A, which binds to VEGFR2, is the target of the anti-VEGF drugs described above. Besides VEGFR1-3 several other RTKs are known to induce angiogenesis such as platelet-derived growth factor receptor (PDGFR) activated by PDGF or stem cell growth factor receptor/type III receptor tyrosine kinase (c-Kit) activated by stem cell factor.

Recently, ocular implants have been provided comprising TKI particles dispersed in a hydrogel, which implants are administered by injection e.g. into the vitreous humor of a patient having wet AMD, wherein the TKI is released in a controlled manner from the implant over an extended period of time, such as several months or longer, so that a therapeutically effective amount of the TKI is available over said period of time. These implants are capable of reducing, or at least maintaining (such as in preventing an increase) the central subfield thickness (CSFT) and/or reducing or maintaining (again, preventing an increase) of sub- or intraretinal fluid in patients. See e.g. WO 2021/195163.

Interim results of an ongoing phase 1 clinical trial (among other studies) have shown that implants comprising the TKI axitinib dispersed in a hydrogel made of a polymer network of crosslinked polyethylene glycol (PEG) units have an extended durability in patients with wet AMD, and that the vision (measured by the best corrected visual acuity, BCVA) and CSFT levels of the subjects treated with one single such implant were comparable to the vision and CSFT levels of subjects treated with the anti-VEGF agent aflibercept (repeated injection every 2 months) up to month 10 of the study. The study is still ongoing. In this study so far, 80% of subjects were rescue-free up to 6 months and 73% of subjects were rescue-free up to 10 months following a single injection of such implant. Thereby, a clinically meaningful reduction in treatment burden has been observed up to 10 months post-treatment with one single implant, as compared to the aflibercept injections every 2 months. See e.g. A. A. Moshfeghi, "Update on a Hydrogel-Based Intravitreal Axitinib Implant (OTX-TKI) for the Treatment of Neovascular Age-related Macular Degeneration", Feb. 11, 2023 at the Angiogenesis, Exudation, and Degeneration Meeting (Virtual); or D. S. Dhoot, "Interim Safety and Efficacy Data from a Phase 1 Clinical Trial of Sustained-release Axitinib Hydrogel Implant (OTX-TKI) in Wet AMD Subjects: 7-month Analysis", Sep. 30, 2022 at the AAO 2022 Retina Subspecialty Day in Chicago, IL—both presentations being available inter alia via https://ocutx.gcs-web.com/scientific-medical-presentations.

While known implants comprising TKI have demonstrated in the clinical studies so far to be safe and effective in patients with wet AMD, there is still a desire to provide further implants which have release profiles that differ from those of the known implants. For example, it is desirable to provide implants comprising TKI such as axitinib which have an increased rate of release of the TKI, such as an increased amount of TKI released over a certain period of time, or a faster release rate, particularly in the early phase of the release after injection of the implant. Furthermore, it is on the one hand desirable to provide ocular implants comprising TKI for the treatment of an ocular disease, such as wet AMD, wherein the largest portion of the content of TKI in the implant is released prior to the biodegradation of the implant hydrogel, so that the remaining amount of TKI that is terminally released upon biodegradation is relatively small. On the other hand, however, it is also desired that the release of TKI from the implant is not too fast, so as to avoid or substantially avoid a remaining drug-depleted implant which first has to be cleared from the eye before a new implant can be injected, i.e., it is also desirable that sufficient TKI remains in the implant to be terminally released upon biodegradation of the implant so as to maintain the therapeutic effect until the remainders of the implant have been cleared completely from the eye and a new implant can be placed, thus providing a continuous therapy by means of implant repeat dosing.

Accordingly, there exists a need for ocular implants comprising TKI for the treatment of ocular diseases such as AMD, DME, DR and RVO, which are effective over an extended period of time such as several months and provide for accelerated release of the TKI particularly in the initial phase of the release as compared to previously disclosed ocular implants, and which are suitable for repeat dosing. The present invention addresses this need.

OBJECTS OF THE INVENTION

It is an object of certain embodiments of the present invention to provide a new ocular implant comprising a TKI such as axitinib that provides a sustained release of TKI such as axitinib over an extended period of time, such as at least 3 months, or at least 6 months, such as for a period of about 6 months to about 12 months.

It is an object of certain embodiments of the present invention to provide an ocular implant comprising a TKI such as axitinib that provides for a sustained release of TKI such as axitinib in vivo (in the vitreous) of about 1 μg/day or more over at least 3 months.

It is an object of certain embodiments of the present invention to provide an ocular implant comprising a TKI such as axitinib that provides for a sustained release of TKI such as axitinib wherein the in vitro or in vivo release of TKI from the implant is accelerated as compared to known implants.

It is an object of certain embodiments of the present invention to provide an ocular implant comprising a TKI such as axitinib that provides for a sustained release of TKI such as axitinib wherein the in vitro or in vivo release of the TKI from the implant is faster than from a comparative known implant which contains the same dose of TKI such as axitinib.

It is an object of certain embodiments of the present invention to provide an ocular implant comprising a TKI such as axitinib that provides for a sustained release of TKI such as axitinib wherein the in vitro release rate of the TKI from the implant per day on one or more days, or the average release rate per day over a certain period of time is higher than from a comparative known implant which contains the same dose of the TKI.

It is an object of certain embodiments of the present invention to provide an ocular implant comprising a TKI such as axitinib that provides for sustained release of the TKI, wherein therapeutically effective levels of TKI in the retina, choroid, and/or retinal pigment epithelium (RPE) are reached faster than with a comparative known implant which contains the same dose of the TKI.

It is an object of certain embodiments of the present invention to provide an ocular implant comprising a TKI such as axitinib that provides for sustained release of the TKI, wherein the in vitro release rate per day on one or more days, and/or the average release rate per day over a certain period of time, and/or the amount of the TKI released on one or more days, and/or the cumulative amount of the TKI released over a certain period of time, and/or the percentage of the TKI (based on the total amount of the TKI contained in the implant, or based on the total amount of the TKI released in the in vitro test), is higher than from a comparative known implant which contains the same dose of the TKI.

It is an object of certain embodiments of the present invention to provide an ocular implant fulfilling one or more of the objects stated above for use in the treatment of ocular diseases, including (wet) AMD, DR, DME, and RVO.

It is an object of certain embodiments of the present invention to provide an ocular implant fulfilling one or more of the objects stated above for use in the treatment of ocular diseases, including (wet) AMD, DR, DME, and RVO, wherein the treatment period with one single implant is at least 3 months, such as at least 6, at least 9, at least 10 months, or at least 12 months, such as from about 6 to about 9 months, or from about 6 to about 12 months.

It is an object of certain embodiments of the present invention to provide an ocular implant fulfilling one or more of the objects stated above for use in the treatment of ocular diseases, including (wet) AMD, DR, DME, and RVO, wherein the TKI levels in ocular tissues such as the retina, the choroid, or the retinal pigment epithelium, as well as the vitreous humor are maintained at a therapeutically efficient level, in particular at a level sufficient for inhibition or deceleration of angiogenesis, over a period of at least 3 months, such as at least 6, at least 9, at least 10 months, or at least 12 months, such as from about 6 to about 9 months, or from about 6 to about 12 months.

It is a further object of certain embodiments of the present invention to provide a method of increasing the release rate of TKI such as axitinib from an ocular implant.

It is a further object of certain embodiments of the present invention to provide forms of axitinib for use in an ocular implant, wherein these forms of axitinib have a solubility of greater than 0.3 μg/mL as measured in phosphate-buffered saline (PBS) at a pH of 7.2 to 7.4 and 37° C. after five days of incubation, and ocular implants comprising such forms of axitinib.

It is a further object of certain embodiments of the present invention to provide ocular implants having an increased hydrated surface area of at least 25 $mm^2$ as measured in phosphate-buffered saline (PBS) at a pH of 7.2 to 7.4 and 37° C. after 24 hours of incubation.

It is a further object of certain embodiments of the present invention to provide methods of manufacturing ocular implants fulfilling one or more of the objects stated above.

It is a further object of certain embodiments of the present invention to provide a method of treating ocular diseases, the method comprising administering an ocular implant fulfilling one or more of the objects stated above.

It is a further object of certain embodiments of the present invention to provide a method of treating (wet) AMD, DR, DME, or RVO, the method comprising administering an ocular implant fulfilling one or more of the objects stated above.

It is a further object of certain embodiments of the present invention to provide a method of treating (wet) AMD, DR, DME, or RVO, the method comprising administering an ocular implant fulfilling one or more of the objects stated above to a patient, wherein the treatment period with one single implant is at least 3 months, such as at least 6, at least 9, at least 10 months, or at least 12 months, such as from about 6 to about 9 months, or from about 6 to about 12 months, wherein rescue medication is required to be administered only rarely, such as 1, 2 or 3 times, during the treatment period.

It is a further object of certain embodiments of the present invention to provide a method of treating an ocular disease such as (wet) AMD, DR, DME, or RVO, particularly (wet) AMD, and an ocular implant for use in such method, wherein the method provides a continuous treatment by means of repeat dosing of an ocular implant.

It is a further object of certain embodiments of the present invention to provide a method of treating an ocular disease such as (wet) AMD, DR, DME, or RVO, particularly (wet) AMD, and an ocular implant for use in such method, wherein the ocular implant containing a TKI such as axitinib allows for repeat dosing of an implant, such as every 6 to 12 months, such as every 8 to 11 months, or every 6 months, or every 9 months.

It is a further object of certain embodiments of the present invention to provide a method of treating an ocular disease such as (wet) AMD, DR, DME, or RVO, particularly (wet) AMD, and an ocular implant for use in such method wherein the ocular implant containing a TKI such as axitinib allows for repeat dosing of an implant, such as every 6 to 12 months, such as every 8 to 11 months, or every 6 months such that a continuous therapeutic effect is achieved without having to re-dose at a point in time when residual drug-depleted implant is still present.

It is a further object of certain embodiments of the present invention to provide a method of treating an ocular disease such as (wet) AMD, DR, DME, or RVO, particularly (wet) AMD, and an ocular implant for use in such method, wherein the ocular implant contains a TKI such as axitinib dispersed in a hydrogel, where the implant provides for a release rate of the TKI such as axitinib into the vitreous (and consequently delivery of the TKI such as axitinib to ocular tissue such as the retina or the choroid) such that the cumulative amount of TKI such as axitinib released prior to the degradation of the hydrogel (i.e., when the implant/the hydrogel is still intact) is higher than the amount of TKI such as axitinib released upon degradation of the hydrogel.

It is a further object of certain embodiments of the present invention to provide a method of treating an ocular disease such as (wet) AMD, DR, DME, or RVO, particularly (wet) AMD, and an ocular implant for use in such method, wherein the ocular implant contains a TKI such as axitinib dispersed in a hydrogel, where the implant provides for a release rate of the TKI such as axitinib into the vitreous (and consequently delivery of the TKI such as axitinib to ocular tissue such as the retina or the choroid) such that the $C_{max}$ of TKI such as axitinib in said tissue occurs before biodegradation of the implant.

It is a further object of certain embodiments of the present invention to provide a method of treating an ocular disease such as (wet) AMD, DR, DME, or RVO, particularly (wet) AMD, and an ocular implant for use in such method, wherein the ocular implant contains a TKI such as axitinib dispersed in a hydrogel, wherein the implant provides for a release rate of the TKI such as axitinib into the vitreous humor (and consequently delivery of the TKI such as axitinib to ocular tissue such as the retina or the choroid) such that the $t_{max}$ of TKI such as axitinib in said tissue occurs before biodegradation of the implant and/or is shorter than the $t_{mix}$ of TKI such as axitinib as provided by known implants.

It is a further object of certain embodiments of the present invention to provide a method of treating (wet) AMD, DR, DME, or RVO, the method comprising administering an ocular implant fulfilling one or more of the objects stated above to a patient who has a history of anti-VEGF treatment, or a patient who is anti-VEGF treatment naïve.

It is a further object of certain embodiments of the present invention to provide a method of treating an ocular disease, including (wet) AMD, DR, DME, or RVO, the method comprising administering an ocular implant fulfilling one or more of the objects stated above in combination with an anti-VEGF agent.

It is a further object of certain embodiments of the present invention to provide a kit comprising one or more ocular implants fulfilling one or more of the objects stated above and optionally comprising a means for injecting the ocular implant.

One or more of these objects of the present invention and others are solved by one or more embodiments as disclosed and claimed herein.

SUMMARY OF THE INVENTION

In one general aspect, the present invention relates to a sustained release biodegradable ocular implant comprising a hydrogel and a tyrosine kinase inhibitor (TKI), wherein tyrosine kinase inhibitor particles are dispersed within the hydrogel, characterized in that the solubility of the tyrosine kinase inhibitor is greater than 0.3 μg/ml as measured in phosphate-buffered saline (PBS) at a pH of 7.2 to 7.4 and 37° C. after five days of incubation.

For example, in certain embodiments the present invention relates to a sustained release biodegradable ocular implant comprising a hydrogel and axitinib polymorph IV in an amount of from about 400 μg to about 500 μg, wherein axitinib particles are dispersed within the hydrogel.

In another general aspect, the present invention relates to a sustained release biodegradable ocular implant comprising a hydrogel and a tyrosine kinase inhibitor, wherein tyrosine kinase inhibitor particles are dispersed within the hydrogel, characterized in that the hydrated surface area of the implant is at least 25 $mm^2$ as measured in phosphate-buffered saline (PBS) at a pH of 7.2 to 7.4 and 37° C. after 24 hours of incubation.

In a further general aspect, the present invention relates to a sustained release biodegradable ocular implant comprising a hydrogel and a tyrosine kinase inhibitor, wherein tyrosine kinase inhibitor particles are dispersed within the hydrogel, wherein the cumulative amount of tyrosine kinase inhibitor released from the implant over a period defined by any initial number of days up to the day when 80% of the tyrosine kinase inhibitor contained in the implant is released is higher than the cumulative amount of tyrosine kinase inhibitor released over the same period of time from a comparative implant, wherein the comparative implant differs from the sustained release biodegradable ocular implant only in that the solubility of the tyrosine kinase inhibitor in the comparative implant is lower as measured in PBS at a pH of 7.2 to 7.4 and 37° C. after five days of incubation, and wherein the release of tyrosine kinase inhibitor from both implants is measured under identical conditions.

In a further general aspect, the present invention relates to a sustained release biodegradable ocular implant comprising a hydrogel and a tyrosine kinase inhibitor, wherein tyrosine kinase inhibitor particles are dispersed within the hydrogel, wherein the average release rate of tyrosine kinase inhibitor per day from the implant over a period defined by any initial number of days up to the day when 80% of the tyrosine kinase inhibitor contained in the implant is released is higher than the average release rate of tyrosine kinase inhibitor per day from a comparative implant over the same period of time, wherein the comparative implant differs from the sustained release biodegradable ocular implant only in that the solubility of the tyrosine kinase inhibitor in the comparative implant is lower as measured in PBS at a pH of 7.2 to 7.4 and 37° C. after five days of incubation, and wherein the release of tyrosine kinase inhibitor from both implants is measured under identical conditions.

In a further aspect, the present invention relates to a sustained release biodegradable ocular implant comprising a hydrogel and axitinib, wherein axitinib particles are dispersed within the hydrogel, wherein the implant comprises axitinib polymorph IV and the implant contains axitinib in an amount corresponding to about 250 to about 700 μg axitinib free base, such as about 400 to about 500 μg axitinib free base, wherein the hydrogel comprises crosslinked PEG units.

In a further aspect, the present invention relates to a sustained release biodegradable ocular implant comprising a hydrogel and axitinib, wherein axitinib particles are dispersed within the hydrogel, wherein the implant comprises axitinib polymorph IV in an amount of from about 360 μg to about 562.5 μg, or from about 405 μg to about 495 μg, such as about 450 μg, wherein the hydrogel comprises crosslinked multi-armed PEG units having a number average molecular weight of about 20,000 Daltons, wherein the crosslinks between the PEG units include a group represented by the following formula

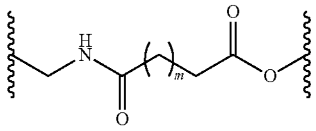

wherein m is 6.

wherein the implant is cylindrical and in its dried state has a length of 10 mm or less, such as from 6 to 9 mm, and a diameter of from 0.25 to 0.45 mm and/or in its hydrated state (after 24 hours in PBS at a pH of 7.2 to 7.4 at 37° C.) has a length of 12 mm or less, 10 mm or less, such as from 8 to 9 mm and a diameter of from 0.5 to 0.9 mm, and wherein the axitinib particles have a d90 particle size of less than 8 μm and a d50 particle size of less than 3 μm.

In a further aspect, the present invention relates to a sustained release biodegradable ocular implant comprising a hydrogel and axitinib, wherein axitinib particles are dispersed within the hydrogel, wherein the implant comprises axitinib polymorph IV in an amount of from about 480 μg to about 750 μg, or from about 540 μg to about 660 μg, such as about 600 μg, wherein the hydrogel comprises cross-linked multi-armed PEG units having a number average molecular weight of about 20,000 Daltons, wherein the crosslinks between the PEG units include a group represented by the following formula

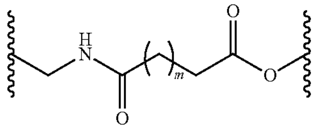

wherein m is 6, wherein the implant is cylindrical and in its dried state has a length of 10 mm or less, such as from 6 to 9 mm, and a diameter of from 0.25 to 0.45 mm and/or in its hydrated state (after 24 hours in PBS at a pH of 7.2 to 7.4 at 37° C.) has a length of 10 mm or less, such as from 8 to 9 mm and a diameter of from 0.5 to 0.9 mm, and wherein the axitinib particles have a d90 particle size of less than 8 μm and a d50 particle size of less than 3 μm.

In a further aspect, the present invention relates to a sustained release biodegradable ocular implant comprising a hydrogel and axitinib, wherein axitinib particles are dispersed within the hydrogel, wherein the implant comprises axitinib polymorph IV and the implant contains axitinib in an amount corresponding to from about 360 μg to about 562.5 μg, or from about 405 μg to about 495 μg, such as about 450 μg axitinib free base, and releases at least about 60 μg axitinib over the initial day, and/or at least about 100 μg axitinib over the initial 2 days, and/or at least about 130 μg axitinib over the initial 3 days, and/or at least about 220 μg axitinib over the initial 7 days and/or at least about 275 μg axitinib over the initial 10 days in an in vitro test performed at 37° C. in an 25%/75% (v/v) ethanol/water mixture under 2× sink conditions.

In a further aspect, the present invention relates to a sustained release biodegradable ocular implant comprising a hydrogel and axitinib, wherein axitinib particles are dispersed within the hydrogel, wherein the implant comprises axitinib polymorph IV and the implant contains axitinib in an amount corresponding to from about 360 μg to about 562.5 μg, or from about 405 μg to about 495 μg, such as about 450 μg axitinib free base, and releases at least about 35 μg axitinib over the initial day, and/or at least about 60 μg axitinib over the initial 2 days, and/or at least about 100 μg axitinib over the initial 4 days, and/or at least about 180 μg axitinib over the initial 7 days and/or at least about 200 μg axitinib over the initial 9 days in an in vitro test performed at 37° C. in an 25%/75% (v/v) ethanol/water mixture under 3× sink conditions.

In a further aspect, the present invention relates to a sustained release biodegradable ocular implant comprising a hydrogel and axitinib, wherein axitinib particles are dispersed within the hydrogel, wherein the implant comprises axitinib polymorph IV and the implant contains axitinib in an amount corresponding to from about 480 μg to about 750 μg, or from about 540 μg to about 660 μg, such as about 600 μg axitinib free base, and releases at least about 70 μg axitinib over the initial day, and/or at least about 130 μg axitinib over the initial 2 days, and/or at least about 180 μg axitinib over the initial 3 days, and/or at least about 300 μg axitinib over the initial 7 days and/or at least about 375 μg axitinib over the initial 10 days in an in vitro test performed at 37° C. in an 25%/75% (v/v) ethanol/water mixture under 2× sink conditions.

In a further aspect, the present invention relates to a sustained release biodegradable ocular implant comprising a hydrogel and axitinib, wherein axitinib particles are dispersed within the hydrogel, wherein the implant comprises axitinib polymorph IV and the implant contains axitinib in an amount corresponding to from about 480 μg to about 750 μg, or from about 540 μg to about 660 μg, such as about 600 μg axitinib free base, and releases at least about 50 μg axitinib over the initial day, and/or at least about 100 μg axitinib over the initial 2 days, and/or at least about 180 μg axitinib over the initial 4 days, and/or at least about 280 μg axitinib over the initial 7 days and/or at least about 300 μg axitinib over the initial 9 days in an in vitro test performed at 37° C. in an 25%/75% (v/v) ethanol/water mixture under 3× sink conditions.

In a further aspect, the present invention relates to a sustained release biodegradable ocular implant comprising a hydrogel and axitinib, wherein axitinib particles are dispersed within the hydrogel, wherein the implant comprises axitinib polymorph IV and the implant contains axitinib in an amount corresponding to from about 360 μg to about 562.5 μg, or from about 405 μg to about 495 μg, such as about 450 μg axitinib free base, and releases at least 50% of the total released amount of axitinib over the initial 3 days in an in vitro test, and/or releases at least 80% of the total released amount of axitinib over the initial 7 days in an in vitro test, and/or releases at least 92% of the total released amount of axitinib over the initial 10 days in an in vitro test performed at 37° C. in an 25%/75% (v/v) ethanol/water mixture under 2× sink conditions.

In a further aspect, the present invention relates to a sustained release biodegradable ocular implant comprising a hydrogel and axitinib, wherein axitinib particles are dispersed within the hydrogel, wherein the implant comprises axitinib polymorph IV and the implant contains axitinib in an amount corresponding to from about 360 μg to about 562.5 μg, or from about 405 μg to about 495 μg, such as about 450 μg axitinib free base, and releases at least 30% of the total released amount of axitinib over the initial 3 days in an in vitro test, and/or releases at least 60% of the total released amount of axitinib over the initial 7 days in an in vitro test, and/or releases at least 80% of the total released amount of axitinib over the initial 10 days in an in vitro test performed at 37° C. in an 25%/75% (v/v) ethanol/water mixture under 2× sink conditions.

In a further aspect, the present invention relates to a sustained release biodegradable ocular implant comprising a hydrogel and axitinib, wherein axitinib particles are dispersed within the hydrogel, wherein the implant comprises axitinib polymorph IV and the implant contains axitinib in an amount corresponding to from about 360 μg to about 562.5 μg, or from about 405 μg to about 495 μg, such as about 450 μg axitinib free base, and releases at least 15% of the total released amount of axitinib over the initial 2 days in an in vitro test, and/or releases at least 30% of the total released amount of axitinib over the initial 4 days in an in vitro test, and/or releases at least 50% of the total released amount of axitinib over the initial 7 days in an in vitro test, wherein the in vitro test is performed at 37° C. in an 25%/75% (v/v) ethanol/water mixture under 3× sink conditions.

In a further aspect, the present invention relates to a sustained release biodegradable ocular implant comprising a hydrogel and axitinib, wherein axitinib particles are dispersed within the hydrogel, wherein the implant comprises axitinib polymorph IV and the implant contains axitinib in an amount corresponding to from about 480 μg to about 750 μg, or from about 540 μg to about 660 μg, such as about 600 μg axitinib free base, and releases at least 50% of the total released amount of axitinib over the initial 3 days in an in vitro test, and/or releases at least 80% of the total released amount of axitinib over the initial 7 days in an in vitro test, and/or releases at least 92% of the total released amount of axitinib over the initial 10 days in an in vitro test performed at 37° C. in an 25%/75% (v/v) ethanol/water mixture under 2× sink conditions.

In a further aspect, the present invention relates to a sustained release biodegradable ocular implant comprising a hydrogel and axitinib, wherein axitinib particles are dispersed within the hydrogel, wherein the implant comprises axitinib polymorph IV and the implant contains axitinib in an amount corresponding to from about 480 μg to about 750 μg, or from about 540 μg to about 660 μg, such as about 600 μg axitinib free base, and releases at least 30% of the total released amount of axitinib over the initial 3 days in an in vitro test, and/or releases at least 60% of the total released amount of axitinib over the initial 7 days in an in vitro test, and/or releases at least 80% of the total released amount of axitinib over the initial 10 days in an in vitro test performed at 37° C. in an 25%/75% (v/v) ethanol/water mixture under 2× sink conditions.

In a further aspect, the present invention relates to a sustained release biodegradable ocular implant comprising a hydrogel and axitinib, wherein axitinib particles are dispersed within the hydrogel, wherein the implant comprises axitinib polymorph IV and the implant contains axitinib in an amount corresponding to from about 480 μg to about 750 μg, or from about 540 μg to about 660 μg, such as about 600 μg axitinib free base, and releases at least 15% or at least 20% of the total released amount of axitinib over the initial 2 days in an in vitro test, and/or releases at least 35% of the total released amount of axitinib over the initial 4 days in an in vitro test, and/or releases at least 55% of the total released amount of axitinib over the initial 7 days in an in vitro test, wherein the in vitro test is performed at 37° C. in an 25%/75% (v/v) ethanol/water mixture under 3× sink conditions.

In a further aspect, the present invention relates to a sustained release biodegradable ocular implant comprising a hydrogel and axitinib polymorph IV in an amount of from about 400 μg to about 500 μg, wherein axitinib particles are dispersed within the hydrogel, wherein the implant is an Intravitreal implant and has a composition on a dry basis (in % w/w) of about 30 to about 75% axitinib, about 20 to about 50% PEG units, and about 0.5 to about 15% sodium phosphate salt and on a wet basis (in % w/w) of about 5 to about 17% axitinib, about 4 to about 12% PEG units, and about 0.2 to about 5% sodium phosphate salt, wherein the hydrogel comprises a PEG hydrogel network formed by crosslinking 4a20kPEG-SAZ and 8a20kPEG-$NH_2$ units, wherein the implant has a length that is greater than its width, and in its dried state has a length of 11 mm or less, such as from 5 to 11 mm, and a width of from 0.2 to 0.4 mm, such as 0.28 to 0.38 mm and/or in its hydrated state (after 24 hours in PBS at a pH of 7.4 at 37° C.) has a length of 11 mm or less, such as from 5 to 11 mm and a width of from 0.4 to 2 mm, and wherein the axitinib particles have a d90 particle size of less than 8 μm and a d50 particle size of less than 3 μm.

In a further aspect, the present invention relates to a sustained release biodegradable ocular implant comprising a hydrogel and axitinib polymorph IV in an amount of from about 400 μg to about 500 μg, wherein axitinib particles are dispersed within the hydrogel, wherein the implant is an intravitreal implant and has a composition on a dry basis (in % w/w) of about 30 to about 75% axitinib, about 20 to about 50% PEG units, and about 0.5 to about 15% sodium phosphate salt and on a wet basis (In % w/w) of from about 5 to about 17% axitinib, about 4 to about 12% PEG units, and about 0.2 to about 5% sodium phosphate salt, wherein the hydrogel comprises a PEG hydrogel network formed by crosslinking 4a20kPEG-SAZ and 8a20kPEG-$NH_2$ precursors, wherein the implant in its dried state has a width of from 0.20 to 0.40 mm, and in its hydrated state (after 24 hours in PBS at a pH of 7.4 at 37° C.) has a length of 11 mm or less, and wherein the implant has a hydrated surface area (after 24 hours incubation in PBS at a pH of 7.2 to 7.4 at 37° C.) of from 10 to 30 $mm^2$.

In a further aspect, the present invention relates to a sustained release biodegradable ocular implant comprising a hydrogel and axitinib polymorph IV in an amount of from about 400 μg to about 500 μg, wherein axitinib particles are dispersed within the hydrogel, wherein the implant is an Intravitreal implant and has a composition on a dry basis (In % w/w) of about 30 to about 75% axitinib, about 20 to about 50% PEG units, and about 0.5 to about 15% sodium phosphate salt and on a wet basis (in % w/w) of about 5 to about 17% axitinib, about 4 to about 12% PEG units, and about 0.2 to about 5% sodium phosphate salt, wherein the hydrogel comprises a PEG hydrogel network formed by crosslinking 4a20kPEG-SAZ and 8a20kPEG-$NH_2$ units, wherein the implant in its dried state has a length of from 5 to 11 mm and a width of from 0.28 to 0.38 mm and/or in its hydrated state (after 24 hours in PBS at a pH of 7.4 at 37° C.) has a length of from 5 to 11 mm and a width of from 0.4 to 2 mm.

In a further aspect, the present invention relates to a sustained release biodegradable ocular implant comprising a hydrogel and axitinib polymorph IV in an amount of from about 400 μg to about 500 μg, wherein axitinib particles are dispersed within the hydrogel, wherein the implant is an intravitreal implant and has a composition on a dry basis (in % w/w) of about 54 to about 69% axitinib, a PEG hydrogel network formed by crosslinking about 17 to 26% 4a20kPEG-SAZ with about 8 to about 13% 8a20kPEG-$NH_2$, about 3 to about 5% dibasic sodium phosphate, and about 1 to about 3% monobasic sodium phosphate.

In a further aspect, the present invention relates to a sustained release biodegradable ocular implant comprising a hydrogel and axitinib polymorph IV in an amount of from about 400 μg to about 500 μg, such as about 450 μg, wherein axitinib particles are dispersed within the hydrogel, wherein the hydrogel comprises a PEG hydrogel, wherein the implant in its dry state has a width of from 0.30 to 0.36 mm, and wherein the implant provides for a release of axitinib in an in vitro test performed at 35° C.±0.5° C. in 0.01N HCl with 0.25% cetyl trimethyl ammonium bromide (CTAB) in a USP apparatus 4 that is characterized in that the percentage of axitinib released from the implant (wherein the percentage of released axitinib is based on the maximum amount of axitinib released from the implant representing 100%) is:

at least about 10% after 0.5 hours,
at least about 30% after 2 hours,
at least about 58% after 6 hours,
at least about 75% after 10 hours,
at least about 80% after 12 hours,
and/or at least about 90% after 16 hours;
such as:
at least about 10% after 0.5 hours,
at least about 19% after 1 hour,
at least about 30% after 2 hours,
at least about 45% after 4 hours,
at least about 58% after 6 hours,
at least about 70% after 8 hours,
at least about 75% after 10 hours,
at least about 80% after 12 hours,
and/or at least about 90% after 16 hours.

In a further aspect, the present invention relates to a sustained release biodegradable ocular implant comprising a hydrogel and axitinib polymorph IV in an amount of from about 400 μg to about 500 μg, such as about 450 μg, wherein axitinib particles are dispersed within the hydrogel, wherein the hydrogel comprises a hydrogel network formed by crosslinking 4a20kPEG-SAZ and 8a20kPEG-$NH_2$ units, wherein the implant has a composition (dry basis; in % w/w) as follows: from about 60% to about 70% axitinib and from about 25% to about 35% PEG units, wherein the implant in its dry state has a width of from 0.30 to 0.36 mm and a total weight of from about 0.6 mg to about 1 mg, and wherein the implant provides for a release of axitinib in an in vitro test performed at 35° C.±0.5° C. in 0.01N HCl with 0.25% cetyl trimethyl ammonium bromide (CTAB) in a USP apparatus 4 that is characterized in that the percentage of axitinib released from the implant (wherein the percentage of released axitinib is based on the maximum amount of axitinib released from the implant representing 100%) is:

from about 10 to about 20% after 0.5 hours,
from about 30 to about 45% after 2 hours,
from about 58 to about 81% after 6 hours,
from about 75 to about 98% after 10 hours,
at least about 80% after 12 hours,
and/or at least about 90% after 16 hours,
such as:
from about 10 to about 20% after 0.5 hours,
from about 19 to about 30% after 1 hour,
from about 30 to about 45% after 2 hours,
from about 45 to about 65% after 4 hours,
from about 58 to about 81% after 6 hours,
form about 70 to about 90% after 8 hours,
from about 75 to about 98% after 10 hours,
at least about 80% after 12 hours,
and/or at least about 90% after 16 hours.

In a further aspect, the present invention relates to a sustained release biodegradable ocular implant comprising a hydrogel and axitinib polymorph IV in an amount of from about 400 μg to about 500 μg, wherein axitinib particles are dispersed within the hydrogel, wherein the hydrogel comprises a PEG hydrogel, wherein the implant in its dry state has a width of from 0.30 to 0.36 mm, and wherein the implant is characterized in that the amount of axitinib released from the implant in an in vitro test performed at 35° C.±0.5° C. in 0.01N HCl with 0.25% cetyl trimethyl ammonium bromide (CTAB) in a USP apparatus 4 is:
at least about 50 μg after 0.5 hours,
at least about 140 μg after 2 hours,
at least about 270 μg after 6 hours,
at least about 350 μg after 10 hours,
at least about 400 μg after 12 hours,
and/or at least about 410 μg after 16 hours,
such as:
at least about 50 μg after 0.5 hours,
at least about 90 μg after 1 hour,
at least about 140 μg after 2 hours,
at least about 230 μg after 4 hours,
at least about 270 μg after 6 hours,
at least about 340 μg after 8 hours,
at least about 350 μg after 10 hours,
at least about 400 μg after 12 hours,
and/or at least about 410 μg after 16 hours.

In a further aspect, the present invention relates to a sustained release biodegradable ocular implant comprising a hydrogel and axitinib polymorph IV in an amount of from about 400 μg to about 500 μg, wherein axitinib particles are dispersed within the hydrogel, wherein the hydrogel comprises a PEG hydrogel network formed by crosslinking 4a20kPEG-SAZ and 8a20kPEG-$NH_2$ units, wherein the implant has a composition (dry basis; in % w/w) as follows: from about 60% to about 70% axitinib and from about 25% to about 35% PEG units, wherein the implant in its dry state has a width of from 0.30 to 0.36 mm and a total weight of from about 0.6 mg to about 1 mg, and wherein the implant is characterized in that the amount of axitinib released from the implant in an in vitro test performed at 35° C.±0.5° C. in 0.01N HCl with 0.25% cetyl trimethyl ammonium bromide (CTAB) in a USP apparatus 4 is:

from about 50 to about 80 μg after 0.5 hours,
from about 140 to about 210 μg after 2 hours,
from about 270 to about 380 μg after 6 hours,
from about 350 to about 470 μg after 10 hours,
at least about 400 μg after 12 hours,
and/or at least about 410 μg after 16 hours,
such as:
from about 50 to about 80 μg after 0.5 hours,
from about 90 to about 130 μg after 1 hour,
from about 140 to about 210 μg after 2 hours,
from about 230 to about 290 μg after 4 hours,
from about 270 to about 380 μg after 6 hours,
from about 340 to about 440 μg after 8 hours,
from about 350 to about 470 μg after 10 hours,
at least about 400 μg after 12 hours,
and/or at least about 410 μg after 16 hours.

In a further aspect, the present invention relates to a sustained release biodegradable ocular implant comprising a hydrogel and axitinib polymorph IV in an amount of from about 400 μg to about 500 μg, wherein axitinib particles are dispersed within the hydrogel, wherein the hydrogel comprises crosslinked PEG units, wherein the amount of axitinib being released upon final degradation of the hydrogel in the vitreous humor is less than 200 μg, wherein the implant in its dry state (prior to injection) has a width of from about 0.3 to about 0.4 mm, such as about 0.33 to about 0.36 mm, and a length of less than about 11 mm, and in its hydrated state (after 24 hours in PBS at a pH of 7.4 at 37° C.) has a length of less than about 11 mm, such as a length of from about 8 to about 10 mm.

In a further aspect, the present invention relates to a method of treating an ocular disease in a patient in need thereof, the method comprising administering to the patient's eye a sustained release biodegradable ocular implant according to one aspect of the invention, such as by means of intravitreal injection.

In a further aspect, the present invention relates to a sustained release biodegradable ocular implant as disclosed herein, for use in a method of treating an ocular disease in a patient in need thereof, the method comprising administering to the patient's eye a sustained release biodegradable ocular implant according to an aspect of the invention.

In a further aspect, the present invention relates to a use of a sustained release biodegradable ocular implant as disclosed herein, for the preparation of a medicament for use in a method of treating an ocular disease in a patient in need thereof, the method comprising administering to the patient's eye a sustained release biodegradable ocular implant according to an aspect of the invention.

In a further aspect, the present invention relates to a method of manufacturing a sustained release biodegradable ocular implant according to the invention, the method comprising the steps of forming a hydrogel comprising a polymer network and axitinib particles dispersed within the hydrogel, shaping the hydrogel and drying the hydrogel.

In a further aspect, the present invention relates to another method of manufacturing a sustained release biodegradable ocular implant according to the invention, the method comprising melt extruding or injection molding a composition comprising polymer or polymer (such as PEG) precursors and axitinib to form the implant.

In a further aspect, the present invention relates to a kit comprising one or more sustained release biodegradable ocular implant(s) of the present invention and one or more needles for injection, wherein each implant is loaded in a needle, such as in a needle having a gauge size of 25 or thinner.

In a further aspect, the present invention relates to a method of increasing the release rate and/or the average release rate and/or the released amount of total TKI contained in an ocular implant and/or the released share of the total TKI contained in the implant or the total TKI released from an implant in a certain period of time.

The individual aspects of the present invention are disclosed in the specification and claimed in the independent claims, while the dependent claims claim particular embodiments and variations of these aspects of the invention. Details of the various aspects of the present invention are provided in the detailed description below.

DEFINITIONS

Figure 1:
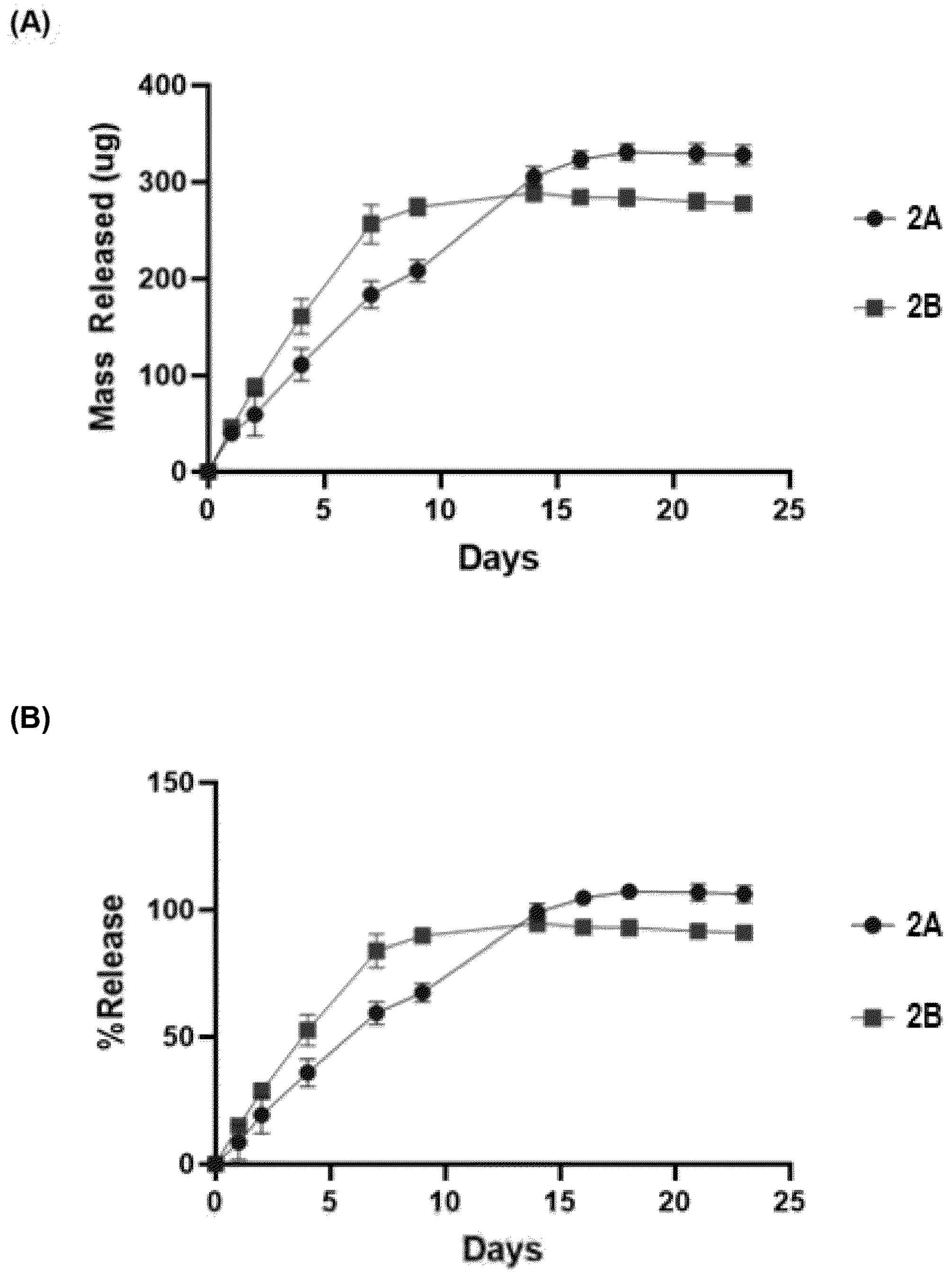
FIG. 1: TKI release profile (In Vitro Method B) from implants manufactured by HME or wet casting: (A) Mass released; (B) % Release.

The term "implant" as used herein (sometimes also referred to as "depot") refers to an object that contains an active agent, specifically a tyrosine kinase inhibitor (TKI) such as axitinib, and/or other compounds as disclosed herein, and that is administered into the human or animal body, e.g., to the vitreous humor of the eye (also called "vitreous chamber" or "vitreous body") where it remains for a certain period of time while it releases the active agent into the surrounding environment. An implant can have any predetermined shape (such as disclosed herein) before being injected, which shape is maintained to a certain degree upon placing the implant into the desired location, although dimensions of the implant (e.g. length and/or diameter) may change after administration due to hydration as further disclosed herein. In other words, in case of a pre-shaped implant, what is injected into the eye is not a solution or suspension, but an already shaped, coherent object. The implant in this case has thus been completely formed as disclosed herein prior to being administered, and is not created in situ at the desired location in the eye. In certain alternative embodiments of the invention, however, the implant may be created in situ at the desired location by means of injection of a solution of precursor compounds that form into an implant once injected.

Once administered, over the course of time an implant of the present invention is biodegraded (as disclosed herein) in physiological environment, may thereby change its shape while it decreases in size until it has been completely dissolved/resorbed.

Herein, the term "implant" is used to refer both to an implant in a hydrated (also referred to herein as "wet") state when it contains water, e.g. after the implant has been hydrated or re-hydrated once administered to the eye or otherwise immersed into an aqueous environment (such as in vitro), as well as to an implant in its/a dry (also referred to herein as "dried" or "dehydrated") state, i.e., after the implant has been produced and dried and just prior to being loaded into a needle, or after having been loaded into a needle as disclosed herein, or wherein the implant has been manufactured in a dry state without the need for dehydration. In other words, the term "dry" or "dried" in connection with an implant of the Invention refers to the implant prior to being injected (into physiological or other environment). In the art, in the dried state a "hydrogel" (such as the hydrogel contained in the implant of the invention) is sometimes also referred to as a "xerogel". Thus, in certain embodiments, an implant in its dry/dried state in the context of the present invention may contain no more than about 1% by weight water. The water content of an implant in its dry/dried state may be measured e.g. by means of a Karl Fischer coulometric method. Whenever dimensions of an implant (i.e., length, diameter, surface area, or volume) are reported herein for the hydrated state, these dimensions are measured after the implant has been immersed in phosphate-buffered saline (PBS) at 37° C. for 24 hours. Whenever dimensions of an implant are reported herein in the dry state, these dimensions are measured after the implant has been fully dried (and thus, in certain embodiments, contain no more than about 1% by weight water) and the implant is in a state to be loaded into a needle for subsequent administration. In certain embodiments, the implant is kept in an inert atmosphere glove box containing below 20 ppm of both oxygen and moisture for at least about 7 days.

The term "ocular" as used in the present invention refers to the eye in general, or any part or portion of the eye (as an "ocular implant" according to the invention can in principle be administered to any part or portion of the eye) or any disease of the eye (as in one aspect the present invention generally refers to treating any diseases of the eye ("ocular diseases")), of various origin and nature. The present invention in certain embodiments is directed to intravitreal injection of an ocular implant (in this case the "ocular implant" is thus an "intravitreal implant"), and to the treatment of ocular diseases affecting the posterior segment of the eye, as further disclosed below.

The term "patient" herein includes both human and animal patients. The implants according to the present invention are therefore suitable for human or veterinary medicinal applications. The patients enrolled and treated in a clinical study may also be referred to as "subjects". Generally, a "subject" is a (human or animal) individual to which an implant according to the present invention is administered, such as during a clinical study. An animal subject in a study may be e.g. a non-human primate, such as a monkey, such as a *Cynomolgus* monkey, or may be a rodent, such as a rabbit, such as a Dutch Belted rabbit. A "patient" is a subject in need of treatment due to a particular physiological or pathological condition. In embodiments of the invention, the patient is a human.

The term "biodegradable" refers to a material or object (such as the ocular implant according to the present invention) which becomes degraded in vivo, i.e., when placed in the human or animal body. In the context of the present invention, as disclosed in detail herein below, the implant comprising the hydrogel within which particles of a TKI such as particles of axitinib, are dispersed, slowly biodegrades over time once deposited within the eye, e.g., within the vitreous humor. This means that the hydrogel gets dissolved and is bioresorbed after a certain period of time (as indicated herein). In certain embodiments biodegradation takes place at least in part via ester hydrolysis of the polymer network forming the hydrogel, which takes place in physiological environment. The implant slowly degrades (i.e., the hydrogel dissolves/degrades) until it is fully resorbed and is no longer visible in the vitreous. Herein, the term "biodegradation" or "degradation" in respect of an implant is used interchangeably with the term "dissolution", "dissociation", "resorption" or "bioresorption" of an implant.

The time until full dissolution of the hydrogel, i.e., the full degradation of the implant (in vivo or in vitro) is referred to herein also as the "persistence" of the implant.

A "hydrogel" can be defined as "a polymeric material which exhibits the ability to swell in water and retain a significant fraction (e.g., >20%) of water within its structure, but which will not dissolve in water. Included in this definition are a wide variety of natural materials of both plant and animal origin, materials prepared by modifying naturally occurring structures, and synthetic polymeric materials." (B. D. Ratner, A. S. Hoffmann, in: Hydrogels for Medical and Related Applications (Andrade, J. D., Ed.); ACS Symposium Series; American Chemical Society, Washington, D.C., 1976; Vol. 31; Chapter 1, 1-36).

Thus, a "hydrogel" is a three-dimensional network of hydrophilic natural or synthetic polymers (as disclosed herein), optionally also containing hydrophobic domains, that can swell in water and hold an amount of water while maintaining or substantially maintaining its structure, e.g., due to chemical or physical cross-linking of individual polymer chains. Due to their high water content, hydrogels are soft and flexible, which makes them very similar to natural tissue. In the present invention the term "hydrogel" is used to refer both to a hydrogel in the hydrated/"wet" state when it contains water (e.g. after the hydrogel has been formed in an aqueous solution, or after the hydrogel has been (re-)hydrated once implanted into the eye or other part of the body or otherwise immersed into an aqueous environment) as well as to a hydrogel in its dry (dried/dehydrated) state when it has been dried to a low water content of e.g. not more than 1% by weight. A dried form of a hydrogel is sometimes also referred to in the art as "xerogel", which is a dried hydrogel that can convert to a hydrogel upon exposure to and imbibition of water. The process of drying to form the xerogel can be accomplished in multiple ways and can result in various degrees of shrinkage and various degrees of porosity.

In the present invention, wherein an active principle is contained (e.g. dispersed) in a hydrogel, the hydrogel may also be referred to as a "matrix".

The term "polymer network" describes a structure formed of polymer chains (of the same or different molecular structure and of the same or different molecular weight) that are crosslinked with each other. The types of polymers suitable for the purposes of the present invention are disclosed herein. The polymer network may also be formed with the aid of a crosslinking agent as also disclosed herein.

The term "amorphous" refers to a polymer or polymer network or other chemical substance or entity which does not exhibit crystalline structures in X-ray or electron scattering experiments.

The term "semi-crystalline" refers to a polymer or polymer network or other chemical substance or entity which possesses some crystalline character, i.e., exhibits some crystalline properties in X-ray or electron scattering experiments.

The term "crystalline" refers to a polymer or polymer network or other chemical substance or entity which has crystalline character as evidenced by X-ray or electron scattering experiments.

The term "precursor" herein refers to those molecules or compounds that are reacted with each other and that are thus connected via crosslinks to form the polymer network and thus the hydrogel matrix. While other materials might be present in the hydrogel, such as active agents or buffers, they are not referred to as "precursors".

The parts of the precursor molecules that are still present in the final polymer network are also called "units" herein. The "units" are thus the building blocks or constituents of the polymer network forming the hydrogel. For example, a polymer network suitable for use in the present invention may contain identical or different polyethylene glycol units as further disclosed herein.

The molecular weight of a polymer precursor as used for the purposes of the present invention and as disclosed herein may be determined by analytical methods known in the art. The molecular weight of polyethylene glycol may for example be determined by any method known in the art, including gel electrophoresis such as SDS-PAGE (sodium dodecyl sulphate-polyacrylamide gel electrophoresis), gel permeation chromatography (GPC), including GPC with dynamic light scattering (DLS), liquid chromatography (LC), as well as mass spectrometry such as matrix-assisted laser desorption/ionization-time of flight (MALDI-TOF) spectrometry or electrospray ionization (ESI) mass spectrometry. The molecular weight of a polymer, including a polyethylene glycol precursor as disclosed herein, is an average molecular weight (based on the polymer's molecular weight distribution), and may therefore generally be indicated by means of various average values, including the weight average molecular weight (Mw) and the number average molecular weight (Mn). In the case of polyethylene glycol precursors as used in the present invention, the molecular weight indicated herein is the number average molecular weight (Mn).

When referring herein to particle size of an active agent, the "d90" (also referred to as "D90" herein) value means that 90 volume-% of all particles within the measured bulk material (which has a certain particle size distribution) have a particle size below the indicated value. For example, a d90 particle size of less than about 10 μm means that 90 volume-% of the particles in the measured bulk material have a particle size below about 10 μm. Corresponding definitions apply to other "d" values, such as the "d10", "d50" or the "d100" values (also referred to herein as the "D10", "D50" and "D100" values, respectively). Thus, whenever any particle size values (d10, d50 or d90) are reported herein, they refer to volume-%. The particle size may be measured by laser diffraction. If nothing else is disclosed herein in connection with a certain particle size, the d10, d50 and d90 particle size is measured by laser diffraction.

In certain embodiments of the present invention, the term "fiber" (used interchangeably herein with the term "rod") characterizes an object (i.e., in the present case the implant according to the present invention) that in general has an elongated shape. Specific dimensions of implants of the present invention are disclosed herein. The implant may have a cylindrical or essentially cylindrical shape, or may have a non-cylindrical shape as further disclosed herein. The cross-sectional area of the fiber or the implant may be either round or essentially round, but may in certain embodiments also be oval or oblong, or may in other embodiments have different geometries, such as cross-shaped, star-shaped or other as further disclosed herein.

In certain embodiments of the present invention, also the term "filament" is used to refer to a fiber, especially in cases where an implant comprises several fibers or filaments to form a "multi-filament" implant. In these cases, the composite diameter of the multi-filament implant is essentially in the same range as the diameter of a single-fiber implant. In other words, in such multi-filament implants the individual filaments—although being generally in the shape of a fiber—may be relatively thin so that the composite diameter of the multi-filament implant is not excessively large. Embodiments of multi-filament implants are disclosed herein.

The "hydrated surface area" of an implant is calculated based on its hydrated dimensions. For example, the hydrated surface area of cylindrical or essentially cylindrical implants ("fibers" in accordance with the present invention) is calculated from the hydrated length and diameter according to the formula for the surface area of cylinders $A=2\pi rh+2\pi r^2$ (with h being the height, i.e., the length of the cylinder, in the hydrated state and r being the radius, i.e., half the diameter/width of the cylinder, in the hydrated state), Whenever dimensions of an implant (i.e., length, diameter) and values derived therefrom (such as surface area or volume) are reported herein for the hydrated state, these dimensions are measured after the implant has been immersed in phosphate-buffered saline (PBS, at a pH of 7.2 to 7.4) at 37° C. for 24 hours.

The term "release" (and accordingly the terms "released", "releasing" etc.) as used herein refers to the provision of agents such as an API from an implant of the present invention to the surrounding environment. The surrounding environment may be an in vitro or in vivo environment as described herein. In certain specific embodiments, the surrounding environment is the vitreous humor and/or ocular tissue, such as the retina or the choroid. Thus, whenever it is herein stated that the implant, "releases" or "provides for (sustained) release" of a TKI such as axitinib, this not only refers to the provision of TKI such as axitinib directly from the implant while the hydrogel has not yet (fully) biodegraded, but also refers to the continued provision of TKI such as axitinib to the surrounding environment following full degradation of the hydrogel when remaining undissolved TKI is still present in this surrounding environment (e.g. as individual or agglomerated particles) for a period of time in which the TKI continues to exert its therapeutic effect. Herein, the "vitreous humor" (VH) is sometimes also simply referred to as the "vitreous".

In the context of in vivo studies, such as in vivo studies in animals, the terms "$C_{max}$" and "$t_{max}$" have the following meaning: The term "$C_{max}$" denotes the maximum concentration of active agent as measured in a specific (ocular) tissue, such as the retina or the choroid (as indicated e.g. in the Examples 10 and 13 herein relating to in vivo studies). Generally, $C_{max}$ refers to the maximum average concentration of all corresponding samples measured in a certain study (again, as in the Examples 10 and 13). The unit of $C_{max}$ in a tissue is ng/g, unless indicated otherwise. If $C_{max}$ is measured in plasma, the unit is ng/mL. The term "$T_{max}$" (or "$t_{max}$", which is interchangeably used herein with "$T_{max}$") denotes the time to maximum plasma concentration ($C_{max}$). $T_{max}$ can be indicated in days, weeks, or months, as the case may be. The "AUC" (Area Under the Curve) value corresponds to the area of the tissue (or plasma, as the case may be) drug concentration versus time curve. The AUC is indicated for a certain time period. In the present invention e.g. an $AUC_{0\text{-}9\ months}$ refers to the area of drug concentration versus the time curve from injection of an implant of the present invention through 9 months.

The "treatment period" referred to herein is the period during which a certain therapeutic effect (as described herein) is achieved. It may extend to a period of time even after the implant/the hydrogel has fully biodegraded/dissolved as further disclosed herein.

The term "sustained release" is defined for the purposes of the present invention to characterize products (in the case of the present invention the products are implants) which are formulated to make a drug available over an extended period of time, thereby allowing a reduction in dosing frequency compared to an immediate release dosage form (such as e.g. a solution of an active principle that is injected into the eye). Other terms that may be used herein interchangeably with "sustained release" are "extended release" or "controlled release". "Sustained release" thus characterizes the release of an API, specifically, the TKI, such as axitinib, that is contained in an implant according to the present invention. The term "sustained release" per se is not associated with or limited to a particular rate of (in vitro or in vivo) release, although in certain embodiments of the invention an implant may be characterized by a certain average rate of (in vitro or in vivo) release or a certain release profile as disclosed herein. Within the specific meaning of the present invention, the term "sustained release" also comprises a period of constant or substantially constant (i.e., above a certain level) tyrosine kinase inhibitor release per day when this period of constant or substantially constant release is followed by a period of tapered tyrosine kinase inhibitor release. In such specific case, an overall sustained release provided by an implant of the present invention may mean that the release rate is not necessarily constant or essentially constant throughout the entire period of TKI release, but may change over time as just described (e.g., with an initial period of constant or essentially constant sustained release, followed by a period of tapered release), Within the meaning of the invention, the term "tapered" or "tapering" refers to a decreasing release of tyrosine kinase inhibitor such as axitinib over time until the tyrosine kinase inhibitor is completely released. In some specific cases, the release profile may also show an initial drug burst and/or a terminal drug burst, indicated by a short-term increase of the respective release rate (in vitro or in vivo), As an implant of the present invention (whether explicitly referred to herein as a "sustained release" implant or simply as an "implant") provides for sustained release of the API, an implant of the present invention may therefore also be referred to as a "depot".

In certain embodiments of the invention, implants are characterized by the release profile of the TKI, such as axitinib, as measured in certain in vitro tests. In such in vitro tests, which are further disclosed herein, the amount of TKI released during a particular period of time, such as over a period of one or more days, may be determined in terms of the absolute amount (such as in μg) released per day on any given day during the course of the in vitro test (the amount released per day also defines the "release rate per day" or "rate of release per day"), or the cumulative absolute amount (again, such as in μg or mg) released over that period of time, such as the cumulative amount released over a period of 10 days. In in vitro tests, also the percentage of release may be determined, either the percentage released per day (or over a period of several days), or the cumulative percentage released over a certain period of time, such as over e.g. 10 days. The percentage may be defined as being a percentage (ratio/share) of the entire amount (drugload) contained in a certain implant, or it may be defined as being a percentage (ratio/share) of the total amount released from a certain implant in the respective in vitro test (which in certain cases is lower than the actual total amount of active contained in the implant, e.g. in cases where the release determined in an in vitro test approaches an equilibrium amount of drug released, which is lower than the actual drugload of the implant for a variety of reasons, or in cases where the in vitro test is terminated before all of the contained drugload has been released).

In the context of in vitro release tests, the "amount" herein refers to a weight, such as μg or mg, while the "percentage" (or "share" or "ratio") refers to a percentage (%).

The "average release rate" (such as in μg/day) is the average amount (such as in μg) released per day over a certain number of days. It is calculated by dividing the absolute (cumulative) amount of active agent released over a certain number of days by that number of days. By means of example, if one implant according to the invention releases a total (cumulative) amount of 100 μg axitinib over a period of 5 days, the average release rate would be 20 μg/day for this period of 5 days. The actual release rate on any single given day within this period of 5 days may of course differ from the average release rate over the entire period.

Whenever in the context of in vitro tests and determining the release (rate) of an active agent from an implant of the invention it is referred herein to an "initial" number of days, or an "initial" period, e.g. an "initial period of 5 days", this means the period covering the respective number of days from the very start of the respective in vitro test (e.g., the first 5 days of the in vitro test).

In vitro tests may be conducted in various solvents and under various conditions (e.g. using "Method A" or "Method B" or "Method C", (see the subsection "In vitro release" in the section "I, The implant")), as disclosed herein in detail whenever referring to any particular release characteristics. Generally, for Methods A and B one implant (or several implants simultaneously if specifically mentioned) is placed into a certain volume of solvent or solvent mixture and at a certain temperature (which is maintained over the course of the in vitro test) as disclosed herein, and the release amount or percentage is determined on pre-determined days. The volume of solvent (mixture) into which the implant is placed for such an in vitro test is determined by a "sink factor" by which a "sink volume" is multiplied. The "sink volume" is calculated by dividing the amount (such as in μg) of active agent contained in the implant to be studied by the solubility of that active agent (such as in μg/mL) in the solvent (mixture) in which the test is to be conducted. For example, if the in vitro test for an implant according to the invention that contains axitinib as the TKI is conducted in a solvent mixture of 25% ethanol/75% water (v/v), the amount of axitinib contained in the implant studied is divided by the solubility of the axitinib in this solvent mixture to determine the sink volume. The solubility of the active agent may differ depending on which form of the active agent is used, as further disclosed herein. For example, different polymorphic forms of an active agent may have different solubilities in the same solvent (mixture). Also, different salts, or co-crystals, or derivatives of an active agent may have different solubilities in the same solvent (mixture). Depending on the purpose of the test and the specific details of the test method applied, either these specific solubility values for the different forms of the active agent are used to calculate the "sink volume", or for certain simplified or comparative tests also an average solubility for the given active agent is used to calculate the "sink volume", as disclosed herein. In vitro tests reported in the present invention may be conducted under various sink conditions, as disclosed herein, such as under 2× sink conditions, or under 3× sink conditions, or with a higher sink factor, such as under 4× or higher sink conditions, "2× sink conditions" means that the volume of solvent (mixture) into which an implant according to the invention is immersed (or several implants if so indicated) for the specific test is two times the "sink volume" (as defined above), i.e., the "sink factor" in this case would be 2; "3× sink conditions" means that the volume of solvent (mixture) into which an implant according to the invention is immersed (or several implants if so indicated) for the specific test is three times the "sink volume" (as defined above), i.e., the "sink factor" in this case would be 3; and so on for other sink factors. Further details on in vitro tests performed with implants according to the invention in which the TKI is axitinib (specifically, on the sink factor and sink volume) are provided in the present description in the sub-section "In vitro release" within the section "The implant". A further method of measuring the in vitro release of axitinib from implants of the present invention is "Method C" as also disclosed herein in detail (see e.g. the subsection "In vitro release" in the section "I. The implant" and Example 7.3).

Whenever it is stated herein that a certain administration or injection is performed "concurrently with" or "simultaneously to" or "at the same time as" an administration or injection of an implant according to the present invention, this means that the respective injection of either two or more implants or the injection of one or more implant(s) together with the administration of another agent, such as the injection of a suspension or solution e.g. of an anti-VEGF agent as disclosed herein, is normally performed immediately one after the other, i.e., without any significant delay. By means of example, if a total dose of about 400 μg axitinib is to be administered to one eye and that total dose is comprised in two implants according to the invention, each containing about 200 μg of axitinib, these two implants are normally injected Into the vitreous chamber Immediately one after the other within the same treatment session (and thus "simultaneously"), of course by respecting all precautions for a safe and precise injection at the desired site, but without any unnecessary delay. The same applies to the administration of one or more implant(s) according to the present invention concurrently with/simultaneously to/at the same time with the administration of an additional anti-VEGF agent as described herein. In case the additional anti-VEGF agent is administered by an intravitreal injection of a suspension or solution containing the anti-VEGF agent, this injection is also normally intended to take place immediately (as disclosed above) before or after the intravitreal injection of the one or more implant(s) according to the present invention, i.e., ideally during one treatment session, if a concurrent/simultaneous treatment is intended.

However, under specific circumstances, e.g. in case complications during the administration of the first implant are experienced and/or the physician carrying out the injection concludes that a second planned injection during the same session on the same day (such as in case the intended dose is contained in two or more implants), or within the following days, may not be advisable, the second implant may in exceptional cases also be administered e.g. within one or two weeks after the first implant. Since, as will be disclosed in more detail herein, the implants may persist in the vitreous of a human eye for a duration of an extended period of time, such as for about 6 to about 12 months, or about 6 to about 9 months, the administration of two implants e.g. one or two weeks apart may still bel regarded as "concurrently" in the context of the present invention. Similar considerations apply for the "concurrent" administration of an implant according to the present invention and an anti-VEGF agent (or other agent). Thus, an anti-VEGF agent can be administered concurrently, i.e., at or around the same time as described herein, with the intravitreal administration of an implant of the present invention.

In certain other embodiments, however, an anti-VEGF agent can also be administered in combination with an intravitreal implant of the present invention, wherein the administration of the implant of the present invention and the anti-VEGF agent are not concurrent or simultaneous as defined above. In these cases, the anti-VEGF agent is administered either later or prior to, such as within 1 month, or 2 months, or 3 months after or prior to the intravitreal injection of an implant according to the present invention. Such combined administration of an anti-VEGF agent, such as aflibercept or bevacizumab, with an implant according to the present invention may also be referred to as "combination therapy".

The term "rescue medication" generally refers to a medication that may be administered to a patient under predefined conditions (e.g. to a subject during a study in case a subject does not sufficiently respond to investigational treatment; or to a patient under specified conditions that are either pre-determined or determined by the physician treating the patient), or to manage an emergency situation. In certain embodiments of the present invention, "rescue medication" refers to one dose of an anti-VEGF agent as disclosed herein, administered as an intravitreal injection of a solution or suspension of the anti-VEGF agent. In certain specific embodiments, the rescue medication is one dose (2 mg) of aflibercept administered by means of intravitreal injection.

As used herein, the term "about" in connection with a measured quantity (Including a period of time, a weight, a volume) refers to the normal variations in the respective measured quantity, as expected by one of ordinary skill in the art in making the measurement and exercising a level of care commensurate with the objective of measurement and the precision of the measuring equipment. If not otherwise mentioned, all values of measured or measurable quantities (again, including periods of time, weights, volumes etc.) disclosed herein-even in cases where these are not preceded by an "about"—are meant to include the said normal variations in the respective measured quantity.

The term "at least about" in connection with a measured quantity refers to the normal variations in the measured quantity, as expected by one of ordinary skill in the art in making the measurement and exercising a level of care commensurate with the objective of measurement and precisions of the measuring equipment and any quantities higher than that.

The term "average" as used herein refers to a central or typical value in a set of data (points), which is calculated by dividing the sum of the data (points) in the set by their number (i.e., the mean value of a set of data).

As used herein, the singular forms "a," "an", and "the" include plural references unless the context clearly indicates otherwise.

The term "and/or" as used in a phrase such as "A and/or B" herein is intended to include both "A and B" and "A or B".

Open terms such as "include," "including," "contain," "containing" and the like as used herein mean "comprising" and are intended to refer to open-ended lists or enumerations of elements, method steps, or the like and are thus not intended to be limited to the recited elements, method steps or the like but are intended to also include additional, unrecited elements, method steps or the like.

The term "up to" when used herein together with a certain value or number is meant to include the respective value or number.

The terms "from A to B", "of from A to B", and "of A to B" are used interchangeably herein and all refer to a range from A to B, including the upper and lower limits A and B.

For the purpose of the present disclosure, any ranges defined by an upper limit and a lower limit are also meant to include all individual values or ranges between these limits.

Specifically, this also applies to ranges of pH values given in this description. For example, if a pH range of 7.2 to 7.4 is indicated, this specifically means a pH of 7.2; or a pH of 7.4; or a pH inbetween such as 7.3.

The terms "API", "active (pharmaceutical) ingredient", "active (pharmaceutical) agent", "active (pharmaceutical) principle", "(active) therapeutic agent", "active", and "drug" are used interchangeably herein and refer to the substance used in a finished pharmaceutical product (FPP) as well as the substance used in the preparation of such a finished pharmaceutical product, intended to furnish pharmacological activity or to otherwise have direct effect in the diagnosis, cure, mitigation, treatment or prevention of a disease, or to have direct effect in restoring, correcting or modifying physiological functions in a patient.

The term "polymorph" as used herein refers to any crystalline form of an active agent such as axitinib. Frequently, active agents that are solid at room temperature exist in a variety of different crystalline forms, i.e., polymorphs, with one polymorph being the thermodynamically most stable at a given temperature and pressure. Axitinib polymorphs for use in the present invention are further disclosed herein.

The term "derivative" of an active agent as used herein generally refers to a compound that is derived from an active agent by a chemical reaction, specifically a compound that is synthesized from the active agent by means of substitution/functionalization/replacement at one or more sites, structural moieties or atoms within the active agent's structure. By means of example. If the active agent's structure has an —NH group in the molecule, the hydrogen atom in such-NH group may be replaced by a substituent group of various nature as disclosed herein. In certain cases, a derivative may also be a compound that is synthesized from the active agent by removal of certain substituents, groups or moieties.

The term "prodrug" as used herein refers to a bioreversible derivative of a drug molecule that undergoes an enzymatic and/or chemical transformation in vivo to the active (parent) drug, which can then exert its desired pharmacological effect. A prodrug may alter the physicochemical, biopharmaceutical or pharmacokinetic properties of a drug in order to alter, and in certain cases to improve, one or more aspects of the therapeutic applicability, availability and usefulness of the respective drug. For example, a prodrug may be more readily soluble than the parent drug, and by using such prodrug the bioavailability of the parent drug may be increased. A "prodrug" in certain embodiments may be a derivative of a drug, as defined above. For example, a prodrug may be a derivative of a drug wherein at one or more sites of the drug molecule groups are attached which are cleaved again upon immersion in a physiological environment. In other embodiments, a "prodrug" may also be a precursor of the active (parent) drug comprising a portion of the active drug molecule, wherein the precursor reacts in physiological environment with other components being present in said physiological environment, or being intentionally administered for that purpose, to build the structure of the active (parent) drug.

For the purpose of the present disclosure, the term "alkyl" as used by itself or as part of another group refers to a straight- or branched-chain aliphatic hydrocarbon containing one to twelve carbon atoms (i.e., $C_{1-12}$ alkyl) or any other number of carbon atoms designated (i.e., a $C_1$ alkyl such as methyl, a $C_2$ alkyl such as ethyl, a $C_3$ alkyl such as propyl or isopropyl, etc.). In one embodiment, the alkyl group is chosen from a straight chain $C_{1-10}$ alkyl group. In another embodiment, the alkyl group is chosen from a branched chain $C_{1-10}$ alkyl group. In another embodiment, the alkyl group is chosen from a straight chain $C_{1-6}$ alkyl group. In another embodiment, the alkyl group is chosen from a branched chain $C_{1-6}$ alkyl group. In another embodiment, the alkyl group is chosen from a straight chain $C_{1-4}$ alkyl group. In another embodiment, the alkyl group is chosen from a branched chain $C_{1-4}$ alkyl group. In another embodiment, the alkyl group is chosen from a straight or branched chain $C_{2-4}$ alkyl group, Non-limiting exemplary $C_{1-10}$ alkyl groups include methyl, ethyl, propyl, isopropyl, butyl, sec-butyl, tert-butyl, iso-butyl, 3-pentyl, hexyl, heptyl, octyl, nonyl, decyl, and the like, Non-limiting exemplary $C_{1-4}$ alkyl groups include methyl, ethyl, propyl, isopropyl, butyl, sec-butyl, tert-butyl, and iso-butyl.

For the purpose of the present disclosure, the term "optionally substituted alkyl" as used by itself or as part of another group means that the alkyl as defined above is either unsubstituted or substituted with one, two, or three substituents independently chosen from nitro, haloalkoxy, aryloxy, aralkyloxy, alkylthio, sulfonamido, alkylcarbonyl, arylcarbonyl, alkylsulfonyl, arylsulfonyl, ureido, guanidino, carboxy, carboxyalkyl, cycloalkyl, and the like. In one embodiment, the optionally substituted alkyl is substituted with two substituents. In another embodiment, the optionally substituted alkyl is substituted with one substituent. Non-limiting exemplary optionally substituted alkyl groups include $—CH_2CH_2NO_2$, $—CH_2CH_2CO_2H$, $—CH_2CH_2SO_2CH_3$, $—CH_2CH_2COPh$, $—CH_2C_6H_{11}$, and the like.

For the purpose of the present disclosure, the term "aryl" as used by itself or as part of another group refers to a monocyclic or bicyclic aromatic ring system having from six to fourteen carbon atoms (i.e., $C_{6-14}$ aryl). Non-limiting exemplary aryl groups include phenyl (abbreviated as "Ph"), naphthyl, phenanthryl, anthracyl, indenyl, azulenyl, biphenyl, biphenylenyl, and fluorenyl groups. In one embodiment, the aryl group is chosen from phenyl or naphthyl. The term "aryl" also comprises "heteroaryl", which means an "aryl" group in which one or more carbon atoms are replaced by one or more other atom(s), which can be identical or different, including oxygen, nitrogen, and/or sulfur. The "aryl" group may comprise one aromatic ring, or may comprise more than one aromatic rings.

For the purpose of the present disclosure, the term "optionally substituted aryl" as used herein by itself or as part of another group means that the aryl as defined above is either unsubstituted or substituted with one or more substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, or (heteroaryl)alkyl. In one embodiment, the optionally substituted aryl is an optionally substituted phenyl. In one embodiment, the optionally substituted phenyl has four substituents. In another embodiment, the optionally substituted phenyl has three substituents. In another embodiment, the optionally substituted phenyl has two substituents. In another embodiment, the optionally substituted phenyl has one substituent. Non-limiting exemplary substituted aryl groups include 2-methylphenyl, 2-methoxyphenyl, 2-fluorophenyl, 2-chlorophenyl, 2-bromophenyl, 3-methylphenyl, 3-methoxyphenyl, 3-fluorophenyl, 3-chlorophenyl, 4-methylphenyl, 4-ethylphenyl, 4-methoxyphenyl, 4-fluorophenyl, 4-chlorophenyl, 2,6-di-fluorophenyl, 2,6-di-chlorophenyl, 2-methyl, 3-methoxyphenyl, 2-ethyl, 3-methoxyphenyl, 3,4-di-methoxyphenyl, 3,5-di-fluorophenyl 3,5-di-methylphenyl, 3,5-dimethoxy, 4-methylphenyl, 2-fluoro-3-chlorophenyl, and 3-chloro-4-fluorophenyl. The term "optionally substituted aryl" is meant to include groups having fused optionally substituted cycloalkyl and fused optionally substituted heterocyclo rings. Examples include (but are not limited to):

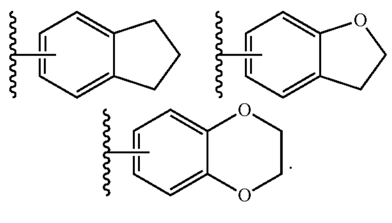

The term "salt," as used herein, can include, but is not limited to, inorganic acid salts such as hydrochloride, hydrobromide, hydroiodite, sulfate, phosphate and the like; organic acid salts such as formate, acetate, trifluoroacetate, maleate, tartrate, glutarate and the like; sulfonates such as methanesulfonate, benzenesulfonate, p-toluenesulfonate, and the like; and metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like. Any TKI, such as axitinib, salt used herein is meant to be a pharmaceutically acceptable salt.

The term "co-crystal" as used herein refers to a combination of an active pharmaceutical ingredient (API) and one or more co-formers, such as acids (such as carboxylic acids) in the same lattice through non-covalent interactions, such as hydrogen bonds, electrostatic interactions, π-π stacking, van der Waals interactions, etc. Co-crystals are thus multicomponent solids. The difference between co-crystals and salts is that the former are only composed of neutral components, while the latter contain ionic components. Suitable co-formers for axitinib co-crystals are further disclosed herein. Cocrystallization may alter, and in certain cases and for certain applications optimize, the physicochemical properties of an API, for example regarding stability, solubility, dissolution rate, mechanical properties etc.

As used herein, the term "therapeutically effective" refers to the amount of drug or active agent needed to produce a certain desired therapeutic result after administration. For example, in the context of the present invention, one desired therapeutic result would be the reduction of the central subfield thickness (CSFT) as measured by optical coherence tomography in a patient suffering from neovascular AMD as patients suffering from neovascular AMD have elevated CSFT. A "therapeutically effective" amount of an active agent in the context of the present invention may also be a multiple of the $IC_{50}$ this active agent provides against a particular substrate, such as 50 or more times the $IC_{50}$.

The abbreviation "PBS" when used herein means "phosphate-buffered saline".

The abbreviation "TBS" when used herein means "tris-buffered saline".

The abbreviation "PEG" when used herein means "polyethylene glycol".

The abbreviation "HME" when used herein means "hot melt extrusion".

The abbreviation "HST" when used herein means "heat-stretch-twist".

The abbreviation "NHP" when used herein means "non-human primates".

The abbreviation "TLA" when used herein means "trilysine acetate".

All references disclosed herein are hereby incorporated by reference in their entireties for all purposes. In case of conflicts between an incorporated reference and the present disclosure, the present disclosure prevails.

DETAILED DESCRIPTION®

I. The Implant

The Active Principle:

One aspect of the present invention is a sustained release biodegradable ocular implant comprising a hydrogel and a tyrosine kinase inhibitor (TKI), wherein TKI particles are dispersed within the hydrogel, as disclosed herein. The active principle contained in an implant of this aspect of the invention is thus a TKI. Examples for suitable TKIs are axitinib, sorafenib, sunitinib, nintedanib, pazopanib, regorafenib, cabozantinib, and vandetanib. In particular embodiments, the TKI used in this and other aspects of the present invention is axitinib.

In embodiments of the present invention, the implant contains axitinib as the tyrosine kinase inhibitor. Axitinib free base is the active ingredient in INLYTA® (Pfizer, NY), indicated for the treatment of advanced renal cell carcinoma. It is a small molecule (386.47 Daltons) synthetic tyrosine kinase inhibitor. The primary mechanism of action is inhibition of angiogenesis (the formation of new blood vessels) by inhibition of receptor tyrosine kinases, primarily:

VEGFR-1, VEGFR-2, VEGFR-3, PDGFR-β and c-Kit (Keating. Axitinib: a review in advanced renal cell carcinoma. 2015, Drugs, 75(16): 1903-13; Kernt et al., Inhibitory activity of ranibizumab, sorafenib, and pazopanib on light-induced overexpression of platelet-derived growth factor and vascular endothelial growth factor A and the vascular endothelial growth factor receptors 1 and 2 and neuropilin 1 and 2. 2012, Retina, 32(8): 1652-63), which are involved in pathologic angiogenesis, tumor growth, and cancer progression. Axitinib is therefore a multi-target inhibitor that inhibits both VEGF and PDGF pathways.

Axitinib inhibits VEGF signaling and it also inhibits PDGF signaling. In addition to inhibiting VEGF/PDGF, it inhibits c-kit, a survival factor for developing blood vessels with a clearance half-life ($t_{1/2}$) of a few hours (Rugo et al., Phase I trial of the oral antiangiogenesis agent AG-013736 in patients with advanced solid tumors. 2005, J Clin Oncol., 23(24): 5474-83), whereas ranibizumab and aflibercept each have $t_{1/2}$ of several days in the human eye. Longer $t_{1/2}$ of these large molecule antibodies enable them to maintain efficacious tissue concentrations for weeks, whereas small molecules are cleared more quickly. However, due to the low solubility of axitinib and its inclusion in the hydrogel implant of the present invention which remains in the vitreous humor (VH) for an extended period of time, such as for months, therapeutically effective amounts of axitinib are delivered over the period the implant persists in the VH. Therefore, intravitreal sustained delivery of axitinib provides a multi-target inhibitor that can in principle inhibit both VEGF and PDGF pathways without the need of combination therapies and without the need for frequent intravitreal injections.

The molecular formula of axitinib free base is $C_{22}H_{18}N_4OS$, and its IUPAC name is N-methyl-2-[3-((E)-2-pyridin-2-yl-vinyl)-1H-indazol-6-ylsulfanyl]-benzamide. It has the following chemical structure:

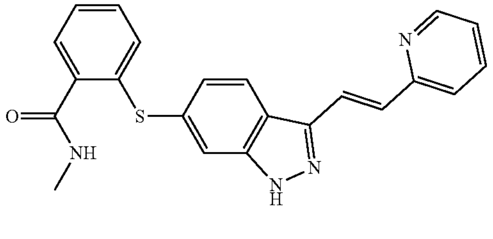 [SMILES: CNC(=O)c1ccccc1Sc1ccc2c(/C=C/c3ccccn3)n[nH]c2c1]

For the purposes of the present invention in all its aspects, axitinib in all its possible forms, including any axitinib polymorphs, salts, anhydrates, hydrates, other solvates, derivatives or prodrugs of axitinib, can be used. Whenever in this description or in the claims it is referred to "axitinib", if not otherwise explicitly stated this refers to any axitinib polymorph, salt, anhydrate, solvate (including hydrates), co-crystal, derivative or prodrug of axitinib. For the purpose of the present invention, all forms of axitinib used in implants are intended to be pharmaceutically acceptable.

In certain embodiments of the present invention, specific forms of axitinib are used.

The solubility of axitinib free base in biorelevant media (e.g. PBS, pH 7.2 to 7.4, e.g. at 37° C.) has been determined to be low. Different forms of axitinib, including different forms of the axitinib free base such as different axitinib polymorphs have different solubility. Solubility measurements are reported in Example 6.

The present invention in one aspect relates to a sustained release biodegradable ocular implant comprising a hydrogel and a tyrosine kinase inhibitor (TKI), such as axitinib, wherein tyrosine kinase inhibitor particles are dispersed within the hydrogel, characterized in that the solubility of the tyrosine kinase inhibitor is greater than 0.3 μg/mL as measured in phosphate-buffered saline (PBS) at a pH of 7.2 to 7.4 and 37° C. after five days of incubation. In specific embodiments, the TKI is axitinib.

According to this aspect of the invention, any forms of axitinib, such as axitinib polymorphs, co-crystals, derivatives and prodrugs, including but not limited to those further disclosed herein may be used that have a solubility of greater than 0.3 μg/mL as measured in phosphate-buffered saline (PBS) at a pH of 7.2 to 7.4 and 37° C. after five days of incubation.

Another aspect of the present invention relates to a sustained release biodegradable ocular implant comprising a hydrogel and a tyrosine kinase inhibitor, such as axitinib, wherein tyrosine kinase inhibitor particles are dispersed within the hydrogel, characterized in that the hydrated surface area of the implant is at least 25 $mm^2$ as measured in phosphate-buffered saline (PBS) at a pH of 7.2 to 7.4 and 37° C. after 24 hours of incubation. According to this aspect of the invention, generally all forms of axitinib may be used, regardless of their solubility, including but not limited to the axitinib polymorphs, co-crystals, derivatives and prodrugs as further disclosed herein, as long as the hydrated surface area of the implant is at least 25 $mm^2$ as measured in phosphate-buffered saline (PBS) at a pH of 7.2 to 7.4 and 37° C. after 24 hours of incubation.

The above two aspects of the present invention may also be combined, i.e., the present invention also relates to a sustained release biodegradable ocular implant comprising a hydrogel and a tyrosine kinase inhibitor, such as axitinib, wherein tyrosine kinase inhibitor particles are dispersed within the hydrogel, characterized in that the solubility of the tyrosine kinase inhibitor is greater than 0.3 μg/mL as measured in phosphate-buffered saline (PBS) at a pH of 7.2 to 7.4 and 37° C. after five days of incubation, and further characterized in that the hydrated surface area of the implant is at least 25 $mm^2$ as measured in phosphate-buffered saline (PBS) at a pH of 7.2 to 7.4 and 37° C. after 24 hours of incubation.

Axitinib Polymorphs for Use in the Present Invention:

With respect to axitinib, suitable solid forms and polymorphs of axitinib including anhydrous forms and solvates are disclosed in the scientific literature, e.g. A. M. Campeta et al., Journal of Pharmaceutical Sciences, Vol. 99, No. 9, September 2010, 3874-3886; B. P. Chekal et al., Organic Process Research & Development 2009, 13, 1327-1337; and in the patent literature, including, but not limited to U.S. Pat. No. 8,791,140 B2, US 2006/0094763 A1, and WO 2016/178150 A1. The most thermodynamically stable polymorph of axitinib is referred to as form XLI in e.g. U.S. Pat. No. 8,791,140 B2. XLI is an anhydrous crystalline form of axitinib. In certain embodiments of the invention, the axitinib used for preparing the implants according to the present invention is the anhydrous crystalline form XLI. In addition to the anhydrous forms, there exist numerous solvates of axitinib with various solvents, as also described in the cited art, which can all be used for preparing implants according to the present invention. Any of the axitinib polymorphic forms known and disclosed in the art, specifically (but not limited to) the references cited herein, may generally be used in the present invention (unless the specific aspect of the invention requires a particular solubility, as explained above, in which case only those axitinib polymorphs that meet this requirement may be used).

In certain aspects and embodiments of the invention, the non-solvated crystalline form SAB-I of axitinib disclosed in WO 2016/178150 may be used for preparing the implants according to the present invention. It is characterized by an XRD pattern comprising at least three, or at least four, or at least five characteristic 2θ° peaks selected from 8.3, 15.6, 16.5, 18.6, 21.0, 23.1, 24.1 and 26.0 2θ° (all values±0.3), and/or $^{13}C$ NMR in DMSO solvent comprising chemical shifts at 26.1, 114.7, 154.8 and 167.8, each shift±0.2 ppm, and/or $^{13}C$ solid state NMR comprising chemical shifts at 171.1, 153.2, 142.6, 139.5, 131.2, 128.1 and 126.3, each shift±0.2 ppm, and/or characterized by a DSC isotherm comprising two endothermic peaks ranging between 213° C. to 217° C. (Peak 1) and 219° C. to 224° C. (Peak 2).

The solubility of axitinib polymorph SAB-I measured at 37° C. in PBS with a pH of 7.2 to 7.4 after 5 days of incubation has been determined to be below 0.3 μg/mL, see Example 6.

In those aspects and embodiments of the present invention, in which the solubility of the tyrosine kinase inhibitor is greater than 0.3 μg/mL as measured in phosphate-buffered saline (PBS) at a pH of 7.2 to 7.4 and 37° C. after five days of incubation, polymorph form IV is a particularly suitable polymorph of axitinib. Polymorph IV is disclosed for example in US 2006/0094763 A1. In specific, embodiments, axitinib polymorph IV is used for preparing the implants according to this aspect of the present invention. Additionally, axitinib polymorph IV is also suitable for preparing the implants according any other aspect of the invention, including aspects wherein the solubility of the TKI is not required to be in a certain range, such as the aspect of the invention wherein the hydrated surface area of the implant is at least 25 $mm^2$ as measured in phosphate-buffered saline (PBS) at a pH of 7.2 to 7.4 and 37° C. after 24 hours of incubation. Axitinib polymorph IV is thus a particular form of axitinib used in all aspects of the present invention.

The solubility of axitinib polymorph IV is about twice the solubility of e.g. axitinib polymorph SAB-I, and at 37° C. in PBS with a pH of 7.2 to 7.4 (or at a pH of 7.2) after 5 days of incubation has been determined to be above 0.3 μg/mL, and is at least 0.4 μg/mL under these conditions. See Example 6 and FIG. 17. In one embodiment, axitinib polymorph IV is used for preparing the implants according to this aspect of the invention requiring a solubility of greater than 0.3 μg/ml as measured in phosphate-buffered saline (PBS) at a pH of 7.2 to 7.4 and 37° C. after five days of incubation, but may also be used for preparing implants according to any other aspect of the present invention.

In certain specific embodiments, the axitinib, specifically the axitinib polymorph IV, contained in or used for preparing the implants according to the present invention alternatively is characterized by a powder X-ray diffraction pattern comprising at least two, such as at least three, or at least four, or at least five of the following peaks at diffraction angles (2θ) of 8.90, 9.40, 9.50, 12.0, 14.60, 15.25, 15.75, 17.80, 19.30, 20.65, 24.95, 26.10 (all values±0.2). Particularly, the axitinib, specifically the axitinib polymorph IV, used for preparing the implants according to this aspect of the present invention may be characterized by a powder X-ray diffraction pattern comprising the following peaks at diffraction angles (2θ) of: 8.90, 12.0, 14.60, 15.75, and 19.30 (all ±0.2), and/or characterized by a DSC peak at about 221° C. at a scan rate of 5° C./min (over a range of 25 to 300° C.).

In certain embodiments, the axitinib used for preparing the implants according to the present invention is polymorph IV as characterized in US 2006/0094763 A1, which discloses axitinib polymorph IV (e.g. in paragraphs [0021], and [0119], [0119], and in claims 3 to 5 of US 2006/0094763 A1, also with reference to FIGS. 4A and 4B of US 2006/0094763 A1). Thus, the axitinib having a solubility of greater than 0.3 μg/ml as measured in phosphate-buffered saline (PBS) at a pH of 7.2 to 7.4 and 37° C. after five days of incubation, specifically the axitinib polymorph IV, used for preparing the implants according to certain embodiments of the present invention may be characterized by a powder X-ray diffraction pattern comprising peaks at diffraction angles (2θ) of 8.9, 14.6, 15.7, and 19.2 (all±0.1), or by a powder X-ray diffraction pattern comprising peaks at diffraction angles (2θ) of 8.9 and 15.7 (all±0.1).

In one embodiment, an implant according to the present invention comprises axitinib, and at least 90%, or at least 95% by weight of the entire axitinib contained in the implant is polymorph IV.

Polymorph IV has been demonstrated to be chemically and physically stable in an implant according to the invention throughout 6 months (see Example 11).

Photostability studies with implants containing axitinib polymorph IV have demonstrated that the XRD patterns post-sterilization and after light exposure (visible light of wavelength of 380-700 nm, and UV-A light of wavelength 315 to 400 nm) did not change with respect to the respective XRD patterns at the start of these studies, before light exposure. These results were the same as those obtained with implants containing axitinib polymorph SAB-I.

Further photostability studies comparing axitinib polymorph IV powder, implants according to the present invention containing axitinib polymorph IV, such implants loaded in needles for injection, and such implant-loaded needles sealed in secondary foil packaging have been conducted using visible light and UV light as described above, and have been compared to no light exposure (control). The major impurity that can result from axitinib polymorph IV being exposed to light is dimerization of axitinib polymorph IV API (while with the axitinib polymorph SAB-I API the two major impurities—although to a lesser extent than with the polymorph IV API—are the dimer and the cis-isomer). In Example 15, the axitinib polymorph IV API powder showed light-induced degradation resulting in impurities (dimer) of above 30% (for both visible and UV light). When axitinib polymorph IV was dispersed in a PEG hydrogel within an implant according to the present invention, less dimerization was observed upon light exposure (both visible and UV light) than for the axitinib polymorph IV API powder itself, namely only about 25% (visible light) and about 14% (UV light). Without wishing to be bound by theory, these data suggest that the hydrogel, such as the PEG hydrogel, exerts a protective effect on the axitinib polymorph form IV when in an implant.

The present invention therefore also provides a method of increasing the photostability of an active agent, such as a TKI, such as axitinib, such as axitinib polymorph IV, by incorporating it into a PEG hydrogel to form an implant according to the present invention. The present invention further provides axitinib polymorph IV in a form that is more photostable than axitinib polymorph IV in powder form, such as at least 10%, such as at least 15%, such as at least 20% more stable in visible light than axitinib polymorph IV in powder form after the same exposure time and at the same exposure conditions, and/or such as at least 10%, such as at least 20%, such as at least 30%, such as at least 40% more stable in UV light than axitinib polymorph IV in powder form after the same exposure time and at the same exposure conditions. The term "at least 10%" higher photostability means that at least 10% less total impurities (i.e., mainly dimer) are detected for the axitinib polymorph IV in an implant according to the present invention (such as dispersed in PEG hydrogel), as compared to the amount of impurities (again, mainly dimer) detected for the axitinib polymorph IV API as a powder. The same meaning applies to the other percentages indicated herein. In certain embodiments, exposure to visible light as referred to herein means exposure to light at wavelength 380 to 700 nm, such as for at least 1 day, or for at least 2 days, such as for at least 0.5 million lux hours/$m^2$, such as for at least 1 million lux hours/$m^2$, such as for at least 1.2 million lux hours/$m^2$. In certain embodiments, exposure to UV light means exposure to UV A light at wavelength 315 to 400 nm, such as for at least 4 hours, such as for at least 8 hours, such as for at least 10 hours, such as for at least 100 watt hours/$m^2$, or at least 150 hours/$m^2$, or at least 200 hours/$m^2$.

It has been demonstrated that axitinib polymorph IV withstands significant photo-degradation (mainly dimerization) under conditions required to manufacture implants containing axitinib polymorph IV according to the present invention. In particular, once axitinib polymorph IV is included in the hydrogel, such as the PEG hydrogel, dimerization is significantly reduced. Furthermore, once an implant is loaded into a needle for injection, and/or sealed in a foil pouch, this further significantly shields the implant and thus the API to protect the API during storage and shipping.

Without wishing to be limited by this theory, the increased solubility of the axitinib polymorph IV as disclosed herein may result in a faster release of axitinib from the implants according to the invention, as compared to comparative implants wherein the axitinib that is present in the implant (such as axitinib polymorph SAB-I) has a lower solubility.

In certain specific embodiments, an implant of the invention contains axitinib polymorph IV in an amount of from 300 to 600 μg, such as from about 360 μg to about 562.5 μg, or from about 405 μg to about 495 μg, or about 450 μg. In certain other specific embodiments, an implant of the invention contains axitinib polymorph IV in an amount of from about 480 μg to about 750 μg, or from about 540 μg to about 660 μg, or about 600 μg.

In other embodiments, further axitinib polymorphic forms that also have a solubility of above 0.3 μg/mL measured at 37° C. in PBS with a pH of 7.2 to 7.4 after 5 days of incubation may be used in this aspect of the invention.

In terms of the manufacturing of an implant according to the invention (any aspect thereof), the manufacturing process and conditions, as well as the composition/amount of the ingredients of the implant, are generally independent of which axitinib polymorphic form is used. Therefore, generally, all amounts and compositions, as well as all manufacturing steps and conditions disclosed herein with respect to a TKI, or axitinib specifically, equally apply to any of the axitinib polymorphs disclosed herein, specifically axitinib polymorph IV and axitinib polymorphs SAB-I or XLI.

Axitinib Co-Crystals for Use in the Present Invention:

In certain embodiments of the present invention, an implant contains axitinib in the form of an axitinib co-crystal. Specifically, in the aspect of the present invention in which the TKI (such as axitinib) has a solubility of greater than 0.3 μg/ml as measured in phosphate-buffered saline (PBS) at a pH of 7.2 to 7.4 and 37° C. after five days of incubation, one or more axitinib co-crystals may be used (including those further disclosed herein) in the implants according to the present invention, as long as they fulfill this solubility criterion. Alternatively, if axitinib co-crystals do not meet this solubility criterion, they may still be used in all other aspects of the present invention in which this solubility criterion does not have to be fulfilled.

Axitinib co-crystals with carboxylic acids as co-formers are particularly suitable to be used in the present invention, as the carboxylic acid generally increases the hydrophilicity and thereby the solubility of the axitinib is increased. Any carboxylic acids are generally suitable for forming co-crystals with axitinib in the context of the present invention. Particular carboxylic acids that may be used for forming axitinib co-crystals are $C_1$ to $C_{12}$ carboxylic acids, such as $C_2$ to $C_{10}$ carboxylic acids, and specifically $C_2$, $C_3$, $C_4$, $C_5$, $C_6$, $C_7$, $C_8$, $C_9$ or $C_{10}$ carboxylic acids. The carboxylic acids may be saturated or unsaturated. They may contain one or more aryl groups, including heteroaryl groups. The carboxylic acids may either be free of, or may contain one or more additional functional groups, in particular functional groups that either further increase the hydrophilicity, or at least do not significantly decrease 30 the hydrophilicity. Suitable such groups are for example hydroxyl groups. If the carboxylic acid that forms a co-crystal with axitinib can have one or more enantiomeric forms or one or more other configurations (such as cis/trans), it can be present in the co-crystal in any enantiomeric form and/or in any configuration. Co-crystals of axitinib are disclosed for example in B-Y Ren et al., Cryst Eng Comm. 2021, 23, 5504-5515.

Specific examples of carboxylic acids suitable for forming a co-crystal with axitinib is one or more of citric acid, fumaric acid, (+)-L- or (−)-D tartaric acid, glutaric acid, (trans- or cis) cinnamic acid, suberic acid, succinic acid, adipic acid, pimelic acid, salicylic acid. This list is not intended to be limiting, and further carboxylic acids or other compounds as mentioned above may be used in the present invention to form axitinib co-crystals. In the co-crystal lattice also more than one molecule of co-former, such as a carboxylic acid, may be present per one molecule of axitinib. In such a case, the more than one molecule of co-former may be the same co-former, such as the same carboxylic acid, or may be different co-formers, such as different carboxylic acids.

Axitinib co-crystals can be prepared for example by crystallizing the co-crystals from a solution or slurry, for example by combining a certain amount of axitinib and the chosen co-former in a 1:1 molar ratio, adding a solvent (such as acetonitrile), and stirring the resulting slurry for a certain number of days (such as 3 days) and optionally at elevated temperature (such as at least 30° C., or at least 40° C.). After that, the solids can be isolated e.g. by filtration or centrifugation and analyzed. Alternatively, the co-crystals can also be prepared by seeding (once a desired co-crystal is already available for a seeding procedure) co-crystals in a low amount of solvent, and allowing the seeded mixture to stir for a number of days (such as at least 1 day) and optionally at elevated temperature (again, such as at least 30° C., or at least 40° C.). After that, the solids can be isolated as described above. Examples of the preparation of certain axitinib co-crystals are provided in Example 4, and solubility data is provided in Example 6.

In certain embodiments, an axitinib co-crystal may have a solubility that is at least 2 times, at least 5 times, at least 10 times, at least 25 times, at least 50 times, at least 75 times, or at least 100 times the solubility of axitinib free base.

In particular embodiments, an axitinib co-crystal has a solubility in PBS at pH 7.4 after 24 hours at 37° C. of at least 10 μg/mL, such as at least 12 μg/mL, at least 15 μg/mL, or at least 18 µg/mL. An axitinib co-crystal with citric acid has a mean solubility in PBS at pH 7.4 after 24 hours at 37° C. of about 19 µg/mL; an axitinib co-crystal with fumaric acid has a mean solubility in PBS at pH 7.4 after 24 hours at 37° C. of about 12 µg/mL; and an axitinib co-crystal with (+)-L-tartaric acid has a mean solubility in PBS at pH 7.4 after 24 hours at 37° C. of between about 19 and 20 µg/mL.

Without wishing to be limited by this theory, the increased solubility of the axitinib co-crystals as disclosed herein may result in a faster release of axitinib from the implants according to the invention, as compared to comparative implants wherein the axitinib that is present in the implant (such as axitinib free base) has a lower solubility, Axitinib Derivatives and Prodrugs for Use in the Present Invention:

In all aspects of the present invention, derivatives or prodrugs of the TKI, such as axitinib, may be used in the implants. However, in the aspect of the present invention in which the solubility of the TKI is greater than 0.3 µg/mL as measured in phosphate-buffered saline (PBS) at a pH of 7.2 to 7.4 and 37° C. after five days of incubation, prodrugs are particularly suitable if they increase the solubility of the parent TKI compound. In embodiments of the invention where the TKI is axitinib, axitinib prodrugs with increased solubility as compared to the axitinib free base are particularly suitable. The axitinib prodrugs are converted in vivo to axitinib.

Prodrugs of axitinib with increased solubility may be derivatives of axitinib, in which one or more atoms or moieties of the axitinib are replaced by one or more substituent groups which render the resulting derivative (i.e., the prodrug) more soluble, such as by the introduction of hydrophilic groups in these substituent groups. Upon immersion of physiological environment, which can be simulated by in vitro tests, these substituent group(s) may be enzymatically or chemically removed, thus releasing the parent drug molecule. In the present invention, examples for particularly suitable axitinib prodrugs are those wherein the axitinib molecule is functionalized at one or more of the nitrogen atoms of the axitinib free base. For example, in an axitinib prodrug for use according to the present invention one or more of the nitrogen atoms in the axitinib free base may be independently substituted with one or more of the following groups: acyl, alkylcarbonyl, arylcarbonyl, alkylthiocarbonyl, arylthiocarbonyl, alkylcarbamoyl, arylcarbamoyl, substituted or unsubstituted acetyl, substituted or unsubstituted aminoalkanoyl, substituted or unsubstituted α-aminoalkanoyl, an acyl group derived from a natural or an unnatural amino acid with or without substitution, an acyl group of a peptide residue, phosphonyl, phosphinyl, aminophosphinyl, alkylaminophosphinyl, sulfonyl, cycloalkanecarbonyl, heterocycloalkane-carbonyl, alkoxycarbonyl, aryloxycarbonyl, heteroalkoxycarbonyl heteroaryloxycarbonyl, and an O-substituted hydroxymethyl group with or without substituents.

In certain embodiments, an axitinib prodrug for use in the present invention is a compound of general formula (I) depicted below, or a salt or solvate thereof:

(I)

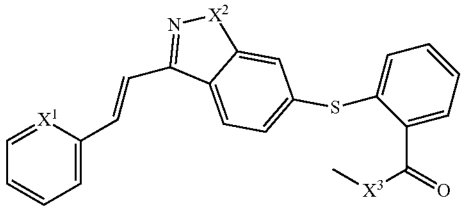

wherein:

$X^1$ is selected from N or $N^+Y^1$;

$X^2$ is selected from NH or $NY^2$;

$X^3$ is selected from NH or $NY^3$:

$Y^1$ is selected from $-CH_2OCO(OCH_2CH_2)n^1OM^1$; or $-CH_2OCO(CH_2CH_2O)n^{1a}Z^1$; or $-CH_2OCO(CH_2)n^{1b}COOH$;

$Y^2$ is selected from $-CH_2OCO(OCH_2CH_2)n^2OM^2$; or $-CH_2OCO(CH_2CH_2O)n^{2a}Z^2$; or $-CH_2OCO(CH_2)n^{2b}COOH$;

$Y^3$ is selected from $-CH_2OCO(OCH_2CH_2)n^3OM^3$; or $-CH_2OCO(CH_2CH_2O)n^{3a}Z^3$; or $-CH_2OCO(CH_2)n^{3b}COOH$;

$n^1$, $n^{1a}$, $n^{1b}$, $n^2$, $n^{2a}$, $n^{2b}$, $n^3$, $n^{3a}$ and $n^{3b}$ are independently 0 or an integer from 1 to 8;

$M^1$, $M^2$, $M^3$, $Z^1$, $Z^2$ and $Z^3$ are independently selected from H, optionally substituted $C_{1-6}$ alkyl and optionally substituted aryl;

wherein at least one of $X^1$, $X^2$ and $X^3$ is not N or NH;

wherein at least one of $Y^1$, $Y^2$ or $Y^3$ is/are the respective $-CH_2OCO(CH_2CH_2O)nZ$.

In certain other embodiments, in the above general formula (I) $Y^1$, $Y^2$ and $Y^3$ are independently selected from the respective $-(CH_2)p^1OCO(O(CH_2)p^2)n^1OM$; or $-(CH_2)p^{1a}OCO((CH_2)p^2O)n^1(CH_2)Z$; or $-(CH_2)p^1OCO(CH_2)q^1COOH$; wherein $p^1$, $p^{1a}$ and $p^2$ are independently selected from an integer from 1 to 4, and $q^1$ is independently selected from an integer from 0 to 4, with the other meanings as defined above for formula (I).

In certain embodiments, the following prodrugs are suitable in the present invention, wherein in the above formula (I):

$X^1$ is $N^+Y^1$; $X^2$ is NH; $X^3$ is NH; and $Y^1$ is $-CH_2OCO(CH_2CH_2O)n^{1a}Z^1$ or $-CH_2OCO(CH_2)n^{1b}COOH$, or:

$X^1$ is N; $X^2$ is $NY^2$; $X^3$ is NH; and $Y^2$ is $-CH_2OCO(CH_2CH_2O)n^{2a}Z^2$ or $-CH_2OCO(CH_2)n^{2b}COOH$, or:

$X^1$ is N; $X^2$ is NH; $X^3$ is $NY^3$; and $Y^3$ is $-CH_2OCO(CH_2CH_2O)n^{3a}Z^3$ or $-CH_2OCO(CH_2)n^{3b}COOH$.

In certain embodiments, in the above formula (I):

$n^1$ 0, 1, 2, 3, 4, 5, 6, 7 or 8; or 1-3 or 4-6 or 7-8;

$n^2$ is 0, 1, 2, 3, 4, 5, 6, 7 or 8; or 1-3 or 4-6 or 7-8;

$n^3$ is 0, 1, 2, 3, 4, 5, 6, 7 or 8; or 1-3 or 4-6 or 7-8;

$n^{1a}$ is 0, 1, 2, 3, 4, 5, 6, 7 or 8; or 1-3 or 4-6 or 7-8;

$n^{2a}$ is 0, 1, 2, 3, 4, 5, 6, 7 or 8; or 1-3 or 4-6 or 7-8;

$n^{3a}$ is 0, 1, 2, 3, 4, 5, 6, 7 or 8; or 1-3 or 4-6 or 7-8;

$n^{1b}$ is 0, 1, 2, 3, 4, 5, 6, 7 or 8; or 1-3 or 4-6 or 7-8;

$n^{2b}$ is 0, 1, 2, 3, 4, 5, 6, 7 or 8; or 1-3 or 4-6 or 7-8;

$n^{3b}$ is 0, 1, 2, 3, 4, 5, 6, 7 or 8; or 1-3 or 4-6 or 7-8.

In certain embodiments, in the above formula (I):

$M^1$ is methyl, ethyl, propyl or phenyl;

$M^2$ is methyl, ethyl, propyl or phenyl;

$M^3$ is methyl, ethyl, propyl or phenyl;

$Z^1$ is methyl, ethyl, propyl or phenyl;

$Z^2$ is methyl, ethyl, propyl or phenyl;

$Z^3$ is methyl, ethyl, propyl or phenyl.

In certain further embodiments, $n^1$, $n^2$ or $n^3$ is 2, 3 or 4, and/or $n^{1a}$, $n^{2a}$ or $n^{3a}$ is 2, 3 or 4 and/or $n^{1b}$, $n^{2b}$ or $n^{3b}$ is 2, 3 or 4.

In certain specific embodiments, an axitinib prodrug to be used in the implants according to the present invention is selected from: axitinib-N-succinoyloxymethyl prodrug, axitinib-N-mPEG-oxymethyl prodrug, including but not limited to axitinib-N-m$(PEG)_1$-oxymethyl, axitinib-N-m$(PEG)_2$ -oxymethyl, axitinib-N-m$(PEG)_3$-oxymethyl, axitinib-N-m$(PEG)_4$-oxymethyl, or a salt or solvate thereof, as shown below.

Axitinib prodrugs, especially prodrugs with a hydrophilic substituent as disclosed herein, may exhibit a higher solubility than axitinib free base. Such prodrugs may have a solubility that is at least 2 times, at least 5 times, at least 10 times, at least 25 times, at least 50 times, at least 75 times, at least 100 times, at least 150 times, at least 200 times, at least 250 times, or at least 500 times, or at least 1000 times the solubility of axitinib free base. Without wishing to be limited by this theory, the increased solubility of the axitinib prodrugs as disclosed herein may result in a faster release of axitinib from the implants according to the invention, as compared to comparative implants wherein the axitinib that is present in the implant (such as axitinib free base) has a lower solubility than the axitinib prodrugs.

Axitinib prodrugs for use in implants of the present invention may have a solubility in PBS at pH 7.4 after 24 hours at 22° C. of at least 50 μg/mL, or at least 90 μg/mL, or at least 150 μg/mL, or at least 200 μg/mL.

The following are exemplary axitinib prodrugs to be used in implants of the present invention:

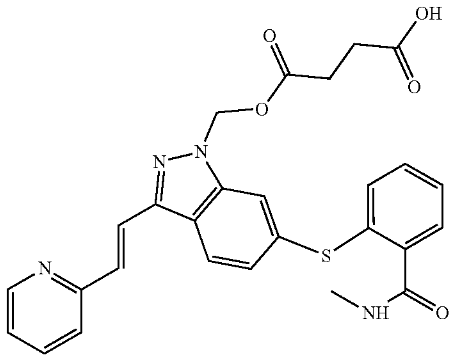 [SMILES: CNC(=O)c1ccccc1Sc1ccc2c(/C=C/c3ccccn3)nn(COC(=O)CCC(=O)O)c2c1]

axitinib-N-succinoyloxymethyl prodrug (total Mw: 516.57)

solubility in PBS at pH 7.2 to 7.4 after 24 hours incubation at 22° C.: 217.4 μg/mL

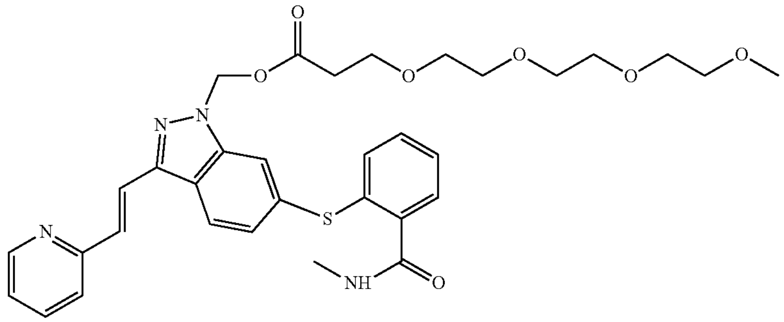 [SMILES: CNC(=O)c1ccccc1Sc1ccc2c(/C=C/c3ccccn3)nn(COC(=O)CCOCCOCCOCCOC)c2c1]

axitinib-N-m(PEG)$_4$-oxymethyl prodrug (total Mw: 634.74)

solubility in PBS at pH 7.2 to 7.4 after 24 hours incubation at 22° C.: 99.37 μg/mL

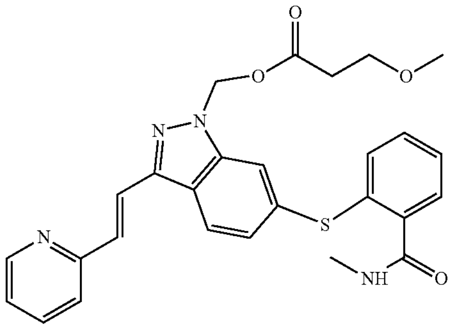 [SMILES: CNC(=O)c1ccccc1Sc1ccc2c(/C=C/c3ccccn3)nn(COC(=O)CCOC)c2c1]

Axitinib-N-m(PEG)$_1$-oxymethyl prodrug. IUPAC Name: 3-Methoxy-propionic acid 6-(2-methylcarbamoyl-phenylsulfanyl)-3-((E)-2-pyridin-2-yl-vinyl)-indazol-1-ylmethyl ester (total Mw: 502.28)

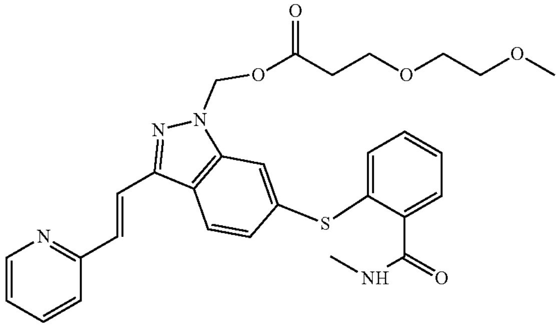 [SMILES: CNC(=O)c1ccccc1Sc1ccc2c(/C=C/c3ccccn3)nn(COC(=O)CCOCCOC)c2c1]

Axitinib-N-m(PEG)$_2$-oxymethyl prodrug, IUPAC Name: 3-(2-Methoxy-ethoxy)-propionic acid 6-(2-methylcarbamoyl-phenylsulfanyl)-3-((E)-2-pyridin-2-yl-vinyl)-indazol-1-ylmethylester (total Mw: 546.63)

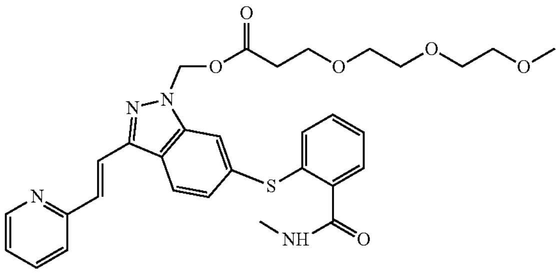 [SMILES: CNC(=O)c1ccccc1Sc1ccc2c(/C=C/c3ccccn3)nn(COC(=O)CCOCCOCCOC)c2c1]

Axitinib-N-m(PEG)$_3$-oxymethyl prodrug. IUPAC Name: 3-[2-(2-Methoxy-ethoxy)-ethoxy]-propionic acid 6-(2-methylcarbamoyl-phenylsulfanyl)-3-((E)-2-pyridin-2-yl-vinyl)-indazol-1-ylmethyl ester (total Mw: 590.68)

Exemplary syntheses and solubilities of axitinib prodrugs are disclosed in Examples 5.1 and 5.2. The solubilities of axitinib prodrugs are presented in Example 6.

Suitable axitinib prodrugs for use in the implants according to the present invention as well as their synthesis and properties are disclosed in co-pending international application PCT/US2023/035121 and in co-pending international application PCT/US2022/046750 (published as WO 2023/064578 A1), which are incorporated by reference. Further suitable axitinib prodrugs for use in the implants according to the present invention are disclosed in US 2021/0078970. All of the axitinib prodrugs disclosed in any of these references, but not limited to these, are generally suitable for use in the present invention.

Solubility

The solubility of the TKI, and in particular the solubility of axitinib in certain embodiments of the present invention, is one of the factors that influences the release profile of axitinib from an implant according to the present invention. The solubility of axitinib free base, in particular the polymorph SAB-I, is relatively low in physiologic environment, or similar aqueous solvent systems such as PBS, which limits the release rate of the drug from implants containing hydrogel where the release is solubility and diffusion-driven.

In particular embodiments the present invention therefore relates to sustained release biodegradable ocular implants comprising a TKI, wherein the solubility of the TKI, such as axitinib, including any forms of axitinib as disclosed herein, is 0.3 μg/mL or greater than 0.3 μg/mL, such as at least 0.4 μg/mL, or at least 0.5 μg/mL, or at least 0.6 μg/mL, at least 0.7 μg/mL, at least 0.8 μg/mL, at least 1 μg/mL, at least 2.5 μg/mL, at least 5 μg/mL, at least 10 μg/mL, at least 20 μg/mL, at least 50 μg/mL, at least 100 μg/mL, at least 150 μg/mL, or at least 200 μg/mL in phosphate-buffered saline (PBS) at a pH of 7.2 to 7.4 and 37° C. after five days of incubation. A pH value of 7.2 to 7.4 as mentioned herein includes the individual values of 7.2, 7.3 and 7.4. In particular embodiments of the present invention, wherein the TKI is axitinib, the solubility of the axitinib used in the sustained release biodegradable ocular implants of the invention is higher than the solubility of axitinib polymorph SAB-I, such as at least 1.5 times the solubility of axitinib polymorph SAB-I, such as at least about 2 times the solubility of axitinib polymorph SAB-I, such as at least 2.3 times the solubility of axitinib polymorph SAB-I.

In particular embodiments, the solubility of the TKI such as axitinib in any and all embodiments of the invention which refer to it is 0.3 μg/mL or greater (such as at least 0.4 μg/mL, or at least 0.5 μg/mL, or at least 0.6 μg/mL, at least 0.7 μg/mL, at least 0.8 μg/mL, at least 1 μg/mL, at least 2.5 μg/mL, at least 5 μg/mL, at least 10 μg/mL, at least 20 μg/mL, at least 50 μg/mL, at least 100 μg/mL, at least 150 μg/mL, or at least 200 μg/mL) in PBS at a pH of 7.2 and 37° C. after five days of incubation. Axitinib forms (including axitinib polymorphs, co-crystals and prodrugs as disclosed herein) meeting any of these solubility ranges thus have a higher solubility than axitinib (free base) polymorph SAB-I, which has a solubility under these same conditions of around 0.2 μg/ml and below 0.3 μg/mL, as shown in Example 6, which also contains details on the conditions of measurement of the solubility, as well as FIG. 17, Specifically, axitinib polymorph SAB-I has an equilibrium solubility in PBS after five days at a pH of 7.4 and 37° C. of from about 0.191 to about 0.252 μg/ml (measured by UPLC), or of an average of about 0.223 μg/mL under these conditions, depending on its particle size, i.e., whether or not it is in micronized form (or the degree of micronization). For example, non-micronized, micronized, and super-micronized axitinib polymorph SAB-I has an equilibrium solubility of about 0.191, about 0.226, and about 0.252 μg/mL (measured by UPLC), respectively, in PBS after five days at a pH of 7.4 and 37° C., see Example 6. Polymorph IV is a particularly suitable axitinib polymorph for use in the present invention in all its aspects. Its solubility is about two times the solubility of e.g. polymorph SAB-I, as disclosed herein (again, see Example 6 and FIG. 17), Specifically, axitinib polymorph IV has an equilibrium solubility in PBS after 5 days at a pH of 7.4 and 37° C. of about 0.435 μg/mL (measured by UPLC), e.g. when in micronized form (as defined herein), see Example 6. Thus, in certain embodiments, the implants of the present invention comprise axitinib polymorph IV. In certain embodiments, at least 90%, such as at least 95% by weight of the axitinib contained in an implant of the invention is axitinib polymorph IV.

Without wishing to be limited by this theory, any increased solubility of axitinib (e.g. in form of a particular prodrug, co-crystal or polymorph) as disclosed herein may result in a faster release of axitinib from the implants according to the invention, as compared to comparative implants wherein the axitinib that is present in the implant (such as axitinib free base, for example polymorph SAB-I) has a lower solubility. This increase solubility may manifest itself in in vitro release tests as disclosed herein in a higher release rate (released amount of axitinib per day) on one or more days of the in vitro test, and/or a higher average release rate per day (as defined herein) over a certain number of days, and/or an increased cumulative amount of axitinib released over a certain period of time (such as one or more days), and/or an increased share/ratio (in %) of the total amount of axitinib contained in the implant released per day or over a certain period of time (any number of days), and/or an increased share/ratio (in %) of the total released amount of axitinib in a certain in vitro test.

Thus, providing an implant containing a TKI with an increased solubility constitutes a method of increasing the release rate per day and/or the average release rate per day over a certain period of time, and/or the percentage of released TKI on one or more individual days, and/or the cumulative percentage of released TKI (based on the total released TKI) over a certain period of time, and/or the absolute amount of TKI released on one or more individual days or over a certain period of time (in vivo or in vitro). Thus, the present invention also relates to such a method of increasing the release rate and/or the average release rate and/or the released amount of total TKI contained in the implant and/or the released share of the total TKI contained in the implant or the total TKI released from an implant in a certain period of time, as compared to known implants containing TKI.

Amount/Dose

The TKI is present in the implants of the invention in a range of doses. The amount of TKI contained in an implant is indicated herein in the units "μg" or "mg". In case the TKI used according to the present invention is axitinib, the amounts/doses of axitinib indicated herein refer to the amounts (in μg or mg, as the case may be) of axitinib free base, including any (anhydrous) axitinib polymorphs such as those that are further disclosed herein, particularly polymorph IV. In case axitinib salts, co-crystals, derivatives or prodrugs are used (which have a different molecular weight than axitinib free base), the amount indicated is the corresponding amount of axitinib free base, unless otherwise stated.

The TKI, such as axitinib, is contained in the implant of the invention generally in a range of doses of at least 150 μg, such as from about 150 μg to about 1000 μg, from about 150 μg to about 900 μg, or from about 200 μg to about 800 μg, or from about 250 μg to about 700 μg, or from about 300 to about 650 μg. Any TKI, such as axitinib, amount within these ranges may be contained in an implant of the invention. In case axitinib is used in a form other than the free base, an implant of the invention may contain a dose that corresponds to the mentioned doses of axitinib free base. For the purpose of the present disclosure, when talking about TKI, such as axitinib, doses contained in an implant, all mentioned values are meant to include a variance of +25% and −20%, or a variance of +/−10%.

In certain particular embodiments, doses of axitinib (which doses are meant to refer to axitinib free base, or the respective amount of another form of axitinib, such as an axitinib co-crystal or prodrug corresponding to these recited amounts of axitinib free base) contained in an implant of the invention are:

- a range from about 120 μg to about 187.5 μg, or from about 135 μg to about 165 μg, or about 150 μg (i.e., including a variance of +25% and −20%, or a variance of +/−10% of 150 μg)
- a range from about 240 μg to about 375 μg, or from about 270 μg to about 330 μg, or about 300 μg (i.e., including a variance of +25% and −20%, or a variance of +/−10% of 300 μg)
- a range from about 360 μg to about 562.5 μg, or from about 400 μg to about 500 μg, or from about 405 μg to about 495 μg, or about 450 μg (i.e., including a variance of +25% and −20%, or a variance of +/−10% of 450 μg)
- a range from about 480 μg to about 750 μg, or from about 540 μg to about 660 μg, or about 600 μg (i.e., including a variance of +25% and −20%, or a variance of +/−10% of 600 μg)

In one particular embodiment, a dose of axitinib contained in one implant of the invention is from 100 to 200 μg, or about 150 μg. In further particular embodiments, the axitinib in such implants is in the form of axitinib free base.

In one particular embodiment, a dose of axitinib contained in one implant of the invention is from 200 to 400 μg, such as from 250 to 350 μg, or about 300 μg. In further particular embodiments, the axitinib in such implants is in the form of axitinib free base.

In one particular embodiment, a dose of axitinib contained in one implant of the Invention is from 300 to 600 μg, such as from about 360 μg to about 562.5 μg, or from 400 to 500 μg, or is about 450 μg. In further particular embodiments, the axitinib in such implants is in the form of axitinib free base.

In another particular embodiment, a dose of axitinib contained in one implant of the invention is from about 400 to 800 μg, from about 480 μg to about 750 μg, or from 500 to 700 μg, or is about 600 μg. In further particular embodiments, the axitinib in such implants is in the form of axitinib free base.

In another particular embodiment, a dose of axitinib contained in one implant of the invention is from about 400 to 1000 μg, from about 480 μg to about 800 μg, from about 480 μg to about 750 μg, or from 500 to 700 μg, or is about 600 μg. In further particular embodiments, the axitinib in such implants is in the form of axitinib free base. In particular embodiments, a target dose of axitinib, such as axitinib polymorph IV, in an implant of the present invention is 600 μg, which means an actual amount of −20% and +25% thereof, i.e., from about 480 μg to about 720 μg.

In one particular embodiment, a dose of axitinib contained in one implant of the invention is from 200 to 1000 μg.

In particular embodiments, a dose of axitinib contained in one implant of the invention is from about 250 to about 750 μg, such as from about 300 to about 600 μg, such as from about 350 to about 550 μg, such as from about 380 to about 520 μg, such as from about 420 to about 480 μg, such as from about 400 to about 500 μg, such as from about 420 to about 480 μg, such as about 450 μg. In particular embodiments, a target (also referred to as "label") dose of axitinib, such as axitinib polymorph IV, in an implant of the present invention is 450 μg, which means an actual amount of −20% and +25% thereof, i.e., from about 360 μg to about 562.5 μg.

In most particular embodiments, an implant according to the present invention contains axitinib in the form of polymorph IV in a dose of from about 400 μg to about 500 μg, such as from about 405 μg to about 495 μg, such as from about 410 μg to about 490 μg, or from about 420 μg to about 490 μg, such as from about 420 μg to about 480 μg, such as from about 430 μg to about 480 μg, such as from about 425 μg to about 475 μg, such as from about 430 μg to about 470 μg, such as from about 440 μg to about 460 μg, such as about 450 μg. In an implant of the present invention having a nominal (i.e., theoretical/label) content of 450 μg or about 450 μg axitinib (specifically, axitinib polymorph IV), the actual (assay) amount of axitinib contained in the implant may vary within the limits of the ranges disclosed in the preceding sentence.

If axitinib is not in the form of the free base, but in the form of e.g. a co-crystal or prodrug, one implant may contain an amount of such other axitinib form that corresponds to the mentioned doses of axitinib free base.

The disclosed amounts of TKI, such as axitinib, including the mentioned variances, refer to both the final content of the active principle in the implant, as well as to the amount of active principle used as a starting component per implant when manufacturing the implant. The total dose of the TKI, such as axitinib, to be administered to a patient, may in certain embodiments be contained in two or more implants administered concurrently as further disclosed herein. The dose may also be contained in an implant according to the invention that is a multi-filament implant, i.e., is made of several filaments combined and optionally stretched and twisted to form one composite strand as further disclosed herein.

TKI Particles

The TKI, such as axitinib, is contained in the implant of the invention and is dispersed or distributed in the hydrogel that is comprised of a polymer network as further disclosed herein. In certain embodiments, the particles are homogeneously or essentially homogeneously dispersed in the hydrogel. The hydrogel may prevent the particles from agglomerating and may provide a matrix for the particles which holds them in the desired location in the eye while gradually releasing drug.

In certain embodiments of the invention, the TKI particles such as the axitinib particles may be microencapsulated. The term "microcapsule" (also referred to as "microparticle") is sometimes defined as a roughly spherical particle with a size varying between e.g. about 50 nm to about 2 mm. Microcapsules have at least one discrete domain (or core) of active agent encapsulated in a surrounding material, sometimes also referred to as a shell. One suitable agent (without limiting the present disclosure to this) for microencapsulating the TKI, such as the axitinib, if that is desired for the purposes of the present invention, is poly (lactic-co-glycolic acid).

In other embodiments, the TKI particles comprise additional compounds beside the TKI. These may be for example be processing aids, stabilizers, fillers, etc. Sometimes active agents are routinely stabilized by the supplier by adding minute amounts of e.g. an antioxidant or other stabilizer, which may also be the case for the TKI such as axitinib particles as used herein.

However, in certain embodiments, the TKI particles such as the axitinib particles are not microencapsulated and/or do not comprise any additional compounds, but are dispersed in the hydrogel and thus in the implant of the invention as they are, i.e., as received from a supplier, i.e., without being further admixed to or adjoined with or microencapsulated by another material.

In one embodiment, the TKI particles, such as the axitinib particles, may be micronized or even nanonized particles. Micronization refers to the process of reducing the average diameter of particles of a solid material. In another embodiment, the TKI particles, such as the axitinib particles, may not be micronized. In the composite materials field, particle size is known to affect the mechanical properties when combined with a matrix, with smaller particles providing superior reinforcement for a given mass fraction. Thus, a hydrogel matrix filled with micronized TKI particles may have improved mechanical properties (e.g. brittleness, strain to failure, etc.) compared to a similar mass fraction of larger TKI particles. Such properties are important in manufacturing, during implantation, and during degradation of the implant. Micronization may also promote a more homogeneous distribution of the active ingredient in the chosen dosage form or matrix. The particle size distribution can be generally measured by methods known in the art, including sieving, laser diffraction or dynamic light scattering.

Without wishing to be bound by theory, the particle size of the TKI particles may influence the release kinetics of the TKI from an implant according to the invention. Particles with reduced diameters may in certain instances have inter alia higher dissolution and erosion rates, which may in certain instances increase the rate of release from implants and thus increase the bioavailability of the TKI in the desired tissue. Furthermore, smaller particles such as micronized particles, may have a reduced tendency to agglomerate during manufacturing and processing operations, which could in certain instances result in a more homogenous distribution of the TKI particles within the hydrogel. Additionally, again without wishing to be bound by theory, when TKI particles are still residing in the eye, e.g. in case the hydrogel has already completely dissolved before the complete TKI drugload has been released from the implant, smaller particles could in certain instances have a lower tendency to agglomerate, and could also be cleared faster from the vitreous. This could be advantageous for repeat dosing, such as to avoid accumulation of uncleared TKI particles in the vitreous over time.

In certain embodiments, the TKI, such as the axitinib, particles have a d90 particle size of less than 10 μm, or less than 8 μm, or less than 7 μm, or 7.5 μm or less, or 6.5 μm or less, or 5 μm or less, or less than 1 μm, or less than 0.5 μm, or less than 0.4 μm as determined by laser diffraction.

In certain embodiments, the TKI, such as the axitinib, particles have a d50 particle size of less than 5 μm, less than 3 μm, less than 2.6 μm, less than 2 μm, less than 1.5 μm, less than 1 μm, less than 0.5 μm, less than 0.25 μm, or less than 0.2 μm, as determined by laser diffraction. In specific embodiments, the d50 particle size of the TKI particles, such as the axitinib particles, contained in an implant of the invention is 0.15 μm or less, as determined by laser diffraction. In the latter case, the particles may be referred to herein as "nanonized particles".

In certain embodiments, the TKI, such as the axitinib, particles have a d10 particle size of less than 1 μm, or less than 0.5 μm, or 0.25 μm or less, or 0.2 μm or less, or less than 0.1 μm as determined by laser diffraction.

In specific embodiments, the TKI present in the implants of the invention is axitinib free base (any polymorphic form as disclosed herein), wherein the axitinib particles have a d10 particle size of less than 8 μm, a d50 particle size of less than 20 μm, and/or a d90 particle size of less than 50 μm. These particles may sometimes be referred to herein as "non-micronized particles".

In other specific embodiments, the TKI present in the implants of the invention is axitinib free base (any polymorphic form as disclosed herein, including axitinib polymorph IV), wherein the axitinib particles have a d10 particle size of less than 0.25 μm, a d50 particle size of less than 3 μm or less than 2.6 μm, and a d90 particle size of less than 8 μm or less than 6.5 μm. These particles may also be referred to herein as "micronized particles". In particular embodiments, the particle size of axitinib, particularly axitinib polymorph IV, contained in implants of the present invention, is as follows: a d10 particle size of less than 0.25 μm, a d50 particle size of less than 2.6 μm, and a d90 particle size of less than 8 μm as determined by laser diffraction.

In other specific embodiments, the TKI present in the implants of the invention is axitinib free base (any polymorphic form as disclosed herein), wherein the axitinib particles have a d10 particle size of less than 0.2 μm, a d50 particle size of less than 1.5 μm, and a d90 particle size of less than 5 μm as determined by laser diffraction. These particles may also be referred to herein as "super micronized particles".

In other specific embodiments, the TKI present in the implants of the invention is axitinib free base (any polymorphic form as disclosed herein, particularly including polymorph IV), wherein the axitinib particles have a d10 particle size of less than 0.1 μm, a d50 particle size of less than 0.2 μm, and a d90 particle size of less than 0.4 μm as determined by laser diffraction. These particles may also be referred to herein as "nanonized particles".

Generally, micronized TKI such as axitinib particles may be purchased per specification from the supplier, or may be prepared e.g. according to an exemplary procedure for axitinib as disclosed in WO 2016/183296 A1, Example 13:1800 ml of sterile Water For Injection (WFI) is measured into a 2 L beaker and placed on a stir plate stirring at 600 RPM with a stir bar, creating a large WFI vortex in the center of the beaker. One 60 mL BD syringe containing axitinib in ethanol is placed on a syringe pump which is clamped above the WFI beaker. A hypodermic needle (21G, BD) is connected to the syringe and aimed directly into the center of the vortex for dispensation of the axitinib solution. The syringe pump is then run at 7.5 mL/min in order to add the axitinib solution dropwise to the WFI to precipitate micronized axitinib. After micronization, the axitinib is filtered, e.g. through a 0.2 μm vacuum filter and rinsed with WFI. After filtration, the axitinib powder is collected from the filter e.g. by using a spatula and vacuum dried for an extended period of time, such as for about 12 or about 24 hours, in order to remove excess solvent. Another exemplary method of micronizing axitinib is disclosed in Example 9 of WO 2017/091749. The described method of micronization is not limiting, and other methods of micronizing the active agent such as axitinib may equally be used. The disclosed micronization method (or other methods) may also be used for other TKI than axitinib.

The Polymer Network:

The sustained release biodegradable ocular implants of the present invention comprise a hydrogel, and TKI particles dispersed within the hydrogel. The hydrogel provides for a steady release of the active agent embedded in the hydrogel over time. In certain embodiments, this is achieved by one single material forming the hydrogel, such as by forming the hydrogel from PEG precursors according to the present invention as further disclosed herein. Without wishing to be bound by theory, this steady release is achieved inter alia because the release rate of the active agent from a hydrogel is controlled by dissolution (and not by erosion or degradation/channel forming as in other matrix materials, such as e.g. PLGA), and because release happens in all directions, Generally, hydrogels are inert as they do not interact or react with the physiological environment they are placed in, and have good biocompatibility as they essentially do not change, or at least do not significantly change, the local pH in physiological environment, such as in the eye. Furthermore, hydrogels have low rigidity and high softness, which provides high compliance with the physical environment such as body tissue when Inserted into a human or animal body. This is particularly advantageous in the context of the present application for injection/insertion of an implant according to the present invention comprising a hydrogel, such as a PEG hydrogel, within which TKI particles are dispersed, into the vitreous humor. Generally, due to the softness of the hydrogel of which the implant of the present invention is formed, the possibility of irritation (including foreign body sensation) or of causing harm to ocular tissue such as the retina, is greatly reduced.

One way of evaluating the stiffness or softness of an implant of the present invention is for example by measuring its elastic modulus.

In certain embodiments, the hydrogel may be formed from precursors having functional groups that form crosslinks to create a polymer network. These crosslinks between polymer strands or arms may be chemical (i.e., may be covalent bonds) and/or physical (such as ionic bonds, hydrophobic association, hydrogen bridges etc.) in nature.

The polymer network may be prepared from any precursors capable of forming a polymer network that is a hydrogel, either from one type of precursor or from two or more types of precursors that are allowed to react. Precursors are chosen in consideration of the properties that are desired for the resultant hydrogel. There are various suitable precursors for use in making the hydrogels. Generally, any pharmaceutically acceptable and crosslinkable polymers forming a hydrogel may be used for the purposes of the present invention. The polymers forming the hydrogel may be homopolymers or copolymers. The copolymers may be random or block copolymers. The hydrogel and thus the components incorporated into it, including the polymers used for making the polymer network, should be physiologically safe such that they do not elicit e.g. an immune response or other adverse effects, Hydrogels may be formed from natural, synthetic, or biosynthetic polymers.

Natural polymers may include glycosaminoglycans, polysaccharides (e.g. dextran), polyaminoacids and proteins or mixtures or combinations thereof.

Synthetic polymers may generally be any polymers that are synthetically produced from a variety of feedstocks by different types of polymerization, including free radical polymerization, anionic or cationic polymerization, chain-growth or addition polymerization, condensation polymerization, ring-opening polymerization etc. The polymerization may be initiated by certain initiators, by light and/or heat, and may be mediated by catalysts. Synthetic polymers may in certain embodiments be used to lower the potential of allergies in implants that do not contain any ingredients from human or animal origin.

Generally, for the purposes of the present invention one or more synthetic polymers of the following list (which is not intended to be limiting) may be used for forming a hydrogel in accordance with the present invention: one or more (Identical or different) units of polyalkylene glycol, such as polyethylene glycol (PEG), polypropylene glycol, poly(ethylene glycol)-block-poly(propylene glycol) copolymers, polyethylene imine, polyalkyl ethers, such as polyethylene oxide, polypropylene oxide, polyacrylic acid, acrylate polymers, poly(electrolyte complexes), starch-graft polymers, polymaleic acid, polyvinylamine polyacrylamide(s), poly (hydroxyethyl-methylacrylate) (PHEMA), polybutylene terephthalate (PBT), polyvinyl alcohol, poly(vinylacetate), poly(vinylpyrrolidinone), poly(vinylpyrrolidone) (PVP), polyglycolic acid, polylactic acid (PLA), polylactic-co-glycolic acid (PLGA), water-swellable N-vinyl lactams, ester-crosslinked polyglucan, polydioxanone, polytrimethylene carbonate. These may be used alone or in combination, as the case may be, for forming a hydrogel. Any polymer capable of forming a hydrogel and being biocompatible may be used for implants according to the present invention.

The polymers forming the hydrogel may be in the form of homopolymers, or of copolymers, such as random or block copolymers. Any combinations/mixtures of any of the mentioned monomers can be used for forming a hydrogel. As the above list is not intended to be limiting, other polymers/polymer combinations not specifically listed but capable of forming a hydrogel may equally be used.

In the present invention, PEG polymers are particularly suitable for forming hydrogels for the implants according to the present invention, as further disclosed below. Thus, in certain embodiments of the present invention, the hydrogel comprises a network formed by crosslinking PEG units (i.e., is a PEG hydrogel). Specific PEG units that may be crosslinked to form the hydrogel according to the present invention are disclosed herein. However, hydrogels formed of polymer networks other than PEG, are also suitable for implants of the present invention if such other hydrogels provide comparable or similar properties as the PEG hydrogels as disclosed herein.

To form covalently crosslinked polymer networks, the precursors may be covalently crosslinked with each other. In certain embodiments, precursors with at least two reactive centers (for example, in free radical polymerization) can serve as crosslinkers since each reactive group can participate in the formation of a different growing polymer chain.

The precursors may have biologically inert and hydrophilic portions, e.g., a core. In the case of a branched polymer, a core refers to a contiguous portion of a molecule joined to arms that extend from the core, where the arms carry a functional group, which is often at the terminus of the arm or branch. Multi-armed PEG precursors are examples of such precursors and are further disclosed herein below.

The precursors may have functional groups as further disclosed herein that can react with each other, i.e., a first functional group capable of reacting with a second functional group. The functional groups can react with each other, e.g., in electrophile-nucleophile reactions or are configured to participate in other polymerization reactions. Nucleophiles that can be used for the present invention may comprise an amine such as a primary amine, a hydroxyl, a thiol, a carboxyl, a dibenzocyclooctyne, or a hydrazide. Electrophiles that can be used for the present invention may comprise succinimidyl esters, succinimidyl carbonates, nitrophenyl carbonates, aldehydes, ketones, acrylates, acrylamides, maleimides, vinylsulfones, iodoacetamides, alkenes, alkynes, azides, norbornenes, epoxides, mesylates, tosylates, tresyls, cyanurates, orthopyridyl disulfides, or halides. Suitable electrophilic and nucleophilic group-containing precursors to form the polymer network are further disclosed herein.

Besides classical electrophile-nucleophile condensation reactions other chemical reaction types based on electrophiles and nucleophiles may also be used in the present invention. For example, precursors may be crosslinked via so-called click-chemistry reactions. Functional groups suitable for click chemistry are those functional groups that enable click chemistry reactions such as strain promoted alkyne-azide cycloaddition (SPAAC), also termed as the Cu-free click reaction, or inverse electron demand Diels-Alder ligation (IEDDA) type click chemistry coupling reactions. An overview of such types of reaction is given in H. C. Kolb; M. G. Finn; K. B. Sharpless (2001). "Click Chemistry: Diverse Chemical Function from a Few Good Reactions", Angewandte Chemie International Edition, 40 (11): 2004-2021), incorporated herein by reference. SPAAC and IEDDA coupling reactions are bioorthogonal reactions with selective and quantitative yields under mild conditions that can occur even inside of living systems without interfering with native biochemical processes. These click chemistry reactions utilize a pair of functional groups that exclusively and efficiently react with each other while remain inert to naturally occurring functional groups. Suitable functional groups comprise moieties selected from the group consisting of alkyne, cycloalkyne such as a dibenzocyclooctyne (DBCO), or a bicyclo[6.1.0]-nonyne (BCN), strained or terminal alkene such as norbornene, or a trans-cyclooctene (TCO), azide or tetrazine (Tz).

A hydrogel for use in the present invention can be made e.g. from one multi-armed precursor with a first (set of) functional group(s) and another multi-armed precursor having a second (set of) functional group(s). By way of example, a multi-armed precursor may have hydrophilic arms, e.g., polyethylene glycol units, terminated with primary amines (nucleophile), or may have activated ester end groups (electrophile). The polymer network according to the present invention may contain identical or different polymer units crosslinked with each other.

Certain functional groups can be made more reactive by using an activating group. Such activating groups include (but are not limited to) carbonyldiimidazole, sulfonyl chloride, aryl halides, sulfosuccinimidyl esters, N-hydroxysuccinimidyl ester, succinimidyl ester, epoxide, aldehyde, maleimides, imidoesters, acrylates and the like. The N-hydroxysuccinimide esters (NHS) are useful groups for crosslinking of nucleophilic polymers, e.g., primary amine-terminated or thiol-terminated polyethylene glycols. An NHS-amine crosslinking reaction may be carried out in aqueous solution and in the presence of buffers, e.g., phosphate buffer (pH 5.0-7.5), triethanolamine buffer (pH 7.5-9.0), borate buffer (pH 9.0-12), or sodium bicarbonate buffer (pH 9.0-10.0).

In certain embodiments, each precursor may comprise only nucleophilic or only electrophilic functional groups, so long as both nucleophilic and electrophilic precursors are used in the crosslinking reaction. Thus, for example, if a crosslinker has only nucleophilic functional groups such as amines, the precursor polymer may have electrophilic functional groups such as N-hydroxysuccinimides. On the other hand, if a crosslinker has electrophilic functional groups such as sulfosuccinimides, then the functional polymer may have nucleophilic functional groups such as amines or thiols. Thus, functional polymers such as proteins, poly (allyl amine), or amine-terminated di- or multifunctional poly(ethylene glycol) can be also used to prepare the polymer network of the present invention.

In one embodiment a first reactive precursor has about 2 to about 16 nucleophilic functional groups each (termed functionality), and a second reactive precursor allowed to react with the first reactive precursor to form the polymer network has about 2 to about 16 electrophilic functional groups each. Reactive precursors having a number of reactive (nucleophilic or electrophilic) groups as a multiple of 4, thus for example 4, 8 and 16 reactive groups, are particularly suitable for the present invention. Any number of functional groups, such as including any of 2, 3, 4, 5, 6, 7, 8, 9, 10, 11, 12, 13, 14, 15, or 16 groups, is possible for precursors to be used in accordance with the present invention, while ensuring that the functionality is sufficient to form an adequately crosslinked network. It is particularly suitable if the molar ratio of nucleophilic groups in one precursor to the electrophilic groups in the second precursor is about equal.

PEG Hydrogels:

In certain embodiments of the present invention, the polymer network forming the hydrogel contains polyethylene glycol (PEG) units. PEGs are known in the art to form hydrogels when crosslinked, and these PEG hydrogels are generally biocompatible and therefore suitable for pharmaceutical applications e.g. as matrix for drugs intended to be administered to all parts of the human or animal body.

The PEG hydrogels are particularly suitable for forming an implant for insertion into ocular tissue, such as the vitreous humor. They are soft and gentle to ocular tissue and therefore reduce the potential for local irritation, uncomfortable feeling (such as foreign body sensation), or damage to ocular tissue (such as retina). Furthermore, the PEG hydrogel provides for a steady release of the TKI such as axitinib into the vitreous humor, and from there a steady delivery to ocular tissue such as the retina and the choroid/RPE. The release of TKI such as axitinib from a PEG hydrogel is essentially diffusion-controlled. Upon final biodegradation of the hydrogel (as further described herein) the remaining TKI such as axitinib is released into the vitreous humor, where it is dissolved and further delivered into ocular tissue to bridge the window until a new implant is administered. Implants according to the present invention comprising a PEG hydrogel as described herein and axitinib, such as axitinib polymorph IV as also further described herein, can be repeatedly administered. In certain embodiments, a re-dosing period is about 6 to about 12 months, such as about 9 months in human patients.

The polymer network of the hydrogel implants of the present invention may comprise one or more, i.e., identical or different, multi-arm PEG units. They may have from 2 to 10 arms, or 4 to 8 arms, or may have 4, 5, 6, 7 or 8 arms. The PEG units may have a different or the same number of arms. Any combination of multi-armed PEG precursors is possible. In certain embodiments, the PEG units used in the hydrogel of the present invention have 4 and/or 8 arms. In certain particular embodiments, a combination of 4- and 8-arm PEG units is utilized.

The number of arms of the PEG used contributes to controlling the flexibility or softness of the resulting hydrogel. For example, hydrogels formed by crosslinking 4-arm PEGs are generally softer and more flexible than those formed from 8-arm PEGs of the same molecular weight. In particular, if stretching the hydrogel prior to or after drying as disclosed herein below in the section relating to the manufacture of the implant is desired, a more flexible hydrogel may be used, such as a 4-arm PEG, optionally in combination with another multi-arm PEG, such as an 8-arm PEG as disclosed above.

In certain embodiments of the present invention, polyethylene glycol units used as precursors have an average molecular weight in the range from about 2,000 to about 100,000 Daltons, or in a range from about 5,000 to about 60,000 Daltons, or in a range from about 10,000 to about 60,000 Daltons, or in a range from about 10,000 to about 50,000 Daltons. In certain particular embodiments the polyethylene glycol units have an average molecular weight in a range from about 10,000 to about 40,000 Daltons, or from about 15,000 to about 40,000 Daltons, or from about 15,000 to about 30,000 Daltons or of about 15,000 Daltons or about 20,000 Daltons. PEG precursors of the same average molecular weight may be used, or PEG precursors of different average molecular weight may be combined with each other. Again, any combination of PEG precursors with any molecular weights as disclosed herein is possible. The average molecular weight of the PEG precursors used in the present invention is given as the number average molecular weight (Mn), which, in certain embodiments, may be determined by MALDI.

In a 4-arm PEG, each of the arms may have an average arm length (or molecular weight) of the total molecular weight of the PEG divided by 4. A 4a20kPEG precursor, which is one particular precursor that can be utilized in the present invention thus has 4 arms with an average molecular weight of about 5,000 Daltons each. An 8a20k PEG precursor, which may be also be used in the present invention, such as by itself or in addition to the 4a20kPEG precursor in the present invention, thus has 8 arms each having an average molecular weight of about 2,500 Daltons. An 8a15k PEG precursor, which may be also be used in the present invention, such as by itself or in addition to the 4a20kPEG and/or the 8a20k PEG precursor, thus has 8 arms each having an average molecular weight of about 1,875 Daltons.

Longer arms may provide increased flexibility as compared to shorter arms. PEGs with longer arms may swell more as compared to PEGs with shorter arms. A PEG with a lower number of arms also may swell more and may be more flexible than a PEG with a higher number of arms. In certain particular embodiments, combinations of PEG precursors with different numbers of arms, such as a combination of a 4-arm PEG precursor and an 8-arm precursor, may be utilized in the present invention. In addition, longer PEG arms have higher melting temperatures when dry, which may provide more dimensional stability during storage.

When referring to a PEG precursor having a certain average molecular weight, such as a 15kPEG- or a 20kPEG-precursor, the indicated average molecular weight (i.e., a Mn of 15,000 or 20,000, respectively) refers to the PEG part of the precursor, before end groups are added ("20k" here means 20,000 Daltons, and "15k" means 15,000 Daltons—the same abbreviation is used herein for other average molecular weights of PEG precursors). In certain embodiments, the average molecular weight of the PEG precursors used in the present invention is given as the number average molecular weight (Mn), which, in certain embodiments, may be determined by MALDI. The degree of substitution with end groups as disclosed herein may be determined by means of $^1$H-NMR after end group functionalization.

In certain embodiments, electrophilic end groups for use with PEG precursors for preparing the hydrogels of the present invention are N-hydroxysuccinimidyl (NHS) esters, including but not limited to one or more of a succinimidylazelate (SAZ) group, a succinimidyladipate group (SAP), a succinimidylglutarate group (SG), succinimidylglutaramide (SGA) group, a succinimidylcarbonate group (SC), or a succinimidylsuccinate group (SS), particularly a succinimidylazelate (SAZ) group. PEG precursors with different ones of these groups may be combined, such as SAZ and SG, for example.

In certain embodiments, nucleophilic end groups for reaction with electrophilic group-containing with PEG precursors for preparing the hydrogels of the present invention are amine (denoted as "$NH_2$") end group-containing crosslinking agents. Thiol (—SH) end groups or other nucleophilic end groups are also possible. In certain embodiments, the nucleophilic group containing crosslinking agent may be an amine, multi-arm amine or salt of any of these, or may be an amine-substituted PEG. In specific embodiments, the nucleophilic group-containing crosslinking agent is trilysine, or a salt or derivative thereof, such as trilysine acetate (TLA). In other specific embodiments, the nucleophilic group-containing agent is an amine-group containing multi-arm PEG precursor, such as 8a20kPEG-$NH_2$ or a similar type of amine-group containing precursor with a different number of arms and/or different molecular weight.

In certain preferred embodiments, 4-arm PEGs with an average molecular weight of about 20,000 Daltons and an electrophilic end group as disclosed above, such as an N-hydroxysuccinimidyl (NHS) ester end group, and 8-arm PEGs also with an average molecular weight of about 20,000 Daltons and with a nucleophilic end group as disclosed above, such as an amine (—$NH_2$) end group, are crosslinked for forming the polymer network and thus the hydrogel according to the present invention.

Reaction of nucleophilic group-containing PEG units and electrophilic group-containing PEG units, such as amine end-group containing PEG units and activated ester-group containing PEG units, results in a plurality of PEG units being crosslinked by a hydrolyzable linker having the formula:

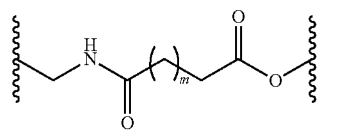

wherein m is an integer from 0 to 10, and specifically is 1, 2, 3, 4, 5, 6, 7, 8, 9, or 10. In one particular embodiment, m is 6, e.g. in the case a SAZ-end group-containing PEG is used. For a SAP-end group, m would be 3, for a SG-end group, m would be 2 and for an SS-end group m would be 1. All crosslinks within the polymer network may be the same, or may be different. Any combination of crosslinks in the polymer network are possible.

The same hydrolysable linker with the same meaning for m also results from the reaction of activated ester-group containing PEG units and a multi-amine as the nucleophilic crosslinking agent, such as trilysine or trilysine acetate.

In certain preferred embodiments, the SAZ end group of PEG precursors is utilized in the present invention. This end group may provide for increased persistence of the hydrogel in the eye. The implant of certain embodiments of the present invention comprising a hydrogel comprising PEG-SAZ units is biodegraded in the eye, such as in the vitreous humor of a human eye, after an extended period of time, e.g., from about 6 to about 12 months as further disclosed below, and may in certain circumstance persist even longer. The SAZ group is more hydrophobic than e.g. the SAP-, SG- or SS-end groups because of a higher number of carbon atoms in the chain (m being 6, and the total of carbon atoms between the amide group and the ester group being 7), which makes this linker group less prone to ester cleavage in aqueous (such as physiological) environment as compared to other, shorter linker groups.

In certain particular embodiments, a 4-arm 20,000 Dalton PEG precursor is combined with an 8-arm 20,000 Dalton PEG precursor, such as a 4-arm 20,000 Dalton PEG precursor having a SAZ group (as disclosed above) combined with an 8-arm 20,000 Dalton PEG precursor having an amine group (as disclosed above). These precursors are also abbreviated herein as 4a20kPEG-SAZ and 8a20kPEG-$NH_2$, respectively. Thus, in certain particular embodiments the polymer network according to the present is a PEG hydrogel network formed by crosslinking 4a20kPEG-SAZ and 8a20kPEG-$NH_2$. The chemical structure of 4a20kPEG-SAZ is:

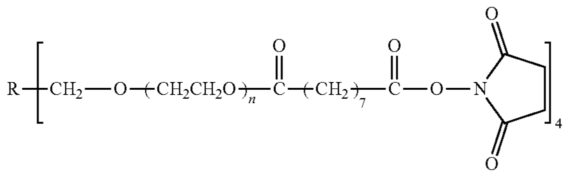

wherein R represents a pentaerythritol core structure. The chemical structure of 8a20kPEG-$NH_2$ (with a hexaglycerol core) is:

$$R\left[O\left(CH_2CH_2O\right)_n CH_2CH_2-NH_2\right]_8$$

R = hexaglycerol core structure

In the above formulae, n is determined by the molecular weight of the respective PEG-arm.

Another possible PEG precursor with an electrophilic group is a 4a20kPEG-SG precursor. A schematic chemical structure of 4a20kPEG-SG is reproduced below:

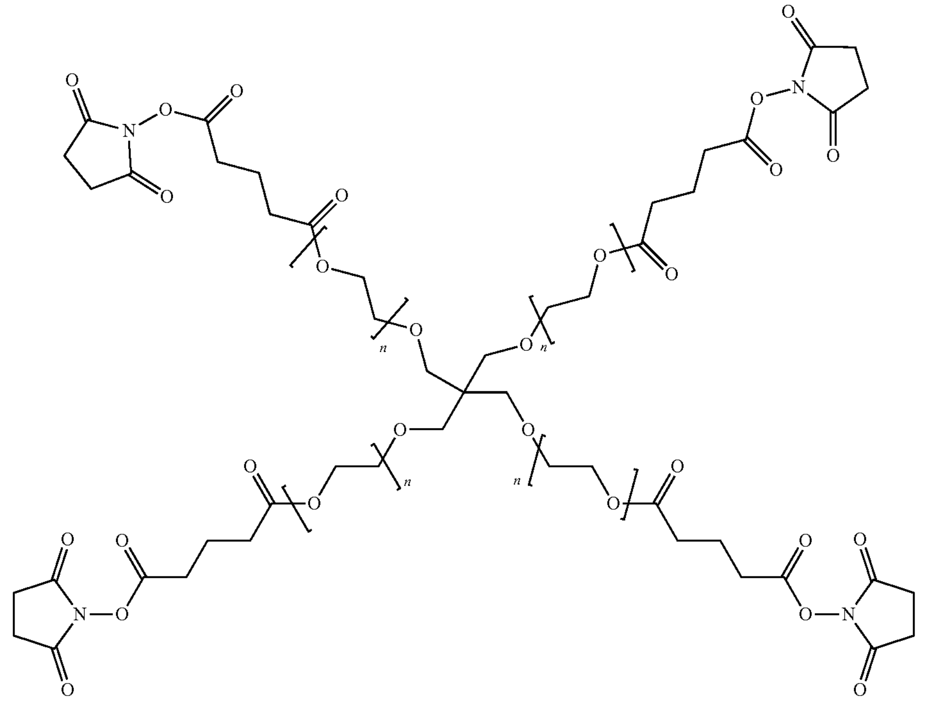

In the above formula, n is determined by the molecular weight of the respective PEG-arm.

In certain particular embodiments, the crosslinking agent (herein also referred to as "crosslinker") used is a low-molecular weight component containing nucleophilic end groups, such as amine or thiol end groups. In certain embodiments, the nucleophilic group-containing crosslinking agent is a small molecule amine with a molecular weight below 1,000 Da. In certain embodiments, the nucleophilic-group containing crosslinking agent comprises two, three or more primary aliphatic amine groups. Suitable crosslinking agents for use in the present invention are (without being limited to) spermine, spermidine, lysine, dilysine, trilysine, tetralysine, polylysine, ethylenediamine, polyethylenimine, 1,3-diaminopropane, 1,3-diaminopropane, diethylenetriamine, trimethylhexamethylenediamine, 1,1,1-tris(aminoethyl) ethane, their pharmaceutically acceptable salts, hydrates or other solvates and their derivatives such as conjugates (as long as sufficient nucleophilic groups for crosslinking remain present), and any mixtures thereof. A particular crosslinking agent for use in the present invention is a lysine-based crosslinking agent, such as trilysine or a trilysine salt or derivative. In particular embodiments of the present invention, the nucleophilic crosslinking agent for use with the electrophilic group-containing PEG precursor(s) is trilysine or trilysine acetate (TLA). Other low-molecular weight multi-arm amines may be used as well. The chemical structure of trilysine is as follows:

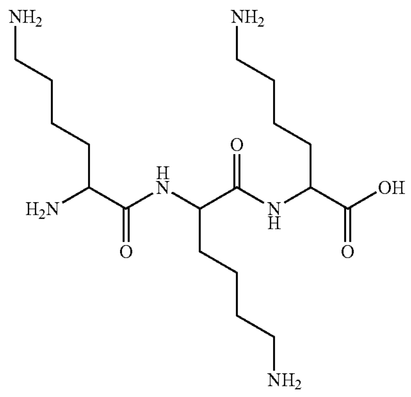 [SMILES: NCCCCC(N)C(=O)NC(CCCCN)C(=O)NC(CCCCN)C(=O)O]

In certain embodiments, the molar ratio of the nucleophilic and the electrophilic end groups reacting with each other is about 1:1, i.e., one amine group is provided per one SAZ group. In the case of 4a20kPEG-SAZ and 8a20kPEG-$NH_2$ this results in a weight ratio of about 2:1, as the 8-arm PEG contains double the amount of end groups as the 4-arm PEG. However, an excess of either the electrophilic (e.g. the NHS end groups, such as the SAZ) end groups or of the nucleophilic (e.g. the amine) end groups may be used. In particular, an excess of the nucleophilic, such as the amine-end group containing precursor may be used, i.e., the weight ratio of 4a20kPEG-SAZ and 8a20kPEG-$NH_2$ may also be less than 2:1.

Each and any combination of electrophilic- and nucleophilic-group containing PEG precursors disclosed herein may be used for preparing the implant according to the present invention. For example, any 4-arm or 8-arm PEG-NHS precursor (e.g. having a SAZ, SAP, SG or SS end group) may be combined with any 4-arm or 8-arm PEG-$NH_2$ precursor (or any other PEG precursor having a nucleophilic group). Furthermore, the PEG units of the electrophilic- and the nucleophilic group-containing precursors may have the same, or may have a different average molecular weight.

Additional Ingredients:

The implant of the present invention may contain, in addition to the polymer units forming the polymer network as disclosed above and the active principle, other additional ingredients. Such additional ingredients are for example salts originating from buffers used during the preparation of the hydrogel, such as phosphates, borates, bicarbonates, or other buffer agents such as triethanolamine. In certain embodiments of the present invention sodium phosphate buffers (specifically, mono- and dibasic sodium phosphate) and/or sodium borate buffers are used. Any other buffers known in the art may generally be used in addition to or instead of sodium phosphate and/or sodium borate buffers in order to provide a pH value of about 6.5 to about 8.5, i.e., around neutral. The afore-said applies for final combined solutions of electrophilic group-containing precursors and nucleophilic-group containing precursors, such as for example a combined solution of 4a20kPEG-SAZ and 8a20kPEG-$NH_2$ in buffer. The individual precursor solutions may have pH values different from each other, for example the electrophilic group containing precursor (such as 4a20kPEG-SAZ) may be provided in a solution buffered to a pH of about 3.5 to about 5.5, and the nucleophilic group containing precursor (such as 8a20kPEG-$NH_2$) may be provided in a solution buffered to a pH of about 6.5 to about 8.

In a specific embodiment, the implant of the present invention is free of anti-microbial preservatives or at least does not contain a substantial amount of anti-microbial preservatives (including, but not limited to benzalkonium chloride (BAK), chlorobutanol, sodium perborate, and stabilized oxychloro complex (SOC)).

In a further specific embodiment, the implant of the present invention does not contain any ingredients of animals or human origin but only contains synthetic ingredients.

If an in situ gelation is desired in an embodiment of the invention, possible additional ingredients may be other agents used during manufacture of the hydrogel, such as (without being limited to) viscosity-influencing agents (such as hyaluronic acid etc.), surfactants etc.

In certain embodiments, the implants of the present invention may contain a visualization agent. In other embodiments, the implants of the present invention do not contain a visualization agent. An implant according to the present invention can be visualized when residing in the patient's eye by imaging techniques such as slit lamp (biomicroscopy), which can be performed e.g. by an ophthalmologist. Another technique for visualizing an implant in the eye is cSLO (confocal scanning laser ophthalmoscopy, sometimes also referred to as IR or OCT). For neither of these two techniques a visualization agent such as a fluorescent agent is required.

Nevertheless, in case a visualization agent is used in the context of the invention, all agents that can be conjugated with the components of the hydrogel or can be entrapped within the hydrogel, and that are visible, or may be made visible when exposed e.g. to light of a certain wavelength, or that are contrast agents, may be used. Suitable visualization agents for use in the present invention are (but are not limited to) e.g. fluorophores. Suitable visualization agents for use in the present invention are (but are not limited to) e.g. fluoresceins, rhodamines, coumarins, cyanines, europium chelate complexes, boron dipyrromethenes, benzofrazans, dansyls, bimanes, acridines, triazapentalenes, pyrenes and derivatives thereof. In certain embodiments the visualization agent is a fluorophore, such as fluorescein or comprises a fluorescein moiety. Visualization of the fluorescein-containing implant is possible by illumination with blue light and a yellow filter. The fluorescein illuminates when excited with blue light enabling confirmation of implant presence.

In certain embodiments, the nucleophilic group-containing crosslinking agent may be bound to or be conjugated with a visualization agent, e.g. through some of the nucleophilic groups of the crosslinking agent. Since a sufficient amount of the nucleophilic groups are necessary for crosslinking, "conjugated" or "conjugation" in general includes partial conjugation, meaning that only a part of the nucleophilic groups are used for conjugation with the visualization agent, such as about 1% to about 20%, or about 5% to about 10%, or about 8% of the nucleophilic groups of the crosslinking agent may be conjugated with a visualization agent. In other embodiments, a visualization agent may also be conjugated with the polymer precursor, e.g. through certain reactive (such as electrophilic) groups of the polymer precursors.

Formulation

In certain embodiments, implants according to the present invention comprise a TKI, a polymer network made from one or more polymer precursors as disclosed herein above in the form of a hydrogel, and optionally additional components such as salts etc. remaining in the implant from the production process (such as phosphate salts used as buffers etc.). In particular embodiments, the TKI is axitinib. In particular specific embodiments the axitinib is axitinib free base. In further particular specific embodiments the axitinib is axitinib polymorph IV.

The implants according to the present invention may have a composition (dry basis; in % w/w) as follows: from about 10% to about 80%, or from about 20% to about 70% by weight TKI, such as axitinib, and from about 10% to about 80%, or from about 20% to about 70% by weight polymer units, such as PEG units.

In certain embodiments, the implants of the invention may have a composition (dry basis; in % w/w) as follows: from about 10% to about 40% by weight, or from about 15% to about 25% by weight axitinib, and from about 55% to about 75% by weight, or from about 60% to about 70% by weight PEG units. In certain specific embodiments, the implants may have a composition (wet basis; in % w/w) as follows: from about 1% to about 8% by weight, or from about 2% to about 7% by weight axitinib, and from about 5% to about 15% by weight, or from about 6% to about 10% by weight PEG units. These compositions are particularly applicable to implants according to the invention that contain axitinib (i.e., axitinib free base in the form of any polymorph thereof, such as polymorph IV, or in the form of e.g. a co-crystal or prodrug thereof) in an amount corresponding to 100 to 200 μg, or from about 120 μg to about 187.5 μg, or about 150 μg axitinib free base.

In certain other embodiments, the implants of the invention may have a composition (dry basis; in % w/w) as follows: from about 30% to about 50% by weight, or from about 40% to about 57% by weight axitinib, and from about 25% to about 50% by weight, or from about 35% to about 45% by weight PEG units. In certain specific embodiments, the implants may have a composition (wet basis; in % w/w) as follows: from about 4% to about 14% by weight, or from about 7% to about 12% by weight axitinib, and from about 5% to about 15% by weight, or from about 6% to about 10% by weight PEG units. These compositions are particularly applicable to implants according to the invention that contain axitinib (i.e., axitinib free base in the form of any polymorph thereof, such as polymorph IV, or in the form of e.g. a co-crystal or prodrug thereof) in an amount corresponding to 200 to 400 μg, or from about 240 μg to about 375 μg, or about 300 μg axitinib free base.

In certain other embodiments, the implants of the invention may have a composition (dry basis; in % w/w) as follows: from about 30% to about 70%, such as from about 40% to about 70% by weight, or from about 45% to about 65% by weight, or from about 50 to about 60% by weight, or from about 60 to 70% by weight axitinib (such as axitinib polymorph IV), and from about 20% to about 50% by weight, or from about 25% to about 45% by weight, or from about 30% to about 43% by weight, or from about 33% to about 43% by weight PEG units, or from about 25% to about 35% by weight PEG units. In particular embodiments, an implant of the present invention comprising axitinib in the form of axitinib polymorph IV in an amount of about 400 μg to about 500 μg may have a composition (dry basis; in % w/w) as follows: from about 60% to about 70% by weight axitinib and from about 25% to about 35% by weight PEG units.

In certain specific embodiments, the implants may have a composition (wet basis; in % w/w) as follows: from about 5% to about 20% by weight, or from about 6% to about 12% by weight, or from about 6% to about 15% by weight, or from about 8 to about 10% by weight or from about 5 to 17% by weight axitinib, and from about 4% to about 12% by weight, or from about 5% to about 10% by weight, or from about 6% to about 8% by weight PEG units. In particular embodiments, an implant of the invention may have a composition (dry basis; in % w/w) as follows: from about 30% to about 70% axitinib and from about 20% to about 50% PEG units. In particular embodiments, an implant of the invention may have a composition (wet basis; in % w/w) as follows: from about 5 to about 17% axitinib, and from about 4 to about 12% PEG units. These compositions are particularly applicable to implants according to the invention that contain axitinib (i.e., axitinib free base in the form of any polymorph thereof, such as polymorph IV, or in the form of e.g. a co-crystal or prodrug thereof) in an amount corresponding to 200 to 1000 μg, 300 to 1000 μg, 300 to 600 μg, or from about 360 μg to about 562.5 μg, or from about 400 to about 500 μg, or to about 450 μg axitinib free base.

In particular embodiments, implants of the invention may have a composition (dry basis; in % w/w) as follows: from about 50% to about 70% by weight axitinib (specifically, axitinib polymorph IV), and from about 25% to about 45% by weight PEG units, specifically PEG units obtained from crosslinking 4a20kPEG-SAZ with 8a20kPEG-$NH_2$. These implants may have a composition (wet basis; in % w/w) as follows: from about 7% to about 17% by weight axitinib (specifically, axitinib polymorph IV), and from about 5% to about 10% by weight PEG units, specifically PEG units obtained from crosslinking 4a20kPEG-SAZ with 8a20kPEG-$NH_2$. These composition ranges are particularly applicable to implants according to the invention that contain axitinib, specifically axitinib polymorph IV, in an amount of from about 360 μg to about 562.5 μg, or from about 400 μg to about 500 μg, or of about 450 μg. Exemplary implants according to these embodiments of the present invention are presented in Table 1C in the Examples section.

In certain other embodiments, the implants of the invention may have a composition (dry basis; in % w/w) as follows: from about 30% to about 80% by weight, or from about 50% to about 70% by weight, or from about 55% to about 70% by weight axitinib, and from about 20% to about 60% by weight, or from about 20% to about 50% by weight, or from about 25% to about 35% by weight PEG units. In certain specific embodiments, the implants may have a composition (wet basis; in % w/w) as follows: from about 10% to about 22% by weight, or from about 12% to about 18% by weight, or from about 14% to about 17% by weight axitinib, and from about 2% to about 12% by weight, or from about 4% to about 10% by weight, or from about 5% to about 8% by weight PEG units. These compositions are particularly applicable to implants according to the invention that contain axitinib (i.e., axitinib free base in the form of any polymorph thereof, such as polymorph IV, or in the form of e.g. a co-crystal or prodrug thereof) in an amount corresponding to from 200 to 1000 μg, 300 to 1000 μg, 300 to 800 μg, or from about 480 μg to about 750 μg, or from about 540 μg to about 660 μg, or about 600 μg axitinib free base.

In certain other embodiments, wherein an implant of the invention comprises at least two filaments, such as from 2 to 10, or from 3 to 7 filaments, the implant, or any of the filaments of which it is composed, may have a composition (dry basis; in % w/w) as follows: from about 30% to about 70% by weight, or from about 30% to about 60% by weight axitinib, and from about 20% to about 60% by weight, or from about 30% to about 60% by weight PEG units. In certain specific embodiments, wherein an implant of the invention comprises at least two filaments, such as from 2 to 10, or from 3 to 7 filaments, the implant may have a composition (wet basis; in % w/w) as follows: from about 5% to about 20% by weight, or from about 5% to about 15% by weight axitinib, and from about 3% to about 20% by weight, or from about 5% to about 10% by weight PEG units.

In certain other embodiments, wherein an implant of the invention has a cross-sectional geometry that is not round or oblong, in particular a cross-sectional geometry that is cross- or star-shaped, including but not limited to 5-arm star shaped, the implant may have a composition (dry basis; in % w/w) as follows: from about 30% to about 70% by weight, or from about 40% to about 70% by weight axitinib, and from about 20% to about 60% by weight, or from about 20% to about 40% by weight PEG units. In certain specific embodiments, wherein an implant of the invention has a cross-sectional geometry that is not round or oblong, in particular a cross-sectional geometry that is cross- or star-shaped, including but not limited to 5-arm star shaped, the implant may have a composition (wet basis; in % w/w) as follows: from about 5% to about 20% by weight, or from about 8% to about 18% by weight axitinib, and from about 3% to about 20% by weight, or from about 5% to about 10% by weight PEG units.

In certain embodiments, on a dry weight basis the axitinib to PEG ratio in an implant according to the invention may be from about 1:1 to about 3:1. In certain embodiments, the maximum amount of drug within the formulation is about two times the amount of the polymer (e.g., PEG) units, but may be higher in certain cases, as long as the mixture comprising, e.g., the precursors, buffers and drug (in the state before the hydrogel has gelled completely) can be uniformly cast into a mold or tubing (in case the implant according to the invention is produced by wet casting as further disclosed herein).

In certain embodiments, the balance of the implant in its dried state (i.e., the remainder of the formulation when TKI, such as axitinib, and polymer units, such as PEG units, have already been taken account of) may be salts remaining from buffer solutions as disclosed above. In certain embodiments, such salts are phosphate, borate or (bi) carbonate salts. In one embodiment the buffer salt is sodium phosphate (mono- and/or dibasic).

In certain embodiments, a solids content of about 10% to about 50%, or of about 25% to about 50% (w/v) (wherein "solids" means the combined weight of polymer precursor(s), salts and the drug in solution/suspension) may be utilized in the wet composition when forming the hydrogel for the implants according to the present invention by wet casting as further disclosed herein. Thus, in certain embodiments, the total solids content of the wet hydrogel composition to be cast into a mold or tubing in order to shape the hydrogel may be no more than about 60%, or no more than about 50%, or no more than about 40%, such as equal to or lower than about 35% (w/v). The content of TKI, such as axitinib, may be no more than about 40%, or no more than about 30%, such as equal to or lower than about 25% (w/V) of the wet composition. The solids content may influence the viscosity and thus may also influence the castability of the wet hydrogel composition.

In certain embodiments, the water content of the hydrogel implant in its dry (dehydrated/dried) state, e.g. prior to being loaded into a needle, or when already loaded in a needle, may be very low, such as not more than 1% by weight of water. The water content may in certain embodiments also be lower than that, possibly not more than 0.25% by weight or even not more than 0.1% by weight. In the present invention the term "implant" is used to refer both to an implant in a hydrated state when it contains water (e.g. after the implant has been (re) hydrated once administered to the eye or otherwise immersed into an aqueous environment) as well as to an implant in its dry (dried/dehydrated) state, e.g., when it has been dried to a low water content of e.g. not more than about 1% by weight or when the preparation results in such a low water content implant without the necessity of a drying step. In certain embodiments, an implant in its dry state is an implant that after production is kept under inert nitrogen atmosphere (containing less than 20 ppm of both oxygen and moisture) in a glove box for at least about 7 days prior to being loaded into a needle. The water content of an implant may be e.g. measured using a Karl Fischer coulometric method.

In certain embodiments, the total weight (also referred to herein as "total mass") of an implant according to the present invention in its dry state may be from about 200 μg (i.e., 0.2 mg) to about 1.5 mg, or from about 400 μg to about 1.2 mg, or from about 500 μg to about 1 mg. In particular embodiments, the total weight of an implant according to the present invention in its dry state is from about 0.6 mg to about 1 mg, such as from about 600 μg to about 900 μg, or is between about 600 μg and about 900 μg, such as from about 700 μg to about 875 μg. In case an implant is a composite (multi-filament) implant, the total weight of the composite implant may be higher, depending on the number of individual filaments of which it is composed, and their total weights. In particular embodiments, when the TKI in the implant is axitinib, such as axitinib polymorph IV, and is present in a dose of from about 400 to about 500 μg, such as from about 405 to about 495 μg, such as from about 410 to about 490 μg, and wherein the axitinib particles are micronized particles as defined herein, the total weight of the implant may by from about 0.6 to about 1 mg, or between about 0.6 and about 0.9 mg, and the hydrated surface area (as defined herein) of such an implant may be at least 16 $mm^2$, such as from 16.0 to 23.0 $mm^2$.

In certain embodiments, an implant according to the present invention in its dry state may contain from about 200 μg to about 1000 μg TKI, such as axitinib, per $mm^3$ (i.e., per 1 $mm^3$ volume of the dry implant). In certain specific embodiments, an implant according to the present invention in its dry state may contain from about 200 μg to about 300 μg axitinib per $mm^3$, e.g. in case the implant contains axitinib in an amount of from about 160 μg to about 250 μg. In certain other specific embodiments, an implant according to the present invention in its dry state may contain from about 500 μg to about 800 μg axitinib per $mm^3$, e.g. in case the implant contains axitinib in an amount of from about 480 μg to about 750 μg.

The implants of the present invention may thus have different densities. The densities of the final implants (i.e., in their dry state) may be controlled and determined by various factors, including but not limited to the concentration of the ingredients in the wet composition (in case of wet casting) when forming the hydrogel, and certain conditions during manufacturing of the implant. For example, the density of the final implant in certain embodiments can be increased by means of sonication or degassing, e.g. using vacuum, at certain points during the manufacturing process. In certain embodiments, the density of implants produced by means of hot melt extrusion may be higher than the density of comparable implants (in terms of their content of TKI and polymer, respectively) produced by means of wet casting.

In certain embodiments, implants according to the invention contain a therapeutically effective amount of TKI such as axitinib for release over an extended period of time, but are nevertheless relatively small in length and/or diameter. This is advantageous both in terms of ease of administration (injection) as well as in terms of reducing possible damage to ocular tissue and reducing a possible impact of the patient's vision while the implant is in place. The implants of the present invention combine the benefits of a suitably high dose of the TKI (i.e., a therapeutically effective dose adjusted to a particular patient's need) with a relatively small implant size. Furthermore, the implants of the present invention achieve a relatively high rate of release of the TKI, particularly in the early phases of the release, i.e., during an initial period of time after administration (or, in case of in vitro release tests, during an initial period of time after start of the test).

Exemplary implants of various aspects of the present invention are disclosed in the Examples section (including prophetic examples of implants), Dimensions of the Implant and Dimensional Change Upon Hydration Through Stretching:

Single Implant:

The dried implant may have different geometries, depending on the method of manufacture, such as the use of a mold or tubing into which the mixture comprising the hydrogel precursors including the TKI is cast prior to complete gelling (in case a wet casting method as disclosed herein is used for manufacturing the implant), or depending on the shape and dimensions of the die through which the melt mixture of polymer precursors and TKI prepared in a hot melt extrusion process (as also disclosed herein) is expelled.

The implant according to the present invention may also be referred to herein as a "fiber" (which term is used interchangeably herein with the term "rod"), wherein the fiber is an object that has in general an elongated shape. The implant (or the fiber) may have different geometries, with specific dimensions as disclosed herein. The implant (or the fiber) is an elongated object that generally has a length and a width, wherein the width is the largest cross-sectional dimension of the elongated object and the length is the longest elongation of the object. Generally, in implants of the present invention the length is longer than the width.

In one embodiment, the implant is cylindrical or has an essentially cylindrical shape. In this case, the implant has a round or an essentially round cross-section. It has a length and a width/diameter. In other embodiments of the invention, the implant Is non-cylindrical, wherein the implant is optionally elongated in its dry state.

Whether cylindrical or non-cylindrical, the length of the implant is generally greater than the width of the implant, wherein the width (also referred to as "diameter" in implants with a round or essentially round cross-section) is the largest cross-sectional dimension that is substantially perpendicular to the length. The length is generally the longest elongation of an implant. In certain embodiments, the width (or diameter) of an implant of the invention may be about 0.1 mm to about 0.5 mm in its dried state. Various geometries of the outer implant shape or its cross-section may be used in the present invention. For example, instead of a round diameter fiber (i.e., a cylindrical implant), also a cross-shaped fiber (i.e., wherein the cross-sectional geometry is cross-like) may be used. Other cross-sectional geometries, such as oval, oblong, elliptical, quadrangular, square, diamond-shaped, cross-shaped, triangular, star-shaped (stars with any number of arms), or asterisk-shaped (again, with any number of arms) etc. may generally be used. The implant may also be in the form of a thin-film or gear-shaped.

The cross-sectional geometry of an implant also determines its hydrated surface area. For example, implants that have a cross-shaped or star-shaped cross-sectional geometry have an increased hydrated surface area as compared to implants of the same length but with a round or oval cross-section. The hydrated surface area of an implant is calculated for the purposes of the present invention from the hydrated dimensions of the implant as measured in phosphate-buffered saline (PBS) at a pH of 7.2 to 7.4 and 37° C. after 24 hours.

In one aspect of the present invention, an implant has a hydrated surface area (as defined herein) of at least 25 $mm^2$, such as from 25 $mm^2$ to 100 $mm^2$, or from 25 $mm^2$ to 60 $mm^2$. In this aspect of the present invention (i.e., wherein the hydrated surface area is at least 25 mm*), the TKI such as axitinib may have any solubility, i.e., may have a solubility of greater than 0.3 μg/mL, such as greater than 0.4 μg/mL, or may have a solubility of 0.3 μg/mL or lower, as measured in phosphate-buffered saline (PBS) at a pH of 7.2 to 7.4 and 37° C. after five days of incubation.

In another aspect of the present invention, an implant can have any hydrated surface area as long as the solubility of the TKI, such as axitinib, contained therein is greater than 0.3 μg/mL, such as greater than 0.4 μg/mL as measured in phosphate-buffered saline (PBS) at a pH of 7.2 to 7.4 and 37° C. after five days of incubation (as disclosed herein). In embodiments of this aspect in which the TKI such as axitinib has the mentioned greater solubility, including but not limited to embodiments wherein the TKI is axitinib in the form of polymorph IV, the hydrated surface area of the implant (as defined herein) may be least 10 $mm^2$, such as at least 15 $mm^2$, such as at least 16 $mm^2$, such as at least 19 $mm^2$, or at least 25 $mm^2$, advantageously from 15 $mm^2$ to 100 $mm^2$, or from 15 $mm^2$ to 90 $mm^2$, or from 16.0 $mm^2$ to 25.0 $mm^2$, or from 16.0 $mm^2$ to 23.0 $mm^2$. Alternatively, if the solubility of the TKI, such as axitinib, contained in an implant of the present invention is greater than 0.3 μg/ml as measured in phosphate-buffered saline (PBS) at a pH of 7.2 to 7.4 and 37° C. after five days of incubation (as disclosed herein), the hydrated surface area of the implant may be from 19 $mm^2$ to 90 $mm^2$, or from 25 $mm^2$ to 90 $mm^2$ as measured in phosphate-buffered saline (PBS) at a pH of 7.2 to 7.4 and 37° C. after 24 hours of incubation. In particular embodiments, the hydrated surface area of an implant of the present invention of any of the two just mentioned aspects may be from 25 $mm^2$ to 90 $mm^2$ or from 25 $mm^2$ to 40 $mm^2$ as measured in phosphate-buffered saline (PBS) at a pH of 7.2 to 7.4 and 37° C. after 24 hours of incubation.

In specific embodiments of the invention, wherein the solubility of the TKI, such as axitinib, contained in the implant is greater than 0.3 μg/mL as measured in phosphate-buffered saline (PBS) at a pH of 7.2 to 7.4 and 37° C. after five days of incubation, and in case the implant is a single-stranded implant, the hydrated surface area may be from 10 $mm^2$ to 60 $mm^2$, such as from 15 $mm^2$ to 40 $mm^2$, or from 16.0 $mm^2$ to 25.0 $mm^2$, or from 16.0 $mm^2$ to 23.0 $mm^2$, as measured in phosphate-buffered saline (PBS) at a pH of 7.2 to 7.4 and 37° C. after 24 hours of incubation in case the implant's cross-section is round or essentially round (i.e., in case the implant has a cylindrical or essentially cylindrical shape). In case the implant's cross-section has an shape with "arms", such as a cross shape (4 arms) or a star shape (5, 6 or more arms), the hydrated surface area may be from 30 $mm^2$ to 90 $mm^2$ as measured in phosphate-buffered saline (PBS) at a pH of 7.2 to 7.4 and 37° C. after 24 hours of incubation.

The hydrated surface area of an implant is calculated from the respective hydrated dimensions of an implant as defined herein (i.e., as measured in phosphate-buffered saline (PBS) at a pH of 7.2 to 7.4 and 37° C. after 24 hours of incubation), by means of the formula for calculating the surface area of the respective geometrical body, e.g. a cylinder in case of a cylindrical implant, whose surface area is $A=2\pi rh+2\pi r^2$ (with h being the height, i.e., the length of the cylinder, and r being the radius, i.e., half the diameter/width of the cylinder). The hydrated dimensions (length and diameter/width) of an implant thus determine its hydrated surface area which inter alia controls the rate of release of the active agent from the implant. Very generally said, a larger surface area provides for a faster release (if the drug/the solubility of the drug and the implant composition stays the same).

In case of multi-filament implants as further disclosed herein, the hydrated surface area of the composite implant is the sum of the hydrated surface area of the filaments, e.g. the hydrated surface are of one filament multiplied by the number of filaments in case the filaments all have the same dimensions (as the filaments are intended to unfurl upon contact with physiological environment as further disclosed herein). In case the filaments have different dimensions, the hydrated surface area of the composite implant is the sum of the hydrated surface are of all filaments.

Figure 3:
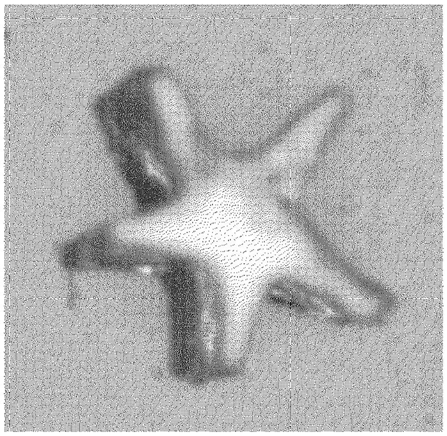
FIG. 3: Star shaped implant and example calculation of dimensions.
Figure 3:
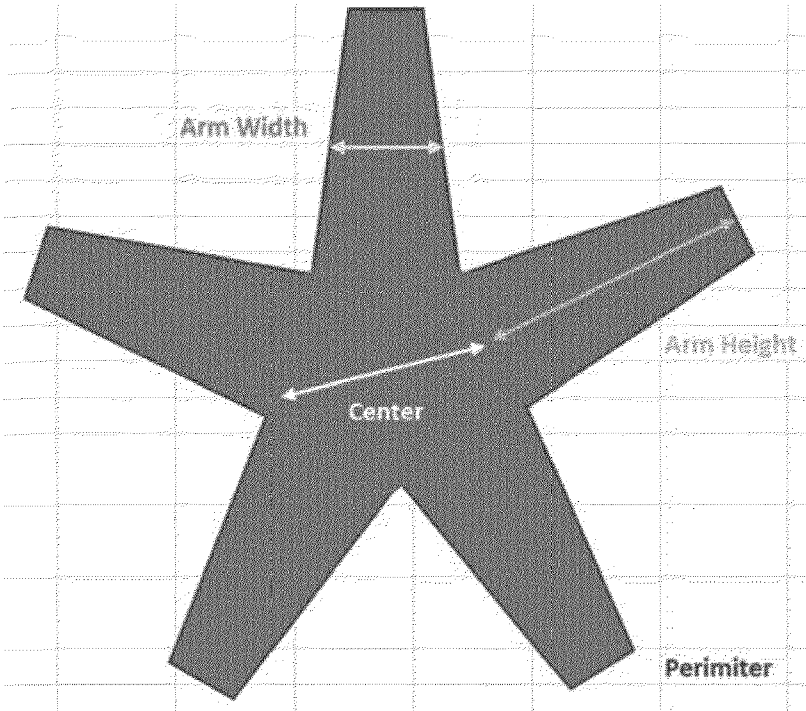

In case of other geometries of implants, such as other cross-sectional geometries, again the respective hydrated dimensions have to be taken for calculating the hydrated surface area. For example, for a 5-arm star-shaped cross-sectional geometry of an implant, the hydrated surface area is calculated as shown in FIG. 3 by the following formulae:

$$\text{"surface area end face"} = \text{arm width} \times \text{arm length} \times 5 + \text{center}^2$$

$$\text{hydrated surface area (also referred to as total implant surface area)} = \text{perimeter} \times \text{implant length} + 2 \times \text{"surface area end face"}$$

The "arm width" is the width of each arm; the "arm length" is the length of each arm, and the "center" is the cross-sectional dimension of the centerpiece. Irregular multiple-arm shapes may also be used, and their hydrated surface area may be calculated correspondingly.

In certain embodiments, the ratio between the hydrated surface area as defined herein and the amount of TKI contained in the implant multiplied by 100, i.e., (hydrated surface area/TKI amount)×100, may be at least 2, such as at least 3, or at least 5, or may be from about 2 to about 10 $mm^2/\mu g$.

Generally speaking, a larger hydrated surface area provides for an Increased rate of release of the API from an implant (within certain limits). Increasing the hydrated surface area by either using a different cross-sectional geometry or by e.g. combining multiple filaments into one combined strand as further disclosed herein is another method of increasing the release rate per day and/or the average release rate per day over a certain period of time, and/or the percentage of released API on one or more individual days, and/or the cumulative percentage of released API (based on the total released API or based on the total contained API) over a certain period of time, and/or the absolute amount of API released on one or more individual days or over a certain period of time (in vivo or in vitro). Thus, the present invention also relates to such a method of increasing the release rate and/or the average release rate and/or the released amount of total TKI contained in the implant and/or the released share of the total TKI contained in the implant or the total TKI released from an implant in a certain period of time, as compared to known implants containing TKI, by increasing the hydrated surface area of the implant.

In certain embodiments, the fiber may also be twisted or coiled, both in case of a single-strand as well as in case of a multi-filament fiber as disclosed herein. In other embodiments, the fiber is linear.

In embodiments where the implant is administered to the eye by means of a needle, the dimensions of the implant (i.e., its length and diameter/width) and its cross-sectional geometry must be such as to enable loading the implant into a needle, particularly a fine-diameter needle such as a 25-gauge, or 26-gauge, or 27-gauge, or 30-gauge needle as further disclosed herein. Particularly suitable implant sizes are those that fit into a 25-gauge needle. The dimensions of the implant in its dry state, in particular its width, are thus of relevance when it comes to selecting an appropriate needle for injecting the implant into the eye, such as the vitreous humor. A small needle diameter generally means a lower potential for irritation and tissue trauma upon injection.

The polymer network, such as the PEG network, of the hydrogel implant according to certain embodiments of the present invention may be semi-crystalline in the dry state at or below room temperature, and amorphous in the wet state. Even in the stretched form, the dry implant may be dimensionally stable at or below room temperature, which may be advantageous for loading the implant into the needle and for quality control.

Upon hydration of the implant in the eye (which can be simulated by immersing the implant into PBS, pH 7.2 to 7.4 at 37° C. for 24 hours) the dimensions of the implant according to the invention may change: for example, the diameter of the implant may increase, while its length may decrease or at least may stay essentially the same. An advantage of this dimensional change is that, while the implant in its dry state is sufficiently thin to be loaded into a fine diameter needle (such as a 25-, or 27-, or in some cases even a smaller diameter needle, such as a 30-gauge needle) to be injected into the eye, once it has been placed in eye, e.g., in the vitreous humor, the implant may become shorter to better fit within the limited, small volume of the eye. The needles used for injection of the implants of the present invention as disclosed herein, such as the 25- or 27-gauge needles in certain embodiments, are small in diameter (and e.g. may have an inner diameter of about 0.4 mm). As the implant also softens upon hydration, injuries of any ocular tissue may be prevented or minimized even when the implant comes into contact with such tissue. In certain embodiments, the dimensional change is enabled at least in part by the "shape memory" effect introduced into the implant by means of stretching the implant in the longitudinal direction during its manufacture (as also disclosed below in the section "Method of manufacture"). In certain embodiments, the stretching may either be performed in the dry or in the wet state, i.e., after drying the hydrogel implant, or before drying. It is noted that if no stretching is performed, and the hydrogel implant is only dried and cut into a desired length, the implant may increase in both diameter and length upon hydration.

In pre-formed dried hydrogels, a degree of molecular orientation may be imparted by "dry-stretching" the material then allowing it to solidify, promoting crystallization and locking in the molecular orientation. This can be accomplished in certain embodiments by drawing the material (optionally while heating the material to a temperature above the melting point of the crystallizable regions of the material), then allowing the crystallizable regions to crystallize. Alternatively, in certain embodiments the glass transition temperature of the dried hydrogel can be used to lock in the molecular orientation for polymers such as PVA that have a suitable glass transition temperature. Still another alternative is to stretch the gel prior to complete drying (also referred to as "wet stretching") and then drying the material while under tension. The molecular orientation provides one mechanism for anisotropic swelling upon introduction into a hydrating medium such as the vitreous. Upon hydration the implant of certain embodiments will swell only in the radial dimension, while the length will either decrease or be essentially maintained. The term "anisotropic swelling" means swelling preferentially in one direction as opposed to another, as in a cylinder that swells predominantly in diameter, but does not appreciably expand (or does even contract) in the longitudinal dimension.

The "locking in" of the molecular orientation is reversible upon (re) hydration. The degree of dimensional change upon hydration may depend inter alia on the stretch factor. As an example, stretching at e.g. a low stretch factor of around (e.g. by means of wet stretching) may have a less pronounced effect or may not change the length during hydration to a large extent. In contrast, stretching at a higher stretch factor of about 1.5 or more, such as about 2 or more may result in a markedly shorter length during hydration.

Stretching at a high stretch factor of 4 (e.g. by means of dry stretching) could result in a much shorter length upon hydration (such as, for example, a reduction in length from 15 to 8 mm). No stretching may result in certain instances in a maintenance or even an increase of the implant length upon hydration. One skilled in the art will appreciate that other factors besides stretching can also affect swelling behavior.

In one or more embodiment(s), the implants of the present invention are treated by wet stretching at a stretch factor of about 0.5 to about 5, or a stretch factor of about 1 to about 4, or a stretch factor of about 1.3 to about 3.5, or a stretch factor of about 1.7 to about 3, or a stretch factor of about 2 to about 2.5. In particular embodiments, wet stretching is performed with a stretch factor of from about 1.3 to about 1.5.

Among other factors influencing the possibility to stretch the hydrogel and to elicit dimensional change of the implant upon hydration is the composition of the polymer network. In the case PEG precursors are used, those with a lower number of arms (such as 4-armed PEG precursors) contribute in providing a higher flexibility in the hydrogel than those with a higher number of arms (such as 8-armed PEG precursors). If a hydrogel contains more of the less flexible components (e.g. a higher amount of PEG precursors containing a larger number of arms, such as the 8-armed PEG units), the hydrogel may be firmer and less easy to stretch without fracturing. On the other hand, a hydrogel containing more flexible components (such as PEG precursors containing a lower number of arms, such as 4-armed PEG units) may be easier to stretch and softer, but may also swell more upon hydration. Thus, the behavior and properties of the implant once it has been placed into the eye (i.e., once the hydrogel becomes (re-)hydrated) can be tailored by means of varying structural features as well as by modifying the processing, such as the stretching, of the implant after it has been initially formed.

Exemplary dimensions of implants used in the Examples herein below are provided in the Examples section. Implants may however also have dimensions (i.e., lengths and/or diameters) differing from the dimensions disclosed in the Tables in the Examples, even in case they contain a similar TKI drugload. The dried implant dimensions inter alia depend on the amount of TKI incorporated as well as the ratio of TKI to polymer units and can also be controlled by the diameter and shape of the mold or tubing in which the hydrogel is allowed to gel. Furthermore, the diameter of the implant is additionally influenced inter alia by (wet or dry) stretching of the hydrogel strand once formed. The dried strand (after stretching) is cut into segments of the desired length to form the implant; the length can thus be chosen as desired.

In certain embodiments, the implants of the present invention have a high aspect ratio, i.e., a high ratio of length to width (the width being the largest cross-sectional dimension and the length being the longest elongation of an implant). In certain embodiments, the aspect ratio may be at least 5:1, such as at least 10:1, such as at least 15:1, such as at least 20:1.

In certain embodiments of the invention where the implant does not have a round or essentially round cross-section (such as in the case an implant is not a cylinder or essentially a cylinder), the respective cross-sectional dimension is referred to as the “width”. All values and value ranges disclosed herein for the diameter of an implant are expressly and equally applicable to the width of an implant in case the implant is not cylindrical or essentially cylindrical.

In certain embodiments, an implant of the present invention may have in its dry state a length of less than about 17 mm. In specific embodiments, the length of an implant in its dry state may be less than about 15 mm, or less than or equal to about 12 mm, or less than or equal to about 11 mm, or less than or equal to about 10 mm, or less than or equal to about 9, or less than or equal to about 8.5 mm. In specific embodiments, an implant of the present invention may have in its dry state a length of about 6 mm to about 10 mm or of about 6 mm to about 9 mm.

In certain embodiments, an implant of the present invention may have in its dry state a diameter/width of less than about 0.7 mm, such as from about 0.1 mm to about 0.65 mm, or from about 0.20 mm to about 0.55 mm, or from about 0.2 mm to about 0.5 mm, or from about 0.20 mm to about 0.45 mm, or from about 0.30 mm to about 0.45 mm, or from about 0.30 to about 0.40 mm, or from about 0.31 to about 0.36 mm.

In particular embodiments, an implant in its dry state may have a length of about 5 mm to about 12 mm and a diameter of about 0.2 to about 0.7 mm.

In further particular embodiments, an implant in its dry state may have a length of about 6 mm to about 10 mm and a diameter of about 0.2 to about 0.5 mm. In very particular embodiments, an implant in its dry state may have a length of from about 6 mm to about 9 mm and a diameter of from about 0.25 mm to about 0.45 mm.

In yet more particular embodiments, an implant in its dry state may have a length of from 6.5 mm to 8.5 mm, such as from 6.7 to 7.8 mm, and a diameter of from 0.30 to 0.40 mm, such as from 0.31 to 0.36 mm.

In certain embodiments, an implant of the present invention may have in its well hydrated state (i.e., after 24 hours in phosphate-buffered saline at a pH of 7.2-7.4 at 37° C.) a length of about 14 mm or less.

In particular embodiments, an implant of the present invention may have in its wet/hydrated state a length of equal to or less than about 12 mm, or equal to or less than about 11 mm, or equal to or less than about 10 mm, or may have a length of from about 4 mm to about 12 mm, or from about 4 mm to about 11 mm, or from about 6 mm to about 11 mm, or from about 6 mm to about 10 mm, or from about 6 mm to about 9 mm. Particularly suitable implants of the present invention are those that have a hydrated length of less than about 11 mm, such as about 10 mm or less.

In certain embodiments, an implant of the present invention may have in its wet/hydrated state a diameter of about 1.2 mm or less, or of about 1 mm or less, or of about 0.8 mm or less. In particular embodiments, an implant of the present invention may have a diameter in its wet/hydrated state of from about 0.5 mm to about 0.9 mm, or from about 0.5 mm to about 0.8 mm, of from about 0.7 mm to about 0.8 mm. In very particular embodiments, an implant in its wet/hydrated state may have a length of from about 7 mm to 10 mm and a diameter of from about 0.5 mm to 0.9 mm.

In yet more particular embodiments, an implant of the present invention may have in its wet/hydrated state a length of from about 8 mm to about 9 mm and a diameter of from about 0.70 mm to about 0.80 mm.

Whenever herein a length or a diameter/width of an implant of the invention in the wet/hydrated state is disclosed (in mm), this disclosure refers to the implant’s length or the diameter/width, respectively, determined after 24 hours in PBS at 37° C. at pH 7.2 to 7.4. The dimensions of an implant may further change (e.g. the length may increase slightly again) over the course of time (i.e., after 24 hours) when the implant remains in these conditions. However, whenever hydrated dimensions of an implant are reported herein, these are measured after 24 hours at a pH of 7.2 to 7.4 at 37° C. in PBS as disclosed above.

In embodiments of the present invention, the diameter or width of an implant in its dry state is ideally such that the implant can be loaded into a thin-diameter needle as disclosed herein, such as a 25-gauge or 27-gauge needle. Specifically, in one embodiment an implant containing from about 480 μg to about 750 μg axitinib, or containing from about 360 μg to about 562.5 μg axitinib, such as about 450 μg axitinib may have a diameter such that it can be loaded into a 25-gauge needle. In another embodiment, such implant can be loaded into a 27-gauge needle without afflicting any damage to the implant while loading, and such that the implant remains stably in the needle during further handling (including packaging, sterilization, shipping etc.).

In case several measurements of the length or diameter of one implant are conducted, or several datapoints are collected during the measurement, the average (i.e., mean) value is reported as defined herein. The length and diameter of an implant according to the invention (whether in the dry or in the hydrated/wet state) may be measured e.g. by means of microscopy, or by means of an (optionally automated) camera system as described in Example 6.1 of WO 2021/195163.

In certain embodiments, an implant of the present invention may have a ratio of the diameter in the hydrated state to the diameter in the dry state of less than about 5 mm, or less than about 4 mm, or less than about 3.25 mm, or less than about 2.5 mm, or less than about 2.25 mm, or about 2.0 mm to about 2.5 mm.

In certain same or other embodiments, an implant of the present invention may have a ratio of the length in the dry state to the length in the hydrated state of greater than about 0.6, or greater than about 0.7, or greater than about 0.8, or greater than about 0.9, or greater than about 1.0. This ratio of length in the dry state to length in the hydrated state may apply in addition to, or independently of, the ratio of the diameter in the hydrated state to the diameter in the dry state disclosed above.

In one embodiment, an implant of the present invention contains from about 360 μg to about 562.5 μg axitinib, or from about 405 μg to about 495 μg, or about 450 μg axitinib free base in the form of polymorph IV, is in the form of a fiber (cylinder) and has a length of from about 6 mm to about 9 mm and a diameter of from about 0.25 mm to about 0.45 mm in the dried state. Such an implant upon hydration in vivo in the eye, such as in the vitreous humor, or in vitro (wherein hydration in vitro is measured in phosphate-buffered saline at a pH of 7.2 at 37° C. after 24 hours) may have a length of from about 7 mm to about 9 mm and a diameter of from about 0.65 mm to about 0.80 mm. In one embodiment, this dimensional change may be achieved by wet stretching as disclosed herein at a stretch factor of between 1.25 and 3.

In another embodiment, an implant of the present invention contains from about 360 μg to about 562.5 μg axitinib, or from about 400 μg to about 500 μg, or from about 405 μg to about 495 μg, or about 450 μg axitinib free base in the form of polymorph IV, and has a length of from about 5 mm to about 11 mm and a diameter of from about 0.28 mm to about 0.38 mm in the dried state. Such an implant upon hydration in vivo in the eye, such as in the vitreous humor, or in vitro (wherein hydration in vitro is measured in phosphate-buffered saline at a pH of 7.2 at 37° C. after 24 hours) may have a hydrated length of from about 5 mm to about 11 mm and a hydrated diameter/width of from about 0.4 mm to about 2 mm. In certain embodiments, this dimensional change may be achieved by wet stretching as disclosed herein at a stretch factor of between 1.0 and 3.0.

In particular embodiments, an implant of the present invention contains from about 360 μg to about 562.5 μg axitinib, or from about 400 μg to about 500 μg, or from about 405 μg to about 495 μg, or about 450 μg axitinib free base in the form of polymorph IV, is in the form of a fiber (cylinder) and has a length of from about 6 mm to about 9 mm and a diameter of from about 0.30 mm to about 0.35 mm in the dried state. Such an implant upon hydration in vivo in the eye, such as in the vitreous humor, or in vitro (wherein hydration in vitro is measured in phosphate-buffered saline at a pH of 7.2 at 37° C. after 24 hours) may have a hydrated length of from about 6 mm to about 10 mm and a hydrated diameter of from about 0.5 mm to about 0.90 mm. In one embodiment, this dimensional change may be achieved by wet stretching as disclosed herein at a stretch factor of between 1.2 and 1.5. Such an implant may have a hydrated surface area of from about 17.0 to about 23.0 $mm^2$.

In another embodiment, an implant of the present invention contains from about 200 to 1000 μg, 300 to 1000 μg, 480 μg to about 750 μg, or from about 540 μg to about 660 μg, or about 600 μg axitinib free base in the form of polymorph IV, is in the form of a fiber (cylinder) and has a length of from about 7 mm to less than 10 mm and a diameter of from about 0.25 mm to about 0.45 mm in the dried state. Such an implant upon hydration in vivo in the eye, such as in the vitreous humor, or in vitro (wherein hydration in vitro is measured in phosphate-buffered saline at a pH of 7.2 at 37° C. after 24 hours) may have a length of from about 8 mm to less than 10 mm and a diameter of from about 0.65 mm to about 0.9 mm. In one embodiment, this dimensional change may be achieved by wet stretching as disclosed herein at a stretch factor of between 1.25 and 3.

In one embodiment, the length of an implant of the present invention that contains from about 300 to about 700 μg of axitinib, such as about 300 μg, about 450 μg or about 600 μg axitinib in the dried state is no longer than 10 mm, and in the hydrated state (as measured in phosphate-buffered saline at a pH of 7.2 at 37° C. after 24 hours) is also no longer or not substantially longer than about 11 mm, or no longer than about 10 mm, or no longer than about 9 mm.

In certain embodiments of the invention, particularly when the implant contains axitinib, such as axitinib polymorph IV, in an amount of about 400 to about 500 μg (or any subrange or dose within that range as disclosed herein) the implant has a hydrated surface area (which is calculated from the hydrated dimensions, as measured in vitro in phosphate-buffered saline at a pH of 7.2-7.4 at 37° C. after 24 hours, as explained above) of at least 15.0 $mm^2$, such as at least 16.0 $mm^2$, such as from about 16.0 to about 25.0 $mm^2$, such as from about 16.0 to about 23.0 $mm^2$. In certain further embodiments, the hydrated surface area may also be from about 17.0 to about 23.0 $mm^2$, particularly from about 18.0 to about 22.5 $mm^2$. In any of these embodiments, the implant may be cylindrical or essentially cylindrical, i.e., may have a round or essentially round cross-sectional area.

In an alternative embodiment, an implant of the present invention is created in situ in the eye, such as in the vitreous. In this case, solutions containing the precursors (such as those disclosed herein for manufacturing implants by means of wet casting) are combined only shortly before the combined solutions are injected into the eye. After combining the precursor (TKI and polymer precursors, and optionally buffer) solutions, optionally already in a syringe or another injection device, the combined solution has to be injected into the eye prior to complete gelling of the hydrogel, i.e., while the content of the syringe is still liquid enough to be readily and completely injected without plugging the needle. Alternatively, in situ gelation can be triggered to occur after injection, e.g. by means of exposure to physiological conditions such as moisture, pH, temperature, light etc. The gelling/crosslinking of the hydrogel is then completed inside the eye, such as inside the vitreous, and an implant is formed which has a roughly spheroidal shape but no defined dimensions such as a defined length and diameter, or a defined hydrated surface area.

Multi-Filament:

In certain embodiments, an implant according to the present invention is composed of/comprises at least two filaments. In specific embodiments, such an implant comprises at least 3 or at least 4 filaments, and/or up to 20, or up to 15, or up to 12 filaments. In particular embodiments, an implant comprises from 2 to 8, or from 3 to 7 filaments, or comprises 2, 3, 4, 5, 6, 7, or 8 filaments. The individual filaments may have a composition (amount/percentage of TKI and of PEG units etc.) as disclosed herein for (single stranded) implants of the invention and may also be produced in the same way as the (single-stranded) implants, as disclosed herein (i.e., either by wet casting or by hot melt extrusion). The filaments comprised in one composite implant may be identical, or may be different (including but not limited to differences in their composition and/or their (wet and/or dry) dimensions and/or their geometry). The individual filaments may for example also contain different forms (Including, but not limited to different polymorphic forms) of the same active and/or may contain different actives.

In certain embodiments, the individual filaments may then be combined into the composite strand by means of a heat-stretch-twist procedure as exemplified in Example 3. In another embodiment, the individual filaments are braided to form one braided strand. In a further embodiment, the individual filaments are attached to each other by other means, such as by adhering them via another material, for example a linear PEG. Said adhesive material may or may not dissolve after injection of the implant into physiological environment (such as the eye, such as the vitreous humor). In case said adhesive material dissolves, the individual filaments dissociate from one another once the implant has been placed into the physiological environment. Multi-filaments can also be attached to each other or be formed in a shape where there are connected to one another by other means.

The filaments may be combined into one composite implant by twisting them, so as to form one twisted strand. Such composite (twisted) strand may have a composite diameter in the dried state that is within the same range as the diameter of a single-stranded implant, as disclosed herein. In certain embodiments, the composite diameter of the twisted strand in its dried state is from 0.2 to 0.8 mm, or from 0.2 to 0.5 mm, or from 0.3 to 0.4 mm, or from 0.33 to 0.38 mm. In certain same or other embodiments, the diameter of an individual filament in the dried state is less than 0.3 mm, or less than 0.25 mm, or less than 0.2 mm, or less than 0.15 mm. Like a single-stranded implant, a multi-filament implant may also be loaded into a needle for injection into the eye, such as into the vitreous, with needle gauges ranging from 20 to 30, such as from 25 to 27, or 25, or 27, or 30.

In certain embodiments, in a twisted composite implant of the present invention comprising at least two filaments, upon hydration (in vivo or in vitro) the twisted strand may completely or partially unfurl, thus exposing the individual filaments. Thereby, a multi-filament implant effectively provides for an increased hydrated surface area (corresponding to the sum of the hydrated surface areas of the individual filaments) thereby increasing the rate of release of the TKI from the implant. In particular embodiments, the hydrated surface area of a multi-filament implant may be at least 2 times, such as at least 3 times, or at least 4 times larger than the hydrated surface area of a single-stranded implant containing the same drugload of TKI and having essentially similar composite dimensions (composite diameter and length) in the dry state. Accordingly, the release rate (amount of TKI released per day, and/or the average release rate per day over a certain number of days) of a multi-filament implant containing the same drugload of TKI and having essentially similar composite dimensions (composite diameter and length) in the dry state as a single-stranded implant is higher, such as at least 10%, or at least 20%, or at least 30% higher than that of the corresponding single-stranded implant. In other words, by means of a multi-filament composite implant multiple implants can be administered by one single injection, resulting in an increased release rate of the API.

In certain embodiments of a twisted multi-filament implant according to the present invention, the number of twists per cm (of the final twisted implant) is at least about 1 or at least about 2, or at least about 5, or is at least about 8, or is at least about 10 and/or is up to about 20, or up to about 15.

The multi-filament implants are produced from individual filaments (that are produced in accordance with the manufacturing methods disclosed herein) as disclosed in the section "Manufacture of the implant".

Multi filament implants can be used with any aspect of the invention, as long as the respective requirements are met, e.g. as long as the solubility of the TKI is greater than 0.3 μg/ml as measured in phosphate-buffered saline (PBS) at a pH of 7.2 to 7.4 and 37° C. after five days of incubation (for this particular aspect of the invention), or as long as the hydrated surface area of the implant is at least 25 $mm^2$ as measured in phosphate-buffered saline (PBS) at a pH of 7.2 to 7.4 and 37° C. after 24 hours of incubation (for this particular aspect of the invention). In case the TKI Incorporated in these multi-filament implants is axitinib, axitinib in any of its forms disclosed herein can be contained (again, as long as the respective features of the particular aspects of the invention are fulfilled).

In certain embodiments multifilament implants comprise a linear PEG at 5% to 30% (w/w) such as 10% to 20% (w/w) of the dried implant.

In Vitro Release:

The in vitro-release of TKI such as axitinib from the implants of the invention can be determined by various in vitro methods (see also the Examples section, and see the Definitions section of this application for further explanations):

In one particular in vitro test, the study implant(s) is/are placed into a certain volume of a solvent mixture of 25% ethanol/75% water (v/v), and at a certain temperature (37° C., or another temperature if this is specifically mentioned) as disclosed herein. The released amount or percentage of TKI such as axitinib is determined on several pre-determined days. The volume of solvent is calculated by using the "sink factor" as defined in the "Definitions" section. In vitro tests reported in the present invention may be conducted under various sink conditions. In certain embodiments, the in vitro tests may be performed, as disclosed herein, under 2× sink conditions, or under 3× sink conditions, or with a higher sink factor. "2× sink conditions" means that the volume of solvent (mixture) into which an implant according to the invention is immersed (or several implants if so indicated) for the specific test is two times the "sink volume" (as defined above), i.e., the "sink factor" in this case would be 2. The same applies analogously to any other sink factors. The sink volume is the ratio of the amount of TKI contained in the implant [μg] to the solubility of the TKI in the employed solvent (mixture), i.e., in 25% ethanol/75% water (v/v) as also defined in the "Definitions" section.

In certain embodiments, for in vitro tests reported in the present application that use 2× sink conditions (such as "Method A" referred to in the Examples), the sink volume is calculated by dividing the amount (in μg) of axitinib contained in the study implant by a mean solubility value of 18.3 μg/mL. In these embodiments, this mean solubility value is thus used regardless of which axitinib polymorph is employed in the study implant, for example regardless of whether polymorph IV or polymorph SAB-I is used.

In certain embodiments, for in vitro tests reported in the present application that use 3× sink conditions (such as "Method B" referred to in the Examples), the sink volume is calculated by dividing the amount (in μg) of axitinib contained in the study implant by a solubility value of 13.41 μg/ml (in case axitinib polymorph SAB-I is used) or a solubility value of 20.09 μg/ml (in case axitinib polymorph IV is used).

Concretely, an in vitro test in accordance with the invention for implants containing axitinib is conducted as follows ("Method A" or "Method B"): 1 L of the 25%: 75% ethanol/water solvent mixture (also referred to herein as "buffer") is created and allowed to equilibrate. The study implant is put in an amber jar. For 2× sink conditions, the volume of buffer added to the implant equals 2 times the volume corresponding to the ratio of the TKI amount [μg] divided by the axitinib solubility [μg/mL] (which, in certain embodiments, is a mean value 18.3 μg/ml for axitinib free base as explained above). For 3× sink conditions, the volume of buffer added to the implant equals 3 times the volume corresponding to the ratio of the TKI amount [μg] divided by the axitinib solubility [μg/mL] (which, in certain embodiments, is 13.41 μg/mL for the case the TKI is axitinib polymorph SAB-I or is 20.09 μg/mL for the case the TKI is axitinib polymorph IV). By means of example, in case an implant contains 600 μg axitinib polymorph SAB-L, and the in vitro test is to be run under 3× sink conditions, 134 ml of 25%/75% ethanol/water mixture is used as the volume in which the study implant is immersed (i.e., 600 μg divided by 13.41 μg/mL, multiplied by a factor of 3). While the in vitro test is running, the jar containing the implant in the respective volume of buffer is stored in a 37° C. incubator on a rocker plate to provide moderate agitation, 1 ml of buffer solution is taken and replaced on each of the sampling days. The buffer solution is analyzed either by UV-VIS (in certain embodiments, for the tests performed under 2× sink conditions) or by UPLC (in certain embodiments, for the tests performed under 3× sink conditions) against analytical standards prepared within the last 2 weeks.

Furthermore, the in vitro-release of TKI, and particularly of axitinib, from the implants of the invention can also be determined by another accelerated in vitro method ("Method C"), as follows (see also the Examples section):

The dissolution medium for this accelerated in vitro release test is 0.01N HCl with 0.25% cetyl trimethyl ammonium bromide (CTAB). The test is performed in a USP apparatus 4 at a temperature of 35° C. Suitable test parameters are specified in the following:

| Parameters | Description |
|---|---|
| Apparatus | USP Apparatus 4 (Flow-through cell) setup as closed system |
| Cell type | 22.6 mm diameter |
| Cell setup laminar flow | laminar flow with 1 implant between two scoops of glass beads |
| Medium | 0.01N HCl with 0.25% CTAB |
| Volume | 100 mL |
| Speed rate | 8 mL/min |
| Temperature | 35° C. (±0.5° C.) |
| Sample | 1 implant |
| Filtration | non |

Sampling time points may be chosen as desired, such as at one or more time points of the following: 0.5, 1, 2, 4, 6, 8, 10, 12, 16, 24, 36, 48, 60, and 83 hours. The samples are analyzed by UPLC against analytical standards. If several (such as n=6) samples of one product (e.g. same production lot) are measured, an average release can be determined.

In Vitro Release of Implants Containing Axitinib in an In Vitro Test Performed at 37° C. in an 25%/75% (v/v) Ethanol/Water Mixture Under 2× Sink Conditions as Disclosed Herein:

In certain embodiments of the present invention, an implant contains axitinib as the TKI, in any of the forms disclosed herein, and exhibits one or more of the following release characteristics in the in vitro release test performed at 37° C. in an 25%/75% (v/v) ethanol/water mixture under 2× sink conditions as disclosed herein (this test is also referred to as "Method A" in the Examples):

In certain embodiments, an implant of the present invention releases axitinib at an average rate of at least about 60 μg/day over the initial day, and/or of at least about 55 μg/day over the initial 2 days, and/or at least about 45 μg/day over the initial 5 days, and/or at least about 40 μg/day over the initial 7 days, and/or at least about 40 μg/day over the initial 10 days.

In certain same or other embodiments, the implant releases at least 40%, or at least 44% of the total released amount of axitinib over the initial 3 days, and/or releases at least 70% of the total released amount of axitinib over the initial 7 days, and/or releases at least 90% of the total released amount of axitinib over the initial 10 days.

In certain particular embodiments, the implant contains axitinib in an amount corresponding to from about 480 μg to about 750 μg, or about 600 μg axitinib free base and releases at least 40% of the total released amount of axitinib over the initial 3 days, and/or the implant contains axitinib in an amount corresponding to from about 360 μg to about 562.5 μg, or about 450 μg axitinib free base and releases at least 50% of the total released amount of axitinib in the implant over the initial 3 days, and/or the implant contains axitinib in an amount corresponding to from about 240 μg to about 375 μg, or about 300 μg axitinib free base and releases at least 60% of the total released amount of axitinib over the initial 3 days, and/or the implant contains axitinib in an amount corresponding to from about 120 μg to about 187.5 μg, or about 150 μg axitinib free base and releases at least 90% of the total released amount of axitinib over the initial 3 days.

In certain same or other particular embodiments, the implant contains axitinib in an amount corresponding to from about 480 μg to about 750 μg, or about 600 μg axitinib free base and releases at least 70% of the total released amount of axitinib over the initial 7 days, and/or the implant contains axitinib in an amount corresponding to from about 360 μg to about 562.5 μg, or about 450 μg axitinib free base and releases at least 80% of the total released amount of axitinib over the initial 7 days, and/or the implant contains axitinib in an amount corresponding to from about 240 μg to about 375 μg, or about 300 μg axitinib free base and releases at least 85% of the total released amount of axitinib over the initial 7 days, and/or the implant contains axitinib in an amount corresponding to from about 120 μg to about 187.5 μg, or about 150 μg axitinib free base and releases at least 95% of the total released amount of axitinib over the initial 7 days.

In certain same or other particular embodiments, the implant contains axitinib in an amount corresponding to from about 480 μg to about 750 μg, or about 600 μg axitinib free base and releases at least 90% of the total released amount of axitinib over the initial 10 days, and/or the implant contains axitinib in an amount corresponding to from about 360 μg to about 562.5 μg, or about 450 μg axitinib free base and releases at least 92% of the total released amount of axitinib over the initial 10 days, and/or the implant contains axitinib in an amount corresponding to from about 240 μg to about 375 μg, or about 300 μg axitinib free base and releases at least 95% of the total released amount of axitinib over the initial 10 days, and/or the implant contains axitinib in an amount corresponding to from about 120 μg to about 187.5 μg, or about 150 μg axitinib free base and releases at least 98% of the total released amount of axitinib over the initial 10 days.

In certain embodiments, an implant releases at least about 65 μg axitinib in the initial day, and/or at least about 120 μg over the initial 2 days.

In certain particular embodiments, an implant of the present invention contains axitinib corresponding to an amount of from about 480 μg to about 750 μg axitinib, or about 600 μg axitinib free base, and releases at least about 75 μg, or at least about 90 μg, or at least about 100 μg axitinib over the initial day, and/or releases at least about 125 μg, or at least about 150 μg, or at least about 140 μg axitinib over the initial 2 days, and/or releases at least about 150 μg, or at least about 180 μg, or at least about 200 μg axitinib over the initial 3 days, and/or releases at least about 275 μg, or at least about 300 μg, or at least about 375 μg axitinib over the initial 7 days, and/or releases at least about 350 μg, or at least about 400 μg, or at least about 450 μg axitinib over the initial 10 days.

In certain other particular embodiments, an implant of the present invention contains axitinib corresponding to an amount of from about 360 μg to about 562.5 μg axitinib, or about 450 μg axitinib free base, and releases at least about 60 μg, or at least about 70 μg, or at least about 80 μg axitinib over the initial day, and/or releases at least about 100 μg, or at least about 120 μg, or at least about 130 μg axitinib over the initial 2 days, and/or releases at least about 130 μg, or at least about 150 μg, or at least about 180 μg axitinib over the initial 3 days, and/or releases at least about 220 μg, or at least about 260 μg, or at least about 290 μg axitinib over the initial 7 days, and/or releases at least about 275 μg, or at least about 300 μg, or at least about 350 μg axitinib over the initial 10 days.

In certain other particular embodiments, an implant of the present invention contains axitinib corresponding to an amount of from about 240 μg to about 375 μg axitinib, or about 300 μg axitinib free base, and releases at least about 60 μg, or at least about 65 μg, or at least about 70 μg axitinib over the initial day, and/or releases at least about 90 μg, or at least about 110 μg, or at least about 130 μg axitinib over the initial 2 days, and/or releases at least about 120 μg, or at least about 140 μg, or at least about 180 μg axitinib over the initial 3 days, and/or releases at least about 200 μg, or at least about 240 μg, or at least about 270 μg axitinib over the initial 7 days, and/or releases at least about 250 μg, or at least about 275 μg, or at least about 300 μg axitinib over the initial 10 days.

In certain other particular embodiments, an implant of the present invention contains axitinib corresponding to an amount of from about 120 μg to about 187.5 μg axitinib, or about 150 μg axitinib free base, and releases at least about 75 μg, or at least about 85 μg, or at least about 90 μg, or at least about 100 μg axitinib over the initial day, and/or releases at least about 90 μg, or at least about 100 μg, or at least about 115 μg axitinib over the initial 2 days.

In certain embodiments the implant contains from about 240 μg to about 375 μg axitinib and releases at least about 90% of the total released amount of axitinib over the initial 7, or the initial 10 days.

In certain embodiments the implant contains from about 480 μg to about 750 μg axitinib and releases at least about 90% of the total released amount of axitinib over the initial 10 days, or the initial 14 days.

In certain embodiments the implant contains from about 120 μg to about 187.5 μg axitinib and releases at least about 90% of the total released amount of axitinib over the initial 2, or the initial 3 days.

In certain embodiments the implant contains from about 360 μg to about 562.5 μg axitinib and releases at least about 90% of the total released amount of axitinib over the initial 8 days, or the initial 9 days.

In certain embodiments, for the release characteristics determined in the in vitro test under 2× sink conditions as reported above in this section, the volume of the 25%/75% (v/v) ethanol/water solvent mixture is twice the volume calculated by the ratio of the amount of axitinib contained in the implant [μg] divided by a mean solubility value [μg/mL] of axitinib of 18.3 μg/mL.

In Vitro Release of Implants Containing Axitinib in an In Vitro Test Performed at 37° C. in an 25%/75% (v/v) Ethanol/Water Mixture Under 3× Sink Conditions as Disclosed Herein:

In certain embodiments of the present invention, an implant contains axitinib as the TKI, in any of the forms disclosed herein, and exhibits one or more of the following release characteristics in the in vitro release test performed at 37° C. in an 25%/75% (v/v) ethanol/water mixture under 3× sink conditions as disclosed herein (this test is also referred to as "Method B" in the Examples):

In certain embodiments, the implant of the present invention comprises axitinib and releases axitinib at an average rate of at least about 40 μg/day over the initial day and/or of at least about 35 μg/day over the initial 2 days and/or at least about 30 μg/day over the initial 4 days and/or at least about 25 μg/day over the initial 7 days.

In certain embodiments, the implant of the present invention comprises axitinib and releases at least 25%, or at least 30%, or at least 34% of the total released amount of axitinib over the initial 4 days.

In certain embodiments, the implant of the present invention contains axitinib in an amount corresponding to from about 480 μg to about 750 μg, or about 600 μg axitinib free base and releases at least 35% of the total released amount of axitinib over the initial 4 days, and/or the implant contains axitinib in an amount corresponding to from about 360 μg to about 562.5 μg, or about 450 μg axitinib free base and releases at least 30% of the total released amount of axitinib over the initial 4 days, and/or the implant contains axitinib in an amount corresponding to from about 240 μg to about 375 μg, or about 300 μg axitinib free base and releases at least 30% of the total released amount of axitinib over the initial 4 days, and/or the implant contains axitinib in an amount corresponding from about 120 μg to about 187.5 μg, or about 150 μg axitinib free base and releases at least 60% of the total released amount of axitinib over the initial 4 days.

In certain embodiments, the implant of the present invention contains axitinib and releases at least 40%, or at least 50% of the total released amount of axitinib over the initial 7 or the initial 9 days.

In certain embodiments, the implant contains axitinib in an amount corresponding to from about 480 μg to about 750 μg, or about 600 μg axitinib free base and releases at least 50% of the total released amount of axitinib over the initial 7 or the initial 9 days, and/or the implant contains axitinib in an amount corresponding to from about 360 μg to about 562.5 μg, or about 450 μg axitinib free base and releases at least 50% of the total released amount of axitinib over the initial 7 or the initial 9 days, and/or the implant contains axitinib in an amount corresponding to from about 240 μg to about 375 μg, or about 300 μg axitinib free base and releases at least 50% of the total released amount of axitinib over the initial 7 or the initial 9 days, and/or the implant contains axitinib in an amount corresponding to from about 120 μg to about 187.5 μg, or about 150 μg axitinib free base and releases at least 90% of the total released amount of axitinib over the initial 7 or the initial 9 days.

In certain embodiments, the implant contains axitinib in an amount corresponding to an amount of from about 480 μg to about 750 μg, or about 600 μg axitinib free base, and releases at least about 40 μg, or at least about 50 μg, or at least about 55 μg axitinib over the initial day, and/or releases at least about 80 μg, or at least about 100 μg, or at least about 120 μg axitinib over the initial 2 days, and/or releases at least about 160 μg, or at least about 190 μg, or at least about 200 μg axitinib over the initial 4 days, and/or releases at least about 290 μg, or at least about 300 μg, or at least about 350 μg axitinib over the initial 7 days, and/or releases at least about 300 μg, or at least about 330 μg axitinib over the initial 9 days.

In certain embodiments, the implant contains axitinib in an amount corresponding to an amount of from about 360 μg to about 562.5 μg, or about 450 μg axitinib free base, and releases at least about 35 μg, or at least about 40 μg, or at least about 45 μg axitinib over the initial day, and/or releases at least about 60 μg, or at least about 70 μg, or at least about 80 μg axitinib over the initial 2 days, and/or releases at least about 100 μg, or at least about 120 μg, or at least about 150 μg axitinib over the initial 4 days, and/or releases at least about 180 μg, or at least about 200 μg, or at least about 240 μg axitinib over the initial 7 days, and/or releases at least about 200 μg, or at least about 250 μg, or at least about 270 μg axitinib over the initial 9 days.

In certain embodiments, the implant contains axitinib in an amount corresponding to an amount of from about 240 μg to about 375 μg, or about 300 μg axitinib free base, and releases at least about 30 μg, or at least about 35 μg, or at least about 40 μg axitinib over the initial day, and/or releases at least about 50 μg, or at least about 60 μg, or at least about 70 μg axitinib over the initial 2 days, and/or releases at least about 80 μg, or at least about 100 μg, or at least about 120 μg axitinib over the initial 4 days, and/or releases at least about 150 μg, or at least about 160 μg, or at least about 180 μg axitinib over the initial 7 days, and/or releases at least about 160 μg, or at least about 180 μg, or at least about 200 μg axitinib over the initial 9 days.

In certain embodiments, the implant contains axitinib in an amount corresponding to an amount of from about 120 μg to about 187.5 μg, or about 150 μg axitinib free base, and releases at least about 60 μg, or at least about 70 μg, or at least about 80 μg axitinib over the initial day, and/or releases at least about 90 μg, or at least about 100 μg, or at least about 120 μg axitinib over the initial 2 days.

In certain embodiments the implant contains about 240 μg to about 375 μg axitinib and releases at least about 85%, or at least about 90% of the total released amount of axitinib over the initial 14 days.

In certain embodiments the implant contains from about 480 μg to about 750 μg axitinib and releases at least about 90% of the total released amount of axitinib over the initial 16 days, or the initial 18 days.

In certain embodiments the implant contains about 120 μg to about 187.5 μg axitinib and releases at least about 90% of the total released amount of axitinib over the initial 7 days.

In certain embodiments the implant contains from about 360 μg to about 562.5 μg axitinib and releases at least about 90% of the total released amount of axitinib over the initial 14 to 16 days.

In certain embodiments, for the release characteristics determined in the in vitro test under 3× sink conditions as reported above in this section, the volume of the 25%/75% (v/v) ethanol/water solvent mixture is three times the volume determined by the ratio of the amount of axitinib contained in the implant [μg] divided by the solubility of axitinib polymorph SAB-I in the said solvent mixture of 13.41 μg/mL (if polymorph SAB-I is used), and for the solubility of axitinib polymorph IV of 20.09 μg/mL (if polymorph IV is used).

Any in vitro release tests, especially the accelerated in vitro release tests described herein, may also be used inter alia to compare different implants (e.g. of different production batches, of different composition, and of different dosage strength etc.) with each other, for example for the purpose of quality control or other qualitative assessments.

In Vitro Release of Implants Containing Axitinib in an Accelerated In Vitro Test Performed at 35° C.±0.5° C. in 0.01N HCl with 0.25% CTAB in a USP Apparatus 4 as Disclosed Herein ("Method C"):

In some embodiments of the present invention, an implant containing axitinib is characterized in that the percentage of axitinib released from the implant in an in vitro test performed at 35° C.±0.5° C. in 0.01N HCl with 0.25% cetyl trimethyl ammonium bromide (CTAB) in a USP apparatus 4 is:

from about 10 to about 25% after 0.5 hours,
from about 30 to about 50% after 2 hours,
from about 60 to about 90% after 6 hours,
from about 79 to about 100% after 10 hours,
at least about 90% after 12 hours,
and/or at least about 92% after 16 hours;

or is characterized in that the percentage of axitinib released from the implant in an in vitro test performed at 35° C.±0.5° C. in 0.01N HCl with 0.25% cetyl trimethyl ammonium bromide (CTAB) in a USP apparatus 4 is:

from about 10 to about 25% after 0.5 hours,
from about 19 to about 35% after 1 hour,
from about 30 to about 50% after 2 hours,
from about 55 to about 70% after 4 hours,
from about 60 to about 90% after 6 hours,
from about 78 to about 95% after 8 hours,
from about 79 to about 100% after 10 hours,
at least about 90% after 12 hours,
and/or at least about 92% after 16 hours.

In certain embodiments of the present invention, an implant containing axitinib is characterized in that the percentage of axitinib released from the implant in an in vitro test performed at 35° C.±0.5° C. in 0.01N HCl with 0.25% cetyl trimethyl ammonium bromide (CTAB) in a USP apparatus 4 is:

from about 10 to about 18% after 0.5 hours,
from about 30 to about 45% after 2 hours,
from about 60 to about 80% after 6 hours,
from about 79 to about 98% after 10 hours,
at least about 90% after 12 hours,
and/or at least about 92% after 16 hours;

or is characterized in that the percentage of axitinib released from the implant in an in vitro test performed at 35° C.±0.5° C. in 0.01N HCl with 0.25% cetyl trimethyl ammonium bromide (CTAB) in a USP apparatus 4 is:

from about 10 to about 18% after 0.5 hours,
from about 19 to about 27% after 1 hour,
from about 30 to about 45% after 2 hours,
from about 55 to about 65% after 4 hours,
from about 60 to about 80% after 6 hours,
from about 78 to about 90% after 8 hours,
from about 79 to about 98% after 10 hours,
at least about 90% after 12 hours,
and/or at least about 92% after 16 hours.

In certain embodiments of the present invention, an implant containing axitinib is characterized in that the percentage of axitinib released from the implant in an in vitro test performed at 35° C.±0.5° C. in 0.01N HCl with 0.25% cetyl trimethyl ammonium bromide (CTAB) in a USP apparatus 4 is:

from about 12 to about 17% after 0.5 hours,
from about 32 to about 42% after 2 hours,
from about 62 to about 78% after 6 hours,
from about 83 to about 97% after 10 hours,
and/or at least about 94% after 16 hours;

or is characterized in that the percentage of axitinib released from the implant in an in vitro test performed at 35° C.±0.5° C. in 0.01N HCl with 0.25% cetyl trimethyl ammonium bromide (CTAB) in a USP apparatus 4 is:

from about 12 to about 17% after 0.5 hours,
from about 23 to about 25% after 1 hour, from about 32 to about 42% after 2 hours,
from about 57 to about 62% after 4 hours,
from about 62 to about 78% after 6 hours,
from about 80 to about 88% after 8 hours,
from about 83 to about 97% after 10 hours,
at least about 94% after 12 hours,
and/or at least about 94% after 16 hours.

In certain embodiments of the present invention, an implant containing axitinib is characterized in that the percentage of axitinib released from the implant in an in vitro test performed at 35° C.±0.5° C. in 0.01N HCl with 0.25% cetyl trimethyl ammonium bromide (CTAB) in a USP apparatus 4 is:

from about 12 to about 16% after 0.5 hours,
from about 34 to about 41% after 2 hours,
from about 66 to about 77% after 6 hours,
from about 85 to about 96% after 10 hours,
and/or at least about 95% after 16 hours;

or is characterized in that the percentage of axitinib released from the implant in an in vitro test performed at 35° C.±0.5° C. in 0.01N HCl with 0.25% cetyl trimethyl ammonium bromide (CTAB) in a USP apparatus 4 is:

from about 12 to about 16% after 0.5 hours,
from about 23 to about 25% after 1 hour,
from about 34 to about 41% after 2 hours,
from about 57 to about 62% after 4 hours,
from about 66 to about 77% after 6 hours,
from about 80 to about 88% after 8 hours,
from about 85 to about 96% after 10 hours,
at least about 94% after 12 hours,
and/or at least about 95% after 16 hours.

In all of the above implant embodiments of in vitro release measured according to method C and defined by the percentage of axitinib release, the axitinib contained in the implant is axitinib free base, and is or comprises axitinib polymorph IV. In particular embodiments, the axitinib contained in the implant is axitinib polymorph IV. In embodiments where the implant comprises axitinib polymorph IV, at least 90 weight-% of the axitinib free base contained in the implant is polymorph IV. In certain embodiments, the amount of axitinib contained in these implants is from about 300 to about 600 µg, such as from about 400 to about 500 µg, such as about 450 µg. In specific embodiments, the implant is a single-stranded implant, such as a single-stranded implant having an essentially cylindrical shape, and has a hydrated surface area (as measured in PBS at a pH of 7.2 to 7.4 and 37° C. after 24 hours of incubation) of at least 16 $mm^2$, such as from about 16.0 to about 23.0 $mm^2$.

In particular ones of these embodiments, the implant contains axitinib polymorph IV in an amount of from about 400 to about 500 µg, such as about 450 µg, and the percentage of released axitinib is based on the maximum amount of axitinib released from the implant representing 100% (referred to herein also as "normalized % release"), as explained in Example 7.3 with respect to in vitro Method C. In other particular embodiments, the implant contains axitinib polymorph IV in an amount of from about 400 to about 500 µg, such as about 450 µg, and the percentage of axitinib released is based on a theoretical (label) amount of 450 µg axitinib representing 100%. This means that if the theoretical (label) axitinib amount of an implant is 450 µg, but the actual axitinib content (assay) is for example slightly higher than 450 µg, the percentage (%) of axitinib released after a certain period of time as indicated above still refers to the 450 µg of theoretical/label content, as also explained in Example 7.3 with respect to Method C.

In some embodiments of the present invention, an implant containing axitinib is characterized in that the amount of axitinib released from the implant in an in vitro test performed at 35° C.±0.5° C. in 0.01N HCl with 0.25% cetyl trimethyl ammonium bromide (CTAB) in a USP apparatus 4 is:

from about 50 to about 80 μg after 0.5 hours,
from about 140 to about 200 μg after 2 hours,
from about 270 to about 360 μg after 6 hours,
from about 350 to about 450 μg after 10 hours,
and/or at least about 410 μg after 16 hours;

or is characterized in that the amount of axitinib released from the implant in an in vitro test performed at 35° C.±0.5° C. in 0.01N HCl with 0.25% cetyl trimethyl ammonium bromide (CTAB) in a USP apparatus 4 is:

from about 50 to about 80 μg after 0.5 hours,
from about 100 to about 120 μg after 1 hour,
from about 140 to about 200 μg after 2 hours,
from about 240 to about 295 μg after 4 hours,
from about 270 to about 360 μg after 6 hours,
from about 350 to about 410 μg after 8 hours,
from about 350 to about 450 μg after 10 hours,
at least about 400 μg after 12 hours,
and/or at least about 410 μg after 16 hours.

In certain embodiments of the present invention, an implant containing axitinib is characterized in that the amount of axitinib released from the implant in an in vitro test performed at 35° C.±0.5° C. in 0.01N HCl with 0.25% cetyl trimethyl ammonium bromide (CTAB) in a USP apparatus 4 is:

from about 55 to about 72 μg after 0.5 hours,
from about 147 to about 190 μg after 2 hours,
from about 280 to about 350 μg after 6 hours,
from about 360 to about 440 μg after 10 hours,
and/or at least about 420 μg after 16 hours;

or is characterized in that the amount of axitinib released from the implant in an in vitro test performed at 35° C.±0.5° C. in 0.01N HCl with 0.25% cetyl trimethyl ammonium bromide (CTAB) in a USP apparatus 4 is:

from about 55 to about 72 μg after 0.5 hours,
from about 105 to about 112 μg after 1 hour,
from about 147 to about 190 μg after 2 hours,
from about 250 to about 280 μg after 4 hours,
from about 280 to about 350 μg after 6 hours,
from about 360 to about 400 μg after 8 hours,
from about 360 to about 440 μg after 10 hours,
at least about 420 μg after 12 hours,
and/or at least about 420 μg after 16 hours.

In certain embodiments of the present invention, an implant containing axitinib is characterized in that the amount of axitinib released from the implant in an in vitro test performed at 35° C.±0.5° C. in 0.01N HCl with 0.25% cetyl trimethyl ammonium bromide (CTAB) in a USP apparatus 4 is:

from about 57 to about 70 μg after 0.5 hours,
from about 150 to about 180 μg after 2 hours,
from about 290 to about 345 μg after 6 hours,
from about 370 to about 430 μg after 10 hours,
and/or at least about 420 μg after 16 hours;

or is characterized in that the amount of axitinib released from the implant in an in vitro test performed at 35° C.±0.5° C. in 0.01N HCl with 0.25% cetyl trimethyl ammonium bromide (CTAB) in a USP apparatus 4 is:

from about 57 to about 70 μg after 0.5 hours,
from about 105 to about 112 μg after 1 hour,
from about 150 to about 180 μg after 2 hours,
from about 250 to about 280 μg after 4 hours,
from about 290 to about 345 μg after 6 hours,
from about 360 to about 400 μg after 8 hours,
from about 370 to about 430 μg after 10 hours,
at least about 420 μg after 12 hours,
and/or at least about 420 μg after 16 hours.

In all of the above implant embodiments of in vitro release measured according to method C and defined by the amount (in μg) of axitinib released, the axitinib contained in the implant is axitinib free base, and is or comprises axitinib polymorph IV. In particular embodiments, the axitinib contained in the implant is axitinib polymorph IV. In embodiments where the implant comprises axitinib polymorph IV, at least 90 weight-% of the axitinib free base contained in the implant is polymorph IV. In certain embodiments, the amount of axitinib contained in these implants is from about 300 to about 600 μg, such as from about 400 to about 500 μg, such as about 450 μg. In particular ones of these embodiments, the implant contains axitinib polymorph IV in an amount of from about 400 to about 500 μg, such as about 450 μg. In specific ones of these embodiments, the implant is a single-stranded implant, such as a single-stranded implant having an essentially cylindrical shape, and has a hydrated surface area (as measured in PBS at a pH of 7.2 to 7.4 and 37° C. after 24 hours of incubation) of at least 16 $mm^2$, such as from about 16.0 to about 23.0 $mm^2$.

In certain specific embodiments of the present invention, the implant contains axitinib in the form of polymorph IV (such as micronized axitinib polymorph IV particles as defined herein) in an amount of from about 400 μg to about 500 μg, optionally is a single-stranded implant that has a hydrated surface area (as measured in PBS at a pH of 7.2 to 7.4 and 37° C. after 24 hours of incubation) of at least 16 $mm^2$, such as from about 16.0 to about 23.0 $mm^2$, and optionally has a total weight in the dry state of from about 0.6 mg to about 1 mg, wherein the implant is further characterized in that the amount of axitinib released from the implant in an in vitro test performed at 35° C.±0.5° C. in 0.01N HCl with 0.25% cetyl trimethyl ammonium bromide (CTAB) in a USP apparatus 4 is:

at least about 50 μg, such as at least about 51 μg after 0.5 hours,
at least about 140 μg, such as at least about 150 μg after 2 hours,
at least about 270 μg, such as at least about 290 μg after 6 hours,
at least about 350 μg, such as at least about 370 μg after 10 hours,
at least about 400 μg, such as at least about 410 μg after 12 hours,
and/or at least about 410 μg, such as at least about 430 μg after 16 hours,
or the implant is further characterized in that the amount of axitinib released from the implant in an in vitro test performed at 35° C.±0.5° C. in 0.01N HCl with 0.25% cetyl trimethyl ammonium bromide (CTAB) in a USP apparatus 4 is:
at least about 50 μg, such as at least about 51 μg after 0.5 hours,
at least about 90 μg, such as at least about 95 μg after 1 hour,
at least about 140 μg, such as at least about 150 μg after 2 hours,
at least about 230 μg, such as at least about 240 μg after 4 hours,
at least about 270 μg, such as at least about 290 μg after 6 hours, at least about 340 μg, such as at least about 350 μg after 8 hours, at least about 350 μg, such as at least about 370 μg after 10 hours, at least about 400 μg, such as at least about 410 μg after 12 hours, and/or at least about 410 μg, such as at least about 430 μg after 16 hours.

In these or other specific embodiments, wherein the implant contains axitinib in the form of polymorph IV (such as micronized axitinib polymorph IV particles as defined herein) in an amount of from about 400 μg to about 500 μg, such as about 450 μg, is a single-stranded implant that has a hydrated surface area (as measured in PBS at a pH of 7.2 to 7.4 and 37° C. after 24 hours of incubation) of at least 16 $mm^2$, such as from about 16.0 to about 23.0 $mm^2$, and has a total weight in the dry state of from about 0.6 mg to about 1 mg, the implant is further characterized in that the percentage of axitinib released from the implant in an in vitro test performed at 35° C.±0.5° C. in 0.01N HCl with 0.25% cetyl trimethyl ammonium bromide (CTAB) in a USP apparatus 4 (wherein the percentage of released axitinib is based on the maximum amount of axitinib released from the implant representing 100%) is:

at least about 10%, such as at least about 12%, after 0.5 hours, at least about 30%, such as at least about 32%, after 2 hours, at least about 58%, such as at least about 60%, after 6 hours, at least about 75%, such as at least about 80%, after 10 hours, at least about 80%, such as at least about 85% after 12 hours, and/or at least about 90%, such as at least about 95% after 16 hours;

or the implant is further characterized in that the percentage of axitinib released from the implant in an in vitro test performed at 35° C.±0.5° C. in 0.01N HCl with 0.25% cetyl trimethyl ammonium bromide (CTAB) in a USP apparatus 4 (wherein the percentage of released axitinib is based on the maximum amount of axitinib released from the implant representing 100%) is:

at least about 10%, such as at least about 12%, after 0.5 hours, at least about 19%, such as at least about 20%, after 1 hour, at least about 30%, such as at least about 32%, after 2 hours, at least about 45%, such as at least about 50%, after 4 hours, at least about 58%, such as at least about 60%, after 6 hours, at least about 70%, such as at least about 74%, after 8 hours, at least about 75%, such as at least about 80%, after 10 hours, at least about 80%, such as at least about 85% after 12 hours, and/or at least about 90%, such as at least about 95% after 16 hours.

In certain more specific embodiments, the implant contains axitinib in the form of polymorph IV (such as micronized axitinib polymorph IV particles as defined herein) in an amount of from about 400 μg to about 500 μg, optionally is a single-stranded implant that has a hydrated surface area (as measured in PBS at a pH of 7.2 to 7.4 and 37° C. after 24 hours of incubation) of at least 16 $mm^2$, such as from about 16.0 to about 23.0 $mm^2$, and optionally has a total weight in the dry state of from about 0.6 mg to about 1 mg, wherein the implant is further characterized in that the amount of axitinib released from the implant in an in vitro test performed at 35° C.±0.5° C. in 0.01N HCl with 0.25% cetyl trimethyl ammonium bromide (CTAB) in a USP apparatus 4 is:

from about 50 to about 80 μg, such as from about 55 to about 75 μg, such as from about 57 to about 72 μg after 0.5 hours, from about 90 to about 130 μg, such as from about 95 to about 120 μg, such as from about 100 to about 120 μg after 1 hour, from about 140 to about 210 μg, such as from about 140 μg to about 200 μg, such as from about 147 to about 195 μg after 2 hours, from about 230 to about 290 μg, such as from about 235 to about 290 μg, such as from about 240 to about 280 μg after 4 hours, from about 270 to about 380 μg, such as from about 295 to about 370 μg, such as from about 300 to about 360 μg after 6 hours, from about 340 to about 440 μg, such as from about 350 to about 430 μg, such as from about 355 to about 420 μg after 8 hours, from about 350 to about 470 μg, such as from about 380 to about 460 μg, such as from about 390 to about 450 μg after 10 hours, at least about 400 μg, such as at least about 410 μg after 12 hours, and/or at least about 410 μg, such as at least about 430 μg after 16 hours.

In these or other more specific embodiments of the present invention, wherein the implant contains axitinib in the form of polymorph IV (such as micronized axitinib polymorph IV particles as defined herein) in an amount of from about 400 μg to about 500 μg, such as about 450 μg, is a single-stranded implant that has a hydrated surface area (as measured in PBS at a pH of 7.2 to 7.4 and 37° C. after 24 hours of incubation) of at least 16 $mm^2$, such as from about 16.0 to about 23.0 $mm^2$, has a total weight of from about 0.6 mg to about 1 mg, the implant is further characterized in that the percentage of axitinib released from the implant in an in vitro test performed at 35° C.±0.5° C. in 0.01N HCl with 0.25% cetyl trimethyl ammonium bromide (CTAB) In a USP apparatus 4 (wherein the percentage of released axitinib is based on the maximum amount of axitinib released from the implant representing 100%) is;

from about 10 to about 20%, such as from about 10 to about 18%, such as from about 12 to about 17% after 0.5 hours, a from about 19 to about 30%, such as from about 20 to about 27%, such as from about 20 to about 26% after 1 hour, from about 30 to about 45%, such as from about 31 to about 43%, such as from about 32 to about 41% after 2 hours, from about 45 to about 65%, such as from about 48 to about 63%, such as from about 49 to about 60% after 4 hours, from about 58 to about 81%, such as from about 60 to about 80%, such as from about 62 to about 78% after 6 hours, from about 70 to about 90%, such as from about 73 to about 87%, such as from about 74 to about 86% after 8 hours, from about 75 to about 98%, such as from about 78 to about 95%, such as from about 80 to about 95% after 10 hours, at least about 80%, such as at least about 85% after 12 hours, and/or at least about 90%, such as at least about 95% after 16 hours.

In Vivo Release and Hydrogel Persistence:

In an embodiment of the present invention, when the dried implant of the present invention is administered to the eye, such as the vitreous humor, it becomes hydrated and changes its dimensions as disclosed herein, and the hydrogel is then over time biodegraded until it has been fully resorbed. When the implant is biodegraded, such as through ester hydrolysis, it gradually may swell and soften, then become smaller, softer and more liquid until it is fully dissolved and no longer visible, After full degradation of the hydrogel, undissolved TKI particles may remain at the former site of the implant and in certain instances may agglomerate, i.e., merge into a monolithic structure. These remaining undissolved axitinib particles may continue to dissolve slowly at a rate sufficient to provide therapeutically effective TKI levels. If in certain embodiments two or more implants are administered to achieve a desired total dose, they are equally biodegraded over time, and the remaining axitinib particles also merge into one single monolithic structure.

In certain embodiments, the hydrogel implant softens over time as it degrades, which may depend inter alia on the structure, i.e. the hydrophilicity or hydrophobicity of the carbon chain in proximity to the degradable ester group, of the linker that crosslinks the PEG units in the hydrogel. For example, in the implants used in the Examples herein, that carbon chain comprises 7 carbon atoms when it stems from a SAZ functional group at the PEG, such as a 4a20k PEG, precursor. This carbon chain may provide an extended persistence in the human eye of up to about 9 or up to about 12 months, as compared to a shorter carbon chain when using e.g. a SG functional group providing for a shorter carbon chain in said linker.

In the human eye, such as in the vitreous humor, the implant of the invention in certain embodiments biodegrades (i.e., the hydrogel dissolves) within about 2 to about 15 months after administration, or within about 4 to about 13 months after administration, or within about 6 to about 12 months after administration, or within about 6 to about 18 months after administration, specifically within about 6 to about 9 months after administration, such as within about 8 months after administration, or within about 9 to about 12 months after administration. In particular embodiments (such as in embodiments where the hydrogel comprises crosslinked PEG units, such as crosslinked 4a20kPEG-SAZ and 8a20kPEG-$NH_2$ units), the hydrogel degrades (bioresorbs) within about 8 to 9 months after injection into the vitreous humor of a human. In other species, the implant of the invention may biodegrade later or earlier than in human vitreous humor. For example, in non-human primates, such as in monkeys, specifically in *Cynomolgus* monkeys, the hydrogel dissolves (specifically, in embodiments where the hydrogel comprises crosslinked PEG units, such as crosslinked 4a20kPEG-SAZ and 8a20kPEG-$NH_2$ units) within about 5 to 6 months; and in rabbits, specifically in Dutch Belted rabbits, the hydrogel dissolves (specifically, in embodiments where the hydrogel comprises crosslinked PEG units, such as crosslinked 4a20kPEG-SAZ and 8a20kPEG-$NH_2$ units) within about 4 to 5 months. Without wishing to be bound by theory, the degradation of the hydrogel (such as via ester hydrolysis) is determined to a large extent by the temperature in the vitreous. The mid-vitreal temperature in humans is about 33° C., in monkey is about 35° C., and in rabbit is about 37° C. (F. Lorget et al., *Molecular pharmaceutics,* 13(9), pp. 2891-2896; and M. B. Landers III et al., Retina 32 (1), p. 172-176 (January/2012), which provides for certain differences in hydrogel persistence between different species such as rabbits, monkeys and humans. The solubility of the drug such as TKI such as axitinib per se is not affected to the same degree by these temperate differences.

In one embodiment, the implant after administration to the vitreous humor releases (as defined herein) the TKI, such as a therapeutically effective amount of TKI, such as axitinib, over a period of at least about 3 months, at least about 6 months, at least about 9 months, at least about 10 months, at least about 11 months, or at least about 12 months, or at least about 13 months or even longer after administration (i.e., injection). In particular embodiments, the implant releases the TKI, such as axitinib, for a period of about 6 to about 9 months after administration.

In one embodiment of the invention, the implant provides for a treatment period of at least about 3 months, at least about 6 months, at least about 9 months, at least about 10 months, at least about 11 months, at least about 12 months, or at least about 13 months or longer after administration (injection) of the (i.e., a single) implant into the vitreous humor of a patient. In certain embodiments, an implant of the present invention provides for a treatment period of from about 6 to about 12 months, such as from about 8 to about 11 months, or of about 6 months. In particular embodiments, an implant of the present invention provides for a treatment period of about 9 months.

After one treatment period a fresh implant of the present invention can be injected as disclosed herein, which sequence can be repeated as many times as needed. For example, about 9 months after injection of the first implant a second, fresh implant can be injected. Specifically in embodiments of the invention wherein the hydrogel comprises crosslinked PEG units, such as an implant being obtained by crosslinking 4a20kPEG-SAZ and 8a20kPEG-$NH_2$ precursors, and wherein the amount of TKI such as axitinib contained in the implant (specifically, axitinib polymorph IV) is from about 400 to about 500 μg, a new implant can be injected into the vitreous humor about 9 months after injection of the first implant, because by that time the hydrogel has fully biodegraded, and the remaining axitinib has been released into the vitreous to be delivered to the retina and/or choroid/RPE.

In one embodiment of the invention, TKI, such as axitinib is released from the implant in vivo into the vitreous generally at an average rate of about 0.1 μg/day to about 10 μg/day, or about 0.5 μg/day to about 5 μg/day, or about 0.5 μg/day to about 2 μg/day. In particular embodiments of the invention, TKI such as axitinib is released from the implant in vivo (in the vitreous humor, such as in the vitreous humor of a human) at an average release rate of at least 0.8 μg/day, such as from about 0.8 μg/day to about 1.5 μg/day, or from about 0.9 μg/day to about 1.3 μg/day, such as about 1.2 μg/day over a time period of at least 3 months, such as least 6, or at least 9, or at least 10 months after injection. In particular embodiments such release of TKI, such as axitinib, is maintained for at least about 3 months, such as about 6 to about 9 months, or from about 6 to about 12 months after injection of the implant. In certain embodiments, the mentioned average release rates apply to the vitreous of a non-human primate, such as a monkey (in particular, but not limited thereby, a *Cynomolgus* monkey). In certain embodiments, the mentioned average release rates apply to the vitreous of a human. In particular embodiments, an implant of the invention, such as an implant comprising a hydrogel and axitinib particles, wherein the hydrogel comprises cross-linked PEG units obtained by crosslinking 4a20kPEG-SAZ and 8a20kPEG-$NH_2$ precursors, and wherein the amount of axitinib contained in the implant (specifically, axitinib polymorph IV) is from about 400 to about 500 μg, provides for the release of axitinib into the vitreous of a human at an average rate of from about 0.8 μg/day to about 1.5 μg/day, such as from about 0.9 μg/day to about 1.3 μg/day, or from about 1.0 μg/day to about 1.2 μg/day, such as about 1.0 μg/day. In certain embodiments, the release rate stays essentially constant over at least about 3 months, or over the first quarter or the first half of the treatment period.

In Vivo Release and Pre-Clinical Studies in Non-Human Primates (NHP)

Pre-clinical studies in non-human primates (NHP) have been conducted inter alia with an implant containing about 300 μg axitinib in the form of polymorph IV and having a hydrated surface area of about 20 $mm^2$. To briefly summarize, in this ocular distribution and pharmacokinetic study the in vivo release following a single intravitreal injection of such an implant is determined in *Cynomolgus* monkeys, and is then compared to the results obtained with reference implants containing axitinib in the form of polymorph SAB-I, in the following doses: about 600 μg, about 300 μg, and 3 implants each containing about 200 μg axitinib. Results of these studies are reported and compared in Example 10. It was found that 3 months after an intravitreal injection of a single implant according to the present invention containing about 300 μg axitinib polymorph IV the axitinib levels in the retina, the choroid and retinal pigment epithelium (RPE) are higher as compared to the reference implants (containing axitinib polymorph SAB-I). Without wishing to be bound by this theory, these increased levels of axitinib in the mentioned ocular tissues are believed to be due to the solubility of axitinib polymorph IV, which solubility is about twice the solubility of axitinib polymorph SAB-I, as disclosed herein, and which thus provides for a faster release of axitinib from the implant into the vitreous humor. Based on an $IC_{50}$ value for VEGFR-2 from cell-based assays of 0.077 ng/mL, and taking into account a vitreous half-life of axitinib of 2 hours, it had been determined (In US 2020/0375889 A1, paragraph [0048] to [0050]) that 256 ng/day of axitinib would have to be released from an intravitreal implant in order to provide for therapeutically effective concentrations of axitinib in the vitreous. In the present study in NHP so far, a release rate of 986 ng/day from the implant containing about 300 μg axitinib (polymorph IV) has been measured, which is almost 4 times the said required release rate of 256 ng/day.

Example 10 also provides further data on the in vivo release of implants according to the present invention in NHP (specifically, *Cynomolgus* monkeys) beyond 3 months, namely at 6 months and 9 months. It is demonstrated in this example that the retina and choroid/RPE $t_{max}$ for an implant containing axitinib polymorph IV (such as implant 10D in Example 10, containing a dose of about 300 μg axitinib) occurred during the sustained release period at 3 months, while for the implants containing axitinib polymorph SAB-I (implants 10A, 10B, and 10C) the retina and choroid/RPE $t_{max}$ occurred at 6 or 9 months. The hydrogel of the implants according to the invention used in this study biodegrades in NHP within about 5 to 6 months. This means that in certain embodiments of the present invention for implants containing a more soluble form of axitinib such as axitinib polymorph IV, a larger portion of the drug payload contained in the implant is released prior to the terminal release that happens upon final biodegradation of the hydrogel, as compared to the release from comparative implants that contain a less soluble form of axitinib (such as axitinib polymorph SAB-I) but are otherwise comparable to the implants of the present invention (e.g. as regards the implant composition and the drug dose contained in the implant), Thus, in certain embodiments of the present invention, in which the axitinib contained in the sustained release biodegradable ocular implant is axitinib having a solubility of at least 0.3 μg/mL as measured in phosphate-buffered saline (PBS) at a pH of 7.2 to 7.4 and 37° C. after five days of incubation (such as axitinib polymorph IV), the maximal axitinib concentration in the retina and/or the choroid/RPE at the time of final hydrogel degradation provided by the sustained release biodegradable ocular implant is less than the maximal axitinib concentration in the retina and/or the choroid/RPE at the time of final hydrogel degradation, respectively, provided by a comparative implant in which the axitinib has a solubility of lower than 0.3 μg/mL as measured in phosphate-buffered saline (PBS) at a pH of 7.2 to 7.4 and 37° C. after five days of incubation. In certain of these embodiments, the total amount of axitinib contained in the comparative implant differs by no more than 10% from the total amount of axitinib contained in the sustained release biodegradable ocular implant.

Thus, in certain embodiments of the present invention, specifically when an implant contains axitinib polymorph IV in an amount of from about 400 to about 500 μg, the cumulative amount of axitinib released prior to the biodegradation of the hydrogel is higher than the amount of axitinib being terminally released upon biodegradation. In certain embodiments, the amount of a terminal release of axitinib upon biodegradation of the hydrogel in the vitreous humor is not higher or not substantially higher than the cumulative amount of axitinib released by the implant prior to biodegradation when the implant is still intact. In certain embodiments, the amount of axitinib remaining in the vitreous humor at 6 months after implant injection (which includes the amount of axitinib that is present in the implant residing in the vitreous humor) is 250 μg or less, such as 200 μg or less. In certain embodiments, after injection into the vitreous humor the concentration of axitinib in the retina or the choroid/RPE provided in a terminal release upon biodegradation of the hydrogel is not higher, or not substantially higher, such as no more than about 25% higher, such as no more than about 10% higher, than the maximum concentration of axitinib in the retina or the choroid/RPE, respectively, provided by the implant at any time after injection and prior to biodegradation of the hydrogel when the implant is still intact.

In certain embodiments of the present invention, the maximum concentration of TKI, specifically axitinib, in NHP retina and choroid/RPE is reached with an implant according to the present invention containing a more soluble TKI (such as axitinib polymorph IV, such as in an amount of from about 400 to about 500 μg) before the hydrogel biodegrades, while in implants containing a less soluble TKI (such as axitinib polymorph SAB-I) the maximum concentration of TKI in NHP retina and choroid/RPE is reached only upon/after hydrogel degradation (which happens at around 5 to 6 months in NHP as explained herein), See e.g. Example 10, implant 10D containing about 0.3 mg axitinib polymorph IV, compared to implants 10A to 10C containing various amounts of axitinib polymorph SAB-I. The implant according to the present invention containing about 0.3 mg axitinib in the form of the more soluble axitinib polymorph IV (sample 10D) reached steady state earlier than the implants containing the less soluble axitinib polymorph SAB-I, and maintained it without any increased release at the time of hydrogel biodegradation. The maximal exposure of axitinib to the retina and the choroid/RPE after hydrogel biodegradation in Example 10 was significantly less with the implant containing the more soluble axitinib polymorph IV (implant 10D) due to less remaining drug upon hydrogel biodegradation. The average daily release rate (μg/day) over the first 3 months after implant injection reflects the faster release of axitinib from the 0.3 mg dose axitinib polymorph IV implant (10D) used in this study as compared to a corresponding implant containing the less soluble axitinib polymorph SAB-I.

In certain embodiments, an implant of the present invention may release TKI such as axitinib into the vitreous, wherein the cumulative amount of TKI (such as axitinib) released prior to the biodegradation of the hydrogel is higher than the amount of TKI (such as axitinib) being terminally released upon final biodegradation. In these embodiments, the amount of axitinib being released upon biodegradation may be less than about 200 μg, such as less than about 150 μg, about 130 μg or less, or about 100 μg or less, or the terminal amount of axitinib being released upon final biodegradation of the hydrogel is from about 50 to about 200 μg, such as from about 100 to about 170 μg, such as from about 110 to 150 g. In these or other embodiments, the maximum TKI (such as axitinib) concentration in ocular tissue ($C_{max}$), such as in the retina or the choroid, reached prior to the biodegradation of the hydrogel is within +/−50%, such as within +/−30% of the concentration of TKI (such as axitinib) delivered to that ocular tissue upon biodegradation.

In some embodiments, an implant according to the present invention delivers a concentration of TKI (such as axitinib) to an ocular tissue (such as the retina or choroid), wherein the $t_{max}$ of that TKI in that tissue is earlier, such as at least about 1 month or at least about 2 months earlier, than the tax achieved with a comparative implant and/or wherein the maximum concentration of that TKI (such as axitinib) delivered to that tissue is higher than the maximum concentration of that TKI delivered by a comparative implant, wherein the comparative implant contains that TKI in a total amount of within +/−10%, such as within +/−5% of the total amount of that TKI contained in the implant of the invention and differs from the implant of the invention in that (such as only in that) the comparative implant contains that TKI in a form that has a lower solubility as measured in PBS at a pH of 7.2 to 7.4 and 37° C. after five days of incubation than the form of that TKI contained in the sustained release biodegradable ocular implant, and wherein the comparative implant has a hydrated surface area (as defined herein) of within +/−20%, such as within +/−10% of the hydrated surface area of the sustained release biodegradable ocular implant of the invention. In certain embodiments, the comparative implant contains a different polymorphic form of the same TKI as the implant of the invention, which has a lower solubility of the polymorph of that TKI as contained in the sustained release biodegradable ocular implant of the invention, specifically the sustained release biodegradable ocular implant of the invention may contain axitinib polymorph IV, and the comparative implant may contain axitinib polymorph SAB-I.

In some embodiments the implant of the invention provides for substantially or near zero-order release of the TKI (such as axitinib) for at least one month, such as at least two months, such as at least three months, such as at least four months, such as at least five months.

In certain embodiments, the concentration of TKI (such as axitinib) in an ocular tissue (such as the retina or choroid) provided in a terminal release upon biodegradation of the hydrogel is not higher or not substantially higher, or is not more than about 25% higher, such as no more than about 10% higher than the concentration of TKI (such as axitinib) in the ocular tissue provided by the implant at any time after injection and prior to biodegradation when the implant is still intact. For example, the increase of the concentration of TKI (such as axitinib) in the ocular tissue provided by a terminal release of TKI (such as axitinib) upon biodegradation of the hydrogel is no more than about 110%, such as no more than about 100%, such as no more than about 80%, such as no more than about 30%, such as no more than about 20%, such as no more than about 10% of the concentration of TKI in that ocular tissue reached at any time prior to said terminal release.

In certain embodiments, the terminal release of the TKI (such as axitinib) upon biodegradation of the hydrogel of an implant of the present invention (such as an implant containing axitinib polymorph IV in an amount of from about 400 to about 500 μg) is less than the terminal release of TKI from a comparative implant upon its biodegradation, wherein the comparative implant contains the TKI in a total amount of within +/−10%, such as within +/−5% of the total amount of the TKI contained in the sustained release biodegradable ocular implant and differs from the sustained release biodegradable ocular implant in that (such as only in that) the comparative implant contains the TKI in a form that has a lower solubility as measured in PBS at a pH of 7.2 to 7.4 and 37° C. after five days of incubation than the form of the TKI contained in the sustained release biodegradable ocular implant, and wherein the comparative implant has a hydrated surface area (as defined herein) of within +/−20%, such as within +/−10% of the hydrated surface area of the sustained release biodegradable ocular implant.

In certain embodiments, an implant of the present invention (such as an implant containing axitinib polymorph IV in an amount of from about 400 to about 500 μg) provides for a higher $C_{max}$ of the TKI in an ocular tissue (such as the retina or the choroid) than the $C_{max}$ of the TKI as provided by a comparative implant, prior to biodegradation of the hydrogel, wherein the comparative implant contains the TKI in a total amount of within +/−10%, such as within +/−5% of the total amount of the TKI contained in the sustained release biodegradable ocular implant and differs from the sustained release biodegradable ocular implant in that (such as only in that) the comparative implant contains the TKI in a form that has a lower solubility as measured in PBS at a pH of 7.2 to 7.4 and 37° C. after five days of incubation than the form of the TKI contained in the sustained release biodegradable ocular implant, and wherein the comparative implant has a hydrated surface area (as defined herein) of within +/−20% the hydrated surface area of the sustained release biodegradable ocular implant.

In these or other certain embodiments, the elimination rate (in μg/day) of the TKI (such as axitinib) from the vitreous humor provided by a sustained release biodegradable ocular implant of the present invention at any time point selected from 3 or 6 months after implant injection is higher as compared to the elimination rate (in μg/day) of the TKI from the vitreous humor at any time point selected from 3 or 6 months after injection of a comparative implant, wherein the comparative implant differs from the sustained release biodegradable ocular implant only in that the solubility of the TKI in the comparative implant is lower as measured in PBS at a pH of 7.2 to 7.4 and 37° C. after five days of incubation than that of the TKI contained in the implant of the invention, and wherein the elimination rate is calculated by dividing the difference between (i) the total amount of TKI contained in the respective implant and the remaining geometric mean TKI amount in the vitreous humor (which includes the remaining amount of TKI contained in the respective implant residing in the vitreous humor) determined at 3 months, or (ii) the difference between the remaining geometric mean TKI amount in the vitreous humor determined at 3 months and the remaining geometric mean TKI amount in the vitreous humor determined at 6 months, by the number of days elapsed in the respective time period, wherein the time period is (i) from 0 to 3 months or (ii) from 3 to 6 months.

In more specific embodiments of the embodiments of the preceding paragraph, the comparative implant differs from the sustained release biodegradable ocular implant of the present invention only in that:

(a) the solubility of the TKI in the comparative implant is lower as measured in PBS at a pH of 7.2 to 7.4 and 37° C. after five days of incubation than that of the TKI contained in the implant of the invention,
(b) the hydrated surface area (as defined herein) of the comparative implant differs by no more than 5%, and
(c) the total amount of the TKI contained in the comparative implant differs by no more than 5; or in that:
(a) the solubility of the TKI in the comparative implant is lower as measured in PBS at a pH of 7.2 to 7.4 and 37° C. after five days of incubation than that of the TKI contained in the implant of the invention,
(b) the total amount of the TKI contained in the comparative implant is at least 1.5 times higher, and
(c) the hydrated surface area (as defined herein) of the comparative implant differs by no more than 10%; or in that:
(a) the solubility of the TKI in the comparative implant is lower as measured in PBS at a pH of 7.2 to 7.4 and 37° C. after five days of incubation than that of the TKI contained in the implant of the invention,
(b) the hydrated surface area (as defined herein) of the comparative implant differs by no more than 10%, and
(c) the total amount of the TKI contained in the comparative implant is at least two times higher.

In more specific embodiments, the comparative implant mentioned in the preceding paragraphs may contain the less soluble axitinib polymorph SAB-I, and the implant according to the present invention may contain the more soluble axitinib polymorph IV.

In yet further embodiments, the elimination rate (in μg/day) of the TKI (such as axitinib) from the vitreous humor provided by an implant of the present invention (such as an implant containing axitinib polymorph IV in an amount of from about 400 to about 500 μg) is substantially the same at 6 months after implant injection as compared to the elimination rate (in μg/day) of the TKI from the vitreous humor at 6 months after injection of a comparative implant, wherein the comparative implant differs from the sustained release biodegradable ocular implant only in that (a) the solubility of the TKI in the comparative implant is lower as measured in PBS at a pH of 7.2 to 7.4 and 37° C. after five days of incubation than that of the TKI contained in the implant of the invention,
(b) the total amount of the TKI contained in the comparative implant is at least 1.5 times higher, and
(c) the hydrated surface area (as defined herein) of the comparative implant is at least 2.5 times higher.

wherein the elimination rate is calculated by dividing the difference between the remaining geometric mean TKI amount in the vitreous humor determined at 3 months and the remaining geometric mean TKI amount in the vitreous humor determined at 6 months by the number of days elapsed in the time period from 3 to 6 months.

In certain embodiments, with an implant of the present invention (such as an implant containing axitinib polymorph IV in an amount of from about 400 to about 500 μg) the geometric mean amount (in μg) of the TKI (such as axitinib) in the vitreous humor (which includes the amount of the TKI present in the sustained release biodegradable ocular implant residing in the vitreous humor after injection) is lower at any time point selected from 3, 6 or 9 months after implant injection as compared to the geometric mean amount (in μg) of the TKI in the vitreous humor at the respective time point selected from 3, 6 or 9 months after injection of a comparative implant, wherein the comparative implant differs from the sustained release biodegradable ocular implant only in that the solubility of the tyrosine kinase inhibitor in the comparative implant is lower as measured in PBS at a pH of 7.2 to 7.4 and 37° C. after five days of incubation than that of the TKI contained in the implant of the invention.

In particular embodiments, the said axitinib concentrations mentioned above in ocular tissue (vitreous humor, retina, or choroid) are measured in a non-human primate, such a monkey, such as a *Cynomolgus* monkey.

In Vivo Release and Pre-Clinical Studies in Rabbit

The findings in the in vivo studies in rabbit (Example 13) were generally consistent with the findings in NHP (Example 10). The implants of the present invention (containing the more soluble form of axitinib, polymorph IV) also achieved higher axitinib levels in the retina and choroid/RPE of rabbit (Dutch Belted rabbit) earlier than comparative implants containing the less soluble form of axitinib (polymorph SAB-I), see e.g. the data at week 6 comparing an implant containing about 0.3 mg axitinib polymorph IV (sample 13E) with an implant containing also about 0.3 mg axitinib, but polymorph SAB-I while having a comparable hydrated surface area (sample 13A).

It is demonstrated in Example 13 that in rabbit (such as Dutch Belted rabbit), implants according to the present invention containing axitinib polymorph IV (including the implants containing an axitinib dose of about 0.3 mg and those containing about 0.6 mg axitinib polymorph IV, see implants 13E and 13F in Example 13) delivered sustained concentrations of axitinib to the retina and choroid/RPE, and reduced the maximal exposure in these tissues at the time of final hydrogel bioresorption. Based on the average axitinib concentration measured in the retina of Dutch Belted rabbits provided by implants of the present invention containing axitinib (in the form of axitinib polymorph IV) doses of about 0.3 mg and about 0.6 mg, respectively, and interpolation thereof, one implant according to the present invention containing a dose of axitinib (again, in the form of axitinib polymorph IV) of about 450 μg (such as from about 400 to about 500 μg) may provide an $AUC_{0\text{-}5.5\ months}$ in the retina of Dutch Belted rabbits in the range of from about 125,000 to about 165,000 ng·day/g, such as from about 130,000 to about 160,000 ng·day/g, such as from about 135,000 to about 155,000 ng·day/g, and may provide an $AUC_{0\text{-}5.5\ months}$ in the choroid/RPE of Dutch Belted rabbits in the range of from about 130,000 to about 190,000 ng·day/g, such as from about 140,000 to about 180,000 ng·day/g, such as from about 150,000 to about 175,000 ng·day/g. These estimates may apply in particular to implants according to the present Invention in which the hydrogel comprises crosslinked PEG units, such as those obtained from crosslinking 4a20kPEG-SAZ and 8a20kPEG-$NH_2$ precursors as disclosed herein, and wherein the implant has a hydrated surface area of from about 16 to about 25 $mm^2$.

In certain embodiments, the geometric mean concentration (in ng/g) of the TKI (such as axitinib) in an ocular tissue (such as the retina and/or the choroid) provided by an implant of the present invention (such as an implant containing axitinib polymorph IV in an amount of from about 400 to about 500 μg) is higher at week 6 after injection of the sustained release biodegradable ocular implant as compared to the geometric mean concentration (in ng/g) of the TKI in that ocular tissue at week 6 after injection of a comparative implant, wherein the comparative implant differs from the sustained release biodegradable ocular implant only in that the solubility of the TKI in the comparative implant is lower as measured in PBS at a pH of 7.2 to 7.4 and 37° C. after five days of incubation than that of the TKI contained in the implant of the invention. In these or other certain embodiments, the sum of the geometric mean concentrations (in ng/g) of TKI (such as axitinib) determined in an ocular tissue at week 6, week 13, and week 24 after injection of the implant is higher than the sum of the geometric mean concentrations (in ng/g) of TKI determined at week 6, week 13, and week 24 after injection of a comparative implant, wherein the comparative implant differs from the sustained release biodegradable ocular implant only in that the solubility of the tyrosine kinase inhibitor in the comparative implant is lower as measured in PBS at a pH of 7.2 to 7.4 and 37° C. after five days of incubation than that of the TKI contained in the implant of the invention. In certain embodiments, the said geometric mean concentrations are determined in a subject that is a rabbit, such as a Dutch Belted rabbit. In more specific embodiments of the embodiments of the preceding paragraph, the comparative implant differs from the sustained release biodegradable ocular implant only in that:

(a) the solubility of the TKI in the comparative implant is lower as measured in PBS at a pH of 7.2 to 7.4 and 37° C. after five days of incubation than that of the TKI contained in the implant of the invention,
(b) the hydrated surface area (as defined herein) of the comparative implant differs by no more than 5%, and
(c) the total amount of the TKI contained in the comparative implant differs by no more than 5; or in that:
(a) the solubility of the TKI in the comparative implant is lower as measured in PBS at a pH of 7.2 to 7.4 and 37° C. after five days of incubation than that of the TKI contained in the implant of the invention,
(b) the total amount of the TKI contained in the comparative implant is at least 1.5 times higher, and
(c) the hydrated surface area (as defined herein) of the comparative implant differs by no more than 10%; or in that:
(a) the solubility of the TKI in the comparative implant is lower as measured in PBS at a pH of 7.2 to 7.4 and 37° C. after five days of incubation than that of the TKI contained in the implant of the invention,
(b) the hydrated surface area (as defined herein) of the comparative implant differs by no more than 10%, and
(c) the total amount of the TKI contained in the comparative implant is at least two times higher.

In more specific embodiments, the comparative implant mentioned in the preceding paragraphs may contain the less soluble axitinib polymorph SAB-I, and the implant according to the present invention may contain the more soluble axitinib polymorph IV.

It was demonstrated in an in vivo challenge study (Example 14, FIG. 29) in rabbit, specifically in Dutch Belted rabbit, that VEGF-induced retinal vascular leakage was reduced or delayed for at least up to about 1 month, such as at least up to about 2 months, such as at least up to about 3 months after injection of an implant of the present invention (containing axitinib polymorph IV in an amount of about 400 to about 500 μg, such as about 450 μg), as compared to the VEGF-induced retinal leakage in the respective same period after administering bevacizumab (Avastin). The study described in Example 14 comprised the intravitreal injection of a sustained release biodegradable ocular implant according to the present invention (containing axitinib polymorph IV in an amount of about 400 to about 500 μg, such as about 450 μg) to an eye of a rabbit, wherein the rabbit was thereafter also administered 1 μg of VEGF to the eye at least three times over a period of 3 months. The efficacy of the administration of the implant of the present invention was compared to the administration of 50 μL of 25 mg/ml bevacizumab under the same conditions including the VEGF challenges, and also compared to the administration of a comparative implant containing a less soluble form of axitinib, namely axitinib polymorph SAB-I, but in a higher amount (about 600 μg). The implant of the present invention containing about 450 μg axitinib polymorph IV showed comparable or better efficacy in inhibiting VEGF-induced leakage than the comparative implant containing a higher amount of axitinib, but of a less soluble axitinib polymorph (see in particular FIG. 29).

$t_{max}$ of Axitinib

In certain embodiments, the $t_{max}$ of TKI (such as axitinib) provided by an implant of the present invention, such as an implant containing axitinib polymorph IV in an amount of about 400 to about 500 μg, such as about 450 μg, in an ocular tissue is earlier than about 6 months, such as earlier than about 5 months, such as earlier than about 4 months, such as earlier than about 3 months, such as earlier than about 2 months after injection of the implant into the eye of a non-human primate, such as a monkey, such as a *Cynomolgus* monkey; and/or the $t_{max}$ of TKI (such as axitinib) in an ocular tissue is earlier than about 6 months, such as at about 5.5 months or earlier, or earlier than about 5 months, such as earlier than about 4 months, such as earlier than about 3 months, such as earlier than about 2 months, such as earlier than about 1 month after infection of the implant into the eye of a rodent, such as a rabbit, such as a Dutch Belted rabbit; and/or the $t_{max}$ (such as axitinib) of TKI in an ocular tissue is earlier than about 9 months, such as earlier than about 8 months, such as earlier than about 7 months, such as earlier than about 6 months, such as earlier than about 5 months, such as earlier than about 4 months after injection into the eye of a human patient. In certain of these embodiments, the ocular tissue may be the retina and/or the choroid/RPE.

In certain embodiments, wherein the axitinib contained in a sustained release biodegradable ocular implant of the present invention is axitinib having a solubility of 0.3 μg/ml or greater as measured in phosphate-buffered saline (PBS) at a pH of 7.2 to 7.4 and 37° C. after five days of incubation, the maximum concentration of axitinib in the retina and/or the choroid/RPE (e.g. the retina and/or the choroid/RPE of a monkey, such as a *Cynomolgus* monkey, or of a rabbit, such as a Dutch Belted rabbit) Is reached by the sustained release biodegradable ocular implant earlier than by a comparative implant, wherein the comparative implant differs from the sustained release biodegradable ocular implant in the solubility (such as the polymorphic form) of the axitinib, and wherein the dose of axitinib in the comparative implant is up to two times the dose of axitinib in the sustained release biodegradable ocular implant. In certain of these embodiments, the maximum axitinib concentration in the retina and/or the choroid/RPE is reached by the sustained release biodegradable ocular implant prior to the final hydrogel biodegradation.

In certain embodiments, after injection into the vitreous humor (such as the vitreous humor of a NHP, such as a monkey, such as a *Cynomolgus* monkey) an implant of the present invention (such as an implant containing axitinib polymorph IV in an amount of about 400 to about 500 μg, such as about 450 μg) provides for an earlier $t_{max}$ of axitinib in the retina or the choroid/RPE than the $t_{max}$ of axitinib as provided by a comparative implant, wherein the comparative implant contains axitinib in a total amount of within +/−10%, such as within +/−5% of the total amount of the axitinib contained in the sustained release biodegradable ocular implant and differs from the sustained release biodegradable ocular implant in that (such as only in that) the comparative implant contains axitinib in a form that has a lower solubility as measured in PBS at a pH of 7.2 to 7.4 and 37° C. after five days of incubation than axitinib polymorph IV, and wherein the comparative implant has a hydrated surface area (as measured in phosphate-buffered saline (PBS) at a pH of 7.2 to 7.4 and 37° C. after 24 hours of incubation) of within +/−20%, such as within +/−10% of the hydrated surface area of the sustained release biodegradable ocular implant, Mechanism of Release:

Without wishing to be bound by theory, the mechanism of release of the TKI from an implant of the invention may be explained as follows: In embodiments of the invention, release of the TKI into the eye and specifically into the vitreous humor is dictated by diffusion and drug clearance. An exemplary TKI according to the present invention is axitinib, According to the present invention, the TKI, such as axitinib, is confined in a biodegradable hydrogel having a particular geometry and surface. The liquid in the posterior chamber of the eye is viscous, has a slow clearance and a relatively stagnant flow (at least as compared to the anterior chamber of the eye).

The implant of the present invention comprises a hydrogel made of a polymer network and a TKI dispersed within the hydrogel. The drug gradually gets dissolved and diffuses out of the hydrogel into the eye. This may happen first at the outer region of the hydrogel (i.e., the drug particles that are located in the outermost region of the hydrogel get dissolved and diffuse out first, the innermost last) that is in contact with the liquid environment of the vitreous. Thereby, in certain embodiments, the outer region of the hydrogel becomes devoid of drug particles. This region is therefore also called the “clearance zone”, which is limited to dissolved drug only, with a concentration at or below the solubility of the drug. In certain embodiments, this low surface concentration may protect tissue (retinal or other cells) from potential drug toxicity by physically separating drug particles from the tissue should the implant get in contact with such tissue. In other embodiments, upon hydration the “clearance zone” is an outer region that has a concentration of active agent that is less than the active agent in an inner region of the hydrated hydrogel.

In embodiments with clearance zones, because drug has dissolved and has diffused out of the clearance zone, this area of the hydrogel may develop voids and becomes softer and weaker. Concurrently with the drug diffusing out of the hydrogel, the hydrogel may also be slowly degraded by means of, e.g., ester hydrolysis in the aqueous environment of the eye. This degradation occurs uniformly throughout the bulk of the hydrogel. At advanced stages of degradation, distortion and some erosion of the hydrogel may begin to occur. As this happens, the hydrogel becomes softer and more liquid (and thus its shape becomes distorted) until the hydrogel finally dissolves and is resorbed completely. Whenever it is referred to herein to “before hydrogel biodegradation”, or to “upon biodegradation”, it is always meant before the final biodegradation/bioresorption/dissolution of the hydrogel. As already mentioned herein, the hydrogel of an implant of the present invention, such as a PEG hydrogel, such as a hydrogel obtained by crosslinking 4a20kPEG-SAZ and 8a20kPEG-$NH_2$ precursors, biodegrades in about 5 to about 6 months after injection into the vitreous humor of a monkey (such as a *Cynomolgus* monkey), in about 4 to about 5 months after injection into the vitreous humor of a rabbit (such as a Dutch Belted rabbit), and in about 8 to about 9 months after injection into the vitreous humor of a human. Upon final biodegradation of the hydrogel, the drug particles that still remained up to this final biodegradation in the hydrogel get then released into the vitreous humor, which release may also be referred to herein as “terminal release”, From the vitreous humor, the drug then continues to be dissolved and delivered to ocular tissue such as the retina and choroid.

In certain embodiments, undissolved TKI particles may remain at the former site of the implant after the hydrogel has already fully dissolved. Since these remaining undissolved axitinib particles are no longer fixated and held apart by the hydrogel, they may in certain Instances agglomerate and form a substantially monolithic structure (or several such structures). This monolithic axitinib structure may still continue to release axitinib, at rates sufficient to achieve the therapeutic effect (specifically, to reduce CSFT as disclosed herein), Without wishing to be bound by theory, the agglomeration is believed to be reduced when using TKI particles with a smaller particle size, as disclosed herein, such as micronized TKI particles, such as with a d10 particle size of less than 0.25 μm, a d50 particle size of less than 2.6 μm, and a d90 particle size of less than 8 μm or less than 6.5 μm (or other particle size ranges as disclosed herein). Apart from potentially reduced agglomeration, a smaller particle size may generally be advantageous as such smaller particles may clear faster from the vitreous (and be delivered to ocular tissue such as the retina and choroid) in cases where the hydrogel has fully dissolved before the full drugload of TKI has been released from an implant of the invention so that the remaining TKI particles are freely located or floating in the vitreous.

In one embodiment of the present invention, the entire amount of TKI such as axitinib is released prior to the complete degradation of the hydrogel, i.e., the time to full degradation of the hydrogel is longer than the time to complete release of the TKI such as axitinib. In other embodiments, the time to full degradation of the hydrogel is shorter than the time to complete release of the TKI such as axitinib. In yet other embodiments, the time to full degradation of the hydrogel is essentially equal to the time to complete release of the TKI such as axitinib, so that the TKI is essentially completely released at about the same time as the hydrogel is completely dissolved. In certain embodiments, the ratio of the time to full degradation of the hydrogel to the time to complete release of the TKI is less than about 2.0, or less than about 1.5, such as from about 0.5 to about 1.5, or from about 0.7 to about 1.3 or 1.25. In certain embodiments, the amount of TKI remaining after complete degradation of the hydrogel (in vitro and/or in vivo) is less than about 25% of the initial TKI content of the implant, or less than about 20%, or less than about 15%, or less than about 10% of the initial TKI content of the implant. In certain embodiments, the implant of the present invention provides for substantially zero-order release of the TKI for at least one month, such as at least two months, such as at least three months, such as at least four months, such as at least five months.

In certain embodiments, the amount of TKI such as axitinib (and in particular axitinib polymorph IV) being terminally released upon final biodegradation of the hydrogel when the implant has been placed into the vitreous humor (such as the vitreous humor of a human patient) is from about 50 to about 200 μg, such as from about 100 to about 170 μg, such as from about 110 to about 150 μg. This applies particularly in case the implant contains axitinib polymorph IV in an amount of from about 400 to about 500 μg, such as about 450 μg.

In certain embodiments the therapeutic effect of one single implant of the present invention can be consistently maintained over an extended period of time, such as at least 3 months, or at least 6 months, or at least 9 months, or at least 10 months, or at least 12 months, or even longer, such as up to 15 months. This greatly reduces the treatment burden for patients with wet AMD as compared to the current standard of care, which requires frequent intravitreal injections of an anti-VEGF agent (such as aflibercept) about every two months. In contrast, the implants according to the present invention may need to be injected only at much greater intervals of time, such as once per about 6 months, or once per about 9 months, or once per about 12 months. In certain embodiments of the present invention, the re-dosing frequency is every 6 to 12 months, such as every 8 to 11 months, or is about every 6 months or about every 9 months. In particular embodiments, the re-dosing frequency of an implant according to the present invention (and thus the treatment period provided by one implant) is about every 9 months. In certain embodiments, the hydrogel, particularly the PEG hydrogel, more particularly the hydrogel obtained by crosslinking 4a20kPEG-SAZ and 8a20kPEG-$NH_2$ precursors, biodegrades in human vitreous humor within about 8 months, or within about 8 to about 9 months after injection. Re-dosing is possible not least because of the gentleness of such an implant to ocular tissue, particularly the retina, and generally a good tolerability of the implant. This good tolerability and gentleness is due inter alia to the use of a hydrogel, particularly a PEG hydrogel, as opposed to the use of other, non-hydrogel matrix materials (such as e.g. pure PL(G)A) which are generally more rigid and may be less biocompatible than hydrogels such as PEG hydrogels.

In certain embodiments, the implants according to the present invention enable a continuous therapy, as they provide for a faster release of the TKI such as axitinib such that the greater part of the drug payload contained in an implant is released into the vitreous prior to the degradation of the hydrogel (i.e., while the implant is still intact). In certain embodiments of the present invention, the $t_{max}$ of the TKI in ocular tissue, such as the retina or the choroid, is earlier than the biodegradation of the hydrogel. In other embodiments, the $t_{max}$ of the TKI in ocular tissue, such as the retina or the choroid, is at terminal release of the TKI upon biodegradation of the hydrogel. The remaining TKI such as axitinib content is released into the vitreous when the hydrogel degrades. Without wishing to be bound by theory, the free TKI such as axitinib particles residing in the vitreous after hydrogel degradation then continue to be dissolved and the active agent migrates into ocular tissue such as the retina and the choroid, so that the therapeutic effect is maintained even during the period when the remainders of the hydrogel are being fully cleared from the vitreous, until a new implant can be placed. Once the hydrogel of an implant has essentially biodegraded, a new implant may be injected. The biodegradation of an implant can be determined by means of certain imaging techniques, such as slit-lamp (sometimes also referred to as slit-lamp biomicroscopy) performed by an ophthalmologist. Another technique is or confocal scanning laser ophthalmoscopy (cSLO; sometimes also referred to as IR or OCT). After it has been confirmed that the hydrogel has essentially biodegraded by means of such imaging techniques, a new implant can be injected. Again, without wishing to be bound by theory, this avoids an accumulation of “empty”, i.e., drug-depleted implants in the vitreous, and/or avoids having to place a fresh implant into the vitreous in order to maintain the therapeutic effect when remainders of the drug-depleted implant still reside in the vitreous. Therefore, in certain embodiments of the invention, the cumulative amount of TKI such as axitinib released prior to the degradation of the hydrogel is higher than the remaining amount which is released upon degradation of the hydrogel. This may be achieved by increasing the release rate of the TKI such as axitinib, such as by incorporating a form thereof that has a higher solubility, such as a solubility of at least 0.3 μg/ml as measured in PBS at a pH of 7.2 to 7.4 and 37° C. after five days of incubation.

In certain embodiments of the present invention, the sustained release biodegradable ocular implant contains the axitinib polymorph IV as the active agent. This axitinib polymer IV is, as disclosed herein, more soluble than other forms of axitinib, such as polymorph SAB-I. This increased solubility provides for a faster release of axitinib from an otherwise identical implant (e.g. comprising a hydrogel of a polymer network such as a network of crosslinked PEG units, such as a network of crosslinked 4a20kPEG-SAZ and 8a20kPEG-$NH_2$ units), such that upon biodegradation of the hydrogel (which occurs at about 8 to 9 months after injection of the implant into the vitreous humor of a human) the majority of the total axitinib content has already been released. Upon biodegradation of the hydrogel the remaining amount of axitinib is released, which then resides in the vitreous and slowly dissolves to be delivered to e.g. the retina while the last remainders of the hydrogel are cleared from the vitreous. Thereby, in certain embodiments, the therapeutic effect can be maintained such as to bridge the time period from the beginning of hydrogel degradation until complete clearance of drug-depleted hydrogel portions from the vitreous, until a fresh implant can be placed. In other words, the depletion of drug from the implant is synchronized or essentially synchronized with the bioresorption/biodegradation of the hydrogel such that re-dosing of an implant is possible after the treatment period, such as within about 9 months after injection of an implant. In the human vitreous humor, an implant as defined herein (such as an implant comprising a hydrogel of a polymer network such as a network of crosslinked PEG units, such as a network obtained by crosslinking 4a20kPEG-SAZ and 8a20kPEG-$NH_2$ precursors) biodegrades within about 8 to 9 months. The remaining amount of active agent that has not been released up to then will be terminally released upon final biodegradation of the hydrogel and will remain in the vitreous humor, where it dissolves and is delivered to ocular tissue such as the retina or the choroid, thereby providing a continued therapeutic efficacy even after biodegradation of the hydrogel such that the entire treatment period provided by one implant may be about 9 months (any may thus extend beyond the persistence of the hydrogel/the implant in vitreous humor). In certain embodiments, this described release profile is provided by an intravitreous sustained release biodegradable implant as disclosed herein, containing axitinib form IV in an amount from about 360 μg to about 562.5 or about 540 μg, such as from about 400 μg to about 500 μg, such as about 450 μg dispersed in a hydrogel comprising a network of crosslinked PEG units, such as crosslinked 4a20kPEG-SAZ and 8a20kPEG-$NH_2$ as disclosed herein. A new implant can be injected after the end of the first treatment period provided by a first implant, so that treatment can continue seamlessly with a second implant providing for a second treatment period. Thus, a continued, long-term treatment (e.g. of wet AMD) can be provided. In some embodiments, a new implant may be administered every 6 to 12 months. In certain embodiments, the re-dosing period may be about 6 months, or about 9 months or about 12 months, i.e., a new implant may be administered about 6 months, or about 9 months, or about 12 months after administration of the preceding implant. In other embodiments, a new implant may be administered as soon as the hydrogel of the previous implant has biodegraded or has essentially biodegraded as e.g. assessed by an ophthalmologist. The re-administration of an implant may be repeated as many times as required, e.g. at least twice, or at least three times, or at least four times, or more times.

In particular embodiments, the implant of the present invention providing for such a release profile is a sustained release biodegradable ocular implant comprising a hydrogel and axitinib, wherein axitinib particles are dispersed within the hydrogel, wherein the implant comprises axitinib polymorph IV in an amount of from about 360 μg to about 540 μg, such as from about 400 μg to about 500 μg, such as about 450 μg, wherein the implant has a composition on a dry basis (in % w/w) of about 30 to about 75% axitinib, about 20 to about 50% PEG units, and about 0.5 to about 15% sodium phosphate salt and on a wet basis (in % w/w) of about 5 to about 17% axitinib, about 4 to about 12% PEG units, and about 0.2 to about 5% sodium phosphate salt, wherein the hydrogel comprises crosslinked 4a20kPEG-SAZ and 8a20kPEG-$NH_2$ units, wherein the implant has a length that is greater than its width, and in its dried state has a length of 11 mm or less, such as from 5 to 11 mm and a width of from 0.2 to 0.4, such as from 0.28 to 0.38 mm and/or in its hydrated state (after 24 hours in PBS at a pH of 7.4 at 37° C.) has a length of 11 mm or less, such as from 5 to 11 mm and a width of from 0.4 to 2 mm, and wherein optionally the axitinib particles are micronized, and may have a d90 particle size of less than 8 μm and a d50 particle size of less than 3 μm. Such an implant may provide for a treatment period of about 6 to about 12 months, such as about 8 to about 11 months, i.e., re-dosing of a fresh implant may occur after a period of about 6 to about 12 months, such as about 8 to 11 months, while providing for a continued therapeutic effect and thus a long-term treatment of an ocular disease (such as wet AMD) in a patient, particularly a human patient.

In certain embodiments, the remaining amount of TKI such as axitinib still contained in the implant when biodegradation of the hydrogel starts, and which is thus liberated upon biodegradation of the hydrogel, may be less than about 250 μg, such as less than about 200 μg, such as less than about 150 μg, such as less than about 100 μg. In certain embodiments, the remaining amount of TKI such as axitinib still contained in the implant at month 6 after injection (In non-human primates, or in humans), may be less than about 250 μg, such as less than about 200 μg, such as less than about 150 μg, such as less than about 100 μg.

It is demonstrated in Example 10 that an implant according to the present invention containing about 300 μg axitinib polymorph IV injected into the eyes of *Cynomolgus* monkeys releases axitinib at a rate such that the amount of axitinib delivered to the retina and the choroid at 3 months after injection is higher than the amount delivered at 6 months (which is when the hydrogel degrades as hydrogel degradation occurs at about 5 to 6 months in *Cynomolgus* monkeys). For human patients, in whom the same hydrogel degrades later than in *Cynomolgus* monkeys (hydrogel degradation occurs at about 8 to 9 months, mainly due the lower mid-vitreal temperature in humans as compared to the monkeys) axitinib can be released longer before the hydrogel starts to degrade. Thus, for human patients, a dose that is higher than about 300 μg axitinib polymorph IV (as used in *Cynomolgus* monkeys in Example 10), such as a dose from about 360 μg to about 540 μg, such as from about 400 μg to about 500 μg, such as about 450 μg of axitinib polymorph IV, can be extrapolated to exhibit a comparable release characteristic, i.e., that the cumulative amount of axitinib released before the hydrogel starts to degrade is higher than the remaining amount of axitinib that is released upon hydrogel degradation.

As already mentioned, the degradation of a PEG hydrogel comprising crosslinked 4a20kPEG-SAZ and 8a20kPEG-$NH_2$ occurs in the rabbit, NHP (non-human primates) and humans at different time points: at about 8 to 9 months after injection in humans, at about 5 to 6 months after injection in monkeys (*Cynomolgus* monkeys), and at about 4 to 5 months after injection in rabbits (Dutch Belted rabbits). Hydrogel degradation takes place inter alia via ester hydrolysis. The vitreous volume in rabbit, NHP and humans also differs and is as follows: about 1.15 mL in rabbit, about 2 mL in monkey (*Cynomolgus* monkey) and about 4 mL in humans (B. Short, *Toxicologic Pathology* 49.3 (2021): 673-699). Finally, the mid-vitreal temperature of the rabbit, NHP, and human vitreous also differs among the species and is as follows: 33° C. in humans, 35° C. in monkeys, 37° C. in rabbit (F. Lorget et al., *Molecular pharmaceutics,* 13(9), pp. 2891-2896; and M. B. Landers III et al., Retina 32(1), p. 172-176 (January/2012)).

Based on the results of the NHP in vivo study and the rabbit in vivo study (Examples 10 and 13), a dose of about 450 μg axitinib polymorph IV in an implant of the invention may be postulated as a suitable and effective human clinical dose for an implant comprising axitinib polymorph IV within a PEG hydrogel comprising crosslinked 4a20kPEG-SAZ and 8a20kPEG-$NH_2$.

In summary, without wishing to be bound by theory, the NHP and rabbit in vivo study results allow the following conclusions:

Because of the higher solubility of axitinib polymorph IV (about twice the solubility of axitinib polymorph SAB-I, as demonstrated herein, see Example 6), implants containing polymorph IV release axitinib faster than implants containing SAB-I (see e.g. Example 13). Thereby, they can deliver axitinib faster to ocular tissue and may also provide higher axitinib concentrations in ocular tissue.

In the NHP in vivo study (Example 10) an implant containing about 300 μg axitinib polymorph IV had already released the largest part of its drug payload prior to hydrogel degradation (which occurs at about 5 to 6 months in monkey). The amount of axitinib still remaining in the implant at the start of its degradation was lower than in the case of implants containing axitinib polymorph SAB-I.

Extrapolating from the NHP in vivo results to humans, based on the longer persistence of the hydrogel in humans (hydrogel degradation at about 8 to 9 months) it may be postulated that in a human eye an implant containing about 400 to 500 μg, such as about 450 μg axitinib form IV releases a relatively large portion of the axitinib already prior to hydrogel degradation, such that there is on the one hand still a sufficient remaining amount of axitinib left in the implant to be released upon hydrogel degradation, but that this amount is on the other hand not higher or not substantially higher than the cumulative amount of axitinib released when the implant was still intact. It may be postulated that the remaining amount of axitinib in the implant to be released upon hydrogel degradation is less than about 250 μg, such as less than about 200 μg (when the starting dose is 450 μg axitinib), or less than about 150 μg, or less than about 100 μg.

The implants according to the present invention in certain embodiments achieve the object of providing a faster release of TKI to achieve high TKI tissue concentrations faster than known implants. At the same time, in certain embodiments, since most of the TKI has already been released, a lower amount of TKI is released upon final degradation of the hydrogel, while this amount is sufficient to "bridge" the time until complete hydrogel degradation, at which point a fresh implant can be placed, so as to provide a continuous treatment by implant re-dosing.

Also in cases where the hydrogel degrades at essentially the same time as it takes for the TKI to be released, a new implant can be injected promptly and repeatedly after said complete degradation/release so that a therapeutically effective concentration of TKI in the eye, such as in the vitreous, can be maintained in steady state or at least without any major fluctuations over a very long period of time (e.g. over years), without the build-up of any residues (hydrogel and/or TKI) in the eye, Thus, regular dosing intervals can be established, such as e.g. every 6 months, or every 9 months for a continued long-term therapy. In other words, upon completion of one treatment period with one implant, a new treatment period with a new implant (also referred to herein as "fresh implant") according to the present invention may start immediately and seamlessly so as to ensure a continuous treatment. In certain embodiments, the treatment periods may even slightly overlap. The point in time when a new implant is administered may be determined by an ophthalmologist e.g. by means of visualization of the previous implant, i.e., when the previous implant is no longer detectable and/or when no or only few remaining axitinib particles are detectable, a new implant may be injected.

Specific Implants:

In specific embodiments, the invention relates to a sustained release biodegradable intravitreal implant comprising a hydrogel comprising crosslinked PEG units and axitinib polymorph IV in an amount of from about 360 μg to about 562.5 μg, such as from about 400 μg to about 500 μg axitinib polymorph IV, or from about 405 μg to about 495 μg, or from about 410 to about 490 μg axitinib polymorph IV, such as about 450 μg axitinib polymorph IV.

In certain specific embodiments, the present invention relates to a sustained release biodegradable ocular (such as intravitreal) implant comprising a hydrogel and axitinib, wherein axitinib particles are dispersed within the hydrogel, wherein the implant comprises axitinib polymorph IV and the implant contains axitinib in an amount corresponding to about 250 to about 700 μg axitinib free base, wherein the hydrogel comprises crosslinked PEG units. The implant may contain axitinib polymorph IV in an amount of from about 360 μg to about 562.5 μg, such as from about 405 μg to about 495 μg, particularly about 450 μg. In other embodiments, the implant may contain axitinib polymorph IV in an amount of from about 480 μg to about 750 μg, such as from about 540 μg to about 660 μg, particularly about 600 μg. It can be cylindrical or essentially cylindrical and in its dried state may have a length of from 6 to 9 mm and a diameter of from 0.25 to 0.45 mm, such as length of from 6.7 to 8.7 mm and a diameter of from 0.30 to 0.40 mm. In the hydrated state (after 24 hours in PBS at a pH of 7.2 to 7.4 at 37° C.) it may have a length of from 7 to 10 mm and a diameter of from 0.5 to 0.9 mm, such as a length of from 8 to 9 mm and a diameter of from 0.70 to 0.80 mm. In other embodiments, the implant can be non-cylindrical and in its dried state can have a length of from 5 to 11 mm and a width of from 0.28 to 0.38 mm, and in the hydrated state (after 24 hours in PBS at a pH of 7.2 to 7.4 at 37° C.) may have a length of from 5 to 11 mm and a width of from 0.4 to 2 mm. These may have a hydrated surface area of at least 10 $mm^2$, or at least 16 $mm^2$, or at least 19 mm, such as a hydrated surface area of at least 25 $mm^2$. Particularly for single-stranded cylindrical (or essentially cylindrical) implants, a suitable hydrated surface area for implants of the present invention is from about 10 $mm^2$ to about 30 $mm^2$, such as from about 16 $mm^2$ to about 25 $mm^2$, or from about 17 $mm^2$ to about 22.5 or 23 $mm^2$. This implant may contain a polymer network comprising crosslinked PEG units, wherein the crosslinks between the PEG units include a group represented by the following formula

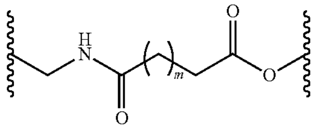

wherein m is an integer from 0 to 10, such as m being 1, 2, 3, or 6, particularly m being 6. In such an implant, the axitinib particles may have a d90 particle size of less than 8 μm, and/or a d50 particle size of less than 3 μm, and/or a d10 particles size of less than 0.5 μm as determined by means of laser diffraction. The implant may biodegrade, i.e., the hydrogel may dissolve, within about 6 to about 12 months after administration, or within about 6 to about 9 months, or within about 7.5 months after administration. In specific embodiments, this implant may release at least about 50% of the total released amount of axitinib over the initial 3 days and/or at least about 80% of the total released amount of axitinib over the initial 7 days and/or at least about 92% of the total released amount of axitinib over the initial 10 days in an in vitro test performed at 37° C. in an 25%/75% (v/v) ethanol/water mixture under 2× sink conditions. Alternatively, the implant may release at least about 30% of the total released amount of axitinib over the initial 4 days and/or at least about 50% of the total released amount of axitinib over the initial 7 days or the initial 9 days in an in vitro test performed at 37° C. in an 25%/75% (v/v) ethanol/water mixture under 3× sink conditions. In terms of the cumulative amount of axitinib released in an in vitro test performed at 37° C. in an 25%/75% (v/v) ethanol/water mixture under 2× sink conditions, the implant may release at least about 60 μg, or at least about 70 μg, or at least about 80 μg axitinib over the initial day, and/or at least about 100 μg, or at least about 120 μg, or at least about 130 μg axitinib over the initial 2 days, and/or at least about 130 μg, or at least about 150 μg, or at least about 180 μg axitinib over the initial 3 days, and/or at least about 220 μg, or at least about 260 μg, or at least about 290 μg axitinib over the initial 7 days, and/or at least about 275 μg, or at least about 300 μg, or at least about 350 μg axitinib over the initial 10 days. Alternatively, in terms of the cumulative amount of axitinib released in an in vitro test performed at 37° C. in an 25%/75% (v/v) ethanol/water mixture under 3× sink conditions, the implant may release at least about 45 μg, or at least about 50 μg, or at least about 55 μg axitinib over the initial day, and/or at least about 80 μg, or at least about 100 μg, or at least about 120 μg axitinib over the initial 2 days, and/or at least about 150 μg, or at least about 160 μg, or at least about 190 μg axitinib over the initial 4 days, and/or at least about 240 μg, or at least about 290 μg, or at least about 300 μg axitinib over the initial 7 days, and/or at least about 270 μg, or at least about 300 μg, or at least about 330 μg axitinib over the initial 9 days.

In further specific embodiments, the invention relates to a sustained release biodegradable ocular implant comprising a hydrogel and axitinib, wherein axitinib particles are dispersed within the hydrogel, wherein the implant comprises axitinib polymorph IV in an amount of from about 360 μg to about 562.5 μg, or from about 405 μg to about 495 μg, such as about 450 μg, wherein the hydrogel comprises crosslinked multi-armed PEG units having a number average molecular weight of about 20,000 Daltons, wherein the crosslinks between the PEG units include a group represented by the following formula

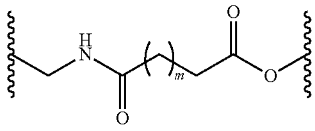

wherein m is 6, wherein the implant is cylindrical and in its dried state has a length of 10 mm or less, such as from 6 to 9 mm and a diameter of from 0.25 to 0.45 mm and/or in its hydrated state (after 24 hours in PBS at a pH of 7.4 at 37° C.) has a length of 10 mm or less, such as from 6 to 9.5 mm and a diameter of from 0.5 to 0.9 mm, and wherein the axitinib particles have a d90 particle size of less than 8 μm and a d50 particle size of less than 3 μm.

In further specific embodiments, the invention relates to a sustained release biodegradable intravitreal implant comprising a hydrogel and axitinib, wherein axitinib particles are dispersed within the hydrogel, wherein the implant comprises axitinib polymorph IV in an amount of from about 250 μg to about 720 μg, such as from 360 μg to about 562.5 μg, such as from about 400 μg to about 500 μg, such as about 450 μg, wherein the implant has a composition on a dry basis (in % w/w) of about 30 to about 75% axitinib, about 20 to about 50% PEG units, and about 0.5 to about 15% sodium phosphate salt and on a wet basis (in % w/w) of about 5 to about 17% axitinib, about 4 to about 12% PEG units, and about 0.2 to about 5% sodium phosphate salt, wherein the hydrogel is a PEG hydrogel network formed by crosslinking 4a20kPEG-SAZ and 8a20kPEG-$NH_2$, wherein the implant has a length that is greater than its width, and in its dry state (prior to injection) has a length of 11 mm or less, such as from 5 to 11 mm and a width of from 0.2 to 0.4 mm, such as from 0.28 to 0.38 mm and/or in its hydrated state (after 24 hours in PBS at a pH of 7.4 at 37° C.) has a length of 11 mm or less, such as from 5 to 11 mm and a width of from 0.4 to 2 mm, and wherein the axitinib particles optionally have a d90 particle size of less than 8 μm and a d50 particle size of less than 3 μm.

In these embodiments, the implant may provide for an average release rate of above about 0.8 μg/day, such as above about 1 μg/day in vitreous humor (of a human patient or of a non-human primate, such as a monkey, such as a *Cynomolgus* monkey). Further, in these embodiments, the amount of axitinib remaining when the hydrogel starts to degrade (and thus the amount of axitinib being released upon final degradation of the hydrogel) may be less than 200 μg, such as less than 150 μg.

In further specific embodiments, the invention relates to a sustained release biodegradable intravitreal implant comprising a hydrogel of cross-linked PEG units and axitinib polymorph IV in an amount of from about 250 to about 750 μg, such as from about 400 to about 500 μg, such as about 450 μg, wherein axitinib particles are dispersed within the hydrogel, wherein the implant has a composition within the following ranges (dry basis, % w/w):

| Ingredient | Implant Composition (% w/w, dry) |
|---|---|
| Axitinib, Polymorph IV | 54-69 |
| 4a20k PEG SAZ | 17-26 |
| 8a20k PEG $NH_2$ | 8-13 |
| Sodium Phosphate Dibasic Dried, USP | 3-5 |
| Sodium Phosphate Monobasic Anhydrous, USP | 1-3 |

and which optionally has the following dry and hydrated (after 24 hours in PBS at a pH of 7.4 at 37° C.) dimensions:

| | Dry dimensions (mm) | Hydrated dimensions (mm) |
|---|---|---|
| Length | 5-11 | 5-11 |
| Width | 0.28-0.38 | 0.4-2 |

and which may be obtainable by wet casting, using a stretch factor of from about 1 to about 3, or alternatively by hot melt extrusion. In these embodiments, the implant may provide for an average release rate of above about 0.8 μg/day, such as above about 1 μg/day in vitreous humor (of a human patient or of a non-human primate, such as a monkey, such as a *Cynomolgus* monkey). Further, in these embodiments, the amount of axitinib remaining when the hydrogel starts to degrade (and thus the amount of axitinib being released upon final degradation of the hydrogel) may be less than 200 μg, such as less than 150 μg.

In further specific embodiments, the invention relates to a sustained release biodegradable intravitreal implant comprising a hydrogel and axitinib polymorph IV in an amount of 360 to 540 μg, such as from about 400 to about 500 μg, such as about 450 μg, where in axitinib particles are dispersed within the hydrogel, the hydrogel comprising crosslinked PEG units (such as a hydrogel formed by crosslinking 4a20kPEG-SAZ and 8a20kPEG-$NH_2$), wherein the amount of axitinib remaining when the hydrogel starts to degrade (and thus the amount of axitinib being released upon final degradation of the hydrogel) is less than 200 μg, such as less than 150 μg, and wherein the implant in its dry state (prior to injection) has a width of from about 0.3 to about 0.4 mm, such as from about 0.33 to about 0.36 mm and a length of less than about 11 mm, and in its hydrated state (after 24 hours in PBS at a pH of 7.4 at 37° C.) has a length of less than about 11 mm, such as a length of from about 6 to about 10 mm, such as from about 8 to about 10 mm. In these embodiments, the implant may provide for an average release rate of above about 0.8 μg/day, such as above about 1 μg/day in vitreous humor (of a human patient or of a non-human primate, such as a monkey, such as a *Cynomolgus* monkey).

In one specific embodiment of an implant of the present invention comprising about 450 μg axitinib polymorph IV in a hydrogel comprising crosslinked PEG units (such as a hydrogel formed by crosslinking 4a20kPEG-SAZ and 8a20kPEG-$NH_2$), having dry dimensions of about 0.35 mm (width)×7.4 mm (length) and hydrated (after 24 hours in PBS at a pH of 7.4 at 37° C.) dimensions of about 0.75 mm (width)×8.4 mm (length), such implant may contain a remaining amount of drug of about 250 μg at month 6, and may exhibit a release rate at month 3 after injection of the implant of about 1.2 μg/day (in non-human primates, such as a monkey, such as a *Cynomolgus* monkey), This is an estimate based on other in vivo studies in non-human primates with other implants (such as those containing axitinib polymorph IV or polymorph SAB-I, and with doses of about 300 and about 600 μg each).

In further specific embodiments, the invention relates to a sustained release biodegradable ocular implant comprising a hydrogel and axitinib, wherein axitinib particles are dispersed within the hydrogel, wherein the implant comprises axitinib polymorph IV in an amount of from about 480 μg to about 750 μg, or from about 540 μg to about 660 μg, such as about 600 μg, wherein the hydrogel comprises crosslinked multi-armed PEG units having a number average molecular weight of about 20,000 Daltons, wherein the crosslinks between the PEG units include a group represented by the following formula

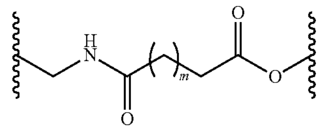

wherein m is 6, wherein the implant is cylindrical and in its dried state has a length of 10 mm or less, such as from 6 to 8 mm and a diameter of from 0.25 to 0.45 mm and/or in its hydrated state (after 24 hours in PBS at a pH of 7.4 at 37° C.) has a length of 10 mm or less, such as from 8 to 9 mm and a diameter of from 0.5 to 0.9 mm, and wherein the axitinib particles have a d90 particle size of less than 8 μm and a d50 particle size of less than 3 μm.

In further specific embodiments, the invention relates to a sustained release biodegradable ocular implant comprising a hydrogel and axitinib, wherein axitinib particles are dispersed within the hydrogel, wherein the implant comprises axitinib polymorph IV and the implant contains axitinib in an amount corresponding to from about 360 μg to about 562.5 μg, or from about 405 μg to about 495 μg, such as about 450 μg axitinib free base, and releases at least about 60 μg axitinib over the initial day, and/or at least about 100 μg axitinib over the initial 2 days, and/or at least about 130 μg axitinib over the initial 3 days, and/or at least about 220 μg axitinib over the initial 7 days and/or at least about 275 μg axitinib over the initial 10 days in an in vitro test performed at 37° C. in an 25%/75% (v/v) ethanol/water mixture under 2× sink conditions.

In other specific embodiments, the invention relates to a sustained release biodegradable ocular implant comprising a hydrogel and axitinib, wherein axitinib particles are dispersed within the hydrogel, wherein the implant comprises axitinib polymorph IV and the implant contains axitinib in an amount corresponding to from about 360 μg to about 562.5 μg, or from about 405 μg to about 495 μg, such as about 450 μg axitinib free base, and releases at least about 35 μg axitinib over the initial day, and/or at least about 60 μg axitinib over the initial 2 days, and/or at least about 100 μg axitinib over the initial 4 days, and/or at least about 180 μg axitinib over the initial 7 days and/or at least about 200 μg axitinib over the initial 9 days in an in vitro test performed at 37° C. in an 25%/75% (v/v) ethanol/water mixture under 3× sink conditions.

In further specific embodiments, the invention relates to a sustained release biodegradable ocular implant comprising a hydrogel and axitinib, wherein axitinib particles are dispersed within the hydrogel, wherein the implant comprises axitinib polymorph IV and the implant contains axitinib in an amount corresponding to from about: 480 μg to about 750 μg, or from about 540 μg to about 660 μg, such as about 600 μg axitinib free base, and releases at least about 70 μg axitinib over the initial day, and/or at least about 130 μg axitinib over the initial 2 days, and/or at least about 180 μg axitinib over the initial 3 days, and/or at least about 300 μg axitinib over the initial 7 days and/or at least about 375 jug axitinib over the initial 10 days in an in vitro test performed at 37° C. in an 25%/75% (v/v) ethanol/water mixture under 2× sink conditions.

In other specific embodiments, the invention relates to a sustained release biodegradable ocular implant comprising a hydrogel and axitinib, wherein axitinib particles are dispersed within the hydrogel, wherein the implant comprises axitinib polymorph IV and the implant contains axitinib in an amount corresponding to from about 480 μg to about 750 μg, or from about 540 μg to about 660 μg, such as about 600 μg axitinib free base, and releases at least about 50 μg axitinib over the initial day, and/or at least about 100 μg axitinib over the initial 2 days, and/or at least about 180 μg axitinib over the initial 4 days, and/or at least about 280 μg axitinib over the initial 7 days and/or at least about 300 μg axitinib over the initial 9 days in an in vitro test performed at 37° C. in an 25%/75% (v/v) ethanol/water mixture under 3× sink conditions.

In further specific embodiments, the invention relates to a sustained release biodegradable ocular implant comprising a hydrogel and axitinib, wherein axitinib particles are dispersed within the hydrogel, wherein the implant comprises axitinib polymorph IV and the implant contains axitinib in an amount corresponding to from about 360 μg to about 562.5 μg, or from about 405 μg to about 495 μg, such as about 450 μg axitinib free base, and releases at least 50% of the total released amount of axitinib over the initial 3 days in an in vitro test, and/or releases at least 80% of the total released amount of axitinib over the initial 7 days in an in vitro test, and/or releases at least 92% of the total released amount of axitinib over the initial 10 days in an in vitro test, wherein the in vitro test is performed at 37° C. in an 25%/75% (v/v) ethanol/water mixture under 2× sink conditions.

In further specific embodiments, the invention relates to a sustained release biodegradable ocular implant comprising a hydrogel and axitinib, wherein axitinib particles are dispersed within the hydrogel, wherein the implant comprises axitinib polymorph IV and the implant contains axitinib in an amount corresponding to from about 360 μg to about 562.5 μg, or from about 405 μg to about 495 μg, such as about 450 μg axitinib free base, and releases at least 30% of the total released amount of axitinib over the initial 3 days in an in vitro test, and/or releases at least 60% of the total released amount of axitinib over the initial 7 days in an in vitro test, and/or releases at least 80% of the total released amount of axitinib over the initial 10 days in an in vitro test, wherein the in vitro test is performed at 37° C. in an 25%/75% (v/v) ethanol/water mixture under 2× sink conditions.

In other specific embodiments, the invention relates to a sustained release biodegradable ocular implant comprising a hydrogel and axitinib, wherein axitinib particles are dispersed within the hydrogel, wherein the implant comprises axitinib polymorph IV and the implant contains axitinib in an amount corresponding to from about 360 μg to about 562.5 μg, or from about 405 μg to about 495 μg, such as about 450 μg axitinib free base, and releases at least 15% of the total released amount of axitinib over the initial 2 days in an in vitro test, and/or releases at least 30% of the total released amount of axitinib over the initial 4 days in an in vitro test, and/or releases at least 50% of the total released amount of axitinib over the initial 7 days in an in vitro test, wherein the in vitro test is performed at 37° C. in an 25%/75% (v/v) ethanol/water mixture under 3× sink conditions.

In further specific embodiments, the invention relates to a sustained release biodegradable ocular implant comprising a hydrogel and axitinib, wherein axitinib particles are dispersed within the hydrogel, wherein the implant comprises axitinib polymorph IV and the implant contains axitinib in an amount corresponding to from about 480 μg to about 750 μg, or from about 540 μg to about 660 μg, such as about 600 μg axitinib free base, and releases at least 50% of the total released amount of axitinib over the initial 3 days in an in vitro test, and/or releases at least 80% of the total released amount of axitinib over the initial 7 days in an in vitro test, and/or releases at least 92% of the total released amount of axitinib over the initial 10 days in an in vitro test, wherein the in vitro test is performed at 37° C. in an 25%/75% (v/v) ethanol/water mixture under 2× sink conditions.

In further specific embodiments, the invention relates to a sustained release biodegradable ocular implant comprising a hydrogel and axitinib, wherein axitinib particles are dispersed within the hydrogel, wherein the implant comprises axitinib polymorph IV and the implant contains axitinib in an amount corresponding to from about 480 μg to about 750 μg, or from about 540 μg to about 660 μg, such as about 600 μg axitinib free base, and releases at least 30% of the total released amount of axitinib over the initial 3 days in an in vitro test, and/or releases at least 60% of the total released amount of axitinib over the initial 7 days in an in vitro test, and/or releases at least 80% of the total released amount of axitinib over the initial 10 days in an in vitro test, wherein the in vitro test is performed at 37° C. in an 25%/75% (v/v) ethanol/water mixture under 2× sink conditions.

In other specific embodiments, the invention relates to a sustained release biodegradable ocular implant comprising a hydrogel and axitinib, wherein axitinib particles are dispersed within the hydrogel, wherein the implant comprises axitinib polymorph IV and the implant contains axitinib in an amount corresponding to from about 480 μg to about 750 μg, or from about 540 μg to about 660 μg, such as about 600 μg axitinib free base, and releases at least 15% or at least 20% of the total released amount of axitinib over the initial 2 days in an in vitro test, and/or releases at least 35% of the total released amount of axitinib over the initial 4 days in an in vitro test, and/or releases at least 55% of the total released amount of axitinib over the initial 7 days in an in vitro test, wherein the in vitro test is performed at 37° C. in an 25%/75% (v/v) ethanol/water mixture under 3× sink conditions.

In other specific embodiments, the invention relates to a sustained release biodegradable ocular implant comprising axitinib polymorph IV particles dispersed in a hydrogel, wherein the implant comprises axitinib polymorph IV in an amount of from about 300 to about 650 μg, such as from about 360 μg to about 562.5 μg, such as from about 400 μg to about 500 μg, such as about 450 μg, wherein the implant has a composition on a dry basis (in % w/w) of about 30 to about 75% axitinib, about 20 to about 50% PEG units, and about 0.5 to about 15% sodium phosphate salt and on a wet basis (in % w/w) of about 5 to about 17% axitinib, about 4 to about 12% PEG units, and about 0.2 to about 5% sodium phosphate salt, wherein the hydrogel comprises a PEG hydrogel network formed by crosslinking 4a20kPEG-SAZ and 8a20kPEG-$NH_2$ units, wherein the implant in its dried state has a length of from 5 to 11 mm and a width of from 0.2 to 0.4 mm, such as from 0.28 to 0.38 mm, and/or in its hydrated state (after 24 hours in PBS at a pH of 7.4 at 37° C.) has a length of from 5 to 11 mm and a width of from 0.4 to 2 mm. In these embodiments, the axitinib may have a d90 particle size of less than 8 μm and a d50 particle size of less than 3 μm.

In other specific embodiments, the invention relates to a sustained release biodegradable ocular implant comprising axitinib polymorph IV particles dispersed in a hydrogel, wherein the implant comprises axitinib polymorph IV in an amount of from about 300 to about 650 μg, such as from about 360 μg to about 562.5 μg, such as from about 400 μg to about 500 μg, such as about 450 μg, wherein the implant has a composition on a dry basis (in % w/w) of about 54 to about 69% axitinib, a PEG hydrogel network formed by crosslinking about 17 to 26% 4a20kPEG-SAZ with about 8 to about 13% 8a20kPEG-$NH_2$, about 3 to about 5% dibasic sodium phosphate, and about 1 to about 3% monobasic sodium phosphate. In these embodiments, the implant in its dried state may have a length of from 5 mm to 11 mm and a width of from 0.28 to 0.38 mm and/or in its hydrated state (after 24 hours in PBS at a pH of 7.4 at 37° C.) may have a length of from 5 to 11 mm and a width of from 0.4 to 2 mm. In these embodiments, the axitinib may have a d90 particle size of less than 8 μm and a d50 particle size of less than 3 μm.

In other specific embodiments, the invention relates to a sustained release biodegradable intravitreal implant comprising a hydrogel and axitinib polymorph IV in an amount of from about 300 to about 650 μg, such as from about 360 μg to about 562.5 μg, such as from about 360 to 540 μg, such as from about 400 to about 500 μg, such as about 450 μg, wherein axitinib particles are dispersed within the hydrogel, the hydrogel comprising crosslinked PEG units (such as crosslinked 4a20kPEG-SAZ and 8a20kPEG-$NH_2$ units), wherein the amount of axitinib remaining when the hydrogel starts to degrade (and thus the amount of axitinib being released upon final degradation of the hydrogel) is less than 200 μg, wherein the implant in its dry state (prior to injection) has a width of from about 0.3 to about 0.4 mm, such as about 0.33 to about 0.36 mm, and a length of less than about 11 mm, and in its hydrated state (after 24 hours in PBS at a pH of 7.4 at 37° C.) has a length of less than about 11 mm, such as a length of from about 8 to about 10 mm.

In other specific embodiments, the present invention relates to a sustained release biodegradable intravitreal implant comprising a hydrogel and axitinib, wherein axitinib particles are dispersed within the hydrogel, wherein the implant comprises axitinib polymorph IV in an amount of from about 300 to about 650 μg, such as from about 360 μg to about 562.5 μg, such as from about 400 μg to about 500 μg, wherein the implant has a composition on a dry basis (in % w/w) of about 30 to about 75% axitinib, about 20 to about 50% PEG units, and about 0.5 to about 15% sodium phosphate salt and on a wet basis (in % w/w) of from about 5 to about 17% axitinib, about 4 to about 12% PEG units, and about 0.2 to about 5% sodium phosphate salt, wherein the hydrogel comprises a PEG hydrogel network formed by crosslinking 4a20kPEG-SAZ and 8a20kPEG-$NH_2$ precursors, wherein the implant in its dried state has a width of from 0.20 to 0.40 mm, and in its hydrated state (after 24 hours in PBS at a pH of 7.4 at 37° C.) has a length of 11 mm or less, and wherein the implant has a hydrated surface area of from 10 to 30 $mm^2$.

In particular ones of these embodiments, the implant of the present invention has a composition on a dry basis (in % w/w) of from about 50% to about 70% by weight axitinib, and from about 25% to about 45% by weight PEG units, and on a wet basis (in % w/w) of from about 7% to about 17% by weight axitinib, and from about 5% to about 10% by weight PEG units, wherein the implant in its dried state has a width of from 0.30 to 0.36 mm, and in its hydrated state (after 24 hours in PBS at a pH of 7.4 at 37° C.) has a length of 10.5 mm or less, and wherein the implant has a hydrated surface area (as defined herein) of from 16 to 25 $mm^2$, such as from 16 to 23 $mm^2$.

In yet other specific embodiments, the present invention relates to a sustained release biodegradable intravitreal implant comprising a hydrogel and axitinib, wherein axitinib particles are dispersed within the hydrogel, wherein the implant comprises axitinib polymorph IV in an amount of from about 400 μg to about 500 μg, wherein the hydrogel comprises a PEG hydrogel network formed by crosslinking 4a20kPEG-SAZ and 8a20kPEG-$NH_2$ precursors, wherein the implant in its dried state has a width of from 0.30 to 0.36 mm, and in its hydrated state (after 24 hours in PBS at a pH of 7.4 at 37° C.) has a length of 10.5 mm or less, and wherein the implant has a hydrated surface area (as defined herein) of from 16 to 25 $mm^2$.

In other specific embodiments, the present invention relates to a sustained release biodegradable ocular implant containing axitinib polymorph IV in a dose of about 400 to about 500 μg, such as about 450 μg, wherein the hydrogel comprises a PEG hydrogel, wherein the implant in its dry state has a width of from 0.30 to 0.36 mm, and wherein the implant provides for a release of axitinib in an in vitro test performed at 35° C.±: 0.5° C. in 0.01N HCl with 0.25% cetyl trimethyl ammonium bromide (CTAB) in a USP apparatus 4 that is characterized in that the percentage of axitinib released from the implant (wherein the percentage of released axitinib is based on the maximum amount of axitinib released from the implant representing 100%) is:

at least about 10% after 0.5 hours,
at least about 30% after 2 hours, at least about 58% after 6 hours,
at least about 75% after 10 hours,
at least about 80% after 12 hours,
and/or at least about 90% after 16 hours;
such as:
at least about 10% after 0.5 hours,
at least about 19% after 1 hour,
at least about 30% after 2 hours,
at least about 45% after 4 hours,
at least about 58% after 6 hours,
at least about 70% after 8 hours,
at least about 75% after 10 hours,
at least about 80% after 12 hours,
and/or at least about 90% after 16 hours.

In these embodiments, the implant may have a hydrated (after 24 hours in PBS at a pH of 7.2-7.4 at 37° C.) surface area of at least 16 $mm^2$, such as from 16 to 23 $mm^2$. In these embodiments, the axitinib particles may have a d90 particle size of less than 8 μm and a d50 particle size of less than 3 μm.

In further specific embodiments, the present invention relates to a sustained release biodegradable ocular implant containing axitinib polymorph IV in a dose of about 400 to about 500 μg, such as about 450 μg, wherein the hydrogel comprises a hydrogel network formed by crosslinking 4a20kPEG-SAZ and 8a20kPEG-$NH_2$ units, wherein the implant has a composition (dry basis; in % w/w) as follows: from about 60% to about 70% axitinib and from about 25% to about 35% PEG units, wherein the implant in its dry state has a width of from 0.30 to 0.36 mm and a total weight of from about 0.6 mg to about 1 mg, and wherein the implant provides for a release of axitinib in an in vitro test performed at 35° C.±0.5° C. in 0.01N HCl with 0.25% cetyl trimethyl ammonium bromide (CTAB) in a USP apparatus 4 that is characterized in that the percentage of axitinib released from the implant (wherein the percentage of released axitinib is based on the maximum amount of axitinib released from the implant representing 100%) is:

from about 10 to about 20% after 0.5 hours,
from about 30 to about 45% after 2 hours,
from about 58 to about 81% after 6 hours,
from about 75 to about 98% after 10 hours,
at least about 80% after 12 hours,
and/or at least about 90% after 16 hours,
such as:
from about 10 to about 20% after 0.5 hours,
from about 19 to about 30% after 1 hour,
from about 30 to about 45% after 2 hours,
from about 45 to about 65% after 4 hours,
from about 58 to about 81% after 6 hours,
from about 70 to about 90% after 8 hours,
from about 75 to about 98% after 10 hours,
at least about 80% after 12 hours,
and/or at least about 90% after 16 hours.

In these embodiments, the implant may have a hydrated (after 24 hours in PBS at a pH of 7.2-7.4 at 37° C.) surface area of at least 16 $mm^2$, such as from 16 to 23 $mm^2$. In these embodiments, the axitinib particles may have a d90 particle size of less than 8 μm and a d50 particle size of less than 3 μm.

In yet other specific embodiments, the present invention relates to a sustained release biodegradable intravitreal implant comprising a hydrogel and axitinib, wherein axitinib particles are dispersed within the hydrogel, wherein the implant comprises axitinib polymorph IV in an amount of from about 400 μg to about 500 μg, wherein the hydrogel comprises a PEG hydrogel (wherein in particular embodiments the hydrogel comprises a PEG hydrogel network formed by crosslinking 4a20kPEG-SAZ and 8a20kPEG-$NH_2$ units), wherein the implant in its dried state has a width of from 0.30 to 0.36 mm and has a hydrated (after 24 hours in PBS at a pH of 7.4 at 37° C.) surface area of from 16 to 25 mm, and wherein the implant provides for a release of axitinib in an in vitro test performed at 35° C.±0.5° C. in 0.01N HCl with 0.25% cetyl trimethyl ammonium bromide (CTAB) in a USP apparatus 4 that is characterized in that the percentage of axitinib released from the implant is:

from 10 to 18% after 0.5 hours,
from 30 to 45% after 2 hours,
from 60 to 80% after 6 hours,
from 79 to 98% after 10 hours,
at least 90% after 12 hours,
and at least 92% after 16 hours, wherein the percentage of released axitinib is based on 450 μg axitinib representing 100%.

In yet other specific embodiments, the present invention relates to a sustained release biodegradable intravitreal implant comprising a hydrogel and axitinib, wherein axitinib particles are dispersed within the hydrogel, wherein the implant comprises axitinib polymorph IV in an amount of from about 400 μg to about 500 μg, wherein the hydrogel comprises a PEG hydrogel network formed by crosslinking 4a20kPEG-SAZ and 8a20kPEG-$NH_2$ units, wherein the implant in its dried state has a width of from 0.20 to 0.40 mm, and in its hydrated state (after 24 hours in PBS at a pH of 7.4 at 37° C.) has a length of 10.5 mm or less (wherein in particular embodiments the implant has a hydrated surface area of from 16 to 25 $mm^2$), and wherein the implant provides for a release of axitinib in an in vitro test performed at 35° C.±0.5° C. in 0.01N HCl with 0.25% cetyl trimethyl ammonium bromide (CTAB) in a USP apparatus 4 that is characterized in that the percentage of axitinib released from the implant is:

from 10 to 18% after 0.5 hours,
from 30 to 45% after 2 hours,
from 60 to 80% after 6 hours,
from 79 to 98% after 10 hours,
at least 90% after 12 hours,
and at least 92% after 16 hours, wherein the percentage of released axitinib is based on 450 μg axitinib representing 100%.

In further specific embodiments, the present invention relates to a sustained release biodegradable ocular implant containing axitinib polymorph IV in a dose of about 400 to about 500 μg, wherein the hydrogel comprises a PEG hydrogel, wherein the implant in its dry state has a width of from 0.30 to 0.36 mm, and wherein the implant is characterized in that the amount of axitinib released from the implant in an in vitro test performed at 35° C.±0.5° C. in 0.01N HCl with 0.25% cetyl trimethyl ammonium bromide (CTAB) in a USP apparatus 4 is:

at least about 50 μg after 0.5 hours,
at least about 140 μg after 2 hours,
at least about 270 μg after 6 hours,
at least about 350 μg after 10 hours,
at least about 400 μg after 12 hours,
and/or at least about 410 μg after 16 hours,
such as:
at least about 50 μg after 0.5 hours,
at least about 90 μg after 1 hour,
at least about 140 μg after 2 hours,
at least about 230 μg after 4 hours,
at least about 270 μg after 6 hours,
at least about 340 μg after 8 hours,
at least about 350 μg after 10 hours,
at least about 400 μg after 12 hours,
and/or at least about 410 μg after 16 hours.

In these embodiments, the implant may have a hydrated (after 24 hours in PBS at a pH of 7.2-7.4 at 37° C.) surface area of at least 16 $mm^2$, such as from 16 to 23 $mm^2$. In these embodiments, the axitinib particles may have a d90 particle size of less than 8 μm and a d50 particle size of less than 3 μm.

In further specific embodiments, the present invention relates to a sustained release biodegradable ocular implant containing axitinib polymorph IV in a dose of about 400 to about 500 μg, wherein the hydrogel comprises a PEG hydrogel network formed by crosslinking 4a20kPEG-SAZ and 8a20kPEG-$NH_2$ units, wherein the implant has a composition (dry basis; in % w/w) as follows: from about 60% to about 70% axitinib and from about 25% to about 35% PEG units, wherein the implant in its dry state has a width of from 0.30 to 0.36 mm and a total weight of from about 0.6 mg to about 1 mg, and wherein the implant is characterized in that the amount of axitinib released from the implant in an in vitro test performed at 35° C.±0.5° C. in 0.01N HCl with 0.25% cetyl trimethyl ammonium bromide (CTAB) in a USP apparatus 4 is:

from about 50 to about 80 μg after 0.5 hours,
from about 140 to about 210 μg after 2 hours,
from about 270 to about 380 μg after 6 hours,
from about 350 to about 470 μg after 10 hours,
at least about 400 μg after 12 hours,
and/or at least about 410 μg after 16 hours,
such as:
from about 50 to about 80 μg after 0.5 hours,
from about 90 to about 130 μg after 1 hour,
from about 140 to about 210 μg after 2 hours,
from about 230 to about 290 μg after 4 hours,
from about 270 to about 380 μg after 6 hours,
from about 340 to about 440 μg after 8 hours,
from about 350 to about 470 μg after 10 hours,
at least about 400 μg after 12 hours,
and/or at least about 410 μg after 16 hours.

In these embodiments, the implant may have a hydrated (after 24 hours in PBS at a pH of 7.2-7.4 at 37° C.) surface area of at least 16 $mm^2$, such as from 16 to 23 $mm^2$. In these embodiments, the axitinib particles may have a d90 particle size of less than 8 μm and a d50 particle size of less than 3 μm.

In further specific embodiments, the present invention relates to a sustained release biodegradable ocular implant containing axitinib polymorph IV in a dose of about 400 to about 500 μg, wherein the hydrogel comprises crosslinked PEG units, wherein the amount of axitinib being released upon final degradation of the hydrogel in the vitreous humor is less than 200 μg, wherein the implant in its dry state (prior to injection) has a width of from about 0.3 to about 0.4 mm, such as about 0.33 to about 0.36 mm, and a length of less than about 11 mm, and in its hydrated state (after 24 hours in PBS at a pH of 7.4 at 37° C.) has a length of less than about 11 mm, such as a length of from about 8 to about 10 mm.

II. Manufacture of the Implant

There are several methods available to manufacture implants in accordance with the present invention, including wet casting and (hot melt) extrusion, which are further explained in the following. Thus, in one aspect the present invention also relates to a method of manufacturing an implant as disclosed herein, either by means of wet casting, or by means of hot melt extrusion as further disclosed herein.

Wet Casting

The wet casting method is disclosed in WO 2021/195163 and is applicable also to the implants according to the present invention. Generally, the method comprises the steps of forming a hydrogel comprising a polymer network and TKI particles dispersed within the hydrogel, shaping the hydrogel and drying the hydrogel. In certain embodiments the method comprises the steps of forming a hydrogel comprising a polymer network from reactive group-containing precursors (e.g., comprising PEG units) and TKI particles dispersed in the hydrogel, shaping the hydrogel and drying the hydrogel, more specifically the polymer network is formed by mixing and reacting an electrophilic group-containing multi-arm PEG precursor with a nucleophilic group-containing multi-arm PEG precursor or another nucleophilic group-containing crosslinking agent (precursors and crosslinking agents are disclosed herein in the sections “The polymer network” and “PEG hydrogels”) in a buffered solution in the presence of TKI particles and allowing the mixture to gel to form the hydrogel. In embodiments of the invention, the hydrogel is shaped into a hydrogel strand as disclosed herein, by casting the mixture into a tubing prior to complete gelling of the hydrogel. In certain embodiments, the hydrogel strand is stretched in the longitudinal direction prior to or after drying as further disclosed herein.

In certain embodiments, the TKI in the method of manufacturing according to the invention in all its aspects is axitinib. In one embodiment the TKI, such as axitinib, may be used in micronized, super-micronized or nanonized form for preparing the implant as disclosed herein, with d10, d50 and d90 particle sizes and particle size ranges as disclosed herein e.g. in the section “The active principle” in sub-section “TKI particles”. Using micronized TKI may have the effect of inter alia reducing the tendency of the TKI particles to agglomerate during casting of the hydrogel strands.

The precursors for forming the hydrogel of certain embodiments have been disclosed in detail above in the section relating to the implant itself (see the section “The polymer network” and the section “PEG hydrogels”). In certain specific embodiments, the hydrogel is made of a polymer network comprising crosslinked polyethylene glycol units as disclosed herein. The polyethylene glycol (PEG) units in particular embodiments are multi-arm, such as 4-arm, PEG units having an average molecular weight from about 2,000 to about 100,000 Daltons, or from about 10,000 to about 60,000 Daltons, or from about 15,000 to about 50,000 Daltons, or of about 20,000 Daltons. In case PEG precursors are used to prepare a crosslinked PEG network, the method of manufacturing the implant in certain embodiments may comprise mixing and reacting an electrophilic group-containing polymer precursor, such as an electrophilic group-containing multi-arm polyethylene glycol, such as 4a20kPEG-SAZ, with a nucleophilic group-containing polymer precursor or another cross-linking agent, such as a nucleophilic group-containing multi-arm polyethylene glycol, such as 8a20kPEG-$NH_2$, in a buffered solution in the presence of the tyrosine kinase inhibitor, and allowing the mixture to gel. Alternatively, the cross-linking may be performed by means of a low molecular (non-PEG) cross-linking agent, such as a multi-amine, such as trilysine or a trilysine salt, such as trilysine acetate. In certain embodiments, the molar ratio of the electrophilic groups to the nucleophilic groups in the PEG precursors (or in the PEG precursor and the other crosslinking agent, as the case may be) is about 1:1, but the nucleophilic groups (such as the amine groups) may also be used in excess of the electrophilic groups. In certain alternative embodiments, the molar ratio of the electrophilic groups to the nucleophilic groups in the precursors may also be in a range from about 2:1 to about 1:2.

In certain embodiments, a mixture of the electrophilic group-containing precursor, the nucleophilic group-containing precursor or other crosslinking agent, the TKI and optionally buffer (and optionally additional ingredients as disclosed in the section “Additional ingredients”) is prepared. This may happen in a variety of orders, including but not limited to first preparing separate mixtures of the electrophilic and the nucleophilic group-containing precursors each in buffer solution, then combining one of the buffer/precursor mixtures, such as the buffer/nucleophilic group-containing precursor mixture, with the TKI and subsequently combining this TKI-containing buffer/precursor mixture with the other buffer/precursor mixture (in this case the buffer/electrophilic group-containing precursor mixture). In certain embodiments, a visualization agent as disclosed herein is included in the mixture forming the hydrogel so that the implant can be visualized once it has been injected into the eye. In certain embodiments, the visualization agent may be firmly conjugated with one or more components of the polymer network so that it remains in the implant until the implant is biodegraded.

After a mixture of all components in the buffered solution has been prepared (i.e., after all components have been combined and the wet composition has been formed), the resulting mixture is cast into a suitable mold or tubing prior to complete gelling of the hydrogel in order to provide the desired final shape of the hydrogel, i.e., a hydrogel strand. The mixture is then allowed to gel. The resulting hydrogel is then dried.

The viscosity of the wet hydrogel composition to be cast into a mold or tubing may depend inter alia on the concentration and the solids content of the hydrogel composition, but may also depend on external conditions such as the temperature. Castability of the wet hydrogel composition especially in case the composition is cast into fine-diameter tubing, may be improved by decreasing the viscosity of the wet composition, including (but not limited to) decreasing the concentration of Ingredients in the solvent and/or decreasing the solids content, or other measures such as increasing the temperature etc. Suitable solids contents are disclosed herein in the section “Formulation”.

In case the implant should have the final shape of a fiber (such as a cylinder), the reactive mixture may be cast into a fine diameter tubing (of e.g. an inner diameter of about 0.5 mm to about 1.5 mm, such as of about 1.0 mm to about 1.5 mm or about 0.7 mm to about 1.3 mm), such as a PU or silicone tubing, in order to provide for the extended cylindrical shape. Different geometries and diameters of the tubing may be used, depending on the desired final cross-sectional geometry of the hydrogel fiber, its initial diameter (which may still be decreased by means of stretching), and depending also on the ability of the reactive mixture to uniformly fill the tubing and the gelled hydrogel to be removed from the tubing. Thus, the inside of the tubing may have a round geometry or a non-round geometry, such as a cross-shaped, star-shaped or other geometry as disclosed herein.

In certain embodiments, after the hydrogel has completely gelled, the hydrogel strand may be longitudinally stretched in the wet or dry state as already disclosed in detail in the section "Dimensions of the implant and dimensional change upon hydration through stretching." In certain embodiments, a stretching factor (also referred to herein as "stretch factor") may be in a range of about 1 to about 4.5, or about 1.3 to about 3.5, or about 2 to about 2.5, or within other ranges also as disclosed herein. In particular embodiments, the stretch factor is from about 1.0 to about 3.0, such as from about 1.2 to about 2.7. The stretch factor indicates the ratio of the length of a certain hydrogel strand after stretching to the length of the hydrogel strand prior to stretching. For example, a stretch factor of 2 for dry stretching means that the length of the dry hydrogel strand after (dry) stretching is twice the length of the dry hydrogel strand before the stretching. The same applies to wet stretching. When dry stretching is performed in certain embodiments, the hydrogel is first dried and then stretched. When wet stretching is performed in certain embodiments, the hydrogel is stretched in the wet (undried) state and then left to dry under tension. Optionally, heat may be applied upon stretching. Further optionally, the hydrogel fiber may additionally be twisted. In certain embodiments, the stretching and/or drying may be performed when the hydrogel is still in the tubing. Alternatively, the hydrogel may be removed from the tubing prior to being stretched. In certain embodiments, the implant maintains its dimensions even after stretching as long as it is kept in the dry state at or below room temperature.

The stretching (wet or dry stretching) and suitable stretching factors to be applied to the implants of the present invention have already been described in the section "Dimensions of the implant and dimensional change upon hydration through stretching" above. After stretching and drying the hydrogel strand is removed from the tubing (if still located inside the tubing) and cut into segments of the desired length for the final implant in its dry state, such as disclosed herein (if cut within the tubing, the cut segments are removed from the tubing after cutting). A particularly desired length of the implant in the dry state for the purposes of the present invention is for example a length of equal to or less than about 12 mm, or equal to or less than about 10 mm, or from about 6 to about 9 mm, or from about 6 to about 8 mm, or other lengths as disclosed herein.

In certain embodiments, the final prepared implant is then loaded into a fine diameter needle. In certain embodiments, the needle has a gauge size of from 22 to 30, such as gauge 22, gauge 23, gauge 24, gauge 25, gauge 26, gauge 27, gauge 28, gauge 29 or gauge 30. In specific embodiments, the needle is a 25- or 27-gauge needle, or an even smaller gauge needle, such as a 30-gauge needle, depending on the diameter of the dried (and optionally stretched) implant.

In certain embodiments, the needles containing implant are then separately packaged e.g. in foil pouches (to keep out moisture), and are sterilized e.g. by means of gamma irradiation.

In certain embodiments, an injection device, such as a syringe or another injection device, may be separately packaged and sterilized e.g. by means of gamma irradiation as disclosed below for the kit (which Is another aspect of the present invention, see the section "Kit").

Hot Melt Extrusion

The hot melt extrusion method is disclosed in co-pending application PCT/US2022/51993 and is applicable also to the implants according to the present invention. This method generally comprises melt extruding, reactive extrusion or injection molding a composition comprising polymer or polymer (such as PEG) precursors and TKI particles, such as axitinib particles, to form the implant. A further method of forming the implant is 3D printing. Single or multiple strand implants (separate or connected) can be manufactured by such methods.

Initially, the polymer or polymer precursors (such as the PEG precursors) and the TKI (such as axitinib) particles are fed into an extruder, a (melt) composition comprising the polymer or polymer precursors and TKI is formed in the extruder, and a strand of the (melt) composition is extruded. The polymer or polymer precursors and the TKI may be fed to the extruder separately, such as via different feeders located at different sites. Alternatively, some or all precursor compounds may be pre-mixed, including melt blended, prior to being fed to the extruder, Such pre-mixing can be done by a method using, e.g., hand-mixing (e.g. in a sealable plastic bag), an orbital mixer, an acoustic mixer or a V-shell blender. In certain embodiments, the precursor compounds are fed to the extruder as powders. In certain embodiments, the polymer composition and TKI are melt blended, milled, optionally sieved, and then fed into the extruder. In certain embodiments, the powder feed rate into the extruder is from about 2 g/min to about 10 g/min. the powder feeder can be a plunger feeder or a K-Tron or Brabender feeder.

As disclosed herein, the polymer precursors may be PEG precursors containing electrophilic groups, such as NHS-ester groups. A second type of polymer precursors such as PEG precursors, containing nucleophilic groups, or other (i.e., non-PEG) crosslinking agents, such as small molecule crosslinking agents e.g. comprising amine groups (such as multi-amines like trilysine, or salts thereof like trilysine acetate) may be used for crosslinking and thus for forming the polymer network.

In certain embodiments, the method comprises melting the polymer or polymer precursors in the extruder at a temperature above the melting temperature of the polymer or polymer precursor, but below the melting point of the active agent. The optimal temperature of the molten polymer or polymer precursor is determined experimentally by its extrusion properties. Advantageously, the unmelted TKI remains unchanged through this melt extrusion process. However, in certain embodiments, the extrusion may be performed above the melting point of the polymer (precursor) and the TKI, which may result in a color change and/or change in form of the TKI, e.g., from amorphous to crystalline. The temperature can be, e.g., less than about 180°, less than about 150°, less than about 130°, less than about 120°, less than about 100°, less than about 90°, less than about 80°, less than about 70°, less than about 60°, less than about 50°. In some embodiments, the temperature in the extruder is moderately high, such as from about 50° to about 80° C. In other embodiments, the temperature is from about 50° to about 200°, about 60° to about 180° or about 80° to about 140°, An exemplary temperature is from about 40° to about 90°. By virtue of certain embodiments of the present invention, the temperature is kept as low as possible to protect excipient powders (if present) and TKI, and to optimize stability. In particular embodiments, if the TKI is axitinib, the extrusion is performed at a temperature from about 57° C. to about 200° C., or from about 65° C. to about 150° C., or from about 70° C. to about 90° C.

In certain embodiments, the screw speed of the extruder is from about 50 rpm to about 200 rpm. In certain embodiments, the extruder may be a twin-screw extruder. In other embodiments, it may be a single-screw extruder.

In certain embodiments, the extrusion may be performed in a solvent. The solvent may be present in less than about 10% by weight (w/w), and may be either an aqueous solvent (such as water) or a non-aqueous solvent (such as a natural or synthetic oil). If an oil is used as solvent, the oil may a biocompatible vegetable oil, a synthetic oil or a mineral oil, a liquid fatty acid or triglyceride composition, or it may be a hydrophobic biodegradable liquid polymer, or combinations thereof. In certain embodiments, the oil may comprise triethyl citrate, acetyl triethyl citrate (ATEC), acetyl tributyl citrate (ATBC), α-tocopherol (vitamin E), α-tocopherol acetate; plant or vegetable oils such as sesame oil, olive oil, soybean oil, sunflower oil, coconut oil, canola oil, rapeseed oil, nut oils such as hazelnut, walnut, pecan, almond, cottonseed oil, corn oil, safflower oil, linseed oil, etc., ethyl oleate, castor oil and derivatives thereof (Cremophor®), lipids being liquid at 37° C. or lower, such as saturated or unsaturated fatty acids, monoglycerides, diglycerides, triglycerides (Myglyols®), phospholipids, glycerophospholipids, sphingolipids, sterols, prenols, polyketides, hydrophobic biodegradable liquid polymers (such as low molecular weight PLGA, PGA or PLA etc.), low melting point waxes such as plant, animal or synthetic waxes, lanolin, jojoba oil, or combinations thereof. In particular embodiments a solvent is used in an amount of less than about 10% w/w, less than about 5% w/w or less than about 1% w/w of the entire composition in the extruder.

In other embodiments, extrusion is performed in the absence of a solvent (such as water), and is specifically performed in the absence of water if a salt (such as a multi-amine salt such as trilysine acetate) is used as a crosslinking agent. By keeping out moisture, it is ensured that no crosslinking happens in the extruder (as the salt is insoluble in the polymer as long as there is no solvent/water present) in order to avoid plugging or blocking the extruder. The mixture formed in the extruder is thus a melt composition of all the precursor compounds and the TKI. In this case, curing takes place in a curing chamber by means of exposure to humidity, after the melt composition has been expelled from the extruder, By this exposure to humidity, the salt (e.g. the nucleophilic-group containing crosslinking agent) solubilizes and reacts with the electrophilic group-containing polymer precursors to crosslink and form the polymer network. Curing may be performed in-line or batch-wise. In certain embodiments, the curing is performed for a period of at least 0.5 hours, or at least 1 hour, or at least 2 hours, or longer. In certain same or other embodiments, curing is performed at a temperature that is higher than ambient temperature, such as a temperature from about 25 to about 50° C., or from about 30 to about 40° C., or at about 30° C. or at about 35° C. In certain same or other embodiments, curing is performed in an atmosphere of at least 50% relative humidity (RH), or at least 60% RH, or at least 80%, or at least 90% RH, or at about 98% RH. After curing is complete, the strands may be cooled and cut to the desired length (as described above in the context of the wet cast method). The curing time, temperature and/or relative humidity may have an influence of the persistence of the hydrogel in physiological environment. For example, a longer curing time, or a higher curing temperature, or a higher relative humidity may provide for increased cross-linking and therefore for a prolonged persistence of the hydrogel. In case the hot melt extrusion process is conducted without solvent, the crosslinking density may be increased due to the higher concentration of the reacting precursors, which—without wishing to be bound by theory—may in certain embodiments result in a longer persistence of the hydrogel. See in this respect Example 12.

In certain embodiments, also the hot melt extrusion method comprises stretching the strand, e.g. prior to cutting the strand. The stretching is generally performed in the same way as disclosed herein in the section “Dimensions of the implant and dimensional change upon hydration through stretching”, or with respect to the wet cast method. In certain embodiments, the stretching is performed under wet or humid conditions, heated conditions, or a combination thereof. In other embodiments, the stretching is performed under dry conditions, heated conditions, or a combination thereof. In certain embodiments, strands that are stretched after crosslinking in a high humidity environment, e.g., a humidity chamber, may have shape memory or partial shape memory when placed in an aqueous environment after drying. In certain embodiments, strands that are stretched or otherwise made to have smaller diameters immediately after extrusion and before crosslinking when still warm may not have shape memory.

In certain embodiments, the hot melt extrusion process may be suitable for scale-up or larger scale manufacturing processes, while the wet cast process may be suitable for small scale manufacturing.

Multi Filament/Heat-Stretch-Twist (HST):

In certain embodiments, individual filaments may be combined by means of a heat-stretch-twist procedure into one composite implant (also referred to herein as “bundle” or “braided implant”) by twisting the filaments, so as to form one twisted strand. In particular embodiments, multiple filaments are combined, heated, stretched and twisted to form a composite twisted strand. Such a twisted multi-filament implant is shown exemplarily in FIG. 2 (side view and also a cross-sectional cut view). Details on the multi-filament implants itself are disclosed in the sub-section “multi-filament” within the section “The implant”. Upon hydration (in vitro or in vivo) the individual filaments may completely or partially unfurl, thereby providing an increased hydrated surface area for a faster release of active agent. The individual filaments may be identical or different. If different, they may differ in e.g. composition, size and/or total weight, geometry including dry and/or wet dimensions, hydrated surface area and other characteristics. Individual filaments in HST bundles may in certain embodiments contain different actives and/or may contain different forms of the same active(s) (such as different polymorphic forms, different prodrugs, different co-crystals, different salts etc. of the same active). For example, the individual filaments of HST implants may contain different actives for the treatment of the same or different ocular diseases or conditions.

In certain embodiments of the invention, multi-filament implants are produced from individual filaments (that are produced in accordance with any of the manufacturing methods disclosed herein, i.e., wet casting or hot melt extrusion) as follows: The desired number of filaments (long filaments obtained from wet casting or extrusion, i.e., not yet cut into the implant size) is combined and secured between two clamps, without pre-stretching or necking the filaments. The clamped filaments are then heated for a certain period of time, such as at least 30 min, at an elevated temperature, such as above 50° C., or above 60° C., or at about or above 70° C., for example in a heating chamber or heating tube. Within this heating chamber or tube, the clamped filaments are first stretched by a pre-determined stretch factor (as disclosed herein, such as a stretch factor of from about 1 to about 2), and then twisted at a pre-set twist time to obtain the desired numbers of twists per cm (of the final twisted implant). After that, the twisted filaments are removed from the heating chamber/tube and left to cool before they are cut to the desired length. An exemplary manufacturing process for multi-filament strands is provided in Example 3, In certain embodiments of a twisted multi-filament implant according to the present invention, the number of twists per cm (of the final twisted implant) is at least about 5, or is at least about 8, or is at least about 10 and/or is up to about 20, or up to about 15.

In certain embodiments, a composite (twisted) strand may have a composite diameter in the dried state that is within the same range as the diameter of a single-stranded implant, as disclosed herein. In certain embodiments, the composite diameter of the twisted strand in its dried state is from 0.2 to 0.8 mm, or from 0.2 to 0.5 mm, or from 0.3 to 0.4 mm, or from 0.33 to 0.38 mm. In certain same or other embodiments, the diameter of the individual filaments in the dried state is less than 0.3 mm, or less than 0.25 mm, or less than 0.2 mm, or less than 0.15 mm. Like a single-stranded implant, a multi-filament implant may also be loaded into a needle for injection into the eye, such as into the vitreous, with needle gauges ranging from 20 to 30, such as from 25 to 27, or 25, or 27, or 30. The filaments may be identical or different, e.g. different as to their composition, their dimensions or their geometry.

In certain embodiments, the individual filaments in a multi-filament implant (such as a HST implant) may be coated with a water-soluble polymer before being stretched and/or twisted. Any water-soluble polymer may be used for such coating, including (but not limited to): polysaccharides (such as cellulose derivatives, such as HPMC, CMC, or amino polysaccharides, such as chitosan and starch derivatives); proteins (such as collagen, gelatin); water soluble synthetic polymers (such as (linear) PEGs, poloxamers, polyacrylamides, polyacrylic acids, polyvinyl alcohol/and homopolymers, copolymers, or block/graft co-polymers thereof such as Kollicoat®). Among these, particularly suitable polymers for such coating are e.g. the following, which are available from BASF: Kollicoat®, Kollidon®, Kolliphor®, and Soluplus® (among others). Other suitable polymers for this purpose would be the same (low molecular weight) PEGs as described in the following section for tipping the needle. In certain embodiments, such water-soluble polymer coating of the individual strands prior to combining/twisting them together (without wishing to be bound by any theory) could act as a protective layer e.g. during (gamma) sterilization of the implants, which protective layer would then dissolve once the implant has been injected into the eye. In certain embodiments, a polymer coating could further contribute to or improve the unfurling of the individual filaments, e.g. after gamma sterilization, once the implants have been immersed into aqueous environment, such as injected into the vitreous humor. An exemplary bundle HST implant with polymer-coated filaments, wherein the individual filaments unfurl after hydration, is disclosed herein e.g. in Example 8 as implant 8E, The polymer coating can be applied onto the implants/filaments for example during wet casting as follows: the casting tube Into which the mixture of hydrogel precursor(s) and active agent is filled is previously filled with a solution of the polymer chosen to form the coating. The hydrogel precursor/active agent mixture is then pumped directly into this polymer-filled tubing during wet casting.

Thereby, most of the polymer solution is pushed out, but a small layer remains against the tube wall because of the no-slip condition. Eventually, this thin polymer solution covers the outside of the implant/filament, and dries when also the implant/filament is dried. In the case of manufacturing implants by means of hot melt extrusion, a polymer could be coated onto the filaments e.g. by means of co-extrusion.

(PEG) Tipping the Needle:

In certain embodiments, after an implant has been loaded into the needle the tip of the needle is blocked with a fast-solidifying molten polymer, such as low-molecular weight PEG. This may be done by dipping the needle into a molten polymer bath. Alternatively, molten polymer, such as molten PEG, may be injected or placed/dripped into the needle tip lumen. This may be done in certain embodiments by means of an automated jet valve system adapted to accurately dispense the molten polymer such as the molten PEG on the needle bevel. The low-molecular PEG is liquid (molten) at body temperature, but solid at room temperature. After applying the molten PEG to the needle tip, either by dipping or dripping, upon cooling the needle a hardened small drop or section (also referred to herein as "tip") of PEG remains at and in the top of the needle which occludes the needle lumen.

The low-molecular weight PEG used in this embodiment may be a linear PEG and may have an average molecular weight of up to about 5000, or up to about 4500, such as from about 3000 to about 5000, such as from about 3350 to about 4500. The low-molecular weight PEG may alternatively have an average molecular weight of about 400, about 600, about 800, about 1000, or about 1500. Also mixtures of PEGs of different average molecular weights as disclosed may be used. In specific embodiments the average molecular weight (Mn) of the PEG used for this purpose of tipping the needle is about 1000. This 1 k (1000) molecular weight PEG has a melting point between about 33° C. and about 40° C. and melts at body temperature when the needle is injected into the eye. In other specific embodiments the embodiments the average molecular weight (Mn) of the PEG used for this purpose of tipping the needle is about 4500, such as in a PEG 4500 NF. In alternative specific embodiments the average molecular weight (Mn) of the PEG used for this purpose of tipping the needle is about 3350.

Alternatively to the PEG materials, any other material for tipping the injection needle may be used that is water soluble and biocompatible (i.e., that may be used in contact with the human or animal body and does not elicit topical or systemic adverse effects, e.g. that is not irritating) and that is solid or hardened at room temperature but liquid or substantially liquid or at least soft at body temperature. Alternatively to PEG, also the following materials may e.g. be used (without being limited to these): poloxamers or poloxamer blends that melt/are liquid at body temperature; crystallized sugars or salts (such as trehalose or sodium chloride), agarose, cellulose, polyvinyl alcohol, poly(lactic-co-glycolic acid), a UV-curing polymer, chitosan or combinations of mixtures thereof.

The plug or tip aids in keeping the implant in place within the needle during packaging, storage and shipping and also further protects the implant from prematurely hydrating during handling as it occludes the needle lumen. It also prevents premature rehydration of the implant within the needle due to moisture ingress during the administration procedure, i.e., during the time the physician prepares the needle and injector for administration, and also at the time when the implant is about to be injected and the needle punctures into the eye (as the positive pressure in the eye could cause at least some premature hydration of the implant just before it is actually injected). The tip or plug additionally provides lubricity when warmed to body temperature and exposed to moisture and thereby allows smooth needle puncture and gliding and thus a successful deployment of the implant. Moreover, by occluding the needle lumen, the needle tipping minimizes the potential for tissue injury, i.e., tissue scoring, a process by which pieces of tissue are removed by a needle as it passes through the tissue.

In order to apply the PEG (or other material) tip/plug to the needle lumen, in one embodiment the needle containing the implant may be manually or by means of an automated apparatus dipped into a container of molten PEG (or the respective other material). The needle may be held dipped in the molten material for a few seconds to enable the molten material to flow upward into the needle through capillary action. The dwell time, the dip depth and the temperature of the molten material determine the final size or length of the tip/plug. In certain embodiments, the length of the PEG (or other) tip/plug at the top end of the needle may be from about 1 to about 5 mm, such as from about 2 to about 4 mm. In certain embodiments, in case a 1 k PEG is used the weight of the tip/plug may be from about 0.1 mg to about 0.6 mg, such as from about 0.15 mg to about 0.55 mg. It was demonstrated that implants according to the present invention can be successfully deployed in vivo and in vitro from an injector carrying a needle with a 1 k PEG tip as disclosed herein.

The tipping of an injection needle as disclosed herein may also be used for the injection of other implants or other medicaments or vaccines to be injected into the human or animal body (including other locations within the eye, or other areas or tissue of the body) by means of a needle, where the effect of protection of the implant (or medicament or vaccine) from moisture and the protective effect on tissue into which the implant (or medicament or vaccine) is injected is desirable and advantageous.

III. Kit

In certain embodiments, the present invention is further directed to a kit (which may also be referred to as a "system") comprising one or more sustained release biodegradable ocular implant(s) as disclosed herein or as manufactured in accordance with the methods as disclosed herein and one or more needle(s) for injection. The one or more needle(s) may be each pre-loaded with one sustained release biodegradable ocular implant in a dried state. In certain embodiments the needle(s) has/have a gauge size of from 20 to 30, such as 20, 21, 22, 23, 24, 25, 26, 27, 28, 29, or 30 gauge. In specific embodiments, the needles may be 25-, 26- or 27-gauge needle(s) or may be smaller gauge, such as 30-gauge needle(s). The diameter of the needle is chosen based on the final diameter of the implant in the dried (and optionally stretched) state. The active contained in the implant is generally a TKI, such as axitinib.

In one embodiment the kit comprises one or more, such as two or three 22- to 30-gauge, such as 25- or 27-gauge needle(s) each loaded with an implant containing a TKI such as axitinib. In certain embodiments, the kit comprises one or more implants of the present invention, wherein each implant is loaded in a needle having a gauge size of 25 or thinner. The needles may be, or may not be pre-connected to an injection device. The injection device may in certain embodiments be a custom-made injection device particularly adapted for injecting an implant of the present invention.

In yet another embodiment the kit comprises one 25-gauge needle loaded with an implant containing axitinib in an amount corresponding to from about 540 μg to about 660 μg, or about 600 μg, axitinib free base, or an implant containing axitinib in an amount corresponding to from about 360 μg to about 562.5 μg, or about 450 μg axitinib free base according to any of the aspects of the present invention as disclosed herein. In another embodiment, the kit comprises one 27-gauge needle loaded with an implant containing axitinib in an amount corresponding to from about 540 μg to about 660 μg, or about 600 μg, axitinib free base, or an implant containing axitinib in an amount corresponding to from about 360 μg to about 562.5 μg, or about 450 μg axitinib free base according to the invention as disclosed herein.

If two or more implants are contained in the kit, these implants may be identical or different, and may contain identical or different doses of TKI such as axitinib. One kit may comprise one or more implants optionally loaded in needle(s), and may optionally comprise one or more injection devices as further disclosed herein.

In certain embodiments, the lumen of the needle containing the implant may be occluded by a material that is solid at room temperature but soft or liquid at body temperature, such as a 1 k PEG material, as disclosed herein in detail in the section "Manufacture of the Implant" and specifically the subsection "(PEG) Tipping the needle" thereof.

In certain embodiments, the kit may further contain an injection device for injecting the implant(s) into the eye of a patient, such as into the vitreous humor of the patient. In certain embodiments the injection device may be provided and/or packaged separately from the one or more needle(s) loaded with implant. In such embodiments the injection device must be connected to the one or more needle(s) loaded with implant prior to injection. In other embodiments, injection devices may be pre-connected to the needle(s).

In certain embodiments the number of injection devices in the kit provided separately or pre-connected to the needles containing implant equals the number of needles loaded with the implant provided in the kit. In these embodiments the injection devices are only used once for injection of one implant. In other embodiments, only one injection device is included in the kit, which is to be re-used in case several implants (pre-loaded in needles) are contained.

In some embodiments the injection device contains a push wire to deploy the implant from the needle into the vitreous humor. The push wire may be a Nitinol push wire or may be a stainless steel/Teflon push wire. The push wire allows deploying the implant from the needle more easily.

In other embodiments the injection device and/or the injection needle may contain a stop feature that controls the injection depth.

A suitable injection device for the purposes of the present invention is the one as disclosed in WO 2022/204374, or as disclosed in WO 2021/195163.

In certain embodiments, the kit may further comprise one or more doses, in particular one dose, of an anti-VEGF agent ready for injection. The anti-VEGF agent may be selected from the group consisting of aflibercept, bevacizumab, pegaptanib, ranibizumab, faricimab, and brolucizumab. In certain embodiments the anti-VEGF agent is bevacizumab. In other embodiments the anti-VEGF agent is aflibercept. In certain embodiments, the dose of aflibercept is 2 mg. The anti-VEGF agent may be provided in a separate injection device connected to a needle, or may be provided as a solution or suspension in a sealed vial, from which the solution or suspension may be aspirated through a needle into a syringe or other injection device prior to administration.

The kit may further comprise an operation manual for the physician who is injecting the ocular implant(s). The kit may further comprise a package insert with product-related information.

IV. Therapy

In certain embodiments, the present invention is further directed to a method of treating an ocular disease in a patient in need thereof, the method comprising administering to the patient's eye a sustained release biodegradable ocular implant comprising a hydrogel and a tyrosine kinase inhibitor (TKI) as disclosed herein.

In specific embodiments, the present invention is directed to a method of treating an ocular disease in a patient in need thereof, the method comprising administering to the patient a sustained release biodegradable ocular implant as disclosed herein, or as claimed in the appended claims or the list of items in the section "ADDITIONAL DISCLOSURE", the implant comprising a hydrogel and axitinib, wherein TKI particles are dispersed within the hydrogel, wherein the implant is administered by intravitreal injection.

The present invention is also directed to an implant as disclosed herein (i.e., any implant as disclosed herein) for use in a method of treating an ocular disease as disclosed herein. Further, the present invention is directed to the use of an implant as disclosed herein (i.e., any implant as disclosed herein) for the manufacture of a medicament for use in a method of treating an ocular disease as disclosed herein.

In the method treatment according to the invention, the dose of TKI such as axitinib per eye administered once during a treatment period, is at least about 150 μg, such as from about 150 μg to about 800 μg, or from about 300 μg to about 700 μg, or from about 300 μg to about 500 μg. In certain specific embodiments the dose of the TKI, and specifically of axitinib, administered per eye once for (i.e., during) the treatment period is in the range from about 100 μg to about 200 μg, such as about 150 μg, or from about 200 μg to about 400 μg, such as about 300 μg, or in the range from about 300 μg to about 500 μg, such as about 400 to about 500 μg, such as about 450 μg, or in the range from about 500 μg to about 700 μg, such as 600 μg. Specific doses of axitinib that may be used according to the present invention are doses per implant of about 300 μg, about 450 μg, or about 600 μg, with the variances as disclosed herein (see the sub-section "Amount/dose" in the section "The Implant"). All doses of TKI such as axitinib as disclosed herein in relation to an implant may be used in the method of treatment. In particular embodiments the tyrosine kinase inhibitor is axitinib, in any of the forms disclosed herein, including polymorphs of axitinib (such as polymorph IV or polymorph SAB-I, particularly polymorph IV), salts, co-crystals, derivatives or prodrugs thereof. The doses indicated herein for therapy are meant to refer to the corresponding amount of axitinib free base (which is the active agent that becomes therapeutically available at the desired site/tissue). The dose administered (per eye) once per treatment period may be contained in one single implant (including an implant comprising multiple filaments that are e.g. twisted to form one composite twisted strand), or in two or more implants administered concurrently, or sequentially. In particular embodiments, the administered dose (per eye) once per treatment period is contained in one single implant.

An implant of the present invention is administered by injection into the eye. The implant can generally be administered by means of intravitreal, subconjunctival, subtenon, suprachoroidal, or intracameral injection.

In certain embodiments, the implant is administered by injection into the anterior or posterior section of the eye, particularly into the posterior section. In particular embodiments, the implant is administered by injection into the vitreous humor of a patient (intravitreal injection).

In alternative embodiments, administration of the implant is suprachoroidal administration.

In particular embodiments, the invention relates to a method of treating an ocular disease in a patient in need thereof, specifically a retinal disease, more specifically wet AMD, the method comprising administering to the patient's eye by means of intravitreal injection a sustained release biodegradable ocular implant comprising a hydrogel and axitinib polymorph IV, wherein axitinib particles are dispersed within the hydrogel, and wherein the axitinib is contained in the implant in a dose of about 400 to about 500 μg. More specifically, in such particular embodiments, such an implant may have a hydrated surface area of at least 15 $mm^2$, such as from about 16.0 $mm^2$ to about 23.0 $mm^2$ (as measured in PBS at a pH of 7.2 to 7.4 and 37° C. after 24 hours of incubation), and may have a total weight in the dry state from about 0.6 to about 1 mg. Other particular features of an implant as used in such particular embodiments are disclosed herein in the section "I. The implant".

In certain embodiments the dry implants are loaded in a needle, such as a needle with a gauge size of from 20 to 30 as disclosed herein, such as a 25-gauge, or a 26-gauge, or a 27-gauge needle, or a smaller gauge needle, and are administered to the eye, such as to the vitreous humor, through this needle. A small needle gauge provides for less potential of irritation or trauma at the injection site.

In certain embodiments, the implant is administered through the needle that is connected to an injection device or injector that is suitable to be connected to a needle preloaded with an implant as disclosed herein and to inject an implant into the eye. For example, a (modified) Hamilton syringe may be used as an injector. Suitable injection devices for the purposes of the present invention are disclosed in WO 2022/204374 and in WO 2021/195163, and are also disclosed above in the section relating to the kit. In specific embodiments relating to suprachoroidal injection, a hollow microneedle may be used as disclosed in U.S. Pat. No. 8,808,225.

Treatment Period and Repeat Dosing:

In certain embodiments, a treatment period for the treatment of an ocular disease as disclosed herein, such as wet AMD, with an implant of the present invention, such as an implant as defined in claim 1, is least 3 months, at least 4.5 months, at least 6 months, at least 9 months, at least 10 months, at least 12 months, at least 14 months or even longer. In particular embodiments, a treatment period may be about 6 to about 12 months, or about 6 to about 9 months, or about 9 to about 12 months, or about 9 to about 13 months. In particular embodiments, a treatment period may be about 9 months. "Treatment period" according to one embodiment of the invention means that a certain therapeutic effect of an implant of the present invention once administered is maintained, essentially maintained or partially maintained over that period of time. In other words, only one injection (of the implant of the present invention or of several implants concurrently in certain cases) is required in certain embodiments for maintaining a therapeutic effect over the treatment period. The therapeutic effect may be reducing or essentially maintaining or preventing a clinically significant increase of the central subfield thickness as measured by optical coherence tomography (CSFT, as further disclosed herein), or increasing or essentially maintaining or preventing a clinically significant reduction of the best corrected visual acuity (BCVA, as further disclosed herein) in a patient's eye during the treatment period.

One implant per eye may be administered per treatment period (although in certain cases the intended dose of TKI may be contained in more than one, such as in two or three implants administered concurrently as disclosed herein). In embodiments wherein two or more implants are administered concurrently, the implants can be the same or different. In cases where an administration during the same session is not possible e.g. due to administration complications or patient-related reasons a successive administration during two or more different sessions may alternatively be applied, such as for instance administration of two implants 7 days apart, i.e., within about 1 or about 2 weeks of the first injection. This may still be considered as a "concurrent" administration in the context of the present invention as disclosed herein.

In embodiments of the invention, a new implant of the invention can be administered for a subsequent treatment period after one treatment period with the previous/preceding implant has been completed or essentially completed. For example, a new implant can be injected promptly and repeatedly after the previous implant has biodegraded or has essentially biodegraded, i.e., after the hydrogel has essentially dissolved and/or the amount of TKI such as axitinib contained in the implant has been essentially released. Without wishing to be bound by theory, by means of the injection of a new implant after said (essentially) complete hydrogel degradation/TKI release from the preceding implant, a therapeutically effective concentration of TKI such as axitinib in ocular tissue, such as in the retina or the choroid, can be maintained over a very long period of time (e.g. over years), and without the build-up of any residues (hydrogel and/or TKI) in the eye. Thus, regular dosing intervals can be established, such as e.g. every 6 to 12 months, such as e.g. every 6 months, or every 9 months, or every 12 months for a continued long-term therapy. In certain embodiments, the treatment periods may even slightly overlap. Thus, upon completion of one treatment period with one implant, a new treatment period with a new implant (sometimes also referred to herein as "fresh implant") according to the present invention can start immediately and seamlessly so as to ensure a continuous treatment. The administration of a new implant may be repeated in principle as often as required, such as at least two times, at least three times, at least four times, or more often.

The time when a new implant is administered may be pre-determined (e.g. a period of every 6 months, or every 9 months, or every 12 months), but may alternatively be individually determined by an ophthalmologist e.g. by means of visualization of the previous implant. For example, when the previous implant is no longer detectable, and/or when no or only few remaining axitinib particles are detectable, a new implant may be injected. An implant according to the present invention can be visualized when residing in the patient's eye by imaging techniques such as slit lamp (biomicroscopy), which can be performed by an ophthalmologist. Another technique for visualizing an implant in the eye is cSLO (confocal scanning laser ophthalmoscopy, sometimes also referred to as IR or OCT). For neither of these two techniques a visualization agent such as a fluorescent agent is required.

In certain embodiments of the present invention, the sustained release biodegradable ocular implant contains forms of the active agent axitinib which are more soluble than other forms of axitinib, such as polymorph SAB-I which has relatively low solubility. In particular embodiments, the more soluble form of axitinib used in the implants of the present invention is axitinib polymorph IV, which is about twice as soluble as axitinib polymorph IV as disclosed herein. This increased solubility provides for a faster release of axitinib from an otherwise identical implant (e.g. comprising a hydrogel of a polymer network such as a network of crosslinked PEG units, such as a network of crosslinked 4a20kPEG-SAZ and 8a20kPEG-$NH_2$ units) as compared to the release of axitinib from such an implant containing a less soluble form of axitinib. A steady state of axitinib concentration in ocular tissue such as the retina or the choroid may be reached earlier, and/or therapeutic concentrations of axitinib in this ocular tissue may be achieved earlier, and/or the therapeutic effect may set in earlier with an implant of the present invention providing for a faster release of axitinib (e.g. by containing a more soluble form of axitinib such as axitinib polymorph IV). In certain embodiments, the majority of the drug load of axitinib in the implant containing the more soluble form of axitinib, such as polymorph IV, may be released when the implant is still intact, i.e., when the hydrogel has not yet (fully) biodegraded. This has been demonstrated in. In vivo studies, see e.g. Examples 10 (NHP) and 13 (rabbit). As a consequence, without wishing to be bound by theory, the release of the active agent axitinib may thus also be more synchronized with the biodegradation/dissolution of the hydrogel, such that upon biodegradation of the hydrogel (which occurs at about 8 to 9 months after injection of the implant into the vitreous humor of a human patient) the majority of the total axitinib content has already been released, Upon biodegradation of the hydrogel the remaining amount of axitinib is then released ("terminal release"). This remaining terminally released amount of axitinib resides in the vitreous humor and continues to be delivered to ocular tissue until fully dissolved. Thereby, in certain embodiments, the therapeutic effect can be maintained to bridge the time period from hydrogel degradation until the administration of a new implant. In certain embodiments, the increased solubility of the axitinib as provided e.g. by polymorph IV and the thus resulting increased synchronization of the hydrogel degradation with drug release may also result in less axitinib being released in a terminal release, i.e., upon final degradation of the hydrogel. Without wishing to be bound by theory, this in turn may lead to less free axitinib particles being present in the vitreous humor after the hydrogel has dissolved. This may facilitate repeat dosing of an implant, as a new implant may be placed e.g. immediately after the previous implant is no longer visible (e.g. by means of any of the visualization methods mentioned herein) without the substantial build-up of free axitinib particles in the vitreous. In certain embodiments, this may provide for a continuous treatment of wet AMD with a constant or essentially constant concentration of axitinib in ocular tissue such as the retina or the choroid over a long period of time, such as one or more years.

In other embodiments of the present invention, a faster release of axitinib may be achieved by more soluble axitinib prodrugs, cocrystals etc. as disclosed herein.

In further embodiments of the present invention, a faster release of axitinib may be achieved, independently of the solubility of the form of axitinib contained in the implant, by means of increasing the hydrated surface area (as defined herein) of the implant. This can be done e.g. by means of different cross-sectional implant geometries (such as star, cross etc.) or by means of multi-filament implants as disclosed herein.

Ocular Diseases and Therapeutic Effect:

In certain embodiments the ocular disease to be treated involves angiogenesis. In certain embodiments, the treatment is effective in inhibiting or slowing down angiogenesis and/or neovascularization at the site of administration.

In certain embodiments the ocular disease may be mediated by one or more receptor tyrosine kinases (RTKs), such as VEGFR-1, VEGFR-2, VEGFR-3, PDGFR-α/β, and/or by c-Kit.

In some embodiments the ocular disease is a retinal disease including Choroidal Neovascularization, Diabetic Retinopathy, Diabetic Macula Edema, Retinal Vein Occlusion, Acute Macular Neuroretinopathy, Central Serous Chorioretinopathy, and Cystoid Macular Edema; wherein the ocular disease is Acute Multifocal Behcet's Disease, Birdshot Placoid Pigment Epitheliopathy, Retinochoroidopathy, Infectious (Syphilis, Lyme, Tuberculosis, Toxoplasmosis), Intermediate Uveitis (Pars Planitis), Multifocal Choroiditis, Multiple Evanescent White Dot Syndrome (MEWDS), Ocular Sarcoidosis, Posterior Scleritis, Serpiginous Choroiditis, Subretinal Fibrosis, Uveitis Syndrome, or Vogt-Koyanagi-Harada Syndrome; wherein the ocular disease is a vascular disease or exudative disease, including Coat's Disease, Parafoveal Telangiectasis, Papillophlebitis, Frosted Branch Angitis, Sickle Cell Retinopathy and other Hemoglobinopathies, Angioid Streaks, and Familial Exudative Vitreoretinopathy; or wherein the ocular disease results from trauma or surgery, including Sympathetic Ophthalmia, Uveitic Retinal Disease, Retinal Detachment, Trauma, Photodynamic Laser Treatment, Photocoagulation, Hypoperfusion During Surgery, Radiation Retinopathy, or Bone Marrow Transplant Retinopathy.

In further aspects, the ocular disease is selected from the group consisting of retinal neovascularisation, choroidal neovascularisation, Wet AMD, Dry AMD, retinal vein occlusion, diabetic macular edema, retinal degeneration, hyphema, presbyopia, corneal graft rejection, retinoblastoma, melanoma, myosis, mydriasis, glaucoma, conjunctivitis, intraocular infections, choroidal neovascularization (CNV), intraocular tumors, retinal neuroinflammation, inflammation, autoimmune uveitis, uveitis, proliferative vitreoretinopathy, and corneal degeneration, acute and chronic macular neuroretinopathy, central serous chorioretinopathy, macular edema, acute multifocal placoid pigment epitheliopathy, Behcet's disease, birdshot retinochoroidopathy, posterior uveitis, posterior scleritis, serpiginous choroiditis, subretinal fibrosis, uveitis syndrome, Vogt-Koyanagi-Harada syndrome, retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemiretinal vein occlusion, papillophlebitis, carotid artery disease (CAD), frosted branch angiitis, sickle cell retinopathy, angioid streaks, familial exudative vitreoretinopathy, Eales disease, proliferative vitreal retinopathy, diabetic retinopathy, retinal disease associated with tumors, congenital hypertrophy of the retinal pigment epithelium (RPE), posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, intraocular lymphoid tumors, myopic retinal degeneration, acute retinal pigment epithelitis, glaucoma, endophthalmitis, cytomegalovirus retinitis, retinal cancers, retinitis pigmentosa, Leber's Congenital Amaurosis, Choroideremia, X-linked retinitis pigmentosa, best vitelliform macular dystrophy, x-linked retinoschisis, achromatopsia CNGA3, achromotopsia CNGB3, LHON, Stargardt disease, Usher syndrome, Norrie disease, Bardet-Biedl syndrome, retinopathy of prematurity and red-green color blindness.

In alternative embodiments the sustained release biodegradable ocular implant comprising the hydrogel and the tyrosine kinase inhibitor (such as axitinib) of the present invention can be applied in treating ocular conditions associated with tumors. Such conditions include e.g., Retinal Disease Associated with Tumors, Solid Tumors, Tumor Metastasis, Benign Tumors, for example, hemangiomas, neurofibromas, trachomas, and pyogenic granulomas, Congenital Hypertrophy of the RPE, Posterior Uveal Melanoma, Choroidal Hemangioma, Choroidal Osteoma, Choroidal Metastasis, Combined Hamartoma of the Retina and Retinal Pigmented Epithelium, Retinoblastoma, Vasoproliferative Tumors of the Ocular Fundus, Retinal Astrocytoma, or Intraocular Lymphoid Tumors.

In particular embodiments, the implant of the present invention is for treatment of neovascular (wet) age-related macular degeneration (AMD), diabetic macular edema, diabetic retinopathy or retinal vein occlusion, more particularly for the treatment of neovascular/wet AMD.

The ocular implants of the present invention can also be applied for treatment of any ocular disease involving vascular leakage, such as retinal vascular leakage. In certain embodiments, the treatment with an implant of the present invention results in inhibition, prevention/delay or substantial prevention, or reduction of VEGF-induced retinal vascular leakage for at least up to about 1 month, such as at least up to about 2 months, such as at least up to about 3 months after injection of the implant (e.g. in a rabbit model as shown in Example 14).

In some embodiments, the treatment with an implant of the present invention is characterized in that VEGF-induced retinal vascular leakage is inhibited, reduced or delayed/prevented during the treatment period as compared to the VEGF-induced retinal vascular leakage during the same time period after administration of an anti-VEGF agent (i.e., a different active agent than axitinib), wherein the anti-VEGF agent is bevacizumab, ranibizumab, faricimab, of aflibercept, and specifically when compared with bevacizumab (Avastin), see Example 14. In this Example 14 it is also demonstrated that an implant of the present invention containing the more soluble axitinib polymorph IV has comparable or better (long-term) efficacy as compared to a comparative implant containing the less soluble axitinib polymorph SAB-I (see e.g. FIG. 29).

In specific embodiments, the treatment is characterized in that VEGF-induced retinal vascular leakage is inhibited, reduced or prevented/delayed for at least up to about 1 month, such as at least up to about 2 months, such as at least up to about 3 months after injection of the implant as compared to the VEGF-induced retinal leakage induced in the respective same period after administering bevacizumab, as measured in a VEGF challenge study in a rabbit (such as Dutch Belted rabbit), the study comprising intravitreal injection of a sustained release biodegradable ocular implant comprising from about 300 to about 650 μg, such as from about 360 μg to about 562.5 μg, such as from about 400 to about 500 μg, or about 450 μg, of TKI (such as axitinib, such as axitinib polymorph IV) to an eye of a rabbit, wherein the rabbit is thereafter also administered 1 μg of VEGF to the eye at least three times over a period of 3 months ("VEGF challenge"), compared to the administration of 50 μL of 25 mg/mL bevacizumab (Avastin) under the same conditions including the VEGF challenges. In particular embodiments, the treatment with such an implant of the present invention is characterized in that VEGF-induced vascular leakage is reduced, inhibited or prevented/delayed after administration of the implant for a longer period of time than after administration of bevacizumab.

In particular embodiments the ocular disease is one selected from the list consisting of neovascular age-related macular degeneration (AMD), diabetic retinopathy (DR), diabetic macula edema (DME), and retinal vein occlusion (RVO). In more particular embodiments the ocular disease is neovascular (wet) age-related macular degeneration. In other more particular embodiments the ocular disease is diabetic retinopathy (DR), such as non-proliferative diabetic retinopathy, or diabetic macular edema (DME). In very particular embodiments the ocular disease is neovascular (wet) age-related macular degeneration, sometimes also referred to herein as "nAMD".

In some embodiments the treatment is effective in reducing the central subfield thickness (CSFT) as measured by optical coherence tomography in a patient whose central subfield thickness is elevated, which is often the case in patients suffering from AMD, Elevated within that context means that the CSFT is higher in the patient when compared to other individuals not suffering from the specific ocular disease, or higher than a certain CSFT level or range as defined by medical professionals and/or professional associations to represent a "normal" CSFT level or range. The elevated CSFT may be caused by retinal fluid such as sub- or intraretinal fluid. The reduction of CSFT in a patient (or the maintenance of CSFT in a patient) may be determined with respect to a baseline CSFT measured in that patient at the start of the treatment, i.e., immediately prior to the administration of the implant of the present invention. In other embodiments, by means of the treatment according to the present invention involving the administration of an implant according to the present invention the CSFT of a patient whose CSFT is elevated due to an ocular disease involving angiogenesis is essentially maintained at a certain given level, or a clinically significant increase of the CSFT is prevented in the patient while sub- or intraretinal fluid is not substantially increased, i.e., is also essentially maintained.

The capacity of implants containing axitinib as the active agent dispersed in a hydrogel formed of crosslinked PEG units to reduce CSFT and to maintain or to substantially maintain a reduced CSFT over an extended period of time in a cohort of human patients has already been clinically demonstrated in WO 2021/195163 and e.g. in A. A. Moshfeghi, "Update on a Hydrogel-Based Intravitreal Axitinib Implant (OTX-TKI) for the Treatment of Neovascular Age-related Macular Degeneration", Feb. 11, 2023 at the Angiogenesis, Exudation, and Degeneration Meeting (Virtual); or D. S. Dhoot, "Interim Safety and Efficacy Data from a Phase 1 Clinical Trial of Sustained-release Axitinib Hydrogel Implant (OTX-TKI) in Wet AMD Subjects: 7-month Analysis", Sep. 30, 2022 at the AAO 2022 Retina Subspecialty Day in Chicago, IL—both presentations being available inter alia via https://ocutx.gcs-web.com/scientific-medical-presentations. The implants of the present invention differ from the known implants disclosed in these references or used in these studies in that the release rate of the active agent (TKI and specifically axitinib) is increased with respect to the known implants. In the implants of the present invention this is achieved by using a TKI, such as axitinib, that has increased solubility in the implant, such as a solubility that is greater than 0.3 μg/mL as measured in phosphate-buffered saline (PBS) at a pH of 7.2 to 7.4 and 37° C. after five days of incubation, and/or by increasing the hydrated surface area of the implant, e.g. such that the hydrated surface area of the implant is at least 25 $mm^2$ as measured in phosphate-buffered saline (PBS) at a pH of 7.2 to 7.4 and 37° C. after 24 hours of incubation. In particular embodiments, the TKI, and specifically the axitinib, that has this increased solubility is axitinib polymorph IV. In other embodiments, the TKI is a co-crystal or prodrug or derivative of axitinib as disclosed herein. In more particular embodiments, the TKI is axitinib polymorph IV, the implant is a single-stranded implant and is cylindrical or essentially cylindrical (i.e., has a round or essentially round cross-section), and the hydrated surface area of the implant is from about 10 to about 30 $mm^2$, such as from about 16 to about 25 $mm^2$.

In a particular embodiment, in the treatment of wet AMD, the CSFT is reduced in a patient and maintained at a reduced level over a period of at least 3 months, at least 4.5 months, at least 6 months, at least 9 months, at least 10 months, at least 11 months, at least 12 months, at least 13 months, at least 14 months or even longer after administration of the implant of the invention. In a very particular embodiment, the CSFT is reduced for at least 6 months or at least 9 months or at least 12 months after administration of the implant with respect to the baseline CSFT of that patient prior to administration of the implant. In other particular embodiments, a reduced amount of retinal fluid and/or a reduced CSFT is maintained in a patient over a treatment period of at least 3 months, at least 4.5 months, at least 6 months, at least 9 months, at least 10 months, at least 11 months, at least 12 months, at least 13 months, at least 14 months or even longer after administration of the implant of the invention.

The need for rescue medication within the treatment period (such as an injection of an anti-VEGF agent) is low. For example, in a population of patients treated with an implant according to the invention, in certain embodiments rescue medication is administered within the treatment period only rarely, such as 1, 2, or 3 times during the treatment period, such as a 6-month treatment period, or a 10-month treatment period. In certain embodiments, at least 80% of the patients having received a single injection of an implant according to the invention may be rescue-medication free up to 6 months after administration, and at least 73% of the patients having received a single injection of an implant according to the invention may be rescue-medication free up to 10 months after administration. In certain embodiments, the rescue medication in the case of wet AMD is an anti-VEGF agent, such as aflibercept or bevacizumab, that may be administered in the form of a suspension or solution by means of intravitreal injection. In certain specific embodiments, the rescue medication is one dose (2 mg) of aflibercept, administered by means of intravitreal injection. In line with the definitions herein, concurrent and/or planned administration of an anti-VEGF agent together (concurrently or within 1, 2 or 3 months) with an implant according to another embodiment of the present invention disclosed herein does not constitute a "rescue medication". In more particular embodiments, the treatment period wherein the level of fluid and/or the CSFT (as reduced by means of the administration of an implant according to the invention) is maintained or essentially maintained without the administration of rescue medication (or with rescue medication administered only rarely as disclosed herein) is from about 4 to about 12 months, or from about 6 months to about 10 months, such as from about 6 to about 9 months after administration of the implant. In certain embodiments, the patients treated with an implant according to the invention do not require the concomitant administration of steroids (e.g., dexamethasone or prednisolone drops) during the treatment period.

In another embodiment, by means of the treatment according to the present invention involving the administration of an implant according to the present invention the CSFT of a patient whose CSFT is elevated due to angiogenesis is reduced, essentially maintained, or a clinically significant increase of the CSFT is prevented while the patient's vision (e.g. expressed by means of the best corrected visual acuity, also referred to herein as "BCVA") is not impaired, or is not significantly impaired. In certain embodiments, by means of the treatment according to the present invention involving the administration of an implant according to the present invention a patient's vision (where the patient's vision is impaired due to an ocular disease involving angiogenesis) as e.g. expressed by the BCVA may improve during the treatment period of at least 3 months, at least 6 months, at least 9 months, at least 10 months, at least 12 months, at least 13 months or at least 14 months.

Thus, in certain embodiments the present invention provides a method of improving the vision of a patient whose vision is impaired e.g. due to retinal fluid caused by an ocular disease involving angiogenesis, wherein the method comprises administering an implant according to the invention to the patient, such as by means of intravitreal injection. The improvement of the vision of a patient may be assessed for instance by means of the BCVA. An improvement of vision may manifest itself by an increase of the patient's BCVA e.g. by at least 10, or at least 15, or even at least 20 ETDRS letters. The Early Treatment Diabetic Retinopathy Study (ETDRS) Letter Score is a representative value for letters that can be read correctly at a certain distance. ETDRS equipment and testing are considered the standard of current-day clinical trials involving vision testing.

In other embodiments, the present invention provides a method of maintaining or essentially maintaining the vision of a patient who is in danger of experiencing vision loss or expected to experience vision loss if untreated, e.g. due to retinal fluid caused by an ocular disease involving angiogenesis, wherein the method comprises administering an implant according to the invention to the patient, such as by means of intravitreal injection.

The invention in certain embodiments is thus further directed to a method of reducing, essentially maintaining or preventing a clinically significant increase of the central subfield thickness as measured by optical coherence tomography in a patient whose central subfield thickness is elevated due to an ocular disease involving angiogenesis, the method comprising administering to the patient the sustained release biodegradable ocular implant containing a tyrosine kinase inhibitor of the present invention as disclosed herein. In certain embodiments the ocular disease involving angiogenesis is neovascular age-related macular degeneration, or is diabetic retinopathy, or diabetic macular edema. In certain embodiments, the patient's vision expressed e.g. by the BCVA is not substantially impaired during the treatment. In certain other embodiments, the patient's vision expressed e.g. by the BCVA may even be improved. Accordingly, the invention in certain embodiments is also directed to a method of improving the vision of a patient whose vision is impaired e.g. due to retinal fluid caused by an ocular disease involving angiogenesis, wherein the method comprises administering an implant according to the invention to the patient, such as by means of intravitreal Injection.

In certain embodiments, in a method of treatment according to the present invention the mean change of the BCVA and CSFT levels from baseline after the injection of one single implant of the present invention up to at least month 10 after administration correspond to the mean change of the BCVA and CSFT levels during the same period of time in which an anti-VEGF agent, such as aflibercept, is administered in regular 2-month intervals according to prescription. The present invention thus may provide for a clinically meaningful reduction in treatment burden up to at least month 10 post-injection of one single implant of the present invention as compared to current standard-of-care treatments which require frequent (e.g. every 2 months) injections of an anti-VEGF agent.

In certain embodiments, in a method of treatment according to the present invention the mean change in CSFT from baseline (at the injection of one single implant of the present invention) over a certain amount of time (such as over the treatment period), such as up to month 6, or up to month 9, or up to month 10, or up to month 12 after injection of the implant is not more than 75 μm, such as not more than 50 μm, or is not more than 25 μm, or is not more than 10 μm, or is not more than 5 μm (with a standard deviation of not more than 28 μm).

In certain same and other embodiments, in a method of treatment according to the present invention the mean change in BCVA from baseline (at the injection of one single implant of the present invention) over a certain amount of time, such as up to month 6, or up to month 9, or up to month 10, or up to month 12 after injection of the implant is less than 15 ETDRS letters, or is less than 10 letters, or is less than 5 letters, or is less than 2 letters (with a standard deviation of not more than 6 letters), compared to the baseline ETDRS value.

In certain embodiments, a method of treatment with an implant according to the present invention (with any, specific or general, implant as disclosed herein) is characterized in that the patient experiences a loss of 15 ETDRS letters of BCVA or less than 15 ETDRS letters (i.e., the patient experiences 15 or less than 15 ETDRS letters of BCVA loss) at 9 months, or during the period of 9 or of 12 months, after injection of the implant as compared to the baseline value, or wherein the treatment is characterized in that the patient experiences an increase of BCVA at 9 months, or during the period of 9 months, after injection of the implant as compared to the baseline value. Such an increase may be an increase of less than or of at least 15 ETDRS letters of BCVA. This applies both to patients having already experienced a loss of vision prior to starting the treatment according to the present invention, and to patients still having relatively good or good vision (such as 20/20 visual acuity). In certain embodiments, no or no more than one rescue medication has been administered during the mentioned period of up to 9 months after injection of the implant.

In certain embodiments, a method of treatment with an implant according to the present invention (with any, specific or general, implant as disclosed herein) is characterized in that the patient experiences a loss of 15 ETDRS letters of BCVA or less than 15 ETDRS letters (i.e., the patient experiences 15 or less than 15 ETDRS letters of BCVA loss) at 12 months, or during the period of 12 months, after injection of the implant as compared to the baseline value, or wherein the treatment is characterized in that the patient experiences an increase of BCVA at 12 months, or during the period of 12 months, after injection of the implant as compared to the baseline value. Such an increase may be an increase of less than or of at least 15 ETDRS letters of BCVA. This applies both to patients having already experienced a loss of vision prior to starting the treatment according to the present invention, and to patients still having relatively good or good vision (such as 20/20 visual acuity).). In certain embodiments, no or no more than one rescue medication has been administered during the mentioned period of up to 12 months after injection of the implant.

The methods of treatment according to the present invention, by injecting an implant according to the present invention, thus may prevent, in certain embodiments, vision loss or impairment, or further vision loss or impairment, or may reduce the risk of vision loss or impairment, in patients being diagnosed with (wet) AMD and/or diagnosis of choroidal neovascularization or subfoveal neovascularization.

In certain same and other embodiments, in a method of treatment according to the present invention subfoveal fluid may essentially be absent (i.e., the CSFT may be 300 μm or lower) in a patient having been treated with an implant of the present invention, within a certain period of time after a single injection of one implant according to the invention, such as within 6 months, or within 9 months, or within 10 months, or within 12 months.

In particular embodiments the invention is directed to a method of treating neovascular age-related macular degeneration in a patient in need thereof, the method comprising administering to the patient a sustained release biodegradable ocular implant as disclosed herein by intravitreous injection, the implant comprising a hydrogel that comprises a polymer network comprising crosslinked PEG units and about 200 to 400 μg, such as 300 μg, or about 400 to 500 μg, such as about 450 μg, or about 500 to 700 μg, such as about 600 μg of axitinib, wherein the axitinib is in the form of polymorph IV, and wherein axitinib particles are dispersed within the hydrogel, wherein one implant per eye is administered once for a treatment period of at least 6 months. In specific embodiments, the patient to be treated has a history of an anti-VEGF treatment. In specific embodiments, the patient to be treated has a history of a treatment of wet AMD. In other specific embodiments, the patient to be treated has no history of a treatment of wet AMD. In specific embodiments, the patient to be treated has a history of an anti-VEGF treatment. In other specific embodiments, the patient to be treated has no history of an anti-VEGF treatment. In particular embodiments, the patient has a diagnosis of extra-foveal choroidal neovascularization (CNV) or subfoveal neovascularization (SFNV) secondary to neovascular AMD.

In particular other embodiments of the invention, each and any of the other sustained release biodegradable ocular implants as specifically disclosed herein may be used in a method of treating neovascular age-related macular degeneration.

Combination Therapy with an Anti-VEGF Agent:

In some embodiments of the method of treatment according to the present invention, an anti-VEGF agent may be administered to the patient in combination with the treatment with the TKI (such as axitinib) containing implant (also referred to herein as "combination therapy"). Such anti-VEGF agent may also be administered by means of an Intravitreal injection, or may be administered at a different site and/or by a different route. The anti-VEGF agent may be selected from the group consisting of aflibercept, bevacizumab, pegaptanib, ranibizumab, faricimab, and brolucizumab. In certain embodiments the anti-VEGF agent is bevacizumab. In certain other embodiments the anti-VEGF agent is aflibercept. In specific embodiments a dose of 2 mg aflibercept is administered as an anti-VEGF treatment in combination with an implant according to the present invention. Whenever it is referred to herein in the context of a combination treatment, or in the context of comparative studies comparing the effect/efficacy of an implant of the present invention (containing a TKI such as axitinib) with a comparative medication containing a known anti-VEGF agent for treatment of e.g. AMD (as disclosed herein, including but not limited to aflibercept and bevacizumab), said other anti-VEGF agent is referred to as "a(n) anti-VEGF agent", or sometimes as "different anti-VEGF agent". Such "anti-VEGF" agent thus does not include axitinib unless specifically indicated otherwise.

In certain embodiments, an anti-VEGF agent may be administered (such as by means of intravitreal administration) some time earlier or later, for example an anti-VEGF agent may be administered within about 1, about 2, or about 3, or more months of the administration of the implant. i.e., may be pre- or post-administered as compared to the implant. In certain embodiments, prior to the administration of the sustained release biodegradable ocular implant an anti-VEGF agent may be administered, for example an anti-VEGF agent may be administered at least once prior to the administration of the sustained release biodegradable ocular implant of the present invention, such as at least once per month for at least 1 month, or at least 2 months, or at least 3 months prior to the administration of the sustained release biodegradable ocular implant. In certain embodiments, prior to the treatment with the sustained release biodegradable ocular implant the patient may have been treated at least once or may have been treated repeatedly with an anti-VEGF agent, such as treated (e.g. monthly) with an anti-VEGF agent for at least 2 months prior to the start of the treatment with the sustained release biodegradable ocular implant of the present invention.

In certain particular embodiments, an anti-VEGF agent (such as aflibercept) is administered prior to the start of the treatment with one or more (e.g. in case of repeat dosing) implant(s) of the present invention. For example, an anti-VEGF agent may be administered once, such as once in the period from about 1 to about 2 months, prior to the start of the treatment with an implant of the present invention. In other embodiments, an anti-VEGF agent may be administered twice or more times prior to the start of the treatment with an implant of the present invention. In the latter case, an anti-VEGF agent may be administered e.g. once every month for two or more months preceding the treatment with an implant of the present invention. In particular embodiments, when the implant of the present invention is an implant comprising a PEG hydrogel as disclosed herein and containing about 400 to 500 μg axitinib polymorph IV, an anti-VEGF agent (such as aflibercept, such as a dose of 2 mg aflibercept) is administered once one month prior to, or once two months as well as once one month prior to the treatment start with the implant for treating wet AMD.

In certain embodiments an anti-VEGF agent may be administered by means of an intravitreal injection concurrently (as defined herein) with the administration of the implant, e.g. in one and the same session. In certain further embodiments, an anti-VEGF agent may be administered concurrently with an implant of the invention and thereafter the anti-VEGF agent may be administered again (once or several times) within certain intervals, such as within 1, or within 2, or within 3 months. The anti-VEGF agent may also be repeatedly administered, such as in regular intervals, during the treatment period with the implant of the present invention. It is noted that such combined (and planned) co-administration of an anti-VEGF agent differs from a rescue medication as defined herein, which is only administered in certain exceptional cases but not planned as a combination therapy from the outset.

Patients:

A patient being treated with an implant of the present invention in certain particular embodiments may be at least 50 or at least 60 years old. The patient may be male or female. The patient may have retinal fluid such as intra-retinal fluid or sub-retinal fluid (for example, such as CSFT of not more than 350 μm). The patient may have macular choroidal neovascularization due to nAMD, The patient may already have vision loss, or may be expected to have vision loss due to nAMD.

In certain embodiments of the present invention the patient may have a diagnosis of primary subfoveal (such as active sub- or juxtafoveal CNV with leakage involving the fovea) neovascularization (SFNV) secondary to nAMD. In certain embodiments of the present invention the patient may have a diagnosis of previously treated or previously untreated subfoveal neovascularization (SFNV) secondary to neovascular AMD with leakage involving the fovea. In such patient, the previous treatment (if the patient has received a treatment) may have been with an anti-VEGF agent.

In some embodiments the patient receiving the implant has a history of an anti-VEGF treatment e.g. such as treatment with LUCENTIS® and/or EYLEA®. In certain embodiments the patient receiving the implant has a history of anti-VEGF treatment but has not responded to this anti-VEGF treatment, Le, the disease state of the patient was not improved by the anti-VEGF treatment. In embodiments where the patient has a history of an anti-VEGF treatment before starting the treatment with the implant according to the present invention, administration of the implant of the present invention may prolong the effect of the prior anti-VEGF treatment over an extended period of time, such as over the treatment period defined above.

In further embodiments the patient receiving the implant has no history of an anti-VEGF and/or AMD treatment (i.e., the patient is anti-VEGF naïve and/or AMD treatment naïve). In further embodiments, the patient is an anti-VEGF responder.

In further embodiments, the patient receiving the implant still has good or relatively good vision before starting treatment with the implant. In certain embodiments, the patient has a visual acuity of approximate 20/20 Snellen equivalent (such as an ETDRS letter score of at least 54, such as at least 84) just before starting the treatment. In particular embodiments, the patient receiving the implant has a diagnosis of choroidal neovascularization or subfoveal neovascularization, is anti-VEGF and/or AMD treatment naïve, and has a visual acuity of 20/20 just before starting the treatment.

Therapy with Specific Implants:

Any of the implants disclosed herein, including the "specific implants" disclosed at the end of the section "I. The implant", may be used in the method of treating an ocular disease, such as wet AMD, according to the present invention.

In a specific embodiment, the present invention relates to a method of treating an ocular disease, such as wet AMD, in a patient in need thereof, the method comprising injecting a sustained release biodegradable intravitreal implant into the vitreous humor of the patient, the implant comprising a hydrogel comprising crosslinked PEG units and axitinib polymorph IV in an amount of from about 360 μg to about 562.5 μg, or from about 405 μg to about 495 μg, such as about 450 μg. In this embodiment, the implant may provide for an average release rate of above about 0.8 μg/day, such as at least about 1 μg/day in vitreous humor (e.g. of a human patient, or of a non-human primate, such as a monkey, such as a *Cynomolgus* monkey). Further, in this embodiment, the amount of axitinib remaining when the hydrogel starts to degrade (and thus the amount of axitinib being released upon final degradation of the hydrogel) may be less than 200 μg. In this embodiment, one implant may provide for a treatment period of about 6 to about 12 months, such as about 8 to about 11 months, so that a fresh implant may be injected about 6 to about 12 months after injection of the first (or previous) implant, thus ensuring a continuous therapy.

In a specific embodiment, the present invention relates to a method of treating an ocular disease, such as wet AMD, in a patient in need thereof, the method comprising injecting a sustained release biodegradable intravitreal implant into the vitreous humor of a patient, the implant comprising a PEG hydrogel network formed by crosslinking 4a20kPEG-SAZ and 8a20kPEG-$NH_2$ and axitinib polymorph IV in an amount of from about 360 μg to about 562.5 μg, or from about 405 μg to about 495 μg, such as about 450 μg. In this embodiment, the implant may provide for an average release rate of above about 0.8 μg/day, such as at least about 1 μg/day in vitreous humor (e.g. of a human patient, or of a non-human primate, such as a monkey, such as a *Cynomolgus* monkey), Further, in this embodiment, the amount of axitinib remaining when the hydrogel starts to degrade (and thus the amount of axitinib being released upon final degradation of the hydrogel) may be less than 200 μg. In this embodiment, one implant may provide for a treatment period of about 6 to about 12 months, such as about 8 to about 11 months, so that a fresh implant may be injected about 6 to about 12 months after injection of the first (or previous) implant, thus ensuring a continuous therapy.

In a specific embodiment, the present invention relates to a method of treating an ocular disease, such as wet AMD, in a patient in need thereof, the method comprising injecting a sustained release biodegradable ocular implant into the vitreous humor of the patient, the implant comprising a hydrogel comprising crosslinked PEG units (as disclosed herein) and axitinib polymorph IV in an amount of from about 360 μg to about 562.5 μg, or from about 405 μg to about 495 μg, such as about 450 μg. In this embodiment, the implant may provide for an average release rate of above about 0.8 μg/day, such as at least about 1 μg/day in vitreous humor (e.g. of a human patient). Further, in this embodiment, the amount of axitinib remaining when the hydrogel starts to degrade (and thus the amount of axitinib being released upon final degradation of the hydrogel) may be less than 200 μg. In this embodiment, one implant may provide for a treatment period of about 6 to about 12 months, such as about 8 to about 11 months, so that a fresh implant may be injected about 6 to about 12 months after injection of the first (or previous) implant, thus ensuring a continuous therapy.

In a specific embodiment, the present invention relates to a method of treating an ocular disease, such as wet AMD, in a patient in need thereof, the method comprising injecting a sustained release biodegradable ocular implant into the vitreous humor of the patient, the implant comprising a hydrogel and axitinib, wherein axitinib particles are dispersed within the hydrogel, wherein the implant comprises axitinib polymorph IV in an amount of from about 250 μg to about 720 μg, such as from 360 μg to about 562.5 μg, such as from about 400 μg to about 500 μg, such as about 450 μg, wherein the implant has a composition on a dry basis (in % w/w) of about 30 to about 75% axitinib, about 20 to about 50% PEG units, and about 0.5 to about 15% sodium phosphate salt and on a wet basis (in % w/w) of about 5 to about 17% axitinib, about 4 to about 12% PEG units, and about 0.2 to about 5% sodium phosphate salt, wherein the hydrogel has been formed by crosslinking 4a20kPEG-SAZ and 8a20kPEG-$NH_2$, wherein the implant has a length that is greater than its width, and in its dry state (prior to injection) has a length of 11 mm or less, such as from 5 to 11 mm and a width of from 0.28 to 0.38 mm and/or in its hydrated state (after 24 hours in PBS at a pH of 7.4 at 37° C.) has a length of 11 mm or less, such as from 5 to 11 mm and a width of from 0.4 to 2 mm, and wherein the axitinib particles optionally have a d90 particle size of less than 8 μm and a d50 particle size of less than 3 μm. In this embodiment, the implant may provide for an average release rate of above about 0.8 μg/day, such as at least about 1 μg/day in vitreous humor (e.g. of a human patient, or of a non-human primate, such as a monkey, such as a *Cynomolgus* monkey). In this embodiment, the amount of axitinib remaining when the hydrogel starts to degrade (and thus the amount of axitinib being released upon final degradation of the hydrogel) may be less than 200 μg. In this embodiment, one implant may provide for a treatment period of about 6 to about 12 months, such as about 8 to about 11 months, so that a fresh implant may be injected about 6 to about 12 months after injection of the first (or previous) implant, thus ensuring a continuous therapy.

In another specific embodiment, the present invention relates to a method of treating an ocular disease, such as wet AMD, in a patient in need thereof, the method comprising injecting a sustained release biodegradable ocular implant into the vitreous humor of the patient, the implant comprising a hydrogel of cross-linked PEG units and axitinib polymorph IV in an amount of from about 250 to about 750 μg, such as from about 400 to about 500 μg, such as about 450 μg, wherein axitinib particles are dispersed within the hydrogel, wherein the implant has a composition within the following ranges (dry basis, % w/w):

| Ingredient | Implant Composition (% w/w, dry) |
|---|---|
| Axitinib, Polymorph IV | 54-69 |
| 4a20k PEG SAZ | 17-26 |
| 8a20k PEG $NH_2$ | 8-13 |
| Sodium Phosphate Dibasic Dried, USP | 3-5 |
| Sodium Phosphate Monobasic Anhydrous, USP | 1-3 |

and which optionally has the following dry and wet dimensions:

| | Dry dimensions (mm | Wet dimensions (mm) |
|---|---|---|
| Length | 5-11 | 5-11 |
| Width | 0.28-0.38 | 0.4-2 |

and which may be obtainable by wet casting, using a stretch factor of from about 1 to about 3, or by hot melt extrusion. In this embodiment, the implant may provide for an average release rate of above about 0.8 μg/day, such as at least about 1.0 μg/day in vitreous humor (e.g. of a human patient). In this embodiment, the amount of axitinib remaining when the hydrogel starts to degrade (and thus the amount of axitinib being released upon final degradation of the hydrogel) may be less than 200 μg. Further, in this embodiment, one implant may provide for a treatment period of about 6 to about 12 months, such as about 8 to about 11 months, so that a fresh implant may be injected about 6 to about 12 months after injection of the first (or previous) implant, thus ensuring a continuous therapy.

In a further specific embodiment, the present invention relates to a method of treating an ocular disease, such as wet AMD, in a patient in need thereof, the method comprising injecting a sustained release biodegradable ocular implant into the vitreous humor of the patient, the implant comprising a hydrogel of cross-linked PEG units and axitinib polymorph IV in an amount of from about about 400 to about 500 μg, wherein axitinib particles are dispersed within the hydrogel, wherein the implant has a composition within the following ranges (dry basis, % w/w):

| Ingredient | Implant Composition (% w/w, dry) |
|---|---|
| Axitinib, Polymorph IV | 54-69 |
| 4a20k PEG SAZ | 17-26 |
| 8a20k PEG $NH_2$ | 8-13 |
| Sodium Phosphate | 1-8 |

and which optionally has the following dry and wet dimensions:

| | Dry dimensions (mm) | Wet/hydrated dimensions (mm) |
|---|---|---|
| Length | 7.00 ± 0.50 mm | 5.0-10.0 mm |
| Width | 0.365 ± 0.025 mm | 0.4-2.0 mm |

In this embodiment, the implant may provide for an average release rate of above about 0.8 μg/day, such as at least about 1.0 μg/day in vitreous humor (e.g. of a human patient). In this embodiment, one implant may provide for a treatment period of about 6 to about 12 months, such as about 8 to about 11 months, so that a fresh implant may be injected about 6 to about 12 months after injection of the first (or previous) implant, thus ensuring a continuous therapy.

In specific embodiments, the present invention relates to a method of treating an ocular disease, such as wet AMD, in a patient in need thereof, the method comprising injecting a sustained release biodegradable ocular implant into the vitreous humor of the patient, the implant comprising a hydrogel and axitinib polymorph IV in an amount of 360 to 540 μg, such as from about 400 to about 500 μg, such as about 450 μg, wherein axitinib particles are dispersed within the hydrogel, the hydrogel comprising crosslinked PEG units (such as a PEG hydrogel network formed by crosslinking 4a20kPEG-SAZ and 8a20kPEG-$NH_2$), wherein the amount of axitinib remaining when the hydrogel starts to degrade (and thus the amount of axitinib being released upon final degradation of the hydrogel) is less than 200 μg, and wherein the implant in its dry state (prior to injection) has a width of from about 0.33 to about 0.36 mm and a length of less than about 11 mm, and in its hydrated state (after 24 hours in PBS at a pH of 7.4 at 37° C.) has a length of less than about 11 mm, such as a length of from about 8 to about 10 mm. In this embodiment, the implant may provide for an average release rate of above about 0.8 μg/day, such as at least about 1 μg/day in vitreous humor (e.g. of a human patient). Further, in this embodiment, the amount of axitinib remaining when the hydrogel starts to degrade (and thus the amount of axitinib being released upon final degradation of the hydrogel) may be less than 200 μg. In this embodiment, one implant may provide for a treatment period of about 6 to about 12 months, such as about 8 to about 11 months, so that a fresh implant may be injected about 6 to about 12 months after injection of the first (or previous) implant, thus ensuring a continuous therapy. In specific embodiments, the present invention relates to a method of treating an ocular disease, such as wet AMD, in a patient in need thereof, the method comprising injecting an implant of the present invention implant into the vitreous humor of the patient, the implant comprising from about 400 to about 500 μg, such as about 450 μg axitinib polymorph IV in a hydrogel comprising crosslinked PEG units (such as a PEG hydrogel network formed by crosslinking 4a20kPEG-SAZ and 8a20kPEG-$NH_2$), having dry dimensions of about 0.35 mm (width)×7.4 mm (length) and hydrated (after 24 hours in PBS at a pH of 7.4 at 37° C.) dimensions of about 0.75 mm (width)×8.4 mm (length), wherein the implant may contain a remaining amount of drug of about 250 μg at month 6, and may exhibit a release rate at month 3 after injection of the implant of about 1.2 μg/day (in non-human primates).

In yet other specific embodiments, the present invention relates to a method of treating an ocular disease in a patient in need thereof, wherein the treatment comprises injection of a sustained release biodegradable ocular implant into the vitreous humor of an eye of the patient in need of treatment, wherein the sustained release biodegradable ocular implant comprises a hydrogel and TKI, with TKI particles being dispersed within the hydrogel, wherein the TKI contained in the sustained release biodegradable ocular implant is axitinib having a solubility of 0.3 μg/mL or greater as measured in phosphate-buffered saline (PBS) at a pH of 7.2 to 7.4 and 37° C. after five days of incubation, and wherein the maximal axitinib concentration in the retina and/or the choroid/RPE at the time of final hydrogel degradation provided by the sustained release biodegradable ocular implant is less than the maximal axitinib concentration in the retina and/or the choroid/RPE at the time of final hydrogel degradation, respectively, provided by a comparative implant in which the TKI is axitinib having a solubility of lower than 0.3 μg/ml as measured in phosphate-buffered saline (PBS) at a pH of 7.2 to 7.4 and 37° C. after five days of incubation. In these embodiments, the comparative implant may differ from the sustained release biodegradable ocular implant only in the solubility and/or the polymorphic form of the axitinib, wherein the total amount of axitinib contained in the comparative implant differs by no more than 10% from the total amount of axitinib contained in the sustained release biodegradable ocular implant. In these embodiments, the maximum TKI (such as axitinib) concentration in the retina and/or the choroid/RPE may be reached by the sustained release biodegradable ocular implant prior to the final hydrogel biodegradation. In these embodiments, the retina and/or the choroid/RPE may be of a monkey, such as a *Cynomolgus* monkey, or of a rabbit, such as a Dutch Belted rabbit. Furthermore, in these embodiments, the solubility of the axitinib contained in the sustained release biodegradable ocular implant may be at least 0.4 μg/ml or greater, and the solubility of the axitinib contained in the comparative implant may be lower than 0.3 μg/mL as measured in phosphate-buffered saline (PBS) at a pH of 7.2 to 7.4 and 37° C. after five days of incubation. Specifically, the higher solubility axitinib in these embodiments may be axitinib polymorph IV, and the lower solubility axitinib (as contained in the comparative implant) may be axitinib polymorph SAB-I.

In yet other specific embodiments, the present invention relates to a method of treating an ocular disease in a patient in need thereof, wherein the treatment comprises injection of a sustained release biodegradable ocular implant into the vitreous humor of an eye of the patient in need of treatment, wherein the sustained release biodegradable ocular implant comprises a hydrogel and TKI, with TKI particles being dispersed within the hydrogel, wherein the TKI contained in the sustained release biodegradable ocular implant is axitinib having a solubility of 0.3 μg/mL or greater as measured in phosphate-buffered saline (PBS) at a pH of 7.2 to 7.4 and 37° C. after five days of incubation, and wherein the maximum concentration of axitinib in the retina and/or the choroid/RPE is reached by the sustained release biodegradable ocular implant earlier than by a comparative implant, wherein the comparative implant differs from the sustained release biodegradable ocular implant in the solubility and/or the polymorphic form of the axitinib, and wherein the dose of axitinib in the comparative implant is up to two times the dose of axitinib in the sustained release biodegradable ocular implant. In these embodiments, the maximum TKI (such as axitinib) concentration in the retina and/or the choroid/RPE may be reached by the sustained release biodegradable ocular implant prior to the final hydrogel biodegradation. In these embodiments, the retina and/or the choroid/RPE may be of a monkey, such as a *Cynomolgus* monkey, or of a rabbit, such as a Dutch Belted rabbit. Specifically, the higher solubility axitinib in these embodiments may be axitinib polymorph IV, and the lower solubility axitinib (as contained in the comparative implant) may be axitinib polymorph SAB-I.

In other specific embodiments, the present invention relates to a method of treating an ocular disease, such as wet AMD, in a patient in need thereof, wherein the treatment comprises injection of a sustained release biodegradable ocular implant into the vitreous humor of an eye of the patient in need of treatment, wherein the sustained release biodegradable ocular implant comprises a hydrogel and axitinib polymorph IV in a dose of about 400 to about 500 μg, such as about 450 μg, with axitinib particles being dispersed within the hydrogel, wherein the hydrogel comprises a PEG hydrogel, wherein the implant in its dry state has a width of from 0.30 to 0.36 mm, and wherein the implant provides for a release of axitinib in an in vitro test performed at 35° C. $0.5° C. in 0.01N HCl with 0.25% cetyl trimethyl ammonium bromide (CTAB) in a USP apparatus 4 that is characterized in that the percentage of axitinib released from the implant (wherein the percentage of released axitinib is based on the maximum amount of axitinib released from the implant representing 100%) is:

at least about 10% after 0.5 hours,
at least about 30% after 2 hours,
at least about 58% after 6 hours,
at least about 75% after 10 hours,
at least about 80% after 12 hours,
and/or at least about 90% after 16 hours;
such as:
at least about 10% after 0.5 hours,
at least about 19% after 1 hour,
at least about 30% after 2 hours, at least about 45% after 4 hours,
at least about 58% after 6 hours,
at least about 70% after 8 hours,
at least about 75% after 10 hours,
at least about 80% after 12 hours,
and/or at least about 90% after 16 hours.

In other specific embodiments, the present invention relates to a method of treating an ocular disease, such as wet AMD, in a patient in need thereof, wherein the treatment comprises injection of a sustained release biodegradable ocular implant into the vitreous humor of an eye of the patient in need of treatment, wherein the sustained release biodegradable ocular implant comprises a hydrogel and axitinib polymorph IV in a dose of about 400 to about 500 µg, such as about 450 µg, with axitinib particles being dispersed within the hydrogel, wherein the hydrogel comprises a hydrogel network formed by crosslinking 4a20kPEG-SAZ and 8a20kPEG-$NH_2$ units, wherein the implant has a composition (dry basis; in % w/w) as follows: from about 60% to about 70% axitinib and from about 25% to about 35% PEG units, wherein the implant in its dry state has a width of from 0.30 to 0.36 mm and a total weight of from about 0.6 mg to about 1 mg, and wherein the implant provides for a release of axitinib in an in vitro test performed at 35° C.±0.5° C. in 0.01N HCl with 0.25% cetyl trimethyl ammonium bromide (CTAB) in a USP apparatus 4 that is characterized in that the percentage of axitinib released from the implant (wherein the percentage of released axitinib is based on the maximum amount of axitinib released from the implant representing 100%) is:

from about 10 to about 20% after 0.5 hours,
from about 30 to about 45% after 2 hours,
from about 58 to about 81% after 6 hours,
from about 75 to about 98% after 10 hours,
at least about 80% after 12 hours,
and/or at least about 90% after 16 hours,
such as:
from about 10 to about 20% after 0.5 hours,
from about 19 to about 30% after 1 hour,
from about 30 to about 45% after 2 hours,
from about 45 to about 65% after 4 hours,
from about 58 to about 81% after 6 hours,
from about 70% to about 90% after 8 hours,
from about 75 to about 98% after 10 hours,
at least about 80% after 12 hours,
and/or at least about 90% after 16 hours.

In other specific embodiments, the present invention relates to a method of treating an ocular disease, such as wet AMD, in a patient in need thereof, wherein the treatment comprises injection of a sustained release biodegradable ocular implant containing axitinib polymorph IV in a dose of about 400 to about 500 µg into the vitreous humor of an eye of the patient in need of treatment, wherein the hydrogel comprises a PEG hydrogel, wherein the implant in its dry state has a width of from 0.30 to 0.36 mm, and wherein the implant is characterized in that the amount of axitinib released from the implant in an in vitro test performed at 35° C.±0.5° C. in 0.01N HCl with 0.25% cetyl trimethyl ammonium bromide (CTAB) in a USP apparatus 4 is:

at least about 50 µg after 0.5 hours,
at least about 140 µg after 2 hours,
at least about 270 µg after 6 hours,
at least about 350 µg after 10 hours,
at least about 400 µg after 12 hours,
and/or at least about 410 µg after 16 hours,
such as:
at least about 50 µg after 0.5 hours,
at least about 90 µg after 1 hour,
at least about 140 µg after 2 hours,
at least about 230 µg after 4 hours,
at least about 270 µg after 6 hours,
at least about 340 µg after 8 hours,
at least about 350 µg after 10 hours,
at least about 400 µg after 12 hours,
and/or at least about 410 µg after 16 hours.

In other specific embodiments, the present invention relates to a method of treating an ocular disease, such as wet AMD, in a patient in need thereof, wherein the treatment comprises injection of a sustained release biodegradable ocular implant containing axitinib polymorph IV in a dose of about 400 to about 500 µg into the vitreous humor of an eye of the patient in need of treatment, wherein the hydrogel comprises a PEG hydrogel network formed by crosslinking 4a20kPEG-SAZ and 8a20kPEG-$NH_2$ units, wherein the implant has a composition (dry basis; in % w/w) as follows: from about 60% to about 70% axitinib and from about 25% to about 35% PEG units, wherein the implant in its dry state has a width of from 0.30 to 0.36 mm and a total weight of from about 0.6 mg to about 1 mg, and wherein the implant is characterized in that the amount of axitinib released from the implant in an in vitro test performed at 35° C.±0.5° C. in 0.01N HCl with 0.25% cetyl trimethyl ammonium bromide (CTAB) in a USP apparatus 4 is:

from about 50 to about 80 µg after 0.5 hours,
from about 140 to about 210 µg after 2 hours,
from about 270 to about 380 µg after 6 hours,
from about 350 to about 470 µg after 10 hours,
at least about 400 µg after 12 hours,
and/or at least about 410 µg after 16 hours,
such as:
from about 50 to about 80 µg after 0.5 hours,
from about 90 to about 130 µg after 1 hour,
from about 140 to about 210 µg after 2 hours,
from about 230 to about 290 µg after 4 hours,
from about 270 to about 380 µg after 6 hours;
from about 340 to about 440 µg after 8 hours,
from about 350 to about 470 µg after 10 hours,
at least about 400 µg after 12 hours,
and/or at least about 410 µg after 16 hours.

In other specific embodiments, the present invention relates to a method of treating an ocular disease, such as wet AMD, in a patient in need thereof, wherein the treatment comprises injection of a sustained release biodegradable ocular implant containing axitinib polymorph IV in a dose of about 400 to about 500 µg into the vitreous humor of an eye of the patient in need of treatment, wherein the hydrogel comprises crosslinked PEG units, wherein the amount of axitinib being released upon final degradation of the hydrogel in the vitreous humor is less than 200 µg, wherein the implant in its dry state (prior to injection) has a width of from about 0.3 to about 0.4 mm, such as about 0.33 to about 0.36 mm, and a length of less than about 11 mm, and in its hydrated state (after 24 hours in PBS at a pH of 7.4 at 37° C.) has a length of less than about 11 mm, such as a length of from about 8 to about 10 mm.

In further specific embodiments, the present invention relates to a method of treating an ocular disease, such as wet AMD. In a patient in need thereof, the method comprising injecting a sustained release biodegradable ocular implant into the vitreous humor of the patient, wherein the implant may be each and any implant specifically disclosed herein in the section "Specific implants:".

The invention is illustrated in the following by means of examples.

ADDITIONAL DISCLOSURE

In addition to the disclosure above, the present invention also discloses the following items:

1. A sustained release biodegradable ocular implant comprising a hydrogel and a tyrosine kinase inhibitor (TKI), wherein tyrosine kinase inhibitor particles are dispersed within the hydrogel, characterized in that the solubility of the tyrosine kinase inhibitor is 0.3 μg/ml or greater as measured in phosphate-buffered saline (PBS) at a pH of 7.2 to 7.4 and 37° C. after five days of incubation.
2. A sustained release biodegradable ocular implant comprising a hydrogel and a tyrosine kinase inhibitor, wherein tyrosine kinase inhibitor particles are dispersed within the hydrogel, characterized in that the hydrated surface area of the implant is at least 25 $mm^2$ as measured in phosphate-buffered saline (PBS) at a pH of 7.2 to 7.4 and 37° C. after 24 hours of incubation.
3. A sustained release biodegradable ocular implant comprising a hydrogel and a tyrosine kinase inhibitor, wherein tyrosine kinase inhibitor particles are dispersed within the hydrogel, wherein the cumulative amount of tyrosine kinase inhibitor released from the implant over a period defined by any initial number of days up to the day when 80% of the tyrosine kinase inhibitor contained in the implant is released is higher than the cumulative amount of tyrosine kinase inhibitor released over the same period of time from a comparative implant, wherein the comparative implant differs from the sustained release biodegradable ocular implant only in that the solubility of the tyrosine kinase inhibitor in the comparative implant is lower as measured in PBS at a pH of 7.2 to 7.4 and 37° C. after five days of incubation, and wherein the release of tyrosine kinase inhibitor from both implants is measured under identical conditions.
4. The sustained release biodegradable ocular implant of item 3, wherein the cumulative amount of tyrosine kinase inhibitor released over said period of time from the implant is at least 10%, or at least 20% higher than the cumulative amount of tyrosine kinase inhibitor released over said period of time from the comparative implant.
5. A sustained release biodegradable ocular implant comprising a hydrogel and a tyrosine kinase inhibitor, wherein tyrosine kinase inhibitor particles are dispersed within the hydrogel, wherein the average release rate of tyrosine kinase inhibitor per day from the implant over a period defined by any initial number of days up to the day when 80% of the tyrosine kinase inhibitor contained in the implant is released is higher than the average release rate of tyrosine kinase inhibitor per day from a comparative implant over the same period of time, wherein the comparative implant differs from the sustained release biodegradable ocular implant only in that the solubility of the tyrosine kinase Inhibitor in the comparative implant is lower as measured in PBS at a pH of 7.2 to 7.4 and 37° C. after five days of incubation, and wherein the release of tyrosine kinase inhibitor from both implants is measured under identical conditions.
6. The sustained release biodegradable ocular implant of item 5, wherein the average release rate of tyrosine kinase inhibitor from the implant over said period of time is at least 10%, or at least 20% higher than the average release rate of tyrosine kinase inhibitor over said period of time from the comparative implant.
7. The sustained release biodegradable ocular implant of any of the preceding items, wherein the tyrosine kinase inhibitor is axitinib.
8. The sustained release biodegradable ocular implant of any of the preceding items, wherein the solubility of the tyrosine kinase inhibitor provides for the sustained release characterized in that
   (A) the total number of days required for 50% release of the total amount of tyrosine kinase inhibitor contained in the implant is less than for a comparative implant,
   (B) the percentage of the total amount of tyrosine kinase inhibitor contained in the implant that is released on day 1 is higher than for a comparative implant, and/or
   (C) the percentage of the total amount of tyrosine kinase inhibitor contained in the implant that is released per day on one or more days from day 2 of the release is higher than for a comparative implant, wherein the comparative implant differs from the sustained release biodegradable ocular implant only in that the solubility of the tyrosine kinase inhibitor in the comparative implant is lower as measured in PBS at a pH of 7.2 to 7.4 and 37° C. after five days of incubation, and wherein the release of tyrosine kinase inhibitor from both implants is measured under identical conditions.
9. The sustained release biodegradable ocular implant of item 8, wherein the solubility of the tyrosine kinase inhibitor provides for the sustained release characterized in that
   (A) the total number of days required for 50% release of the total amount of tyrosine kinase inhibitor contained in the implant is at most 70%, such as at most 60%, or at most 50% of the total number of days required for 50% release of the total amount of tyrosine kinase inhibitor from a comparative implant,
   (B) the percentage of the total amount of tyrosine kinase inhibitor contained in the implant that is released on day 1 is at least 5% higher, or at least 10% higher than for a comparative implant, and/or
   (C) the percentage of the total amount of tyrosine kinase inhibitor contained in the implant that is released per day on one or more days from day 2 of the release is at least 2% higher, or at least 5% higher than for a comparative implant, wherein the comparative implant differs from the sustained release biodegradable ocular implant only in that the solubility of the tyrosine kinase inhibitor in the comparative implant is lower as measured in PBS at a pH of 7.2 to 7.4 and 37° C. after five days of incubation, and wherein the release of tyrosine kinase inhibitor from both implants is measured under identical conditions.
10. The sustained release biodegradable ocular implant of any of items 3 to 9, wherein the solubility of the tyrosine kinase inhibitor in the comparative implant is at least 1.5 times, such as 2 times lower, 11. The sustained release biodegradable ocular implant of any of items 3 to 10, wherein the release of tyrosine kinase inhibitor from both implants is measured in an in vitro release test.
12. The sustained release biodegradable ocular implant of item 11, wherein the release of tyrosine kinase inhibitor from both implants is measured in an in vitro release test in 25%/75% (v/v) ethanol/water at 37° C.
13. The sustained release biodegradable ocular implant of item 12, wherein the release of tyrosine kinase inhibitor from both implants is measured in an in vitro release test in 25%/75% (v/v) ethanol/water at 37° C. under sink conditions, such as under 2× or 3× sink conditions.
14. The sustained release biodegradable ocular implant of any of the preceding items, wherein the solubility of the tyrosine kinase inhibitor is 0.35 μg/mL or greater, such as 0.4 μg/ml or greater as measured in phosphate-buffered saline (PBS) at a pH of 7.2 to 7.4 and 37° C. after five days of incubation.
15. The sustained release biodegradable ocular implant of any of the preceding items, wherein the TKI is axitinib, and axitinib particles are dispersed within the hydrogel, wherein the solubility of the axitinib is at least 0.4 μg/mL, such as at least 0.5 g/mL, or at least 0.6 μg/mL, at least 0.7 μg/mL; at least 0.8 μg/mL, at least 1 μg/mL, at least 2.5 μg/mL, at least 5 μg/mL, at least 10 μg/mL, at least 20 μg/mL, at least 50 μg/mL, at least 100 μg/mL, at least 150 μg/mL, or at least 200 μg/mb in phosphate-buffered saline (PBS) at a pH of 7.2 to 7.4 and 37° C. after five days of incubation.
16. The sustained release biodegradable ocular implant of any of items 1 to 14, wherein TKI is axitinib, and axitinib particles are dispersed within the hydrogel, wherein the solubility of the axitinib is at least 0.4 μg/mL, such as at least 0.5 μg/mL, such as at least 0.6 μg/mL, at least 0.7 μg/mL, at least 0.8 μg/mL, at least 1 μg/mL, at least 2.5 μg/mL, at least 5 μg/mL, at least 10 μg/mL, at least 50 μg/mL, at least 90 μg/mL, at least 150 μg/mL, or at least 200 μg/mL in phosphate-buffered saline (PBS) at a pH of 7.2 to 7.4 and 22° C. after five days of incubation.
17. The sustained release biodegradable ocular implant of any of items 3 to 16, wherein the solubility of the tyrosine kinase inhibitor in the comparative implant is at least 2 times lower.
18. The sustained release biodegradable ocular implant of item 17, wherein the solubility of the tyrosine kinase inhibitor in the comparative implant is from 2 times to 200 times lower, such as 5 times lower, or 10 times lower, or 100 times lower.
19. The sustained release biodegradable ocular implant of any of the preceding items, wherein the TKI is axitinib, and the axitinib is in the form of: its free base, a solvate, a salt, a co-crystal, a derivative, a prodrug, or mixtures of the foregoing,
20. The sustained release biodegradable ocular implant of any of the preceding items, wherein the implant contains an amount of axitinib in the form of its free base, or a solvate, a salt, a co-crystal, a derivative, a prodrug, or mixtures of the foregoing, that corresponds to an amount ranging from 100 to 1200 μg, or from 200 to 1000 μg, or from 200 to 800 μg, or from 300 to 600 μg, or from 400 to 500 μg of axitinib free base.
21. The sustained release biodegradable ocular implant of any of items 1 to 19, containing axitinib free base in an amount ranging from 100 to 1200 μg, from 200 to 1000 μg, or from 200 to 800 μg, or from 300 to 700 μg.
22. The sustained release biodegradable ocular implant of any of items 1 to 19, containing axitinib free base in an amount of from about 300 to about 650 μg, such as from 300 to 600 μg, such as from about 360 μg to about 562.5 μg, such as from 350 to 550 μg, such as from about 360 μg to about 562.5 μg, such as from about 420 to about 480 μg, or from 400 to 500 μg, or of about 450 μg.
23. The sustained release biodegradable ocular implant of any of items 1 to 19, containing axitinib free base in an amount of from 400 to 800 μg, such as from about 480 μg to about 750 μg, or from 500 to 650 μg, or of about 600 μg.
24. The sustained release biodegradable ocular implant of any of items 19 to 23, wherein the axitinib free base, solvate, salt, derivative, or prodrug is contained in the implant in amorphous or crystalline form, or a mixture thereof.
25. The sustained release biodegradable ocular implant of any of the preceding items, wherein the implant contains axitinib free base in crystalline form.
26. The sustained release biodegradable ocular implant of the of the preceding items, wherein the implant contains axitinib free base in the form of one or more axitinib polymorphs.
27. The sustained release biodegradable ocular implant of item 26, wherein the implant contains an axitinib polymorph that is characterized by a powder X-ray diffraction pattern comprising at least one, such as at least two, or at least three, or at least four of the following peaks at diffraction angles (2θ) of 8.90, 9.50, 12.0, 14.60, 15.25, 15.75, 17.80, 19.30, 20.65, 24.95, 26.10 (all ±0.2).
28. The sustained release biodegradable ocular implant of item 27, wherein the implant contains an axitinib polymorph that is characterized by a powder X-ray diffraction pattern comprising the following peaks at diffraction angles (2θ) of 8.90, 12.0, 14.60, 15.75, and 19.30 (all±0.2).
29. The sustained release biodegradable ocular implant of any of the preceding items, wherein the implant contains axitinib polymorph IV.
30. The sustained release biodegradable ocular implant of any of the preceding items, wherein at least 90%, or at least 95% by weight of the axitinib contained in the implant is axitinib polymorph IV.
31. The sustained release biodegradable ocular implant of any of items 1 to 20 and 24 to 30, containing axitinib polymorph IV in an amount of from 200 to 1000 μg, such as 200 to 800 μg, such as from 300 to 600 μg, such as from 400 to 500 μg, or of about 450 μg.
32. The sustained release biodegradable ocular implant of any of items 1 to 20 and 24 to 30, containing polymorph IV in an amount of from 400 to 1000 μg, 400 to 700 μg, such as from 500 to 650 μg, or of about 600 μg.
33. The sustained release biodegradable ocular implant of any of the preceding items, wherein after storage at room temperature° C. for at least 3 months, such as at least 4.5 months or at least 6 months the content of axitinib in the implant is within a range of ±7% of its original content, such as ±6% of its original content.
34. The sustained release biodegradable ocular implant of any of items 1 to 20, wherein the implant contains axitinib in the form of an axitinib co-crystal, 35. The sustained release biodegradable ocular implant of item 34, wherein the axitinib co-crystal is a co-crystal of axitinib and a carboxylic acid.
36. The sustained release biodegradable ocular implant of item 35, wherein the carboxylic acid in the axitinib co-crystal is a $C_1$ to $C_{12}$ carboxylic acid.
37. The sustained release biodegradable ocular implant of any of items 35 or 36, wherein the carboxylic acid has one or more carboxyl groups, or has 2 or 3 carboxyl groups.
38. The sustained release biodegradable ocular implant of any of items 35 to 37, wherein the carboxylic acid is saturated or unsaturated and/or contains aromatic groups.
39. The sustained release biodegradable ocular implant of any of items 35 to 38, wherein the carboxylic acid is free of, or contains one or more additional functional groups, such as hydroxyl groups.
40. The sustained release biodegradable ocular implant of any of items 35 to 39, wherein the carboxylic acid forming the co-crystal with axitinib is present in any enantiomeric form and/or in any (cis/trans) configuration.
41. The sustained release biodegradable ocular implant of any of items 35 to 40, wherein the carboxylic acid forming the co-crystal with the axitinib is one or more of citric acid, fumaric acid, (+)-L- or (−)-D tartaric acid, glutaric acid, (trans- or cis) cinnamic acid, suberic acid, succinic acid, adipic acid, pimelic acid, salicylic acid.
42. The sustained release biodegradable ocular implant of any of items 34 to 41, wherein the axitinib co-crystal has a solubility in PBS at pH 7.4 after 24 hours at 37° C. that is at least twice the solubility of axitinib free base under identical conditions.
43. The sustained release biodegradable ocular implant of item 42, wherein the axitinib co-crystal has a solubility in PBS at pH 7.4 after 24 hours at 37° C. of at least 10 μg/mL, such as at least 15 μg/mL.
44. The sustained release biodegradable ocular implant of any of items 1 to 25, wherein the implant contains axitinib in the form of an axitinib derivative or prodrug,
45. The sustained release biodegradable ocular implant of item 44 wherein the axitinib derivative or prodrug is axitinib functionalized at one or more of the nitrogen atoms of the axitinib free base.
46. The sustained release biodegradable ocular implant of item 45, wherein in the axitinib derivative or prodrug one or more of the nitrogen atoms in the axitinib free base is/are independently substituted with one or more of the following groups: acyl, alkylcarbonyl, arylcarbonyl, alkylthiocarbonyl, arylthiocarbonyl, alkylcarbamoyl, arylcarbamoyl, substituted or unsubstituted acetyl, substituted or unsubstituted aminoalkanoyl, substituted or unsubstituted α-aminoalkanoyl, an acyl group derived from a natural or an unnatural amino acid with or without substitution, an acyl group of a peptide residue, phosphonyl, phosphinyl, aminophosphinyl, alkylaminophosphinyl, sulfonyl, cycloalkanecarbonyl, heterocycloalkane-carbonyl, alkoxycarbonyl, aryloxycarbonyl, heteroalkoxycarbonyl, heteroaryloxycarbonyl, an O-substituted hydroxymethyl group with or without substitution,
47. The sustained release biodegradable ocular implant of item 44 or 45, wherein the axitinib derivative or prodrug is a compound of general formula (I) depicted below, or a salt or solvate thereof:

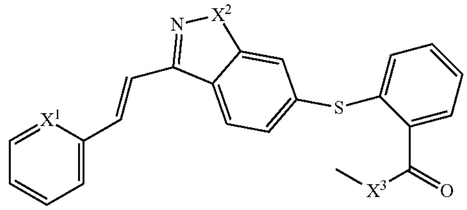

(I)

wherein:

$X^1$ is selected from N or $N^+Y^1$;

$X^2$ is selected from NH or $NY^2$;

$X^3$ is selected from NH or $NY^3$;

$Y^1$ is selected from —$CH_2OCO(OCH_2CH_2)n^1OM^1$; or —$CH_2OCO(CH_2CH_2O)n^{1a}Z^1$; or —$CH_2OCO(CH_2)n^{1b}COOH$;

$Y^2$ is selected from —$CH_2OCO(OCH_2CH_2)n^2OM^2$; or —$CH_2OCO(CH_2CH_2O)n^{2a}Z^2$; or —$CH_2OCO(CH_2)n^{2b}COOH$;

$Y^3$ is selected from —$CH_2OCO(OCH_2CH_2)n^3OM^3$; or —$CH_2OCO(CH_2CH_2O)n^{3a}Z^3$; or —$CH_2OCO(CH_2)n^{3b}COOH$;

$n^1$, $n^{1a}$, $n^{1b}$, $n^2$, $n^{2a}$, $n^{2b}$, $n^3$, $n^{3a}$ and $n^{3b}$ are Independently 0 or an integer from 1 to 8;

$M^1$, $M^2$, $M^3$, $Z^1$, $Z^2$ and $Z^3$ are independently selected from H, optionally substituted $C_{1-6}$ alkyl and optionally substituted aryl;

wherein at least one of $X^1$, $X^2$ and $X^3$ is not N or NH;

wherein at least one of $Y^1$, $Y^2$ or $Y^3$ are the respective —$CH_2OCO(CH_2CH_2O)nZ$;

or wherein:

$Y^1$, $Y^2$ and $Y^3$ are independently selected from the respective —$(CH_2)p^1OCO(O(CH_2)p^2)n^1OM$; or —$(CH_2)_p{}^{1a}OCO((CH_2)p^2O)n^1(CH_2)Z$; or —$(CH_2)p^1OCO(CH_2)q^1COOH$; wherein $p^1$, $p^{1a}$ and $p^2$ are independently selected from an integer from 1 to 4, and $q^1$ is independently selected from an integer from 0 to 4.

48. The sustained release biodegradable ocular implant of item 47, wherein the axitinib derivative or prodrug is a compound wherein:

$X^1$ is $N^+Y^1$; $X^2$ is NH; $X^3$ is NH; and $Y^1$ is —$CH_2OCO(CH_2CH_2O)n^{1a}Z^1$ or —$CH_2OCO(CH_2)n^{1b}COOH$, or wherein:

$X^1$ is N; $X^2$ is $NY^2$; $X^3$ is NH; and $Y^2$ is —$CH_2OCO(CH_2CH_2O)n^{2a}Z^2$ or —$CH_2OCO(CH_2)n^{2b}COOH$, or wherein:

$X^1$ is N; $X^2$ is NH; $X^3$ is $NY^3$; and $Y^3$ is —$CH_2OCO(CH_2CH_2O)n^{3a}Z^3$ or —$CH_2OCO(CH_2)n^{3b}COOH$, 49. The sustained release biodegradable ocular implant of item 47 or 48, wherein in the axitinib derivative or prodrug $n^1$, $n^2$ or $n^3$ is 2, 3 or 4, and/or $n^{1a}$, $n^{2a}$ or $n^{3a}$ is 2, 3 or 4 and/or $n^{1b}$, $n^{2b}$ or $n^{3b}$ is 2, 3 or 4.
50. The sustained release biodegradable ocular implant of item 47, containing axitinib-N-succinyloxymethyl prodrug, axitinib-N-mPEG-oxymethyl prodrug, including but not limited to axitinib-N-m(PEG)$_1$-oxymethyl, axitinib-N-m(PEG)$_2$-oxymethyl, axitinib-N-m(PEG)$_3$-oxymethyl, axitinib-N-m(PEG)$_4$-oxymethyl, or a salt or solvate thereof,
51. The sustained release biodegradable ocular implant of any of items 44 to 50, containing an axitinib derivative or prodrug as defined in these items, wherein the axitinib derivative or prodrug has a solubility that is at least 2 times, at least 5 times, at least 10 times, at least 25 times, at least 50 times, at least 75 times, at least 100 times, at least 150 times, at least 200 times, at least 250 times, or at least 500 times the solubility of axitinib free base.

52. The sustained release biodegradable ocular implant of any of items 44 to 51, wherein the axitinib derivative or prodrug has a solubility in PBS at pH 7.4 after 24 hours at 22° C. of at least 90 μg/mL, or at least 150 μg/mL, or at least 200 μg/mL.

53. The sustained release biodegradable ocular implant of any of items 47 to 52, wherein at least 90% of the entire axitinib contained in the implant is a compound of formula (I) as defined in these items.

54. The sustained release biodegradable ocular implant of any of the preceding items, wherein the TKI particles have a d90 particle size of less than 10 μm, or less than 8 μm, or less than 7 μm, or 7.5 μm or less, or 6.5 μm or less, or 5 μm or less, or less than 1 μm, or less than 0.5 μm, or less than 0.4 μm as determined by laser diffraction.

55. The sustained release biodegradable ocular implant of any of the preceding items, wherein the TKI particles have a d50 particle size of less than 5 μm, less than 3 μm, less than 2.6 μm, less than 2 μm, less than 1.5 μm, less than 1 μm, less than 0.5 μm, or less than 0.25 μm, less than 0.2 μm, as determined by laser diffraction.

56. The sustained release biodegradable ocular implant of item 55, wherein the TKI particles have a d50 particle size of 0.15 μm or less, as determined by laser diffraction.

57. The sustained release biodegradable ocular implant of any of the preceding items, wherein the TKI particles have a d10 particle size of less than 1 μm, or less than 0.5 μm, or 0.25 μm or less, or less than 0.2 μm, or less than 0.1 μm as determined by laser diffraction.

58. The sustained release biodegradable ocular implant of any of items 1 to 53 comprising axitinib, wherein the axitinib particles have a d10 particle size of less than 8 μm, a d50 particle size of less than 20 μm, and a d90 particle size of less than 50 μm.

59. The sustained release biodegradable ocular implant of any of items 1 to 53 comprising axitinib, wherein the axitinib particles have a d10 particle size of less than 0.25 μm, a d50 particle size of less than 2.6 μm, and a d90 particle size of less than 8 or less than 6.5 μm, 60. The sustained release biodegradable ocular implant of any of items 1 to 53 comprising axitinib, wherein the axitinib particles have a d10 particle size of less than 0.2 μm, a d50 particle size of less than 1.5 μm, and a d90 particle size of less than 5 μm.

61. The sustained release biodegradable ocular implant of any of items 1 to 53 comprising axitinib, wherein the axitinib particles have a d10 particle size of less than 0.1 μm, a d50 particle size of less than 0.2 μm, and a d90 particle size of less than 0.4 μm.

62. The sustained release biodegradable ocular implant of any of the preceding items, wherein the implant is in the shape of a fiber, wherein a fiber is an elongated object that has a length and a width, wherein the width is the largest cross-sectional dimension of the elongated object and the length is the longest elongation of the object.

63. The sustained release biodegradable ocular implant of any of the preceding items, wherein in the implant in its dried state the length is longer than the width.

64. The sustained release biodegradable ocular implant of any of the preceding items, wherein the implant in its dried state has a length of less than 17 mm, such as a length 11 mm or less, such as 10 mm or less, such as a length of from 6 mm to 10 mm, or from 6 to 9 mm.

65. The sustained release biodegradable ocular implant of any of the preceding items, wherein in case the implant has a cylindrical or essentially cylindrical shape, the width of the implant is the diameter.

66. The sustained release biodegradable ocular implant of any of the preceding items, wherein the implant in its dried state has a width or (In case of a cylindrical or essentially cylindrical implant) a diameter of less than 0.7 mm, such as less than 0.6 mm, or from 0.1 mm to 0.65 mm, or from 0.20 mm to 0.45 mm.

67. The sustained release biodegradable ocular implant of any of the preceding items, wherein the implant in its dried state has a length of less than about 11 mm and a diameter of from 0.3 to about 0.4 mm, or has a length of from 6 to 8 mm and a diameter of from 0.25 to 0.45 mm.

68. The sustained release biodegradable ocular implant of any of the preceding items, wherein the implant in its dried state has a length of from 6.7 to 7.8 mm and a diameter of from 0.30 to 0.40 mm.

69. The sustained release biodegradable ocular implant of any of the preceding items, wherein the implant in its hydrated state (after 24 hours in phosphate-buffered saline at a pH of 7.2-7.4 at 37° C.) has a length of 12 mm or less, or of 11 mm or less, or of 10 mm or less.

70. The sustained release biodegradable ocular implant of any of the preceding items, wherein the implant in its hydrated state (after 24 hours in phosphate-buffered saline at a pH of 7.2 to 7.4 at 37° C.) has a length of from 4 to 12 mm, or from 4 to 11 mm, or from 6 to 11 mm, or from 6 to 10 mm, or from 6 to 9 mm.

71. The sustained release biodegradable ocular implant of any of the preceding items, wherein the implant in its hydrated state (after 24 hours in phosphate-buffered saline at a pH of 7.2 to 7.4 at 37° C.) has a diameter of 1.2 mm or less, or of 1 mm or less, or of 0.8 mm or less, 72. The sustained release biodegradable ocular implant of any of the preceding items, wherein the implant in its hydrated state (after 24 hours in phosphate-buffered saline at a pH of 7.2 to 7.4 at 37° C.) has a diameter of from 0.5 to 0.9 mm, or from 0.5 to 0.8 mm.

73. The sustained release biodegradable ocular implant of any of the preceding items, wherein the implant in its hydrated state (after 24 hours in PBS at a pH of 7.2 to 7.4 at 37° C.) has a length of less than about 11 mm and a diameter of about 2 mm or less, or has a length of from 7 to 10 mm and a diameter of from 0.5 to 0.9 mm.

74. The sustained release biodegradable ocular implant of any of the preceding items, wherein the implant in its hydrated state (after 24 hours in PBS at a pH of 7.2 to 7.4 at 37° C.) has a length of from 8 to 9 mm and a diameter of from 0.70 to 0.80 mm.

75. The sustained release biodegradable ocular implant of any of the preceding items, wherein the implant has a cross-sectional geometry that is round, essentially round, oval, oblong, elliptical, quadrangular, square, diamond-shaped, cross-shaped, triangular, star-shaped, asterisk-shaped, thin-film shaped or gear shaped.

76. The sustained release biodegradable ocular implant of any of the preceding items, wherein the implant is cylindrical or essentially cylindrical.

77. The sustained release biodegradable ocular implant of any of the preceding items, wherein the implant is non-cylindrical.

78. The sustained release biodegradable ocular implant of item 1 or 3 to 77, wherein the hydrated surface area of the implant is at least 10 $mm^2$, or at least 16 $mm^2$, or at least 19 $mm^2$, or at least 25 $mm^2$ as measured in phosphate-buffered saline (PBS) at a pH of 7.2 to 7.4 and 37° C. after 24 hours of incubation.

79. The sustained release biodegradable ocular implant of item 1 or 3 to 78, wherein the hydrated surface area of the implant is from 15 $mm^2$ to 100 $mm^2$, such as from 19 $mm^2$ to 40 $mm^2$ as measured in phosphate-buffered saline (PBS) at a pH of 7.2 to 7.4 and 37° C. after 24 hours of incubation.

80. The sustained release biodegradable ocular implant of any of items 1 or 3 to 78, wherein the hydrated surface area of the implant is from 10 $mm^2$ to 90 $mm^2$, or from 19 $mm^2$ to 90 $mm^2$, or from 25 $mm^2$ to 90 $mm^2$ as measured in phosphate-buffered saline (PBS) at a pH of 7.2 to 7.4 and 37° C. after 24 hours of incubation.

81. The sustained release biodegradable ocular implant of item 1 or 3 to 80, wherein the hydrated surface area of the implant is from 10 $mm^2$ to 30 $mm^2$, such as from 16 to 25 $mm^2$, as measured in phosphate-buffered saline (PBS) at a pH of 7.2 to 7.4 and 37° C. after 24 hours of incubation, and wherein the implant is single-stranded and is cylindrical.

82. The sustained release biodegradable ocular implant of any of the preceding items, wherein the implant is formed in situ.

83. The sustained release biodegradable ocular implant of any of the preceding items, wherein the implant comprises at least two filaments, 84. The sustained release biodegradable ocular implant of item 83, wherein the implant comprises at least 3 or at least 4 filaments, and/or up to 20, or up to 15 filaments, such as from 2 to 8, or from 3 to 7 filaments.

85. The sustained release biodegradable ocular implant of item 84, wherein the implant is an extruded or an injection molded multi-filament implant.

86. The sustained release biodegradable ocular implant of any of items 83 to 85, wherein in the implant's dried state the multiple filaments are twisted to form one twisted strand, or wherein the multiple filaments are braided to form one braided strand, or wherein the individual strands are adhere to each other (such as by means of linear polyethylene glycol).

87. The sustained release biodegradable ocular implant of item 86, wherein upon hydration (in vivo or in vitro) the twisted strand completely or partially unfurls.

88. The sustained release biodegradable ocular implant of item 86 or 87, wherein the number of twists per cm is at least about 1, or at least about 2, or at least about 5, or is at least about 8, or is at least about 10 and/or is up to about 20, or up to about 15.

89. The sustained release biodegradable ocular implant of any of items 86 to 88, wherein the composite diameter of the twisted strand in its dried state is from 0.2 to 0.8 mm, 0.2 to 0.5 mm, or from 0.3 to 0.4 mm, or from 0.33 to 0.38 mm.

90. The sustained release biodegradable ocular implant of any of items 83 to 89, wherein the diameter of the individual filaments in the dried state is less than 0.3 mm, or less than 0.25 mm, or less than 0.2 mm, or less than 0.15 mm.

91. The sustained release biodegradable ocular implant of any of the preceding items, wherein the implant is loaded in a needle having a gauge of from 20 to 30, such as from 25 to 27.

92. The sustained release biodegradable ocular implant of any of the preceding items, wherein the hydrogel comprises a polymer network comprising one or more units of polyalkylene glycol, polyethylene glycol, polyethylene oxide, polypropylene oxide, polyvinyl alcohol, poly (vinylpyrrolidinone), polylactic acid, polylactic-co-glycolic acid, random or block copolymers or combinations or mixtures of any of these, or one or more units of polyaminoacids, glycosaminoglycans, polysaccharides, or proteins, 93. The sustained release biodegradable ocular implant of any of the preceding items, wherein the hydrogel comprises crosslinked polyethylene glycol (PEG) units.

94. The sustained release biodegradable ocular implant of any of the preceding items, wherein the hydrogel comprises multi-arm PEG units that are identical or different, and that have a number average molecular weight of from about 10,000 to about 60,000 Daltons, or from about 15,000 to about 40,000 Daltons, such as about 20,000 Daltons.

95. The sustained release biodegradable ocular implant of item 93 or 94, wherein the PEG units comprise 4-arm and/or 8-arm PEG units, 96. The sustained release biodegradable ocular implant of any of the preceding items, wherein the polymer network is formed by reacting an electrophilic group-containing PEG precursor with a nucleophilic group-containing crosslinking agent, wherein the crosslinking agent is a nucleophilic group-containing PEG precursor or another nucleophilic group-containing crosslinking agent, such as by crosslinking 4a20kPEG-SAZ with 8a20kPEG-$NH_2$.

97. The sustained release biodegradable ocular implant of item 96, wherein the nucleophilic group is an amine group.

98. The sustained release biodegradable ocular implant of item 96 or 97, wherein the nucleophilic group containing crosslinking agent is an amine, multi-arm amine or salt of any of these.

99. The sustained release biodegradable ocular implant of any of items 96 to 98, wherein the crosslinking agent is trilysine, or a salt or derivative thereof, such as trilysine acetate.

100. The sustained release biodegradable ocular implant of any of items 96 to 99, wherein the electrophilic group is an activated ester group.

101. The sustained release biodegradable ocular implant of any of items 96 to 100, wherein the electrophilic group is an N-hydroxysuccinimidyl (NHS) group and the polymer precursor is a multi-arm PEG precursor, 102. The sustained release biodegradable ocular implant of any of items 96 to 101, wherein the electrophilic group is one or more of a succinimidylazelate (SAZ) group, a succinimidyladipate group (SAP), a succinimidylglutarate group (SG), a succinimidylglutaramide (SGA) group, a succinimidylcarbonate group (SC) or a succinimidylsuccinate group (SS), particularly a succinimidylazelate (SAZ) group.

103. The sustained release biodegradable ocular implant of any of the preceding items, wherein the hydrogel comprises crosslinked PEG units, and the crosslinks between the PEG units include a group represented by the following formula

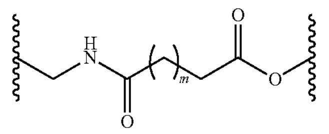

wherein m is an integer from 0 to 10, such as m being 1, 2, 3, or 6, particularly m being 6.

104. The sustained release biodegradable ocular implant of any of the preceding items, wherein the implant further contains a visualization agent.

105. The sustained release biodegradable ocular implant of item 104, wherein the visualization agent is a fluorophore.

106. The sustained release biodegradable ocular implant of any of the preceding items, wherein the implant is free or substantially free of antimicrobial preservatives.

107. The sustained release biodegradable ocular implant of any of the preceding items, having a composition (dry basis; in % w/w) as follows: from about 10% to about 80%, or from about 20% to about 70% by weight axitinib and from about 10% to about 80%, or from about 20% to about 70% by weight PEG units.

108. The sustained release biodegradable ocular implant of any of the preceding items, having a composition (dry basis; in % w/w) as follows: from about 10% to about 40% by weight, or from about 15% to about 25% by weight axitinib, and from about 55% to about 75% by weight, or from about 60% to about 70% by weight PEG units.

109. The sustained release biodegradable ocular implant of any of the preceding items, having a composition (wet basis; in % w/w) as follows: from about 1% to about 8% by weight, or from about 2% to about 7% by weight axitinib, and from about 5% to about 15% by weight, or from about 6% to about 10% by weight PEG units.

110. The sustained release biodegradable ocular implant of item 108 or 109, wherein the implant contains axitinib in an amount corresponding to from about 120 μg to about 187.5 μg, or about 150 μg axitinib free base.

111. The sustained release biodegradable ocular implant of any of items 1 to 107, having a composition (dry basis; in % w/w) as follows: from about 30% to about 50% by weight, or from about 40% to about 57% by weight axitinib, and from about 25% to about 50% by weight, or from about 35% to about 45% by weight PEG units, 112. The sustained release biodegradable ocular implant of any of items 1 to 107 or 111, having a composition (wet basis; in % w/w) as follows: from about 4% to about 14% by weight, or from about 7% to about 12% by weight axitinib, and from about 5% to about 15% by weight, or from about 6% to about 10% by weight PEG units, 113. The sustained release biodegradable ocular implant of item 111 or 112, wherein the implant contains axitinib in an amount corresponding to from about 240 μg to about 375 μg, or about 300 μg axitinib free base.

114. The sustained release biodegradable ocular implant of any of items 1 to 107, having a composition (dry basis; in % w/w) as follows: from about 40% to about 70% by weight, or from about 30% to about 70%, or from about 45% to about 65% by weight, or from about 50 to about 60% by weight or from about 60 to 70% by weight axitinib, and from about 20% to about 50% by weight, or from about 25% to about 45% by weight, or from about 33% to about 43% by weight PEG units.

115. The sustained release biodegradable ocular implant of any of items 1 to 107 or 114, having a composition (wet basis; in % w/w) as follows: from about 5% to about 20% by weight, or from about 6% to about 12% by weight, or from about 8 to about 10% by weight or from about 5 to about 17% by weight axitinib, and from about 4% to about 12% by weight, or from about 5% to about 10% by weight, or from about 6% to about 8% by weight PEG units, 116. The sustained release biodegradable ocular implant of item 114 or 115, wherein the implant contains axitinib in an amount corresponding to from about 360 μg to about 562.5 μg or to about 450 μg axitinib free base.

117. The sustained release biodegradable ocular implant of any of items 1 to 107, having a composition (dry basis; in % w/w) as follows: from about 30% to about 80% by weight, or from about 50% to about 70% by weight, or from about 55% to about 70% by weight axitinib, and from about 20% to about 60% by weight, or from about 20% to about 50% by weight, or from about 25% to about 35% by weight PEG units.

118. The sustained release biodegradable ocular implant of any of items 1 to 107 or 117, having a composition (wet basis; in % w/w) as follows: from about 10% to about 22% by weight, or from about 12% to about 18% by weight, or from about 14% to about 17% by weight axitinib, and from about 2% to about 12% by weight, or from about 4% to about 10% by weight, or from about 5% to about 8% by weight PEG units.

119. The sustained release biodegradable ocular implant of item 117 or 118, wherein the implant contains axitinib in an amount corresponding to from about 480 μg to about 750 μg, or about 600 μg axitinib free base.

120. The sustained release biodegradable ocular implant of any of items 1 to 107, having a composition (dry basis; in % w/w) as follows: from about 30% to about 70% by weight, or from about 30% to about 60% by weight axitinib, and from about 20% to about 60% by weight, or from about 30% to about 60% by weight PEG units, wherein the implant comprises at least two filaments, such as from 2 to 10, or from 3 to 7 filaments.

121. The sustained release biodegradable ocular implant of any of items 1 to 107 or 120, having a composition (wet basis; in % w/w) as follows: from about 5% to about 20% by weight, or from about 5% to about 15% by weight axitinib, and from about 3% to about 20% by weight, or from about 5% to about 10% by weight PEG units, wherein the implant comprises at least two filaments, such as from 2 to 10, or from 3 to 7 filaments.

122. The sustained release biodegradable ocular implant of any of items 1 to 107, having a composition (dry basis; in % w/w) as follows: from about 30% to about 70% by weight, or from about 40% to about 70% by weight axitinib, and from about 20% to about 60% by weight, or from about 20% to about 40% by weight PEG units, wherein the implant has a cross-sectional geometry that is not round or oblong, in particular a cross-sectional geometry that is cross- or star-shaped, including but not limited to 5-arm star shaped.

123. The sustained release biodegradable ocular implant of any of items 1 to 107 or 122, having a composition (wet basis; in % w/w) as follows: from about 5% to about 20% by weight, or from about 8% to about 18% by weight axitinib, and from about 3% to about 20% by weight, or from about 5% to about 10% by weight PEG units, wherein the implant has a cross-sectional geometry that is not round or oblong, in particular a cross-sectional geometry that is cross- or star-shaped, including but not limited to 5-arm star shaped.

124. The sustained release biodegradable ocular implant of any of the preceding items, wherein the implant in its dry state contains axitinib in an amount corresponding to 200 μg to 1000 μg axitinib free base per $mm^3$, or corresponding to 500 μg to 800 μg axitinib free base per $mm^3$, 125. The sustained release biodegradable ocular implant of any of the preceding items comprising axitinib, wherein the implant releases axitinib at an average rate of at least about 60 μg/day over the initial day and/or of at least about 55 μg/day over the initial 2 days and/or at least about 45 μg/day over the initial 5 days and/or at least about 40 μg/day over the initial 7 days and/or at least about 40 μg/day over the initial 10 days in an in vitro test performed at 37° C. in an 25%/75% (v/v) ethanol/water mixture under 2× sink conditions.

126. The sustained release biodegradable ocular implant of any of the preceding items comprising axitinib, wherein the implant releases at least 30% or 40%, or at least 44% of the total released amount of axitinib over the initial 3 days in an in vitro test performed at 37° C. in an 25%/75% (v/V) ethanol/water mixture under 2× sink conditions.

127. The sustained release biodegradable ocular implant of any of the preceding items, wherein the implant contains axitinib in an amount corresponding to from about 480 μg to about 750 μg, or about 600 μg axitinib free base and releases at least 40% of the total released amount of axitinib over the initial 3 days in an in vitro test, and/or wherein the implant contains axitinib in an amount corresponding to from about 360 μg to about 562.5 μg, or about 450 μg axitinib free base and releases at least 50% of the total released amount of axitinib in the implant over the initial 3 days in an in vitro test, and/or wherein the implant contains axitinib in an amount corresponding to from about 240 μg to about 375 μg, or about 300 μg axitinib free base and releases at least 60% of the total released amount of axitinib over the initial 3 days in an in vitro test, and/or wherein the implant contains axitinib in an amount corresponding to from about 120 μg to about 187.5 μg, or about 150 μg axitinib free base and releases at least 90% of the total released amount of axitinib over the initial 3 days in an in vitro test;

wherein said in vitro test is performed at 37° C. in an 25%/75% (v/v) ethanol/water mixture under 2× sink conditions, 128. The sustained release biodegradable ocular implant of any of the preceding items, wherein the implant releases at least 70%, or at least 77% of the total released amount of axitinib over the initial 7 days in an in vitro test performed at 37° C. in an 25%/75% (v/v) ethanol/water mixture under 2× sink conditions.

129. The sustained release biodegradable ocular implant of item 128, wherein the implant contains axitinib in an amount corresponding to from about 480 μg to about 750 μg, or about 600 μg axitinib free base and releases at least 70% of the total released amount of axitinib over the initial 7 days in an in vitro test, and/or wherein the implant contains axitinib in an amount corresponding to from about 360 μg to about 562.5 μg, or about 450 μg axitinib free base and releases at least 80% of the total released amount of axitinib over the initial 7 days in an in vitro test, and/or wherein the implant contains axitinib in an amount corresponding to from about 240 μg to about 375 μg, or about 300 μg axitinib free base and releases at least 85% of the total released amount of axitinib over the initial 7 days in an in vitro test, and/or wherein the implant contains axitinib in an amount corresponding to from about 120 μg to about 187.5 μg, or about 150 μg axitinib free base and releases at least 95% of the total released amount of axitinib over the initial 7 days in an in vitro test;

wherein said in vitro test is performed at 37° C. in an 25%/75% (v/v) ethanol/water mixture under 2× sink conditions.

130. The sustained release biodegradable ocular implant of any of the preceding items, wherein the implant releases at least 90%, or at least 95% of the total released amount of axitinib over the Initial 10 days in an in vitro test performed at 37° C. in an 25%/75% (v/v) ethanol/water mixture under 2× sink conditions, 131. The sustained release biodegradable ocular implant of item 130, wherein the implant contains axitinib in an amount corresponding to from about 480 μg to about 750 μg, or about 600 μg axitinib free base and releases at least 90% of the total released amount of axitinib over the initial 10 days in an in vitro test, and/or wherein the implant contains axitinib in an amount corresponding to from about 360 μg to about 562.5 μg, or about 450 μg axitinib free base and releases at least 92% of the total released amount of axitinib over the initial 10 days in an in vitro test, and/or wherein the implant contains axitinib in an amount corresponding to from about 240 μg to about 375 μg, or about 300 μg axitinib free base and releases at least 95% of the total released amount of axitinib over the initial 10 days in an in vitro test, and/or wherein the implant contains axitinib in an amount corresponding to from about 120 μg to about 187.5 μg, or about 150 μg axitinib free base and releases at least 98% of the total released amount of axitinib over the initial 10 days in an in vitro test;

wherein said in vitro test is performed at 37° C. in an 25%/75% (v/v) ethanol/water mixture under 2× sink conditions, 132. The sustained release biodegradable ocular implant of any of the preceding items, wherein the implant releases at least about 65 μg axitinib in the initial day, and/or at least about 120 μg over the initial 2 days in an in vitro test performed at 37° C. in an 25%/75% (v/v) ethanol/water mixture under 2× sink conditions.

133. The sustained release biodegradable ocular implant of any of items 1 to 132, containing axitinib corresponding to an amount of from about 480 μg to about 750 μg, or about 600 μg axitinib free base, and releasing at least about 75 μg, or at least about 90 μg, or at least about 100 μg axitinib over the initial day, and/or releasing at least about 125 μg, or at least about 150 μg, or at least about 140 μg axitinib over the initial 2 days, and/or releasing at least about 150 μg, or at least about 180 μg, or at least about 200 μg axitinib over the initial 3 days, and/or releasing at least about 275 μg, or at least about 300 μg, or at least about 375 μg axitinib over the initial 7 days, and/or releasing at least about 350 μg, or at least about 400 μg, or at least about 450 μg axitinib over the initial 10 days in an in vitro test, wherein said in vitro test is performed at 37° C. in an 25%/75% (v/v) ethanol/water mixture under 2× sink conditions.

134. The sustained release biodegradable ocular implant of any of items 1 to 132, containing axitinib corresponding to an amount of from about 360 μg to about 562.5 μg, or about 450 μg axitinib free base, and releasing at least about 60 μg, or at least about 70 μg, or at least about 80 μg axitinib over the initial day, and/or releasing at least about 100 μg, or at least about 120 μg, or at least about 130 μg axitinib over the initial 2 days, and/or releasing at least about 130 μg, or at least about 150 μg, or at least about 180 μg axitinib over the initial 3 days, and/or releasing at least about 220 μg, or at least about 260 μg, or at least about 290 μg axitinib over the initial 7 days, and/or releasing at least about 275 μg, or at least about 300 μg, or at least about 350 μg axitinib over the initial 10 days in an in vitro test, wherein said in vitro test is performed at 37° C. in an 25%/75% (v/v) ethanol/water mixture under 2× sink conditions, 135. The sustained release biodegradable ocular implant of any of items 1 to 132, containing axitinib corresponding to an amount of from about 240 μg to about 375 μg, or about 300 μg axitinib free base, and releasing at least about 60 μg, or at least about 65 μg, or at least about 70 μg axitinib over the initial day, and/or releasing at least about 90 μg, or at least about 110 μg, or at least about 130 μg axitinib over the initial 2 days, and/or releasing at least about 120 μg, or at least about 140 μg, or at least about 180 μg axitinib over the initial 3 days, and/or releasing at least about 200 μg, or at least about 240 μg, or at least about 270 μg axitinib over the initial 7 days, and/or releasing at least about 250 μg, or at least about 275 μg, or at least about 300 μg axitinib over the initial 10 days in an in vitro test, wherein said in vitro test is performed at 37° C. in an 25%/75% (v/v) ethanol/water mixture under 2× sink conditions.

136. The sustained release biodegradable ocular implant of any of items 1 to 132, containing axitinib corresponding to an amount of from about 120 μg to about 187.5 μg, or about 150 μg axitinib free base, and releasing at least about 75 μg, or at least about 85 μg, or at least about 90 μg, or at least about 100 μg axitinib over the initial day, and/or releasing at least about 90 μg, or at least about 100 μg, or at least about 115 μg axitinib over the initial 2 days in an in vitro test, wherein said in vitro test is performed at 37° C. in an 25%/75% (v/v) ethanol/water mixture under 2× sink conditions.

137. The sustained release biodegradable ocular implant of any of any of items 1 to 132, wherein the implant contains from about 240 μg to about 375 μg axitinib and releases at least about 90% of the total released amount of axitinib over the initial 7, or the initial 10 days in an in vitro test performed at 37° C. in an 25%/75% (v/v) ethanol/water mixture under 2× sink conditions, 138. The sustained release biodegradable ocular implant of any of any of items 1 to 132, wherein the implant contains from about 480 μg to about 750 μg axitinib and releases at least about 90% of the total released amount of axitinib over the initial 10 days, or the initial 14 days in an in vitro test performed at 37° C. in an 25%/75% (v/v) ethanol/water mixture under 2× sink conditions 139. The sustained release biodegradable ocular implant of any of any of items 1 to 132, wherein the implant contains from about 120 μg to about 187.5 μg axitinib and releases at least about 90% of the total released amount of axitinib over the initial 2, or the initial 3 days in an in vitro test performed at 37° C. in an 25%/75% (v/v) ethanol/water mixture under 2× sink conditions.

140. The sustained release biodegradable ocular implant of any of any of items 1 to 132, wherein the implant contains from about 360 μg to about 562.5 μg axitinib and releases at least about 90% of the total released amount of axitinib over the initial 8 days, or the initial 9 days in an in vitro test performed at 37° C. in an 25%/75% (v/v) ethanol/water mixture under 2× sink conditions, 141. The sustained release biodegradable ocular implant of any of items 125 to 140, wherein the 2× sink conditions in the in vitro test mean that the release of axitinib from an implant is performed by placing the implant in a volume of the 25%/75% (v/v) ethanol/water mixture at 37° C., wherein the volume is twice the volume determined by the ratio of the amount of axitinib contained in the implant [μg] divided by the solubility [μg/mL] of axitinib in the said solvent mixture.

142. The sustained release biodegradable ocular implant of item 141, wherein for the solubility of axitinib in the said solvent mixture a value of 18.3 μg/ml is used under 2× sink conditions.

143. The sustained release biodegradable ocular implant of any of the preceding items comprising axitinib, wherein the implant releases axitinib at an average rate of at least about 40 μg/day over the initial day and/or of at least about 35 μg/day over the initial 2 days and/or at least about 30 μg/day over the initial 4 days and/or at least about 25 μg/day over the initial 7 days in an in vitro test performed at 37° C. in an 25%/75% (v/v) ethanol/water mixture under 3× sink conditions.

144. The sustained release biodegradable ocular implant of any of the preceding items comprising axitinib, wherein the implant releases at least 25%, or at least 30%, or at least 34% of the total released amount of axitinib over the initial 4 days in an in vitro test performed at 37° C. in an 25%/75% (v/v) ethanol/water mixture under 3× sink conditions.

145. The sustained release biodegradable ocular implant of item 144, wherein the implant contains axitinib in an amount corresponding to from about 480 μg to about 750 μg, or about 600 μg axitinib free base and releases at least 30% of the total released amount of axitinib over the initial 4 days in an in vitro test, and/or wherein the implant contains axitinib in an amount corresponding to from about 360 μg to about 562.5 μg, or about 450 μg axitinib free base and releases at least 30% of the total released amount of axitinib over the initial 4 days in an in vitro test, and/or wherein the implant contains axitinib in an amount corresponding to from about 240 μg to about 375 μg, or about 300 μg axitinib free base and releases at least 30% of the total released amount of axitinib over the initial 4 days in an in vitro test, and/or wherein the implant contains axitinib in an amount corresponding from about 120 μg to about 187.5 μg, or about 150 μg axitinib free base and releases at least 60% of the total released amount of axitinib over the initial 4 days in an in vitro test;

wherein said in vitro test is performed at 37° C. in an 25%/75% (v/v) ethanol/water mixture under 3× sink conditions, 146. The sustained release biodegradable ocular implant of any of any of the preceding items, wherein the implant releases at least 40%, or at least 50% of the total released amount of axitinib over the initial 7 or the initial 9 days in an in vitro test performed at 37° C. in an 25%/75% (v/v) ethanol/water mixture under 3× sink conditions.

147. The sustained release biodegradable ocular implant of item 146, wherein the implant contains axitinib in an amount corresponding to from about 480 μg to about 750 μg, or about 600 μg axitinib free base and releases at least 50% of the total released amount of axitinib over the initial 7 or the initial 9 days in an in vitro test, and/or wherein the implant contains axitinib in an amount corresponding to from about 360 μg to about 562.5 μg, or about 450 μg axitinib free base and releases at least 50% of the total released amount of axitinib over the initial 7 or the initial 9 days in an in vitro test, and/or wherein the implant contains axitinib in an amount corresponding to from about 240 μg to about 375 μg, or about 300 μg axitinib free base and releases at least 50% of the total released amount of axitinib over the initial 7 or the initial 9 days in an in vitro test, and/or wherein the implant contains axitinib in an amount corresponding to from about 120 μg to about 187.5 μg, or about 150 μg axitinib free base and releases at least 90% of the total released amount of axitinib over the initial 7 or the initial 9 days in an in vitro test;

wherein said in vitro test is performed at 37° C. in an 25%/75% (v/v) ethanol/water mixture under 3× sink conditions.

148. The sustained release biodegradable ocular implant of any of any of the preceding items containing axitinib corresponding to an amount of from about 480 μg to about 750 μg, or about 600 μg axitinib free base, and releasing at least about 40 μg, or at least about 50 μg, or at least about 55 μg axitinib over the initial day, and/or releasing at least about 80 μg, or at least about 100 μg, or at least about 120 μg axitinib over the initial 2 days, and/or releasing at least about 160 μg, or at least about 190 μg, or at least about 200 μg axitinib over the initial 4 days, and/or releasing at least about 290 μg, or at least about 300 μg, or at least about 350 μg axitinib over the initial 7 days in an vitro test, releasing at least about 300 μg, or at least about 330 μg axitinib over the initial 9 days in an vitro test, wherein said in vitro test is performed at 37° C. in an 25%/75% (v/v) ethanol/water mixture under 3× sink conditions.

149. The sustained release biodegradable ocular implant of any of items 1 to 147, containing axitinib corresponding to an amount of from about 360 μg to about 562.5 μg, or about 450 μg axitinib free base, and releasing at least about 35 μg, or at least about 40 μg, or at least about 45 μg axitinib over the initial day, and/or releasing at least about 60 μg, or at least about 70 μg, or at least about 80 μg axitinib over the initial 2 days, and/or releasing at least about 100 μg, or at least about 120 μg, or at least about 150 μg axitinib over the initial 4 days, and/or releasing at least about 180 μg, or at least about 200 μg, or at least about 240 μg axitinib over the initial 7 days, and/or releasing at least about 200 μg, or at least about 250 μg, or at least about 270 μg axitinib over the initial 9 days in an in vitro test, wherein said in vitro test is performed at 37° C. in an 25%/75% (v/v) ethanol/water mixture under 3× sink conditions.

150. The sustained release biodegradable ocular implant of any of items 1 to 147, containing axitinib corresponding to an amount of from about 240 μg to about 375 μg, or about 300 μg axitinib free base, and releasing at least about 30 μg, or at least about 35 μg, or at least about 40 μg axitinib over the initial day, and/or releasing at least about 50 μg, or at least about 60 μg, or at least about 70 μg axitinib over the initial 2 days, and/or releasing at least about 80 μg, or at least about 100 μg, or at least about 120 μg axitinib over the initial 4 days, and/or releasing at least about 150 μg, or at least about 160 μg, or at least about 180 μg axitinib over the initial 7 days, and/or releasing at least about 160 μg, or at least about 180 μg, or at least about 200 μg axitinib over the initial 9 days in an in vitro test, wherein said in vitro test is performed at 37° C. in an 25%/75% (v/v) ethanol/water mixture under 3× sink conditions, 151. The sustained release biodegradable ocular implant of any of items 1 to 147, containing axitinib corresponding to an amount of from about 120 μg to about 187.5 pig, or about 150 μg axitinib free base, and releasing at least about 60 μg, or at least about 70 μg, or at least about 80 μg axitinib over the initial day, and/or releasing at least about 90 μg, or at least about 100 μg, or at least about 120 μg axitinib over the initial 2 days in an in vitro test, wherein said in vitro test is performed at 37° C. in an 25%/75% (v/v) ethanol/water mixture under 3× sink conditions.

152. The sustained release biodegradable ocular implant of any of any of items 1 to 147, wherein the implant contains about 240 μg to about 375 μg axitinib and releases at least about 85%, or at least about 90% of the total released amount of axitinib over the initial 14 days in an in vitro test performed at 37° C. in an 25%/75% (v/v) ethanol/water mixture under 3× sink conditions.
153. The sustained release biodegradable ocular implant of any of any of items 1 to 147, wherein the implant contains from about 480 μg to about 750 μg axitinib and releases at least about 90% of the total released amount of axitinib over the initial 16 days, or the initial 18 days in an in vitro test performed at 37° C. in an 25%/75% (v/v) ethanol/water mixture under 3× sink conditions
154. The sustained release biodegradable ocular implant of any of any of items 1 to 147, wherein the implant contains about 120 μg to about 187.5 μg axitinib and releases at least about 90% of the total released amount of axitinib over the Initial 7 days in an in vitro test performed at 37° C. in an 25%/75% (v/v) ethanol/water mixture under 3× sink conditions.
155. The sustained release biodegradable ocular implant of any of any of items 1 to 147, wherein the implant contains from about 360 μg to about 562.5 μg axitinib and releases at least about 90% of the total released amount of axitinib over the initial 14 to 16 days in an in vitro test performed at 37° C. in an 25%/75% (v/v) ethanol/water mixture under 3× sink conditions.
156. The sustained release biodegradable ocular implant of any of items 143 to 155, wherein the 3× sink conditions in the in vitro test mean that the release of axitinib from an implant is performed by placing the implant in a volume of the 25%/75% (v/v) ethanol/water mixture at 37° C., wherein the volume is three times the volume determined by the ratio of the amount of axitinib contained in the implant [μg] divided by the solubility [μg/mL] of axitinib in the said solvent mixture.
157. The sustained release biodegradable ocular implant of item 156, wherein for the solubility of axitinib polymorph SAB-I in the said solvent mixture a value of 13.41 μg/mL is used in 3× sink conditions, and for the solubility of axitinib polymorph IV in the said solvent mixture a value of 20.09 μg/ml is used under 3× sink conditions.
158. The sustained release biodegradable ocular implant of any of the preceding items, wherein the implant is obtainable by extrusion, such as by hot melt extrusion.
159. The sustained release biodegradable ocular implant of any of the preceding items obtainable by hot melt extrusion, wherein the hot melt extrusion comprises extruding a composition comprising polymer precursors and the TKI, and optionally curing the extruded composition,
160. The sustained release biodegradable ocular implant of item 159 obtainable by hot melt extrusion, wherein the curing comprises exposing the extruded composition to humidity and/or elevated temperature.
161. The sustained release biodegradable ocular implant of item 160 obtainable by hot melt extrusion, wherein the curing is performed for a period of at least 0.5 hours, such as at least 1 hour, or at least 2 hours, at a temperature that is higher than ambient temperature, such as a temperature from about 25 to about 50° C., or from about 30 to about 40° C., and at least 50% relative humidity (RH), or at least 60% RH, or at least 80%, or at least 90% RH, or at 98% RH.
162. The sustained release biodegradable ocular implant of any of items 1 to 157, wherein the implant is obtainable by wet casting or injection molding.
163. The sustained release biodegradable ocular implant of any of the preceding items, wherein the implant is for administration into the posterior section of the eye, such as to the vitreous humor.
164. The sustained release biodegradable ocular implant of any of the preceding items, wherein the implant is an intravitreal implant.
165. The sustained release biodegradable ocular implant of any of the preceding items, wherein the implant provides for the release of a therapeutically effective amount TKI for a period of at least 3 months after administration, or a period of at least 6 months after administration, or a period of at least 9 months after administration, or a period of at least 12 months after administration, or a period of about 3 to about 12 months after administration, or a period of about 6 months to about 12 months after administration, or a period of about 4 months to about 10 months after administration, or a period of about 6 to about 9 months after administration.
166. The sustained release biodegradable ocular implant of any of the preceding items, wherein the hydrogel biodegrades within about 2 to about 15 months, preferably within about 4 to about 13 months, or within about 6 to about 9 months, or within about 7.5 months after administration.
167. The sustained release biodegradable ocular implant of any of the preceding items, wherein the time to full degradation of the hydrogel is longer, essentially equal to or is shorter than the time to complete release of the TKI from the implant (in vitro or in vivo).
168. The sustained release biodegradable ocular implant of any of the preceding items, wherein the ratio of the time to full degradation of the hydrogel to the time to complete release of the TKI is less than about 2.0, or less than about 1.5.
169. The sustained release biodegradable ocular implant of any of the preceding items, wherein the ratio of the time to full degradation of the hydrogel to the time to complete release of the TKI is from about 0.5 to about 1.5, or from about 0.75 to about 1.25.
170. The sustained release biodegradable ocular implant of any of the preceding items, wherein essentially the entire amount of TKI contained in the implant has been released by the time the hydrogel has completely degraded (in vivo and/or in vitro).
171. The sustained release biodegradable ocular implant of any of the preceding items, wherein the amount of TKI remaining after complete degradation of the hydrogel (In vitro and/or in vivo) is less than about 80%, such as less than about 70%, or less than about 50%, or less than about 25% of the initial TKI content of the implant, or less than about 20%, or less than about 15%, or less than about 10% of the initial TKI content of the implant,
172. The sustained release biodegradable ocular implant of any of the preceding items, wherein the implant provides for an average in vivo release rate in the vitreous of at least 0.5 μg/day, such as at least 0.6 μg/day, or at least 0.7 μg/day, or at least 0.8 μg/day for a period of at least 3 months.
173. The sustained release biodegradable ocular implant of item 172, wherein the in vivo release is in the vitreous of a non-human primate, such as a monkey.

174. The sustained release biodegradable ocular implant of item 172, wherein the in vivo release is in the vitreous of a human.

175. A sustained release biodegradable ocular implant comprising a hydrogel and axitinib, wherein axitinib particles are dispersed within the hydrogel, wherein the implant comprises axitinib polymorph IV and the implant contains axitinib in an amount corresponding to about 200 to about 1000 μg, 250 to about 700 μg axitinib free base, wherein the hydrogel comprises crosslinked PEG units.

176. The sustained release biodegradable ocular implant of item 175, containing axitinib polymorph IV in an amount of from about 300 to about 650 μg, such as from about 360 μg to about 562.5 μg, such as from about 360 μg to about 562.5 μg, such as from about 400 to about 500 μg, particularly about 450 μg.

177. The sustained release biodegradable ocular implant of item 175, containing axitinib polymorph IV in an amount of from about 480 μg to about 750 μg, such as from about 500 to about 700 μg, particularly about 600 μg.

178. The sustained release biodegradable ocular implant of any of items 175 to 177, wherein the implant is cylindrical and in its dried state has a length of from 5 to 12 mm and a diameter of from 0.20 to 0.70 mm, such as a length of from 5 to 11 mm and a diameter from 0.20 to 0.52 mm, such as a length of from 6 to 9 mm and a diameter of from 0.25 to 0.45 mm.

179. The sustained release biodegradable ocular implant of any of item 178, wherein the implant is cylindrical and in its dried state has a length of from 6.7 to 7.8 mm and a diameter of from 0.30 to 0.40 mm.

180. The sustained release biodegradable ocular implant any of items 175 to 179, wherein the implant is cylindrical and in its hydrated state (after 24 hours in PBS at a pH of 7.2 to 7.4 at 37° C.) has a length of from 6 to 11 mm, or from 7 to 10 mm and a diameter of from 0.5 to 0.9 mm.

181. The sustained release biodegradable ocular implant of item 180, wherein the implant is cylindrical and in its hydrated state (after 24 hours in PBS at a pH of 7.2 to 7.4 at 37° C.) has a length of from 8 to 9 mm and a diameter of from 0.70 to 0.80 mm.

182. The sustained release biodegradable ocular implant of any of items 175 to 181, having a hydrated surface area of at least 10 $mm^2$, such as at least 16 $mm^2$, such as at least 18 $mm^2$.

183. The sustained release biodegradable ocular implant of any of items 175 to 182, wherein the crosslinks between the PEG units include a group represented by the following formula

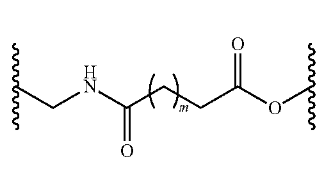

wherein m is an integer from 0 to 10, such as m being 1, 2, 3, or 6, particularly m being 6.

184. The sustained release biodegradable ocular implant of any of items 175 to 183, wherein the axitinib particles have a d90 particle size of less than 10 μm, such as less than 8 μm, and/or a d50 particle size of less than 3 μm, and/or a d10 particles size of less than 0.5 μm as determined by means of laser diffraction.

185. The sustained release biodegradable ocular implant of any of Items 175 to 184, wherein the hydrogel biodegrades within about 5 to about 15 months, such as within about 6 to about 12 months, such as within 8 to 11 months after administration to a human eye, or within about 6 to about 9 months, or within about 7.5 months after administration to a human eye.

186. The sustained release biodegradable ocular implant of any of items 175 to 185, wherein the implant releases at least about 30%, or at least about 50% of the total released amount of axitinib over the initial 3 days and/or at least about 60%, or at least about 80% of the total released amount of axitinib over the initial 7 days and/or at least about 80%, or at least about 92% of the total released amount of axitinib over the initial 10 days in an in vitro test performed at 37° C. in an 25%/75% (v/v) ethanol/water mixture under 2× sink conditions.

187. The sustained release biodegradable ocular implant of any of items 175 to 186, wherein the implant releases at least about 30% of the total released amount of axitinib over the initial 4 days and/or at least about 50% of the total released amount of axitinib over the initial 7 days or the initial 9 days in an in vitro test performed at 37° C. in an 25%/75% (v/v) ethanol/water mixture under 3× sink conditions.

188. The sustained release biodegradable ocular implant of any of items 175 to 187, wherein the implant releases at least about 60 μg, or at least about 70 μg, or at least about 80 μg axitinib over the initial day, and/or at least about 100 μg, or at least about 120 μg, or at least about 130 μg axitinib over the initial 2 days, and/or at least about 130 μg, or at least about 150 μg, or at least about 180 μg axitinib over the initial 3 days, and/or at least about 220 μg, or at least about 260 μg, or at least about 290 μg axitinib over the initial 7 days, and/or at least about 275 μg, or at least about 300 μg, or at least about 350 μg axitinib over the initial 10 days in an in vitro test performed at 37° C. in an 25%/75% (v/v) ethanol/water mixture under 2× sink conditions.

189. The sustained release biodegradable ocular implant of any of items 175 to 188, wherein the implant releases at least about 45 μg, or at least about 50 μg, or at least about 55 μg axitinib over the initial day, and/or at least about 80 μg, or at least about 100 μg, or at least about 120 μg axitinib over the initial 2 days, and/or at least about 150 μg, or at least about 160 μg, or at least about 190 μg axitinib over the initial 4 days, and/or at least about 240 μg, or at least about 290 μg, or at least about 300 μg axitinib over the initial 7 days, and/or at least about 270 μg, or at least about 300 μg, or at least about 330 μg axitinib over the initial 9 days in an in vitro test performed at 37° C. in an 25%/75% (v/v) ethanol/water mixture under 3× sink conditions.

190. A sustained release biodegradable ocular implant comprising a hydrogel and axitinib, wherein axitinib particles are dispersed within the hydrogel, wherein the implant comprises axitinib polymorph IV in an amount of from about 360 μg to about 800 μg, from about 360 μg to about 562.5 μg, or from about 405 μg to about 495 μg, such as about 450 μg, wherein the hydrogel comprises crosslinked multi-armed PEG units having a number average molecular weight of from about 10,000 to about 40,000 Daltons (such as about 20,000

Daltons), wherein the crosslinks between the PEG units include a group represented by the following formula

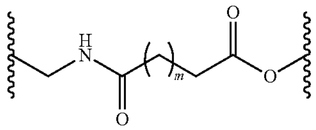

wherein m is 6, wherein the implant is cylindrical and in its dried state has a length of 10 mm or less, such as from 6 to 9 mm and a diameter of from 0.25 to 0.45 mm and/or in its hydrated state (after 24 hours in PBS at a pH of 7.2 to 7.4 at 37° C.) has a length of 10 mm or less, such as from 8 to 9 mm and a diameter of from 0.5 to 0.9 mm, and wherein the axitinib particles have a d90 particle size of less than 10 μm, such as less than 8 μm and/or a d50 particle size of less than 3 μm, 191. A sustained release biodegradable ocular implant comprising a hydrogel and axitinib, wherein axitinib particles are dispersed within the hydrogel, wherein the implant comprises axitinib polymorph IV in an amount of from about 480 μg to about 750 μg, or from about 540 μg to about 660 μg, such as about 600 μg, wherein the hydrogel comprises crosslinked multi-armed PEG units having a number average molecular weight of from about 10,000 to about 40,000 Daltons (such as about 20,000 Daltons), wherein the crosslinks between the PEG units include a group represented by the following formula

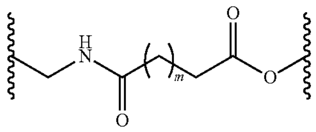

wherein m is 6, wherein the implant is cylindrical and in its dried state has a length of 10 mm or less, such as from 6 to 9 mm and a diameter of from 0.25 to 0.45 mm and/or in its hydrated state (after 24 hours in PBS at a pH of 7.2 to 7.4 at 37° C.) has a length of 10 mm or less, such as from 8 to 9 mm and a diameter of from 0.5 to 0.9 mm, and wherein the axitinib particles have a d90 particle size of less than 10 μm, such as less than 8 μm and/or a d50 particle size of less than 3 μm.

192. A sustained release biodegradable ocular implant comprising a hydrogel and axitinib, wherein axitinib particles are dispersed within the hydrogel, wherein the implant comprises axitinib polymorph IV and the implant contains axitinib in an amount corresponding to from about 360 μg to about 562.5 μg, or from about 405 μg to about 495 μg, such as about 450 μg axitinib free base, and releases at least about 60 μg axitinib over the initial day, and/or at least about 100 μg axitinib over the initial 2 days, and/or at least about 130 μg axitinib over the initial 3 days, and/or at least about 220 μg axitinib over the initial 7 days and/or at least about 275 μg axitinib over the initial 10 days in an in vitro test performed at 37° C. in an 25%/75% (v/v) ethanol/water mixture under 2× sink conditions.

193. A sustained release biodegradable ocular implant comprising a hydrogel and axitinib, wherein axitinib particles are dispersed within the hydrogel, wherein the implant comprises axitinib polymorph IV and the implant contains axitinib in an amount corresponding to from about 360 μg to about 562.5 μg, or from about 405 μg to about 495 μg, such as about 450 μg axitinib free base, and releases at least about 35 μg axitinib over the initial day, and/or at least about 60 μg axitinib over the initial 2 days, and/or at least about 100 μg axitinib over the initial 4 days, and/or at least about 180 μg axitinib over the initial 7 days and/or at least about 200 μg axitinib over the initial 9 days in an in vitro test performed at 37° C. in an 25%/75% (v/v) ethanol/water mixture under 3× sink conditions.

194. A sustained release biodegradable ocular implant comprising a hydrogel and axitinib, wherein axitinib particles are dispersed within the hydrogel, wherein the implant comprises axitinib polymorph IV and the implant contains axitinib in an amount corresponding to from about 480 μg to about 750 μg, or from about 540 μg to about 660 μg, such as about 600 μg axitinib free base, and releases at least about 70 μg axitinib over the initial day, and/or at least about 130 μg axitinib over the initial 2 days, and/or at least about 180 μg axitinib over the initial 3 days, and/or at least about 300 μg axitinib over the initial 7 days and/or at least about 375 μg axitinib over the initial 10 days in an in vitro test performed at 37° C. in an 25%/75% (v/v) ethanol/water mixture under 2× sink conditions.

195. A sustained release biodegradable ocular implant comprising a hydrogel and axitinib, wherein axitinib particles are dispersed within the hydrogel, wherein the implant comprises axitinib polymorph IV and the implant contains axitinib in an amount corresponding to from about 480 μg to about 750 μg, or from about 540 μg to about 660 μg, such as about 600 μg axitinib free base, and releases at least about 50 μg axitinib over the initial day, and/or at least about 100 μg axitinib over the initial 2 days, and/or at least about 180 μg axitinib over the initial 4 days, and/or at least about 280 μg axitinib over the initial 7 days and/or at least about 300 μg axitinib over the initial 9 days in an in vitro test performed at 37° C. in an 25%/75% (v/v) ethanol/water mixture under 3× sink conditions, 196. A sustained release biodegradable ocular implant comprising a hydrogel and axitinib, wherein axitinib particles are dispersed within the hydrogel, wherein the implant comprises axitinib polymorph IV and the implant contains axitinib in an amount corresponding to from about 360 μg to about 562.5 μg, or from about 405 μg to about 495 μg, such as about 450 μg axitinib free base, and releases at least 50% of the total released amount of axitinib over the initial 3 days in an in vitro test, and/or releases at least 80% of the total released amount of axitinib over the initial 7 days in an in vitro test, and/or releases at least 92% of the total released amount of axitinib over the initial 10 days in an in vitro test performed at 37° C. in an 25%/75% (v/v) ethanol/water mixture under 2× sink conditions.

197. A sustained release biodegradable ocular implant comprising a hydrogel and axitinib, wherein axitinib particles are dispersed within the hydrogel, wherein the implant comprises axitinib polymorph IV and the implant contains axitinib in an amount corresponding to from about 360 μg to about 562.5 μg, or from about 405 μg to about 495 μg, such as about 450 μg axitinib free base, and releases at least 15% of the total released amount of axitinib over the initial 2 days in an in vitro test, and/or releases at least 30% of the total released amount of axitinib over the initial 4 days in an in vitro test, and/or releases at least 50% of the total released amount of axitinib over the initial 7 days in an in vitro test, wherein the in vitro test is performed at 37° C. in an 25%/75% (v/v) ethanol/water mixture under 3× sink conditions.

198. A sustained release biodegradable ocular implant comprising a hydrogel and axitinib, wherein axitinib particles are dispersed within the hydrogel, wherein the implant comprises axitinib polymorph IV and the implant contains axitinib in an amount corresponding to from about 480 μg to about 750 μg, or from about 540 μg to about 660 μg, such as about 600 μg axitinib free base, and releases at least 30% or at least 50% of the total released amount of axitinib over the initial 3 days in an in vitro test, and/or releases at least 60% or at least 80% of the total released amount of axitinib over the initial 7 days in an in vitro test, and/or releases at least 92% of the total released amount of axitinib over the initial 10 days in an in vitro test performed at 37° C. in an 25%/75% (v/v) ethanol/water mixture under 2× sink conditions.

199. A sustained release biodegradable ocular implant comprising a hydrogel and axitinib, wherein axitinib particles are dispersed within the hydrogel, wherein the implant comprises axitinib polymorph IV and the implant contains axitinib in an amount corresponding to from about 480 μg to about 750 μg, or from about 540 μg to about 660 μg, such as about 600 μg axitinib free base, and releases at least 15% or at least 20% of the total released amount of axitinib over the initial 2 days in an in vitro test, and/or releases at least 35% of the total released amount of axitinib over the initial 4 days in an in vitro test, and/or releases at least 55% of the total released amount of axitinib over the initial 7 days in an in vitro test, wherein the in vitro test is performed at 37° C. in an 25%/75% (v/v) ethanol/water mixture under 3× sink conditions.

200. A method of treating an ocular disease in a patient in need thereof, the method comprising administering to the patient's eye a sustained release biodegradable ocular implant according to any of the preceding items.

201. The method of item 200, wherein the implant is administered by injection into the anterior or posterior section of the eye.

202. The method of item 200, wherein the administration is suprachoroidal administration.

203. The method of item 200 or 201, wherein the administration is intravitreal injection.

204. The method of any of items 200 to 203, wherein the ocular disease involves angiogenesis.

205. The method of any of items 200 to 204, wherein the ocular disease is mediated by one or more receptor tyrosine kinases (RTKs), specifically VEGFR-1, VEGFR-2, VEGFR-3, PDGFR-α/β, and/or c-Kit.

206. The method of any of items 200 to 205, wherein the ocular disease is a retinal disease including age-related macular degeneration (AMD), Choroidal Neovascularization, Diabetic Retinopathy, Diabetic Macular Edema, Retinal Vein Occlusion, Acute Macular Neuroretinopathy, Central Serous Chorioretinopathy, and Cystoid Macular Edema; wherein the ocular disease is Acute Multifocal Placoid Pigment Epitheliopathy, Behcet's Disease, Birdshot Retinochoroidopathy, Infectious (Syphilis, Lyme, Tuberculosis, Toxoplasmosis), Intermediate Uveitis (Pars Planitis), Multifocal Choroiditis, Multiple Evanescent White Dot Syndrome (MEWDS), Ocular Sarcoidosis, Posterior Scleritis, Serpignous Choroiditis, Subretinal Fibrosis, Uveitis Syndrome, or Vogt-Koyanagi-Harada Syndrome; wherein the ocular disease is a vascular disease or exudative diseases, including Coat's Disease, Parafoveal Telangiectasis, Papillophlebitis, Frosted Branch Angitis, Sickle Cell Retinopathy and other Hemoglobinopathies, Angioid Streaks, and Familial Exudative Vitreoretinopathy; or wherein the ocular disease results from trauma or surgery, Including Sympathetic Ophthalmia, Uveitic Retinal Disease, Retinal Detachment, Trauma, Photodynamic Laser Treatment, Photocoagulation, Hypoperfusion During Surgery, Radiation Retinopathy, or Bone Marrow Transplant Retinopathy.

207. The method of any of items 200 to 206, wherein the ocular disease is neovascular age-related macular degeneration, diabetic macular edema, diabetic retinopathy or retinal vein occlusion, 208. The method of item 203, wherein the disease is neovascular (wet) age-related macular degeneration (AMD), 209. The method of item 203, wherein the disease is diabetic retinopathy (DR).

210. The method of item 203, wherein the disease is diabetic macular edema (DMA).

211. The method of any of items 200 to 210, wherein the treatment is effective in inhibiting or slowing down angiogenesis and/or neovascularization at the site of administration.

212. The method of any of items 200 to 211, wherein the treatment is effective in reducing, essentially maintaining the central subfield thickness (CSFT) or preventing a clinically significant increase of the CSFT as measured by optical coherence tomography in a patient whose central subfield thickness is elevated.

213. The method of any of items 200 to 212, wherein the treatment period with one implant lasts at least about 3 months, at least about 4.5 months, at least about 6 months, at least about 9 months, at least about 11 months, at least about 12 months, at least about 13 months, or at least about 14 months:

214. The method of item 213, wherein the treatment period with one implant lasts about 3 to about 12 months after administration, or about 4 months to about 10 months after administration, or about 6 to about 9 months after administration.

215. The method of any of items 200 to 214, wherein concurrently with the sustained release ocular implant an anti-VEGF agent is administered to the patient.

216. The method of item 215, wherein an anti-VEGF agent is administered within about 1, about 2 or about 3 months prior to or after the administration of the implant.

217. The method of item 215 or item 216, wherein the anti-VEGF agent is selected from the group consisting of aflibercept, bevacizumab, pegaptanib, ranibizumab, faricimab, and brolucizumab.

218. The method of item 215 or item 216, wherein the anti-VEGF agent is bevacizumab.

219. The method of item 215 or item 216, wherein the anti-VEGF agent is aflibercept.

220. The method of any of items 215 to 219, wherein the anti-VEGF agent is administered by means of intravitreal injection.

221. The method of any of items 200 to 220, wherein the patient receiving the implant has a history of an anti-VEGF treatment.
222. The method of any of items 200 to 220, wherein the patient receiving the implant has no history of an anti-VEGF treatment (i.e., is anti-VEGF naïve) and/or no history of an AMD treatment.
223. The method of any of any of items 200 to 222, wherein upon or after completion of one treatment period a new implant according to any of items 1 to 199 is administered to the patient,
224. The method of item 223, wherein a new implant is administered about 6 months, or about 9 months, or about 12 months after administration of the preceding implant.
225. A sustained release biodegradable ocular implant according to any of items 1 to 199, for use in a method according to any of items 200 to 224.
226. Use of a sustained release biodegradable ocular implant according to any of items 1 to 199, for the preparation of a medicament for use in a method according to any of items 200 to 224.
227. A method of manufacturing the sustained release biodegradable ocular implant according to any of items 1 to 199, the method comprising the steps of forming a hydrogel comprising a polymer network and TKI particles dispersed within the hydrogel, shaping the hydrogel and drying the hydrogel.
228. The method of item 227, wherein the polymer network is formed by mixing and reacting an electrophilic group-containing multi-arm polymer (such as PEG) precursor with a nucleophilic group-containing multi-arm polymer (such as PEG) precursor or another nucleophilic group-containing crosslinking agent in a buffered solution in the presence of TKI particles, and allowing the mixture to gel to form the hydrogel.
229. The method of item 227 or 228, comprising shaping the hydrogel by means of casting the mixture into a tube or mould prior to complete gelling of the hydrogel.
230. The method of any of items 227 to 229, comprising casting the mixture into a tube to form a hydrogel strand prior to complete gelling of the hydrogel, drying the hydrogel strand and cutting the strand.
231. A method of manufacturing the sustained release biodegradable ocular implant according to any of items 1 to 199, the method comprising melt extruding, reactive extrusion, 3D printing or injection molding a composition comprising polymer or polymer (such as PEG) precursor and TKI to form the implant.
232. The method of item 231, comprising feeding the polymer or polymer precursor and the TKI into an extruder, forming the composition comprising the polymer or polymer precursor and axitinib in the extruder, and extruding a strand of the composition,
233. The method of item 232, wherein the polymer or polymer precursor and the TKI are fed to the extruder separately, or are pre-mixed prior to being fed to the extruder.
234. The method of any of items 231 to 233, wherein the extrusion is performed at a temperature from about 57° C. to about 200° C., or from about 65° C. to about 150° C., or from about 70° C. to about 90° C.
235. The method of any of items 231 to 234, wherein the extrusion is performed in a solvent.
236. The method of item 235, wherein the solvent is present in less than about 30% by weight (w/w), or 10% by weight (w/w), and the solvent is either an aqueous solvent (such as water) or a non-aqueous solvent (such as a natural or synthetic oil).
237. The method of any of items 231 to 234, wherein the extrusion is performed in the absence of a solvent.
238. The method of item 237, wherein the extrusion is performed in the absence of water.
239. The method of any of items 231 to 238, further comprising the steps of cooling the strand, curing the strand, stretching the strand, and/or drying the strand.
240. The method of item 238 or 239, wherein the extrusion is performed in the absence of water, and the curing comprises exposing the extruded composition to moisture and/or elevated temperature.
241. The method of item 240, wherein the nucleophilic cross-linking agent is a nucleophilic group containing salt, such as an amine or multi-amine salt, and the polymer network forms by means of crosslinking of the polymer precursors during curing in a moist atmosphere.
242. The method of any of items 239 to 241, wherein the curing is performed for a period of at least 0.5 hours, or at least 1 hour, or at least 2 hours.
243. The method of any of items 239 to 242, wherein the curing is performed at a temperature that is higher than ambient temperature, such as a temperature from about 25 to about 50° C., or from about 30 to about 40° C.
244. The method of any of items 239 to 243, wherein the curing is performed in an atmosphere of at least 50% relative humidity (RH), or at least 60% RH, or at least 80%, or at least 90% RH, or at 98% RH.
245. The method of any of items 227 to 244, further comprising stretching the hydrogel strand in the longitudinal direction prior to or after drying the hydrogel (wet stretching or dry stretching).
246. The method of item 245, wherein the stretch factor is in the range of about 1 to about 10, or about 1 to about 6, or about 1 to about 4.5, or about 1.3 to about 3.5.
247. The method of any of Items 227 to 246, wherein the strand is cut into implants of the desired length, the implants are dried and packaged, such as individually packaged, e.g. into foil pouches.
248. The method of any of items 227 to 247, wherein the implants are sterilized, such as by gamma radiation.
249. The method of any of items 227 to 248, wherein the method is performed under conditions of essentially no or only little UV/visual light exposure.
250. The method of manufacturing the sustained release biodegradable ocular implant according to any of items 227 to 248, the method comprising combining at least 2 filaments, and heating, stretching and twisting them to form one twisted composite strand.
251. The method of manufacturing the sustained release biodegradable ocular implant according to item 250, comprising combining at least 3 or at least 4 filaments, and/or up to 20, or up to 15 filaments.
252. The method of manufacturing the sustained release biodegradable ocular implant according to item 251, comprising combining from 2 to 8, or from 3 to 7 filaments.
253. The method of manufacturing the sustained release biodegradable ocular implant according to any of items 250 to 252, wherein the number of twists per cm is at least about 1 or at least about 2, or a at least about 5, or is at least about 8, or is at least about 10 and/or is up to about 20, or up to about 15.

254. The method of manufacturing the sustained release biodegradable ocular implant according to any of items 250 to 253, wherein the composite diameter of the twisted composite strand in its dried state is from 0.2 to 0.5 mm, such as from 0.3 to 0.4 mm, or from 0.33 to 0.38 mm.
255. The method of manufacturing the sustained release biodegradable ocular implant according to item 254, wherein the diameter of the individual filaments in the dried state is less than 0.3 mm, or less than 0.25 mm, or less than 0.2 mm, or less than 0.15 mm.
256. A kit comprising one or more sustained release biodegradable ocular implant(s) of any of items 1 to 199 and one or more needles for injection, wherein each implant is loaded in a needle.
257. The kit of item 256, wherein the needle is a hypodermic needle.
258. The kit of item 256 or 257, wherein the needle is suitable for injection into the eye.
259. The kit of item 258, wherein the needle is suitable for injection into the vitreous humor.
260. The kit of any of items 256 to 259, wherein the needle(s) have a gauge size of from 20 to 30, or from 25 to 27,
261. The kit of any of Items 256 to 260, wherein the lumen of each needle is occluded by a material that is solid at room temperature and soft or liquid at body temperature.
262. The kit of any of items 256 to 261, further comprising one or more injection device(s), wherein each needle is pre-connected or is not pre-connected to an injection device.
263. A method of increasing the release rate and/or the average release rate and/or the released amount of total TKI contained in an ocular implant and/or the released share of the total TKI contained in the implant or the total TKI released from an implant in a certain period of time.
264. The method of item 263, comprising increasing the solubility of the TKI contained in the implant and/or increasing the hydrated surface area of the implant.
265. A method of treating an ocular disease in a patient in need thereof, wherein the treatment comprises injection of a sustained release biodegradable ocular implant into the vitreous humor of an eye of the patient in need of treatment, wherein the implant comprises a hydrogel and TKI (such as axitinib) particles dispersed within the hydrogel, and wherein the implant releases TKI into the vitreous, wherein the cumulative amount of TKI released prior to the biodegradation of the hydrogel is higher than the amount of TKI being terminally released upon biodegradation.
266. The method of item 265, wherein the TKI is axitinib, and the amount of axitinib being released upon biodegradation of the hydrogel is less than about 200 μg, such as less than about 150 μg, such as about 130 μg or less, or about 100 μg or less, or the terminal amount of axitinib being released upon final biodegradation of the hydrogel is from about 50 to about 200 μg, such as from about 100 to about 170 μg, such as from about 110 to about 150 μg.
267. The method of item 265 or 266, wherein the maximum TKI concentration in ocular tissue ($C_{max}$) reached prior to the biodegradation of the hydrogel is within +/−50%, such as within +/−30% of the concentration of TKI delivered to that ocular tissue upon biodegradation.
268. The method of any of items 265 to 267, wherein the $t_{max}$ of TKI in an ocular tissue is earlier than about 6 months, such as earlier than about 5 months, such as earlier than about 4 months, such as at about 3 months, or earlier than about 3 months, such as earlier than about 2 months after injection of the implant into the eye of a non-human primate, such as a monkey, such as a *Cynomolgus* monkey.
269. The method of any of items 265 to 267, wherein the $t_{max}$ of TKI in an ocular tissue is earlier than about 6 months, such as at about 5.5 months or earlier, or earlier than about 5 months, such as earlier than about 4 months, such as at about 3 months or earlier than about 3 months, such as earlier than about 2 months, such as earlier than about 1 month after injection of the implant into the eye of a rodent, such as a rabbit, such as a Dutch Belted rabbit.
270. The method of any of items 265 to 267, wherein the $t_{max}$ of TKI in an ocular tissue is earlier than about 9 months, such as earlier than about 8 months, such as earlier than about 7 months, such as earlier than about 6 months, such as earlier than about 5 months, such as earlier than about 4 months after injection into the eye of a human patient.
271. The method of any of items 265 to 270, wherein the implant contains axitinib polymorph IV in an amount of from about 300 to about 650 μg, such as from about 360 μg to about 562.5 μg, such as from about 380 to about 520 μg axitinib, such as from about 400 to about 500 μg axitinib, such as from about 420 to about 480 μg axitinib, such as about 450 μg axitinib, wherein the axitinib polymorph IV is present in the implant as particles dispersed in a hydrogel (such as a PEG hydrogel), wherein the particles are optionally micronized.
272. A method of treating an ocular disease in a patient in need thereof, wherein the treatment comprises injection of a sustained release biodegradable ocular implant into the vitreous humor of an eye of the patient in need of treatment, wherein the implant comprises a hydrogel and TKI (such as axitinib) particles dispersed within the hydrogel, and wherein the implant delivers a concentration of the TKI to an ocular tissue,
    wherein the $t_{mix}$ of TKI in that tissue is earlier than the $t_{max}$ achieved with a comparative implant and/or wherein the maximum concentration of TKI delivered to that tissue prior to final biodegradation of the hydrogel is higher than the maximum concentration of TKI delivered by a comparative implant,
    wherein the comparative implant contains the TKI in a total amount of within +/−10%, such as within +/−5% of the total amount of the TKI contained in the sustained release biodegradable ocular implant and differs from the sustained release biodegradable ocular implant in that (such as only in that) the comparative implant contains the TKI in a form that has a lower solubility as measured in PBS at a pH of 7.2 to 7.4 and 37° C. after five days of incubation than the form of the TKI contained in the sustained release biodegradable ocular implant, and wherein the comparative implant has a surface area of within +/−20%, such as within +/−10% of the surface area of the sustained release biodegradable ocular implant.
273. The method of item 272, wherein the sustained release biodegradable ocular implant contains a different polymorphic form of the same TKI from the polymorphic form of the TKI contained in the comparative implant.

274. The method of item 272 or 273, wherein the comparative implant contains a form of axitinib having a solubility of below 0.3 μg/mL as measured in PBS at a pH of 7.2 to 7.4 and 37° C. after five days of incubation, and the sustained release biodegradable ocular implant contains a form of axitinib having a solubility of at least 0.3 μg/mL, such as at least 0.4 μg/mL as measured in PBS at a pH of 7.2 to 7.4 and 37° C. after five days of incubation.

275. The method of any of items 272 to 274, wherein the sustained release biodegradable ocular implant contains axitinib polymorph IV, and the comparative implant contains axitinib polymorph SAB-I.

276. The method of any of items 272 to 275, wherein the $t_{max}$ of the TKI provided by the sustained release biodegradable ocular implant in the retina and/or choroid is at least about 1 month earlier, such as at least about 2 months earlier than $t_{max}$ of the TKI in the retina and/or choroid provided by the comparative implant.

277. A method of treating an ocular disease in a patient in need thereof, wherein the treatment comprises injection of a sustained release biodegradable ocular implant into the vitreous humor of an eye of the patient in need of treatment, wherein the implant comprises a hydrogel and TKI (such as axitinib) particles dispersed within the hydrogel, and wherein the implant provides for substantially zero-order release of the TKI for at least one month, such as at least two months, such as at least three months, such as at least four months, such as at least five months.

278. A method of treating an ocular disease in a patient in need thereof, wherein the treatment comprises injection of a sustained release biodegradable ocular implant into the vitreous humor of an eye of the patient in need of treatment, wherein the implant comprises a hydrogel and TKI (such as axitinib) particles dispersed within the hydrogel, and wherein the amount of a terminal release of the TKI upon biodegradation of the hydrogel is not higher or not substantially higher than the cumulative amount of TKI released by the implant prior to biodegradation when the implant is still intact.

279. A method of treating an ocular disease in a patient in need thereof, wherein the treatment comprises injection of a sustained release biodegradable ocular implant into the vitreous humor of an eye of the patient in need of treatment, wherein the implant comprises a hydrogel and TKI (such as axitinib) particles dispersed within the hydrogel, and wherein the concentration of TKI in an ocular tissue provided in a terminal release upon biodegradation of the hydrogel is not higher, or not substantially higher, such as no more than about 25% higher, such as no more than about 10% higher, than the maximum concentration of TKI in the ocular tissue provided by the implant at any time after injection and prior to biodegradation when the implant is still intact.

280. The method of the preceding item 279, wherein an increase of the concentration of TKI in the ocular tissue provided by a terminal release of TKI upon biodegradation of the hydrogel is no more than about 110%, such as no more than about 100%, such as no more than about 80%, such as no more than about 30%, such as no more than about 20%, such as not more than about 10% of the maximum concentration of TKI in that ocular tissue reached at any time prior to said terminal release.

281. A method of treating an ocular disease in a patient in need thereof, wherein the treatment comprises injection of a sustained release biodegradable ocular implant into the vitreous humor of an eye of the patient in need of treatment, wherein the implant comprises a hydrogel and TKI (such as axitinib) particles dispersed within the hydrogel, and wherein a terminal release of the TKI upon biodegradation of the hydrogel is less than the terminal release of TKI from a comparative implant upon its biodegradation, wherein the comparative implant contains the TKI in a total amount of within +/−10%, such as within +/−5% of the total amount of the TKI contained in the sustained release biodegradable ocular implant and differs from the sustained release biodegradable ocular implant in that (such as only in that) the comparative implant contains the TKI in a form that has a lower solubility as measured in PBS at a pH of 7.2 to 7.4 and 37° C. after five days of incubation than the form of the TKI contained in the sustained release biodegradable ocular implant, and wherein the comparative implant has a surface area of within +/−20%, such as within +/−10% of the surface area of the sustained release biodegradable ocular implant.

282. A method of treating an ocular disease in a patient in need thereof, wherein the treatment comprises injection of a sustained release biodegradable ocular implant into the vitreous humor of an eye of the patient in need of treatment, wherein the implant comprises a hydrogel and TKI (such as axitinib) particles dispersed within the hydrogel, and wherein the implant provides for a higher $C_{max}$ of the TKI in an ocular tissue than the Cost of the TKI as provided by a comparative implant, prior to biodegradation of the hydrogel, wherein the comparative implant contains the TKI in a total amount of within +/−10%, such as within +/−5% of the total amount of the TKI contained in the sustained release biodegradable ocular implant and differs from the sustained release biodegradable ocular implant in that (such as only in that) the comparative implant contains the TKI in a form that has a lower solubility as measured in PBS at a pH of 7.2 to 7.4 and 37° C. after five days of incubation than the form of the TKI contained in the sustained release biodegradable ocular implant, and wherein the comparative implant has a surface area of within +/−20%, such as within +/−10% of the surface area of the sustained release biodegradable ocular implant.

283. A method of treating an ocular disease in a patient in need thereof, wherein the treatment comprises injection of a sustained release biodegradable ocular implant into the vitreous humor of an eye of the patient in need of treatment, wherein the implant comprises a hydrogel and TKI (such as axitinib) particles dispersed within the hydrogel, and wherein the implant provides for an earlier $t_{max}$ of the TKI in an ocular tissue than the $t_{max}$ of the TKI as provided by a comparative implant, wherein the comparative implant contains the TKI in a total amount of within +/−10%, such as within +/−5% of the total amount of the TKI contained in the sustained release biodegradable ocular implant and differs from the sustained release biodegradable ocular implant in that (such as only in that) the comparative implant contains the TKI in a form that has a lower solubility as measured in PBS at a pH of 7.2 to 7.4 and 37° C. after five days of incubation than the form of the TKI contained in the sustained release biodegradable ocular implant, and wherein the comparative implant has a surface area of within +/−20%, such as within +/−10% of the surface area of the sustained release biodegradable ocular implant.

284. The method of any of items 267 to 276, 279, 282, and 283, wherein the ocular tissue is the retina or the choroid, 285. The method of any of items 267 to 284, wherein the TKI is axitinib.

286. The method of item 284 or 285, wherein the TKI concentration in the ocular tissue is measured in the retina of a non-human primate, such a monkey, such as a *Cynomolgus* monkey.

287. The method of any of items 267 to 286, wherein the TKI contained in the sustained release biodegradable ocular implant has a solubility of 0.3 μg/ml or greater as measured in phosphate-buffered saline (PBS) at a pH of 7.2 to 7.4 and 37° C. after five days of incubation and/or has a higher solubility than axitinib polymorph SAB-I 288. The method of any of items 267 to 287, wherein the TKI contained in the sustained release biodegradable ocular implant is a form of axitinib that has the same or a higher solubility than axitinib polymorph IV.

289. The method of any of items 267 to 288, wherein the TKI contained in the sustained release biodegradable ocular implant is axitinib polymorph IV.

290. The method of any of items 272 to 276 or 281 to 289, wherein the TKI contained in the comparative implant has a solubility of lower than 0.3 μg/mL as measured in phosphate-buffered saline (PBS) at a pH of 7.2 to 7.4 and 37° C. after five days of incubation.

291. The method of any of items 272 to 276 and 281 to 290, wherein the TKI contained in the comparative implant is axitinib polymorph SAB-I.

292. The method of any of items 265 to 291, wherein the sustained release biodegradable ocular implant contains a dose of axitinib of from about 200 to about 800 μg, such as from about 300 to about 600 μg, such as from about 350 to about 550 μg, such as from about 380 to about 520 μg, such as from about 420 to about 480 μg, such as from about 400 to about 500 μg, such as about 450 μg.

293. The method of any of items 265 to 292, wherein the hydrogel of the sustained release biodegradable ocular implant biodegrades within about 8 to about 9 months after injection into a human eye.

294. The method of any of items 265 to 293, wherein the hydrogel of the sustained release biodegradable ocular implant biodegrades within about 5 to about 6 months after injection into a monkey eye, such as a *Cynomolgus* monkey eye, 295. The method of any of items 265 to 294, wherein the hydrogel of the sustained release biodegradable ocular implant biodegrades within about 4 to about 5 months after injection into a rodent eye, such as a rabbit eye, such as a Dutch Belted rabbit eye.

296. The method of any of items 265 to 295, wherein the ocular disease involves vascular leakage and/or neovascularization.

297. The method of any of items 265 to 296, wherein the ocular disease is a retinal disease.

298. The method of any of Items 265 to 296, wherein the ocular disease Is Choroidal Neovascularization, Diabetic Retinopathy, Diabetic Macular Edema, Retinal Vein Occlusion, Acute Macular Neuroretinopathy, Central Serous Chorioretinopathy, and Cystoid Macular Edema; wherein the ocular disease is Acute Multifocal Placoid Pigment Epitheliopathy, Behcet's Disease, Birdshot Retinochoroidopathy, Infectious (Syphilis, Lyme, Tuberculosis, Toxoplasmosis), Intermediate Uveitis (Pars Planitis), Multifocal Choroiditis, Multiple Evanescent White Dot Syndrome (MEWDS), Ocular Sarcoidosis, Posterior Scleritis, Serpiginous Choroiditis, Subretinal Fibrosis, Uveitis Syndrome, or Vogt-Koyanagi-Harada Syndrome; wherein the ocular disease is a vascular disease or exudative diseases, including Coat's Disease, Parafoveal Telangiectasis, Papillophlebitis, Frosted Branch Angitis, Sickle Cell Retinopathy and other Hemoglobinopathies, Angioid Streaks, and Familial Exudative Vitreoretinopathy; or wherein the ocular disease results from trauma or surgery, including Sympathetic Ophthalmia, Uveitic Retinal Disease, Retinal Detachment, Trauma, Photodynamic Laser Treatment, Photocoagulation, Hypoperfusion During Surgery, Radiation Retinopathy, or Bone Marrow Transplant. Retinopathy.

299. The method of any of items 265 to 296, wherein the ocular disease is age-related macular degeneration (AMD).

300. The method of any of items 265 to 299, wherein the ocular disease is neovascular age-related macular degeneration (AMD).

301. The method of any of items 265 to 295, wherein the ocular disease is diabetic retinopathy (DR).

302. The method of any of items 265 to 295, wherein the ocular disease is diabetic macular edema (DME).

303. The method of any of items 265 to 295, wherein the ocular disease is retinal vein occlusion (RVO).

304. The method of any of items 265 to 303, wherein the patient is a human patient.

305. A method of treating an ocular disease in a patient in need thereof, wherein the treatment comprises injection of a sustained release biodegradable ocular implant into the vitreous humor, wherein the sustained release biodegradable ocular implant comprises a hydrogel and TKI (such as axitinib) particles dispersed within the hydrogel, and wherein the treatment is characterized in that the geometric mean concentration (in ng/g) of the TKI in an ocular tissue is higher at week 6 after injection of the sustained release biodegradable ocular implant as compared to the geometric mean concentration (in ng/g) of the TKI in that ocular tissue at week 6 after injection of a comparative implant, wherein the comparative implant differs from the sustained release biodegradable ocular implant only in that the solubility of the tyrosine kinase inhibitor in the comparative implant is lower as measured in PBS at a pH of 7.2 to 7.4 and 37° C. after five days of incubation.

306. A method of treating an ocular disease in a patient in need thereof, wherein the treatment comprises injection of a sustained release biodegradable ocular implant into the vitreous humor, wherein the sustained release biodegradable ocular implant comprises a hydrogel and TKI (such as axitinib) particles dispersed within the hydrogel, and wherein the treatment is characterized in that the sum of the geometric mean concentrations (in ng/g) of TKI determined in an ocular tissue at week 6, week 13, and week 24 after Injection of the implant is higher than the sum of the geometric mean concentrations (in ng/g) of TKI determined at week 6, week 13, and week 24 after injection of a comparative implant, wherein the comparative implant differs from the sustained release biodegradable ocular implant only in that the solubility of the tyrosine kinase inhibitor in the comparative implant is lower as measured in PBS at a pH of 7.2 to 7.4 and 37° C. after five days of incubation.

307. The method of any of items 305 and 306, wherein the subject is a rabbit, such as a Dutch Belted rabbit.

308. A method of treating an ocular disease in a patient in need thereof, wherein the treatment comprises injection of a sustained release biodegradable ocular implant into the vitreous humor, wherein the sustained release biodegradable ocular implant comprises a hydrogel and TKI (such as axitinib) particles dispersed within the hydrogel, and wherein the treatment is characterized in that the geometric mean amount (in μg) of the TKI in the vitreous humor (which includes the amount of the TKI in the sustained release biodegradable ocular implant residing in the vitreous humor after injection) is lower at any time point selected from 3, 6 or 9 months after implant injection as compared to the geometric mean amount (in μg) of the TKI in the vitreous humor at the respective time point selected from 3, 6 or 9 months after injection of a comparative implant, wherein the comparative implant differs from the sustained release biodegradable ocular implant only in that the solubility of the tyrosine kinase inhibitor in the comparative implant is lower as measured in PBS at a pH of 7.2 to 7.4 and 37° C. after five days of incubation.

309. A method of treating an ocular disease in a patient in need thereof, wherein the treatment comprises injection of a sustained release biodegradable ocular implant into the vitreous humor, wherein the sustained release biodegradable ocular implant comprises a hydrogel and TKI (such as axitinib) particles dispersed within the hydrogel, wherein the sustained release biodegradable ocular implant comprises a total amount of TKI, and wherein the treatment is characterized in that the elimination rate (in μg/day) of the TKI from the vitreous humor at any time point selected from 3 or 6 months after implant injection is higher as compared to the elimination rate (in μg/day) of the TKI from the vitreous humor at any time point selected from 3 or 6 months after injection of a comparative implant, wherein the comparative implant differs from the sustained release biodegradable ocular implant only in that the solubility of the tyrosine kinase inhibitor in the comparative implant is lower as measured in PBS at a pH of 7.2 to 7.4 and 37° C. after five days of incubation, and wherein the elimination rate is calculated by dividing the difference between (i) the total amount of TKI and the remaining geometric mean TKI amount in the vitreous humor (which includes the amount of TKI contained in the implant residing in the vitreous humor) determined at 3 months, or (ii) the difference between the remaining geometric mean TKI amount in the vitreous humor determined at 3 months and the remaining geometric mean TKI amount in the vitreous humor determined at 6 months, by the number of days elapsed in the respective time period, wherein the time period is (i) from 0 to 3 months or (ii) from 3 to 6 months.

310. The method of any of items 305 to 309, wherein the comparative implant differs from the sustained release biodegradable ocular implant only in that
(a) the solubility of the TKI in the comparative implant is lower as measured in PBS at a pH of 7.2 to 7.4 and 37° C. after five days of incubation,
(b) the surface area of the comparative implant differs by no more than 5%, and
(c) the total amount of the TKI contained in the comparative implant differs by no more than 5%.

311. The method any of items 305 to 309, wherein the comparative implant differs from the sustained release biodegradable ocular implant only in that
(a) the solubility of the TKI in the comparative implant is lower as measured in PBS at a pH of 7.2 to 7.4 and 37° C. after five days of incubation,
(b) the total amount of the TKI contained in the comparative implant is at least 1.5 times higher, and
(c) the surface area of the comparative implant differs by no more than 10%.

312. The method of any of items 305 to 309, wherein the comparative implant differs from the sustained release biodegradable ocular implant only in that
(a) the solubility of the TKI in the comparative implant is lower as measured in PBS at a pH of 7.2 to 7.4 and 37° C. after five days of incubation,
(b) the surface area of the comparative implant differs by no more than 10%, and
(c) the total amount of the TKI contained in the comparative implant is at least two times higher.

313. A method of treating an ocular disease in a patient in need thereof, wherein the treatment comprises injection of a sustained release biodegradable ocular implant into the vitreous humor, wherein the implant comprises a hydrogel and TKI (such as axitinib) particles dispersed within the hydrogel, wherein the sustained release biodegradable ocular implant comprises a total amount of TKI, and wherein the treatment is characterized in that the elimination rate (in μg/day) of the TKI from the vitreous humor is substantially the same at 6 months after implant injection as compared to the elimination rate ((in μg/day) of the TKI from the vitreous humor at 6 months after injection of a comparative implant, wherein the comparative implant differs from the sustained release biodegradable ocular implant only in that
(a) the solubility of the TKI in the comparative implant is lower as measured in PBS at a pH of 7.2 to 7.4 and 37° C. after five days of incubation,
(b) the total amount of the TKI contained in the comparative implant is at least 1.5 times higher, and
(c) the surface area of the comparative implant is at least 2.5 times higher,
wherein the elimination rate is calculated by dividing the difference between the remaining geometric mean TKI amount in the vitreous humor determined at 3 months and the remaining geometric mean TKI amount in the vitreous humor determined at 6 months by the number of days elapsed in the time period from 3 to 6 months, 314. The method of any of items 308 to 313, wherein the subject is a non-human primate, such as a monkey, such as a *Cynomolgus* monkey.

315. The method of any of items 305 to 307, wherein the ocular tissue is the retina or the choroid.

316. The method of any of items 305 to 315, wherein the TKI is axitinib,

317. The method of any one of items 305 to 316, wherein the sustained release biodegradable ocular implant comprises axitinib polymorph IV and the comparative implant comprises axitinib polymorph SAB-I.

318. The method of any of items 200 to 224 or 265 to 317, comprising injecting a sustained release biodegradable ocular implant according to any of items 1 to 199 into the vitreous humor, wherein the treatment results in inhibition, prevention or substantial prevention/delay, or reduction of VEGF-induced retinal vascular leakage during the treatment period.

319. The method of item 318, wherein the treatment results in inhibition, prevention or substantial prevention/delay, or reduction of VEGF-induced retinal vascular leakage for at least up to about 1 month, such as at least up to about 2 months, such as at least up to about 3 months after injection of the implant.

320. The method of any of items 318 and 319, wherein the treatment is characterized in that VEGF-induced retinal vascular leakage is inhibited, reduced or delayed/prevented during the treatment period as compared to the VEGF-induced retinal vascular leakage induced during the same time period after administration of an anti-VEGF agent, wherein the anti-VEGF agent is bevacizumab, ranibizumab, faricimab, of aflibercept.

321. The method of any of items 318 to 321, wherein the treatment is characterized in that VEGF-induced retinal vascular leakage is reduced or delayed for at least up to about 1 month, such as at least up to about 2 months, such as at least up to about 3 months after injection of the implant as compared to the VEGF-induced retinal leakage in the respective same period after administering bevacizumab, as measured in a VEGF challenge study in a rabbit (such as Dutch Belted rabbit), the study comprising intravitreal injection of a sustained release biodegradable ocular implant comprising from about 300 to about 650 μg, such as from about 360 μg to about 562.5 μg, such as from about 400 to about 500 μg, or about 450 μg, of TKI (such as axitinib) to an eye of a rabbit, wherein the rabbit is thereafter also administered 1 μg of VEGF to the eye at least three times over a period of 3 months, compared to the administration of 50 μL of 25 mg/mL bevacizumab (Avastin) under the same conditions including the VEGF challenges.

322. The method of any of items 318 to 321, wherein the treatment is characterized in that VEGF-induced vascular leakage is reduced after administration of the implant for a longer period of time than after administration of bevacizumab.

323. A method of treating neovascular age-related macular degeneration (AMD) in a patient, the method comprising administering a sustained release biodegradable ocular implant according to any of items 1 to 199 to the vitreous humor of a patient's eye that is in need of such treatment, wherein the patient has a diagnosis of extrafoveal choroidal neovascularization (CNV) or subfoveal neovascularization (SFNV) secondary to neovascular AMD.

324. The method of item 323, wherein one sustained release biodegradable ocular implant is injected per eye for a treatment period of at least 9 months.

325. The method of item 323 or 324, wherein the duration of the treatment period is from 9 months to 12 or 13 months.

326. The method of any of items 323 to 325, wherein prior to the administration of the sustained release biodegradable ocular implant an anti-VEGF agent is administered.

327. The method of item 326, wherein an anti-VEGF agent is administered at least once prior to the administration of the sustained release biodegradable ocular implant, such as at least once per month for at least 1 month, or at least 2 months, or at least 3 months prior to the administration of the sustained release biodegradable ocular implant.

328. The method of any of items 323 to 327, wherein prior to the treatment with the sustained release biodegradable ocular implant the patient has been treated at least once or has been treated repeatedly with an anti-VEGF agent.

329. The method of any of items 323 to 328, wherein prior to the treatment with the sustained release biodegradable ocular implant the patient has been treated (e.g. monthly) with an anti-VEGF agent for at least 2 months.

330. The method of any of items 323 to 329, wherein the patient's last treatment with an anti-VEGF agent prior to the injection of the sustained release biodegradable ocular implant was at least one month, or was about one month, prior to the injection of the sustained release biodegradable ocular implant.

331. The method of any of items 265 to 330, wherein the patient is an anti-VEGF responder.

332. The method of any of items 323 to 331, wherein after the injection of the sustained release biodegradable ocular implant no further anti-VEGF agent is administered.

333. The method of any of items 326 to 332, wherein the anti-VEGF agent is selected from bevacizumab, ranibizumab, faricimab, and aflibercept.

334. The method of any of items 326 to 332, wherein the anti-VEGF agent is bevacizumab, 335. The method of any of items 326 to 332, wherein the anti-VEGF agent is aflibercept.

336. The method of any of items 326 to 335, wherein one aflibercept dose administered at any time prior to the administration of the sustained release biodegradable ocular implant is 2 mg aflibercept.

337. The method of any of Items 323 to 336, wherein the treatment with the sustained release biodegradable ocular implant maintains or essentially maintains visual acuity during the treatment period.

338. The method of any of items 323 to 337, wherein the treatment with the sustained release biodegradable ocular implant prevents or essentially prevents a reduction in visual acuity during the treatment period, 339. The method of any of items 323 to 338, wherein the treatment is characterized in that the patient experiences a loss of 15 ETDRS letters of BCVA or less than 15 ETDRS letters at 9 months, or during the period of 9 months, after injection of the implant as compared to the baseline value, or wherein the treatment is characterized in that the patient experiences an increase, such as an increase of 15 ETDRS letters, of BCVA or more at 9 months, or during the period of 9 months, after injection of the implant as compared to the baseline value, 340. The method of any of items 323 to 339, wherein the treatment is characterized in that the patient experiences a loss of 15 ETDRS letters of BCVA or less than 15 ETDRS letters at 12 months, or during the period of 12 months after injection of the implant as compared to the baseline value, or wherein the treatment is characterized in that the patient experiences an increase, such as an increase of 15 ETDRS letters, of BCVA or more at 12 months, or during the period of 12 months, after injection of the implant as compared to the baseline value.

341. The method of any of items 323 to 339, wherein the treatment is characterized in that the patient experiences a loss of 15 ETDRS letters of BCVA or less than 15 ETDRS letters at 9 months or at 12 months, or during the period of 9 months or 12 months, after injection of the implant as compared to the baseline value, with no or no more than one rescue medication administration,
342. The method of any of items 323 to 341, wherein the treatment prevents or essentially prevents an increase in the central subfield thickness (CSFT) during the treatment period.
343. The method of any of items 323 to 342, wherein the treatment provides for a CSFT increase of no more than 75 μm, such as no more than 50 μm during the treatment period as compared to the baseline CSFT value.
344. The method of any of items 323 to 343, wherein the treatment provides for a CSFT increase of no more than 75 μm, such as no more than 50 μm at 9 months, or during the period of 9 months, or at 12 months, or during the period of 12 months, after injection of the implant as compared to the baseline CSFT value.
345. The method of any of items 323 to 344, wherein the CSFT of the patient's treated eye is 350 μm or less at 9 months or at 12 months after injection of the implant
346. The method of any of items 323 to 345, wherein the sustained release biodegradable ocular implant comprises a TKI that has a solubility of at least 0.3 μg/mL as measured in phosphate-buffered saline (PBS) at a pH of 7.2 to 7.4 and 37° C. after five days of incubation.
347. The method of any of items 323 to 346, wherein the TKI is axitinib.
348. The method of any of items 323 to 347, wherein the TKI comprises or is axitinib polymorph IV.
349. The method of any of items 323 to 348, wherein the sustained release biodegradable ocular implant contains a dose of axitinib of from about 300 to about 650 μg, such as from about 350 to about 550 μg, such as from about 380 to about 520 μg, such as from about 400 to about 500 μg, such as from about 420 to about 480 μg, such as from about 400 to about 500 μg, such as about 450 μg axitinib.
350. The method of any of items 323 to 349, wherein the sustained release biodegradable ocular implant has in its dry state (prior to injection) a length of less than about 11 mm, and a width of from about 0.3 to about 0.4 mm, or of about 0.4 mm.
351. The method of any of items 323 to 350, wherein the sustained release biodegradable ocular implant has in its hydrated state (after 24 hours in PBS at a pH of 7.4 at 37° C.) a length of less than about 11 mm, or of about 10 mm or less, and a width of about 2 mm or less.
352. The method of any of items 323 to 351, wherein the sustained release biodegradable ocular implant has in its dry state (prior to injection) a width of about 0.33 to about 0.36 mm, and in its hydrated state a length of about 8 to about 10 mm.
353. The method of any of items 323 to 352, wherein the sustained release biodegradable ocular implant is cylindrical or essentially cylindrical
354. The method of any of items 323 to 352, wherein the sustained release biodegradable ocular implant is non-cylindrical.
355. The method of any of items 323 to 354, wherein the sustained release biodegradable ocular implant comprises axitinib polymorph IV particles dispersed in a PEG hydrogel network formed by crosslinking 4a20kPEG-SAZ and 8a20kPEG-$NH_2$ precursors.
356. The method of any of items 323 to 355, wherein the sustained release biodegradable ocular implant comprises axitinib polymorph IV particles dispersed in a hydrogel, wherein the implant comprises axitinib polymorph IV in an amount of from about 300 to about 650 μg, such as from about 360 μg to about 562.5 μg, such as from about 400 μg to about 500 μg, such as about 450 μg, wherein the implant has a composition on a dry basis (in % w/w) of about 30 to about 75% axitinib, about 20 to about 50% PEG units, and about 0.5 to about 15% sodium phosphate salt and on a wet basis (in % w/w) of about 5 to about 17% axitinib, about 4 to about 12% PEG units, and about 0.2 to about 5% sodium phosphate salt, wherein the hydrogel comprises a PEG hydrogel network formed by crosslinking 4a20kPEG-SAZ and 8a20kPEG-$NH_2$ units, wherein the implant in its dried state has a length of from 5 to 11 mm and a width of from 0.28 to 0.38 mm and/or in its hydrated state (after 24 hours in PBS at a pH of 7.4 at 37° C.) has a length of from 5 to 11 mm and a width of from 0.4 to 2 mm.
357. The method of any of items 323 to 356, wherein the sustained release biodegradable ocular implant comprises axitinib polymorph IV particles dispersed in a hydrogel, wherein the implant comprises axitinib polymorph IV in an amount of from about 300 to about 650 μg, such as from about 360 μg to about 562.5 μg, such as from about 400 μg to about 500 μg, such as about 450 μg, wherein the implant has a composition on a dry basis (in % w/w) of about 54 to about 69% axitinib, a PEG hydrogel network formed by crosslinking about 17 to 26% 4a20kPEG-SAZ with about 8 to about 13% 8a20kPEG-$NH_2$, about 3 to about 5% dibasic sodium phosphate, and about 1 to about 3% monobasic sodium phosphate.
358. The method of 357, wherein the implant in its dried state has a length of from 5 mm to 11 mm and a width of from 0.28 to 0.38 mm and/or in its hydrated state (after 24 hours in PBS at a pH of 7.4 at 37° C.) has a length of from 5 to 11 mm and a width of from 0.4 to 2 mm.
359. The method of any of items 347 to 358, wherein the axitinib particles have a d90 particle size of less than 8 μm and a d50 particle size of less than 3 μm.
360. The method of any of items 323 to 359, wherein the implant is obtainable by wet casting and applying a stretch factor of from about 1 to about 3.
361. The method of any of items 323 to 359, wherein the implant is obtainable by hot melt extrusion.
362. A method of increasing the photostability of an active agent by dispersing active agent particles in a hydrogel.
363. The method of item 362, wherein the active agent is a TKI.
364. The method of item 363, wherein the active agent is axitinib.
365. The method of item 364, wherein the active agent is axitinib polymorph IV.
366. The method of any of Items 362 to 365, wherein the hydrogel comprises a polymer network comprising one or more units of polyalkylene glycol, such as polyethylene glycol (PEG),
367. The method of any of items 365 and 366, wherein axitinib polymorph IV is comprised in an implant according to any of items 1 to 199.

368. The method of any of items 365 to 367, wherein the axitinib polymorph IV comprised in the hydrogel and/or implant contains at least about 10% less total impurities, such as at least about 15% less total impurities, such as at least about 20% less total impurities after exposure to visible light than axitinib polymorph IV in powder form after the same exposure time and at the same exposure conditions.
369. The method of item 368, wherein exposure to visible light means exposure to light at wavelength 380 to 700 nm, such as for at least 1 day, or for at least 2 days, such as for at least 0.5 million lux hours/$m^2$, such as for at least 1 million lux hours/$m^2$, such as for at least 1.2 million lux hours/$m^2$.
370. The method of any of items 365 to 369, wherein the axitinib polymorph IV comprised in the hydrogel and/or implant contains at least about 10% less total impurities, such as at least about 20% less total impurities, such as at least about 30% less total impurities, such as at least about 40% less total impurities after exposure to UV light than axitinib polymorph IV in powder form after the same exposure time and at the same exposure conditions.
371. The method of item 370, wherein exposure to UV light means exposure to UV A light at wavelength 315 to 400 nm, such as for at least 4 hours, such as for at least 8 hours, such as for at least 10 hours, such as for at least 100 watt hours/$m^2$, or for at least 150 watt hours/$m^2$, or for at least 200 watt hours/$m^2$.
372. A sustained release biodegradable intravitreal implant comprising a hydrogel comprising crosslinked PEG units and axitinib polymorph IV in an amount of from about 360 μg to about 562.5 μg, or from about 405 μg to about 495 μg, such as about 450 μg.
373. A sustained release biodegradable intravitreal implant comprising a hydrogel comprising a PEG hydrogel network formed by crosslinking 4a20kPEG-SAZ and 8a20kPEG-$NH_2$ units and axitinib polymorph IV in an amount of from about 300 to about 650 μg, such as from about 360 μg to about 562.5 μg, or from about 405 μg to about 495 μg, such as about 450 μg,
374. A sustained release biodegradable intravitreal implant comprising a hydrogel and axitinib, wherein axitinib particles are dispersed within the hydrogel, wherein the implant comprises axitinib polymorph IV in an amount of from about 300 to about 650 μg, such as from about 360 μg to about 562.5 μg, such as from about 400 to about 500 μg, such as about 450 μg, wherein the implant has a composition on a dry basis (in % w/w) of about 30 to about 75% axitinib form IV, about 20 to about 50% PEG units, and about 0.5 to about 15% sodium phosphate salt and on a wet basis (in % w/w) of about 5 to about 17% axitinib, about 4 to about 12% PEG units, and about 0.2 to about 5% sodium phosphate salt, wherein the hydrogel comprises a PEG hydrogel network formed by crosslinking 4a20kPEG-SAZ and 8a20kPEG-$NH_2$ units, wherein the implant in its dried state has a length of from 5 to 11 mm and a width of from 0.2 to 0.4 mm, such as 0.28 to 0.38 mm and in its hydrated state (after 24 hours in PBS at a pH of 7.4 at 37° C.) has a length of from 5 to 11 mm and a width of from 0.4 to 2 mm.
375. A sustained release biodegradable intravitreal implant comprising a hydrogel and axitinib, wherein axitinib particles are dispersed within the hydrogel, wherein the implant comprises axitinib polymorph IV in an amount of from about 300 to about 650 μg, such as from about 360 μg to about 562.5 μg, such as from about 400 to about 500 μg, such as about 450 μg, wherein the implant has a composition on a dry basis (in % w/w) of from about 54 to about 69% axitinib form IV, a PEG hydrogel network formed by crosslinking about 17 to about 26% 4a20kPEG-SAZ with about 8 to about 13% 8a20kPEG-$NH_2$, about 3 to about 5% dibasic sodium phosphate and about 1 to about 3% monobasic sodium phosphate.
376. A sustained release biodegradable intravitreal implant comprising a hydrogel and axitinib, wherein axitinib particles are dispersed within the hydrogel,
 wherein the implant comprises axitinib polymorph IV in an amount of from about 300 to about 650 μg, such as from about 360 μg to about 562.5 μg, such as from about 360 μg to about 540 μg, such as from about 400 μg to about 500 μg, such as about 450 μg,
 wherein the implant has a composition on a dry basis (in % w/w) of about 30 to about 75% axitinib, about 20 to about 50% PEG units, and about 0.5 to about 15% sodium phosphate salt and on a wet basis (in % w/w) of about 5 to about 17% axitinib, about 4 to about 12% PEG units, and about 0.2 to about 5% sodium phosphate salt,
 wherein the hydrogel comprises a PEG hydrogel network formed by crosslinking 4a20kPEG-SAZ and 8a20kPEG-$NH_2$ units,
 wherein the implant has a length that is greater than its width, and in its dried state has a length of 11 mm or less, such as from 5 to 11 mm, and a width of from 0.2 to 0.4 mm, such as 0.28 to 0.38 mm and/or in its hydrated state (after 24 hours in PBS at a pH of 7.4 at 37° C.) has a length of 11 mm or less, such as from 5 to 11 mm and a width of from 0.4 to 2 mm, and wherein the axitinib particles have a d90 particle size of less than 8 μm and a d50 particle size of less than 3 μm,
377. A sustained release biodegradable intravitreal implant comprising a hydrogel and axitinib polymorph IV in an amount of from about 300 to about 650 μg, such as from about 360 μg to about 562.5 μg such as from about 360 to 540 μg, such as from about 400 to about 500 μg, such as about 450 μg, wherein axitinib particles are dispersed within the hydrogel, the hydrogel comprising crosslinked PEG units (such as crosslinked 4a20kPEG-SAZ and 8a20kPEG-$NH_2$ units), wherein the amount of axitinib remaining when the hydrogel starts to degrade (and thus the amount of axitinib being released upon final degradation of the hydrogel) is less than 200 μg, wherein the implant in its dry state (prior to injection) has a width of from about 0.3 to about 0.4 mm, such as about 0.33 to about 0.36 mm, and a length of less than about 11 mm, and in its hydrated state (after 24 hours in PBS at a pH of 7.4 at 37° C.) has a length of less than about 11 mm, such as a length of from about 8 to about 10 mm.
378. A method of treating neovascular AMD in a patient in need thereof, the method comprising administering a sustained release biodegradable intravitreal implant to vitreous humor, wherein the implant is as defined in any of items 372 to 377, and wherein the treatment period provided by one implant is from 6 to 12 months.
379. A method of treating neovascular AMD in a patient in need thereof, the method comprising administering a sustained release biodegradable intravitreal implant to vitreous humor, wherein the implant is as defined in any of items 372 to 377, and wherein the treatment period provided by one implant is from 8 to 11 months.

380. A method of treating neovascular AMD in a patient in need thereof, the method comprising administering a sustained release biodegradable intravitreal implant to vitreous humor, wherein the implant is as defined in any of items 372 to 377, and wherein the treatment period provided by one implant is about 6 months, or is at least 6 months.

381. A method of treating neovascular AMD in a patient in need thereof, the method comprising administering a sustained release biodegradable intravitreal implant to vitreous humor, wherein the implant is as defined in any of items 372 to 377, wherein a fresh implant is administered every 6 to 12 months.

382. A method of treating neovascular AMD in a patient in need thereof, the method comprising administering a sustained release biodegradable intravitreal implant to vitreous humor, wherein the implant is as defined in any of items 372 to 377, wherein a fresh implant is administered every 8 to 11 months, such as every 9 months.

383. A method of treating neovascular AMD in a patient in need thereof, the method comprising administering a sustained release biodegradable intravitreal implant to vitreous humor, wherein the implant is as defined in any of items 372 to 377, wherein the interval between injection of one implant and a subsequent fresh implant is at least 6 months, such as about 9 months.

384. The method of any of items 378 to 383, wherein the cumulative amount of axitinib released prior to the biodegradation of the hydrogel when the implant is still intact is higher than the amount of axitinib being terminally released upon biodegradation.

385. The method of item 384, wherein the amount of axitinib being terminally released upon biodegradation is less than about 200 μg, such as less than about 150 μg, such as about 130 μg or less, or about 100 μg or less, or the amount of axitinib being terminally released upon final biodegradation of the hydrogel is from about 50 to about 200 μg, such as from about 100 to about 170 μg, such as from about 110 to 150 μg.

386. The method of any of items 378 to 383, wherein the amount of axitinib remaining in the implant at 6 months after implant injection is 250 μg or less, such as 200 μg or less.

387. The method of item 386, wherein the implant is injected in the eye of a non-human primate, such as a monkey, such as a *Cynomolgus* monkey.

388. The sustained release biodegradable intravitreal implant according to any of items 372 to 377, or the method of any of items 378 to 387, wherein the implant provides for an average release rate of above about 0.8 μg/day in vitreous humor.

389. The sustained release biodegradable intravitreal implant according to any of items 372 to 377, or the method of any of items 378 to 387, wherein the implant provides for an average release rate of at least about 1.0 μg/day, such as at least about 1.2 μg/day in vitreous humor.

390. The sustained release biodegradable intravitreal implant or the method according to any of items 388 and 389, wherein the release in vitreous humor is in a non-human primate, such as a monkey, such as a *Cynomolgus* monkey, or is in a human.

391. A sustained release biodegradable ocular implant comprising a hydrogel and axitinib, wherein axitinib particles are dispersed within the hydrogel, characterized in that the percentage of axitinib released from the implant is:

from about 10 to about 18% after 0.5 hours,
from about 30 to about 45% after 2 hours,
from about 60 to about 80% after 6 hours,
from about 79 to about 98% after 10 hours,
at least about 90% after 12 hours,
and/or at least about 92% after 16 hours,
in an in vitro test performed at 35° C.±0.5° C. in 0.01N HCl with 0.25% cetyl trimethyl ammonium bromide (CTAB) in a USP apparatus 4.

392. The sustained release biodegradable ocular implant of item 391, characterized in that the percentage of axitinib released from the implant is:

from about 10 to about 18% after 0.5 hours,
from about 19 to about 27% after 1 hour,
from about 30 to about 45% after 2 hours,
from about 55 to about 65% after 4 hours,
from about 60 to about 80% after 6 hours,
from about 78 to about 90% after 8 hours,
from about 79 to about 98% after 10 hours,
at least about 90% after 12 hours,
and/or at least about 92% after 16 hours,
in an in vitro test performed at 35° C.±0.5° C. in 0.01N HCl with 0.25% cetyl trimethyl ammonium bromide (CTAB) in a USP apparatus 4

393. A sustained release biodegradable ocular implant comprising a hydrogel and axitinib, wherein axitinib particles are dispersed within the hydrogel, characterized in that the percentage of axitinib released from the implant is:

from about 12 to about 17% after 0.5 hours,
from about 32 to about 42% after 2 hours,
from about 62 to about 78% after 6 hours,
from about 83 to about 97% after 10 hours,
and/or at least about 94% after 16 hours,
in an in vitro test performed at 35° C.±0.5° C. in 0.01N HCl with 0.25% cetyl trimethyl ammonium bromide (CTAB) in a USP apparatus 4.

394. The sustained release biodegradable ocular implant of item 393, characterized in that the percentage of axitinib released from the implant is:

from about 12 to about 17% after 0.5 hours,
from about 23 to about 25% after 1 hour,
from about 32 to about 42% after 2 hours,
from about 57 to about 62% after 4 hours,
from about 62 to about 78% after 6 hours,
from about 80 to about 88% after 8 hours,
from about 83 to about 97% after 10 hours,
at least about 94% after 12 hours,
and/or at least about 94% after 16 hours,
in an in vitro test performed at 35° C.±0.5° C. in 0.01N HCl with 0.25% cetyl trimethyl ammonium bromide (CTAB) in a USP apparatus 4.

395. A sustained release biodegradable ocular implant comprising a hydrogel and axitinib, wherein axitinib particles are dispersed within the hydrogel, characterized in that the percentage of axitinib released from the implant is:

from about 12 to about 16% after 0.5 hours,
from about 34 to about 41% after 2 hours,
from about 66 to about 77% after 6 hours,
from about 85 to about 96% after 10 hours,
and/or at least about 95% after 16 hours, in an in vitro test performed at 35° C.±0.5° C. in 0.01N HCl with 0.25% cetyl trimethyl ammonium bromide (CTAB) in a USP apparatus 4.

396. The sustained release biodegradable ocular implant of item 395, characterized in that the percentage of axitinib released from the implant is:
from about 12 to about 16% after 0.5 hours,
from about 23 to about 25% after 1 hour,
from about 34 to about 41% after 2 hours,
from about 57 to about 62% after 4 hours,
from about 66 to about 77% after 6 hours,
from about 80 to about 88% after 8 hours,
from about 85 to about 96% after 10 hours,
at least about 94% after 12 hours,
and/or at least about 95% after 16 hours,
in an in vitro test performed at 35° C.±0.5° C. in 0.01N HCl with 0.25% cetyl trimethyl ammonium bromide (CTAB) in a USP apparatus 4.

397. The sustained release biodegradable ocular implant of any of items 391 to 396, containing axitinib in an amount of from about 400 to about 500 µg, such as about 450 µg, wherein the percentage of released axitinib is based on 450 µg axitinib representing 100%.

398. A sustained release biodegradable ocular implant comprising a hydrogel and axitinib, wherein axitinib particles are dispersed within the hydrogel, the implant comprising axitinib free base in an amount of from about 300 to about 600 µg, such as from about 400 to about 500 µg, such as about 450 µg, characterized in that the amount of axitinib released from the implant is:
from about 50 to about 80 µg after 0.5 hours,
from about 140 to about 200 µg after 2 hours,
from about 270 to about 360 µg after 6 hours,
from about 350 to about 450 µg after 10 hours,
and/or at least about 410 µg after 16 hours,
in an in vitro test performed at 35° C.±0.5° C. in 0.01N HCl with 0.25% cetyl trimethyl ammonium bromide (CTAB) in a USP apparatus 4.

399. The sustained release biodegradable ocular implant of item 398, characterized in that the amount of axitinib released from the implant is:
from about 50 to about 80 µg after 0.5 hours,
from about 100 to about 120 µg after 1 hour,
from about 140 to about 200 µg after 2 hours,
from about 240 to about 295 µg after 4 hours,
from about 270 to about 360 µg after 6 hours,
from about 350 to about 410 µg after 8 hours,
from about 350 to about 450 µg after 10 hours,
at least about 400 µg after 12 hours,
and/or at least about 410 µg after 16 hours,
in an in vitro test performed at 35° C.±0.5° C. in 0.01N HCl with 0.25% cetyl trimethyl ammonium bromide (CTAB) in a USP apparatus 4.

400. A sustained release biodegradable ocular implant comprising a hydrogel and axitinib, wherein axitinib particles are dispersed within the hydrogel, the implant comprising axitinib free base in an amount of from about 300 to about 600 µg, such as from about 400 to about 500 µg, such as about 450 µg, characterized in that the amount of axitinib released from the implant is:
from about 55 to about 72 µg after 0.5 hours,
from about 147 to about 190 µg after 2 hours,
from about 280 to about 350 µg after 6 hours,
from about 360 to about 440 µg after 10 hours,
and/or at least about 420 µg after 16 hours,
in an in vitro test performed at 35° C.±0.5° C. in 0.01N HCl with 0.25% cetyl trimethyl ammonium bromide (CTAB) in a USP apparatus 4.

401. The sustained release biodegradable ocular implant of item 400, characterized in that the amount of axitinib released from the implant is:
from about 55 to about 72 µg after 0.5 hours,
from about 105 to about 112 µg after 1 hour,
from about 147 to about 190 µg after 2 hours,
from about 250 to about 280 µg after 4 hours,
from about 280 to about 350 µg after 6 hours,
from about 360 to about 400 µg after 8 hours,
from about 360 to about 440 µg after 10 hours,
at least about 420 µg after 12 hours,
and/or at least about 420 µg after 16 hours,
in an in vitro test performed at 35° C.±0.5° C. in 0.01N HCl with 0.25% cetyl trimethyl ammonium bromide (CTAB) in a USP apparatus 4.

402. A sustained release biodegradable ocular implant comprising a hydrogel and axitinib, wherein axitinib particles are dispersed within the hydrogel, the implant comprising axitinib free base in an amount of from about 300 to about 600 µg, such as from about 400 to about 500 µg, such as about 450 µg, characterized in that the amount of axitinib released from the implant is:
from about 57 to about 70 µg after 0.5 hours,
from about 150 to about 180 µg after 2 hours,
from about 290 to about 345 µg after 6 hours,
from about 370 to about 430 µg after 10 hours,
and/or at least about 420 µg after 16 hours,
in an in vitro test performed at 35° C.±0.5° C. in 0.01N HCl with 0.25% cetyl trimethyl ammonium bromide (CTAB) in a USP apparatus 4, 403. The sustained release biodegradable ocular implant of item 402, characterized in that the amount of axitinib released from the implant is:
from about 57 to about 70 µg after 0.5 hours,
from about 105 to about 112 µg after 1 hour,
from about 150 to about 180 µg after 2 hours,
from about 250 to about 280 µg after 4 hours,
from about 290 to about 345 µg after 6 hours,
from about 360 to about 400 µg after 8 hours,
from about 370 to about 430 µg after 10 hours,
at least about 420 µg after 12 hours,
and/or at least about 420 µg after 16 hours,
in an in vitro test performed at 35° C.±0.5° C. in 0.01N HCl with 0.25% cetyl trimethyl ammonium bromide (CTAB) in a USP apparatus 4.

404. The sustained release biodegradable ocular implant of any of items 391 to 403, wherein the axitinib free base comprises axitinib polymorph IV, such as at least 90 weight-% axitinib polymorph IV, based on the entire amount of axitinib free base contained in the implant.

405. The sustained release biodegradable ocular implant of any of items 391 to 403, wherein the axitinib free base is axitinib polymorph IV.

406. The sustained release biodegradable ocular implant of item 405, containing axitinib polymorph IV in an amount of from about 300 to about 600 µg, such as from about 400 to about 500 µg, such as about 450 µg.

407. The sustained release biodegradable ocular implant of any of items 1 to 199, 372 to 377, 388 to 390, and 391 to 406, wherein the implant has a hydrated surface area (as calculated from the hydrated dimensions as measured in vitro in phosphate-buffered saline at a pH of 7.2 at 37° C. after 24 hours) of from about 10.0 to about 30.0 $mm^2$.

408. The sustained release biodegradable ocular implant of item 407, having a hydrated surface area of from about 16.0 to about 25.0 $mm^2$, such as of from about 17.0 to about 23.0 $mm^2$, such as from about 18.0 to about 22.5 $mm^2$.
409. The sustained release biodegradable ocular implant of item 407 or 408, wherein the implant is cylindrical or essentially cylindrical.
410. The method of any of items 200 to 226, 265 to 361, and 378 to 390, wherein the patient is anti-VEGF and/or AMD treatment naïve, and has good vision prior to starting the treatment with the implant.
411. The method of item 410, wherein the patient has a visual acuity of 20/20 prior to starting the treatment with the implant.
412. The sustained release biodegradable ocular implant according to any of items 1 to 199, 372 to 377, 388 to 390, and 391 to 409, or the method according to any of items 200 to 226, 265 to 361, 378 to 390, 410 and 411, wherein the implant contains an amount of axitinib of from about 400 to about 500 μg, and wherein the axitinib is in the form of polymorph IV, wherein the implant provides for an $AUC_{0\text{-}5.5\ months}$ in the retina in the range of from about 125,000 to about 165,000 ng day/g and/or an $AUC_{0\text{-}5.5\ months}$ in the choroid/RPE from about 130,000 to about 190,000 ng·day/g in rabbit.
413. The sustained release biodegradable ocular implant or method of item 412, wherein the implant provides for an $AUC_{0\text{-}5.5\ months}$ in the retina in the range of from about 130,000 to about 160,000 ng·day/g and/or an $AUC_{0\text{-}5.5\ months}$ in the choroid/RPE from about 140,000 to about 180,000 ng·day/g in rabbit.
414. The sustained release biodegradable ocular implant or method of item 413, wherein the implant provides for an $AUC_{0\text{-}5.5\ months}$ in the retina in the range of from about 135,000 to about 155,000 ng·day/g and/or an $AUC_{0\text{-}5.5\ months}$ in the choroid/RPE from about 150,000 to about 175,000 ng·day/g in rabbit.
415. The sustained release biodegradable ocular implant according to any of items 1 to 199, 372 to 377, 388 to 390, 391 to 409, and 412 to 414 or the method according to any of items 200 to 226, 265 to 361, 378 to 390, 410 to 414, wherein the implant contains an amount of axitinib of from about 400 to about 500 μg, and wherein the axitinib is in the form of polymorph IV, wherein the implant provides for a $C_{max}$ in the retina of less than about 1300 ng/g in rabbit.
416. The sustained release biodegradable ocular implant or method of item 415, wherein the implant provides for a $C_{max}$ in the retina in the range of from about 800 to about 1300 ng/g in rabbit.
417. The sustained release biodegradable ocular implant or method of any of items 412 to 416, wherein the retina and/or the choroid is of a Dutch Belted rabbit.
418. The sustained release biodegradable ocular implant according to any of items 1 to 199, 372 to 377, 388 to 390, 391 to 409, and 412 to 417 or the method according to any of items 200 to 226, 265 to 361, 378 to 390, 410 and 417, wherein the implant when injected into the vitreous humor provides for a release rate during steady state of from about 0.8 μg/day to about 1.2 μg/day, such as from about 0.9 μg/day to about 1.1 μg/day, such as about 1.0 μg/day.
419. The sustained release biodegradable ocular implant or method of item 418, wherein the retina is of a non-human primate, such as a monkey, such as a *Cynomolgus* monkey.
420. A method of treating an ocular disease in a patient in need thereof, wherein the treatment comprises injection of a sustained release biodegradable ocular implant into the vitreous humor of an eye of the patient in need of treatment, wherein the sustained release biodegradable ocular implant comprises a hydrogel and TKI, with TKI particles being dispersed within the hydrogel, wherein the TKI contained in the sustained release biodegradable ocular implant is axitinib having a solubility of 0.3 μg/mL or greater as measured in phosphate-buffered saline (PBS) at a pH of 7.2 to 7.4 and 37° C. after five days of incubation, and wherein the maximal axitinib concentration in the retina and/or the choroid/RPE at the time of final hydrogel degradation provided by the sustained release biodegradable ocular implant is less than the maximal axitinib concentration in the retina and/or the choroid/RPE at the time of final hydrogel degradation, respectively, provided by a comparative implant in which the TKI is axitinib having a solubility of lower than 0.3 μg/mL as measured in phosphate-buffered saline (PBS) at a pH of 7.2 to 7.4 and 37° C. after five days of incubation.
421. The method of item 420, wherein the comparative implant differs from the sustained release biodegradable ocular implant only in the solubility and/or the polymorphic form of the axitinib, wherein the total amount of axitinib contained in the comparative implant differs by no more than 10% from the total amount of axitinib contained in the sustained release biodegradable ocular implant.
422. A method of treating an ocular disease in a patient in need thereof, wherein the treatment comprises injection of a sustained release biodegradable ocular implant into the vitreous humor of an eye of the patient in need of treatment, wherein the sustained release biodegradable ocular implant comprises a hydrogel and TKI, with TKI particles being dispersed within the hydrogel, wherein the TKI contained in the sustained release biodegradable ocular implant is axitinib having a solubility of 0.3 μg/mL or greater as measured in phosphate-buffered saline (PBS) at a pH of 7.2 to 7.4 and 37° C. after five days of incubation, and wherein the maximum concentration of axitinib in the retina and/or the choroid/RPE is reached by the sustained release biodegradable ocular implant earlier than by a comparative implant, wherein the comparative implant differs from the sustained release biodegradable ocular implant in the solubility and/or the polymorphic form of the axitinib, and wherein the dose of axitinib in the comparative implant is up to two times the dose of axitinib in the sustained release biodegradable ocular implant.
423. The method according to any of items 420 to 422, or the method according to any of items 200 to 226, 265 to 361, 378 to 390, and 410 to 419, wherein the maximum TKI (such as axitinib) concentration in the retina and/or the choroid/RPE is reached by the sustained release biodegradable ocular implant prior to the final hydrogel biodegradation.
424. The method of any of items 420 to 423, wherein the retina and/or the choroid/RPE is of a monkey, such as a *Cynomolgus* monkey, or is of a rabbit, such as a Dutch Belted rabbit.

425. The method of any of items 420 to 424, wherein the solubility of the axitinib contained in the sustained release biodegradable ocular implant is at least 0.4 μg/mL or greater, and the solubility of the axitinib contained in the comparative implant is lower than 0.3 μg/ml as measured in phosphate-buffered saline (PBS) at a pH of 7.2 to 7.4 and 37° C. after five days of incubation.
426. The method of any of items 420 to 425, wherein the axitinib contained in the sustained release biodegradable ocular implant is axitinib free base in the form of polymorph IV.
427. The sustained release biodegradable ocular implant of any of items 391 to 409 and 412 to 419, or the method of any of items 412 to 426, wherein the sustained release biodegradable ocular implant and the comparative implant (if applicable) comprise a PEG hydrogel obtained by crosslinking PEG precursors with electrophilic end groups with PEG precursors with nucleophilic end groups.
428. The sustained release biodegradable ocular implant or method of item 427, wherein the hydrogel in the sustained release biodegradable ocular implant and the comparative implant comprises crosslinked 4a20kPEG-SAZ and 8a20kPEG-$NH_2$ precursors.
429. A sustained release biodegradable intravitreal implant comprising a hydrogel and axitinib, wherein axitinib particles are dispersed within the hydrogel,
    wherein the implant comprises axitinib polymorph IV in an amount of from about 300 to about 650 μg, such as from about 360 μg to about 562.5 μg, such as from about 360 μg to about 540 μg, such as from about 400 μg to about 500 μg,
    wherein the implant has a composition on a dry basis (in % w/w) of about 30 to about 75% axitinib, about 20 to about 50% PEG units, and about 0.5 to about 15% sodium phosphate salt and on a wet basis (in % w/w) of from about 5 to about 17% axitinib, about 4 to about 12% PEG units, and about 0.2 to about 5% sodium phosphate salt,
    wherein the hydrogel comprises a PEG hydrogel network formed by crosslinking 4a20kPEG-SAZ and 8a20kPEG-$NH_2$ precursors,
    wherein the implant in its dried state has a width of from 0.20 to 0.40 mm, and in its hydrated state (after 24 hours in PBS at a pH of 7.4 at 37° C.) has a length of 11 mm or less,
    and wherein the implant has a hydrated surface area of from 10 to 30 $mm^2$.
430. The sustained release biodegradable ocular implant of item 429, having a composition on a dry basis (in % w/w) of from about 50% to about 70% by weight axitinib, and from about 25% to about 45% by weight PEG units, and on a wet basis (in % w/w) of from about 7% to about 17% by weight axitinib, and from about 5% to about 10% by weight PEG units,
    wherein the implant in its dried state has a width of from 0.30 to 0.36 mm, and in its hydrated state (after 24 hours in PBS at a pH of 7.4 at 37° C.) has a length of 10.5 mm or less, and wherein the implant has a hydrated surface area of from 16 to 25 $mm^2$.
431. A sustained release biodegradable intravitreal implant comprising a hydrogel and axitinib, wherein axitinib particles are dispersed within the hydrogel,
    wherein the implant comprises axitinib polymorph IV in an amount of from about 400 μg to about 500 μg, wherein the hydrogel comprises a PEG hydrogel network formed by crosslinking 4a20kPEG-SAZ and 8a20kPEG-$NH_2$ precursors,
    wherein the implant in its dried state has a width of from 0.30 to 0.36 mm, and in its hydrated state (after 24 hours in PBS at a pH of 7.4 at 37° C.) has a length of 10.5 mm or less, and wherein the implant has a hydrated surface area of from 16 to 25 $mm^2$.
432. A sustained release biodegradable intravitreal implant comprising a hydrogel and axitinib, wherein axitinib particles are dispersed within the hydrogel,
    wherein the implant comprises axitinib polymorph IV in an amount of from about 400 μg to about 500 μg, wherein the hydrogel comprises a PEG hydrogel,
    wherein the implant in its dried state has a width of from 0.30 to 0.36 mm and has a hydrated (after 24 hours in PBS at a pH of 7.4 at 37° C.) surface area of from 16 to 25 $mm^2$, and wherein the implant provides for a release of axitinib in an in vitro test performed at 35° C.±0.5° C. in 0.01N HCl with 0.25% cetyl trimethyl ammonium bromide (CTAB) in a USP apparatus 4 that is characterized in that the percentage of axitinib released from the implant is:
    from 10 to 18% after 0.5 hours,
    from 30 to 45% after 2 hours,
    from 60 to 80% after 6 hours,
    from 79 to 98% after 10 hours,
    at least 90% after 12 hours,
    and at least 92% after 16 hours,
    wherein the percentage of released axitinib is based on 450 μg axitinib representing 100%.
433. A sustained release biodegradable intravitreal implant comprising a hydrogel and axitinib, wherein axitinib particles are dispersed within the hydrogel,
    wherein the implant comprises axitinib polymorph IV in an amount of from about 400 μg to about 500 μg, wherein the hydrogel comprises a PEG hydrogel network formed by crosslinking 4a20kPEG-SAZ and 8a20kPEG-$NH_2$ units,
    wherein the implant in its dried state has a width of from 0.20 to 0.40 mm, and in its hydrated state (after 24 hours in PBS at a pH of 7.4 at 37° C.) has a length of 11 mm or less, and wherein the implant provides for a release of axitinib in an in vitro test performed at 35° C.±0.5° C. in 0.01N HCl with 0.25% cetyl trimethyl ammonium bromide (CTAB) in a USP apparatus 4 that is characterized in that the percentage of axitinib released from the implant is:
    from 10 to 18% after 0.5 hours,
    from 30 to 45% after 2 hours,
    from 60 to 80% after 6 hours,
    from 79 to 98% after 10 hours,
    at least 90% after 12 hours,
    and at least 92% after 16 hours,
    wherein the percentage of released axitinib is based on 450 μg axitinib representing 100%.
434. A method of treating an ocular disease in a patient in need thereof, wherein the treatment comprises injection of the sustained release biodegradable ocular implant of any of items 429 to 433 into the vitreous humor of an eye of a patient in need of such treatment, and wherein the maximum concentration of axitinib in the retina or the choroid/RPE is reached before the hydrogel finally biodegrades.
435. The method of item 434, wherein the patient is a human patient, and the ocular disease is wet AMD.

436. The method of item 434 or 435, wherein the treatment period with one implant is about 6 to 12 months, such as about 9 months.
437. The method of item 436, wherein a new implant is injected after the treatment period.
438. The method of any of items 265 to 361, 378 to 428, and 434 to 437, wherein the sustained release biodegradable ocular implant is an implant according to any of items 1 to 199, 372 to 377, 388 to 409, 412 to 419, and 427 to 433.
439. The method of any of items 265 to 361, 378 to 428, and 434 to 437, wherein the method is as further defined in any of items 200 to 226.
440. A sustained release biodegradable ocular implant for use in a method of item 438 or 439.
441. Use of a sustained release biodegradable ocular implant according to any of items 1 to 199, 372 to 377, 388 to 409, 412 to 419, and 427 to 433 in the preparation of a medicament for use in a method of any of items 200 to 226, 265 to 361, 378 to 428, and 434 to 437.

EXAMPLES

The following Examples are included to demonstrate certain aspects and embodiments of the invention as described in the claims. It should be appreciated by those of skill in the art, however, that the following description is illustrative only and should not be taken in any way as a restriction of the invention.

Example A: Overview of Implants are Provided in Table 1A, Table 1B, Table 1C and Table 1D Below

TABLE 1

Overview of implants

| Implant type | | Implant #1 | Implant #2 | Implant #3 | Implant # 3* | Implant #8 | Implant #9 | Implant #10 |
|---|---|---|---|---|---|---|---|---|
| Axitinib Type | Polymorph | SAB-I Non Micronized | SAB-I Micronized | SAB-I Micronized | SAB-I Micronized | Polymorph IV micronized | Polymorph IV micronized | Polymorph IV micronized |
| | PSD (μm) Range ± 10% | D10 6.3, D50 16.2, D90 42.5 | D10 0.2, D50 2.2, D90 6.1 | D10 0.2, D50 2.2, D90 6.1 | D10 0.2, D50 2.2, D90 6.1 | D10 0.2, D50 2.5, D90 7.5 | D10 0.2, D50 2.5, D90 7.5 | D10 0.2, D50 2.5, D90 7.5 |
| | Actual or theoretical | Actual | Actual | Actual | Actual | Actual | Actual | Actual |
| (% dry basis w/w) | Axitinib | 49.40% | 52.10% | 68.60% | 68.60% | 52.10% | 21.70% | 62.50% |
| | Target Dose | 200 μg | 300 μg | 600 μg | 600 μg | 300 μg | 150 μg | 600 μg |
| | Actual Dose | 203 μg | 309 μg | 679 μg | 679 μg | 322 μg | 143 μg | 608 μg |
| | PEG Hydrogel | 42.00% | 39.90% | 26.00% | 26.00% | 39.90% | 65.20% | 31.20% |
| | 4a20K PEG-SAZ | 28.00% | 26.60% | 17.33% | 17.33% | 26.60% | 43.50% | 20.80% |
| | 8a20K PEG-NH2 | 14.00% | 13.30% | 8.67% | 8.67% | 13.30% | 21.70% | 10.40% |
| | TLA | 0.00% | 0.00% | 0.00% | 0.00% | 0.00% | 0.00% | 0.00% |
| | Co-Crystal | 0.00% | 0.00% | 0.00% | 0.00% | 0.00% | 0.00% | 0.00% |
| | Sodium phosphate | 8.60% | 8.00% | 5.40% | 5.40% | 8.00% | 13.00% | 6.30% |
| % wet basis (w/w) | Axitinib | 7.50% | 9.80% | 16.50% | 16.50% | 9.80% | 2.50% | 15.00% |
| | PEG Hydrogel | 6.90% | 7.50% | 6.30% | 6.30% | 7.50% | 7.50% | 7.50% |
| | 4a20K PEG-SAZ | 4.60% | 5.00% | 4.20% | 4.20% | 5.00% | 5.00% | 5.00% |
| | 8a20K PEG-NH2 | 2.30% | 2.50% | 2.10% | 2.10% | 2.50% | 2.50% | 2.50% |
| | TLA | 0.00% | 0.00% | 0.00% | 0.00% | 0.00% | 0.00% | 0.00% |
| | Co-Crystal | 0.00% | 0.00% | 0.00% | 0.00% | 0.00% | 0.00% | 0.00% |
| | Sodium phosphate | 1.50% | 1.50% | 1.30% | 1.30% | 1.50% | 1.50% | 1.50% |
| Configuration | Stretching Method | Dry | NA | Wet | Wet | NA | NA | Wet |
| | (Stretch Factor) | 4.5 | NA | 2.1 | 2.1 | NA | NA | 2 |
| Dimensions | Dry Diameter | 0.24 ± 0.013 mm | 0.30 ± 0.013 mm | 0.37 ± 0.008 mm | 0.354 ± 0.010 | 0.31 ± 0.005 mm | 0.33 ± 0.010 mm | 0.35 ± 0.014 mm |
| | Dry Length | 16.5 ± 0.26 mm | 7.1 ± 0.03 mm | 7.4 ± 0.03 mm | 7.53 ± 0.031 | 7.0 ± 0.08 mm | 7.7 ± 0.09 mm | 8.9 ± 0.95 mm |
| | Dry Implant Mass | 0.45 mg | 0.58 mg | 0.88 ± 0.01 mg | 0.99 mg | 0.58 mg | 0.69 mg | 0.96 mg |
| | Wet Diameter | 0.75 mm | 0.63 mm | 0.77 mm | 0.733 ± 0.024 | 0.64 mm | 0.92 mm | 0.72 mm |
| | Wet Length | 7.5 mm | 9.4 mm | 6.8 mm | 7.66 ± 0.18 *same as implant #3 but different dimensions | 9.6 mm | 11.4 mm | 9.7 mm |

TABLE 1-continued

Overview of implants

| Implant type | | Implant #11 | Implant #11.1 | Implant #11.2 | Implant #12 | Implant #13 | Implant #14 |
|---|---|---|---|---|---|---|---|
| Axitinib Type | Polymorph | SAB-I Micronized (HME) | SAB-I Micronized (HME) | Polymorph IV Micronized (HME) | SAB-I Super Micronized | Polymorph IV Nanonized | Co-Crystal - Fumaric Acid |
| | PSD (μm) Range ± 10% | D10 0.2, D50 2.2, D90 6.1 | D10 0.2, D50 2.2, D90 6.1 | D10 0.2, D50 2.5, D90 7.5 | D10 0.17, D50 1.4, D90 4.0 | D10 0.07, D50 0.15, D90 0.30 | NA |
| | Actual or theoretical | Actual | Actual | Theoretical | Actual | Theoretical | Theoretical |
| (% dry basis w/w) | Axitinib | 69.00% | 39.80% | 65.00% | 64.8% | 68.60% | 34.30% |
| | Target Dose | 600 μg | 220 μg | 450 μg | 600 μg | 600 μg | 300 μg |
| | Actual Dose | 614 μg | 220 μg | 450 μg | 692 μg | 600 μg | 300 μg |
| | PEG Hydrogel | 27.00% | 57.50% | 33.00% | 29.40% | 26.00% | 26.00% |
| | 4a20K PEG-SAZ | 27.00% | 57.50% | 33.00% | 19.60% | 17.33% | 17.33% |
| | 8a20K PEG-NH2 | 0.00% | 0.00% | 0.00% | 9.80% | 8.67% | 8.67% |
| | TLA | 0.79% | 1.68% | 0.96% | 0.00% | 0.00% | 0.00% |
| | Co-Crystal | 0.00% | 0.00% | 0.00% | 0.00% | 0.00% | 34.30% |
| | Sodium phosphate | 3.21% | 1.00% | 1.00% | 5.70% | 5.40% | 5.40% |
| % wet basis (w/w) | Axitinib | 14.04% | 6.09% | NA | 16.50% | 16.50% | 8.25% |
| | PEG Hydrogel | 5.49% | 9.05% | NA | 7.50% | 6.30% | 6.30% |
| | 4a20K PEG-SAZ | NA | 8.80% | NA | 5.00% | 4.20% | 4.20% |
| | 8a20K PEG-NH2 | 0.00% | 0.00% | NA | 2.50% | 2.10% | 2.10% |
| | TLA | 0.16% | 0.26% | NA | 0.00% | 0.00% | 0.00% |
| | Co-Crystal | 0.00% | 0.00% | NA | 0.00% | 0.00% | 8.25% |
| | Sodium phosphate | 0.65% | 0.15% | NA | 1.45% | 1.30% | 1.30% |
| Configuration | Stretching Method | NA | NA | NA | Wet | Wet | Wet |
| | (Stretch Factor) | NA | NA | NA | 2.1 | 2.1 | 2.1 |
| Dimensions | Dry Diameter | 0.44 mm | 0.32 mm | 0.35 mm | 0.36 mm | 0.37 mm | 0.37 mm |
| | Dry Length | 4.3 mm | 8.4 mm | 6.0 mm | 7.9 mm | 8.4 mm | 8.4 mm |
| | Dry Implant Mass | 0.89 mg | 0.77 mg | 0.69 mg | 0.96 mg | 0.95 mg | 0.95 mg |
| | Wet Diameter | 1.01 mm | 0.58 mm | 0.60 mm | 0.84 mm | 0.68 mm | 0.68 mm |
| | Wet Length | 6.51 mm | 14.0 mm | 10.0 mm | 6.8 mm | 8.23 mm | 8.23 mm |

| Implant type | | Implant #15 | Implant #16 | Implant #17 | Implant #18 | Implant #19 | Implant #20 | Implant #21 | Implant #22 |
|---|---|---|---|---|---|---|---|---|---|
| Axitinib Type | Supplier | Pro Drug | SAB-I Micronized (HME-HST 3 filaments/implants) | Polymorph IV Micronized | SAB-I Micronized | SAB-I Micronized | SAB-I Micronized HST × 7 filaments/implants | SAB-I Micronized HST × 3 filaments/implants | SAB-I Micronized 5-arm Star |
| | PSD (um) Range ± 10% | NA | D10 0.2, D50 2.2, D90 6.1 | D10 0.2, D50 2.5, D90 7.5 | D10 0.2, D50 2.2, D90 6.1 | D10 0.2, D50 2.2, D90 6.1 | D10 0.2, D50 2.2, D90 6.1 | D10 0.2, D50 2.2, D90 6.1 | D10 0.2, D50 2.2, D90 6.1 |
| | Actual or theoretical | Theoretical | Actual | Actual | Actual | Actual | Actual | Actual | Actual |
| (% dry basis w/w) | Axitinib | 68.60%* (prodrug) | 39.80% | 64.3% | 64.3% | 64.3% | 39.60% | 55.0% | 64.3% |
| | Target Dose | 390 μg | 600 μg | 600 μg | 600 μg | 450 μg | 600 μg | 300 μg | 600 μg |
| | Actual Dose | 390 μg | 684 μg | 570 μg | 610 μg | 450 μg | 520 μg | 367 μg | 640 μg |
| | PEG Hydrogel | 26.00% | 57.50% | 29.20% | 29.20% | 29.20% | 49.50% | 37.50% | 29.20% |
| | 4a20K PEG-SAZ | 17.33% | 57.50% | 19.50% | 19.50% | 19.50% | 33.00% | 25.00% | 19.50% |
| | 8a20K PEG-NH2 | 8.67% | 0.00% | 9.70% | 9.70% | 9.70% | 16.50% | 12.50% | 9.70% |
| | TLA | 0.00% | 1.68% | 0.00% | 0.00% | 0.00% | 0.00% | 0.00% | 0.00% |
| | Co-Crystal | 0.00% | 0.00% | 0.00% | 0.00% | 0.00% | 0.00% | 0.00% | 0.00% |
| | Sodium phosphate | 5.40% | 1.00% | 6.50% | 6.50% | 6.50% | 10.9% | 7.5% | 6.50% |

TABLE 1-continued

Overview of implants

| | | | | | | | | | |
|---|---|---|---|---|---|---|---|---|---|
| (% wet basis w/w) | Axitinib | 16.50%* (prodrug) | 6.09% | 16.50% | 16.50% | 16.50% | 6.00% | 11.00% | 16.50% |
| | PEG Hydrogel | 6.30% | 9.05% | 7.50% | 7.50% | 7.50% | 7.50% | 7.50% | 7.50% |
| | 4a20K PEG-SAZ | 4.20% | 8.80% | 5.00% | 5.00% | 5.00% | 5.00% | 5.00% | 5.00% |
| | 8a20K PEG-NH2 | 2.10% | 0.00% | 2.50% | 2.50% | 2.50% | 2.50% | 2.50% | 2.50% |
| | TLA | 0.00% | 0.26% | 0.00% | 0.00% | 0.00% | 0.00% | 0.00% | 0.00% |
| | Co-Crystal | 0.00% | 0.00% | 0.00% | 0.00% | 0.00% | 0.00% | 0.00% | 0.00% |
| | Sodium phosphate | 1.30% | 0.15% | 1.65% | 1.65% | 1.65% | 1.65% | 1.50% | 1.65% |
| Configuration | Stretching Method | Wet | Heat-Stretch-Twist | Wet | Wet | Wet | NA | Heat-Stretch-Twist | Heat-Stretch Twist |
| | (Stretch Factor) | 2.1 | NA | 2.1 | 2.1 | 2.4 | NA | NA | NA |
| Dimensions | Dry Diameter | 0.37 mm | 0.63 mm | 0.37 mm | 0.40 mm | 0.289 mm | 0.15 mm (per filament/implant) | 0.32 mm (per bundle) | 0.64 mm |
| | Dry Length | 8.4 mm | 6.9 mm | 8.0 mm | 8.0 mm | 10.0 mm | 6.8 mm (per filament/implant) | 10.0 mm (per bundle) | 7.6 mm |
| | Dry Implant Mass | 0.95 mg | 2.62 mg | 0.95 mg | 0.91 mg | 0.69 mg | 0.19 mg (per filament/implant) | 0.67 mg (per bundle) | 0.96 mg |
| | Wet Diameter | 0.68 mm | 0.58 mm | 0.92 mm | 0.90 mm | 0.55 mm | 0.38 mm (per filament/implant) | Did not unfurl | NA |
| | Wet Length | 8.23 mm | 11.6 mm | 7.7 mm | 7.5 mm | 9.6 mm | 9.5 mm (per filament/implant) | 10.1 mm (per filament/implant) | 10.1 mm |

| Implant type | | Implant #23 | Implant #24 | Implant #25 | Implant #26 | Implant #27 | Implant #28 |
|---|---|---|---|---|---|---|---|
| Axitinib Type | Supplier | Polymorph IV Micronized 5-arm Star | Polymorph IV Micronized | Polymorph IV Micronized | Polymorph IV Micronized | SAB-I Micronized | SAB-I Micronized |
| | PSD (um) Range ± 10% | D10 0.2, D50 2.5, D90 7.5 | D10 0.2, D50 2.5, D90 7.5 | D10 0.2, D50 2.5, D90 7.5 | D10 0.2, D50 2.5, D90 7.5 | D10 0.2, D50 2.2, D90 6.1 | D10 0.2, D50 2.2, D90 6.1 |
| | Actual or theoretical | Actual | Actual | Theoretical | Theoretical | Actual | Actual |
| (% dry basis w/w) | Axitinib | 52.6% | 54.10% | 54.10% | 54.10% | 64.3% | 64.3% |
| | Target Dose | 300 µg | 450 µg | 450 µg | 500 µg | 600 µg | 300 µg |
| | Actual Dose | 325 µg | 465 µg | 400 µg | 500 µg | 597 µg | 307 µg |
| | PEG Hydrogel | 39.50% | 38.70% | 38.70% | 38.70% | 29.20% | 29.20% |
| | 4a20K PEG-SAZ | 26.30% | 25.80% | 25.80% | 25.80% | 19.50% | 19.50% |
| | 8a20K PEG-NH2 | 13.20% | 12.90% | 12.90% | 12.90% | 9.70% | 9.70% |
| | TLA | 0.00% | 0.00% | 0.00% | 0.00% | 0.00% | 0.00% |
| | Co-Crystal | 0.00% | 0.00% | 0.00% | 0.00% | 0.00% | 0.00% |
| | Sodium phosphate | 7.9% | 7.20% | 7.20% | 7.20% | 6.50% | 6.50% |
| (% wet basis w/w) | Axitinib | 10.00% | 9.50% | 9.50% | 9.50% | 16.50% | 16.50% |
| | PEG Hydrogel | 7.50% | 6.80% | 6.80% | 6.80% | 7.50% | 7.50% |
| | 4a20K PEG-SAZ | 5.00% | 4.50% | 4.50% | 4.50% | 5.00% | 5.00% |
| | 8a20K PEG-NH2 | 2.50% | 2.30% | 2.30% | 2.30% | 2.50% | 2.50% |
| | TLA | 0.00% | 0.00% | 0.00% | 0.00% | 0.00% | 0.00% |
| | Co-Crystal | 0.00% | 0.00% | 0.00% | 0.00% | 0.00% | 0.00% |
| | Sodium phosphate | 1.50% | 1.30% | 1.30% | 1.30% | 1.65% | 1.65% |

TABLE 1-continued

Overview of implants

| | | | | | | | |
|---|---|---|---|---|---|---|---|
| Configuration | Stretching Method | Heat-Stretch-Twist | Wet | Wet | Wet | Wet | Wet |
| | (Stretch Factor) | NA | 1.5 | 1.5 | 1.5 | 2.1 | 2.1 |
| Dimensions | Dry Diameter | NA | 0.352 mm | 0.352 mm | 0.352 mm | 0.38 mm | 0.38 mm |
| | Dry Length | NA | 7.09 mm | 6.3 mm | 7.9 mm | 8.4 mm | 4.5 mm |
| | Dry Implant Mass | 0.62 mg | 0.87 mg | 0.75 mg | 0.93 mg | 0.93 mg | 0.47 mg |
| | Wet Diameter | Did not unfurl | 0.738 mm | 0.738 mm | 0.738 mm | 0.66 mm | 0.66 mm |
| | Wet Length | 10.3 mm | 8.14 mm | 7.2 mm | 9.0 mm | 8.3 mm | 4.4 mm |

| Implant type | | Implant #29 | Implant #29a | Implant #30 | Implant #30a | Implant #31 | Implant #31a |
|---|---|---|---|---|---|---|---|
| Axitinib Type | Supplier | Polymorph IV Micronized | Polymorph IV Micronized | Polymorph IV Micronized | Polymorph IV Micronized | Polymorph IV Micronized | Polymorph IV Micronized |
| | PSD (um) Range ± 10% | D10 0.2, D50 2.5, D90 7.5 | D10 0.2, D50 2.5, D90 7.5 | D10 0.2, D50 2.5, D90 7.5 | D10 0.2, D50 2.5, D90 7.5 | D10 0.2, D50 2.5, D90 7.5 | D10 0.2, D50 2.5, D90 7.5 |
| | Actual or Theoretical | Theoretical | Actual | Theoretical | Actual | Theoretical | Theoretical |
| (% dry basis w/w) | Axitinib | 54.00% | 54.00% | 63.74% | 63.74% | 63.46% | 63.94% |
| | Actual Dose | 457 µg | 457 µg | 479 µg | 479 µg | 450 µg | 450 µg |
| | Target Dose | 450 µg | 450 µg | 450 µg | 450 µg | 450 µg | 450 µg |
| | PEG Hydrogel | 38.60% | 38.60% | 30.58% | 30.58% | 30.5% | 30.73% |
| | 4a20K PEG-SAZ | 25.70% | 25.70% | 20.39% | 20.39% | 20.3% | 20.49% |
| | 8a20K PEG-NH2 | 12.90% | 12.90% | 10.19% | 10.19% | 10.2% | 10.24% |
| | TLA | 0.00% | 0.00% | 0.00% | 0.00% | 0.00% | 0.00% |
| | Co-Crystal | 0.00% | 0.00% | 0.00% | 0.00% | 0.00% | 0.00% |
| | Sodium phosphate | 8.60% | 7.40% | 5.40% | 5.40% | 7.40% | 5.33% |
| (% wet basis w/w) | Axitinib | 7.50% | 9.50% | 16.50% | 13.51% | 9.50% | 13.50% |
| | PEG Hydrogel | 6.90% | 6.80% | 6.30% | 6.48% | 6.80% | 6.49% |
| | 4a20K PEG-SAZ | 4.60% | 4.53% | 4.20% | 4.32% | 4.53% | 4.33% |
| | 8a20K PEG-NH2 | 2.30% | 2.27% | 2.10% | 2.16% | 2.27% | 2.16% |
| | TLA | 0.00% | 0.00% | 0.00% | 0.00% | 0.00% | 0.00% |
| | Co-Crystal | 0.00% | 0.00% | 0.00% | 0.00% | 0.00% | 0.00% |
| | Sodium phosphate | 1.50% | 1.30% | 1.30% | 1.21% | 1.30% | 1.12% |
| Configuration | Stretching Method | Wet | Wet | Wet | Wet | Wet | Wet |
| | (Stretch Factor) | 1.5 | 1.5 | 1.5 | 1.5 | 1.4 (1.3-1.6) | 1.4 |
| Dimensions | Dry Diameter | 0.364 mm | 0.360 mm | 0.327 mm | 0.327 mm | 0.31-0.33 mm | 0.31-0.33 mm |
| | Dry Length | 6.97 mm | 7.00 mm | 7.13 mm | 7.13 mm | 6-9 mm | 6-9 mm |
| | Dry Implant Mass | 0.83 mg | 0.83 mg | 0.88 mg | 0.75 mg | 0.71 mg | 0.71 mg |
| | Wet Diameter | 0.797 mm | 0.797 mm | 0.650 mm | 0.650 mm | 0.5-0.9 mm | 0.5-0.9 mm |
| | Wet Length | 7.79 mm | 7.79 mm | 8.50 mm | 8.50 mm | 6-9.5 mm | 6-9.5 mm |

| Implant type | | Implant #32 | Implant # 35 | Implant # 36 | Implant # 37 |
|---|---|---|---|---|---|
| Axitinib Type | Supplier | Polymorph IV Micronized | Polymorph IV Nanonized* | Axitinib ProDrug* | SAB-I Micronized |
| | PSD (um) Range ± 10% | D10 0.2, D50 2.5, D90 7.5 | D10 0.2 D50 3.1* D90 17.2* | D10 0.4 D50 4.4 D90 11.6 | D10 0.2, D50 2.2, D90 6.1 |
| | Actual or Theoretical | Actual | Actual | Actual | Actual |
| (% dry basis w/w) | Axitinib | 63.90% | 63.94% | 64.72%* (prodrug) | 63.95% |
| | Actual Dose | 462 µg | 447 µg | 437 µg | 448 µg |
| | Target Dose | 450 µg | 450 µg | 450 µg | 450 µg |
| | PEG Hydrogel | 30.70% | 30.73% | 30.06% | 30.74% |
| | 4a20K PEG-SAZ | 20.50% | 20.49% | 20.04% | 20.50% |

TABLE 1-continued

| Overview of implants | | | | | |
|---|---|---|---|---|---|
| | 8a20K PEG-NH2 | 10.20% | 10.24% | 10.02% | 10.24% |
| | TLA | 0.00% | 0.00% | 0.00% | 0.00% |
| | Co-Crystal | 0.00% | 0.00% | 0.00% | 0.00% |
| | Sodium phosphate | 5.30% | 5.33% | 5.22% | 5.31% |
| % wet basis w/W) | Axitinib | 13.50% | 13.50% | 13.34%* (prodrug) | 13.50% |
| | PEG Hydrogel | 6.50% | 6.49% | 6.20% | 6.49% |
| | 4a20K PEG-SAZ | 4.30% | 4.33% | 4.13% | 4.33% |
| | 8a20K PEG-NH2 | 2.20% | 2.16% | 2.07% | 2.16% |
| | TLA | 0.00% | 0.00% | 0.00% | 0.00% |
| | Co-Crystal | 0.00% | 0.00% | 0.00% | 0.00% |
| | Sodium phosphate | 1.10% | 1.13% | 1.08% | 1.12% |
| Config-uration | Stretching Method | Wet | Wet | Wet | Wet |
| | (Stretch Factor) | 1.4 | 1.4 | 1.0 | 1.5 |
| Dimen-sions | Dry Diameter | 0.33 mm | 0.33 mm | 0.40 mm | 0.33 mm |
| | Dry Length | 6.80 mm | 6.98 mm | 4.75 mm | 7.00 mm |
| | Dry Implant Mass | 0.71 mg | 0.74 mg | 0.68 mg | 0.71 mg |
| | Wet Diameter | 0.67 mm | 0.63 mm | 0.73 mm | 0.74 mm |
| | Wet Length | 7.83 mm | 8.03 mm | 6.32 mm | 7.59 mm |
| | | | * particle size distribution showed two peaks due to agglomeration | *(axitinib-N-m$(PEG)_2$-oxymethyl prodrug of Ex. 5.2) | |

| Implant type | | Implant #38 | Implant #39 | Implant #40 |
|---|---|---|---|---|
| Axitinib Type | Supplier | Polymorph IV Micronized | Polymorph IV Micronized | SAB-I Micronized (HST 3 Implants) |
| | PSD (um) Range ± 10% | D10 0.2, D50 2.5, D90 7.5 | D10 0.2, D50 2.5, D90 7.5 | D10 0.2, D50 2.2, D90 6.1 |
| | Actual or Theoretical | Actual | Actual | Actual |
| (% dry basis w/w) | Axitinib | 63.95% | 66.72% | 44.90% |
| | Actual Dose | 469 µg | 468 µg | 409 µg |
| | Target Dose | 450 µg | 450 µg | 450 µg |
| | PEG Hydrogel | 30.73% | 28.37% | 48.10% |
| | 4a20K PEG-SAZ | 20.47% | 18.89% | 32.10% |
| | 8a20K PEG-NH2 | 10.26% | 9.48% | 16.00% |
| | TLA | 0.00% | 0.00% | 0.00% |
| | Co-Crystal | 0.00% | 0.00% | 0.00% |
| | Sodium phosphate | 5.32% | 4.91% | 7.10% |
| (% wet basis w/w) | Axitinib | 13.49% | 14.97% | 7.00% |
| | PEG Hydrogel | 6.48% | 6.37% | 7.50% |
| | 4a20K PEG-SAZ | 4.32% | 4.24% | 5.00% |
| | 8a20K PEG-NH2 | 2.17% | 2.13% | 2.50% |
| | TLA | 0.00% | 0.00% | 0.00% |
| | Co-Crystal | 0.00% | 0.00% | 0.00% |
| | Sodium phosphate | 1.12% | 1.10% | 1.10% |
| Config-uration | Stretching Method | Wet | Wet | Wet |
| | (Stretch Factor) | 2.0 | 1.8 | 1.7 (during HST) |
| Dimen-sions | Dry Diameter | 0.27 mm | 0.26 mm | 0.37 mm (per bundle) |
| | Dry Length | 9.57 mm | 9.91 mm | 8.94 mm (per bundle) |
| | Dry Implant Mass | 0.76 mg | 0.70 mg | 1.05 mg (per bundle) |
| | Wet Diameter | 0.66 mm | 0.48 mm | 0.54 mm (per implant when unfurled) |
| | Wet Length | 9.01 mm | 9.95 mm | 7.31 mm (per implant when unfurled) |

Example 1: Exemplary Process of Preparing an Implant (Wet Cast Process/Single Strand)

Certain implants according to the present invention were formed by a wet casting process as follows:

The polymer network of the implants was formed by reacting 2 parts 4a20K PEG-SAZ (a 20 kDa PEG with 4 arms with a N-hydroxysuccinimidyl reactive end group, sometimes also referred to as "NHS" end group) with 1 part 8a20K PEG $NH_2$ (a 20 kDa PEG with 8 arms with an amine end group). Therefore, a polyurethane tubing was cut into appropriate length pieces, After that, an 8a20K PEG $NH_2$ sodium phosphate dibasic solution was prepared and (sterile) filtered to remove endotoxins as well as other particles over 0.2 μm (pore size of the filter). The desired volume of the PEG amine solution was then weighed into a syringe. Next, corresponding amounts of solid axitinib depending on the desired final axitinib dose in the implant were weighed into another syringe. The powdered axitinib syringe and the PEG amine syringe were mixed carefully to suspend and disperse the particles and the syringes were degassed. After that, a 4a20K PEG SAZ sodium phosphate monobasic solution was prepared and sterile filtered as described for the PEG amine solution. The desired volume of PEG SAZ solution was then weighed into another syringe. In the next step, the ingredients of both syringes (4a20K PEG SAZ sodium phosphate monobasic solution and axitinib-8a20K PEG $NH_2$ mixture) were mixed to initiate the reaction leading to gelation. The liquid suspension was cast through the prepared polyurethane tubing before the material cross-links and solidifies. Gelling time was confirmed by performing a gel tap test. The gel-comprising tubing was then placed at room temperature for 2 hours. In the chamber, the hydrogel axitinib suspension in the tubing was allowed to cross-link to completion creating a highly 20 reacted and uniform gel, thus forming a hydrogel strand.

After curing, different implant stretching methods were performed as disclosed herein. Implants were either dry stretched or wet stretched as outlined below. For dry stretching, strands were cut into shorter segments after curing and the strands were dried for 48 to 96 hours at 32° C. under nitrogen. After drying, dried strand segments were removed from the tubing and placed on clamps of a custom stretcher. The strands were then slowly dry stretched at a controlled rate to achieve the desired diameter that fits into a small gauge needle (stretch factor of about 2 to about 5, or about 3 to about 4.5). The stretching step was performed in an oxygen and moisture free environment to protect the product. For wet stretching, strands were placed on clamps of a custom stretcher. The strands were then slowly wet stretched at a controlled rate to achieve the desired diameter that fits into a small gauge needle (stretch factor of about 1 to about 3, or about 1.3 to about 2.6), After stretching, the strands were dried under tension under the conditions as described for the dry stretching process.

Stretched hydrogel strands were removed from the stretcher and then cut to the desired final length. The implant fibers were then placed on the inspection station. If the implants passed the quality control, they were loaded into a 25 or 27 gauge needle (e.g. an FDA-approved 25G UTW ½" having an inner diameter of about 0.4 mm, or a 25G UTW 1" or a 27G TW 1.25" needle) using a customized vacuum device and capped safely to avoid any needle tip damage.

The loaded needles were placed into a glove box for about 1 to about 10 days to remove any moisture (the remaining water content in the implant is intended to not exceed 1% water). All steps from then on were performed in the glove box. The loaded needle was dipped into a melted low-molecular weight 1 k PEG to tip the needle. The PEG-tipped needles were then again inspected, needles which did not meet the quality requirements were discarded, Passed needles were again capped to ensure the needles were not suffering any additional damage. Needles were then individually pouched and sealed to protect them from moisture and keep them sterile. The packaged needles and injection devices were removed from the glove box and stored refrigerated (2-8° C.) prior to sterilization using gamma irradiation. After sterilization the packages were stored refrigerated (2-8° C.) or frozen protected from light prior to use and were equilibrated 30 min to room temperature prior to injection.

Different implant geometries can be obtained by using tubing that has the respective desired inner geometry, such as a start-shaped geometry. FIG. 3 shows an image of a star shaped implant and exemplary calculation of its dimensions.

Example 2: Exemplary Process of Preparing an Implant (HME Process/Single Strand)

Certain implants according to the present invention were formed by a melt extrusion process as exemplarily disclosed herein, from the following raw materials: the reactive polymer precursors (4a20K PEG SAZ and trilysine acetate (TLA)), the TKI (in this case axitinib), and Sodium Phosphate Dibasic. Alternatively, the TLA can be substituted with a PEG amine salt.

These materials are first combined and mixed for 10 minutes in the melt or powder form to provide a homogenous pelletized, granulated or blended powder material. The combined material is then loaded into a MiniCTW melt extruder (Thermofisher, Inc.), which has been set to temperature (50-80° C.) and screw rotation speed (20-100 rpm).

The material may be recirculated within the barrel of the twin-screw mixing extruder for about 10 minutes to confirm homogeneity before extrusion. Material can then be extruded through the die of the extruder onto a conveyer belt at a speed of 1000 RPM (1.4 in/sec). The rate of drawing determines the diameter of the extrudate. Drawing keeps material straight and allows it to cool and harden before being cut away from the extruder and collected for downstream processing.

After extrusion, the material can be placed in a humidity chamber to crosslink, typically overnight, for a period of 16-24 hours. After crosslinking, the damp, rubbery material can be stretched to its final length and then dried overnight, at which point it is ready to be cut and inspected in the same manner it would be in a liquid casting process. The process is performed with the exclusion of water during extrusion, which facilitates activation of the PEG crosslinking reaction. The extrusion itself is run at low temperature, 50-80° C., since heat is not required to drive a crosslinking reaction. Exposure to a controlled water vapor environment (>95% humidity) after extrusion allows enough water to penetrate the strand to activate the curing reaction. The dampened strand, once crosslinked, is a rubber, which can be stretched at a stretch factor of e.g., 3×. Evaporative drying with nitrogen sweep leaves a semi-crystalline solid with the same molecular and physical structure of a wet cast implant, albeit not by casting.

Table 2 outlines these steps and considers exemplary equipment for each step as well as exemplary settings for each step.

TABLE 2

| Laboratory bench top process steps | | |
|---|---|---|
| Processing Step | Equipment/Material Required | Equipment/Material Specs |
| Material weights | 4a20K PEG SAZ<br>TLA<br>API<br>Sodium phosphate dibasic<br>Balance | 50%<br>24%<br>47%<br>1%<br>Analytical balance |
| Material melting/mixing | FlackTek SpeedMixer<br>Spatulas<br>Plastic cup | Mix powder for 2 × 30 second bursts at 1000 rpm |
| Extrusion | Thermo Fisher mini CTW extruder<br>Leistritz Nano-16 | Mini-CTW Extruder settings:<br>20 RPM mix/extrude<br>50-80° C. barrel temp |
| Conveying/uptake | Mini-mover conveyer Model/Part #: 20-02036-R-N U1 RI-050N-20-31 | Conveyer settings:<br>1000 RPM = 1.4 in/sec |
| Crosslinking | Passive ® Humidity Chamber or KMF115 (Binder humidity chamber)<br>Crosslinking Mesh<br>RO/DI<br>Extech Instruments RHT20<br>Humidity/Temperature Data logger | Humidity inside chamber: 100%<br>Crosslink time: 16-24 hrs |
| Stretching | Custom Stretcher (modular)<br>Humidity/drying chamber<br>Modified humidifier<br>Extech Instruments RHT20<br>Humidity/Temperature Data logger | Humidity chamber >95% humidity<br>Stretched slow and consistent in humidity chamber |
| Drying | Active humidity/drying chamber<br>Nitrogen | Convert chamber from active humidity chamber to drying chamber<br>Dry at flow of 20 SCFH overnight (16-24 hrs) |
| Downstream Processes | Cutting<br>Inspection<br>Packaging<br>Conditioning<br>Gamma | No changes have been made to these existing processes<br>Future improvements may be made |

Table 3 below outlines the in vitro release of two implants, one manufactured by wet casting (Example 1) and another by HME (present Example 2). The release was measured according to Method B (disclosed in Example 7). The release profile is shown in FIGS. 1A and 1B.

The implant characteristics are shown in Table 4 below.

TABLE 3

| Release profile of implants 2A and 2B | | | | | | | |
|---|---|---|---|---|---|---|---|
| Group | % API Dry | Assay (μg) | Ave Release (μg/day) | Ave Release (%/day) | Hydrated Length (mm) | Hydrated Width (mm) | Day Fully Released |
| 2A (wet casting) | 52 | 308 | 9.41 | 3.05% | 9.38 | 0.63 | 18 |
| 2B (HME) | 40 | 278 | 11.45 | 3.75% | 13.98 | 0.58 | 7 |

TABLE 4

| Implants 2A and 2B | | | |
|---|---|---|---|
| Implant | | 2A | 2B |
| Axitinib Type | Polymorph PSD (um) Range ± 10% | SAB-I Micronized D10 0.2, D50 2.2, D90 6.1 | SAB-I Micronized (HME) D10 0.2, D50 2.2, D90 6.1 |
| (% dry basis w/w) | Axitinib | 52.10% | 39.80% |
| | Dose | 300 µg | 220 µg |
| | Actual Dose | 308 µg | 278 µg |
| | PEG Hydrogel | 39.90% | 57.50% |
| | 4a20K PEG-SAZ | 26.60% | 57.50% |
| | 8a20K PEG-NH2 | 13.30% | 0.00% |
| | TLA | 0.00% | 1.68% |
| | Co-Crystal | 0.00% | 0.00% |
| | Sodium phosphate | 18.00% | 1.00% |
| (% wet basis w/w) | Axitinib | 9.80% | 16.09% |
| | PEG Hydrogel | 7.50% | 9.05% |
| | 4a20K PEG-SAZ | 5.00% | 18.80% |
| | 8a20K PEG-NH2 | 2.50% | 0.00% |
| | ITLA | 0.00% | 0.26% |
| | Fumaric | 0.00% | 0.00% |
| | Sodium phosphate | 1.50% | 0.15% |
| Configuration | Stretching Method | NA | INA |
| | (Stretch Factor) | NA | NA |
| Dimensions | Dry Diameter | 0.30 ± 0.013 mm | 0.32 mm |
| | Dry Length | 7.1 ± 0.03 mm | 8.4 mm |
| | Dry Implant Mass | 0.58 mg | 0.77 mg |
| | Wet Diameter | 0.63 mm | 0.58 mm |
| | Wet Length | 9.4 mm | 14.0 mm |

Example 3: Exemplary Process of Preparing an Implant (Heat-Stretch-Twist Process (HST)/Multi-Filament)

Multi-filament implants are produced from individual filaments (that are produced in accordance with the manufacturing methods disclosed in the previous examples, i.e., wet casting or hot melt extrusion) as follows:

The desired number of filaments (filaments obtained from wet casting or extrusion, i.e., not yet cut into the implant size) is combined and carefully secured between two clamps, without necking or pre-stretching the filaments.

The clamped filaments are then heated for a certain period of time, such as about 30 min, at an elevated temperature (e.g., 60 to 70° C.), for example in a heating chamber or heating tube.

Within this heating chamber or tube, the clamped filaments are first stretched by a pre-determined stretch factor (of e.g., from about 1 to about 4, such as 2), and then twisted at a pre-set twist time to obtain the desired numbers of twists per cm (of the final twisted implant). After that, the twisted filaments are removed from the heating chamber/tube and left to cool for a few minutes before they are cut to the desired length.

The heat-stretch-twist process can be performed with any implant or filament geometry, including round cross-section or also e.g. star-cross section.

Figure 2:
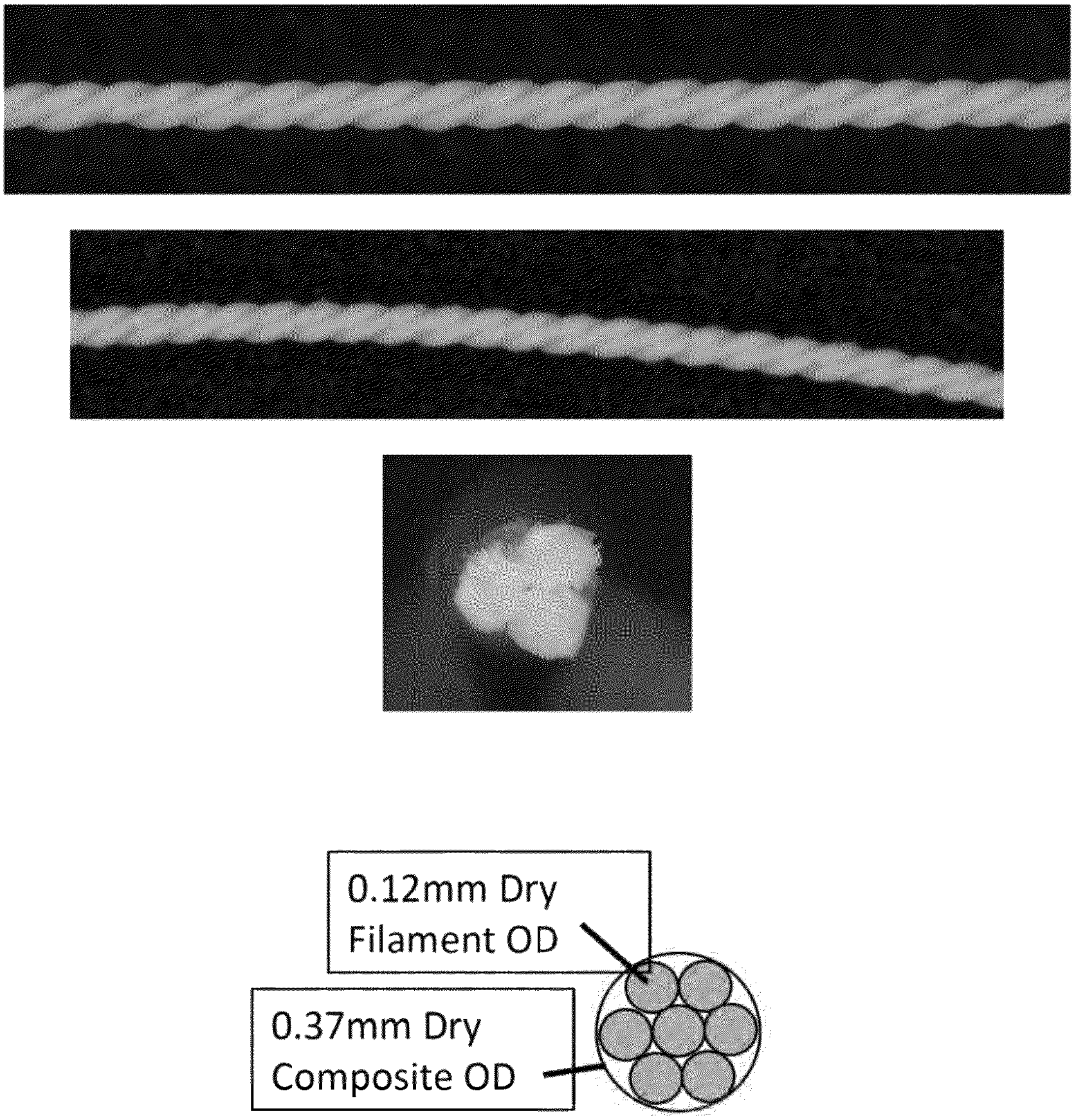
FIG. 2: Implant manufactured by HME (3× filament).

In this example 3 implants, each 0.2 mm diameter, were combined and heated at 73° C. for 35 minutes. 10 twists per cm were obtained at a stretch factor of 1.44×. The combined diameter was 0.33-0.38 mm. Individual implants were cut to the desired length from two multi-filament strands that had an original length of 15 cm each. These implants could be successfully loaded into a 25G needle, FIG. 2 shows an image of this multi-filament implant in the dry state. Upon hydration (such as in vivo or in vitro as described herein) the bundle of twisted filaments may unfurl to result in individual implants, each releasing active agent.

An exemplary braided or bundle-implant is implant #40 in Table 1D. In the case of implant #40, the individual filaments have been coated with a Kollicoat® coating before stretching and twisting as disclosed herein.

Example 4: Preparation of Axitinib Co-Crystals

Example 4.1: Slurry Experiments 3 slurry experiments were performed by weighing ca. 150 mg of free axitinib in 4 mL vials and adding the appropriate co-formers (CF), i.e., either citric acid (CA), fumaric acid (FA) or tartaric acid (TA) in 1:1 molar ratios API:CF (Table 5)

To each experiment a volume of 1.5 mL acetonitrile (ACN) was added, and the slurries were stirred for 3 days at 40° C. and ~1000 rpm. After the elapsed time, the solids were isolated by centrifuge filtration (nylon filters, 0.22 µm pore size, 10000 rpm for 3 min) and they were analyzed by XRPD.

The vials containing the recovered solids were dried at 40° C. under vacuum for 24 hours and reanalyzed by XRPD.

TABLE 5

Experimental conditions and observations of the 3 slurry experiments

| Exp. No. | Acid | Targeted form | Experimental Conditions to follow | $V_{solv}$ (mL) | Observations | XRPD on wet material | XRPD on dry material |
|---|---|---|---|---|---|---|---|
| 1 | Citric Acid | AXI-CA I | Slurry in ACN ~1000 rpm stirring, 40° C. | 1.5 | Yellow solids | AXI-CA I + pks. | AXI-CA I + pks. |
| 2 | Fumaric Acid | AXI-FA II | Slurry in ACN ~1000 rpm stirring, 40° C. | 1.5 | Pale yellow solids | AXI-FA III | AXI-FA IV |

TABLE 5-continued

| Experimental conditions and observations of the 3 slurry experiments | | | | | | | |
|---|---|---|---|---|---|---|---|
| Exp. No. | Acid | Targeted form | Experimental Conditions to follow | $V_{solv}$ (mL) | Observations | XRPD on wet material | XRPD on dry material |
| 3 | (+)-L-Tartaric acid | AXI-TA III | Slurry in ACN ~1000 rpm stirring, 40° C. | 1.5 | Yellow solids | Pattern 9 + pks. | AXI-TA III |

Figure 4:
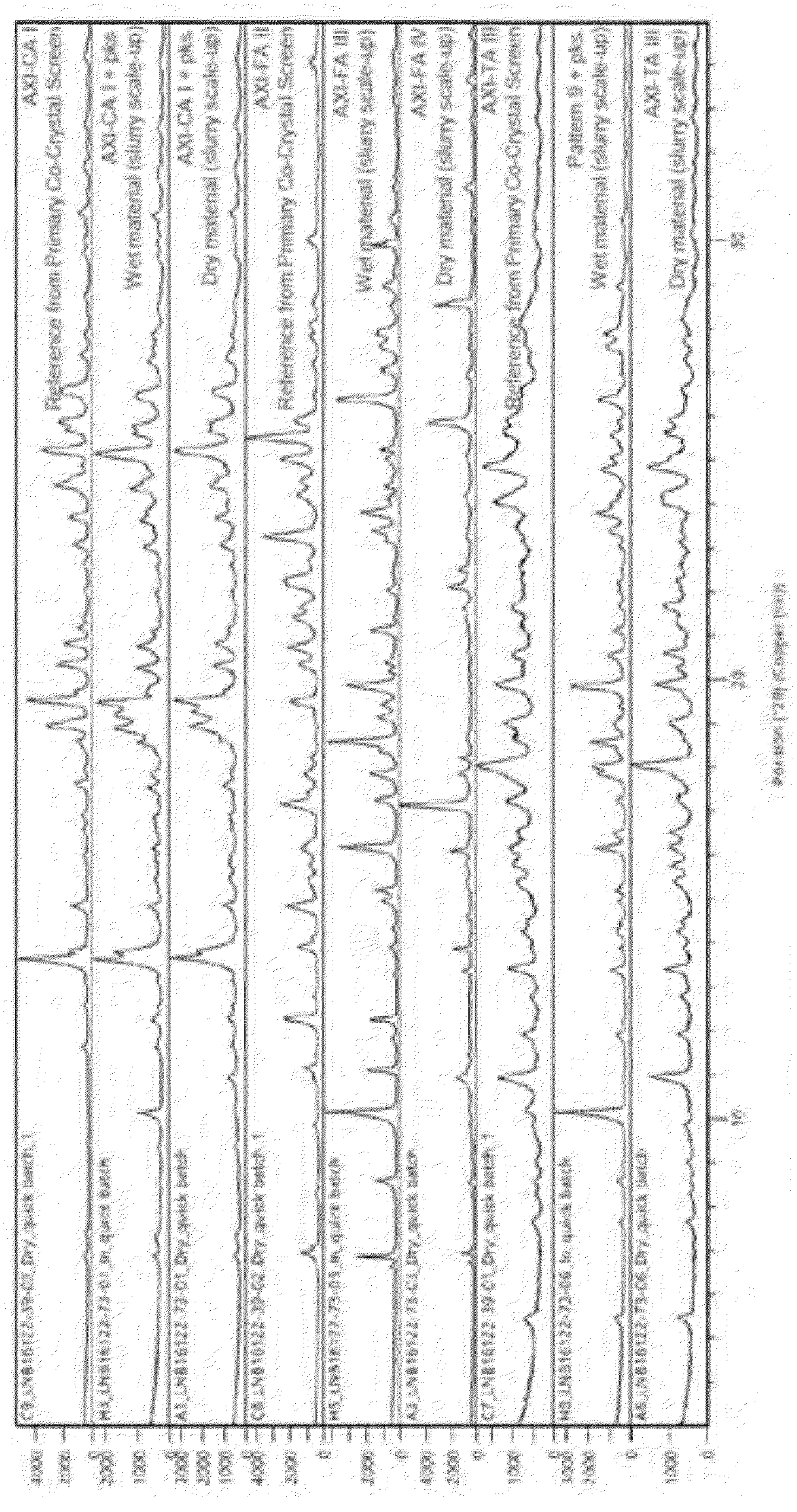
FIG. 4: XPRD results—peaks for citric acid, fumaric acid and tartaric acid.

The XRPD results are shown in FIG. 4. The experiment with citric acid yielded the desired form AXI-CA I with additional peaks for wet and dry solids. The experiment with fumaric acid yielded new crystalline forms-AXI-FA III for wet solids and AXI-FA IV for dry solids. The experiment with tartaric acid, yielded Pattern 9 with extra peaks for wet solids and the targeted co-crystal AXI-TA III on dry solids.

Example 4.2: Seeded Slurry Experiments 2 seeded experiments were performed in the case of the potential co-crystals with citric and fumaric acids (Table 6).

The procedure consisted in reprocessing the solids from the mini scale-up experiments and adding a small amount of AXI-CA I and AXI-FA II obtained in the Primary Co-crystal Screen.

To the mixture 1 mL of acetonitrile was added, and the mixtures were stirred for 24 hours at 40° C.

After the elapsed time, the solids were isolated by centrifuge filtration (nylon filters, 0.22 ym pore size, 10000 rpm for 3 min) and they were analyzed by XRPD.

The vials containing the recovered solids were dried at 40° C. under vacuum for 2 hours and reanalyzed by XRPD.

The purity and solubility in PBS, pH 7.4, were evaluated by HPLC.

TABLE 6

| Experimental conditions and observations of the 3 seeded slurry experiments | | | | | | | |
|---|---|---|---|---|---|---|---|
| Exp. No. | Acid | Targeted form | Experimental Conditions to follow | $V_{solv}$ (mL) | Observations | XRPD on wet material | XRPD on dry material |
| 1 | Citric Acid | AXI-CA I | Slurry in ACN with seeds of co-crystal AXI-CA I from the primary screen ~1000 rpm stirring, 40° C., 24 hours | 1 | Yellow solids | AXI-CA I + 1 pk. | AXI-CA I + pks. |
| 2 | Fumaric Acid | AXI-FA II | Slurry in ACN with seeds of co-crystal AXI-FA II from the primary screen ~1000 rpm stirring, 40° C., 24 hours | 1 | Pale yellow solids | AXI-FA II + AXI-FA III | AXI-FA II + A XI-FA III |
| 3 | (+) = Tartaric: acid | LAXI-TA III | Slurry in ACN ~1000 rpm stirring, 40° C. | 1.5 | Yellow solids | Pattern 9 + pks. | AXI-TA III |

The co-crystallization process with citric acid, fumaric acid, and tartaric acid provides for increased solubility in PBS under the indicated conditions (see Example 6.3 below).

Example 4.3: Glutaric Acid Co-Crystal

An overview of co-crystallization with glutaric acid is provided in Table 7 below

TABLE 7

Overview of experimental conditions for glutaric acid co-crystal

| Acid | Targeted form | Experimental Conditions to follow | Aspect/color | XRPD on wet material | XRPD on dry material | HPLC Purity (%) | Thermodynamic solubility in PBS, pH 7.4 (μg/mL) at 37° C. 2 hours | 4 hours | 24 hours |
|---|---|---|---|---|---|---|---|---|---|
| Glutarci acid | AXI-GA I | Grinding with EtOH : Bead mill Standard Program: Speed 4500 rpm Cycle 10 x 90s Pause 10s x 4 cycles | White solids | Pattern | AXI-GA I | 99.66 | < LOD | < LOD | < LOD |

Example 4.4: Stability Study

Stability studies of the co-crystals were performed as shown in Table 8 below. The results are also depicted in Table 8.

TABLE 8

Stability Studies of co-crystals and results

| Acid | Aspect/color | XRPD | TG/DSC | H NMR | XRPD post solubility | XRPD after stability | HPLC Initial purity (%) | HPLC Purity after stability studies 25° C./60% RH | 40° C./75% RH | 80° C. | Stability-3 days slurry in H2O (25° C.) and 4 days drying at 32° C./0% RH XRPD | HPLC |
|---|---|---|---|---|---|---|---|---|---|---|---|---|
| Citric Acid | Yellow solids | AXI-CA | DSC curve-1 endothermic. event: Onset Temperature = 192.8° C. Peak Temperature = 198.8° C. TG curve 0.85% mass loss (ca. 0.08 eq. ACN). | 1:1 ratio API: CF Residual solvent theoretically equal with ca. 0.01 eq. acetonitrile. | New crystal-line pattern. | 25° C./60% RH-AXI-CA low crystallinity 40° C./75% RH-AXI-CA I low crystallinity 80° C-AXI-CAI | 1st scale up: 97.9 2nd scale up: 95.77 | 90.78 | 93.23 | 86.88 | New crystalline pattern (common peaks with the pattern obtained from solubility in PBS) | 96.24 |
| Fumarc Acid | Pale yellow solids | AXI-FA II | DSC curve = 1 overlapped endothermic event: Onset Temperature = 199.7° C. Peak | 1:1.8 ratio API:CF Solvent theoretically equal with ca. 0.2 eq. acetonitrile | Pattern 1 + pks. | *25° C./60% RH-AXI-FA II with traces of AXI-FA II. *40° C./75% RH-AXI-FA II with traces of AXI-FA III. | 1st scale up: 99.91 2nd scale up: 99.81 | 99.60 | 99.64 | 99.47 | AXI-FA II + peaks | 99.76 |

TABLE 8-continued

Stability Studies of co-crystals and results

| Acid | Aspect/ color | XRPD | TG/DSC | H NMR | XRPD post solubility | XRPD after stability | HPLC: Initial purity (%) | HPLC: Purity after stability studies: 25° C./ 60% RH | HPLC: Purity after stability studies: 40° C./ 75% RH | HPLC: Purity after stability studies: 80° C. | Stability-3 days slurry in H2O (25° C.) and 4 days drying at 32° C./0% RH: XRPD | Stability-3 days slurry in H2O (25° C.) and 4 days drying at 32° C./0% RH: HPLC |
|---|---|---|---|---|---|---|---|---|---|---|---|---|
| | | | Temperature 210.8° C. TG curve 2.2% mass loss (ca. 0.21 eq. ACN). | | | *80° C-AXI-FA II with traces of AXI-FA III. | | | | | | |
| (+)-L Tartaric acid | Yellow solids | AXI-TA III | DSC curve-1 broad endothermic: event: Onset Temperature 162.3° C. Peak Temperature 178.5° C. TG curve = 2% mass loss (ca. 0.19 eq. ACN). | 1:1.06 ratio API:CF No residual solvent | Pattern 1 + pks. | 25° C./60% RH-AXI-TA low crystallinity, 40° C./75% RH-AXI-TA III 80° C.-AXI-TA III. | $1^{st}$ scale up: 99.53 $2^{nd}$ scale up: 98.79 | 96.66 | 96.24 | 93.24 | Pattern 30 | 97.50 |
| Glutaric acid | White solids | AXI-GA I | DSC curve-1 endothermic event: Onset Temperature = 179.9° C. Peak Temperature = 182.7° C. TG curve 1.2%\mass loss (ca. 0.1 eq. EtOH) | 1:1.06 ratio API:CF No residual solvent | Similar to Pattern 1 | 25° C./60% RH-AXI-GA I 40° C./75% RH-AXI-GAI 80° C -AXI-GA I low crystallinity | $1^{st}$ scale up: 99.66 $2^{nd}$ scale up: 99.76 | 90.81 | 99.31 | 99.44 | Similar with Pattern 2 (anhydrous form) | 99.80 |

*Note:
The first three stability conditions (25° C./60 % RH, 40° C./75 % RH and 80° C.) were done on the first mini scale-up experiments, where the potential co-crystal with fumaric acid was obtained as a mixture between AXI-FA II and AXI-FA III, while the last stability condition (slurry in H2O for 3 days at RT and drying at 32° C./0 % RH) for 4 days was done with the second mini scale-up where pure AXI-FA II was obtained

Example 4.5: Trans-Cinnamic Acid Co-Crystal

An overview of co-crystallization with trans-cinnamic acid co-crystal is provided in Table 9 below.

TABLE 9

Overview of experimental conditions for trans-cinnamic acid co-crystal

| No. | Acid | Experimental Conditions | Observations | XRPD on initial material | XRPD on vacuum dried material |
|---|---|---|---|---|---|
| 1 | trans-Cinnamic | Approx. 1000 rpm stirring | White slurry | Pattern 30 | Pattern 30 |
| 2 | acid | days at 40° C. | White slurry | Pattern 31 | Pattern 5 |
| 3 | | | White slurry | Pattern 10 | Pattern 32 |
| 1 | trans-Cinnamic acid | Grinding Bead Mill Standard Program: | White solids | AXI-TCA I | AXI-TCA I |

TABLE 9-continued

Overview of experimental conditions for trans-cinnamic acid co-crystal

| No. | Acid | Experimental Conditions | Observations | XRPD on initial material | XRPD on vacuum dried material |
|---|---|---|---|---|---|
| 2 | | Speed 4500 rpm Cycle 10 × 90 s | White solids | AXI-TCA I | AXI-TCA I |
| 3 | | Pause 10 s x 4 cycles | White solids | AXI-TCA I | AXI-TCA I |

Example 4.6: Suberic Acid Co-Crystal

A Volume of 50 UL of acetone was added, and the grinding program was the following:

4500 rpm
10×90 s cycles
10 second hold
Repeat×2
Total mill time ca. 30 minutes

An initial XPRD analysis was performed on the material after the additional milling cycles.

The vial containing the solids was dried at 40° C. under vacuum for 24 hours and reanalyzed by XPRD.

An overview of co-crystallization with trans-cinnamic acid co-crystal is provided in Table 10 below.

TABLE 10

Overview of experimental conditions for suberic acid co-crystal

| No. | Acid | Targeted form | Experimental Conditions | $V_{solv}$ (mL) | Observ-ations | XRPD on initial material | XRPD on vacuum dried material |
|---|---|---|---|---|---|---|---|
| 1 | Suberic acid | AXI-SbA I | Seeds of AXI-SbA I<br>Grinding with acetone<br>Bead Mill Program:<br>Speed 4500 rpm<br>10 x 90 s cycles<br>Pause 10 s<br>x2 cycles | 0.05 | White solids<br>White slurry | AXI-SbA + Pattern 31<br>Pattern: 10 | AXI-SbA with low crystallinity<br>Pattern 32 |

Example 5: Preparation of Axitinib Prodrugs

Example 5.1—Axitinib N-succinyloxymethyl Prodrug

The axitinib N-succinyloxymethyl prodrug (compound 3 in the reaction scheme depicted in this same paragraph below) was synthesized according to the following reaction scheme, under the conditions as also disclosed in co-pending PCT/US2022/046750, from axitinib (compound 1):

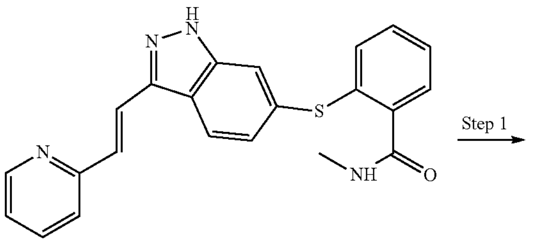

1

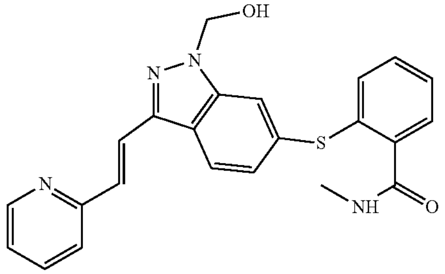

2

-continued

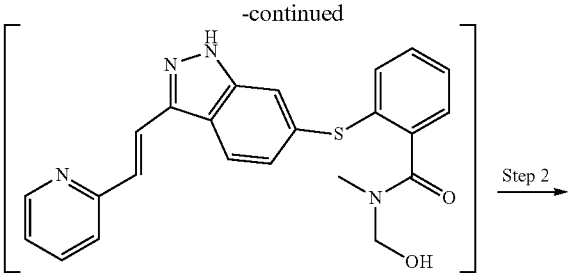

2a

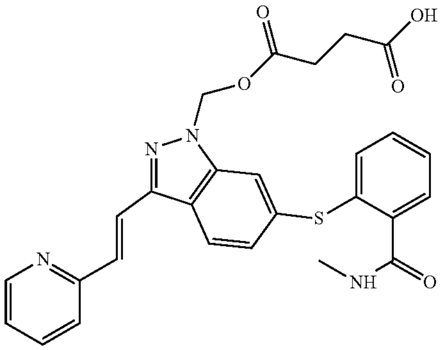

3

The sample number, batch size, conditions, reagents, yield and discussion for the above reaction sequence are set forth below for each step of the process:

| S. No | Batch size | Conditions | Yield | Discussion |
|---|---|---|---|---|
| | | Step 1 | | |
| 1 | 500 mg (1) | 37% formaldehyde (4.0 eq.), TEA (4.0 eq.), DMF, 0° C-RT, 16 h | 400 mg (crude) | Formation of intermediate compound 2 was confirmed by LCMS(98.2%).<br>$^1$H NMR shows a mixture of regio-isomers 2 and 2a in the ratio (60:40). |

-continued

| S. No | Batch size | Conditions | Yield | Discussion |
|---|---|---|---|---|
| | | Step 1 | | |
| 2 | 500 mg (1) | 37% formaldehyde (3.0 eq.), TEA (3.0 eq.), DMF, 0° C, 3 h. | 1.3 g (80%) | Formation of compound 2 was confirmed by LCMS and NMR. $^1$H NMR confirms the compound 2 with only traces of compound 2a (~4%). Isolated compound 2 in 1.3 g scale with 99.1% purity by LCMS. |
| 3 | 1.0 g (1) | | | |

| S. No | Batch size | Conditions | Yield | Discussion |
|---|---|---|---|---|
| | | Step 2 | | |
| 1 | 350 mg (2) | Succinic anhydride (1.3 eq.), DMAP (0.1 eq.), DMSO, 0° C-RT, 16 h Purification: The compound 3 with 85% purity by LCMS was purified by slurring with isopropyl alcohol at 40° C. for 1 h and filtered the solid. The obtained solid quantity was 160 mg. | 160 mg (37%) | Formation of compound 3 was confirmed by LCMS and $^1$HNMR. Isolated compound 3 in 160 mg scale with 95% purity by LCMS. Purity by HPLC is 94.3%. Nature of the compound: Off-white solid. |

Figure 6:
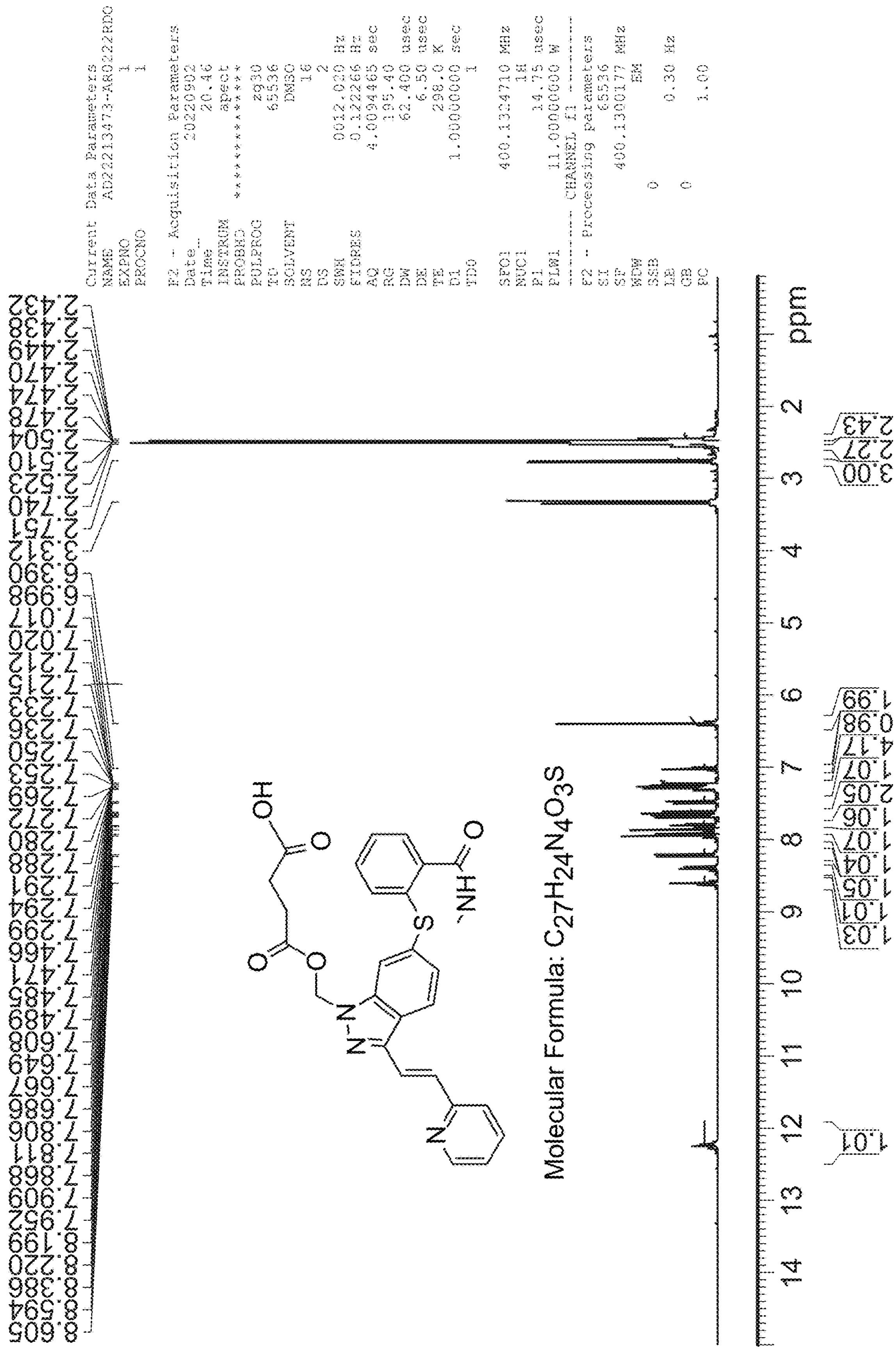
FIG. 6: $^1$H-NMR of the prodrug of Example 5.1
Figure 7:
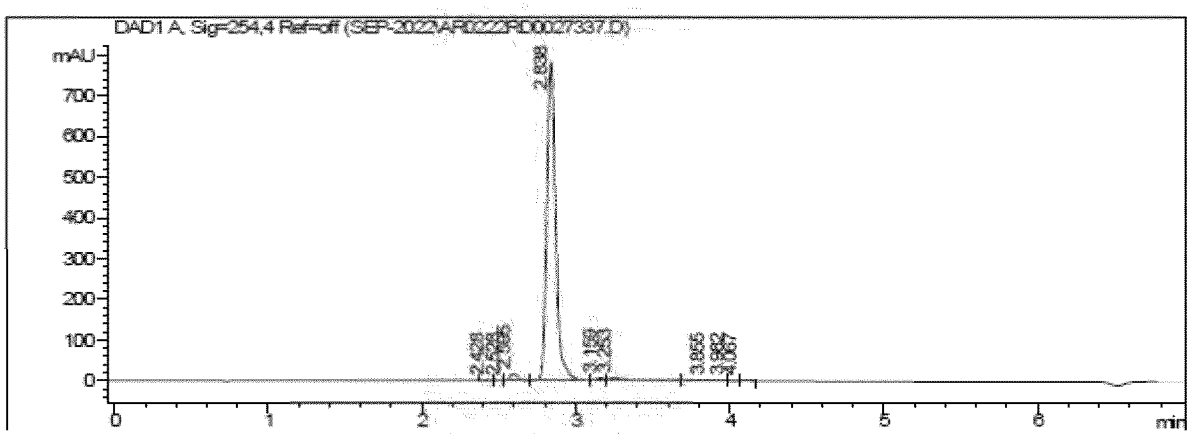
FIG. 7: LCMS of the prodrug of Example 5.1
Figure 8:
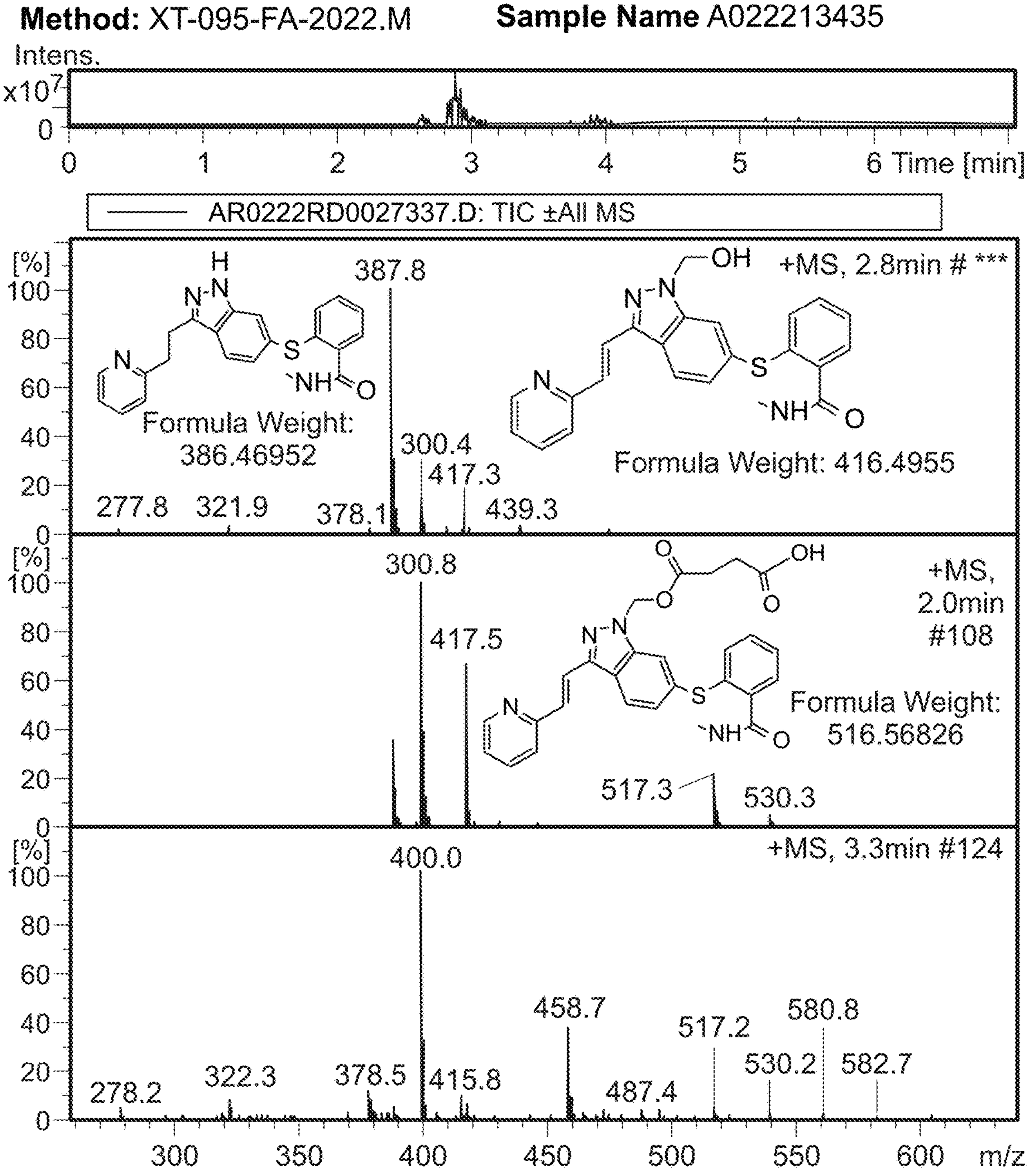
FIG. 8: HPLC of the prodrug of Example 5.1
Figure 9:
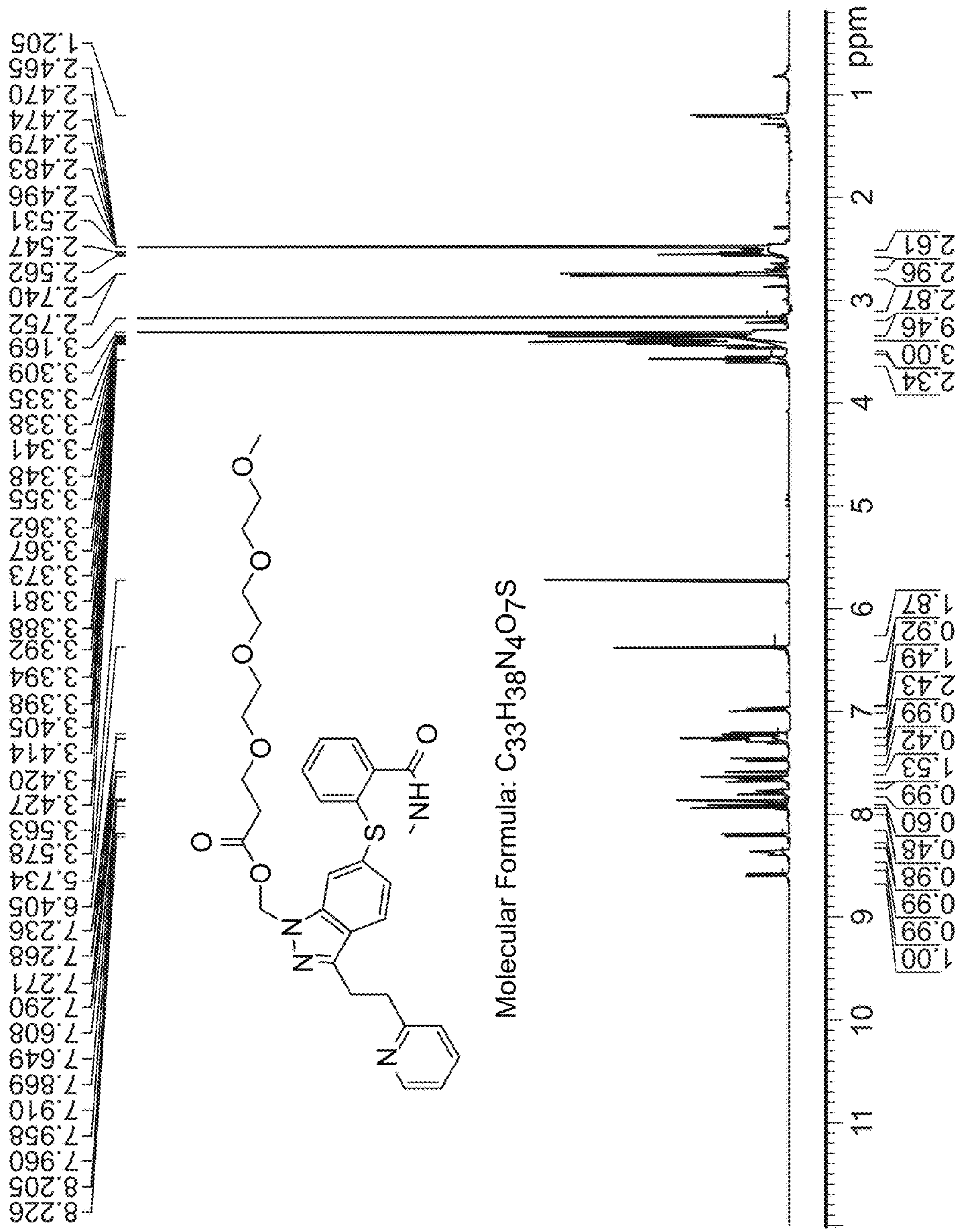
FIG. 9: $^1$H-NMR of axitinib N-m(PEG)$_4$-oxymethyl prodrug of Example 5.2
Figure 10:
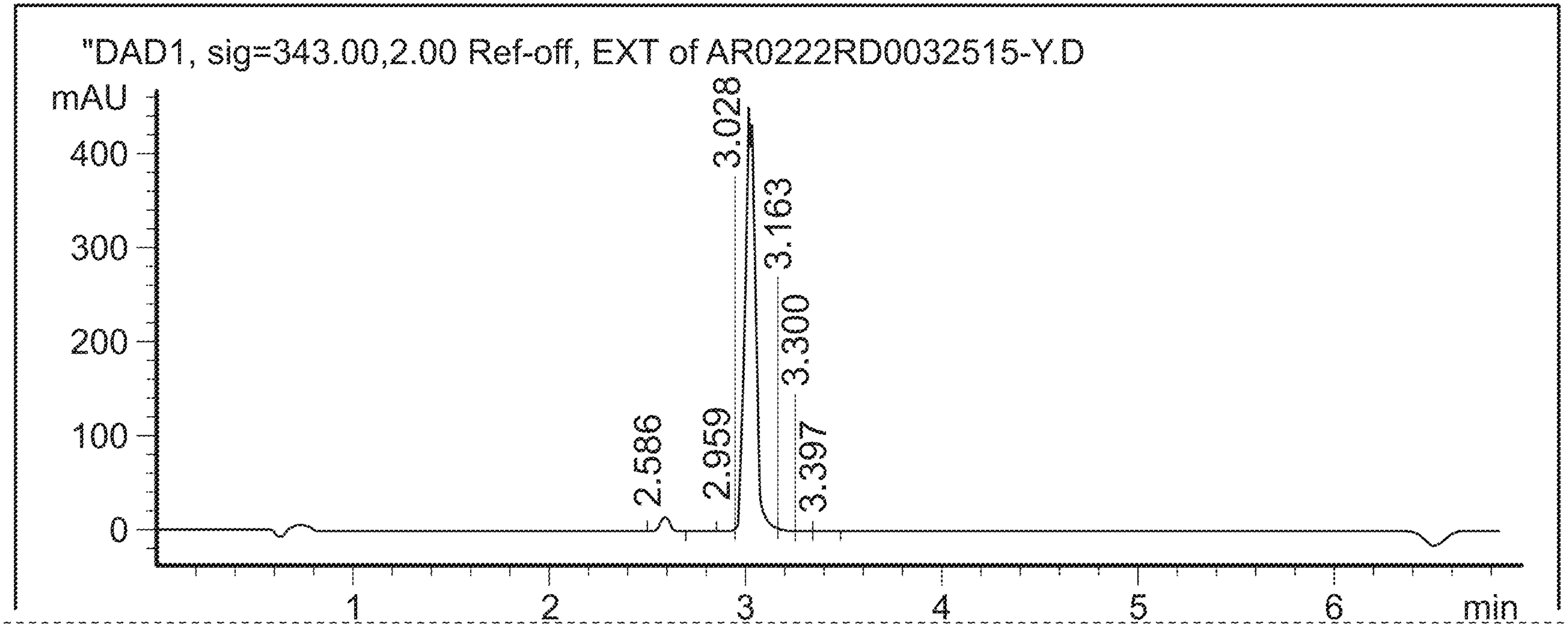
FIGS. 10 and 11: LCMS of axitinib N-m(PEG)$_4$-oxymethyl prodrug Example 5.2
Figure 11:
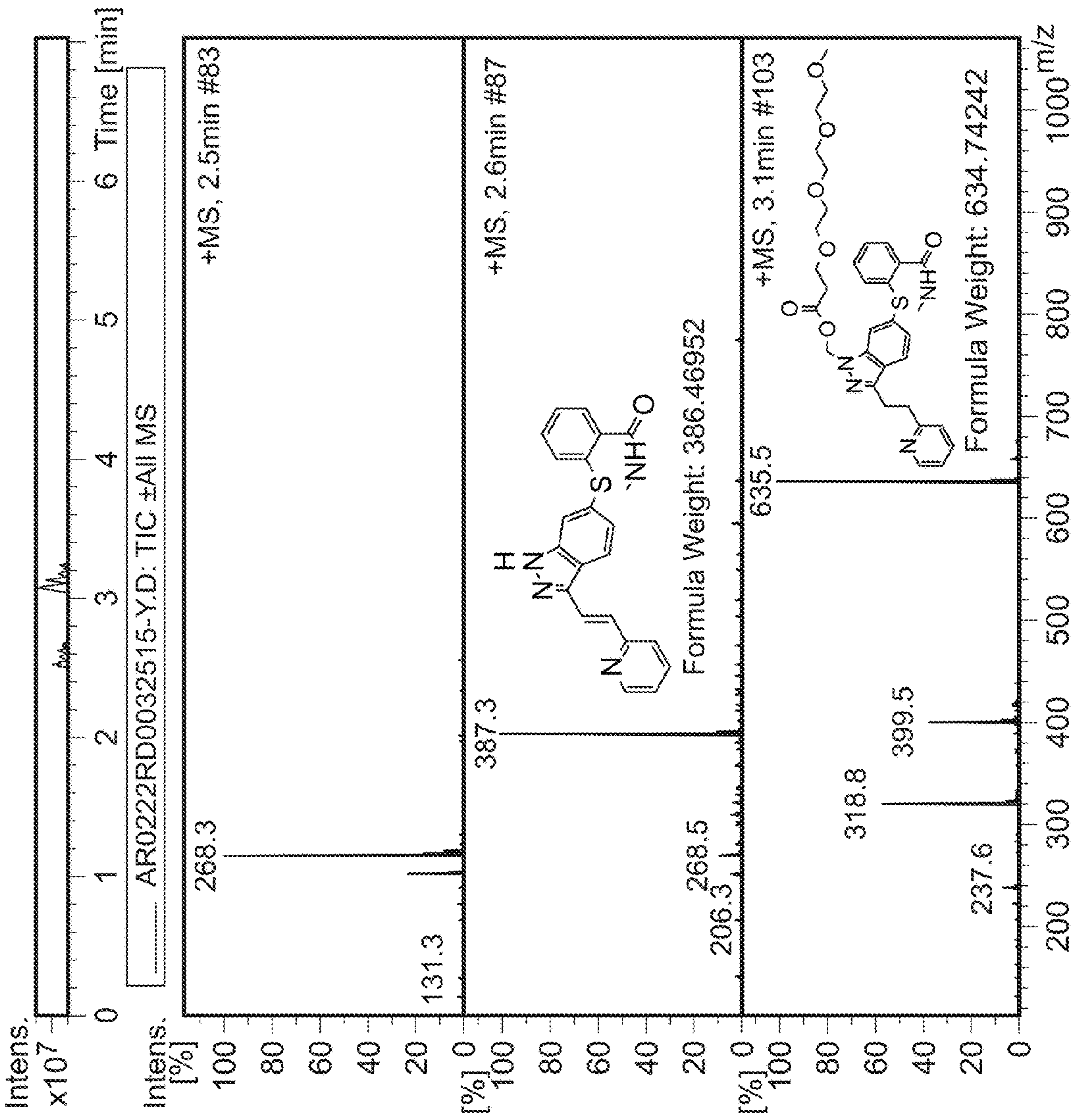
Figure 12:
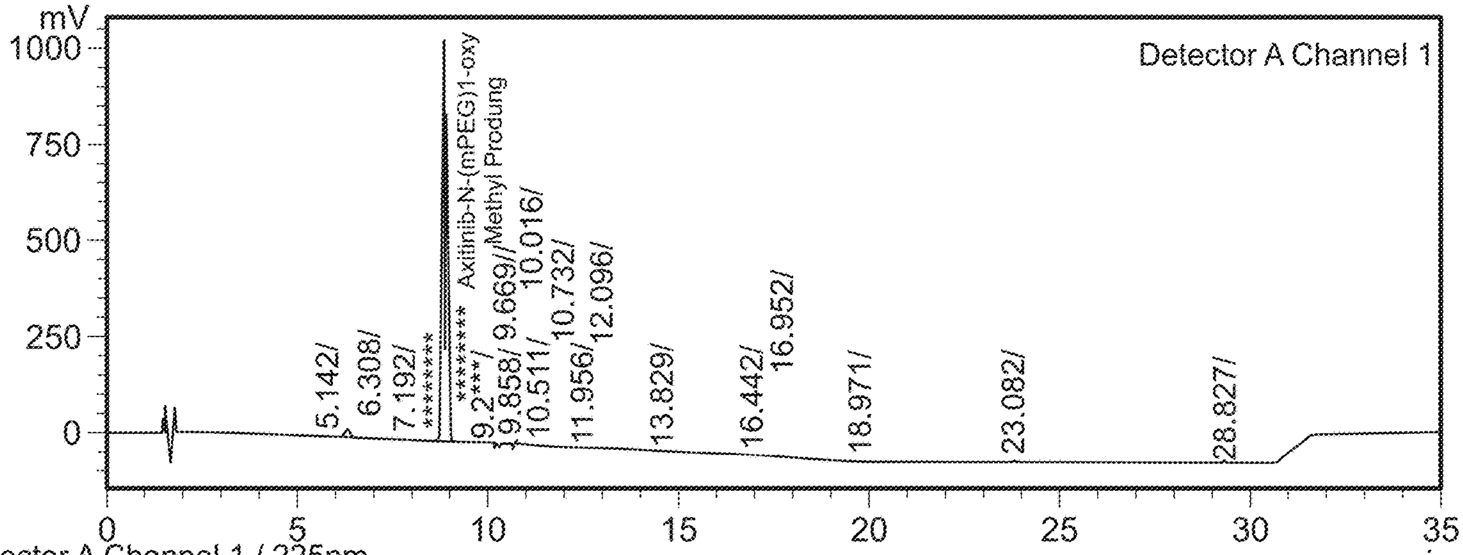
FIG. 12: HPLC of axitinib N-m(PEG)$_4$-oxymethyl prodrug Example 5.2
Figure 13:
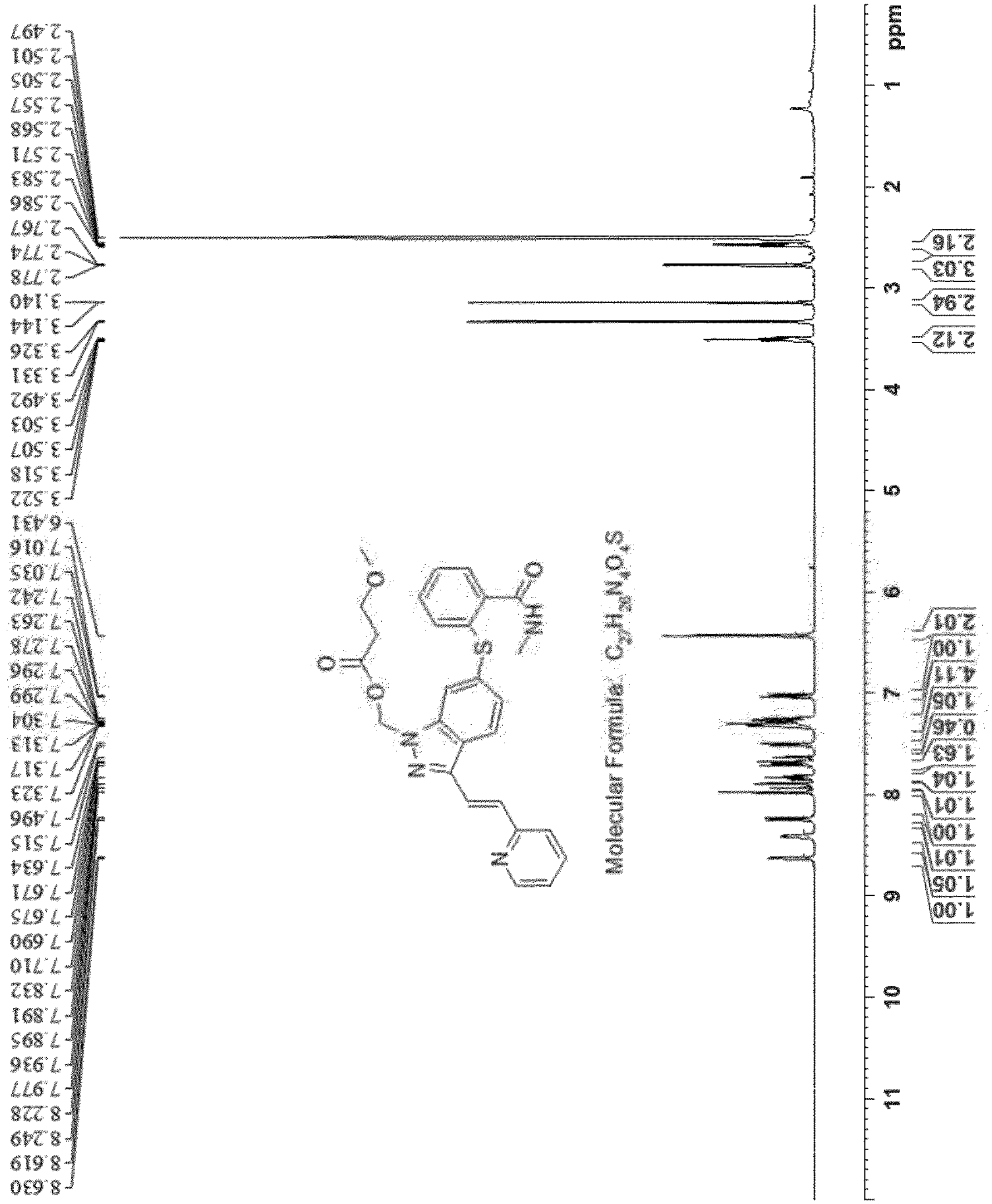
FIG. 13: $^1$H-NMR of axitinib-N-m(PEG)$_1$-oxymethyl prodrug of Example 5.2
Figure 14:
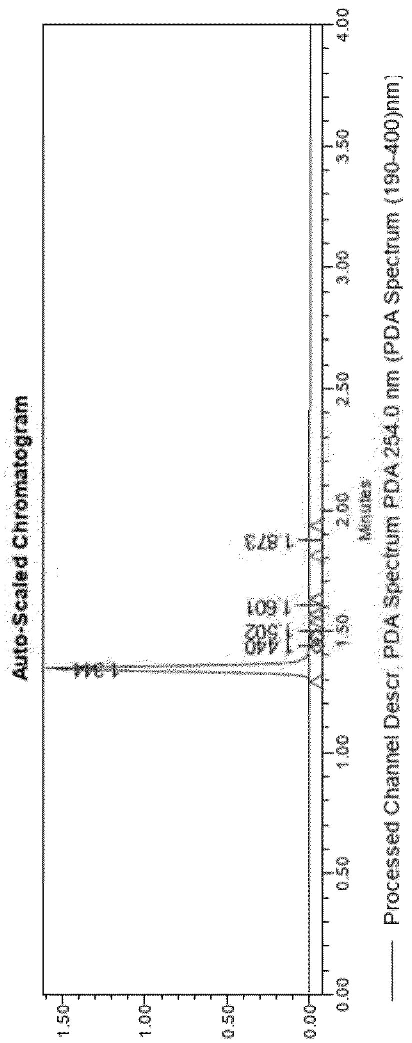
FIGS. 14 and 15: LCMS of axitinib-N-m(PEF)$_1$-oxymethyl prodrug Example 5.2
Figure 14:
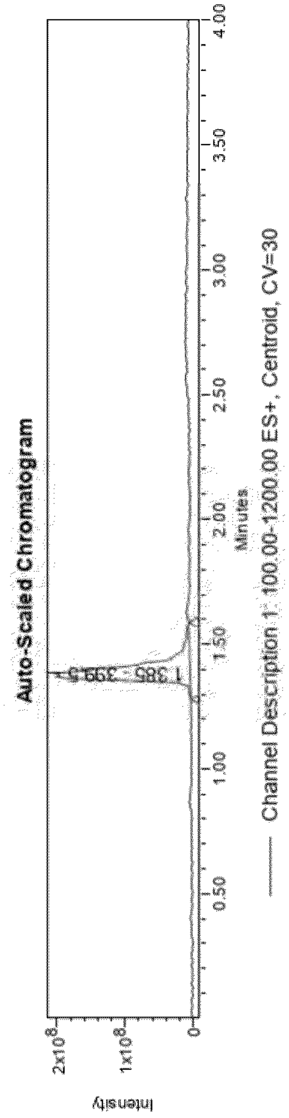
Figure 15:
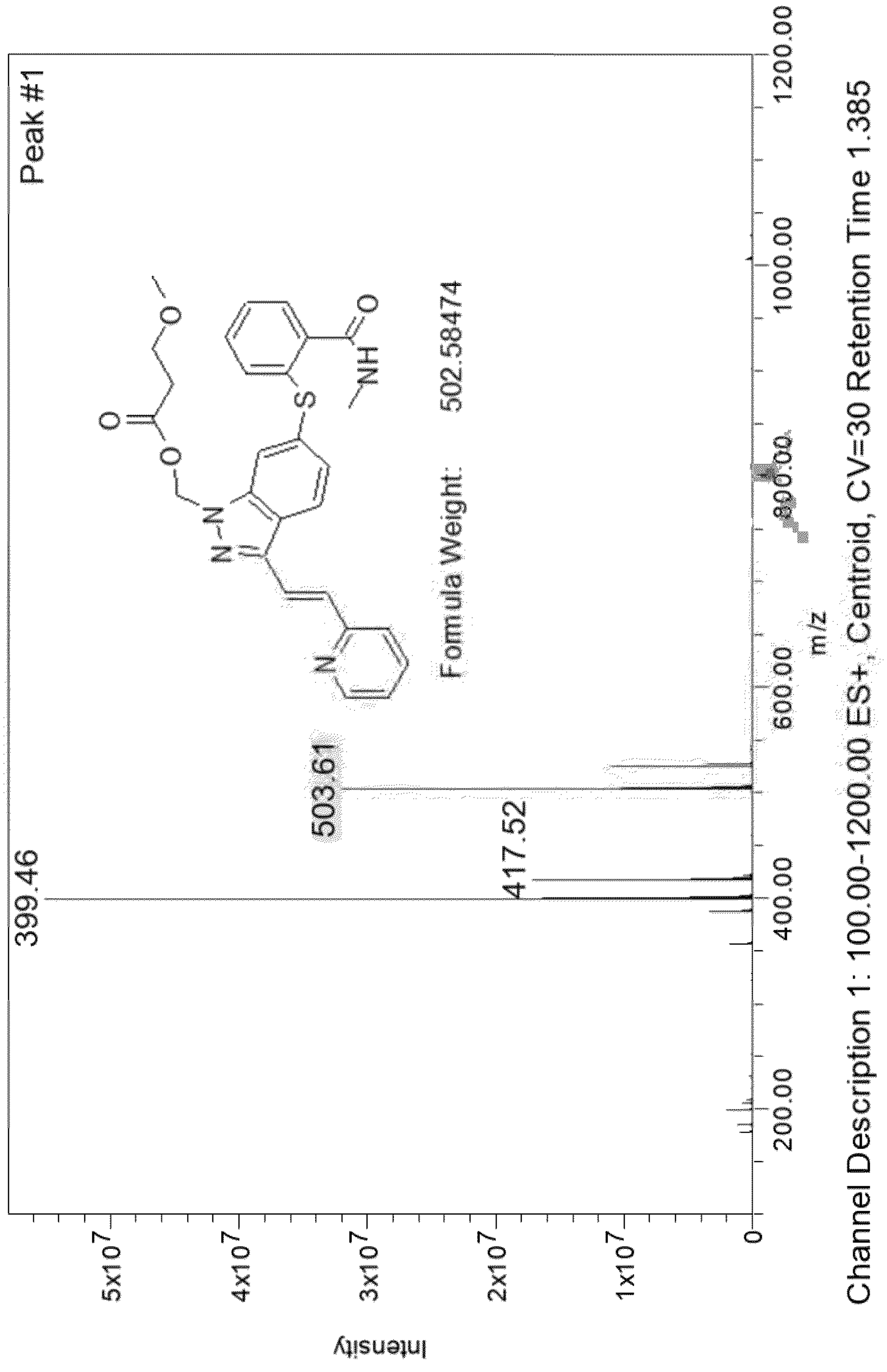
Figure 16:
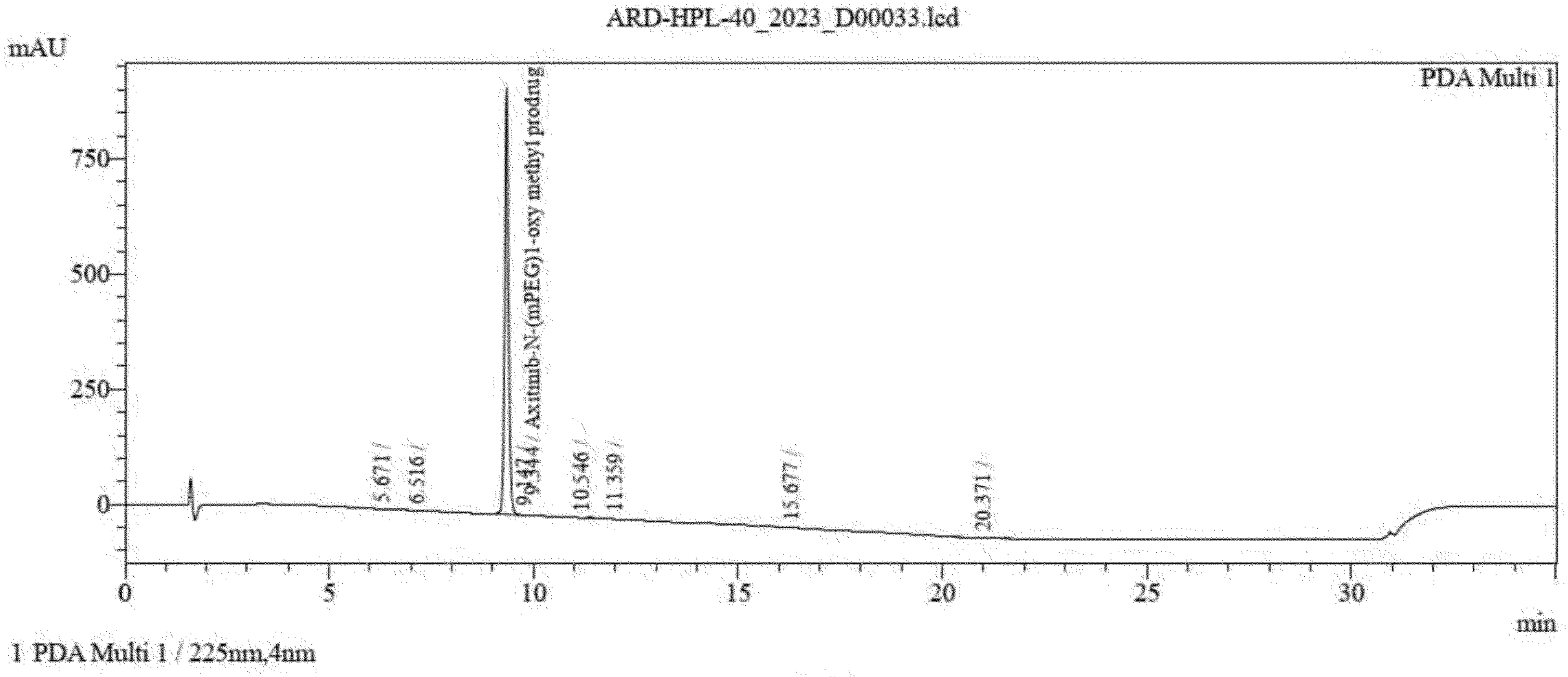
FIG. 16: HPLC of axitinib-N-m(PEG)$_1$-oxymethyl prodrug Example 5.2

Analytical data for the axitinib N-succinoyloxymethyl prodrug (compound 3 in the above reaction scheme) is disclosed in PCT/US2022/046750 and reproduced in FIGS. 6 to 8.

Example 5.2—Axitinib N-mPEG-oxymethyl Prodrugs

Axitinib N-m(PEG)$_4$-oxymethyl prodrug (compound 3 in the reaction scheme depicted in this same paragraph below) was synthesized according to the following reaction scheme, under the conditions as also disclosed in co-pending U.S. Provisional application 63/416,292, from axitinib (compound 1) via the synthesis of intermediate compound 6 (Int-1):

Scheme A: Preparation of Intermediate Compound 6 (Int-1):

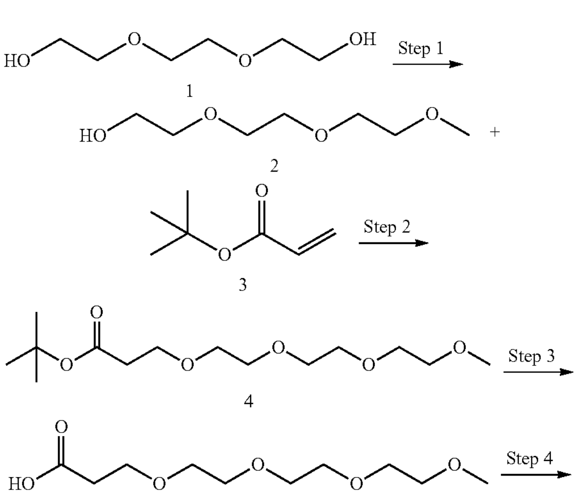

1 2 3 4 5

-continued

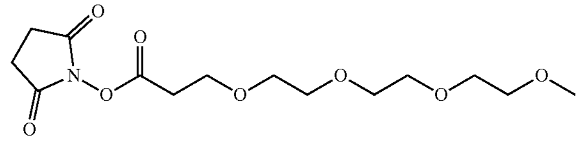

6 (Int-1)

Scheme B: Preparation of Axitinib N-m(PEG)$_4$-Oxymethyl Prodrug (Compound 3):

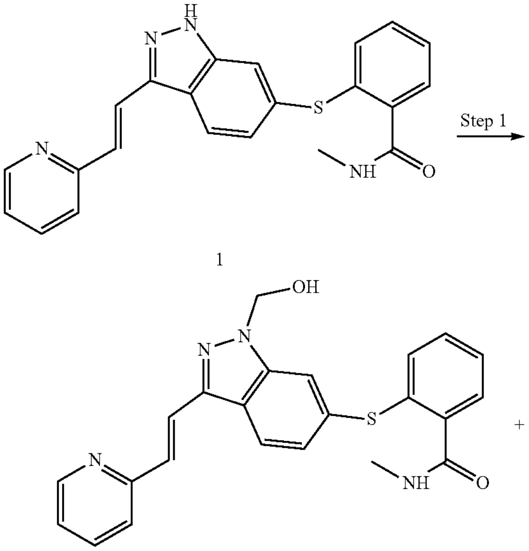

1 2

-continued

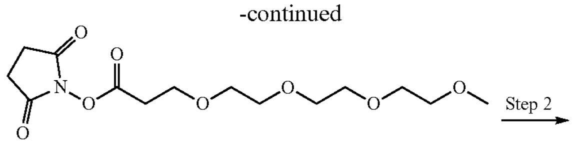

6 (Int-1)

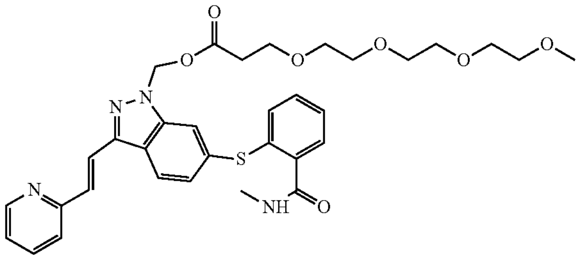

3

The sample number, batch size, conditions, reagents, yield and discussion for the above reaction sequence are set forth below for each step of the process:

| S. No | Batch size | Conditions | Yield | Discussion |
|---|---|---|---|---|
| | | Scheme A: Step 1 | | |
| 1 | 2.0 g (1) | Methyl iodide (0.5 eq.), KOH (0.55 eq.), THF, 0° C-RT, 16 h | 400 mg (20%) | Formation of compound 2 was confirmed by MS and NMR Isolated compound 2 by silica gel column chromatography in 400 mg scale. |
| | | Scheme A: Step 2 | | |
| 2 | 2.0 g (2) | t-Butyl acrylate(3.0 eq.), Triton-B (40% in methanol) (0.4 eq.), 0° C-RT, 2 h. | 150 g (42%) | Formation of compound 4 was confirmed by NMR. Isolated compound 4 by silica gel column chromatography in 1.5 g scale. |

| S. No | Batch size: | Conditions | Yield | Discussion |
|---|---|---|---|---|
| | | Scheme A: Step 3 | | |
| 2 | 1.5 g (4) | Triflouroacetic acid (5 V), DCM (5 V), 0° C-RT, 2 h | 850 mg (70%) | Formation of compound 5 was confirmed by MS and NMR. Isolated compound 5 by silica gel column chromatography in 850 mg scale. |

| S. No | Batch size | Conditions | Yield | Comments |
|---|---|---|---|---|
| | | Scheme A: Step 4 | | |
| 1 | 0.1 g (5) | N-Hydroxy succinimide (1.2 eq.), DIPEA (3.0 eq), DCC (1.2 eq.), DMAP (0.1 eq.), THF 0° C-RT, 12 h | 110 mg (crude) | Attempt to convert compound 5 to compound 6 (Int-1) was successful. Crude compound was taken forward to next step without purification. |

-continued

| S. No | Batch size | Conditions | Yield | Comments |
|---|---|---|---|---|
| | | Scheme A: Step 4 | | |
| 2 | 0.1 g (5) | DSC (1.2 eq.), DIPEA (2.0 eq), DMF 45° C, 16 h. | — | Attempt to convert compound 5 to compound 6 (Int-1) was not successful. SM intact by TLC. |
| 4 | 0.2 g (5) | N-Hydroxy succinimide (1.1 eq.), EDC•HCl (1.0 eq.), DCM, 0° C-RT, 12 h | 0.44 g (crude) | Formation of compound 6 (Int-1) was confirmed by NMR Isolated compound 6 (Int-1) in 0.44 g scale. |

| S. No | Batch size | Conditions | Yield | Comments |
|---|---|---|---|---|
| | | Scheme B: Step 2 (Scheme B Step 1 is identical to Step 1 in Example 5.1, above) | | |
| 2 | 0.1 g (2) | 6 (Int-1) (1.2 eq), DIPEA (2.0 eq), DMF 0° C-RT, 16 h. | 30 mg | Formation of compound 3 was confirmed by LCMS (83.8%). Isolated compound 3 by silica gel column chromatography in 30 mg scale |
| 3 | 0.1 g (2) | 6 (Int-1) (1.2 eq), TEA (2.0 eq), DMF | 120 mg (16%) | Formation of compound 3 was confirmed by LCMS and NMR. Isolated compound 3 by silica gel column chromatography in 120 mg scale with 95.53% LCMS purity. Purity by HPLC is 93.57%. Nature of the compound: viscous liquid. Traces of DCM by 1H-NMR were observed and further drying is in order. |
| 4 | 0.4 g (2) | 0° C-RT, 16 h. | | |

An alternative route to axitinib N-m(PEG)$_4$-oxymethyl prodrug 3 is via intermediate 5 (synthesized according to Scheme A above), via modified Scheme B':

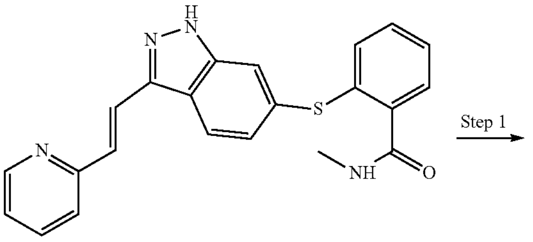

1

-continued

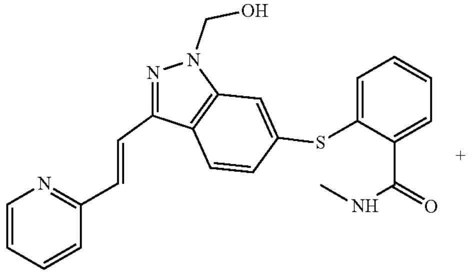

2

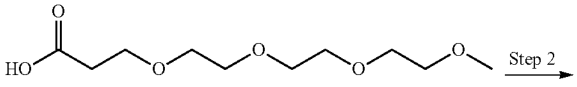

5

-continued

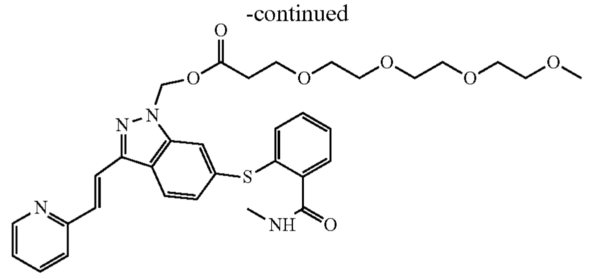

3

| S. No | Batch Size | Conditions | Yield | Comments |
|---|---|---|---|---|
| | | Scheme B': Step-2 | | |
| 1 | 0.1 g (2) | 5 (1.1 eq), EDC•HCl (1.2 eq.), DIPEA (2.0 eq), DMAP (0.1 eq.), DMF 0° C-RT, 16 h. | 20 mg | Formation of compound 3 was confirmed by LCMS(83%) and NMR. Isolated compound 3 by silica gel column chromatography in 20 mg scale. |

Analytical data for the axitinib N-m(PEG)$_4$ oxymethyl prodrug (compound 3 in the above reaction scheme) is disclosed in U.S. Provisional application 63/416,292 and reproduced in FIGS. 9-12.

Further axitinib N-m(PEG)-oxymethyl prodrugs were synthesized analogously (mutatis mutandis) from axitinib (compound 1) via the synthesis of corresponding intermediate compounds, according to the same reaction Schemes A and B (or B') as shown above:

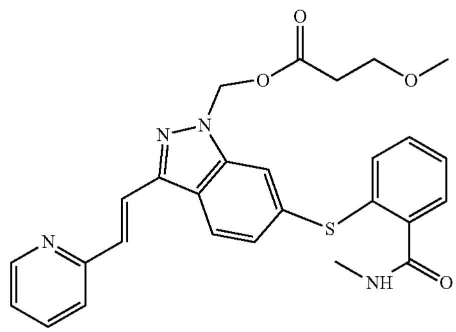 [SMILES: CNC(=O)c1ccccc1Sc1ccc2c(/C=C/c3ccccn3)nn(COC(=O)CCOC)c2c1]

Axitinib-N-m(PEG)$_1$-oxymethyl prodrug (total Mw: 502.28 g/mol; $C_{27}H_{26}N_4O_4S$).

IUPAC Name: 3-Methoxy-propionic acid 6-(2-methylcarbamoyl-phenylsulfanyl)-3-((E)-2-pyridin-2-yl-vinyl)-indazol-1-ylmethyl ester This axitinib-N-m(PEG)$_1$-oxymethyl prodrug was synthesized in 180 mg scale with 99.34% purity by HPLC

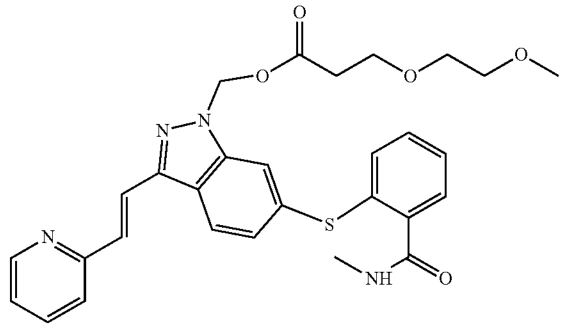 [SMILES: CNC(=O)c1ccccc1Sc1ccc2c(/C=C/c3ccccn3)nn(COC(=O)CCOCCOC)c2c1]

Axitinib-N-m(PEG)$_2$-oxymethyl prodrug (total Mw: 546.63 g/mol; $C_{29}H_{30}N_4O_5S$)

IUPAC Name: 3-(2-Methoxy-ethoxy)-propionic acid 6-(2-methylcarbamoyl-phenylsulfanyl)-3-((E)-2-pyridin-2-yl-vinyl)-indazol-1-ylmethylester This axitinib-N-m(PEG)$_2$-oxymethyl prodrug was synthesized in 220 mg scale with 99.1% purity by HPLC

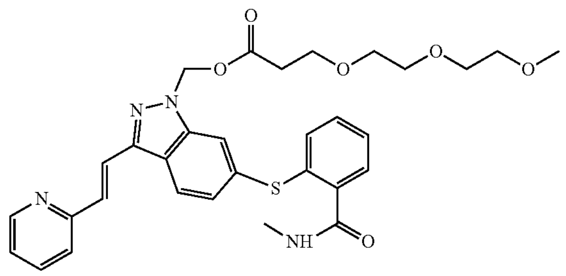 [SMILES: CNC(=O)c1ccccc1Sc1ccc2c(/C=C/c3ccccn3)nn(COC(=O)CCOCCOCCOC)c2c1]

Axitinib-N-m(PEG)$_3$-oxymethyl prodrug (total Mw: 590.68 g/mol; $C_{31}H_{34}N_4O_6S$)

Figure 5:
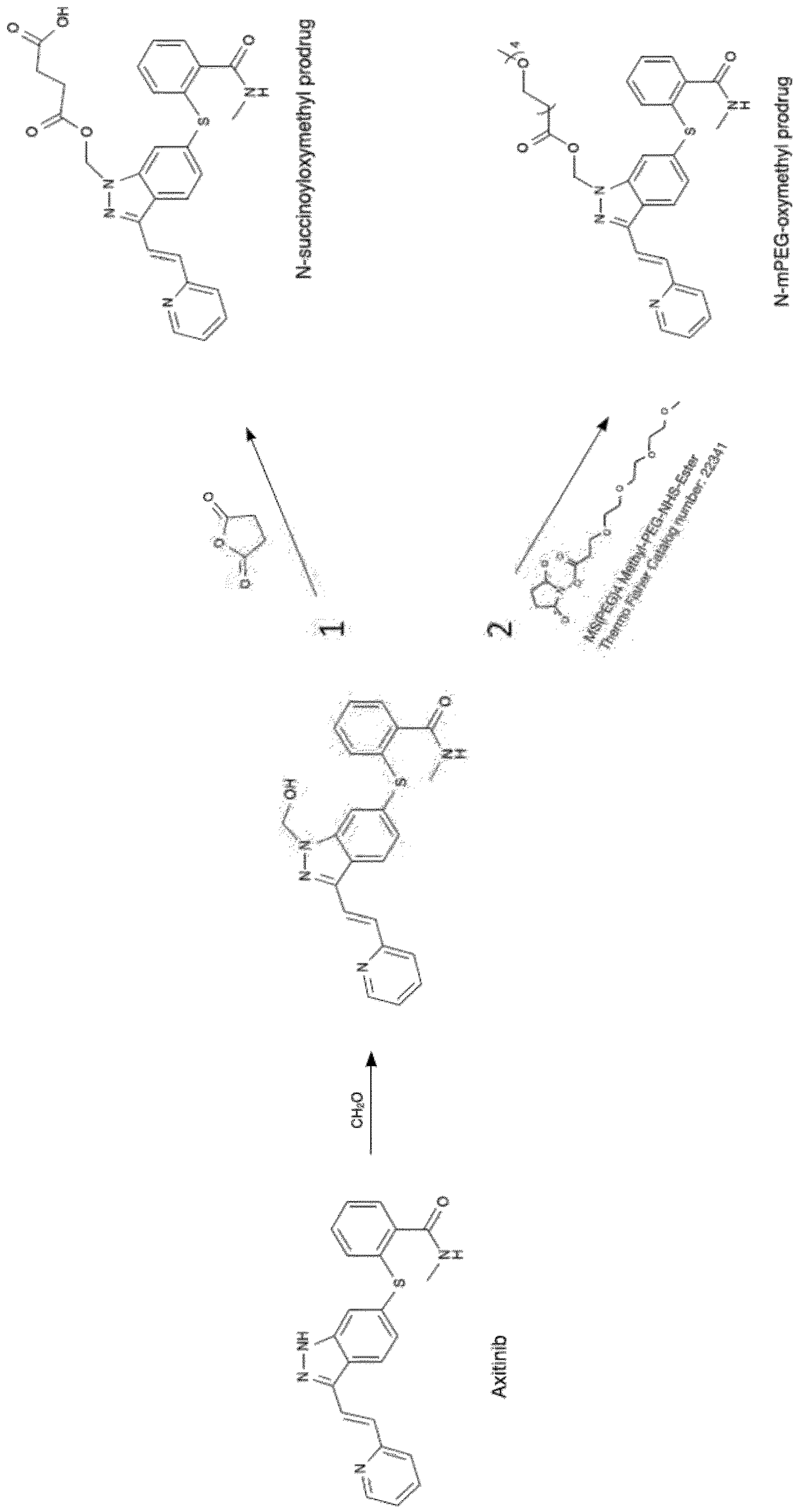
FIG. 5: Synthetic schemes of prodrugs of Example 5

IUPAC Name: 3-[2-(2-Methoxy-ethoxy)-ethoxy]-propionic acid 6-(2-methylcarbamoyl-phenylsulfanyl)-3-((E)-2-pyridin-2-yl-vinyl)-indazol-1-ylmethylester This axitinib-N-m$(PEG)_3$-oxymethyl prodrug was synthesized in 350 mg scale with 94.9% purity by HPLC Analytical data for the axitinib-N-m$(PEG)_1$-oxymethyl prodrug are provided in FIGS. 13-16. ($^1$H NMR, LC/MS). FIG. 5 provides an overview of the reaction schemes for prodrugs of Examples 5.1 and 5.2.

Example 6: Solubility of TKI

Example 6.1: Axitinib Free Base

In this study, solubility of different polymorphs of axitinib was measured (Table 11).

TABLE 11

| Particle size of SAB-I and Polymorph IV | | | | |
|---|---|---|---|---|
| | SAB-I non-micronized | SAB-I micronized | SAB-I super micronized | Polymorph IV micronized |
| PSD (μm) Range ± 10% | D10 6.3, D50 16.2, D90 42.5 | D10 0.2, D50 2.2, D90 6.1 | D10 0.17, D50 1.4, D90 4.0 | D10 0.2, D50 2.5 D90 7.5 |

Materials and Methods

Reagents:
- 1×PBS, pH 7.2
- Water
- 100 ml amber sample bottle

Equipment:
- Eppendorf Microcentrifuge 5424
- Capacity 1.5-2.2 mL microcentrifuge tubes
- Max. Speed 15,000 rpm
- Max. RCF 21,130 rcf Add approximately 10-20 mg of the axitinib into ~75 ml of 1×PBS pH 7.2-7.4. Place on rocker table at 37° C. at 200 rpm. Remove 1-2 mL at each time interval and transfer to 2 ml centrifuge tube. Centrifuge at 15,000 RPM for 30 minutes. Aliquot 1 ml of supernatant to a UPLC vial. Samples are placed in a 37° C. incubator for the duration of the study. Care is taken to sample through a clear area as much as possible. The pipet tip is wiped clean for this transfer step.

An Example injection sequence is shown below:

TABLE 12

| Example injection for UPLC | | |
|---|---|---|
| Sample Description | Number of injections | Purpose |
| Mobile Phase | 1 | Blank/Carryover |
| Repeatability Standard | 6 | System Suitability |
| Mobile Phase | 1 | Blank |
| Std Curve | 1 ea | System Suitability |
| Check Std | 1 | System Suitability |
| Sample 1 | 1 | Sample |
| Sample 2 | 1 | Sample |
| Sample 3 | 1 | Sample |
| Sample 4 | 1 | Sample |
| Sample 5 | 1 | Sample |
| Bracket Std | 1 | System Suitability/Bracket |

Note:
A bracket standard should be analyzed after every 10 sample injections.

TABLE 12a

| UPLC conditions | |
|---|---|
| Analytical column | Acquity UPLC BEH C18, 1.7 μm, 2.1 × 150 mm |
| Mobile Phase A | 0.1% Formic acid in $H_2O$ |
| Mobile Phase B | 0.1% Formic acid in 90/10 methanol/acetonitrile |
| Column temperature | 50° C. |
| Sample temperature | 20° C. |
| Injection volume | 6 μL |
| Mobile phase gradient | Isocratic A/B 52.5/47.5 |
| Flow rate | 0.3 mL/min |
| Wavelength | 360 nm |
| Run time | 4 min |
| Retention time | ca. 2-3 min |

Figure 17:
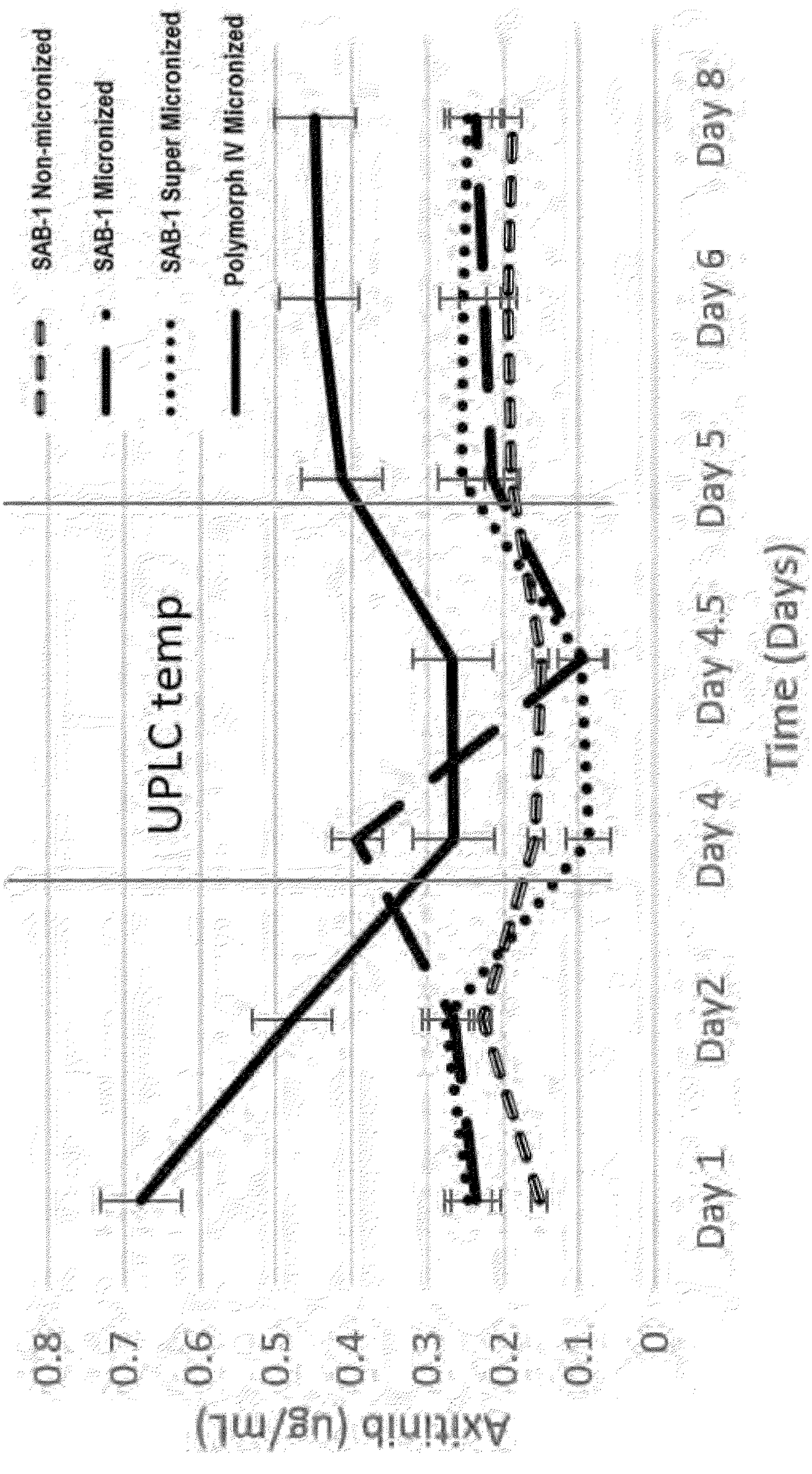
FIG. 17: Solubility of SAB-I (micronized, non-micronized, and super micronized) and Polymorph IV in PBS, pH 7.2 at 37° C.

The solubility results are shown in FIG. 17, as follows: Axitinib polymorph IV has a solubility in PBS at 37° C. and pH 7.2 to 7.4 after five days of incubation of greater than 0.3 μg/mL, and even greater than 0.4 μg/mL. Axitinib polymorph SAB-I (all particles sizes tested) has a solubility in PBS at 37° C. and pH 7.2 to 7.4 of less than 0.3 μg/mL. From the solubility results shown in FIG. 17 and presented in Table 12b, it can be taken that after five days of incubation an equilibrium state is achieved. An average equilibrium solubility could be determined (equilibrium of days 5, 6 and 8 in Table 12b) for each polymorph. The equilibrium solubility of axitinib SAB-I in PBS at 37° C. and pH 7.2 to 7.4 was an average of 0.191, 0.226 and 0.252 μg/mL, depending on the particle size (non-micronized, micronized and super-micronized). The equilibrium solubility of axitinib polymorph IV (micronized) was 0.435 μg/mL.

TABLE 12b

| Equilibrium solubility of axitinib SAB-I and Polymorph IV in PBS | | | | | | |
|---|---|---|---|---|---|---|
| Sample | Day 1 | Day2 | Day 5 | Day 6 | Day 8 | Average (Days 5-8) |
| SAB-I non-micronized | 0.153 | 0.228 | 0.190 | 0.194 | 0.188 | 0.191 |
| SAB-I micronized | 0.236 | 0.265 | 0.216 | 0.226 | 0.237 | 0.226 |
| SAB-I super-micronized | 0.246 | 0.277 | 0.256 | 0.253 | 0.247 | 0.252 |
| Polymorph IV micronized | 0.678 | 0.479 | 0.413 | 0.443 | 0.449 | 0.435 |

Example 6.2: Axitinib Prodrug

In this study, solubility of different axitinib prodrugs was measured (Table 13)

TABLE 13

| Prodrugs | |
|---|---|
| No. | Prodrug |
| 1 | N-Succinoyloxymethyl |
| 2 | N-m$(PEG)_4$-oxymethyl |

Materials and Methods

- PBS, pH 7.2
- 24 h at 22° C. with continuous shaking
- Solubility of test item was determined by HPLC analysis with calibration curve HPLC conditions are provided in the Table 14 below:

TABLE 14

| HPLC conditions | |
|---|---|
| HPLC | PCR-HPLC-003 (Shimadzu) |
| Column Specification | Kinetex , C18, 100 × 4.6 mm, 2.6 μM particle size, 100 Å |
| Mobile Phase A | 0.05% Acetic Acid in Ultrapure Water Type-I |
| Mobile Phase B | Acetonitrile (100%) |
| Flow Rate | 1.0 mL/min |
| Run Time (Minutes) | 18 |
| Column oven Temperature (° C.) | 40 |
| Calibration Range (μg/mL) Axitinib | 0.78-200 |
| Calibration Range (μg/mL) N-Succinoyloxymethyl | 0.78-200 |
| Calibration Range (μg/mL) N-mPEG-oxymethyl | 0.78-100 |
| Retention time of Analyte (Minutes) N-Succinoyloxymethyl | ~7.5 |
| Retention time of Analyte (Minutes) N-mPEG-oxymethyl | ~8.0 |
| Lamda Max | 225 nm |
| Autosampler Temperature (° C.) | 4 |
| Injection Volume (μL) N-Succinoyloxymethyl | 10 |
| Injection Volume (μL) N-mPEG-oxymethyl | 5 |

The solubility of Axitinib N-Succinoyloxymethyl Prodrug is shown in Table 15 below:

TABLE 15

Solubility of Axitinib N-Succinoyloxymethyl Prodrug

| Sample ID | Area | Conc. (μg/mL) | Dilution factor | Obtained Conc. (μg/mL) | Mean Solubility (μg/mL) |
|---|---|---|---|---|---|
| Solubility in PBS-R1 | 644476 | 44.411 | 5 | 222.06 | 217.44 |
| Solubility in PBS-R2 | 617628 | 42.564 | 5 | 212.82 | |

The solubility of the above axitinib N-m(PEG)-oxymethyl prodrugs is shown in Tables 16a to 16d below ("BLOQ" means "below limit of quantification", i.e., <0.781 μg/mL):

TABLE 16a

Solubility of Axitinib N-m(PEG)$_1$-oxymethyl Prodrug in PBS, pH 7.4

| Sample ID | Area | Dilution factor | Conc. (μg/mL) | Mean Solubility (μg/mL) |
|---|---|---|---|---|
| Solubility in PBS-R1 | 14030 | NA | BLOQ | Not soluble |
| Solubility in PBS-R2 | 13739 | NA | BLOQ | |

TABLE 16b

Solubility of Axitinib N-m(PEG)$_2$-oxymethyl Prodrug in PBS, pH 7.4

| Sample ID | Area | Dilution factor | Conc. (μg/mL) | Mean Solubility (μg/mL) |
|---|---|---|---|---|
| Solubility in PBS-R1 | 30842 | NA | 1.112 | 1.10 |
| Solubility in PBS-R2 | 30115 | NA | 1.086 | |

TABLE 16c

Solubility of Axitinib N-m(PEG)$_3$-oxymethyl Prodrug in PBS, pH 7.4

| Sample ID | Area | Dilution factor | Conc. (μg/mL) | Mean Solubility (μg/mL) |
|---|---|---|---|---|
| Solubility in PBS-R1 | 144126 | NA | 6.179 | 6.16 |
| Solubility in PBS-R2 | 143361 | NA | 6.146 | |

TABLE 16d

Solubility of Axitinib N-m(PEG)$_4$-oxymethyl Prodrug

| Sample ID | Area | Conc. (μg/mL) | Dilution factor | Obtained Conc. (μg/mL) | Mean Solubility (μg/mL) |
|---|---|---|---|---|---|
| Solubility in PBS-R1 | 99962 | 5.008 | 20 | 100.16 | 99.37 |
| Solubility in PBS-R2 | 98366 | 4.929 | 20 | 98.58 | |

Example 6.3: Axitinib Co-Crystals

The purity and solubility in PBS, pH 7.4 at 37° C., were evaluated by HPLC (Table 17)

TABLE 17

| Solubility of co-crystals | | | | | |
|---|---|---|---|---|---|
| | | HPLC | | | |
| | | | Thermodynamic solubility in PBS, pH 7.4 (μg/mL) at 37° C. | | |
| Exp. No. | Acid | Purity (%) | 2 hours | 4 hours | 24 hours |
| 1 | Citric Acid | 97.95 | 2.0 | 3.6 | 19.1 |
| 2 | Fumaric Acid | 99.91 | 0.6 | 0.4 | 12.2 |
| 3 | (+)-L-Tartaric acid | 99.53 | 2.3 | 3.3 | 19.7 |

The co-crystallization process with citric acid, fumaric acid, and tartaric acid seem to cause solubility enhancement.

Example 7: In Vitro Release of the TKI Implant-Axitinib Solubility can be Selected to Control the Release Profile Example 7.1: In Vitro Method A In this study, the influence of solubility on in vitro release kinetics of the TKI implant was investigated, PEG $NH_2$ (8a20k) and PEG SAZ (4a20k) were used to form the PEG hydrogels. (Table 18).

The implants contained either the SAB-I or the polymorph IV axitinib. As demonstrated in Example 6, SAB-I and polymorph IV differ in their solubilities by a factor of at least 2, i.e., the polymorph IV is about two times more soluble than the SAB-I (FIG. 17).

1 L of 25:75 Ethanol:Water (v/v) using a graduated cylinder was prepared and allowed to equilibrate. Each implant was placed in an amber jar. The amount of 25:75 Ethanol:Water equal to 2 times the sink volume (sink volume is the axitinib amount in the implant per assay/axitinib solubility) was added for a 2× sink factor. The samples were stored in a 37° C. incubator on a rocker plate to provide moderate agitation. 1 mL of the solution was sampled on pre-determined days until the drug is fully released. Samples were run on either a UV-Vis spectrometer or a UPLC against analytical standards prepared within the last 2 weeks.

In this method A, one (mean) solubility value of 18.3 μg/ml was used for both SAB-I and Polymorph-IV in order to calculate the sink volume.

Figure 18A:
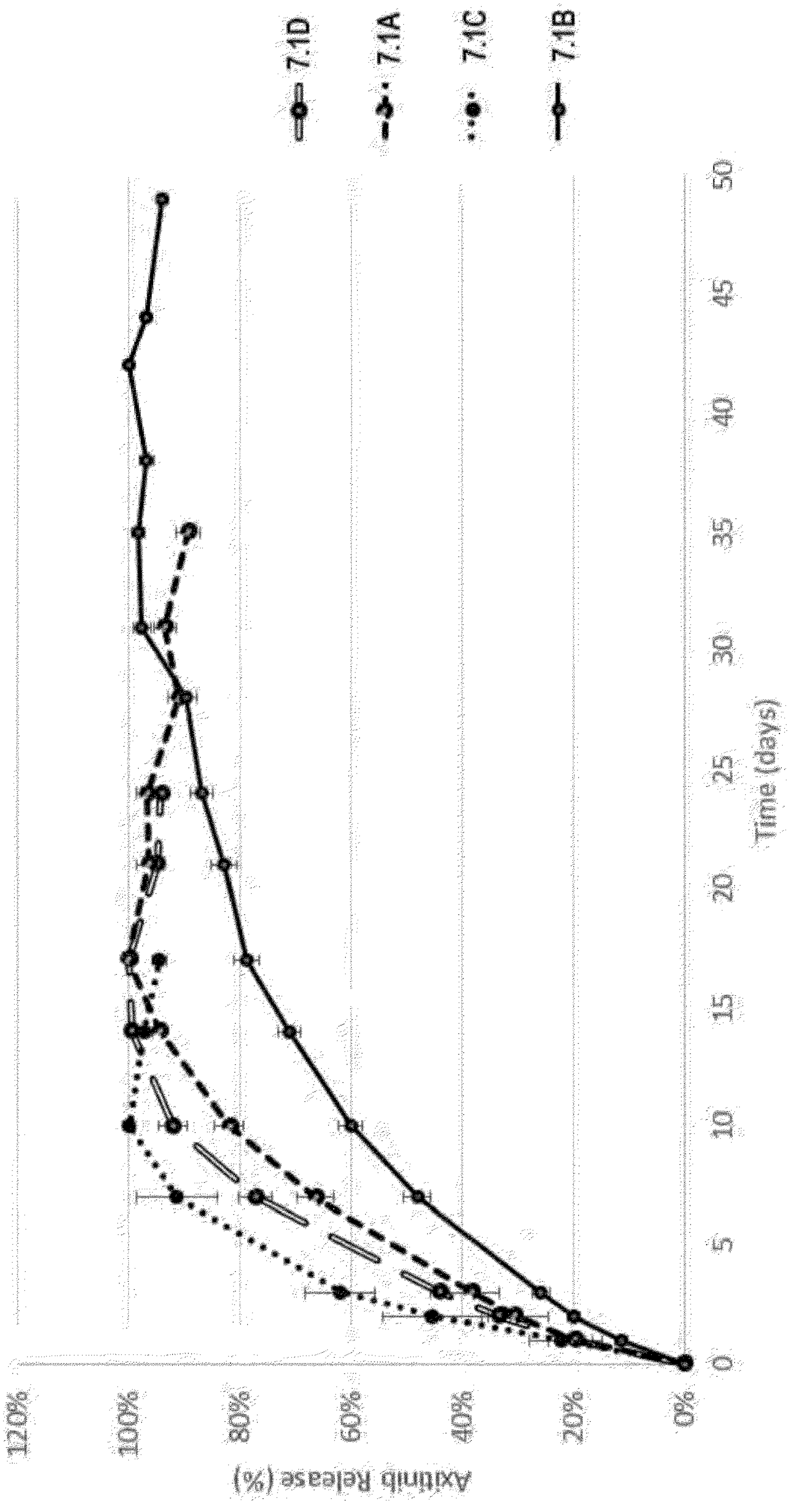
FIG. 18: TKI release profile (In Vitro Method A) from implants 7.1A, 7.1B, 7.1C, and 7.1D showing the effect of axitinib solubility: (A) % Release; (B) Mass Released; (C) TKI release profile from implant 7.1E.
Figure 18B:
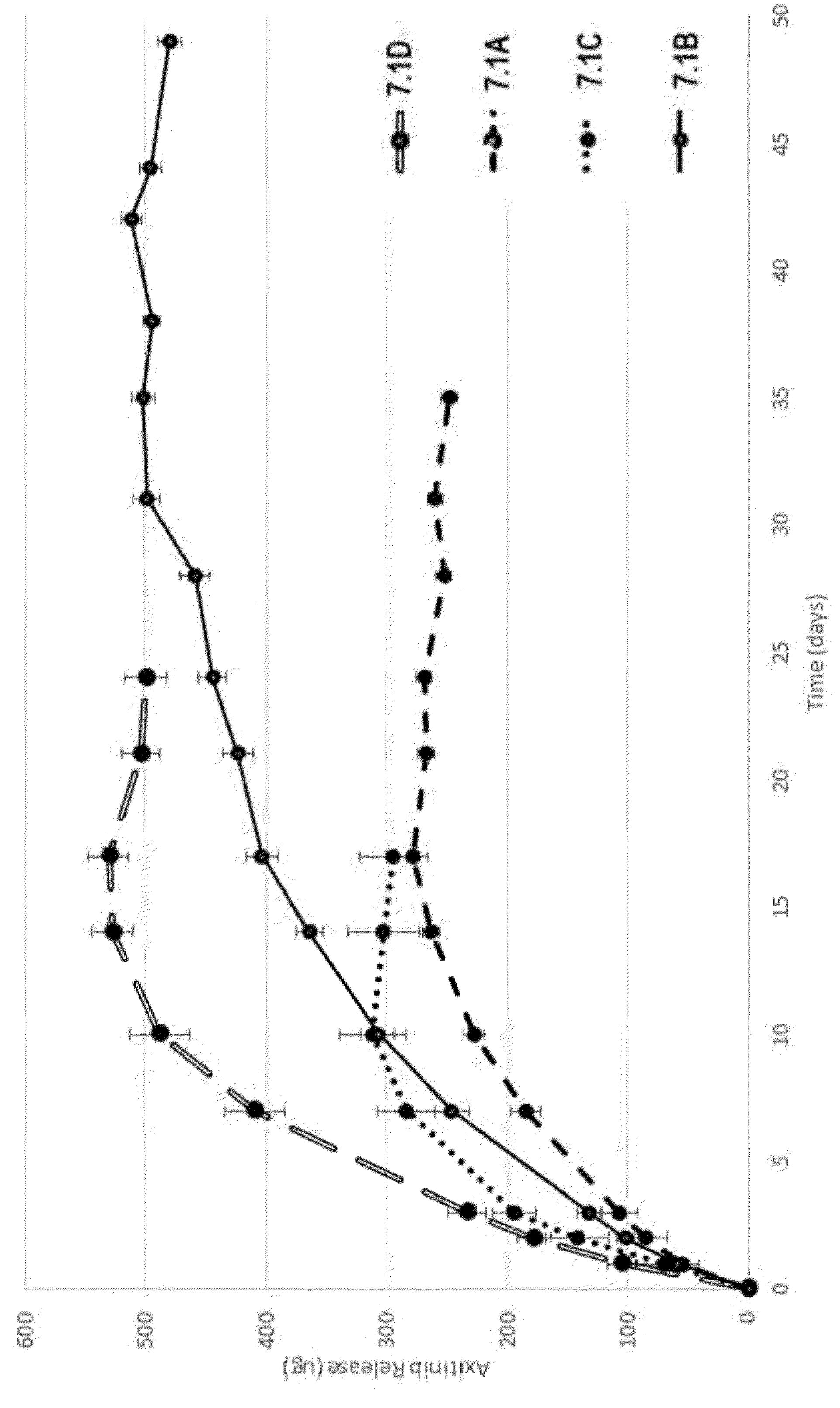
Figure 18C:
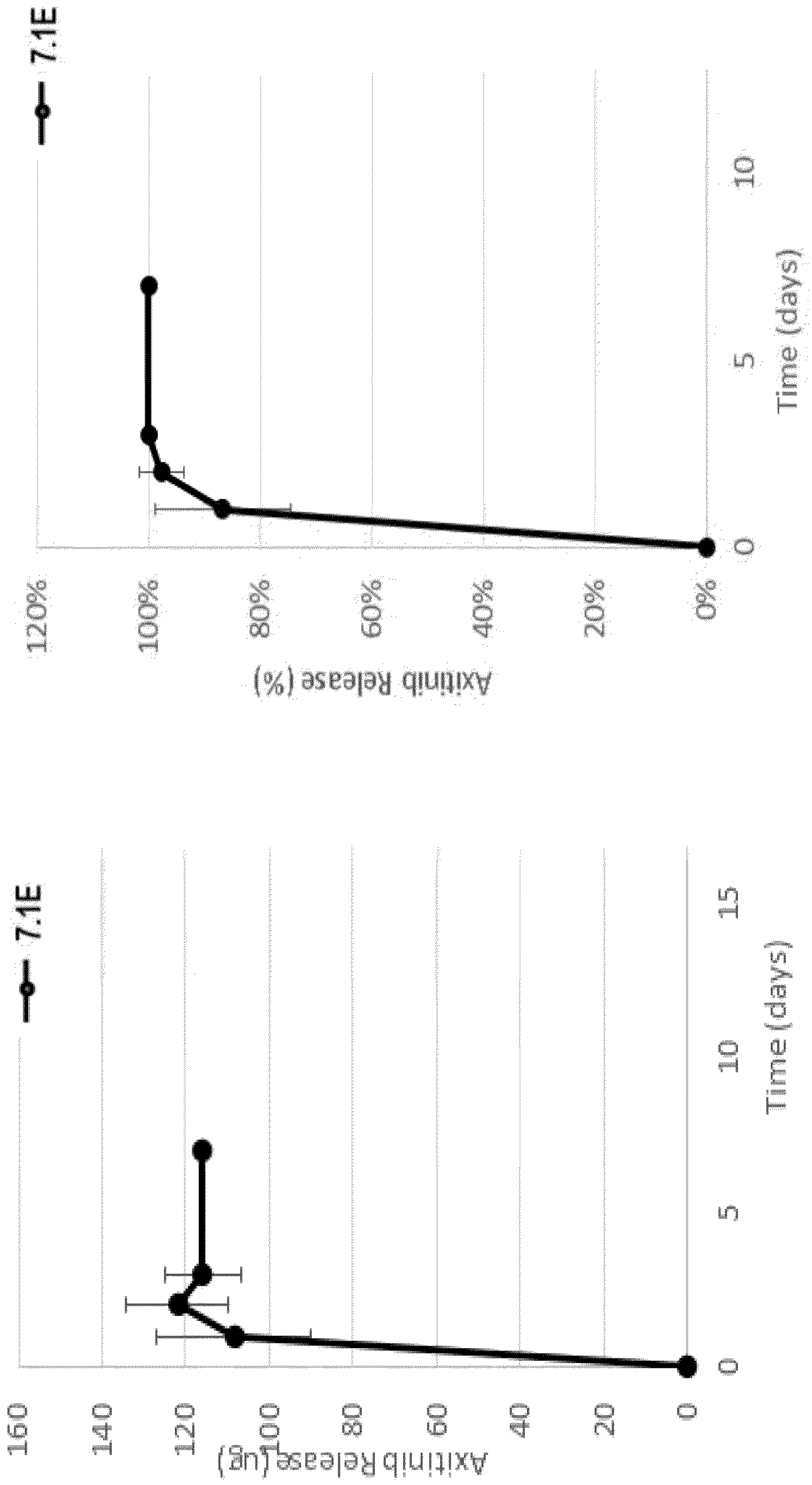

The results are shown in FIGS. 18A, 18B, and 18C.

TABLE 18

| Implants 7.1A, 7.1B, 7.1C, 7.1D, and 7.1E | | | | | | |
|---|---|---|---|---|---|---|
| Implant | | 7.1A | 7.1B | 7.1C | 7.1D | 7.1E |
| Axitinib Type | Free Base | SAB-I | SAB-I | Polymorph IV | Polymorph IV | Polymorph IV |
| | Solubility in PBS pH 7.2-7.4 (37° C., 5 days) | 0.2 μg/mL | 0.2 μg/mL | 0.4 μg/mL | 0.4 μg/mL | 0.4 μg/mL |
| Particle size | PSD (μm) Range + 10% | D10 0.2, D50 2.2, D90 6.1 | D10 0.2, D50 2.2, D90 6.1 | D10 0.2, D50 2.5, D90 7.5 | D10 0.2, D50 2.5, D90 7.5 | D10 0.2, D50: 2.5, D90 7.5 |
| (% dry | Axitinib | 52.10% | 68.60% | 52.10% | 62.50% | 21.70% |
| basis | Target Dose | 300 μg | 600 μg | 300 μg | 600 μg | 150 |
| w/w) | Actual Dose | 308.6 μg | 679.0 μg | 322.3 μg | 608.1 μg | 143 μg |
| | PEG Hydrogel | 39.90% | 26.00% | 39.90% | 31.20% | 65.20% |
| | 4a20K PEG-SAZ | 26.60% | 17.40% | 26.60% | 20.80% | 43.50% |
| | 8a20K PEG-NH2 | 13.30% | 8.70% | 13.30% | 10.40% | 21.70% |
| | TLA | 0.00% | 0.00% | 0.00% | 0.00% | 0.00% |
| | Co-Crystal | 0.00% | 0.00% | 0.00% | 0.00% | 0.00% |
| | Sodium phosphate | 8.00% | 5.40% | 8.00% | 6.30% | 13.00% |
| (% wet | Axitinib | 9.80% | 16.50% | 9.80% | 15.00% | 2.50% |
| basis | PEG Hydrogel | 7.50% | 6.30% | 7.50% | 7.50% | 7.50% |
| w/w) | 4a20K PEG-SAZ | 5.00% | 4.20% | 5.00% | 5.00% | 5.00% |
| | 8a20K PEG-NH2 | 2.50% | 2.10% | 2.50% | 2.50% | 2.50% |
| | TLA | 0.00% | 0.00% | 0.00% | 0.00% | 0.00% |
| | Fumaric® | 0.00% | 0.00% | 0.00% | 0.00% | 0.00% |
| | Sodium phosphate | 1.50% | 1.30% | 1.50% | 1.50% | 1.50% |

TABLE 18-continued

| Implants 7.1A, 7.1B, 7.1C, 7.1D, and 7.1E | | | | | | |
|---|---|---|---|---|---|---|
| Implant | | 7.1A | 7.1B | 7.1C | 7.1D | 7.1E |
| Dimensions | Dry Diameter | 0.300 ± 0.013 | 0.354 ± 0.010 | 0.306 ± 0.005 | 0.350 ± 0.014 | 0.334 ± 0.010 |
| | Dry Length | 7.09 ± 0.025 | 7.53 ± 0.031 | 7.02 ± 0.083 | 8.93 ± 0.948 | 7.65 ± 0.085 |
| | Dry Implant Mass | 0.58 mg | 0.99 mg | 0.58 | 0.96 mg | 0.69 mg |
| | Wet Diameter | 0.629 ± 0.020 | 0.733 ± 0.024 | 0.642 ± 0.030 | 0.717 ± 0.031 | 0.917 ± 0.036 |
| | Wet length | 9.38 ± 0.13 | 7.66 ± 0.18 | 9.56 ± 0.13 | 9.69 ± 0.16 | 11.38 ± 0.40 |

Example 7.2: In Vitro Method B

Also in this study, the influence of solubility on release kinetics of the TKI implant was investigated, with a slightly different in vitro method than in Example 7.1. PEG $NH_2$ (8a20k) and PEG SAZ (4a20k) were used to form the PEG hydrogels. (Table 19).

The implants contained either the SAB-I or the polymorph IV axitinib. As demonstrated in Example 6, SAB-I and polymorph IV differ in their solubilities by a factor of at least 2, i.e., the polymorph IV is about two times more soluble than the SAB-I (FIG. 17).

1 L of 25:75 Ethanol:Water (v/v) using a graduated cylinder was prepared and allowed to equilibrate. Each implant was placed in an amber jar. The amount of 25:75 Ethanol:Water equal to three times the sink volume (sink volume is the axitinib amount in the implant per assay/axitinib solubility) was added for a 3× sink factor. The samples were stored in a 37° C. incubator on a rocker plate to provide moderate agitation. 1 mL of the solution was sampled on pre-determined days until the drug is fully released. Samples were run on either a UV-Vis spectrometer or a UPLC against analytical standards prepared within the last 2 weeks.

In this method B, two different solubility values were used for SAB-I and Polymorph-IV, namely 13.41 and 20.09 μg/mL, respectively, to calculate the sink volume.

Figure 19A:
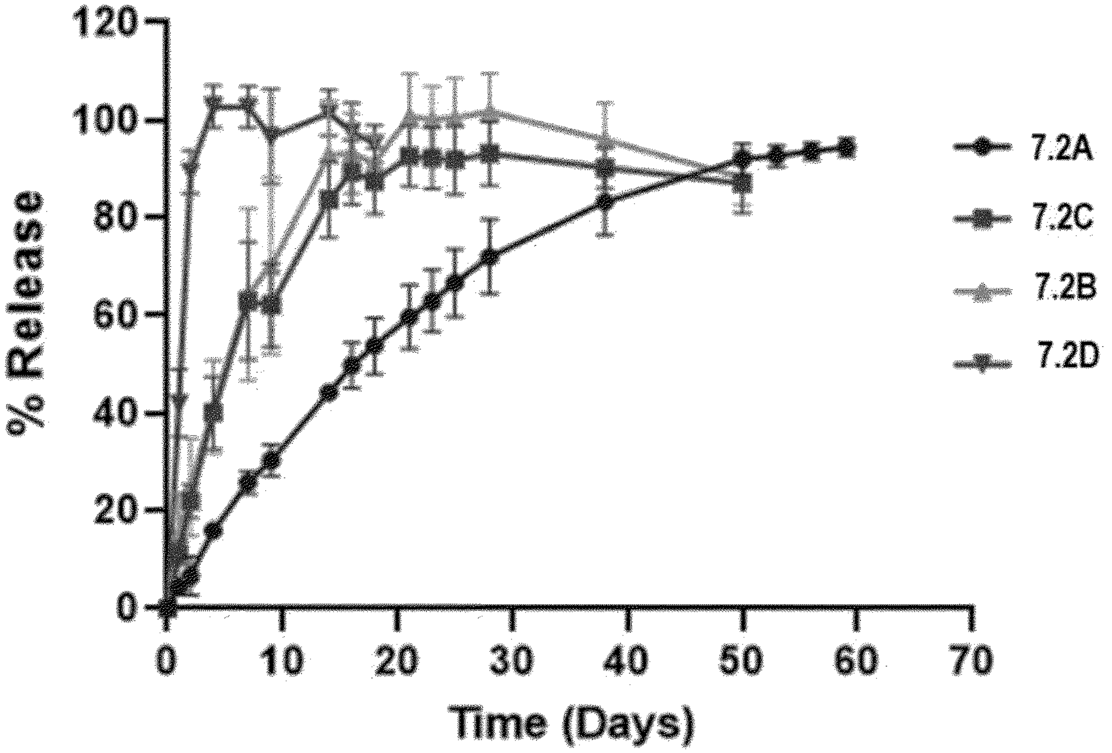
FIG. 19: TKI release profile (In Vitro Method B) from implants 7.2A, 7.28, 7.2C and 7.2D showing the effect of axitinib solubility: (A) % Release; (B) Mass Released.
Figure 19B:
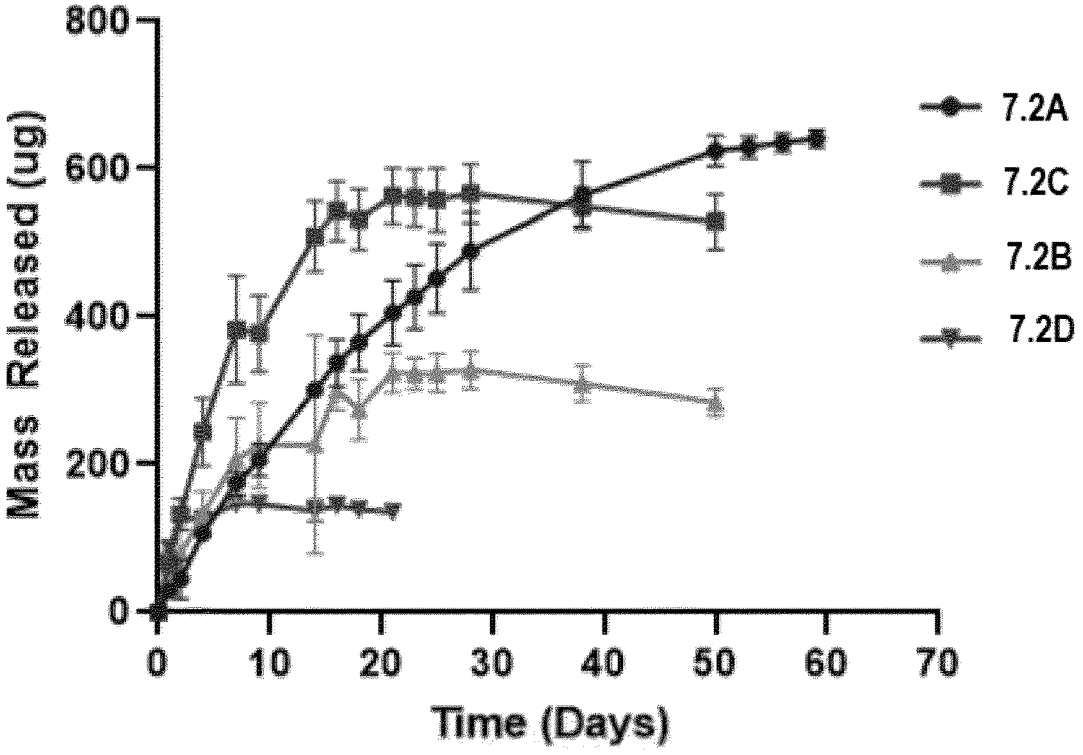

The results are shown in FIGS. 19A and 19B.

TABLE 19

| Implants 7.2A, 7.2B, 7.2C, and 7.2D | | | | | |
|---|---|---|---|---|---|
| | Implant | 7.2A | 7.2B | 7.2C | 7.2D |
| Axitinib Type | Free Base | SAB-I | Polymorph IV | Polymorph IV | Polymorph IV |
| | Solubility in PBS pH 7.2-7.4 (37° C., 5 days) | 0.2 μg/mL | 0.4 μg/mL | 0.4 μg/mL | 0.4 μg/mL |
| Particle size | PSD (μm) Range ± 10% | D10 0.2, D50 2.2, D90 6.1 | D10 0.2, D50 2.5, D90 7.5 | D10 0.2, D50 2.5, D90 7.5 | D10 0.2, D50 2.5, D90 7.5 |
| (% dry basis w/w) | Axitinib | 68.60% | 52.10% | 62.50% | 21.70% |
| | Target Dose | 600 μg | 300 μg | 600 μg | 150 |
| | Actual Dose | 679.0 μg | 322.3 μg | 608.1 μg | 143 μg |
| | PEG Hydrogel | 26.00% | 39.90% | 31.20% | 65.20% |
| | 4a20K PEG-SAZ | 17.40% | 26.60% | 20.80% | 43.50% |
| | 8a20K PEG-NH2 | 8.70% | 13.30% | 10.40% | 21.70% |
| | TLA | 0.00% | 0.00% | 0.00% | 0.00% |
| | Co-Crystal | 0.00% | 0.00% | 0.00% | 0.00% |
| | Sodium phosphate | 5.40% | 8.00% | 6.30% | 13.00% |
| (% wet basis w/w) | Axitinib | 16.50% | 9.80% | 15.00% | 2.50% |
| | PEG Hydrogel | 6.30% | 7.50% | 7.50% | 7.50% |
| | 4a20K PEG-SAZ | 4.20% | 5.00% | 5.00% | 5.00% |
| | 8a20K PEG-NH2 | 2.10% | 2.50% | 2.50% | 2.50% |
| | TLA | 0.00% | 0.00% | 0.00% | 0.00% |
| | Fumaric | 0.00% | 0.00% | 0.00% | 0.00% |
| | Sodium phosphate | 1.30% | 1.50% | 1.50% | 1.50% |
| Dimensions | Dry Diameter | 0.354 ± 0.010 | 0.306 ± 0.005 | 0.350 ± 0.014 | 0.334 ± 0.010 |
| | Dry Length | 7.53 ± 0.031 | 7.02 ± 0.083 | 8.93 ± 0.948 | 7.65 ± 0.085 |
| | Dry Implant Mass | 0.99 mg | 0.58 | 0.96 mg | 0.69 mg |
| | Wet Diameter | 0.733 ± 0.024 | 0.642 ± 0.030 | 0.717 ± 0.031 | 0.917 ± 0.036 |
| | Wet length | 7.66 ± 0.18 | 9.56 ± 0.13 | 9.69 ± 0.16 | 11.38 ± 0.40 |

Example 7.3: In Vitro Method C

Also in this accelerated in vitro test, the influence of solubility on release kinetics of the TKI implant was investigated, with a different in vitro method than in Examples 7.1 and 7.2. Exemplary implants for which results are presented herein are listed in Table 19C.

The implants contained either the SAB-I or the polymorph IV axitinib. As demonstrated in Example 6, SAB-I and polymorph IV differ in their solubilities by a factor of at least 2, i.e., the polymorph IV is about two times more soluble than the polymorph SAB-I (FIG. 17).

The method steps for measuring the axitinib release by means of the accelerated in vitro Method C were according to the following procedure:

7.3.1 Solution Preparations

Dilute Phosphoric Acid: Accurately measure 88 ml of water using a suitably sized graduated cylinder and add approximately 65 ml of water to a suitable container. Add 12 mL of concentrated phosphoric acid and stir to mix completely. Add remaining water, mix well, and allow the solution to return to room temperature.

10 mM Sodium Phosphate Buffer, pH 3.5: Weigh about 1.36 g of potassium dihydrogen phosphate ($KH_2PO_4$) into a suitable vessel. Add 1000 ml of water to the vessel and stir to dissolve. Adjust the pH to 3.50±0.5 with dilute phosphoric acid or 1N NaOH if needed.

Mobile Phase Preparation (1 L): Add 500 ml of the 10 mM sodium phosphate buffer, pH 3.5 prepared as explained above to a 1 L media bottle. Add 250 ml of acetonitrile. Add 250 mL methanol. Mix and allow to equilibrate to room temperature.

Dissolution Media (1 L): Add 10 mL of 1N HCl to a 1 L graduated cylinder containing 900 ml of water. Fill to 1 L with water and transfer to a media bottle. Weigh approximately 2.5 grams of cetyl trimethyl ammonium bromide (CTAB) and add to the media bottle. Mix well and filter to degas.

Stock Standard Diluent (90:10 Ethanol:Water): Combine 100 ml of water and 900 ml of ethanol and mix. Equilibrate to room temperature.

7.3.2 Standard Preparations

Stock Standard Preparation (125 μg/mL): Accurately weigh approximately 12.5 mg axitinib reference standard and quantitatively transfer to an amber 100 mL volumetric flask. Record the exact weight. Add approximately 60 ml of diluent and sonicate until completely dissolved. Allow solution to come to room temperature if sonication was required. Dilute to volume with diluent and mix well. For stock check standard preparation repeat the steps described above for the mobile phase preparation.

Working Standard Preparation (6 μg/mL): Pipette 5.0 ml of the stock standard into a 100 ml amber volumetric flask. Fill to near volume with dissolution media and allow to equilibrate to room temperature. Dilute to volume with dissolution media and mix.

7.3.3 Sample Preparation (n=6)

Prepare the samples and system according to Table 19A.

TABLE 19A

| Preparation of samples and system | |
|---|---|
| Parameters | Description |
| Apparatus | USP App 4 (Flow through cell) setup as closed system |
| Cell type | 22.6 mm diameter |
| Cell setup | Laminar flow with 1 implant between two scoops of glass beads. |
| Medium | 0.01N HCl with 0.25% CTAB |
| Volume | 100 mL |
| Speed rate | 8 mL/min |
| Temperature | 35° C. ± 0.5° C. |
| Sample | 1 Implant |
| Filtration | None |
| Sampling profile (hours) | For this study:<br>Form IV: 0.5, 1, 2, 4, 6, 8, 12, 16, 24, 36, 48<br>SAB-I: 2, 4, 6, 8, 12, 16, 24, 36, 48, 60, 72 |
| Run initiation Prep I | Prep I |

7.3.4 Analysis Procedure

UPLC Conditions: UPLC is run according to the following conditions:

TABLE 19B

| UPLC conditions | |
|---|---|
| Injection Volume | 10 μL |
| Needle Wash | 90:10 Ethanol:Water |
| Seal Wash | 10:90 Acetonitrile:Water |
| Purge Solvent | 50:25:25 Water:Acetonitrile:Methanol |
| Column | Waters X-Bridge BEH C18, 2.1 × 50, 1.7 μm |
| Column Temperature | 40° C. |
| Detection Wavelength | 330 nm |
| Run Time | 4 minutes |
| Mobile Phase | 50:25:25 10 mM Sodium Phosphate Buffer, pH 3.5:ACN:MeOH |
| Flow Rate | 0.35 mL/min |
| Flow Composition | Isocratic |
| Sample temp. | Ambient |
| Axitinib retention time | Approximately 1.0 minutes |

Exemplary implants for which the accelerated in vitro Method C was performed are listed in the following Table 19C:

TABLE 19C

| Implants 7.3A, 7.3B, 7.3C, 7.3D, 7.3E, 7.3F, 7.3G, 7.3H | | | | | | | | | |
|---|---|---|---|---|---|---|---|---|---|
| Implant | | 7.3A | 7.3B | 7.3C | 7.3D | 7.3E | 7.3F | 7.3G | 7.3H |
| Axitinib Type | Free Base | Polymorph IV micronized | Polymorph IV micronized | SAB-I Micronized | Polymorph IV micronized | SAB-I Micronized | Polymorph IV micronized | Polymorph IV micronized | Polymorph IV micronized |
| | Solubility in PBS pH (37° C., 5 days) 7.2-7.4 | 0.4 μg/mL | 0.4 μg/mL | 0.2 μg/ml | 0.4 μg/mL | 0.2 μg/mL | 0.4 μg/mL | 0.4 μg/mL | 0.4 μg/mL |

TABLE 19C-continued

| Implants 7.3A, 7.3B, 7.3C, 7.3D, 7.3E, 7.3F, 7.3G, 7.3H | | | | | | | | | |
|---|---|---|---|---|---|---|---|---|---|
| Implant | | 7.3A | 7.3B | 7.3C | 7.3D | 7.3E | 7.3F | 7.3G | 7.3H |
| Particle size | PSD (μm) Range ± 10% | D10 0.2, D50 2.5 D90 7.5 | D10:0.2, D50 2.5, D90 7.5 | D10 0.2, D50 2.2, D90 6.1 | D10 0.2, D50 2.5, D90 7.5 | D10 0.2, D50 2.2, D90 6.1 | D10 0.2, D50 2.5, D90 7.5 | D10 0.2, D50 2.5, D90 7.5 | D10 0.2, D50 2.5, D90 7.5 |
| | Axitinib | 62.50% | 21.70% | 52.10% | 52.10% | 68.60% | 54.00% | 54.00% | 63.74% |
| | Target Dose | 600 μg | 150 μg | 300 μg | 300 μg | 600 μg | 450 μg | 450 μg | 450 μg |
| (% dry basis w/w) | Actual Dose | 608 μg | 143 μg | 309 μg | 322 μg | 598 μg | 446 μg | 457 μg | 479 μg |
| | PEG Hydrogel | 31.20% | 65.20% | 39.90% | 39.90% | 26.00% | 38.60% | 38.60% | 30.58% |
| | 4a20K PEG-SAZ | 20.80% | 43.50% | 26.60% | 26.60% | 17.33% | 25.70% | 25.70% | 20.39% |
| | 8a20K PEG-NH2 | 10.40% | 21.70% | 13.30% | 13.30% | 8.67% | 12.90% | 12.90% | 10.19% |
| | TLA | 0.00% | 0.00% | 0.00% | 0.00% | 0.00% | 0.00% | 0.00% | 0.00% |
| | Co-Crystal | 0.00% | 0.00% | 0.00% | 0.00% | 0.00% | 0.00% | 0.00% | 0.00% |
| | Sodium phosphate | 6.30% | 13.00% | 8.00% | 8.00% | 5.40% | 7.40% | 7.40% | 5.40% |
| (% wet basis w/w) | Axitinib | 15.00% | 2.50% | 9.80% | 9.80% | 16.50% | 9.50% | 9.50% | 13.51% |
| | PEG Hydrogel | 7.50% | 7.50% | 7.50% | 7.50% | 6.30% | 6.80% | 6.80% | 6.48% |
| | 4a20K PEG-SAZ | 5.00% | 5.00% | 5.00% | 5.00% | 4.20% | 4.53% | 4.53% | 4.32% |
| | 8a20K PEG-NH2 | 2.50% | 2.50% | 2.50% | 2.50% | 2.10% | 2.27% | 2.27% | 2.16% |
| | TLA | 0.00% | 0.00% | 0.00% | 0.00% | 0.00% | 0.00% | 0.00% | 0.00% |
| | Fumaric | 0.00% | 0.00% | 0.00% | 0.00% | 0.00% | 0.00% | 0.00% | 0.00% |
| | Sodium phosphate | 1.50% | 1.50% | 1.50% | 1.50% | 1.30% | 1.30% | 1.30% | 1.21% |
| Dimensions | Dry Diameter | 0.35 ± 0.014 mm | 0.33 ± 0.010 mm | 0.306 mm | 0.31 ± 0.005 mm | 0.37 ± 0.008 mm | 0.360 mm | 0.360 mm | 0.327 mm |
| | Dry Length | 9.43 mm | 7.7 ± 0.09 mm | 7.1 ± 0.03 mm | 7.1 ± 0.08 mm | 7.01 mm | 6.98 mm | 7.00 mm | 7.13 mm |
| | Dry Implant Mass | 0.96 mg | 0.69 mg | 0.58 mg | 0.58 mg | 0.88 ± 0.01 mg | 0.83 mg | 0.83 mg | 0.75 mg |
| | Wet Diameter | 0.72 mm | 0.92 mm | 0.63 mm | 0.64 mm | 0.712 mm | 0.840 mm | 0.797 mm | 0.650 mm |
| | Wet length | 9.70 mm | 11.4 mm | 9.4 mm | 9.6 mm | 6.75 mm | 7.79 mm | 7.79 mm | 8.50 mm |

Figure 27A:
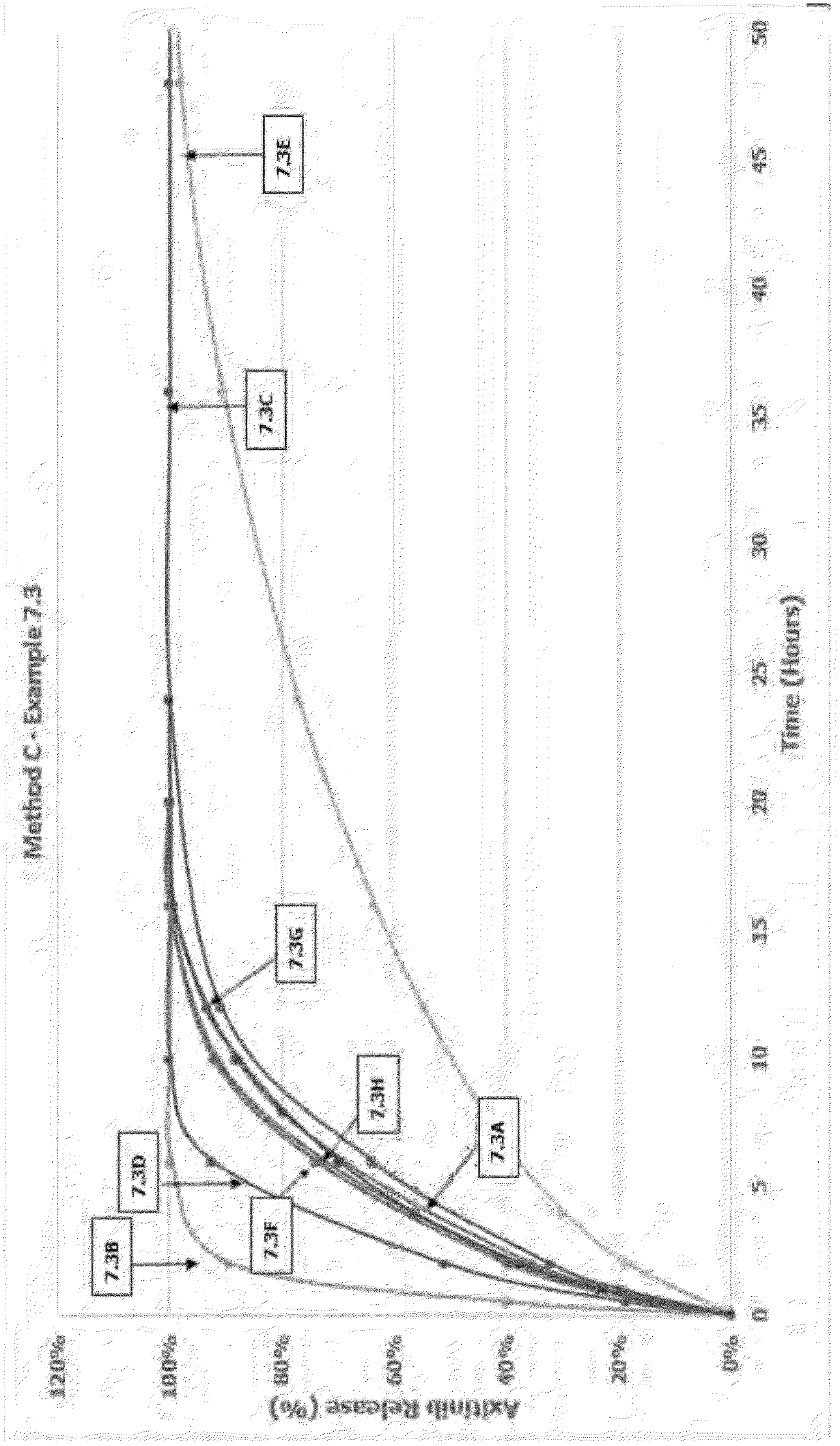
FIG. 27: TKI release profile from implants 7.3A to 7.3H (% release over time, In Vitro Method C), shown through about 50 hours (A) and through about 11 hours (B), Example 7.3
Figure 27B:
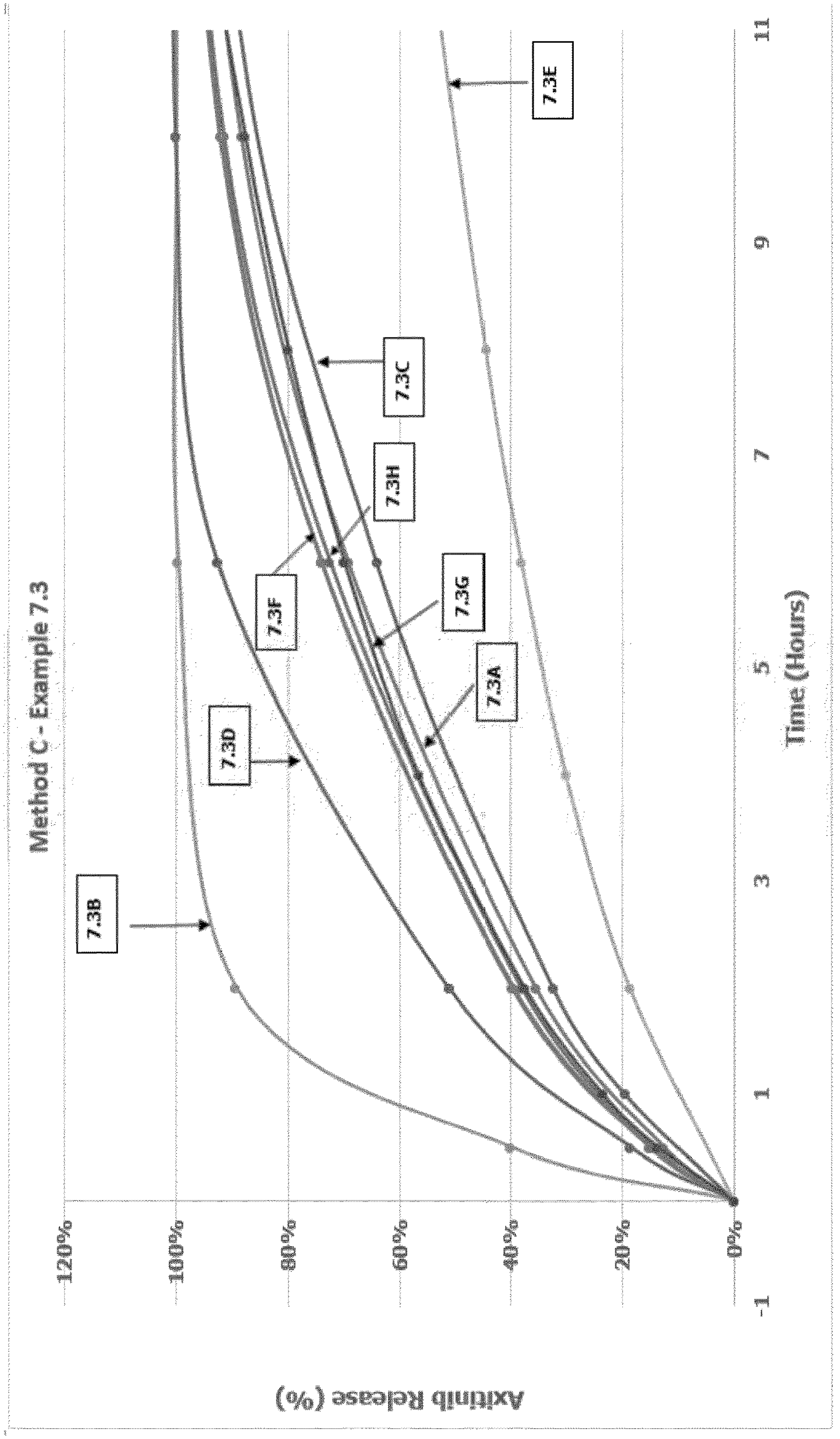
Figure 28:
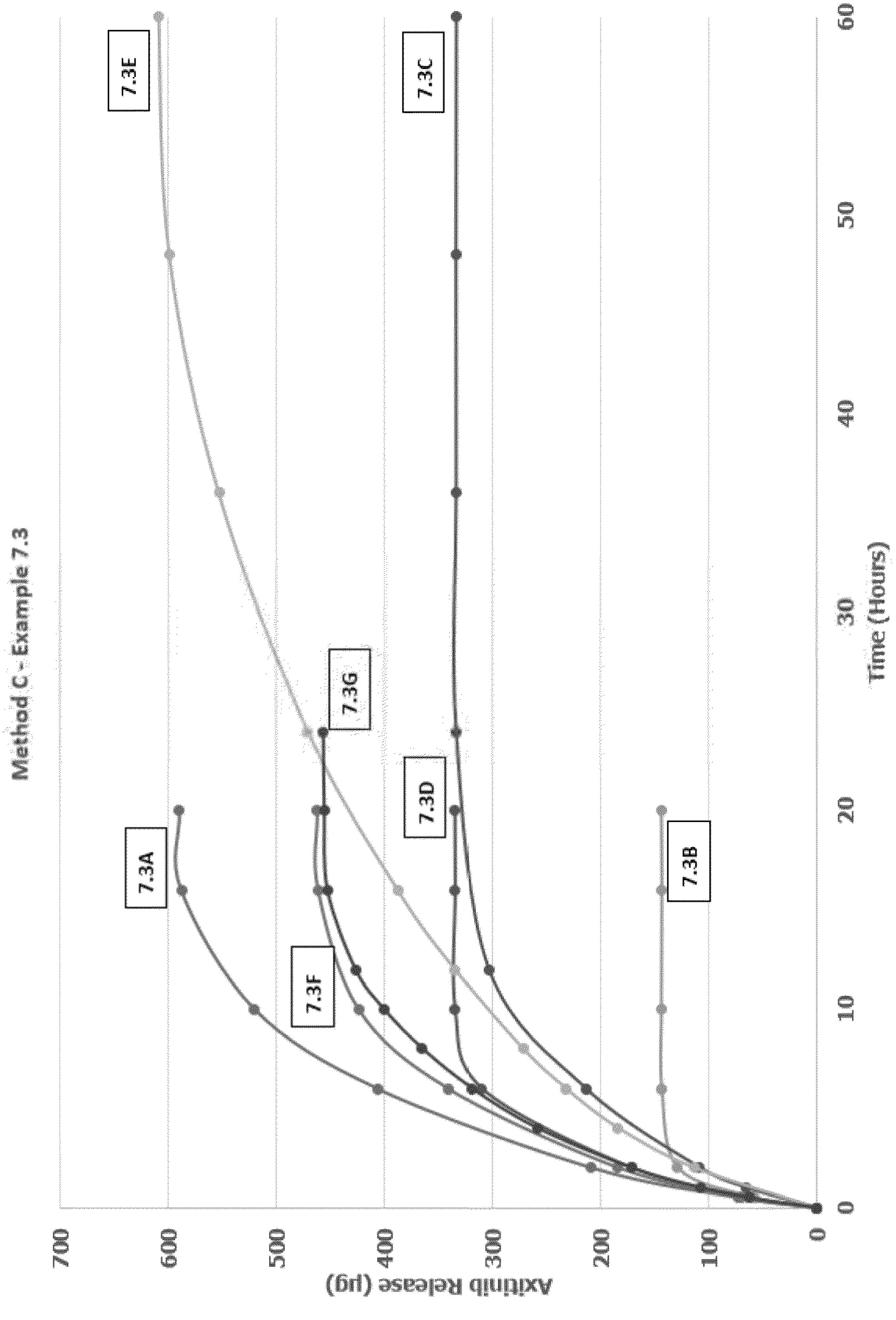
FIG. 28: TKI release profile from implants 7.3A to 7.3H (mass released over time, In Vitro Method C), Example 7.3; TKI release profile from implants 7.3G to 7.3K of Example 7.3 (mass released over time, In Vitro method C—FIG. 28A; and % released over time, In Vitro Method C—FIG. 28B)

The results of the accelerated in vitro test (Method C) from the implants of Table 19C are provided in FIGS. 27A, 27B and 28.

For the in vitro release using method Cas disclosed herein, the axitinib concentration, % axitinib release and cumulative % release was determined as follows:

$$\text{Sample Axitinib Concentration } (C) = (A_{sam} \times C_{Std})/A_{Std}$$

Where:

$A_{sam}$=peak area of the sample $A_{Std}$=average peak area of the 6 consecutive injections for each standard $C_{Std}$=concentration of Axitinib in the standard solution (μg/mL)

$$\text{Axitinib \% Released} = \{(C_n - C_{n-1}) \times (V_i[(n-1) \times V_r]) \times 100\%\}/(\text{Label Claim})$$

Where:

n=Time point number (first sample taken: n=1, second sample taken: n=2, etc.)

$C_n$=Axitinib concentration of sample at timepoint n $C_{n-1}$=Axitinib concentration of sample at timepoint n−1

$V_i$=Dissolution media volume at start of analysis (mL)

$V_r$=Sampling volume removed per sample taken (mL)

Label Claim means the target dose of axitinib in an implant, e.g. 450 μg in the case of implant 7.3F (and not the actual amount of axitinib contained in the implant, which would be 446 pig in the case of implant 7.3F).

$$\text{Cumulative \% Release} = \text{\% Released}_n + \text{\% Released}_{n-1}$$

Where:

% $\text{Released}_n$=Axitinib % released at a certain timepoint

% $\text{Released}_{n-1}$=% released from previous timepoint

The average (i.e., cumulative) % of axitinib released (as shown in all the tables/graphs herein relating to in vitro release measurements by Method C) is calculated herein (per the formula above) from six samples measured for each timepoint.

The normalized average % released (as shown in all the tables/graphs herein relating to in vitro release measurements by Method C) is based on the maximum release of axitinib from the respective sample representing 100% (independent of the label/target amount of axitinib or the actual amount of axitinib contained in the respective implant).

The "actual µg released" (as shown in all the tables/graphs herein relating to in vitro release measurements by Method C) represents the actual mass of axitinib released over time, again measured from six samples for each timepoint.

TABLE 19C.1:

In vitro release from implants 7.3A, 7.3B, 7.3C, 7.3D, 7.3E, 7.3F, 7.3G, 7.3H:

| Time (hours) | Concentration (µg/mL) | Avg % Released | Normalized Average % Released | StDev | Average µg Released | StDev µg Released |
|---|---|---|---|---|---|---|
| Implant 7.3A (in vitro release) | | | | | | |
| 0 | 0.0000 | 0 | 0 | 0 | 0 | 0 |
| 0.5 | 0.734 | 12.238 | 12 | 0.276 | 73 | 2 |
| 2 | 2.103 | 34.827 | 35 | 1.198 | 209 | :7 |
| 6 | 4.121 | 67.782 | 69 | 1.918 | 407 | 12 |
| 10 | 5.288 | 86.643 | 88 | 1.483 | 520 | 9 |
| 16 | 5.995 | 97.966 | 100 | 0.890 | 588 | 5 |
| 20 | 6.012 | 98.230 | 100 | 0.925 | 589 | 6 |
| Implant 7.3B (in vitro release) | | | | | | |
| 0 | 0.000 | 0 | 0 | 0 | 0 | 0 |
| 0.5 | 0.578 | 38.555 | 40 | 1.209 | 58 | 2 |
| 2 | 1.294 | 85.789 | 89 | 3.279 | 129 | 5 |
| 6 | 1.445 | 95.654 | 100 | 4.257 | 143 | 6 |
| 10 | 1.450 | 95.999 | 100 | 3.785 | 144 | 6 |
| 16 | 1.446 | 95.743 | 100 | 3.746 | 144 | 6 |
| 20 | 1.451 | 96.018 | 100 | 3.791 | 144 | 6 |
| Implant 7.3C (in vitro release) | | | | | | |
| 0 | 0.000 | 0 | 0 | 0 | 0 | 0 |
| 1 | 0.654 | 21.811 | 20 | 0.892 | 65 | 3 |
| 2 | 1.087 | 36.094 | 32 | 1.681 | 108 | 5 |
| 6 | 2.164 | 71.282 | 64 | 3.385 | 214 | 10 |
| 12 | 3.089 | 101.185 | 91 | 4.560 | 304 | 14 |
| 24 | 3.405 | 111.297 | 100 | 4.982 | 334 | 15 |
| 36 | 3.406 | 111.318 | 100 | 4.950 | 334 | 15 |
| 48 | 3.408 | 111.386 | 100 | 4.942 | 334 | 15 |
| 60 | 3.404 | 111.267 | 100 | 5.043 | 334 | 15 |
| Implant 7.3D (in vitro release) | | | | | | |
| 0 | 0.000 | 0 | 0 | 0 | 0 | 0 |
| 0.5 | 0.612 | 20.666 | 18 | 0.640 | 62 | 2 |
| 2 | 1.726 | 57.151 | 51 | 0.939 | 171 | 3 |
| 6 | 3.169 | 103.361 | 92 | 2.307 | 310 | 7 |
| 10 | 3.476 | 111.723 | 100 | 3.824 | 335 | 11 |
| 16 | 3.478 | 111.723 | 100 | 3.868 | 335 | 12 |
| 20 | 3.479 | 111.805 | 100 | 3.889 | 335 | 12 |
| Implant 7.3E (in vitro release) | | | | | | |
| 0 | 0.000 | 0 | 0 | 0 | 0 | 0 |
| 2 | 1.138 | 18.966 | 19 | 0.467 | 114 | 3 |
| 4 | 1.844 | 30.607 | 30 | 0.413 | 184 | 2 |
| 6 | 2.338 | 38.684 | 38 | 1.344 | 232 | 8 |
| 8 | 2.746 | 45.282 | 44 | 2.125 | 272 | 13 |
| 12 | 3.404 | 55.808 | 55 | 3.104 | 335 | 19 |
| 16 | 3.961 | 64.622 | 63 | 3.674 | 388 | 22 |
| 24 | 4.843 | 78.450 | 77 | 3.418 | 471 | 21 |
| 36 | 5.729 | 92.178 | 91 | 3.522 | 553 | 21 |
| 48 | 6.227 | 99.814 | 98 | 3.123 | 599 | 19 |
| 60 | 6.333 | 101.424 | 100 | 1.378 | 609 | 8 |
| 72 | 6.360 | 101.822 | 100 | 0.896 | 611 | 5 |

TABLE 19C.1:-continued

In vitro release from implants 7.3A, 7.3B, 7.3C, 7.3D, 7.3E, 7.3F, 7.3G, 7.3H:

| Time (hours) | Concentration (μg/mL) | Avg % Released | Normalized Average % Released | StDev | Average μg Released | StDev μg Released |
|---|---|---|---|---|---|---|
| Implant 7.3F (in vitro release) | | | | | | |
| 0 | 0.000 | 0 | 0 | 0 | 0 | 0 |
| 0.5 | 0.697 | 15.481 | 15 | 0.333 | 70 | 2 |
| 2 | 1.850 | 40.843 | 40 | 0.678 | 184 | 3 |
| 6 | 3.456 | 75.826 | 74 | 1.768 | 341 | 8 |
| 10 | 4.308 | 94.195 | 92 | 2.339 | 424 | 11 |
| 16 | 4.698 | 102.504 | 100 | 2.732 | 461 | 12 |
| 20 | 4.705 | 102.669 | 100 | 2.514 | 462 | 11 |
| Implant 7.3G (in vitro release) | | | | | | |
| 0 | 0.000 | 0 | 0 | 0 | 0 | 0 |
| 0.5 | 0.625 | 13.892 | 14 | 0.352 | 63 | 2 |
| 1 | 1.079 | 23.869 | 24 | 0.853 | 107 | 4 |
| 2 | 1.734 | 38.134 | 38 | 1.031 | 172 | 5 |
| 4 | 2.628 | 57.408 | 57 | 1.269 | 258 | 6 |
| 6 | 3.259 | 70.880 | 70 | 1.704 | 319 | 8 |
| 8 | 3.743 | 81.091 | 80 | 2.184 | 365 | 10 |
| 10 | 4.121 | 88.987 | 88 | 2.514 | 400 | 11 |
| 12 | 4.407 | 94.897 | 93 | 2.898 | 427 | 13 |
| 16 | 4.689 | 100.669 | 99 | 3.621 | 453 | 16 |
| 20 | 4.722 | 101.330 | 100 | 3.633 | 456 | 16 |
| 24 | 4.732 | 101.533 | 100 | 3.283 | 457 | 15 |
| Implant 7.3H (in vitro release) | | | | | | |
| 0 | 0.000 | 0 | 0 | 0 | 0 | 0 |
| 0.5 | 0.675 | 14.996 | 14 | 0.451 | 67 | 2 |
| 2 | 1.867 | 41.220 | 38 | 0.797 | 185 | 4 |
| 6 | 3.574 | 78.394 | 73 | 1.484 | 353 | 7 |
| 10 | 4.500 | 98.355 | 92 | 2.087 | 443 | 9 |
| 16 | 4.926 | 107.443 | 100 | 2.206 | 483 | 10 |
| 20 | 4.907 | 107.042 | 100 | 2.324 | 482 | 10 |

TABLE 19D

Implants 7.3G, 7.3H, 7.31, 7.3J and 7.3K

| Implant | | 7.3G | 7.3H | 7.3I | 7.3J | 7.3K |
|---|---|---|---|---|---|---|
| Axitinib Type | Free Base | Polymorph IV micronized | Polymorph IV micronized | Polymorph IV Micronized | SAB-I Micronized | Polymorph IV Micronized |
| | Solubility in: PBS pH 7.2-7.4 (37° C., 5 days) | 0.4 μg/mL | 0.4 μg/mL | 0.4 μg/mL | 0.2 μg/mL | 0.4 μg/mL |
| Particle size | PSD (um) Range ± 10% | D90 7.5 D10 0.2, D50 2.5, | D10 0.2, D50 2.5, D90 7.5 | D10 0.2, D50 2.5, D90 7.5 | D10 0.2, D50 2.2, D90 6.1 | D10 0.2, D50 2.5, D90 7.5 |
| (% dry basis w/w) | Axitinib | 54.00% | 63.74% | 63.90% | 63.95% | 63.95% |
| | Target Dose | 450 μg | 450 μg | 450 μg | 450 μg | 450 μg |
| | Actual Dose | 457 μg | 479 μg | 462 μg | 448 μg | 416 μg |
| | PEG Hydrogel | 38.60% | 30.58% | 30.70% | 30.74% | 30.73% |
| | 4a20K PEG-SAZ | 25.70% | 20.39% | 20.50% | 20.50% | 20.47% |
| | 8a20K PEG-NH2 | 12.90% | 10.19% | 10.20% | 10.24% | 10.26% |
| | TLA | 0.00% | 0.00% | 0.00% | 0.00% | 0.00% |
| | Co-Crystal | 0.00% | 0.00% | 0.00% | 0.00% | 0.00% |
| | Sodium phosphate | 7.40% | 5.40% | 5.30% | 5.31% | 5.32% |
| (% wet basis w/w) | Axitinib | | | | | |
| | PEG Hydrogel | 6.80% | 6.48% | 6.50% | 6.49% | 6.48% |
| | 4a20K PEG-SAZ | 4.53% | 4.32% | 4.30% | 4.33% | 4.32% |
| | 8a20K PEG-NH2 | 2.27% | 2.16% | 2.20% | 2.16% | 2.17% |
| | TLA | 0.00% | 0.00% | 0.00% | 0.00% | 0.00% |
| | Fumaric | 0.00% | 0.00% | 0.00% | 0.00% | 0.00% |
| | Sodium phosphate | 1.30% | 1.21% | 1.10% | 1.12% | 1.12% |

TABLE 19D-continued

| Implants 7.3G, 7.3H, 7.31, 7.3J and 7.3K | | | | | | |
|---|---|---|---|---|---|---|
| Implant | | 7.3G | 7.3H | 7.3I | 7.3J | 7.3K |
| Dimensions | Dry Diameter | 0.360 mm | 0.327 mm | 0.33 mm | 0.33 mm | 0.27 mm |
| | Dry Length | 7.00 mm | 7.13 mm | 6.80 mm | 7.00 mm | 9.57 mm |
| | Dry Implant Mass | 0.83 mg | 0.75 mg | 0.71 mg | 0.71 mg | 0.76 mg |
| | Wet Diameter | 0.797 mm | 0.650 mm | 0.67 mm | 0.74 mm | 0.66 mm |
| | Wet length | 7.79 mm | 8.50 mm | 7.83 mm | 7.59 mm | 9.01 mm |

Figure 28A:
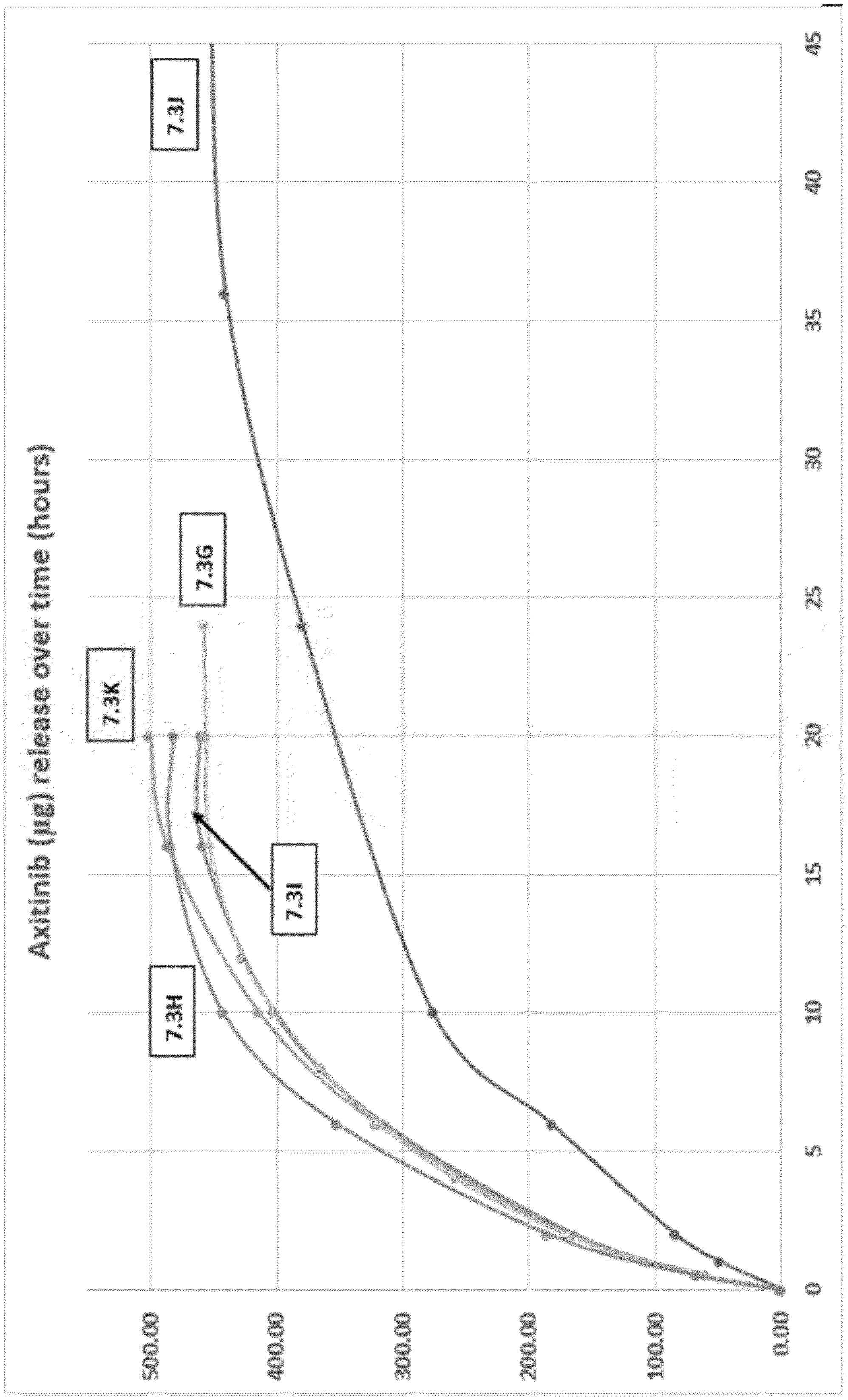
Figure 28B:
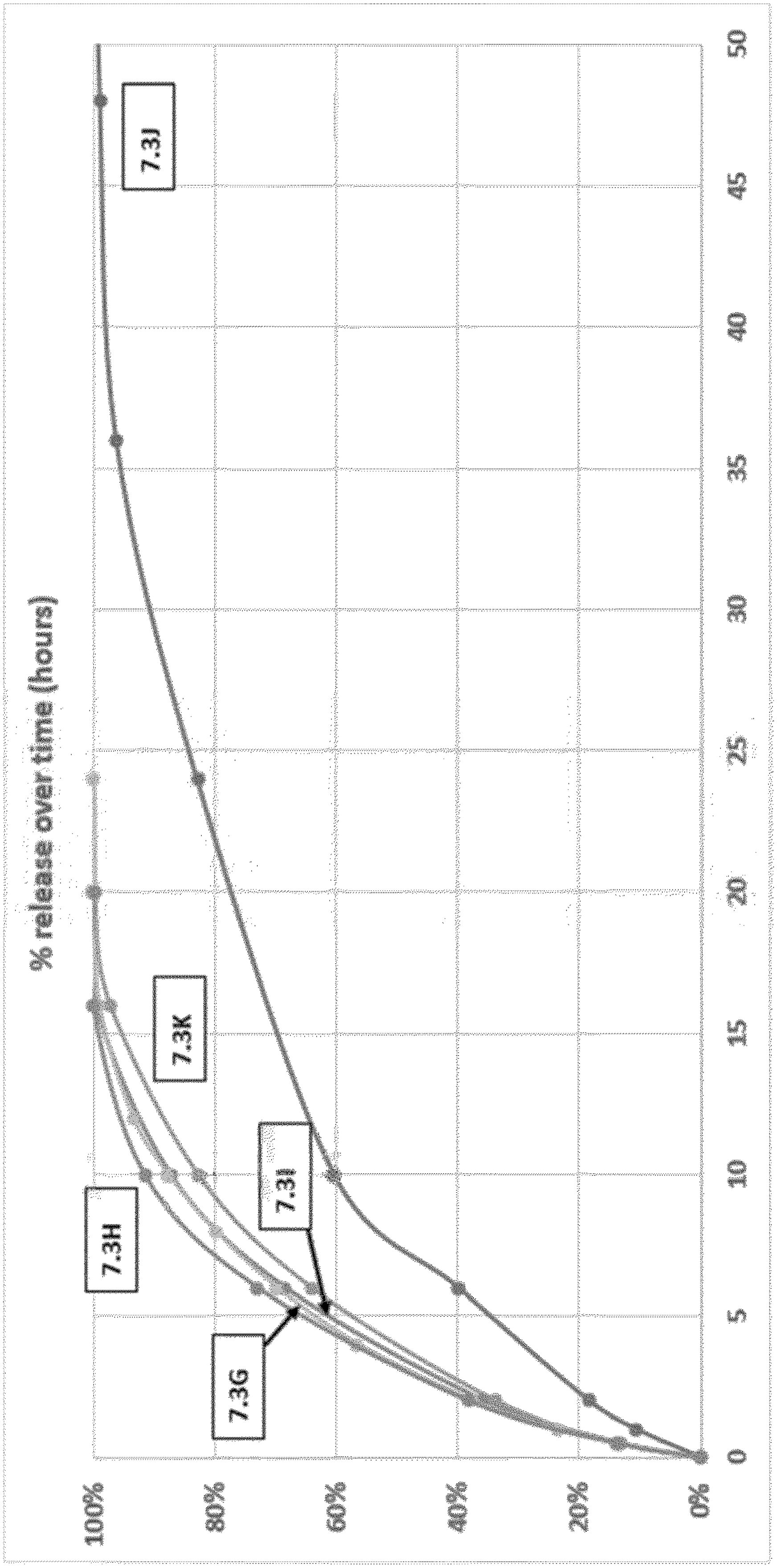

The results of the accelerated in vitro test (Method C) from the implants of Table 19D are provided in FIGS. 28A and 28B and shown in the Tables below.

TABLE 19D.1

In vitro release from implants 7.3G, 7.3H, 7.31, 7.3J and 7.3K:

Implant 7.3I (in vitro release)

| Time (hours) | Concentration (μg/mL) | Avg % Released | Normalized Average % Released | StDev | Average μg Released | StDev μg Released |
|---|---|---|---|---|---|---|
| 0 | 0 | 0 | 0 | 0 | 0 | 0 |
| 0.5 | 0.606 | 13.462 | 13 | 0.501 | 61 | 2.257 |
| 2 | 1.652 | 36.467 | 36 | 0.585 | 164 | 2.635 |
| 6 | 3.190 | 69.969 | 68 | 0.463 | 315 | 2.084 |
| 10 | 4.085 | 89.268 | 87 | 1.267 | 402 | 5.704 |
| 16 | 4.677 | 101.890 | 100 | 2.239 | 459 | 10.076 |
| 20 | 4.694 | 102.246 | 100 | 1.861 | 460 | 8.378 |

Implant 7.3J (in vitro release)

| Time (hours) | Concentration (μg/mL) | Average % Released | Normalized Average % Released | StDev | Average μg Released | StDev μg Released |
|---|---|---|---|---|---|---|
| 0 | 0 | 0 | 0 | 0 | 0.00 | 0 |
| 1 | 0.485 | 10.78 | 11 | 2.07 | 48.53 | 9.32 |
| 2 | 0.837 | 18.70 | 18 | 2.94 | 84.16 | 13.22 |
| 6 | 1.812 | 40.55 | 40 | 3.07 | 182.47 | 13.81 |
| 10 | 2.732 | 61.40 | 60 | 1.70 | 276.28 | 7.67 |
| 24 | 3.736 | 84.33 | 83 | 1.53 | 379.49 | 6.87 |
| 36 | 4.309 | 97.88 | 96 | 1.29 | 440.45 | 5.79 |
| 48 | 4.387 | 100.58 | 99 | 0.68 | 452.61 | 3.06 |
| 60 | 4.397 | 101.77 | 100 | 0.95 | 457.95 | 4.29 |

Implant 7.3K (in vitro release)

| Time (hours) | Concentration (μg/mL) | Average Released | Normalized Average % Released | StDev | Average μg Released | StDev μg Released |
|---|---|---|---|---|---|---|
| 0 | 0 | 0 | 0 | 0 | 0 | 0 |
| 0.5 | 0.670 | 14.32 | 13 | 1.58 | 67.18 | 7.41 |
| 2 | 1.684 | 36.13 | 34 | 4.26 | 169.46 | 19.98 |
| 6 | 3.182 | 68.49 | 64 | 7.04 | 321.21 | 33.02 |
| 10: | 4.082 | 88.40 | 83 | 7.46 | 414.59 | 34.99 |
| 16 | 4.764 | 103.85 | 97 | 4.95 | 487.06 | 23.22 |
| 20 | 4.855 | 106.81 | 100 | 2.89 | 500.92 | 13.55 |

TABLE 19E

| Implants 7.3L, 7.3M | | | |
|---|---|---|---|
| | Implant | 7.3L | 7.3M |
| Axitinib Type | Free Base | Polymorph IV Nanonized | Axitinib ProDrug* (axitinib N-m(PEG)$_2$-oxymethyl of Ex. 5.2) |
| | Solubility in PBS pH 7.2-7.4 (37° C., 5 days) | 0.4 μg/mL | 1.10 μg/mL |
| Particle size | PSD (μm) Range ± 10% | D10 0.2 D50 3.1 D90 17.2 (particle size distribution showed two peaks due to agglomeration) | D10 0.4 D50 4.4 D90 11.6 |
| (% dry basis w/w) | Axitinib | 63.94% | 64.72%* (prodrug) |
| | actual Dose | 447 μg | 437 μg |
| | target Dose | 450 μg | 450 μg |
| | PEG Hydrogel | 30.73% | 30.06% |
| | 4a20K PEG-SAZ | 20.49% | 20.04% |
| | 8a20K PEG-NH2 | 10.24% | 10.02% |
| | TLA | 0.00% | 0.00% |
| | Prodrug | 0.00% | 64.72% |
| | Sodium phosphate | 5.33% | 5.22% |
| (% wet basis w/w) | Axitinib | 13.50% | 13.34%* (prodrug) |
| | PEG Hydrogel | 6.49% | 6.20% |
| | 4a20K PEG-SAZ | 4.33% | 4.13% |
| | 8a20K PEG-NH2 | 2.16% | 2.07% |
| | TLA | 0.00% | 0.00% |
| | Fumaric | 0.00% | 0.00% |
| | Sodium phosphate | 1.13% | 1.08% |
| Dimensions | Dry Diameter | 0.33 mm | 0.40 mm |
| | Dry Length | 6.98 mm | 4.75 mm |
| | Dry Implant Mass | 0.74 mg | 0.68 mg |
| | Wet Diameter | 0.63 mm | 0.73 mm |
| | Wet length | 8.03 mm | 6.32 mm |

TABLE 19E.1

1: In vitro release from implants 7.3L, 7.3M:

Implant 7.3L (in vitro release)

| Time (hours) | Concentration (μg/mL) | Average % Released | Normalized Average % Released | StDev | Average Released | StDev μg Released |
|---|---|---|---|---|---|---|
| 0 | 0.000 | 0 | 0 | 0 | 0 | 0 |
| 0.5 | 0.715 | 15.89 | 15 | 0.13 | 71.50 | 0.58 |
| 2 | 1.865 | 41.60 | 40 | 0.43 | 187.22 | 1.92 |
| 6 | 3.455 | 77.35 | 74 | 0.47 | 348.08 | 2.10 |
| 10 | 4.293 | 96.73 | 92 | 0.37 | 435.29 | 1.68 |
| 16 | 4.573 | 103.91 | 99 | 0.93 | 467.58 | 4.18 |
| 20 | 4.565 | 104.76 | 100 | 1.10 | 471.40 | 4.96 |

TABLE 19E.1-continued

| Implant 7.3M ( in vitro release) | | | | | | |
|---|---|---|---|---|---|---|
| Time (hours) | Con-cen-tration (µg/mL) | Average 0% Re-leased | Nor-malized Average % Released | StDev | Average µg Re-leased | StDev µg Re-leased |
| 0 | 0 | 0 | 0 | 0 | 0 | 0 |
| 0.5 | 0.737 | 16.37 | 17 | 0.64 | 73.67 | 2.89 |
| 2 | 1.807 | 40.31 | 41 | 1.57 | 181.40 | 7.05 |
| 6 | 3.333 | 74.64 | 76 | 2.25 | 335.88 | 10.11 |
| 10 | 4.143 | 93.38 | 95 | 2.64 | 420.21 | 11.87 |
| 16 | 4.337 | 98.60 | 100 | 1.53 | 443.69 | 6.90 |
| 20 | 4.283 | 98.38 | 100 | 2.11 | 442.69 | 9.47 |

Example 8: In Vitro Release of the TKI Implant-Hydrated Surface Area can be Selected to Control the Release Profile In this study, the influence of the hydrated surface area on release kinetics of the TKI implant was investigated. PEG $NH_2$ (8a20k) and PEG SAZ (4a20k) were used to form the PEG hydrogels. (Tables 20 and 21).

The implants contained the SAB-I axitinib. The hydrated surface area of the implants is indicated in Tables 20 and 21. Implant 8B was a 5-arm star implant. The formula for calculating the hydrated surface area of such an implant is provided e.g., in FIG. 3. Implant 8A is a cylindrical implant. The hydrated surface area of this implant is calculated from the hydrated dimensions, as indicated, by means of the formula for a surface are of a cylinder.

In Table 20 below, implant 8C was a 7-filament heat-stretch-twist implant, which was 4 compared in this in vitro release study to three implants 8D. The hydrated surface area is calculated in both cases from the hydrated surface area of a single implant/filament (based on the hydrated dimension as explained above) multiplied by the number of implants/filaments.

The release was measured according to Method B described in Example 7.2 except for implant 8E that was measured according to Method C described in Example 7.3. Implant 8E was a HST (heat-stretch-twist) bundle implant made of 3 individual (but identical) filaments, see Table 21A below. In implant 8E, the individual filaments were coated with a Kollicoat® coating before stretching and twisting as disclosed herein. This coating contributed to the unfurling of the individual filaments upon hydration in vitro and in vivo, so that in the hydrated state (as defined herein) there were 3 individual, unfurled implants providing an increased hydrated surface area for a faster release rate of the active agent.

Figure 20:
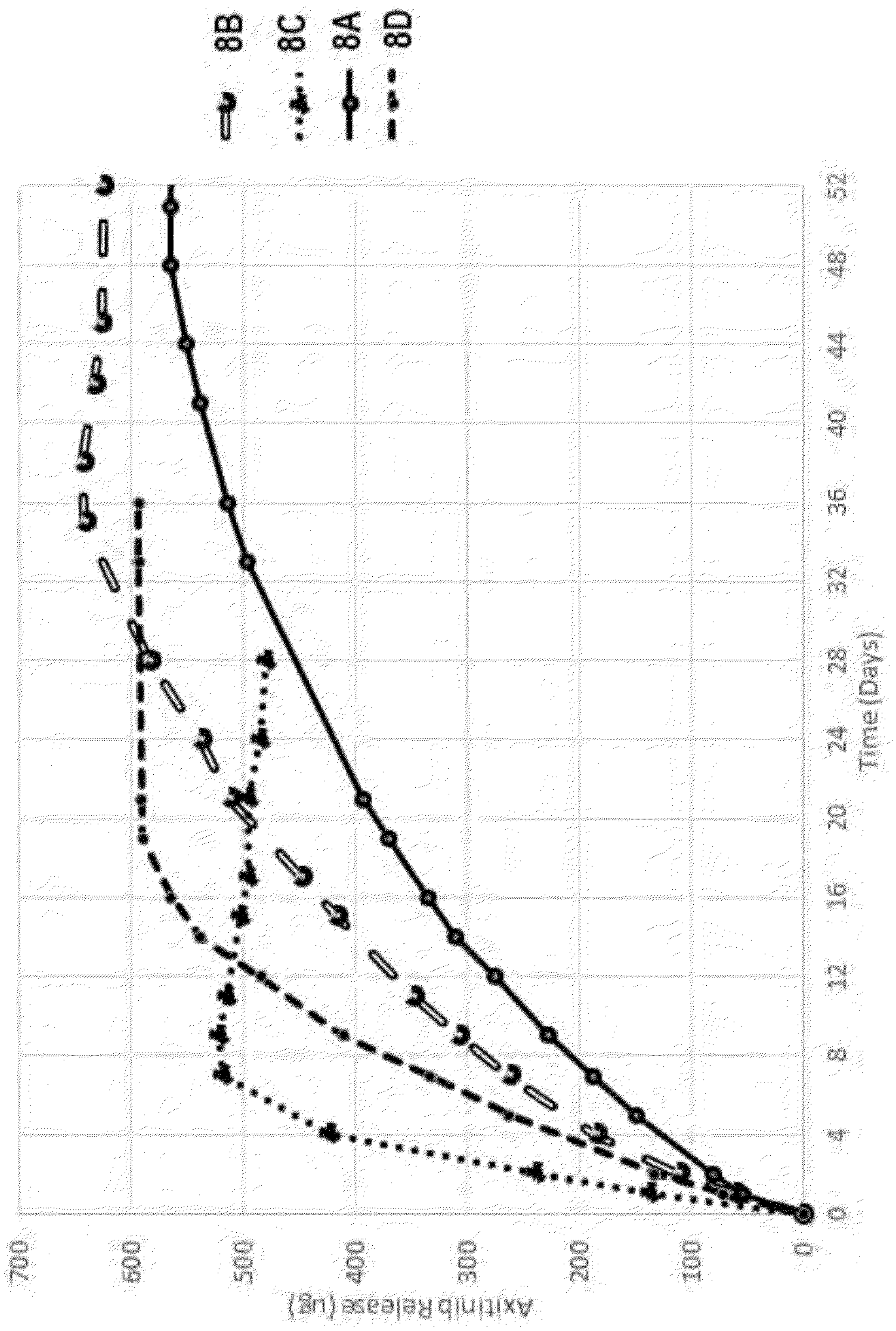
FIG. 20: TKI release profile (In Vitro Method B) from implants 8A, 8B, 8C and 8D showing the effect of hydrated surface area.

The results for implants 8A to 8D (Method B) are shown in FIG. 20

TABLE 20

| Implants 8A and 8B | | | |
|---|---|---|---|
| | Implant | 8A | 8B |
| Axitinib Type | Free Base | SAB-I | SAB-I 5-arm star shaped implant |
| | Solubility in PBS pH 7.2-7.4 (37° C., 5 days) | 0.2 µg/mL | 0.2 µg/mL |

TABLE 20-continued

| Implants 8A and 8B | | | |
|---|---|---|---|
| | Implant | 8A | 8B |
| Particle size | PSD (µm) Range ± 10% | D10 0.2, D50 2.2, D90 6.1 | D10 0.2, D50 2.2, D90 6.1 |
| (% dry basis) w/w) | Axitinib | 64.3% | 64.3% |
| | Target Dose | 600 µg | 600 µg |
| | Actual Dose | 610 µg | 640 µg |
| | PEG Hydrogel | 29.20% | 29.20% |
| | 4a20K PEG-SAZ | 19.50% | 19.50% |
| | 8a20K PEG-NH2 | 9.70% | 9.70% |
| | TLA | 0.00% | 0.00% |
| | Co-Crystal | 0.00% | 0.00% |
| | Sodium phosphate | 6.50% | 6.50% |
| (% wet basis w/w) | Axitinib | 16.50% | 16.50% |
| | PEG Hydrogel | 7.50% | 7.50% |
| | 4a20K PEG-SAZ | 5.00% | 5.00% |
| | 8a20K PEG-NH2 | 2.50% | 2.50% |
| | TLA | 0.00% | 0.00% |
| | Fumaric | 0.00% | 0.00% |
| | Sodium phosphate | 1.65% | 1.65% |
| Dimensions | Dry Diameter | 0.40 mm | 0.64 mm |
| | Dry Length | 8.0 mm | 7.6 mm |
| | Dry Implant Mass | 0.91 mg | 0.96 mg |
| | Wet Diameter | 0.90 mm | NA* |
| | Wet length | 7.5 mm | 10.1 mm |
| | Hydrated surface area | 23 $mm^2$ | 49 $mm^2$ |

TABLE 21

| Implants 8C and 8D | | | |
|---|---|---|---|
| | Implant | 8D | 8C |
| Axitinib Type | Free Base | SAB-I 3 implants | SAB-I HST × 7 implants |
| | Solubility in PBS pH 7.2-7.4 (37° C., 5 days) | 0.2 µg/mL | 0.2 µg/mL |
| Particle size | PSD (µm) Range ± 10% | D10 6.3, D50 16.2, D90 42.5 | D10 0.2, D50 2.2, D90 6.1 |
| (% dry basis w/w) | Axitinib | 49.40% | 39.60% |
| | Target Dose | 3 × 200 µg | 600 µg |
| | Actual Dose | 608 µg | 520 µg |
| | PEG Hydrogel | 42.00% | 49.50% |
| | 4a20K PEG-SAZ | 28.00% | 33.00% |
| | 8a20K PEG-NH2 | 14.00% | 16.50% |
| | TLA | 0.00% | 0.00% |
| | Co-Crystal | 0.00% | 0.00% |
| | Sodium phosphate | 8.60% | 10.9% |
| (% wet basis w/w) | Axitinib | 7.50% | 6.00% |
| | PEG Hydrogel | 6.90% | 7.50% |
| | 4a20K PEG-SAZ | 4.60% | 5.00% |
| | 8a20K PEG-NH2 | 2.30% | 2.50% |
| | TLA | 0.00% | 0.00% |
| | Fumaric | 0.00% | 0.00% |
| | Sodium phosphate | 1.50% | 1.65% |
| Dimen-sions | Dry Diameter | 0.24 ± 0.013 mm | 0.15 mm (per filament) |
| | Dry Length | 16.5 ± 0.26 mm | 6.8 mm (per filament) |
| | Dry Implant Mass | 0.45 mg | 0.19 mg (per filament) |
| | Wet Diameter | 0.75 mm | 0.38 mm (per filament) |
| | Wet length | 7.5 mm | 9.5 mm (per filament) |
| | Hydrated surface area | 63 $mm^2$ | 80 $mm^2$ |

TABLE 21A

| Implant 8E | | |
|---|---|---|
| Implant | | 8E |
| Axitinib Type | Free Base | SAB-I Micronized (HST 3 Implants) |
| | Solubility in PBS pH 7.2-7.4 (37° C., 5 days) | 0.2 μg/mL |
| Particle size | PSD (μm) Range ± 10% | D10 0.2, D50 2.5, D90 7.5 |
| (% dry basis w/w) | Axitinib | 44.90% |
| | Target Dose | 450 μg |
| | Actual Dose | 409 μg |
| | PEG Hydrogel | 48.10% |
| | 4a20K PEG-SAZ | 32.10% |
| | 8a20K PEG-NH2 | 16.00% |
| | TLA | 0.00% |
| | Co-Crystal | 0.00% |
| | Sodium phosphate | 7.10% |
| (% wet basis w/w) | Axitinib | 7.00% |
| | PEG Hydrogel | 7.50% |
| | 4a20K PEG-SAZ | 5.00% |
| | 8a20K PEG-NH2 | 2.50% |
| | TLA | 0.00% |
| | Fumaric | 0.00% |
| | Sodium phosphate | 1.10% |
| Dimensions | Dry Diameter | 0.37 mm (per implant) |
| | Dry Length | 8.94 mm (per implant) |
| | Dry Implant Mass | 1.05 mg (per implant) |
| | Wet Diameter | 0.54 mm (per implant) |
| | Wet length | 7.31 mm (per implant) |
| | Hydrated surface area | 38.6 $mm^2$ (calculated from 3x the hydrated surface area of the individual unfurled implants) |

TABLE 21A.1

In vitro release (Method C) of implant 8E from Table 21A: Implant 8E (in vitro release)

| Time (hours) | Concentration μg/mL) | Average % Released | Normalized Avg % Released | StDev | Average μg Released | StDev μg Released |
|---|---|---|---|---|---|---|
| 0 | 0 | 0 | 0 | 0 | 0 | 0 |
| 1 | 0.938 | 20.84 | 21 | 1.17 | 93.80 | 5.28 |
| 2 | 1.499 | 33.53 | 34 | 1.62 | 150.87 | 7.28 |
| 6 | 2.863 | 64.17 | 65 | 2.84 | 288.77 | 12.80 |
| 10 | 3.942 | 88.77 | 90 | 3.85 | 399.47 | 17.33 |
| 24 | 4.312 | 97.88 | 99 | 3.73 | 440.48 | 16.77 |
| 36 | 4.315 | 98.89 | 100 | 3.95 | 445.02 | 17.79 |
| 48 | 4.239 | 98.16 | 99 | 3.57 | 441.74 | 16.07 |
| 60 | 4.241 | 99.16 | 100 | 4.10 | 446.24 | 18.45 |

Example 9: In Vitro Release of the TKI Implant—Comparison of Particle Sizes

In this further in vitro study, the influence of particle size on release kinetics of the TKI implant was investigated. PEG $NH_2$ (8a20k) and PEG SAZ (4a20k) were used to form the PEG hydrogels. (Table 22).

The implants contained the SAB-I axitinib. The varying particle size is depicted in Table 22.

The release was measured according to Method B as described in Example 7.2.

Figure 21:
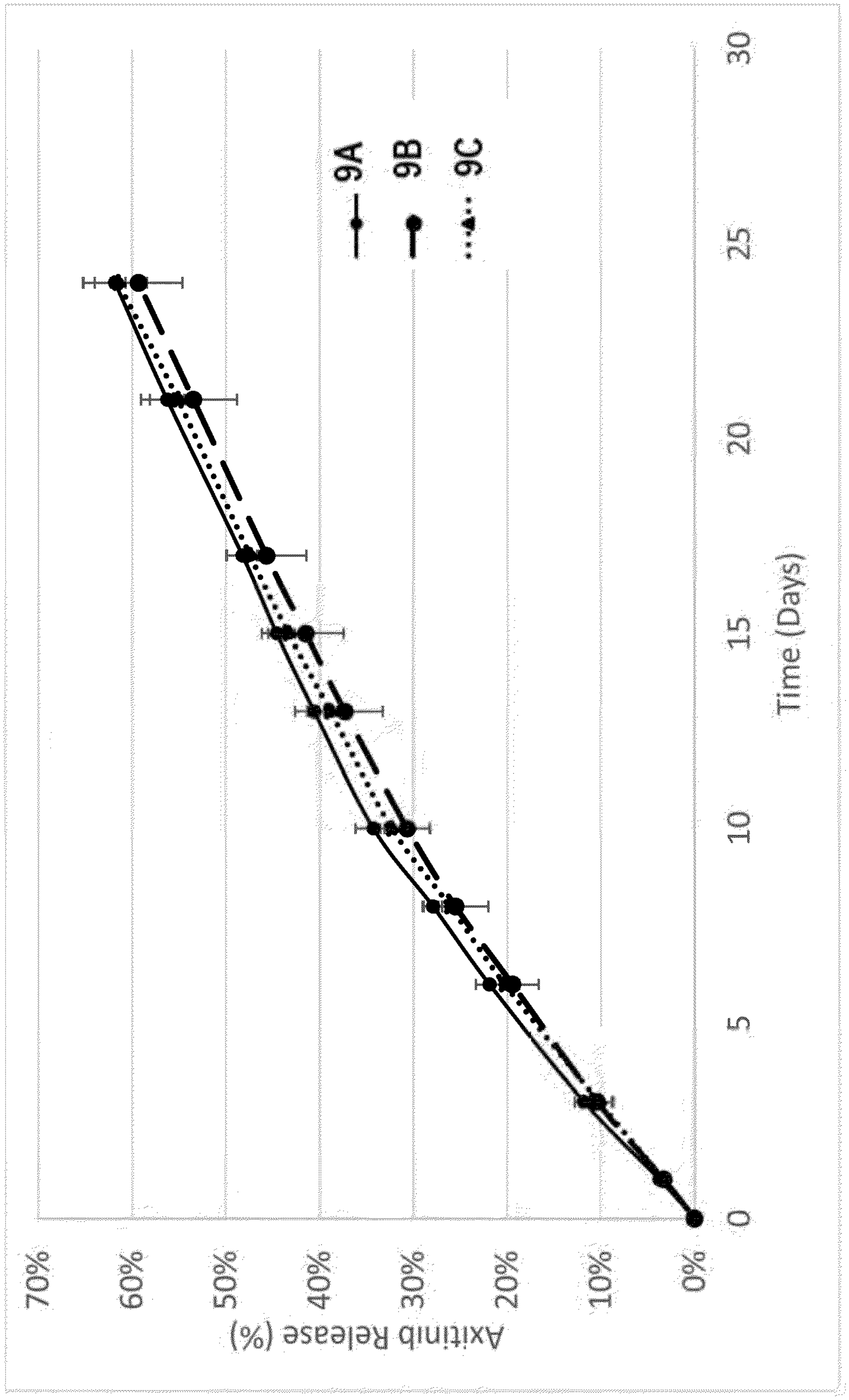
FIG. 21: TKI release profile (In Vitro Method B) of implants 9A, 9B, and 9C showing particle size comparison.

The results are shown in FIG. 21.

TABLE 22

| Implants 9A, 9B, and 9C | | | | |
|---|---|---|---|---|
| | Implant | 9A | 9B | 9C |
| Axitinib Type | Polymorph | SAB-1 non-micronized | SAB-1 micronized | SAB-1 super-micronized |
| | PSD (um) Range ± 10% | D10 6.3, D50 16.2, D90 42.5 | D10 0.2, D50 2.2, D90 6.1 | D10 0.17, D50 1.4, D90 4.0 |
| (% dry basis w/w) | Axitinib | 49.40% | 68.60% | 64.8% |
| | Dose | 651 μg | 690 μg | 692 μg |
| | PEG Hydrogel | 29.40% | 29.40% | 29.40% |
| | 4a20K PEG-SAZ | 19.60% | 19.60% | 19.60% |
| | 8a20K PEG-NH2 | 9.80% | 9.80% | 9.80% |
| | TLA | 0.00% | 0.00% | 0.00% |
| | Co-Crystal | 0.00% | 0.00% | 0.00% |
| | Sodium phosphate | 5.70% | 5.70% | 5.70% |
| (% wet basis w/w) | Axitinib | 16.50% | 16.50% | 16.50% |
| | PEG Hydrogel | 7.50% | 7.50% | 7.50% |
| | 4a20K PEG-SAZ | 5.00% | 5.00% | 5.00% |
| | 8a20K PEG-NH2 | 2.50% | 2.50% | 2.50% |
| | TLA | 0.00% | 0.00% | 0.00% |
| | Fumaric | 0.00% | 0.00% | 0.00% |
| | Sodium phosphate | 1.45% | 1.450% | 1.45% |
| Configuration | Stretching Method | Wet | Wet | Wet |
| | (Stretch Factor) | 2.3 | 2.3 | 2.3 |
| Dimensions | Dry Diameter | 0.40 mm | 0.35 mm | 0.36 mm |
| | Dry Length | 7.8 mm | 7.8 mm | 7.8 mm |
| | Dry Implant Mass | 0.92 mg | 0.97 mg | 0.95 mg |
| | Wet Diameter | 1.00 mm | 0.82 mm | 0.84 mm |
| | Wet Length | 6.4 mm | 6.8 mm | 6.8 mm |

Example 10: In Vivo Release of TKI—Non-Human Primate (NHP) Study

The non-human primate study was designed according to Table 23 below:

TABLE 23

| NHP study | | | | |
|---|---|---|---|---|
| | | Test Material | | Actual |
| GN | No. An. | Right Eye (OD) | Left Eye (OS) | dose (μg/eye) |
| 10A × 3 | 2 (3 months)<br>2 (6 months)<br>2 (9 months) | SAB-I<br>(3 × Implant 10A) | | 608 |
| 10B | 2 (3 months)<br>2 (6 months)<br>2 (9 months) | SAB-I<br>(Implant 10B) | | 307 |
| 10C | 2 (3 months)<br>2 (6 months)<br>2 (9 months) | SAB-I<br>(Implant 10C) | | 597 |
| 10D | 3 (3 months)<br>2 (6 months)<br>1 (9 months) | Polymorph-IV<br>(Implant 10D) | | 322 |

The implants used for each of the above groups are further characterized herein below:

TABLE 24

| Implants 10A, 10B, 10C, 10D | | | | | |
|---|---|---|---|---|---|
| | Implant | 10A | 10B | 10C | 10D |
| Axitinib Type | Axitinib Type | SAB-I | SAB-I | SAB-I | Polymorph IV |
| | PSD (um) Range ± 10% | D10 6.3, D50 16.2, D90 42.5 | D10 0.2, D50 2.5, D90 7.5 | D10 0.2, D50 2.5, D90 7.5 | D10 0.2, D50 2.5, D90 7.5 |
| (% dry basis w/w) | Axitinib | 49.40% | 64.3% | 64.3% | 52.10% |
| | Target Dose | 200 μg | 300 μg | 600 μg | 300 μg |
| | Actual Dose | 202.7 μg * | 307 μg | 597 μg | 322 μg |
| | PEG Hydrogel | 42.00% | 29.20% | 29.20% | 39.90% |
| | 4a20K PEG-SAZ | 28.00% | 19.50% | 19.50% | 26.60% |
| | 8a20K PEG-NH2 | 14.00% | 9.70% | 9.70% | 13.30% |
| | TLA | 0.00% | 0.00% | 0.00% | 0.00% |
| | Co-Crystal | 0.00% | 0.00% | 0.00% | 0.00% |
| | Sodium phosphate | 8.60% | 6.50% | 6.50% | 8.00% |
| (% wet basis w/w) | Axitinib | 7.50% | 16.50% | 16.50% | 9.80% |
| | PEG Hydrogel | 6.90% | 7.50% | 7.50% | 7.50% |
| | 4a20K PEG-SAZ | 4.60% | 5.00% | 5.00% | 5.00% |
| | 8a20K PEG-NH2 | 2.30% | 2.50% | 2.50% | 2.50% |
| | TLA | 0.00% | 0.00% | 0.00% | 0.00% |
| | Fumaric | 0.00% | 0.00% | 0.00% | 0.00% |
| | Sodium phosphate | 1.50% | 1.65% | 1.65% | 1.50% |
| Dimensions | Dry Diameter | 0.24 ± 0.013 mm | 0.38 mm | 0.38 mm | 0.31 ± 0.005 mm |
| | Dry Length | 16.5 ± 0.26 mm | 4.5 mm | 8.4 mm | 7.0 ± 0.08 mm |
| | Dry Implant Mass | 0.45 mg | 0.47 mg | 0.93 mg | 0.58 mg |
| | Wet Diameter | 0.75 mm | 0.66 mm | 0.66 mm | 0.64 mm |
| | Wet Length | 7.5 mm | 4.4 mm | 8.3 mm | 9.6 mm |

* 3x = 608

Surgical Dosing Procedure and Taking of Samples

The test implants were packaged in two separately foil pouched sub-assemblies. A needle sub-assembly contained the test article drug implant pre-loaded in the needle cannula (bottom image) and an injector sub-assembly (top image). The user connected the needle sub-assembly to the injector and the implant was ready to be dosed. The injector and needle assemblies were provided in separate foil pouches.

The study animals were *Cynomolgus* monkeys 2 to 4 years old and weighed 1.5 to 3.0 kg (equal share of male/female) at the start of the study. The monkeys received a bilateral intravitreal injection of test implants (i.e., one implant in each eye). The monkeys were sedated/anesthetized to effect and placed in dorsal recumbency. Topical proparacaine was be applied to the eyes. The conjunctival fomices were flushed with a 1:50 dilution of betadine solution/saline and the eyelid margins swabbed with undiluted 5% betadine solution. The eyes were draped and a wire eyelid speculum placed. A caliper was used to mark a spot 3.0 mm posterior to the limbus on the inferotemporal bulbar conjunctiva. The conjunctiva at the marked spot was swabbed with undiluted 5% betadine solution. Conjunctival forceps were used to fixate the globe position while the needle of the injection device was inserted at the marked spot, through the sclera and advanced into the vitreous humor. The intravitreal injection was made to a full depth of the needle and a dwell time of 8 seconds was counted and then the implant was manually deployed with the depression of the plunger. Subsequently, the needle was be removed and the episcleral tissues approximated to the site of insertion grasped with the conjunctival forceps to lessen reflux of vitreous. 20 (Second and third injections were be performed for Group 1 only). The contralateral eye had an identical injection procedure performed.

At week 13 (±4 days) the animals were euthanized by euthanasia solution administration, under sedation if necessary (e.g. ketamine), followed by a Testing Facility SOP approved method to ensure death, e.g. exsanguination.

Whole eyes were collected from all animals. All extraneous tissue was removed from the eye. The eyes were placed in a tube, then immediately stored frozen at −60° C. to −90° C.

Tissue Processing and Bioanalytical Procedures

Frozen eyes were dissected and processed in compartments for quantification of axitinib in ocular tissues using qualified methods described here.

Figure 22:
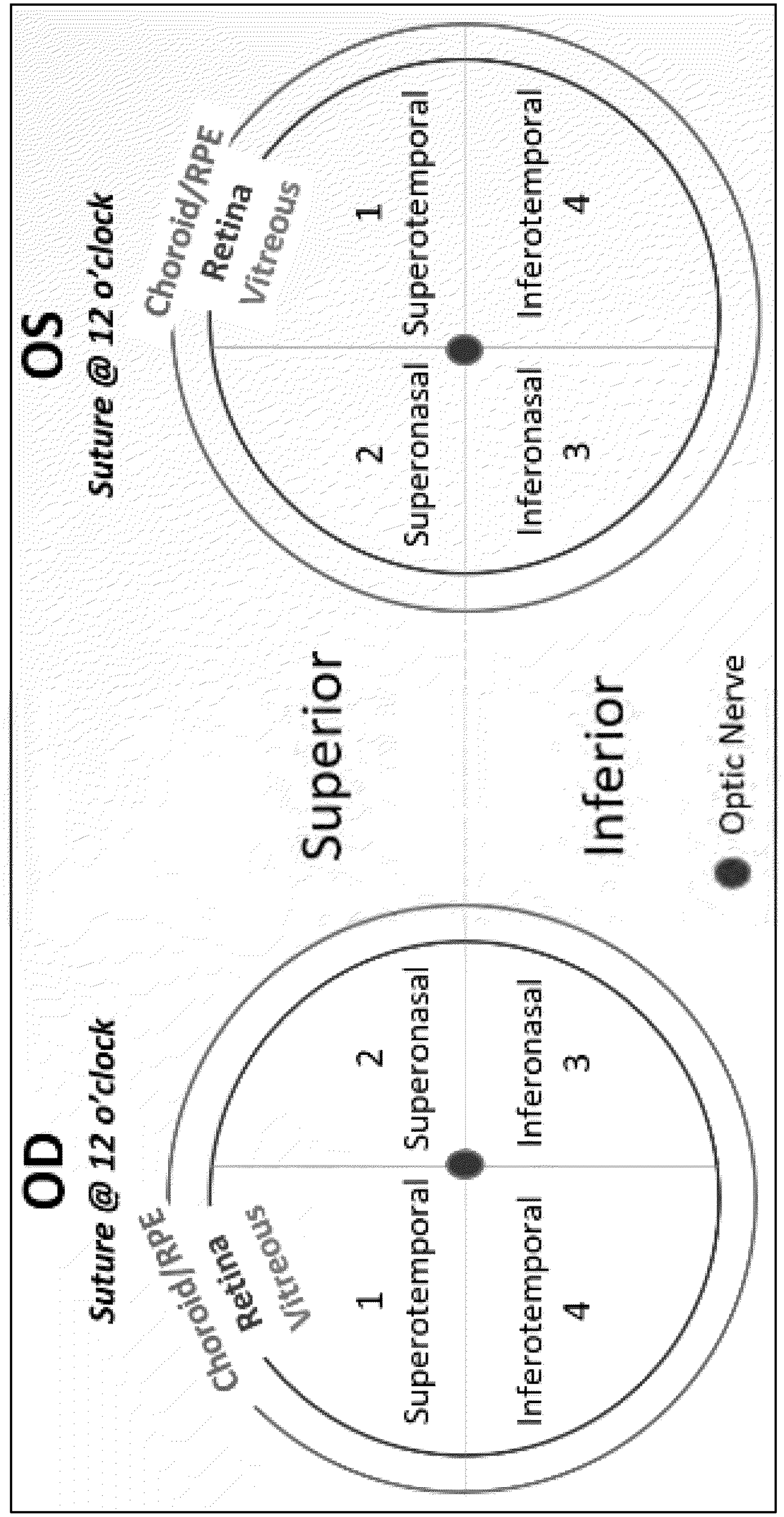
FIG. 22: NHP eye quadrants and suture position.

The eyes were bisected 3-4 mm distal to the limbus and the anterior tissues (cornea, iris ciliary body, aqueous humor) and posterior tissues (vitreous humor, retina, choroid/RPE) were separated. FIG. 22 shows the location of these tissues in the eye. In the posterior eye cup, superior was identified using a suture at 12 o'clock and center of the posterior eye cup was identified using the optic nerve (FIG. 22).

Within the frozen vitreous in the eye cup, fully intact implant was identified and removed from the vitreous to quantify remaining drug in the vitreous humor implant. Cuts were made through the sclera horizontally and vertically through the optic nerve to create four quadrants. The remaining vitreous humor was separated into superior and inferior halves from the retina/choroid/RPE and collected to quantify drug in soluble vitreous humor. Then, the retina was removed one quadrant at a time followed by choroid/RPE to quantify drug in retina and choroid/RPE quadrants. To extract aqueous humor, the cornea and iris ciliary body were separated, and the aqueous humor (ice crystal between) was removed to quantify drug in the aqueous humor.

Vitreous humor with implants were further prepared in ethanol and retina/choroid/RPE tissues were prepared in methanol:water (50:50, v/v) per milligram of tissue. All samples were placed in Precellys lysing tubes with ceramic beads and homogenized at 5500 rpm for 3×30 second cycles, with 20 second pauses between cycles at 4° C. Vitreous with implant samples were further agitated overnight, devoid of light, at ambient temperature. Each standard, blank, or unknown aqueous humor, vitreous humor (soluble), diluted vitreous humor implants (insoluble), retina or choroid tissue homogenate sample was vortex mixed for 4 minutes and centrifuged for 10 minutes, 4000 rpm, at 4° C.

Two-hundred (200) µL (retina and choroid) or three-hundred (300) µL (aqueous and vitreous humor) supernatant was transferred to a new 96-well collection plate. The samples were dried down under nitrogen gas at 35° C. Samples were then reconstituted in 200 µL of methanol: water (50:50, v/v) and vortexed for four minutes. Reconstituted samples were transferred to a 96-well autosampler plate and analyzed by LC-MS/MS.

The concentration of axitinib in the tissue samples were determined using the calibration curve parameters and further corrected for tissue weight and appropriate dilution factors. Descriptive statistics were applied during data analysis and axitinib concentrations in aqueous and vitreous humor, retina and choroid/RPE tissues in each study group were presented as geometric means. The drug release rate was derived by subtracting the remaining drug mass in the vitreous from the starting implant drug mass and dividing the difference by number of days of drug release (90 days for 3-months).

The results (based on geometric mean concentrations) are shown in Table 25 below.

TABLE 25

In vivo NHP study results at 3 months

| Study Arm | Starting Dose (µg) | Dose Remaining at month 3 (µg) | Drug release rate from VH from 0 to 3 months, Geometric Mean (µg/day) | Release Rate/Day (ng/day) | Soluble $C_{vitreous}$ (ng/mL) | AH Geometric Mean (ng/ml) | Geometric Retina Mean (ng/g) | Choroid/RPE Geometric mean (ng/g) |
|---|---|---|---|---|---|---|---|---|
| 10A × 3 | 608 | 496 | 1.2 | 1229 | 290* | 39 | 475 | 3873 |
| 10B | 307 | 239 | 0.75 | 527 | 9 | 2 | 72 | 653 |
| 10C | 597 | 523 | 0.8 | 766 | 22 | 4 | 160 | 1198 |
| 10D | 322 | 232 | 1.0 | 986 | 91 | 6 | 698 | 4683 |

*High-likely due to free particles in VH (exceeds solubility)

As can be seen from Table 25 above, the effect of increased solubility of the axitinib polymorph IV on the release from the implants demonstrated in Example 7 in vitro could be reproduced in vivo (compare implants 10B and 10D—see the dose remaining at month 3, in particular also the drug release rates from VH and the release rate per day).

The soluble concentration in vitreous humor resulting from the implant containing polymorph IV (implant 10D) was much higher than for the implant containing SAB-I (implant 10B).

It was also found that the faster release of a more soluble polymorph led to increased quantification of the polymorph in eye tissues (compare implant 10B and 10D and the quantified polymorph in retina and choroid/retinal pigment epithelium (RPE)).

Figure 23A:
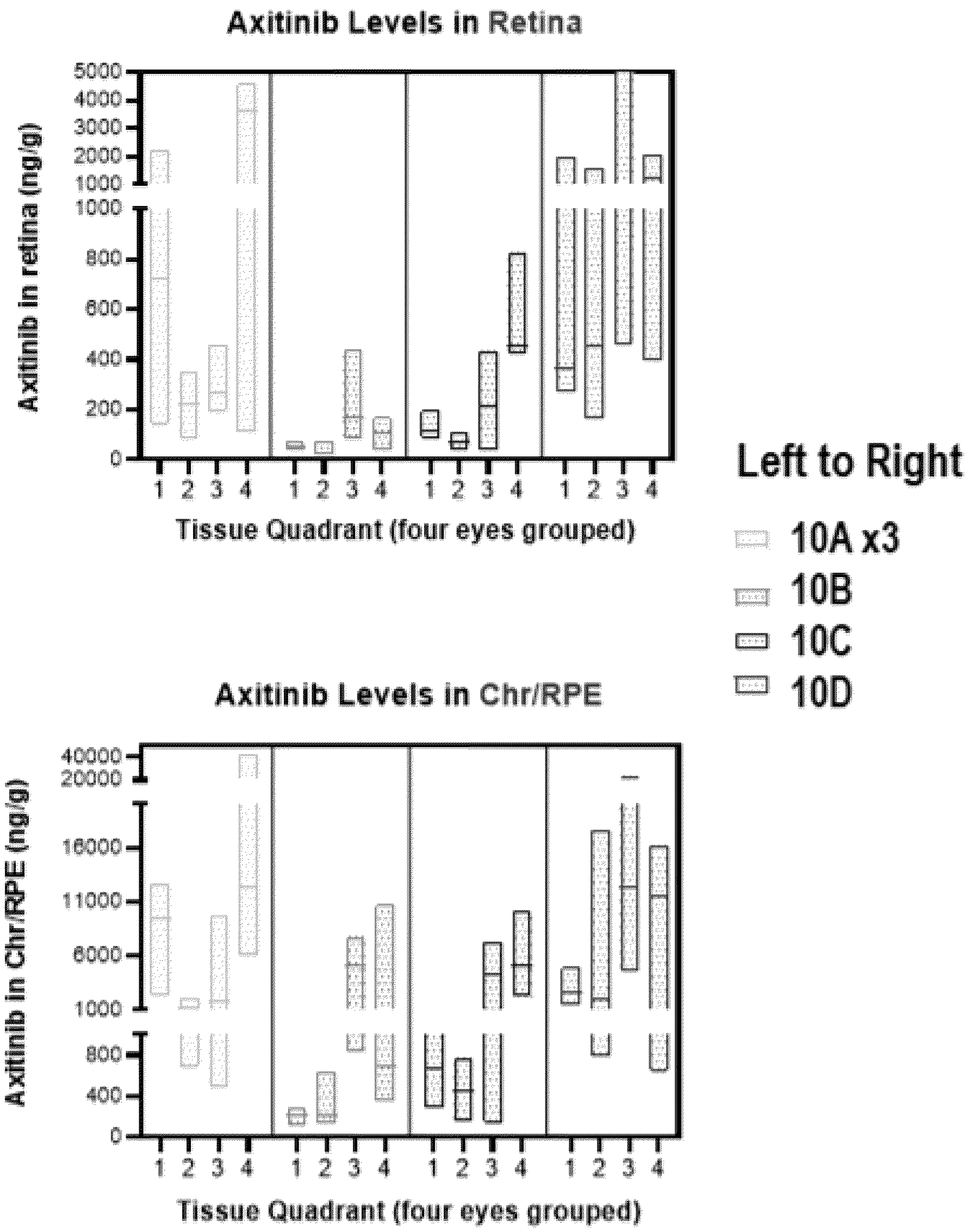
FIG. 23: TKI Distribution in NHP Retina/Chr/RPE at 3 months: (A) Retina and Choroid/RPE—Tissue Quadrant (four eyes grouped); (B) Retina and Choroid/RPE—four quadrants grouped
Figure 23B:
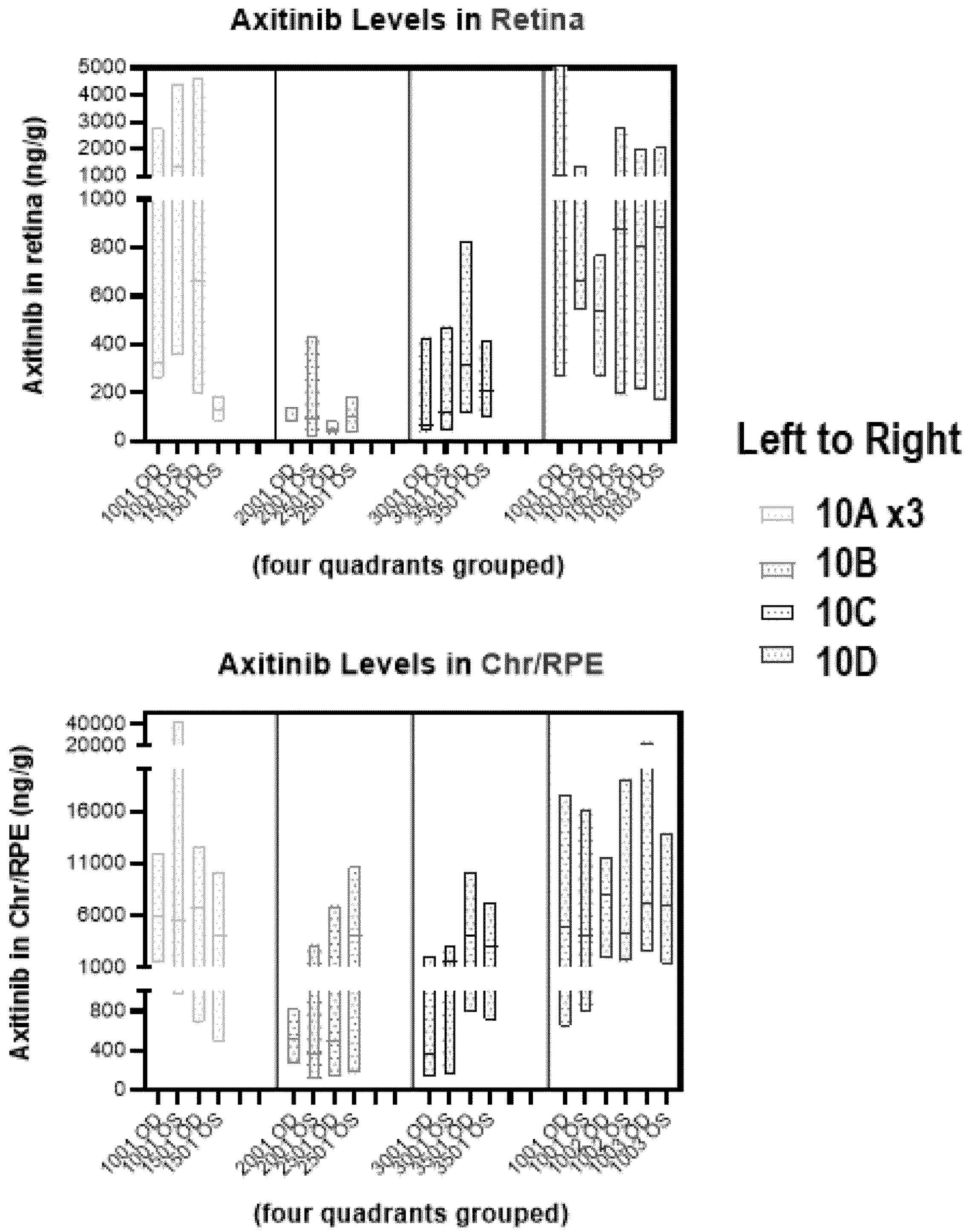

FIGS. 23 A and 23 B show the distribution of the respective polymorphs in retina and choroid/RPE.

As can be seen from Table 25 above, the effect of increased hydrated surface area on the release of the TKI from the implants demonstrated in Example 8 in vitro could be reproduced in vivo (compare implants 10A and 10C—dose remaining at month 3, the drug release rates from VH and the release rate per day).

The results for the 6 and 9 month time points (based on geometric mean concentrations) are provided in Tables 26 and 27 below.

TABLE 26

In vivo NHP study results at 6 months

| Study Arm | Starting Dose (μg) | Dose Remaining at month 6 μg) | Drug release rate from VH from 3 to 6 months, Geometric Mean (μg/day) | AH Geometric Mean (ng/ml) | Retina Geometric Mean (ng/g) | Choroid/RPE Geometric mean (ng/g) |
|---|---|---|---|---|---|---|
| 10A × 3 | 608 | 305 | 2.1 | 75 7 | 2338 | 6088 |
| 10B | 307 | 125 | 1.3 | 37 | 3243 | 8218 |
| 10C | 597 | 381 | 1.6 | 1864 | 1793 | 6281 |
| 10D | 322 | 40 | 2.1 | 61 | 598 | 3475 |

TABLE 27

In vivo NHP study results at 9 months

| Study Arm | Starting Dose (μg) | Dose Remaining at month 9 (μg) | Drug release rate from VH from 6 to 9 months, Geometric Mean (μg/day) | AH Geometric Mean (ng/mL) | Retina Geometric Mean (ng/g) | Choroid/RPE Geometric mean (ng/g) |
|---|---|---|---|---|---|---|
| 10A × 3 | 608 | 96 | 2.3 | 20 | 746 | 4765 |
| 10B | 307 | 30 | 1.0 | 12 | 838 | 3535 |
| 10C | 597 | 95 | 3.2 | 14 | 581 | 4887 |
| 10D | 322 | 1 | 0.4 | 3 | 60 | 716 |

Clinical Observations

There were no TKI implant-related effects on clinical observations. Clinical signs that were observed during the study were incidental and unrelated to TKI implants. These observations were generally sporadic/transient and/or common observations of animals this age/species.

Body Weights

The TKI implant did not adversely impact animal body weights over the study duration. Body weight gain throughout the study was consistent with expected values and normal biological variation.

IOP

Intraocular pressure values were within normal limits for all animals at all time points on study, except an isolated low IOP value (5 mmHg) for one animal on day 39, which however returned to the normal range at day 85.

Ophthalmic Examination and Imaging

The implants were visualized and implants within the posterior chamber were observed using ultra widefield cSLO imaging. Based on implant observations and cSLO images the implants reside principally in the inferior region. The hydrogel component of the implant stays intact and then fully bioresorbs by hydrolysis within the vitreous at approximately 5 to 6 months. At 6 months, the hydrogel component of the implant has fully degraded liberating axitinib particles for release into the vitreous.

Ocular Scoring

The ocular (uveitis) scoring parameters and numerical scores were assigned using a modification of the Standardization of Uveitis Nomenclature (SUN) and SPOTS systems performed by a Staff Ophthalmologist as part of the ophthalmic examination. There were no statistically significant differences identified for ocular scoring, all study eyes were graded a zero over the study duration.

Bioanalysis (Plasma)

Axitinib concentrations were measured in the plasma of animals at sacrifice time points using a qualified method with a LLOQ of 0.100 ng/mL. No measurable amount of axitinib was detected in any plasma samples over the study duration.

Pharmacokinetic Analysis

The study arm 10D formulated with the polymorph IV had an axitinib starting dose of 322 µg. The geometric mean remaining axitinib dose in the VH at 3, 6, and 9 months was 232, 40, and 1 µg, respectively (see Tables 25, 26 and 27). Results demonstrated a clearance rate (i.e., elimination rate) from VH during the initial 3 month period prior to hydrogel bioresorption of 1.0 µg/day (see Table 25). That rate represents diffusion of the drug through the implant into the vitreous and distribution to the surrounding ocular tissues. Following hydrogel bioresorption at approximately 5.5 months, the remaining drug disperses and clears faster, and drug clearance (elimination) from the VH Is near complete by 9 months. In the present disclosure, the terms “elimination” from the vitreous humor (VH) and “clearance” from the vitreous humor (VH) are used interchangeably.

The study arms 10A×3, 10B, and 10C formulated with the SAB-I polymorph had an axitinib starting dose of 608 µg, 307 µg and 597 µg (see Tables 23, 24, 25, 26 and 27). Results demonstrated clearance rates (i.e., elimination rates) from the VH during the initial 3-month period prior to hydrogel degradation of 1.2, 0.75, and 0.8 µg/day for 10A×3, 10B and 10C, respectively (see Table 25). These results demonstrate that the implant formulated with polymorph IV (10D) provides for a higher daily release rate prior to hydrogel degradation compared to 10B and 10C.

A single 0.3 mg dose implant formulated with the Form IV axitinib polymorph delivered (at month 3) 1.0 µg/day into the vitreous and surrounding ocular tissues, which is almost similar to three 0.2 mg implants formulated with SAB-I axitinib polymorph which delivered 1.2 µg/day. The data supports the hypothesis that a lower dose implant formulated with the more soluble axitinib polymorph IV can deliver a comparable daily release rate in vivo as a higher dose implant formulated with axitinib polymorph SAB-I.

Further, implant 10D formulated with axitinib form IV resulted in less drug released at the time of hydrogel bioresorption into the vitreous and surrounding ocular tissues in the subjects compared to the formulations containing axitinib polymorph SAB-I, thus reducing the maximal drug exposure at 6 months (upon degradation of the hydrogel). Thus, in the case of implant 10D containing axitinib polymorph IV, the largest part of the drugload of the implant had already been released prior to the start of the hydrogel degradation. This may also be derived from the geometric mean concentrations in the retina and the choroid at 3 months (implant still intact) vs. 6 months (degradation of implant). Implant 10D containing axitinib form IV delivered steady axitinib concentrations into the retina at 3 and 6 months (698 and 598 ng/g, respectively). Similarly, steady concentrations in the choroid/RPE were observed at months 3 and 6 (4683 and 3475 ng/g, respectively).

The average concentrations in retina and choroid/RPE are provided in Tables 27A and 27B below. The PK parameters (based on the average concentrations) in these tissues are summarized again in Table 27C below.

TABLE 27A

Average concentrations in retina
Axitinib Concentrations in Retina (Avg ± SD)

| | Polymorph SAB-I | | | Polymorph IV |
|---|---|---|---|---|
| Time (months) | 10A × 3<br>3 × 0.2 mg | 10B<br>1 × 0.3 mg | 10C<br>1 × 0.6 mg | 10D<br>1 × 0.3 mg |
| 3 | 1120 ± 1553 | 103 ± 103 | 241 ± 221 | 1073 ± 1177 |
| 6 | 6567 ± 13791 | 5282 ± 7061 | 2621 ± 2413 | 770 ± 557 |
| 9 | 3430 ± 9302 | 3256 ± 7507 | 2022 ± 3673 | 106 ± 112 |
| $AUC_{0\text{-}9\ mo.}$ (ng*day/g)[1] | 907662 | 642973 | 363650 | 222431 |

TABLE 27B

| Average concentrations in choroid/RPE Axitinib Concentrations in Choroid/RPE (Avg ± SD) | | | | |
|---|---|---|---|---|
| | Polymorph SAB-I | | | Polymorph IV |
| Time (months) | 10A × 3<br>3 × 0.2 mg | 10B<br>1 × 0.3 mg | 10C<br>1 × 0.6 mg | 10D<br>1 × 0.3 mg |
| 3 | 7915 ± 10518 | 2088 ± 3361 | 2697 ± 3169 | 7586 ± 6816 |
| 6 | 9104 ± 7737 | 10899 ± 8164 | 9953 ± 10299 | 6779 ± 7991 |
| 9 | 11319 ± 15838 | 8414 ± 9726 | 9554 ± 11704 | 1326 ± 1333 |
| $AUC_{0\text{-}9\ mo.}$ (ng*day/g)[1] | 2431791 | 1661746 | 1711268 | 1720297 |

TABLE 27C

| PK parameters in retina and choroid/RPE | | | | | |
|---|---|---|---|---|---|
| | | Polymorph SAB-I | | | Polymorph IV |
| PK Parameter | | 10A × 3<br>3 × 0.2 mg | 10B<br>1 × 0.3 mg | 10C<br>1 × 0.6 mg | 10D<br>1 × 0.3 mg |
| Axitinib in Retina | $C_{max}$ (Avg ± SD) | 6567 ± 13791 | 5282 ± 7061 | 2621 ± 2413 | 1073 ± 1177 |
| | $T_{max}$ | 6 mo. | 6 mo. | 6 mo. | 3 mo. |
| | $AUC_{0\text{-}9\ mo.}$ (ng*day/g)[1] | 907662 | 642973 | 363650 | 222431 |
| Axitinib in Choroid/RPE | $C_{max}$ (Avg ± SD) | 11319 ± 15838 | 10899 ± 8164 | 9953 ± 10299 | 7586 ± 6816 |
| | $T_{max}$ | 9 mo. | 6 mo. | 6 mo. | 3 mo. |
| | $AUC_{0\text{-}9\ mo.}$ (ng*day/g)[1] | 2431791 | 1661746 | 1711268 | 1720297 |

[1]For Tables 27A to 27C: AUC trapezoid calculation assumes steady state from time zero to 3 months.

Example 11: Stability of Axitinib in Implants Over Time (Comparison of Different Polymorphic Forms of Axitinib)

Stability of SAB-I and Polymorph IV in implants was tested over a period of 6 months at RT. The relative humidity (RH) was not controlled. The study is still ongoing.

Implants were manufactured using the wet casting process outlined in Example 1. The same formulation was used for each lot (Table 28 below). The only difference was the polymorph of the axitinib (form SAB-I and form IV). Implants were loaded into 25G JBP needles with cowls and sealed under nitrogen in heat sealed foil pouches. After implants were received back from gamma sterilization they were stored in a room temperature chamber with a LogTag to monitor temperature and relative humidity throughout the study. After 6 months of storage, the XRD patterns for both the polymorphic forms of axitinib in the respective implants were identical to their corresponding initial reference patterns.

Average storage temperature through 6 months was 25.2° C.±0.12° C. and average relative humidity was 14.4%±0.52%. The range of values for temperature and % RH were 22.1-25.5° C. and 13.0-54.3%, respectively. Axitinib purity was measured using TM-0099 at T=0, T=1.5 months, T=3 months, T=4.5 months, and T=6 months. Values must be equal to or greater than 0.1% of peak area on the UPLC curve to be considered reported impurities.

The implants used in this study are shown in Table 28 below.

The results are shown in Table 29 below.

TABLE 28

| Implants 11A and 11B | | | |
|---|---|---|---|
| | Implant | 11A | 11B |
| Axitinib Type | Polymorph | SAB-1 Micronized | Polymorph IV |
| | PSD (um) Range ± 10% | D10 0.2, D50 2.2, D90 6.1 | D10 0.2, D50 2.5, D90 7.5 |
| (% dry basis w/w) | Axitinib | 52.10% | 52.10% |
| | Target Dose | 300 μg | 300 μg |
| | Actual Dose | 309 μg | 322 μg |
| | PEG Hydrogel | 39.90% | 39.90% |
| | 4a20K PEG-SAZ | 26.60% | 26.60% |
| | 8a20K PEG-NH2 | 13.30% | 13.30% |
| | TLA | 0.00% | 0.00% |
| | Co-Crystal/ Pro-Drug | 0.00% | 0.00% |
| | Sodium phosphate | 8.00% | 8.00% |
| (% wet basis w/w) | Axitinib | 9.80% | 9.80% |
| | PEG Hydrogel | 7.50% | 7.50% |
| | 4a20K PEG-SAZ | 5.00% | 5.00% |
| | 8a20K PEG-NH2 | 2.50% | 2.50% |
| | TLA | 0.00% | 0.00% |
| | Co-Crystal/ Pro-Drug | 0.00% | 0.00% |
| | Sodium phosphate | 1.50% | 1.50% |
| Dimensions | Dry Diameter | 0.30 ± 0.013 mm | 0.31 ± 0.005 mm |
| | Dry Length | 7.1 ± 0.03 mm | 7.0 ± 0.08 mm |
| | Dry Implant Mass | 0.58 mg | 0.58 mg |
| | Wet Diameter | 0.63 mm | 0.64 mm |
| | Wet Length | 9.4 mm | 9.6 mm |

TABLE 29

| Stability of polymorphs SAB-I and polymorph IV in implants 11A and 11B, respectively | | |
|---|---|---|
| time point | Purity of SAB-I [%] | Purity of Polymorph IV [%] |
| 0 | 99.6 | 99.8 |
| 1.5 months | 100.0 | 99.7 |
| 3 months | 99.9 | 99.7 |
| 4.5 months | 99.9 | 99.7 |
| 6 months | 99.9 | 99.7 |

Example 12: Implant Synthesis Via Hot Melt Extrusion and Curing-Influence of the Curing Time and Temperature A study was performed to investigate the influence of the curing time on persistence of the hydrogel in tris-buffered saline (TBS) at pH 8.5 and at 22° C. An implant (specifically, implant no. 12A, see Table 30 below), was prepared by the hot melt extrusion process described in Example 2, with curing under different conditions as listed below.

TABLE 30

| Implant 12A | | |
|---|---|---|
| Implant type | | 12A |
| Axitinib Type | Free Base | SAB-I Micronized (HME) |
| | Solubility | 0.2 µg/ml |
| Particle size | PSD (µm) Range ± 10% | D10 0.2, D50 2.2, D90 6.1 |
| (% dry basis w/w) | Axitinib | 69.00% |
| | Theoretical Dose | 600 µg |
| | Actual Dose | 614 µg |
| | PEG Hydrogel | 27.00% |
| | 4a20K PEG-SAZ | 27.00% |
| | 8a20K PEG-NH2 | 0.00% |
| | TLA | 0.79% |
| | Sodium phosphate | 3.21% |
| (% wet basis w/w) | Axitinib | 14.04% |
| | PEG Hydrogel | 5.49% |
| | 4a20K PEG-SAZ | NA |
| | 8a20K PEG-NH2 | 0.00% |
| | TLA | 0.16% |
| | Sodium phosphate | 0.65% |
| Dimensions | Dry Diameter | 0.44 mm |
| | Dry Length | 4.3 mm |
| | Dry Implant Mass | 0.89 mg |
| | Wet Diameter | 1.01 mm |
| | Wet length | 6.51 mm |

Figure 24:
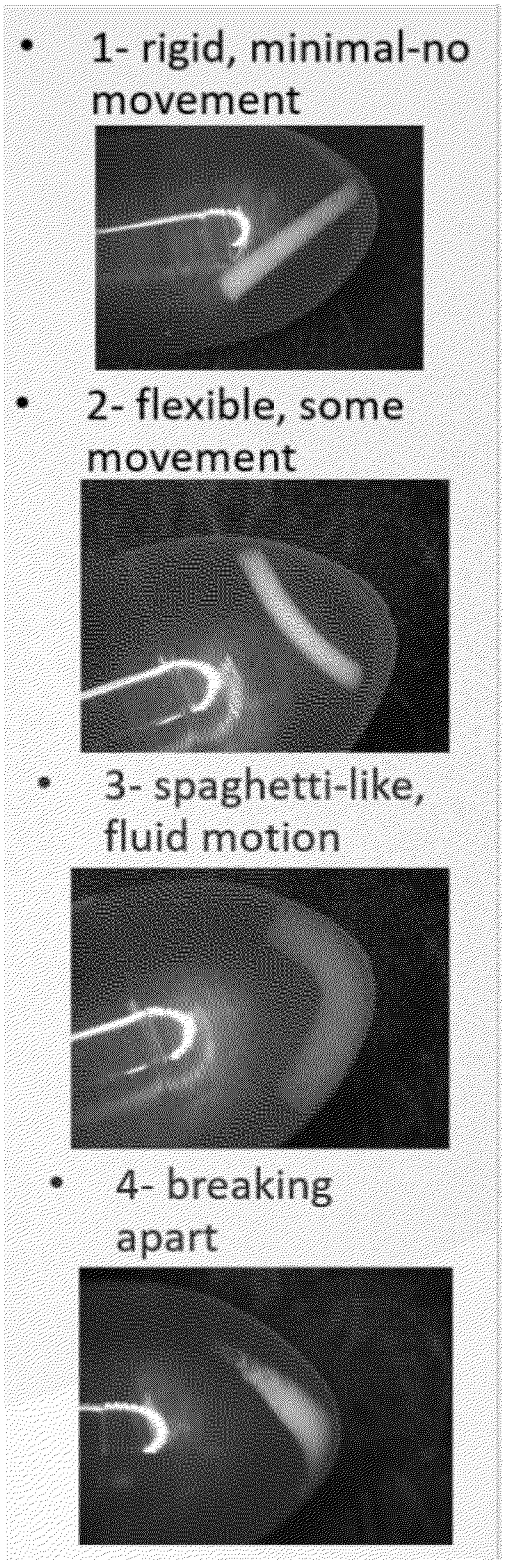
FIG. 24: Hydrogel persistence scores

For the study, various implants of the composition shown above in Table 30 were produced using different curing time and were placed individually in tris-buffered saline (TBS) at pH 8.5 and at 22° C. having Tris-HCl at a concentration of 300 mM. The implant integrity (corresponding to the hydrogel persistence) was judged daily by a score from 1 to 4, the scores being: 1 (rigid implant, minimal to no movement); 2 (implant flexible, some movement); 3 (spaghetti-like, fluid motion); 4 (breaking apart)=see also FIG. 24 to illustrate scores 1 to 4. The following table records the day of the study on which score 4 was reached for implants prepared using different curing times, temperatures and relative humidities (RH). The implants were assessed visually.

TABLE 31

| Curing study | | | | | |
|---|---|---|---|---|---|
| Curing time (at 35° C., 98% RH) | Day of score 4 | Curing time (at 30° C., 60% RH) | Day of score 4 | Curing time (at 30° C., 98% RH) | Day of score 4 |
| No cure | 14.0 | No cure | 16 | No cure | 16 |
| 0.5 h | 26.0 | 2 h | 16 | 2 h | 23 |
| 1.5 h | 25.7 | 8 h | 17 | 8 h | 23 |
| 2 h | 27.0 | 24 h | 19-21 | 24 h | 23 |
| 4 h | 26.0 | 48 h | 19-21 | 48 h | 23 |
| 72 h | 22.7 | 72 h | 19-21 | 72 h | 23 |

It was found that, generally, a higher curing temperature resulted in longer hydrogel persistence (for example, when curing was performed at 35° C. instead of 30° C. at the same relative humidity). Furthermore, it was found that a higher relative humidity resulted in a longer hydrogel persistence (for example, when curing was performed at 98% RH instead of 60% RH at the same temperature). At a curing temperature of 35° C. and at 98% relative humidity it was found that a 2-hour curing time was sufficient to provide for an extended hydrogel persistence in TBS at pH 8.5 and at 22° C. After sufficient cure time was reached, additional curing time did not have a large impact on persistence.

Figure 25:
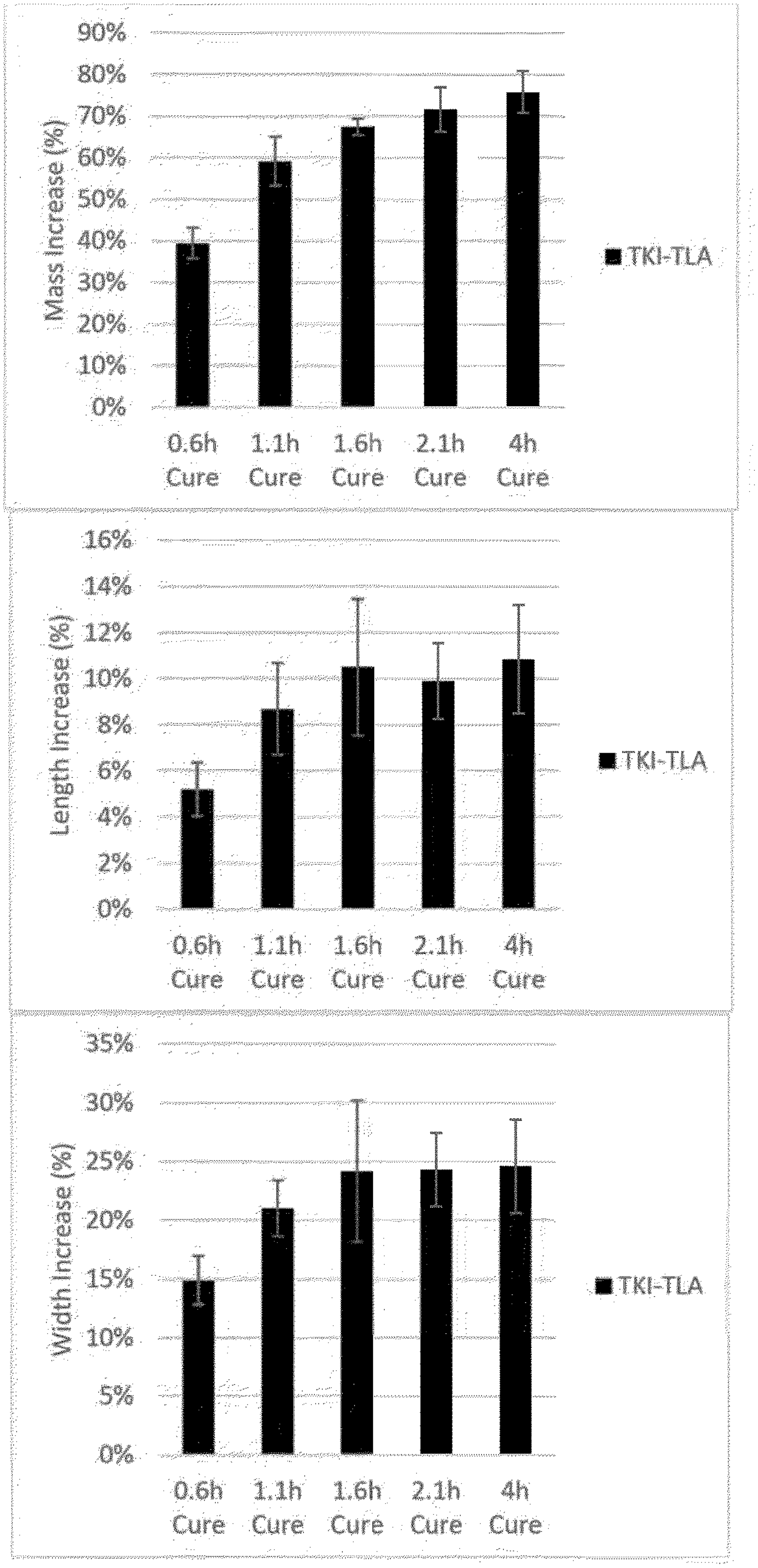
FIG. 25: Effect of curing time on implant dimensions

It was also found that the mass of an implant produced by the hot melt extrusion process increases during curing such that the longer the curing time, the larger the resulting implant mass and increased implant length and diameter (which is assumed to be due to increased crosslinking of the PEG precursors): 3.0% (curing at 30° C./60% RH) vs. 45.3% (curing at 30° C./98% RH) vs. 73.1% (35° C./98% RH). After sufficient cure time was reached, percent mass, width, and length increase during curing reaches an equilibrium value such that increased cure time does not have a significant impact. See also FIG. 25.

Example 13: In Vivo Release of TKI-Rabbit Study

The rabbit study was designed according to Table 32 below:

TABLE 32

| Rabbit study | | | | |
|---|---|---|---|---|
| | | Test Material | | |
| GN | No. Animals | Right Eye (OD) | Left Eye (OS) | Actual dose (µg/eye) |
| 13A | 10 males (6 weeks: 3 males) (12 weeks: 3 males) (24 weeks: 4 males) | SAB-I (Implant 13A) | | 309 |
| 13B | 10 males (6 weeks: 3 males) (12 weeks: 3 males) (24 weeks: 4 males) | SAB-I (Implant 13B) | | 679 |
| 13C × 2 | 10 males (6 weeks: 3 males) (12 weeks: 3 males). (24 weeks: 4 males) | SAB-I (Implant 13C) | | 1358 |
| 13D | 10 males (6 weeks: 3 males) (12 weeks: 3 males) (24 weeks: 4 males) | Polymorph-IV (Implant 13D) | | 143 |

TABLE 32-continued

| Rabbit study | | | | |
|---|---|---|---|---|
| | | Test Material | | |
| GN | No. Animals | Right Eye (OD) | Left Eye (OS) | Actual dose (μg/eye) |
| 13E | 10 males (6 weeks: 3 males) (12 weeks: 3 males) (24 weeks: 4 males) | Polymorph-IV (Implant 13E) | | 322 |
| 13F | 10 males (6 weeks: 3 males) (12 weeks: 3 males) (24 weeks: 4 males) | Polymorph-IV (Implant 13F) | | 608 |

The implants used for each of the above groups are further characterized herein below:

TABLE 33

| Implants 13A, 13B, 13C × 2, 13D, 13E, and 13F | | | | | | | |
|---|---|---|---|---|---|---|---|
| Implant | | 13A | 13B | 13C × 2 | 13D | 13E | 13F |
| Axitinib Type | Axitinib Type | SAB-I | SAB-I | SAB-I | IV Polymorph | IV Polymorph | IV Polymorph |
| | PSD (um) Range # 10% | D10 0.2, D50 2.2 D90 6.1 | D10 0.2, D50 2.2, D90 6.1 | D10 0.2, D50 2.2, D90 6.1 | D10 0.2, D50 2.5, D90 7.5 | D10 0.2, D50 2.5, D90 7.5 | D10 0.2, D50 2.5, D90 7.5 |
| (% dry basis w/w) | Axitinib | 52.10% | 68.60% | 68.6% | 21.7% | 52.10% | 62.5% |
| | Target Dose | 300 μg | 600 μg | 1200 μg (total dose, as 2 × 600 μg) | 150 μg | 300 μg | 600 μg |
| | Actual Dose | 309 μg | 679 μg | 1358 μg (total dose) | 143 μg | 322 μg | 608 μg |
| | PEG Hydrogel | 39.90% | 26.00% | 26.1% | 65.2% | 39.90% | 31.20% |
| | 4a20K PEG-SAZ | 26.6% | 17.40% | 17.4% | 43.5% | 26.60% | 20.8% |
| | 8a20K PEG-NH2 | 13.3% | 8.70% | 8.7% | 21.7% | 13.30% | 10.4% |
| | TLA | 0.00% | 0.00% | 0.00% | 0.00% | 0.00% | 0.00% |
| | Co-Crystal | 0.00% | 0.00% | 0.00% | 0.00% | 0.00% | 0.00% |
| | Sodium phosphate | 8.00% | 5.40% | 5.4 % | 13.00 % | 8.00% | 6.3% |
| (% wet basis w/w) | Axitinib | 9.80% | 16.50% | 16.50% | 2.50% | 9.80% | 15.00% |
| | PEG Hydrogel | 7.50% | 6.30% | 6.30% | 7.50% | 7.50% | 7.50% |
| | 4a20K PEG-SAZ | 5.00% | 4.20% | 4.20% | 5.00% | 5.00% | 5.00% |
| | 8a20K PEG-NH2 | 2.50% | 2.10% | 2.10% | 2.50% | 2.50% | 2.50% |
| | TLA | 0.00% | 0.00% | 0.00% | 0.00% | 0.00% | 0.00% |
| | Fumaric | 0.00% | 0.00% | 0.00% | 0.00% | 0.00% | 0.00% |
| | Sodium phosphate | 1.50% | 1.30% | 1.30% | 1.50% | 1.50% | 1.50% |
| Dimensions | Dry Diameter | 0.30 ± 0.013 mm | 0.354 ± 0.010 mm | 0.354 ± 0.010 mm | 0.33 ± 0.010 mm | 0.31 ± 0.005 mm | 0.35 ± 0.014 mm |
| | Dry. Length | 7.1 ± 0.03 mm | 7.53 ± 0.031 mm | 2 × 7.53 ± 0.031 mm | 7.7 ± 0.09 mm | 7.0 ± 0.08 mm | 8.9 ± 0.95 mm |
| | Dry Implant Mass | 0.58 mg | 0.99 mg | 2 × 0.99 mg | 0.69 mg | 0.58 mg | 0.96 mg |
| | Wet Diameter | 0.63 mm | 0.733 ± 0.02 mm | 0.73 mm | 0.92 mm | 0.64 mm | 0.72 mm |
| | Wet Length | 9.4 mm | 7.66 ± 0.18 mm | 7.7 mm | 11.4 mm | 9.64 mm | 9.7 mm |
| | Surface area | 19.16 $mm^2$ | 18.48 $mm^2$ | 36.96 $mm^2$ | 34.1 $mm^2$ | 19.93 $mm^2$ | 22.6 $mm^2$ |

Surgical Dosing Procedure

Bilateral intravitreal injections of the test articles were performed in male Dutch Belted rabbits by means of an injector with a 25G needle assembly. The needle was inserted into the eye at a 45-degree angle to the sclera 3-4 mm away from the limbus via pars plana, while care was taken to not hit the lens or retina. Specifically, the needle was advanced inferotemporal at an angle, redirected to mid-vitreous before injecting, and after injection the needle was directed back to the entry angle/position before exiting the eye. The intravitreal injection was made to a full depth of the needle and then the implant was manually deployed with the depression of the plunger. Subsequently, the needle was removed and the episcleral tissues approximated to the site of insertion were grasped with conjunctival forceps to lessen reflux of vitreous. The study arms, OTX-TKI implant dosing and animal assignments are summarized in Table 32 above.

Tissue Processing and Bioanalytical Procedures

At the selected necropsy time points, whole eyes were sutured at 12 o-clock position, enucleated and frozen. The eyes were stored and shipped frozen prior to frozen dissection and subsequent bioanalysis. Care was taken to maintain orientation of the eye through dissections. Dissection of the eye followed the schematic shown in FIG. 22. Frozen eyes were bisected, and the anterior chamber was separated off. Four quadrants of retina and choroid were separated from the VH. The VH was bisected into superior and inferior and placed in collection tubes. Retina was removed and placed in collection tubes followed by choroid. Samples were weighed and frozen on dry ice until homogenization. Prior to homogenization, the originally dissected four quadrants of retina and choroid were pooled into one Precellys® tube for each respective tissue. Prior to homogenization, superior vitreous humor, inferior vitreous humor, and implant were pooled into one Precellys® tube.

To homogenize ocular tissue samples, weighed amounts of control bovine retina and choroid were homogenized in 7 ml Precellys® lysing tubes containing 1.4 and 2.8 mm mixed ceramic beads. Unknown Dutch Belted rabbit retina and choroid samples were homogenized in USA scientific impact resistant 7 mL microtubes containing ceramic beads (2.8 mm). A consistent aliquot of methanol:water (50:50, v/v) per milligram of tissue was added to each tube. Retina unknowns were diluted at an average of 1:19 (parts tissue to parts diluent). Choroid unknowns were diluted at an average of 1:21 (parts tissue to parts diluent). Vitreous humor was diluted with 4 mL of ethanol prior to homogenization. Tissues and ocular fluids were homogenized (Precellys® Evolution temperature 4° C.) at 5500 rpm for 3×30 second cycles with 20 second pauses between cycles until homogenized.

The prepared matrices were then dried under nitrogen at 35° C. and reconstituted with 200 μl methanol/water (50:50 v/v) and are analyzed via LC-MS/MS with a water/formic acid/acetonitrile gradient. Axitinib and the internal standard (IS) were separated on a YMC-Pack Pro C4 column (50×3.0 mm I.D.) and quantitated using ESI selective reaction monitoring mode with a total run time of approximately 6 min. The peak area of the m/z 387.1→356.3 for axitinib and m/z 390.3→356.1 for axitinib-D3 (IS) transition of axitinib was measured versus that of the internal standard transition to generate the standard curve. All standard curves were linear over the range of 0.100 to 500 ng/mL with the correlation coefficient (r2)>0.99. The LLOQ was 0.100 ng/mL.

Results

Body Weight

The TKI implant did not adversely impact animal body weights over the study duration. Body weight gain throughout the study was consistent with expected values and normal biological variation.

Ophthalmic Examinations

Ophthalmic examinations were used to aide in the description of the breakdown of the test article. TKI implants were visualized within the inferior vitreous of all eyes. Based on implant observations and cSLO images the implants reside principally in the inferior region. The hydrogel component of the implant stays intact and then fully bioresorbs by hydrolysis within the vitreous at approximately 4 to 5 months. Once the hydrogel fully degrades any undissolved axitinib particles (white amorphous/flocculent material) are released into the vitreous.

IOP

Following IVT injection, IOP (intraocular pressure) was relatively consistent throughout the study. All IOP measurements remained consistent with what is considered normal IOP for a rabbit.

Ocular Scoring

The ocular (uveitis) scoring parameters and numerical scores were assigned using a modification of the Standardization of Uveitis Nomenclature (SUN) and SPOTS systems as part of the ophthalmic examination. There were no statistically significant differences identified for ocular scoring, all study eyes were graded a zero to mild scores over the study duration.

Axitinib concentrations were measured in entire retina, choroid/RPE, vitreous humor and aqueous humor following dissection of the animal eye tissues.

The results for the concentrations of axitinib in aqueous humor are presented in Table 34.

TABLE 34

Summary of Axitinib concentration in Aqueous Humor (AH)

| Study Arm | Starting Dose (μg) | Time Point | Geometric Mean (ng/ml) |
|---|---|---|---|
| 13A | 309 | 6 Weeks | 3.0 |
| | | 13 Weeks | 22.1 |
| | | 24 Weeks | 2.7 |
| 13B | 679 | 6 Weeks | 1.9 |
| | | 13 Weeks | 26.2 |
| | | 24 Weeks | 1.1 |
| 13C × 2 | 1358 | 6 Weeks | 7.6 |
| | | 13 Weeks | 55.8 |
| | | 24 Weeks | 49.2 |
| 13D | 143 | 6 Weeks | 7.5 |
| | | 13 Weeks | 7.2 |
| | | 24 Weeks | 0.6 |
| 13E | 322 | 6 Weeks | 15.6 |
| | | 13 Weeks | 4.4 |
| | | 24 Weeks | 2.4 |
| 13F | 608 | 6 Weeks | 10.2 |
| | | 13 Weeks | 21.6 |
| | | 24 Weeks | 8.3 |

The highest geometric mean concentration of axitinib for SAB-I formulations was noted at 13-week time point for three dose levels, whereas for polymorph IV formulations the highest axitinib concentration for 150 and 300 μg dose groups (13D and 13E, respectively) was noted at 6 weeks and for 600 μg dose (13F) at 13 weeks. All the geometric mean concentrations of axitinib in aqueous humor are well below its solubility (400 ng/mL) in aqueous medium indicating very low drug movement to anterior chamber. In general, low peak concentration of axitinib was noted for polymorph IV formulations compared to SAB-I for similar dose.

The results for the concentrations of axitinib in retina and choroid/RPE (geometric mean concentrations) are presented in Table 35.

TABLE 35

In vivo Rabbit study results at 6 weeks, 13 weeks, and 24 weeks

| Study Arm | Starting Dose (μg) | Time point | Retina Geometric Mean (ng/g) | Choroid/ RPE Geometric mean (ng/g) |
|---|---|---|---|---|
| 13A | 309 | Week 6 | 353 | 271 |
| | | Week 13 | 529 | 496 |
| | | Week 24 | 500 | 377 |
| 13B | 679 | Week 6 | 125 | 178 |
| | | Week 13 | 115 | 288 |
| | | Week 24 | 965 | 492 |
| 13C × 2 | 1358 | Week 6 | 413 | 541 |
| | | Week 13 | 382 | 635 |
| | | Week 24 | 3089 | 764 |
| 13D | 143 | Week 6 | 456 | 514 |
| | | Week 13 | 226 | 849 |
| | | Week 24 | 159 | 123 |
| 13E | 322 | Week 6 | 588 | 861 |
| | | Week 13 | 460 | 660 |
| | | Week 24 | 900 | 493 |
| 13F | 608 | Week 6 | 488 | 823 |
| | | Week 13 | 736 | 1335 |
| | | Week 24 | 760 | 410 |

The retina concentrations of axitinib at 13 and 24 weeks appeared generally more stable in polymorph IV formulations groups compared to SAB-I formulations.

As can be seen from Table 35 above, the study with implants formulated with polymorph IV axitinib (13D, 13E, and 13F) in all cases resulted in higher geometric means in retina and choroid at week 6 than for the study group with implants formulated with SAB-I axitinib (13A, 13B, and 13C×2) at week 6, irrespective of the starting dose. This is particularly surprising, for example because the geometric mean concentration resulting from axitinib polymorph IV in the retina at week 6 was higher than the axitinib SAB-I polymorph even with an eight times higher dose of the axitinib SAB-I as compared to axitinib polymorph IV (compare groups 13C×2 and 13D in Table 35 above). This supports that a higher solubility polymorph of axitinib leads to a faster delivery of axitinib to the ocular tissues such as retina after intravitreal injections.

Groups 13A and 13E in Table 35 show the results of the study with implants comprising SAB-I axitinib and polymorph IV axitinib, respectively, with substantially the same surface area (within 5% of each other) and substantially the same dose (within 5% of each other) (19.16 and 19.93 $mm^2$, and 309 and 322 μg, respectively). The geometric mean concentrations of axitinib in ocular tissues after week 6 show that the polymorph IV is able to reach the tissues faster and provides for a higher concentration at week 6.

Further, the sum of the geometric mean concentrations determined in week 6, 13, and 24 of each of the two groups, 13A, and 13E show that a higher concentration of axitinib overall reaches the ocular tissues when using polymorph IV as compared to SAB-I.

Further, the results of the two groups, 13A, and 13E show that the $C_{max}$ of axitinib up to week 24 is higher in ocular tissues when using polymorph IV as compared to SAB-I (900 ng/g in retina and 529 ng/g in retina, respectively and 861 ng/g in the choroid and 496 ng/g in the choroid, respectively).

Groups 13B and 13E in Table 35 show the results of the study with implants comprising SAB-I axitinib and polymorph IV axitinib, respectively, with substantially the same surface area (within 10% of each other) (18.48 and 19.93 $mm^2$, respectively) but the SAB-I dose being almost 1.5 times the form IV dose. Even with such a high dose of SAB-I (13B) as compared to the polymorph IV (13E), the geometric mean concentrations of axitinib in ocular tissues at week 6 clearly show that the polymorph IV is able to reach the tissues faster and at a higher concentration at week 6.

Further, even with such a high dose of SAB-I as compared to the polymorph IV (13B and 13E) the sum of the geometric mean concentrations measured at week 6, 13, and 24 of each of the two groups, 13B, and 13E show that a higher concentration of axitinib overall reaches the ocular tissues when using polymorph IV as compared to SAB-I.

The average concentrations in retina and choroid/RPE measured in this study are provided in Tables 35A and 35B below. The PK parameters (based on the average concentrations) in these tissues are summarized again in Table 35C below.

TABLE 35A

Average concentrations in retina

Axitinib Concentrations in Retina (Avg ≤ SD)

| | Polymorph SAB-I | | | Polymorph IV | | | |
|---|---|---|---|---|---|---|---|
| Time | 13A 1 × 0.3 mg | 13B 1 × 0.6 mg | 13C 2 × 0.6 mg | 13D 1 × 0.15 mg | 13E 1 × 0.3 mg | Interpolation 1 × 0.45 mg | 13F 1 × 0.6 mg |
| 1.4 mo. | 538 ± 428 | 212 ± 234 | 611 ± 713 | 609 ± 543 | 722 ± 530 | 631 | 539 ± 294 |
| 3 mo. | 991 ± 914 | 143 ± 96 | 406 ± 178 | 272 ± 120 | 470 ± 106 | 933 | 1395 ± 1754 |
| 5.5 mo. | 1316 ± 2508 | 1589 ± 1971 | 8877 ± 10423 | 390 ± 717 | 1230 ± 957 | 1167 | 1103 ± 1271 |
| $AUC_{0-5.5\ mo.}$ (ng*day/g)[1] | 148856 | 84264 | 407954 | 72677 | 125003 | 145599 | 166194 |

TABLE 35B

Average concentrations in choroid/RPE
Axitinib Concentrations in Choroid/RPE (Avg # SD)

| Time | Polymorph SAB-I 13A 1 × 0.3 mg | 13B 1 × 0.6 mg | 13C 2 × 0.6 mg | Polymorph IV 13D 1 × 0.15 mg | 13E 1 × 0.3 mg | Interpolation 1 × 0.45 mg | 13F 1 × 0.6 mg |
|---|---|---|---|---|---|---|---|
| 1.4 mo. | 348 ± 238 | 245 ± 189 | 1501 ± 2858 | 525 ± 132 | 915 ± 406 | 932 | 949 ± 527 |
| 3 mo. | 901 ± 956 | 321 ± 179 | 664 ± 203 | 953 ± 559 | 751 ± 478 | 1264 | 1777 ± 1532 |
| 5.5 mo. | 460 ± 332 | 501 ± 102 | 825 ± 312 | 195 ± 211 | 584 ± 353 | 534 | 484 ± 300 |
| $AUC_{0.5\ mo.}$ (ng*day/g)[1] | 97590 | 55769 | 173427 | 102476 | 130653 | 162167 | 193682 |

TABLE 35C

PK parameters in retina and choroid/RPE

| | Time | Polymorph SAB-I 13A 1 × 0.3 mg | 13B 1 × 0.6 mg | 13C 2 × 0.6 mg | Polymorph IV 13D 1 × 0.15 mg | 13E 1 × 0.3 mg | Interpolation 1 × 0.45 mg | 13F 1 × 0.6 mg |
|---|---|---|---|---|---|---|---|---|
| Axitinib in Retina | $C_{max}$ (Avg ± SD) | 1316 ± 2508 | 1589 ± 1971 | 8877 ± 10423 | 609 ± 543 | 1230 ± 957 | 1167 | 1395 ± 1754 |
| | $T_{max}$ | 5.5 mo. | 5.5 mo. | 5.5 mo. | 1.4 mo. | 5.5 mo. | 5.5 mo. | 3 mo. |
| | $AUC_{0\text{-}5.5\ mo.}$ (ng*day/g) | 148856 | 84264 | 407954 | 72677 | 125003 | 145599 | 166194 |
| Axitinib in Choroid/ RPE | $C_{max}$ (Avg ± SD) | 901 ± 956 | 501 ± 102 | 1501 ± 2858 | 953 ± 559 | 915 ± 406 | 1264 | 1777 ± 1532 |
| | $T_{max}$ | 3 mo. | 5.5 mo. | 1.4 mo. | 3 mo. | 1.4 mo. | 3 mo. | 3 mo. |
| | $AUC_{0\text{-}5.5\ mo.}$ (ng*day/g) | 97590 | 55769 | 173427 | 102476 | 130653 | 162167 | 193682 |

[1]: For Tables 35A to 35C: AUC trapezoid calculation assumes steady state from time zero to 3 months.

Example 14: In Vivo VEGF Challenge Study—Rabbit

An in vivo challenge study in rabbit was designed according to Table 36 below, comparing an implant containing 0.6 mg axitinib polymorph SAB-I (14C; corresponding to implant #3 in Table 1A, Example A) and an implant according to the present invention containing 0.45 mg axitinib polymorph IV (14D; corresponding to implant #29a in Table 1C, Example A) with control and Avastin (bevacizumab):

TABLE 36

VEGF challenge study

| GN | No. Animals | Test Material (both eyes) | Intravitreal VEGF-Challenge (both eyes) | FA imaging (leakage evaluation) | IR imaging (implant evaluation) | Termination and tissue collection |
|---|---|---|---|---|---|---|
| 14A | 6 Cohort A: N = 3 Cohort B: N = 3 | Control (untreated) | Cohort A: Day 4, 28 (±2), 56 (±4), 84 (±5) | N = 3/group/ Cohort | None | Day 84 (±5) No tissue collection |
| 14B | 6 Cohort A: N = 3 Cohort B: N = 3 | Avastin 25 mg/ml 50 μL | Cohort B: Day 14 (±1), 42 (±2), 70 (±5) | 3 days after VEGF challenge at all corresponding | None | Day 84 (±5) No tissue collection: |
| 14C | 6 Cohort A: N = 3 Cohort B: N = 3 | SAB-I 1 × 0.6 mg | 1 μg/eye | timepoints | N = 6/group Days 28 (±2) 56(±4) 84(±5) | Day 84 (±5): Ocular tissues for bioanalysis (fresh collection) AH, VH, retina, chr/RPE, iris, implants |

TABLE 36-continued

| VEGF challenge study | | | | | | |
|---|---|---|---|---|---|---|
| GN | No. Animals | Test Material (both eyes) | Intravitreal VEGF-Challenge (both eyes) | FA imaging (leakage evaluation) | IR imaging (implant evaluation) | Termination and tissue collection |
| 14D | 6 Cohort A: N = 3 Cohort B: N = 3 | Polymorph-IV 1 × 0.45 mg | | | | |

The expected results are shown in Table 37 below.

| GN | | Cohort A | Cohort B |
|---|---|---|---|
| 14A | Control (untreated) | 1 week (full leakage)<br>1 month (full leakage).<br>2 months (full leakage)<br>3 months (full leakage) | 2 weeks (full leakage)<br>1.5 months (full leakage)<br>2.5 months (full leakage) |
| 14B | Avastin 25 mg/ml 50 μL | 1 week (No leakage)<br>1 month (No leakage)<br>2 months (Some leakage)<br>3 months (full leakage) | 2 weeks (No leakage)<br>1.5 months (No leakage)<br>2.5 months (Some leakage) |
| 14C | SAB-I 1 × 0.6 mg | 1 week (No leakage)<br>1 month (No leakage)<br>2 months (No leakage)<br>3 months (No leakage) | 2 weeks (No leakage)<br>1.5 months (No leakage)<br>2.5 months (No leakage) |
| 14D | Polymorph IV 1 × 0.45 mg | 1 week (No leakage)<br>1 month (No leakage)<br>2 months (No leakage)<br>3 months (No leakage) | 2 weeks (No leakage)<br>1.5 months (No leakage)<br>2.5 months (No leakage) |

Leakage was measured by fluorescein angiography on a scale of 0.4, with 0 meaning "no leakage" and 4 meaning "no inhibition of leakage" (see Table 37B).

Figure 29:
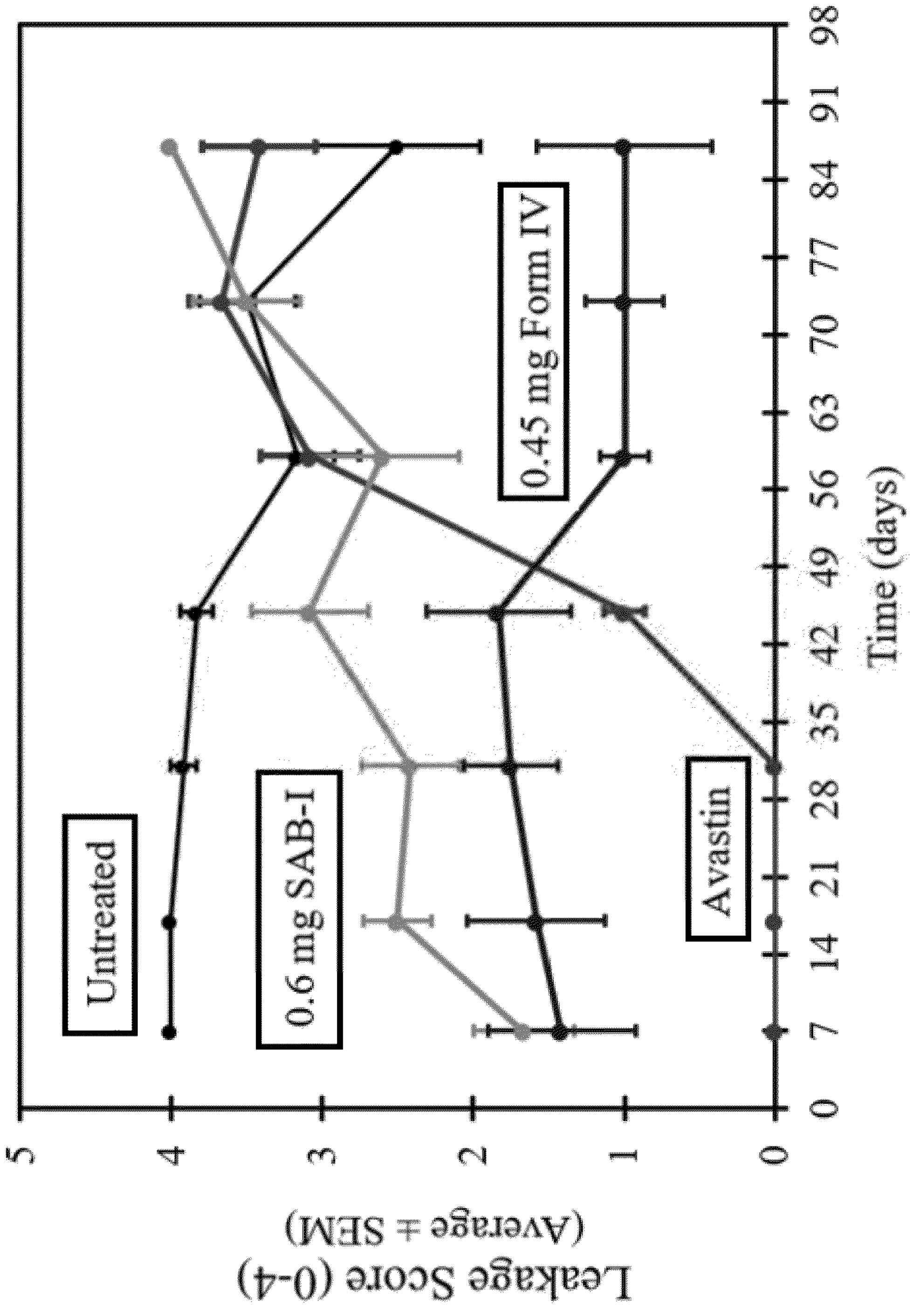
FIG. 29: Results of VEGF challenge study (leakage score over time), Example 14

The results of the measurement are shown in Table 37A and FIG. 29. The scoring criteria is based on Table 37B.

TABLE 37A

| Scoring Results | | | | | | |
|---|---|---|---|---|---|---|
| | Leakage Scores (average) | | | | | |
| Days | 7 | 17 | 31 | 45 | 59 | 73 |
| Untreated (− control), 14A | 4.0 | 4.0 | 3.9 | 3.8 | 3.2 | 3.5 |
| Avastin (+ control), 14B | 0.0 | 0.0 | 0.0 | 1.0 | 3.1 | 3.7 |
| 0.45 mg implant, axitinib polymorph IV, 14D | 1.4 | 1.6 | 1.8 | 1.8 | 1.2 | 1.0 |
| 0.6 mg implant, axitinib SAB-I, 14C | 1.7 | 2.5 | 2.4 | 3.1 | 2.8 | 3.5 |

TABLE 37B

| Scoring Criteria | |
|---|---|
| Score | Descriptor |
| 0 | Major vessels straight some tortuosity of smaller vessels, no vessel dilation |
| 1 | Increased tortuosity of major vessels and/or some vessel dilation |
| 2 | Leakage between major vessels, significant vessel dilation |
| 3 | Leakage between major and minor vessels, minor vessels still visible |

TABLE 37B-continued

| Scoring Criteria | |
|---|---|
| Score | Descriptor |
| 4 | Leakage between major and minor vessels, minor vessels poorly/not visible |

The axitinib polymorph IV implants (14D) according to the present invention substantially reduced retinal vessel leakage for at least 60 days following dosing compared to untreated controls. These implants maintained low leakage scores (mean: 1.2 to 1.8) throughout this period, with even a further decrease in leakage score thereafter, while untreated controls exhibited increased tortuosity and leakage (mean: 3.2 to 4.0). Bevacizumab-treated eyes showed no vascular leakage for up to 31 days (mean: 0.0), after which effectiveness waned. Even after 60 days, the axitinib implant according to the present invention continued to suppress vascular leakage effectively (mean: 1.2), whereas the bevacizumab group showed similar leakage scores (mean 3.1) to untreated eyes (mean 3.2). There were no implant-related effects on clinical observations through 60 days. Going further, the axitinib implant according to the present invention even further suppressed vascular leakage (mean: 1.0), while the effect of bevacizumab further decreased (mean: 3.7). The polymorph IV 450 μg axitinib intravitreal implant according to the present invention showed a sustained pharmacodynamic effect for at least 60 days, surpassing the duration of bevacizumab's effectiveness. These findings up to 60 days and beyond demonstrate the axitinib intravitreal implant's steady inhibition of VEGF activity and potential to continuously control retinal vascular diseases.

Example 15: Photostability Study of Polymorph IV

The axitinib form IV polymorph is known to be a photoreactive compound (Schmidt, D. et al, 2018. Axitinib: A photoswitchable approved Tyrosine Kinase inhibitor. ChemMedChem, 13(22), pp. 2415-2426; Garrett, M. et al., 2014. Population pharmacokinetic analysis of axitinib in healthy volunteers. British journal of clinical pharmacology, 77(3), pp. 480-492) requiring light protection for example when in tableted form (Gierer, D. S. et al, Pfizer Inc, 2014. Pharmaceutical compositions of n-methyl-2-[3-((e)-2-pyridin-2-yl-vinyl)-1h-indazol-6-ylsulfanyl]-benzamide. U.S. patent application Ser. No. 14/348,415).

A photostability study was conducted of polymorph IV API and PEG hydrogel implants prepared with the polymorph IV under different packaging configurations to determine the effect of light exposure on purity and crystal structure by X-ray powder diffraction (XRPD or XRD).

Implants for the photostability study targeting a 0.45 mg axitinib dose using polymorph IV were prepared (see Table 38). Time of light exposure of the implants and API during casting and aliquoting was tracked. The build process from casting to needle loading took three days in an inactive environmentally controlled area. During the cutting and loading, the implants were exposed for a maximum of six hours of ambient light exposure. On day three, the implants were loaded into needles, and they were left to condition for two days in the foil pouches and then heat sealed in a glove box under nitrogen. Once sealed, the samples were packaged according to Table 39 in labelled re-closable bags.

Implants were sterilized by gamma irradiation at 26.2-32.8 kGy. After sterilization, the controlled light exposure of each group was initiated. After the light exposure was completed, samples were either tested on XRD or tested for purity. The configurations of axitinib polymorph IV that were studied include the API powder, implants containing axitinib polymorph IV, such implants loaded in needles, and such implants loaded in needles with secondary foil packaging. All these configurations were tested with visible light, UV light, and no light exposure (control), following ICH Q1B Stability Testing Option 2 guidelines. The experimental setup included two light chambers for UV and visible light, and each had internal dimensions of 26.0" W×23.1" D×8" H. The UV light was exposed to the groups for 200-watt hours/$m^2$ for 10 hours. The visible light groups were exposed to 1.2 million lux hours/$m^2$ for 2 days, 16 h, and 43 m.

The polymorph IV samples experienced some light induced dimerization as expected. For the polymorph IV powder sample, the dimer (RRT~1.1286) converted from the control 0.564% to 31.29% (visible light) and 31.06% (UV light) impurity. In the exposed implant samples, the dimer converted from 0.115% to 24.72% (visible light) to 14.05% (UV light) impurities (see Table 40). In Table 40, "NR" means "not reported" (because the value was too small to report per limit), and "ND" means "not detected" (did not show up on the chromatogram). Without wishing to be bound by theory, there may be a protective effect of the PEG hydrogel network because the polymorph IV axitinib API experienced more dimerization than the polymorph IV implants (API 31.29% versus implant 24.72% after visible light exposure). There is no cis-isomer in the polymorph IV API sample because this polymorph does not exhibit cis-trans isomerization.

The XRPD analysis of polymorph IV samples demonstrated maintenance of their XRD diffraction peaks under all lighting conditions. Polymorph IV when contained in an implant according to the present invention can be considered photostable when the implant is in its primary packaging (i.e., the implant is loaded in an injector which is sealed in a pouch), as no change in impurities or crystal structure have been determined by XRPD.

Figure 30:
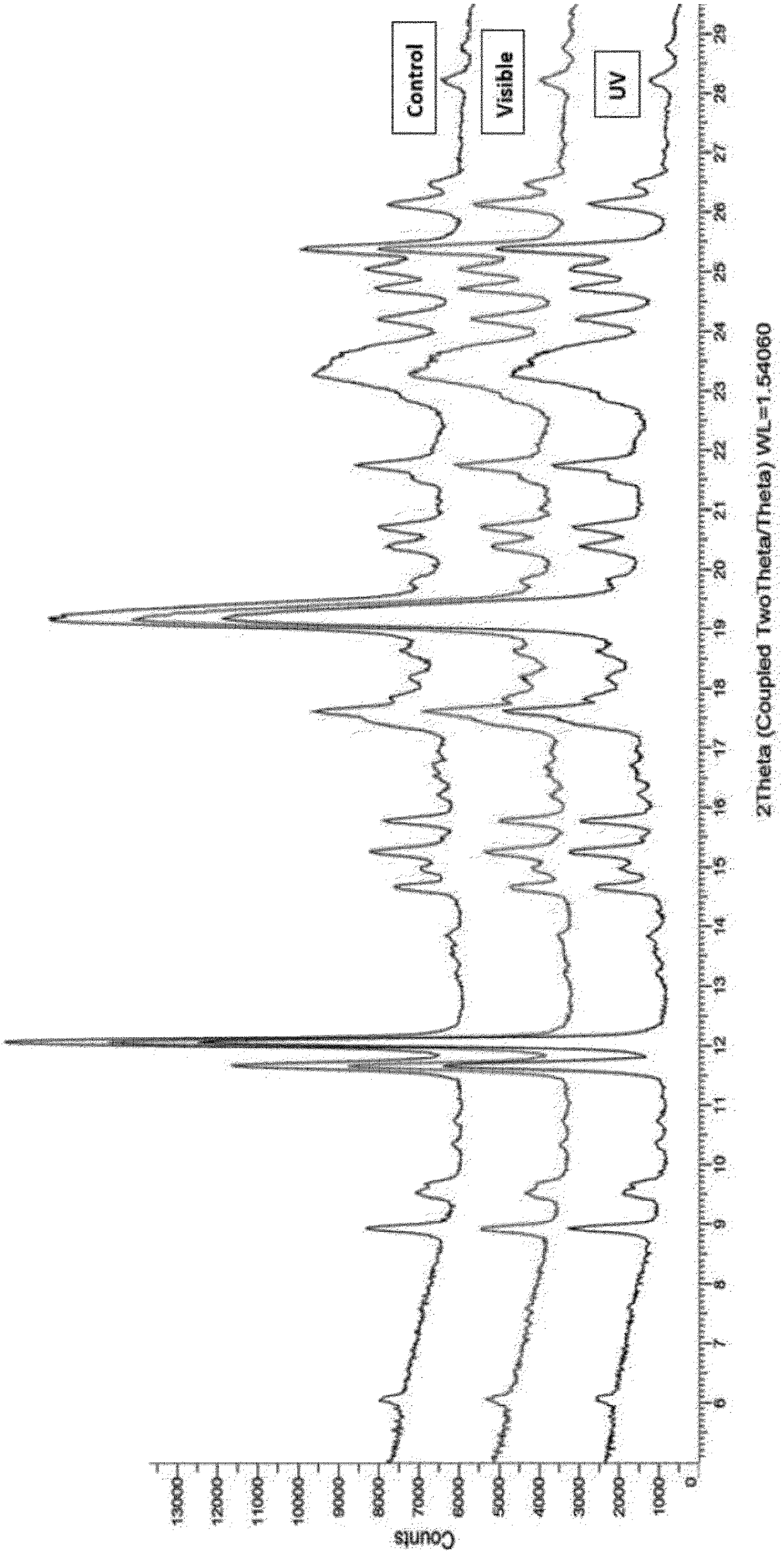
FIG. 30: XRD relating to photostability test, Example 15

A comparative XRD chart (for control, Visible light exposure, UV light exposure) is shown in FIG. 30.

The degradation of polymorph IV to intense light exposure per ICH conditions produced expected results compared to the findings previously reported in the literature. Results suggest that the exposure during a three-day implant build process to detrimental light is minimal. The low impurities found in the loaded needle and pouch sealed groups suggest that once loaded, there is significant light shielding to protect the implant.

TABLE 38

OTX-TKI Stability Build Formulations with Dimension and Assay Results

| Manufacturing | | | Wet Basis Formulation (w/w) | | | Dry Basis Formulation (w/w) | | | Dry Dimensions | | Assay | Hydrated Dimensions | |
|---|---|---|---|---|---|---|---|---|---|---|---|---|---|
| Axitinib | Tubing ID (mm) | Stretch Factor (X) | Axitinib (%) | PEG (%) | Sodium Phosphate (%) | Axitinib (%) | PEG (%) | Sodium Phosphate(%) | Width (mm) | Length (mm) | Axitinib (μg) | Width (mm) | Length (mm) |
| Polymorph IV | 1.18 | 1.70 | 9.5% | 7.5% | 0.85% | 53.2% | 42.0% | 4.80% | 0.337 | 8.18 | 489 | NA | NA |

TABLE 39

| Experimental Design for the Photostability Study | | | | |
|---|---|---|---|---|
| Group No. | Group | Study 0-No Light Exposure (Control) | Study 1-Visible Light 380-700 nm | Study 2-UV A 315-400 nm |
| 15A | Polymorph IV Raw API | 2 × 20 mg | 2 × 20 mg | 2 × 20 mg |
| 15B | Polymorph IV Implant (Implant of Table 38) | 12 | 12 | 12 |
| 15C | Polymorph IV implant in Needle (Implant of Table 38) | 12 | 12 | 12 |
| 15D | Polymorph IV implant in Needle in Pouch (Implant of Table 38) | 12 | 12 | 12 |

TABLE 40

| Photostability Purity Testing Results | | | | | | | | | | | | | |
|---|---|---|---|---|---|---|---|---|---|---|---|---|---|
| | | Reportable Impurities (% Area) | | | | | | | | | | | |
| Group No. and condition | Assay (μg) | RRT ~0.644 | RRT ~0.683 | RRT ~0.735 | RRT ~0.766 | RRT ~0.955 | RRT ~1.116 | RRT ~1.172 | RRT ~1.286 (Dimer) | RRT ~1.350 | RRT ~1.543 | RRT ~1.579 | Total Reportable Impurities |
| 15A-Control | NA | ND | ND | 0.13% | 0.06% | ND | ND | ND | 0.56% | ND | 0.07% | 0.05% | 0.88% |
| 15A-Visible | NA | 0.06% | ND | 0.14% | 0.07% | 0.07% | 0.05% | 0.06% | 32.29% | 0.14% | 0.09% | NR | 32.98% |
| 15A-UV | NA | ND | ND | 0.15% | 0.08% | ND | NR | NR | 31.06% | 0.20% | 0.09% | NR | 31.58% |
| 15B-Control | 488 | ND | ND | NR | NR | ND | ND | ND | 0.12% | ND | NR: | NR | 0.10% |
| 15B-Visible | 327 | ND | NR | 0.22% | NR | ND | 0.17% | ND | 24.72% | 0.13% | 0.13% | NR | 25.40% |
| 15B-UV | 392 | ND | ND | 0.15% | NR | ND | NR | ND | 14.05% | NR | NR | NR | 14.20% |
| 15C-Visible | 479 | NR | ND | NR | NR | ND | ND | ND | 0.24% | ND | NR | NR | 0.20% |
| 15C-UV | 440 | ND | ND | NR | NR | ND | ND | ND | 1.50% | ND | NR | NR | 1.50% |
| 15D-Visible | 490 | NR | ND | NR | NR | ND | ND | ND | 0.13% | ND | NR | NR | 0.10% |
| 15D-UV | 488 | ND | ND | NR | NR | ND | ND | ND | 0.11% | ND | NR | NR | 0.10% |

Example 16: Planned Phase 3, Multicenter, Double-Masked, Randomized, Parallel-Group Study to Evaluate the Efficacy and Safety of Intravitreal OTX-TKI (Axitinib Implant) in Subjects with Neovascular Age-Related Macular Degeneration Indication:

Neovascular age-related macular degeneration (nAMD).

Study Objective:

To evaluate the efficacy and safety of Intravitreal OTX-TKI (0.45 mg axitinib polymorph IV implant) in subjects who have nAMD.

Number of Subjects:

300 subjects (150 per group).

Study Population:

Subjects who are treatment naïve with a diagnosis of extra-foveal choroidal neovascularization (CNV) or subfoveal neovascularization (SFNV) secondary to nAMD, who are older than 50 years of age and are expected to develop visual loss.

Study Design:

This planned study is a multicenter, double-masked, randomized, parallel group study. Two treatment groups will be evaluated.

| Treatment Group | N | Route of Delivery | Day 1 Admin |
|---|---|---|---|
| OTX-TKI-Polymorph IV | 150 | Intravitreal injection | 0.45 mg OTX-TKI* |
| Control | 150 | Intravitreal injection: | 2 mg (0.05 mL) aflibercept |

Abbreviations: Admin = administration, N = number of subjects, OTX-TKI = OTX-TKI (0.45 mg axitinib implant) for intravitreal use; *see information herein below regarding the implant composition and amount of axitinib form IV contained therein.

Study Overview:

The screening period will have two visits that occur 8 weeks and 4 weeks prior to Day 1. During screening, after investigator confirms initial eligibility, all subjects will receive 1 injection of 2 mg (0.05 mL) aflibercept 8 weeks prior to Day 1 and 1 injection of 2 mg (0.05 mL) aflibercept 4 weeks prior to Day 1 in the potential study eye(s). At Day 1 after investigator's confirmation of continued eligibility, subjects will be randomized 1:1 to one of two treatment groups: OTX-TKI (axitinib implant) 0.45 mg for intravitreal injection (OTX-TKI) or control. Subjects randomized to the OTX-TKI treatment group will receive an injection of 0.45 mg OTX-TKI on Day 1, and subjects randomized to the control group will receive an injection of 2 mg (0.05 mL) aflibercept on Day 1. All subjects will be monitored for at least 10 minutes immediately following injections. Subjects can have only one eye treated with OTX-TKI. The contralateral eye, if needed, will be treated at the Investigator's discretion. The fellow eye treatment will be standard of care and in no case should another investigational drug be used for the contralateral eye. The study eye will be the eye meeting the inclusion and none of the exclusion criteria at Day 1. For subjects with bilateral nAMD, if both eyes meet the criteria at Day 1, the study eye will be the eye clinically judged to be the more severely affected eye as determined by the Investigator. If the eyes are symmetrically affected, the study eye will be the right eye.

Figure 26:
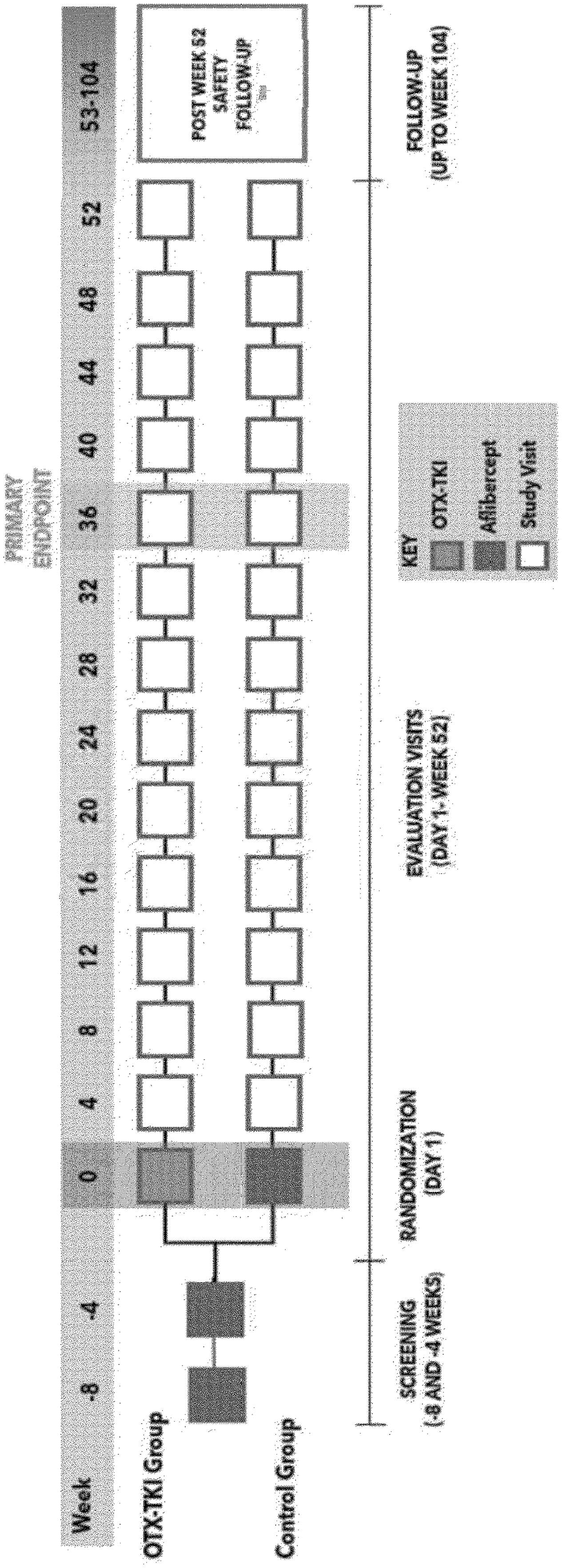
FIG. 26: Planned study overview (Example 16)

Follow-up evaluations will occur at Week 4 (Visit 4), Week 8 (Visit 5), Week 12 (Visit 6), Week 16 (Visit 7), Week 20 (Visit 8), Week 24 (Visit 9), Week 28 (Visit 10), Week 32 (Visit 11), Week 36 (Visit 12), Week 40 (Visit 13), Week 44 (Visit 14), Week 48 (Visit 15), and Week 52 (Visit 16), at which time subject will be followed up for safety at least every 3 months for an additional 52 weeks with a final visit at Week 104 post Day 1. The study scheme also showing the study treatment duration is provided in FIG. 26.

Subject Treatment Duration

The total expected study duration is 112 weeks for each subject. Duration includes 8 weeks of screening, 52 weeks of initial follow up and 52 weeks of additional safety follow up.

Post Week 52 safety follow up visits may occur monthly or bi-monthly; however, follow-up visits should be no more than 3 months (12 weeks) from the previous visit, per Investigator discretion. Subjects in both groups should be treated with standard of care.

Study Treatment

All subjects in this planned study that meet inclusion/exclusion criteria at screening will receive 1 injection of 2 mg (0.05 mL) aflibercept in potential study eye at 8 weeks and 4 weeks prior to Day 1. If both eyes meet inclusion/exclusion criteria at screening, both eyes will receive the aflibercept injections at the screening visits and study eye will be determined at Day 1.

At Day 1 subjects will be randomized 1:1 to either:

OTX-TKI Treatment Group: This group will receive 1 injection of OTX-TKI (axitinib implant) 0.45 mg for intravitreal injection Control Group: This group will receive 1 injection of 2 mg (0.05 mL) aflibercept OTX-TKI is a dried polyethylene glycol (PEG)-based hydrogel implant containing dispersed particles of the small molecule, tyrosine kinase inhibitor axitinib. OTX-TKI is provided to the Investigator as one 0.45 mg axitinib hydrogel implant pre-loaded in a 25-gauge thin-walled needle with a separately packaged injection device.

Axitinib is the active pharmaceutical ingredient (API) in the OTX-TKI implant. The implant is designed to be injected into the posterior segment (vitreous cavity) of the eye. The implant hydrates and softens upon contact with the vitreous and gradually elutes axitinib. It will remain in place until the hydrogel is eventually resorbed through hydrolysis and cleared from the eye.

OTX-TKI (Axitinib) Implant 0.45 mg Composition and Dimensions

The implant used in this planned study is an implant according to the present invention containing axitinib polymorph IV in a target amount of about 450 μg, which means an actual amount of −20% and +25% thereof, i.e., from about 360 μg to about 562.5 μg, such as from about 400 to about 500 μg. Nevertheless, for simplicity, the implant is designated in this Example 16 as the "0.45 mg OTX-TKI" implant.

The composition of this implant may be within the following ranges:

| Ingredient | Theoretical Implant Composition (% w/w, dry) | Function |
|---|---|---|
| Axitinib, Form IV | 54-69 | API |
| 4A 20k PEG SAZ | 17-26 | Hydrogel matrix |
| 8A 20k PEG Free Amine | 8-13 | Hydrogel matrix |
| Sodium Phosphate Dibasic Dried, USP | 3-5 | Buffer salt |
| Sodium Phosphate Monobasic Anhydrous, USP | 1-3 | Buffer salt |
| Water for Injection (WFI) | * | Solvent |
| Total | 100 | |

The dimensions of such an implant may be within the following ranges:

| | Dry Dimensions | Hydrated Dimensions |
|---|---|---|
| Length | ≤11 mm (such as about 6 to about 9 mm) | ≤11 mm |
| Diameter | 0.2-0.4 mm (such as about 0.31 to about 0.36 mm) | ≤2 mm (such as about 0.4 to about 0.9 mm) |

For Eylea® (aflibercept injection) see Eylea package insert. Regeneron Pharmaceuticals, Inc; (2023) or Bayer (2020)

Endpoints

The primary and secondary endpoints of the planned study are as follows:

Primary:

- Proportion of subjects who maintained visual acuity, defined as <15 ETDRS letters of BCVA loss at Week 36

Key Secondary:

- Proportion of subjects who maintained visual acuity, defined as <15 ETDRS letters of BCVA loss with one rescue injection or fewer at Week 52
- Proportion of subjects who maintained visual acuity, defined as <15 ETDRS letters of BCVA loss at Week 52
- Proportion of subjects who maintained visual acuity, defined as <15 ETDRS letters of BCVA loss with one rescue injection or fewer at Week 36
- BCVA change from baseline at Week 36
- BCVA change from baseline at Week 52

Secondary:

- Central subfield thickness (CSFT) changes from baseline at Week 36 and Week 52
- Proportion of subjects with no increase in CSFT (i.e., CSFT increase to be ≤50 μm) as compared with baseline at Week 36 and Week 52
- Proportion of subjects with CSFT≤350 μm at Week 36 and Week 52
- Number of rescue injections from baseline up to Week 36 and Week 52
- Proportion of subjects receiving rescue injections from baseline up to Week 36 and Week 52
- Mean time to the first rescue injection
- Mean time to the second rescue injection
- Mean number of rescue injections at each study visit
- Proportion of subjects who lose ≥10 letters at Week 36 and Week 52
- Proportion of subjects who gain ≥15 letters at Week 36 and Week 52

Proportion of subjects who gain ≥10 letters at Week 36 and Week 52

Safety:

Incidence and severity of treatment emergent adverse events (AEs)

Severe vision loss defined as a ≥30 ETDRS letter loss in vision from baseline

Intraocular pressure (IOP) changes from baseline

Inclusion Criteria

Individuals must meet the following criteria to be eligible:

At Screening Visits 1 and 2:

1. Treatment naïve for nAMD in either eye at screening.
2. Have macular choroidal neovascularization due to nAMD who have had visual loss or would be expected to develop visual loss during the course of the study.
3. If foveal intraretinal and/or subretinal fluid is present on SD-OCT, it shall not exceed 500 μm (CSFT) as determined by Investigator.
4. Are eligible to receive intraocular aflibercept therapy for the treatment of nAMD.
5. Have a BCVA ETDRS letter score of at least 54, such as 59 or greater (approximately 20/63, or 20/80) in either eye at screening
6. Have adequate ocular media and adequate pupillary dilation in the study eye to permit good quality fundus imaging.
7. Are female who is postmenopausal for at least 12 months prior to screening or surgically sterile; or male or female of childbearing potential willing to use two forms of adequate contraception from screening until they exit the study.
8. Are able and willing to comply with all study requirements and visits.
9, Have provided written informed consent.

At Day 1:

1. Are at least older than 50 years of age at Day 1.
2. Have BCVA of at least 84 ETDRS letter score (approximate 20/20 Snellen equivalent) at Day 1.
3. Have a CSFT of 350 μm or less in study eye at Day 1 as determined by Investigator.

Exclusion Criteria

Individuals are not eligible for study participation if at screening visits and Day 1 they:

1. Have presence of a disease other than CNVM due to AMD in the study eye that could affect vision or safety assessments.
2. Monocular subjects or a BCVA score of 20/200 in fellow eye at screening.
3. Have evidence of a scar, fibrosis, or atrophy of >50% of the total lesion in the study eye.
4. Currently or previously treated Geographic Atrophy in study eye.
5. Have previous laser photocoagulation to the macula in the study eye.
6. Have history of intraocular surgery including cataract surgery or keratorefractive surgery (laser-assisted in-situ keratomileusis [LASIK], photorefractive keratectomy [PRK], etc.) or any anterior segment surgery in the study eye within 6 months of screening or have expectation of penetrating keratoplasty, vitrectomy, cataract surgery, or LASIK or any other intraocular surgery during the study period in the study eye or have a history of vitreoretinal surgery (including vitrectomy) or other ocular surgeries including scleral buckle or glaucoma filtering/shunt surgery in the study eye.
7. Have received gene therapy treatment or PDS in the fellow eye.

8. Have aphakia in the study eye.
9. Have a history of significant ocular infection (bacterial, viral, or fungal) within the previous 3 months, or history of herpetic ocular diseases (including herpes simplex virus, varicella zoster, or cytomegalovirus retinitis) or toxoplasmosis gondii or chronic/recurrent inflammatory eye disease (i.e., scleritis, uveitis, corneal edema) in either eye.
10. Have evidence of a rhegmatogenous retinal detachment or visually significant/severe epiretinal membrane, macular hole, tear of the retinal pigment epithelium in the macula, or other macular pathology deemed significant by the Investigator in the study eye.
11. Have a history of or presence of vitreous hemorrhage in the study eye. Subject is still eligible if history of past hemorrhagic posterior vitreous detachment has resolved.
12. Have advanced glaucoma or uncontrolled IOP≥25 mmHg despite treatment.
13. Have a history of receiving glaucoma filtration surgery in the study eye.
14. Have presence of other causes of CNV, e.g., pathologic myopia (spherical equivalent ≥−8 diopters, or axial length of 26 mm or more), choroidal rupture, ocular histoplasmosis syndrome, or multifocal choroiditis in the study eye.
15. Have any current systemic or ocular treatment with TKIs or systemic treatment with anti-VEGF agents.
16. Have an ocular malignancy including choroidal melanoma in either eye,
17. Are receiving concurrent treatment with medications known to be toxic to the retina, lens, or optic nerve (e.g., chlorpromazine, phenothiazines, tamoxifen, etc.).
18. Have a need for chronic therapy with systemic, intravitreal, or topical ocular corticosteroids or have known allergy to fluorescein (e.g., bronchospasm, rash, etc.), or to any component of the study products.
19. Have symptomatic or unstable coronary artery disease, angina, congestive heart failure, or an arrhythmia requiring active procedural management (management with medications is permissible) within the last 30 days of the injection of the implant.
20. Have uncontrolled hypertension (defined as >160/100 mmHg, despite medical treatment).
21. Have a history of or presence of uncontrolled systemic disease or a debilitating disease.
22. Had a myocardial infarction or other cardiovascular event (e.g., stroke) within the previous 6 months.
23. Have uncontrolled diabetes as deemed by the Investigator.
24. Are female and pregnant or breastfeeding or intend to become pregnant during the study,
25. Have participated in any study involving an investigational drug either in the US or outside the US within the past 30 days,
26. Are an employee of the site that is directly involved in the management, administration, or support of the study, or an immediate family member of the same.

Sample Size Consideration

The study primary endpoint is proportion of subjects who maintained visual acuity, defined as <15 ETDRS letters of BCVA loss at Week 36. N=128 per group will have 90% of power to detect the difference of 75% in OTX-TKI group vs 55% in the control group based on Fisher's exact test at two-sided alpha=0.05. Adjusting for dropout, a total of 300 subjects will be randomized using 1:1 ratio to OTX-TKI 0.45 mg group (N=150) and control group (N=150).

Statistical Methods

The primary endpoint is proportion of subjects who maintained visual acuity, defined as <15 ETDRS letters of BCVA loss at Week 36. The primary estimand is the treatment difference in the proportions of subjects maintaining vision at Week 36 (losing <15 ETDRS letters) between OTX-TKI and control groups. Composite variable estimand will be used. The 5 components of the estimand are as follow.

Target Population:

Subjects with wet AMD who meet the study entry criteria.

Endpoint:

Proportion of subjects maintaining vision at Week 36 (losing <15 ETDRS letters).

Treatment Condition(s):

Treatment condition is based on the randomized treatment.

Population-Level Summary:

The difference in proportions of subjects maintaining vision at Week 36 (losing <15 ETDRS letters) between OTX-TKI and control groups, two-sided 95% confidence interval, and the corresponding two-sided p-value.

Intercurrent Events:

Subjects who received any rescue injections prior to Week 36 or drop out the study due to any reasons prior to or at Week 36 will be imputed as treatment failure.

For the primary endpoint analysis, subjects who received any rescue injections prior to Week 36 or dropout of the study due to any reasons will be imputed as treatment failure (Le, losing ≥15 ETDRS letters). Cochran-Mantel-Haenszel test (without stratification factor) will be used to analyze the primary endpoint. Difference of proportions of subjects maintaining vision at Week 36 between OTX-TKI and control groups will be presented with 95% confidence interval and p-value. Multiple sensitivity analyses of the primary endpoints will be performed. The first 3 key secondary endpoints will be analyzed using the same statistical method as the primary endpoint.

For the analyses of the 4th and 5th key secondary endpoints (BCVA change from baseline at Week 36 and Week: 52), subjects who received any rescue injections, their observed BCVA values after the 1st supplemental injection will be set to missing, BCVA change from baseline will be analyzed by a mixed model for repeated measures (MMRM). Sensitivity analyses using multiple imputation with pattern-mixture models will be performed.

Descriptive statistics by treatment group will be provided for all safety endpoints. Frequency counts and percentage of subjects will be provided by MedDRA System Organ Class (SOC) and preferred term (PT) by treatment group. Concomitant medications will be presented after coding with WHO-Drug Dictionary terms. Clinical laboratory assessments will be presented using descriptive statistics by treatment group.

Rescue Criteria

Subjects receiving rescue therapy will be followed to the last study visit. The following criteria must be met to receive rescue therapy the first time:

1. BCVA loss of 15 ETDRS letters or more from Day 1 due to AMD (letter loss cannot be due to any other ophthalmic reason outside of AMD) OR
2. New macular hemorrhage that would likely to lead irreversible vision loss if left untreated in the opinion of the investigator after discussion with Medical Monitor After the first rescue injection, rescue therapy can be provided at investigator discretion per their clinical judgement.

Prohibited Medications/Procedures

The following are prohibited prior to administration of IP in the study eye:

- Previous therapy for the treatment of nAMD, including no previous anti-VEGF therapy (i.e., aflibercept, ranibizumab, faricimab, brolucizumab, or bevacizumab).
- Intraocular surgery including cataract surgery or keratorefractive surgery (laser-assisted in-situ keratomileusis [LASIK], photorefractive keratectomy [PRK], etc.) or any anterior segment surgery in the study eye within 6 months of screening.
- Any glaucoma surgery including minimally invasive glaucoma surgeries Concomitant use of any investigational medications is prohibited for the duration of the study. Also, concomitant use of any prescription ophthalmic/systemic medications (other than those allowed per protocol) that would affect AMD is prohibited until Week 52. Additionally, concurrent use of medications known to be toxic to the retina, lens, or optic nerve (e.g., chlorpromazine, phenothiazines, tamoxifen, etc.) and concurrent use of ocular or systemic TKIs and systemic treatment with anti-VEGF agents are prohibited.

Chronic therapy with systemic, intravitreal, or topical ocular corticosteroids is also prohibited but a short course of <7 days, if needed during the study, is permissible.

Intraocular anti-VEGF agents can be administered as standard of care to the non-study eye (NSE) if clinically indicated.

Example 17 (Prospective): A Phase 3, Multicenter, Double-Masked, Randomized, Parallel-Group Study to Evaluate the Efficacy and Safety of Intravitreal OTX-TKI (Axitinib Implant) in Subjects with Neovascular Age-Related Macular Degeneration Indication:

Neovascular age-related macular degeneration (nAMD).

Study Objective:

To evaluate the efficacy and safety of Intravitreal OTX-TKI implants according to the invention (containing a target axitinib dose of 0.3 mg, 0.45 mg, 0.6 mg polymorph IV axitinib implant, each −20%/+25%) in subjects who have nAMD.

Number of Subjects:

300 subjects (150 per group).

Study Population:

Subjects with a diagnosis of extra-foveal choroidal neovascularization (CNV) or subfoveal neovascularization (SFNV) secondary to nAMD.

Study Design:

This is a multicenter, double-masked, randomized, parallel group study. Four treatment groups will be evaluated.

| Treatment Group | N | Route of Delivery | Day 1 Admin |
|---|---|---|---|
| OTX-TKI-Polymorph IV | 150 | Intravitreal injection | 0.3 mg OTX-TKI |
| OTX-TKI-Polymorph IV | 150 | Intravitreal injection | 0.45 mg OTX-TKI |
| OTX-TKI-Polymorph IV | 150 | Intravitreal injection | 0.6 mg OTX-TKI |
| Control | 150 | Intravitreal injection | 2 mg (0.05 mL) aflibercept |

Abbreviations: Admin=administration, N=number of subjects, OTX-TKI=OTX-TKI (0.3, 0.45 or 0.6 mg axitinib implant) for intravitreal use.

Subject Treatment Duration

The total expected study duration is 112 weeks for each subject. Duration includes 8 weeks of screening, 52 weeks of initial follow up and 52 weeks of additional safety follow up, Post Week 52 safety follow up visits may occur monthly or bi-monthly; however, follow-up visits should be no more than 3 months (12 weeks) from the previous visit, per Investigator discretion, Subjects in both groups should be treated with standard of care.

OTX-TKI (Axitinib) Implant Dimensions in this Prospective Study

| | Dry Dimensions | Hydrated Dimensions |
|---|---|---|
| Length | ≤11 mm | ≤11 mm |
| Diameter | 0.2 to 0.6 mm | ≤2 mm |

For Eylea ® (aflibercept injection) see Eylea package insert. Regeneron Pharmaceuticals, Inc; (2023) or Bayer (2020)

Endpoints

Primary:

- Proportion of subjects who maintained visual acuity, defined as <15 ETDRS
- letters of BCVA loss at Week 36

Key Secondary:

- Proportion of subjects who maintained visual acuity, defined as <15 ETDRS
- letters of BCVA loss with one rescue injection or fewer at Week 52
- Proportion of subjects who maintained visual acuity, defined as <15 ETDRS
- letters of BCVA loss at Week 52
- Proportion of subjects who maintained visual acuity, defined as <15 ETDRS
- letters of BCVA loss with one rescue injection or fewer at Week 36
- BCVA change from baseline at Week 36
- BCVA change from baseline at Week 52

Secondary:

- Central subfield thickness (CSFT) changes from baseline at Week 36 and Week 52
- Proportion of subjects with no increase in CSFT (i.e., CSFT increase to be ≤50 μm) as compared with baseline at Week 36 and Week 52
- Proportion of subjects with CSFT≤350 μm at Week 36 and Week 52
- Number of rescue injections from baseline up to Week 36 and Week 52
- Proportion of subjects receiving rescue injections from baseline up to Week 36 and Week 52
- Mean time to the first rescue injection
- Mean time to the second rescue injection
- Mean number of rescue injections at each study visit
- Proportion of subjects who lose ≥10 letters at Week 36 and Week 52
- Proportion of subjects who gain ≥15 letters at Week 36 and Week 52
- Proportion of subjects who gain ≥10 letters at Week 36 and Week 52

Safety:

- Incidence and severity of treatment emergent adverse events (AES)·
- Severe vision loss defined as a ≥30 ETDRS letter loss in vision from baseline
- Intraocular pressure (IOP) changes from baseline Inclusion Criteria Subjects with a diagnosis of extra-foveal choroidal neovascularization (CNV) or subfoveal neovascularization (SFNV) secondary to nAMD.

Exclusion Criteria

Subjects without a diagnosis of extra-foveal choroidal neovascularization (CNV) or subfoveal

The invention claimed is:

1. A method of treating an ocular disease in a patient in need thereof, the treatment comprising administering to the patient's eye by intravitreal injection a sustained release biodegradable ocular implant comprising a hydrogel and axitinib, wherein the implant comprises axitinib polymorph IV in an amount of from about 400 μg to about 500 μg.

2. The method of claim 1, wherein the ocular disease involves angiogenesis, neovascularization or a combination thereof.

3. The method of claim 1, wherein the ocular disease is neovascular age-related macular degeneration (AMD), diabetic macular edema, diabetic retinopathy, or retinal vein occlusion.

4. The method of claim 1, wherein the patient is a human patient.

5. The method of claim 4, wherein final biodegradation of the hydrogel occurs within about 6 to about 9 months after injection.

6. The method of claim 4, wherein the treatment period with one implant lasts for about 6 to about 12 months after administration.

7. The method of claim 4, wherein a new implant is administered every 6 to 12 months.

8. The method of claim 4, wherein the ocular disease is neovascular age-related macular degeneration (AMD).

9. The method of claim 1, wherein the percentage of axitinib released from the implant in an in vitro test performed at 35° C.±0.5° C. in 0.01N HCl with 0.25% cetyl trimethyl ammonium bromide (CTAB) in a USP apparatus 4 is:

from about 10 to about 25% after 0.5 hours,
from about 30 to about 50% after 2 hours,
from about 60 to about 90% after 6 hours,
from about 79 to about 100% after 10 hours,
at least about 90% after 12 hours,
or at least about 92% after 16 hours.

10. The method of claim 1, wherein the amount of axitinib released from the implant in an in vitro test performed at 35° C.±0.5° C. in 0.01N HCl with 0.25% cetyl trimethyl ammonium bromide (CTAB) in a USP apparatus 4 is:

from about 50 to about 80 μg after 0.5 hours,
from about 140 to about 200 μg after 2 hours,
from about 270 to about 360 μg after 6 hours,
from about 350 to about 450 μg after 10 hours,
or at least about 410 μg after 16 hours.

11. The method of claim 1, wherein the implant has a composition on a dry basis (in % w/w) of about 30 to about 75% axitinib, about 20 to about 50% polyethylene glycol (PEG) units, and about 0.5 to about 15% sodium phosphate salt, and on a wet basis (in % w/w) of from about 5 to about 17% axitinib, about 4 to about 12% PEG units, and about 0.2 to about 5% sodium phosphate salt, wherein the hydrogel comprises a PEG hydrogel network formed by crosslinking 4a20kPEG-SAZ and 8a20kPEG-$NH_2$ precursors, wherein the implant in its dried state has a width of from about 0.20 to about 0.40 mm, and in its hydrated state (after 24 hours in PBS at a pH of 7.4 at 37° C.) has a length of about 11 mm or less, and wherein the implant has a hydrated surface area of from about 10 to about 30 $mm^2$, and wherein the ocular disease is neovascular age-related macular degeneration (AMD), diabetic macular edema, diabetic retinopathy, or retinal vein occlusion.

12. A method of treating an ocular disease in a patient in need thereof, the treatment comprising administering to the patient's eye by intravitreal injection a sustained release biodegradable ocular implant comprising a hydrogel and axitinib, wherein at least 90% by weight of the entire axitinib contained in the implant is polymorph IV.

* * * * *